(12) United States Patent
Blomgren et al.

(10) Patent No.: US 12,053,462 B2
(45) Date of Patent: Aug. 6, 2024

(54) QUINOLINE DERIVATIVES

(71) Applicant: Gilead Sciences, Inc., Foster City, CA (US)

(72) Inventors: Peter A. Blomgren, Issaquah, WA (US); Taryn Campbell, Seattle, WA (US); Jayaraman Chandrasekhar, Redmond, WA (US); Christopher T. Clark, Seattle, WA (US); Julian A. Codelli, Seattle, WA (US); Kevin S. Currie, North Bend, WA (US); Jeffrey E. Kropf, Issaquah, WA (US); Yasamin Moazami, Seattle, WA (US); Nicole Nava, Seattle, WA (US); Leena Patel, Seattle, WA (US); Stephane Perreault, Brier, WA (US); Jason K. Perry, San Francisco, CA (US); Kassandra F. Sedillo, Princeton, NJ (US); Natalie Seeger, Salt Lake City, UT (US); Kirk L. Stevens, Bothell, WA (US); Jennifer Anne Treiberg, Redmond, WA (US); Suet C. Yeung, Redmond, WA (US); Zhongdong Zhao, Bellevue, WA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/379,175

(22) Filed: Jul. 19, 2021

(65) Prior Publication Data
US 2023/0041518 A1 Feb. 9, 2023

Related U.S. Application Data

(63) Continuation of application No. 16/667,306, filed on Oct. 29, 2019, now Pat. No. 11,116,760.
(Continued)

(51) Int. Cl.
| | | |
|---|---|---|
| C07D 215/02 | (2006.01) |
| A61K 31/4375 | (2006.01) |
| A61K 31/47 | (2006.01) |
| A61K 31/4709 | (2006.01) |
| A61K 31/501 | (2006.01) |

(Continued)

(52) U.S. Cl.
CPC .......... *A61K 31/47* (2013.01); *A61K 31/4375* (2013.01); *A61K 31/4709* (2013.01); *A61K 31/501* (2013.01); *A61K 31/506* (2013.01); *A61K 31/517* (2013.01); *A61K 31/519* (2013.01); *A61K 31/5355* (2013.01); *A61K 31/541* (2013.01); *A61K 45/06* (2013.01); *C07D 215/14* (2013.01); *C07D 401/10* (2013.01); *C07D 401/12* (2013.01); *C07D 401/14* (2013.01); *C07D 405/14* (2013.01); *C07D 407/14* (2013.01); *C07D 409/14* (2013.01); *C07D 413/12* (2013.01); *C07D 413/14* (2013.01); *C07D 417/12* (2013.01); *C07D 471/04* (2013.01); *C07D 487/04* (2013.01); *C07D 215/18* (2013.01); *C07D 401/04* (2013.01); *C07D 413/04* (2013.01); *C07D 417/14* (2013.01); *C07D 475/02* (2013.01); *C07D 491/04* (2013.01);
(Continued)

(58) Field of Classification Search
CPC ................ C07D 413/14; C07D 215/02; A61K 31/5377; A61K 31/47; A61P 29/00
USPC ....... 544/117, 116; 546/152; 514/234.2, 311, 514/314
See application file for complete search history.

(56) References Cited

U.S. PATENT DOCUMENTS

| | | |
|---|---|---|
| 6,511,961 B1 | 1/2003 | Takahashi et al. |
| 6,521,666 B1 | 2/2003 | Sircar et al. |

(Continued)

FOREIGN PATENT DOCUMENTS

| | | |
|---|---|---|
| CN | 105483206 A | 4/2016 |
| CN | 106995439 A | 8/2017 |

(Continued)

OTHER PUBLICATIONS

Examination Report dated Jan. 28, 2022 for Indian Appl. No. 202117019649.
(Continued)

*Primary Examiner* — Charanjit Aulakh

(57) ABSTRACT

The present disclosure provides a compound of Formula (I):

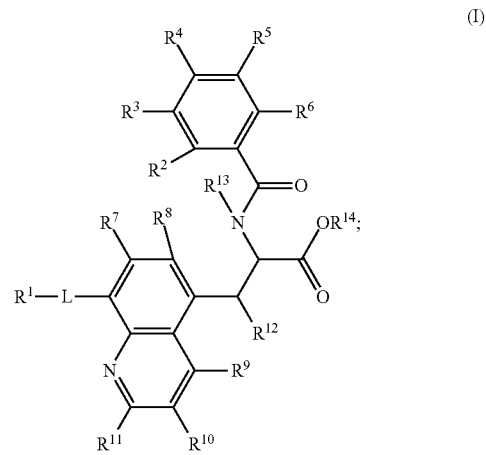

or a pharmaceutically acceptable salt thereof as described herein. The present disclosure also provides pharmaceutical compositions comprising a compound of Formula (I), pro-
(Continued)

cesses for preparing compounds of Formula (I), and therapeutic methods for treating inflammatory disease.

18 Claims, No Drawings

Related U.S. Application Data

(60) Provisional application No. 62/823,987, filed on Mar. 26, 2019, provisional application No. 62/752,805, filed on Oct. 30, 2018.

(51) Int. Cl.

| | | |
|---|---|---|
| *A61K 31/506* | (2006.01) | |
| *A61K 31/517* | (2006.01) | |
| *A61K 31/519* | (2006.01) | |
| *A61K 31/5355* | (2006.01) | |
| *A61K 31/541* | (2006.01) | |
| *A61K 45/06* | (2006.01) | |
| *C07D 215/14* | (2006.01) | |
| *C07D 401/10* | (2006.01) | |
| *C07D 401/12* | (2006.01) | |
| *C07D 401/14* | (2006.01) | |
| *C07D 405/14* | (2006.01) | |
| *C07D 407/14* | (2006.01) | |
| *C07D 409/14* | (2006.01) | |
| *C07D 413/12* | (2006.01) | |
| *C07D 413/14* | (2006.01) | |
| *C07D 417/12* | (2006.01) | |
| *C07D 471/04* | (2006.01) | |
| *C07D 487/04* | (2006.01) | |
| C07D 215/18 | (2006.01) | |
| C07D 401/04 | (2006.01) | |
| C07D 413/04 | (2006.01) | |
| C07D 417/14 | (2006.01) | |
| C07D 475/02 | (2006.01) | |
| C07D 491/04 | (2006.01) | |
| C07D 491/06 | (2006.01) | |
| C07D 491/08 | (2006.01) | |
| C07D 498/10 | (2006.01) | |
| C07D 513/04 | (2006.01) | |

(52) U.S. Cl.
CPC .......... *C07D 491/06* (2013.01); *C07D 491/08* (2013.01); *C07D 498/10* (2013.01); *C07D 513/04* (2013.01)

(56) References Cited

U.S. PATENT DOCUMENTS

| | | | |
|---|---|---|---|
| 6,806,312 B2 | 10/2004 | Sasagawa et al. | |
| 7,105,520 B2 | 9/2006 | Suzuki et al. | |
| 7,335,673 B2 | 2/2008 | Hoshina et al. | |
| 7,361,679 B2 | 4/2008 | Ikegami et al. | |
| 7,566,724 B2 | 7/2009 | Hirano et al. | |
| 8,450,460 B2 | 5/2013 | Hill et al. | |
| 8,546,610 B2 | 10/2013 | Kataoka et al. | |
| 9,216,174 B2 | 12/2015 | Shen et al. | |
| 9,533,985 B2 | 1/2017 | Ueno et al. | |
| 9,822,110 B2 | 11/2017 | Ueno et al. | |
| 11,116,760 B2 | 9/2021 | Blomgren et al. | |
| 11,174,256 B2 | 11/2021 | Blomgren et al. | |
| 11,179,383 B2 | 11/2021 | Blomgren et al. | |
| 11,224,600 B2 | 1/2022 | Blomgren et al. | |
| 11,370,773 B1 | 6/2022 | Bursavich et al. | |
| 11,578,069 B2 | 2/2023 | Blomgren et al. | |
| 2003/0114490 A1 | 6/2003 | Tanaka et al. | |
| 2003/0130320 A1 | 7/2003 | Suzuki et al. | |
| 2003/0149083 A1 | 8/2003 | Tanaka et al. | |
| 2003/0220268 A1 | 11/2003 | Makino et al. | |
| 2003/0220318 A1 | 11/2003 | Suzuki et al. | |
| 2004/0039040 A1 | 2/2004 | Takahashi et al. | |
| 2004/0077693 A1 | 4/2004 | Artis et al. | |
| 2004/0087574 A1 | 5/2004 | Takahashi et al. | |
| 2004/0110945 A1 | 6/2004 | Nakayama et al. | |
| 2004/0132783 A1 | 7/2004 | Ono et al. | |
| 2004/0235848 A1 | 11/2004 | Okuzumi et al. | |
| 2004/0236147 A1 | 11/2004 | Chiba et al. | |
| 2004/0259908 A1 | 12/2004 | Ikegami et al. | |
| 2005/0101779 A1 | 5/2005 | Sagi et al. | |
| 2005/0187284 A1 | 8/2005 | Artis et al. | |
| 2005/0222141 A1 | 10/2005 | Sagi et al. | |
| 2005/0261291 A1 | 11/2005 | Kawahara et al. | |
| 2006/0009476 A1 | 1/2006 | Kataoka et al. | |
| 2006/0204572 A1 | 9/2006 | Higuchi et al. | |
| 2006/0204574 A1 | 9/2006 | Ogawa et al. | |
| 2006/0223836 A1 | 10/2006 | Makino et al. | |
| 2006/0241132 A1 | 10/2006 | Ishigaki et al. | |
| 2007/0105936 A1 | 5/2007 | Ono et al. | |
| 2007/0232601 A1 | 10/2007 | Yoneda et al. | |
| 2007/0269835 A1 | 11/2007 | Katayama et al. | |
| 2008/0075719 A1 | 3/2008 | Chan et al. | |
| 2008/0108634 A1 | 5/2008 | Sagi et al. | |
| 2008/0108637 A1 | 5/2008 | Fujita et al. | |
| 2008/0161566 A1 | 7/2008 | Kotake et al. | |
| 2008/0280909 A1 | 11/2008 | Okuzumi et al. | |
| 2009/0048236 A1 | 2/2009 | Suzuki et al. | |
| 2009/0163715 A1 | 6/2009 | Nagai et al. | |
| 2009/0233901 A1 | 9/2009 | Machinaga et al. | |
| 2009/0318688 A1 | 12/2009 | Kataoka et al. | |
| 2009/0325962 A1 | 12/2009 | Jackson et al. | |
| 2010/0022783 A1 | 1/2010 | Ono et al. | |
| 2010/0137593 A1 | 6/2010 | Takahashi et al. | |
| 2010/0204505 A1 | 8/2010 | Kataoka et al. | |
| 2010/0267754 A1 | 10/2010 | Wakabayashi et al. | |
| 2011/0009434 A1 | 1/2011 | Fujita et al. | |
| 2011/0065918 A1 | 3/2011 | Makino et al. | |
| 2011/0313154 A1 | 12/2011 | Kataoka et al. | |
| 2012/0157437 A1 | 6/2012 | Machinaga et al. | |
| 2012/0253041 A1 | 10/2012 | Makino et al. | |
| 2013/0030013 A1 | 1/2013 | Aburatani et al. | |
| 2013/0065882 A1 | 3/2013 | Machinaga et al. | |
| 2013/0066072 A1 | 3/2013 | Kataoka et al. | |
| 2014/0206705 A1 | 7/2014 | Kataoka et al. | |
| 2015/0045435 A1 | 2/2015 | Scott et al. | |
| 2015/0051395 A1 | 2/2015 | Ueno et al. | |
| 2016/0367517 A1 | 12/2016 | Thompson | |
| 2017/0196870 A1 | 7/2017 | Kageyama et al. | |
| 2018/0244648 A1 | 8/2018 | Harrison et al. | |
| 2018/0312498 A1 | 11/2018 | Biediger et al. | |
| 2020/0155538 A1 | 5/2020 | Blomgren et al. | |
| 2020/0155563 A1 | 5/2020 | Blomgren et al. | |
| 2020/0163953 A1 | 5/2020 | Blomgren et al. | |
| 2020/0165248 A1 | 5/2020 | Blomgren et al. | |
| 2021/0053967 A1 | 2/2021 | Blomgren et al. | |
| 2022/0119383 A1 | 4/2022 | Blomgren et al. | |
| 2022/0135561 A1 | 5/2022 | Blomgren et al. | |
| 2022/0152014 A1 | 5/2022 | Blomgren et al. | |
| 2022/0226337 A1 | 7/2022 | Blomgren et al. | |

FOREIGN PATENT DOCUMENTS

| | | |
|---|---|---|
| EP | 1209147 A1 | 5/2002 |
| EP | 1323711 A1 | 7/2003 |
| EP | 1889827 B1 | 8/2010 |
| EP | 3064491 A1 | 9/2016 |
| EP | 2842945 B1 | 10/2016 |
| IN | 2966/DEL/2005 | 7/2009 |
| JP | 2001089368 A | 4/2001 |
| JP | 2003048889 A | 2/2003 |
| JP | 2003277340 A | 10/2003 |
| JP | 2003321358 A | 11/2003 |
| JP | 2004277338 A | 10/2004 |
| JP | 2007-023029 A | 2/2007 |
| JP | 2015083970 A | 4/2015 |
| JP | 2016037467 A | 3/2016 |
| JP | 2016037468 A | 3/2016 |
| JP | 2019031449 A | 2/2019 |

(56) References Cited

FOREIGN PATENT DOCUMENTS

| | | |
|---|---|---|
| WO | WO-94/012181 A1 | 6/1994 |
| WO | WO-96/000581 A1 | 1/1996 |
| WO | WO-97/003094 A1 | 1/1997 |
| WO | WO-97/005865 A1 | 2/1997 |
| WO | WO-98/004247 A1 | 2/1998 |
| WO | WO-98/042656 A1 | 10/1998 |
| WO | WO-98/053814 A1 | 12/1998 |
| WO | WO-98/053817 A1 | 12/1998 |
| WO | WO-98/053818 A1 | 12/1998 |
| WO | WO-98/058902 A1 | 12/1998 |
| WO | WO-99/006431 A1 | 2/1999 |
| WO | WO-99/006434 A1 | 2/1999 |
| WO | WO-99/006436 A1 | 2/1999 |
| WO | WO-99/006437 A1 | 2/1999 |
| WO | WO-99/010312 A1 | 3/1999 |
| WO | WO-99/010313 A1 | 3/1999 |
| WO | WO-99/013898 A1 | 3/1999 |
| WO | WO-99/025731 A1 | 5/1999 |
| WO | WO-99/026615 A1 | 6/1999 |
| WO | WO-99/026921 A1 | 6/1999 |
| WO | WO-99/030713 A1 | 6/1999 |
| WO | WO-99/036393 A1 | 7/1999 |
| WO | WO-99/052898 A1 | 10/1999 |
| WO | WO-99/061421 A1 | 12/1999 |
| WO | WO-99/062901 A1 | 12/1999 |
| WO | WO-99/064395 A1 | 12/1999 |
| WO | WO-99/067230 A1 | 12/1999 |
| WO | WO-2000/002903 A1 | 1/2000 |
| WO | WO-2000/005223 A2 | 2/2000 |
| WO | WO-2000/015612 A1 | 3/2000 |
| WO | WO-2000/035855 A1 | 6/2000 |
| WO | WO-2000/037444 A1 | 6/2000 |
| WO | WO-2000/043354 A2 | 7/2000 |
| WO | WO-2000/043369 A1 | 7/2000 |
| WO | WO-2000/043371 A2 | 7/2000 |
| WO | WO-2000/043372 A1 | 7/2000 |
| WO | WO-2000/043413 A2 | 7/2000 |
| WO | WO-2000/048994 A1 | 8/2000 |
| WO | WO-2000/051974 A1 | 9/2000 |
| WO | WO-2000/063234 A2 | 10/2000 |
| WO | WO-2000/064866 A1 | 11/2000 |
| WO | WO-2000/067746 A1 | 11/2000 |
| WO | WO-2000/071572 A1 | 11/2000 |
| WO | WO-2001/000206 A1 | 1/2001 |
| WO | WO-2001/007400 A1 | 2/2001 |
| WO | WO-2001/012183 A1 | 2/2001 |
| WO | WO-2001/012186 A1 | 2/2001 |
| WO | WO-2001/014328 A2 | 3/2001 |
| WO | WO-2001/021584 A1 | 3/2001 |
| WO | WO-2001/032610 A1 | 5/2001 |
| WO | WO-2001/042215 A1 | 6/2001 |
| WO | WO-2001/042225 A2 | 6/2001 |
| WO | WO-2001/043774 A1 | 6/2001 |
| WO | WO-2001/047868 A1 | 7/2001 |
| WO | WO-2001/047887 A1 | 7/2001 |
| WO | WO-2001/053279 A1 | 7/2001 |
| WO | WO-2001/053295 A1 | 7/2001 |
| WO | WO-2001/055121 A1 | 8/2001 |
| WO | WO-2001/056994 A1 | 8/2001 |
| WO | WO-2001/068586 A2 | 9/2001 |
| WO | WO-2001/070670 A1 | 9/2001 |
| WO | WO-2002/002556 A2 | 1/2002 |
| WO | WO-2002/008201 A2 | 1/2002 |
| WO | WO-2002/008203 A2 | 1/2002 |
| WO | WO-2002/008206 A1 | 1/2002 |
| WO | WO-2002/014262 A1 | 2/2002 |
| WO | WO-2002/016329 A1 | 2/2002 |
| WO | WO-2002/018320 A2 | 3/2002 |
| WO | WO-2002/022563 A1 | 3/2002 |
| WO | WO-2002/024697 A1 | 3/2002 |
| WO | WO-2002/028830 A1 | 4/2002 |
| WO | WO-2002/053534 A1 | 7/2002 |
| WO | WO-2002/057242 A2 | 7/2002 |
| WO | WO-2002/068393 A1 | 9/2002 |
| WO | WO-2003/008380 A1 | 1/2003 |
| WO | WO-2003/010135 A1 | 2/2003 |
| WO | WO-2003/011815 A1 | 2/2003 |
| WO | WO-2003/024933 A1 | 3/2003 |
| WO | WO-2003/048126 A1 | 6/2003 |
| WO | WO-2003/053926 A1 | 7/2003 |
| WO | WO-2003/070709 A1 | 8/2003 |
| WO | WO-2003/072536 A1 | 9/2003 |
| WO | WO-2003/080611 A1 | 10/2003 |
| WO | WO-2003/089410 A1 | 10/2003 |
| WO | WO-2003/093237 A1 | 11/2003 |
| WO | WO-2003/099231 A2 | 12/2003 |
| WO | WO-2003/099809 A1 | 12/2003 |
| WO | WO-2004/006918 A1 | 1/2004 |
| WO | WO-2004/007428 A1 | 1/2004 |
| WO | WO-2004/007494 A1 | 1/2004 |
| WO | WO-2004/014844 A2 | 2/2004 |
| WO | WO-2004/014859 A2 | 2/2004 |
| WO | WO-2004/062601 A2 | 7/2004 |
| WO | WO-2004/066931 A2 | 8/2004 |
| WO | WO-2004/066932 A2 | 8/2004 |
| WO | WO-2004/074264 A2 | 9/2004 |
| WO | WO-2004/099126 A1 | 11/2004 |
| WO | WO-2004/103967 A2 | 12/2004 |
| WO | WO-2005/000244 A2 | 1/2005 |
| WO | WO-2005/009992 A1 | 2/2005 |
| WO | WO-2005/014532 A1 | 2/2005 |
| WO | WO-2005/040135 A1 | 5/2005 |
| WO | WO-2005/042529 A1 | 5/2005 |
| WO | WO-2005/044817 A1 | 5/2005 |
| WO | WO-2005/061440 A1 | 7/2005 |
| WO | WO-2005/061466 A1 | 7/2005 |
| WO | WO-2005/063705 A1 | 7/2005 |
| WO | WO-2005/070921 A1 | 8/2005 |
| WO | WO-2005/077914 A1 | 8/2005 |
| WO | WO-2005/077915 A1 | 8/2005 |
| WO | WO-2005/087760 A1 | 9/2005 |
| WO | WO-2005/097162 A2 | 10/2005 |
| WO | WO-2005/107762 A2 | 11/2005 |
| WO | WO-2005/121135 A1 | 12/2005 |
| WO | WO-2006/010054 A2 | 1/2006 |
| WO | WO-2006/019632 A2 | 2/2006 |
| WO | WO-2006/023396 A2 | 3/2006 |
| WO | WO-2006/028393 A1 | 3/2006 |
| WO | WO-2006/052962 A2 | 5/2006 |
| WO | WO-2006/066780 A1 | 6/2006 |
| WO | WO-2006/068058 A1 | 6/2006 |
| WO | WO-2006/068213 A1 | 6/2006 |
| WO | WO-2006/081986 A1 | 8/2006 |
| WO | WO-2006/090234 A1 | 8/2006 |
| WO | WO-2006/096807 A1 | 9/2006 |
| WO | WO-2006/112738 A1 | 10/2006 |
| WO | WO-2006/113199 A1 | 10/2006 |
| WO | WO-2006/115918 A2 | 11/2006 |
| WO | WO-2006/126635 A1 | 11/2006 |
| WO | WO-2006/127584 A1 | 11/2006 |
| WO | WO-2006/131200 A1 | 12/2006 |
| WO | WO-2007/004958 A1 | 1/2007 |
| WO | WO-2007/069635 A1 | 6/2007 |
| WO | WO-2007/082809 A1 | 7/2007 |
| WO | WO-2007/100763 A2 | 9/2007 |
| WO | WO-2007/101165 A1 | 9/2007 |
| WO | WO-2008/062859 A1 | 5/2008 |
| WO | WO-2008/064830 A1 | 6/2008 |
| WO | WO-2008/109943 A1 | 9/2008 |
| WO | WO-2008/125210 A1 | 10/2008 |
| WO | WO-2008/138591 A2 | 11/2008 |
| WO | WO-2008/154642 A2 | 12/2008 |
| WO | WO-2009/075806 A1 | 6/2009 |
| WO | WO-2009/124755 A1 | 10/2009 |
| WO | WO-2009/140621 A2 | 11/2009 |
| WO | WO-2010/104306 A2 | 9/2010 |
| WO | WO-2010/105363 A1 | 9/2010 |
| WO | WO-2010/112865 A1 | 10/2010 |
| WO | WO-2010/126914 A1 | 11/2010 |
| WO | WO-2011/048091 A1 | 4/2011 |
| WO | WO-2011/094890 A1 | 8/2011 |
| WO | WO-2011/122619 A1 | 10/2011 |
| WO | WO-2011/143274 A1 | 11/2011 |
| WO | WO-2011/150499 A1 | 12/2011 |

(56) References Cited

FOREIGN PATENT DOCUMENTS

| | | |
|---|---|---|
| WO | WO-2011/159781 A2 | 12/2011 |
| WO | WO-2012/011123 A1 | 1/2012 |
| WO | WO-2012/068251 A2 | 5/2012 |
| WO | WO-2012/106343 A2 | 8/2012 |
| WO | WO-2013/070842 A1 | 5/2013 |
| WO | WO-2013/110680 A1 | 8/2013 |
| WO | WO-2013/110681 A1 | 8/2013 |
| WO | WO-2013/148978 A1 | 10/2013 |
| WO | WO-2013/161904 A1 | 10/2013 |
| WO | WO-2013/178816 A1 | 12/2013 |
| WO | WO-2014/051056 A1 | 4/2014 |
| WO | WO-2014/052605 A1 | 4/2014 |
| WO | WO-2015/064580 A1 | 5/2015 |
| WO | WO-2015/138882 A1 | 9/2015 |
| WO | WO-2015/172196 A1 | 11/2015 |
| WO | WO-2016/040505 A1 | 3/2016 |
| WO | WO-2016/051828 A1 | 4/2016 |
| WO | WO-2016/145258 A1 | 9/2016 |
| WO | WO-2017/006272 A1 | 1/2017 |
| WO | WO-2017/070518 A1 | 4/2017 |
| WO | WO-2017/126637 A1 | 7/2017 |
| WO | WO-2017/132620 A1 | 8/2017 |
| WO | WO-2017/135471 A1 | 8/2017 |
| WO | WO-2017/135472 A1 | 8/2017 |
| WO | WO-2018/049068 A1 | 3/2018 |
| WO | WO-2018/064119 A1 | 4/2018 |
| WO | WO-2018/085552 A1 | 5/2018 |
| WO | WO-2018/085574 A2 | 5/2018 |
| WO | WO-2018/089353 A1 | 5/2018 |
| WO | WO-2018/089355 A1 | 5/2018 |
| WO | WO-2018/089357 A1 | 5/2018 |
| WO | WO-2018/089358 A1 | 5/2018 |
| WO | WO-2018/089360 A1 | 5/2018 |
| WO | WO-2018/160522 A1 | 9/2018 |
| WO | WO-2018/200625 A1 | 11/2018 |
| WO | WO-2018/201167 A2 | 11/2018 |
| WO | WO-2019/085441 A1 | 5/2019 |
| WO | WO-2019/094319 A1 | 5/2019 |
| WO | WO-2019/173653 A1 | 9/2019 |
| WO | WO-2019/178248 A1 | 9/2019 |
| WO | WO-2019/200202 A1 | 10/2019 |
| WO | WO-2019/246455 A1 | 12/2019 |
| WO | WO-2020/033724 A1 | 2/2020 |
| WO | WO-2020/043533 A1 | 3/2020 |
| WO | WO-2020/047207 A1 | 3/2020 |
| WO | WO-2020/047208 A1 | 3/2020 |
| WO | WO-2020/047239 A1 | 3/2020 |
| WO | WO-2020/092375 A1 | 5/2020 |
| WO | WO-2020/092383 A1 | 5/2020 |
| WO | WO-2020/092394 A1 | 5/2020 |
| WO | WO-2020/092401 A1 | 5/2020 |
| WO | WO-2021/030438 A1 | 2/2021 |

OTHER PUBLICATIONS

Non-Final Office Action dated Feb. 10, 2022 for U.S. Appl. No. 16/991,708.
Intl. Preliminary Report on Patentability dated Feb. 24, 2022 for Intl. Appl. No. PCT/US2020/045938.
Examination Report dated Aug. 12, 2021 for GCC Appl. No. 2019-38568.
Examination Report dated Aug. 23, 2021 for Australian Appl. No. 2019373245.
Examination Report dated Aug. 27, 2021 for Australian Appl. No. 2019373244.
Examination Report dated Nov. 15, 2021 for Indian Appl. No. 202117023381.
Examination Report dated Nov. 16, 2021 for Indian Appl. No. 202117023382.
Final Office Action dated Aug. 12, 2021 for U.S. Appl. No. 16/667,373.
Hatley R J D et al. (2019), "The Design of Potent, Selective and Drug-Like RGD αvβ1 Small-Molecule Inhibitors Derived from non-RGD α4β1 Antagonists", Chem MedChem, 14, 1-7.
Intl. Preliminary Report on Patentability dated May 14, 2021 for Intl. Appl. No. PCT/US2019/058573.
Intl. Preliminary Report on Patentability dated May 14, 2021 for Intl. Appl. No. PCT/US2019/058583.
Intl. Preliminary Report on Patentability dated May 14, 2021 for Intl. Appl. No. PCT/US2019/058599.
Intl. Preliminary Report on Patentability dated May 14, 2021 for Intl. Appl. No. PCT/US2019/058610.
Intl. Search Report-Written Opinion dated Jan. 14, 2020 for Intl. Appl. No. PCT/US2019/058610.
Intl. Search Report-Written Opinion dated Jan. 21, 2020 for Intl. Appl. No. PCT/US2019/058573.
Intl. Search Report-Written Opinion dated Jan. 23, 2020 for Intl. Appl. No. PCT/US2019/058583.
Intl. Search Report-Written Opinion dated Jan. 28, 2020 for Intl. Appl. No. PCT/US2019/058599.
Intl. Search Report-Written Opinion dated Jan. 21, 2021 for Intl. Appl. No. PCT/US2020/045938.
Li H et al. (2018), "$\alpha_4\beta_7$ integrin inhibitors: a patent review", Expert Opinion on Therapeutic Patents, 28:12, 903-917.
Non-Final Office Action dated Mar. 19, 2021 for U.S. Appl. No. 16/667,532.
Non-Final Office Action dated Jul. 9, 2021 for U.S. Appl. No. 16/667,373.
Notice of Allowance and Fees Due dated Feb. 24, 2021 for U.S. Appl. No. 16/667,306.
Notice of Allowance and Fees Due dated Mar. 12, 2021 for U.S. Appl. No. 16/667,373.
Notice of Allowance and Fees Due dated Mar. 19, 2021 for U.S. Appl. No. 16/667,572.
Notice of Allowance and Fees Due dated Jun. 14, 2021 for U.S. Appl. No. 16/667,306.
Notice of Allowance and Fees Due dated Jul. 15, 2021 for U.S. Appl. No. 16/667,532.
Notice of Allowance and Fees Due dated Sep. 15, 2021 for U.S. Appl. No. 16/667,373.
Notice of Allowance and Search Report dated Nov. 6, 2020 for Taiwanese Appl. No. 108139338.
Notice of Allowance dated Mar. 26, 2021 for Taiwanese Appl. No. 108139358.
Office Action dated Aug. 4, 2020 for Taiwanese Appl. No. 108139359.
Office Action dated Sep. 11, 2020 for Taiwanese Appl. No. 108139358.
Office Action dated Sep. 18, 2020 for Taiwanese Appl. No. 108139336.
Office Action dated Jul. 14, 2021 for Taiwanese Appl. No. 109127810.
Sircar Ila et al. (2002), "Synthesis and SAR of N-Benzoyl-L-Biphenylalanine Derivatives: Discovery of TR-14035, A Dual α4β7/α4β1 Integrin Antagonist", Bioorganic & Medicinal Chemistry, vol. 10, No. 6, pp. 2051-2066.
Xu Y-Z et al. (2013), "Orally available and efficacious α4β1/α4β7 integrin inhibitors", Bioorganic & Medicinal Chemistry Letters 23:4370-4373.
Office Action dated Apr. 5, 2022 for Panamanian Appl. No. 93479-01.
Examination Report dated Apr. 22, 2022 for Australian Appl. No. 2019373240.
Office Action dated May 10, 2022 for Japanese Appl. No. 2021-548529.
Office Action dated Aug. 1, 2022 for Canadian Appl. No. 3,116,769.
Office Action dated Oct. 4, 2022 for Eurasian Appl. No. 202190689.
Office Action dated Oct. 31, 2022 for Dominican Republic Appl. No. P2021-0077.
Notice of Allowance dated Nov. 8, 2022 for Japanese Appl. No. 2021-548529.
Office Action dated Dec. 15, 2022 for Chilean Appl. No. 202101098.
Office Action dated Dec. 22, 2022 for Eurasian Appl. No. 202190689.
Office Action dated Jan. 24, 2023 for European Appl. No. 19805484.3.
Office Action dated Mar. 15, 2023 for Ukrainian Appl. No. a202101839.
Examination Report dated Mar. 17, 2023 for Australian Appl. No. 2019373240.
Notice of Allowance dated Apr. 5, 2023 for Australian Appl. No. 2019373240.

(56) References Cited

OTHER PUBLICATIONS

Office Action dated Apr. 25, 2023 for Korean Appl. No. 10-2021-7016023.
Office Action dated Jun. 15, 2023 for Chilean Appl. No. 202101098.
Office Action dated Jul. 5, 2023 for Taiwanese Appl. No. 110123631.
Office Action dated Jul. 26, 2023 for Vietnamese Appl. No. 1-2021-02928.
Office Action dated Aug. 3, 2023 for Dominican Republic Appl. No. P2021-0077.
Office Action dated Aug. 11, 2023 for European Appl. No. 19805484.3.
Office Action dated Aug. 15, 2023 for ARIPO Appl. No. AP/P/2021/013095.
Macchiarulo, A. et al. (2004) "Insights into Phenylalanine Derivatives Recognition of VLA-4 Integrin: From a Pharmacophoric Study to 3D-QSAR and Molecular Docking Analyses", J Chem Inf Comput Sci, 44(5):1829-1839.
Office Action dated Aug. 18, 2023 for Indonesian Appl. No. P00202103751.
Notice of Allowance dated Sep. 11, 2023 for Ukrainian Appl. No. A202101839.
Notice of Allowance dated Oct. 23, 2023 for Korean Appl. No. 10-2021-7016023.
Office Action dated Oct. 26, 2023 for Chinese Appl. No. 201980071854.X.
Office Action dated Nov. 19, 2023 for Israeli Appl. No. 282545.
Office Action dated Dec. 5, 2023 for Dominican Republic Appl. No. P2021-0077.
Office Action dated Dec. 28, 2023 for Colombian Appl. No. NC2021/0005532.
Office Action dated Jan. 26, 2024 for Uzbekistan Appl. No. IAP20210267.
Notice of Allowance dated Feb. 23, 2024 for Taiwanese Appl. No. 110123631.
Intention to Grant dated Feb. 27, 2024 for European Appl. No. 19805484.3.
Office Action dated Mar. 22, 2024 for Chinese Appl. No. 201980071854.X.
Office Action dated Mar. 22, 2024 for Mexican Appl. No. MX/a/2021/005050.
Examination Report dated May 17, 2024 for Australian Appl. No. 2023204712.
Office Action dated May 16, 2024 for Dominican Republic Appl. No. P2021-0077.
Notice of Allowance dated Jun. 10, 2024 for Japanese Appl. No. 2022-195576.
Decision to Grant dated Jun. 10, 2024 for ARIPO Appl. No. AP/P/2021/013095.

QUINOLINE DERIVATIVES

CROSS REFERENCE TO RELATED APPLICATIONS

This Application is a Continuation of application Ser. No. 16/667,306 filed on Oct. 29, 2019. Application Ser. No. 16/667,306 claims the benefit of U.S. Provisional Application 62/823,987 filed on Mar. 26, 2019 and U.S. Provisional Application 62/752,805 filed on Oct. 30, 2018. The entire contents of these applications are incorporated herein by reference in their entirety.

FIELD

The present disclosure relates generally to novel compounds that have α4β7 integrin inhibitory action, prodrugs of compounds having α4β7 integrin inhibitory action, and methods of use and manufacture thereof.

BACKGROUND

Integrins are heterodimeric cell surface proteins involved in numerous cellular processes including cell-cell and cell-extracellular matrix interactions. Upon binding of an extracellular ligand, integrins mediate signal transduction to the cell interior resulting in lymphocyte cell capture, adhesion, and infiltration into the tissue.

Integrins are heterodimeric proteins consisting of an alpha and a beta subunit. There are 18 known alpha subunits and 8 known beta subunits. The α4β7 integrin is expressed on the surface of lymphocytes and recognizes the extracellular ligand mucosal addressing cell adhesion molecule-1 (MAdCAM-1). α4β7 integrin governs lymphocyte trafficking to and retention in gut tissues through its interaction with MAdCAM-1, which is expressed on venules in the intestinal mucosa and high endothelial venules (HEV) in the gut-associated lymphoid tissues (GALT). Inhibiting the interactions of integrins with their respective ligands has been proposed as an effective method of treating a variety of autoimmune and inflammatory diseases, and blocking the α4β7-MAdCAM-1 interaction has shown therapeutic benefit in inflammatory bowel disease (Crohn's disease and ulcerative colitis).

There is a need to for improved α4β7 integrin antagonist molecules for the treatment of autoimmune and inflammatory diseases, including inflammatory bowel disease.

SUMMARY

The present disclosure provides compounds that are inhibitors for α4β7 integrin. The disclosure also provides compositions, including pharmaceutical compositions, kits that include the compounds, and methods of using (or administering) and making the compounds. The compounds provided herein are useful in treating diseases, disorders, or conditions that are mediated by α4β7 integrin. The disclosure also provides compounds for use in therapy. The disclosure further provides compounds for use in a method of treating a disease, disorder, or condition that is mediated by α4β7 integrin. Moreover, the disclosure provides uses of the compounds in the manufacture of a medicament for the treatment of a disease, disorder or condition that is mediated by α4β7 integrin.

In one aspect, provided is a compound having the structure of Formula (I), or a pharmaceutically acceptable salt thereof:

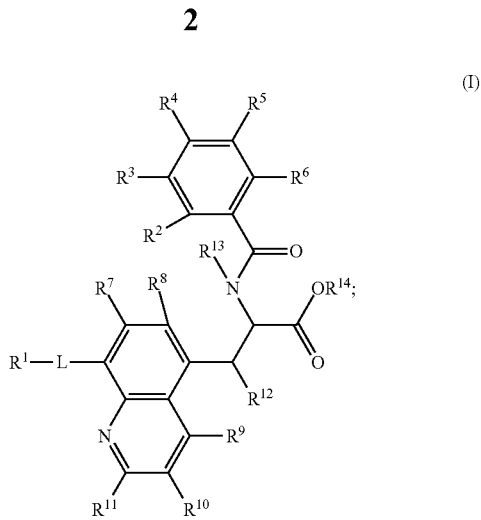

(I)

L is selected from a bond, —O—, —O—C(O)—*, —NH—, —C(O)—N(H)—*, and —N(H)—C(O)—*; wherein * indicates the point of attachment of L to $R^1$;

$R^1$ is selected from $A^1$, $A^2$, $A^3$, and $A^4$;

$A^1$ is 5-10 membered heteroaryl containing one to five heteroatoms independently selected from S, N, and O; wherein $A^1$ optionally comprises one to three C(O); and wherein $A^1$ is optionally substituted with one to six Ra;

$A^2$ is $C_{6-10}$aryl, optionally substituted with one to six $R^a$;

$A^3$ is $C_{5-10}$cycloalkyl or 5-14 membered heterocyclyl; wherein $A^3$ is optionally substituted with one to four groups independently selected from oxo and $R^a$; and $A^4$ is —$NR^{a1}R^{a2}$ wherein each $R^a$ is independently selected from halo, cyano, hydroxyl, —$NR^{a1}R^{a2}$, $C_{1-6}$alkyl, $C_{2-6}$alkenyl, $C_{2-6}$alkynyl, $C_{1-6}$alkoxyl, $C_{1-6}$haloalkyl, $C_{1-6}$ haloalkoxyl, —$S(O)_m$—$C_{1-6}$alkyl, $C_{3-8}$cycloalkyl, 3-6 membered heterocyclyl, $C_{6-10}$aryl, 5-6 membered heteroaryl, —O—$C_{3-8}$cycloalkyl, —O-(3-6 membered heterocyclyl), —O—$C_{1-4}$alkylene-$C_{3-8}$cycloalkyl, and —O-phenyl;

wherein each $C_{3-8}$cycloalkyl, 3-6 membered heterocyclyl, $C_{6-10}$aryl, 5-6 membered heteroaryl, —O—$C_{3-8}$cycloalkyl, —O-(3-6 membered heterocyclyl), —O—$C_{1-4}$alkylene-$C_{3-8}$cycloalkyl, and —O-phenyl of $R^a$ is independently optionally substituted with one to three groups independently selected from halo, cyano, hydroxyl, —$NR^{a1}R^{a2}$, $C_{1-6}$alkyl, $C_{1-6}$haloalkyl, $C_{1-6}$alkoxyl, and $C_{1-6}$haloalkoxyl; and wherein each $C_{1-6}$alkyl, $C_{2-6}$alkenyl, $C_{2-6}$alkynyl, $C_{1-6}$alkoxyl, $C_{1-6}$ haloalkyl, $C_{1-6}$haloalkoxyl, and —$S(O)_m$—$C_{1-6}$alkyl of $R^a$ is optionally substituted with one to three $R^{a3}$, wherein each $R^{a3}$ is independently selected from halo, cyano, hydroxyl, —$NR^{a1}R^{a2}$, $C_{1-6}$alkoxyl, $C_{3-8}$cycloalkyl, and 3-6 membered heterocyclyl;

wherein each $C_{3-8}$cycloalkyl and 3-6 membered heterocyclyl of $R^{a3}$ is optionally substituted with one to three $R^{a4}$; and each $R^{a4}$ is independently selected from halo, cyano, hydroxyl, —NR$^{a1}$R$^{a2}$, C$_{1-6}$alkyl, C$_{1-6}$haloalkyl, C$_{1-6}$alkoxyl, C$_{1-6}$haloalkoxyl, C$_{3-8}$cycloalkyl, and 3-6 membered heterocyclyl;

each R$^2$, R$^3$, R$^4$, R$^5$, and R$^6$ is independently selected from H, halo, cyano, hydroxyl, C$_{1-6}$ alkyl, C$_{2-6}$alkenyl, C$_{2-6}$alkynyl, C$_{1-6}$alkoxyl, C$_{1-8}$haloalkyl, C$_{1-8}$haloalkoxyl, —NR$^{b1}$R$^{b2}$, —R$^{b3}$S(O)$_m$R$^{b4}$, —S(O)$_m$R$^{b4}$, —NR$^{b1}$S(O)$_n$R$^{b4}$, —COOR$^{b1}$, —CONR$^{b1}$R$^{b2}$, —NR$^{b1}$COOR$^{b2}$, —NR$^{b1}$COR$^{14}$, —R$^{b3}$NR$^{b1}$R$^{b2}$, —S(O)$_n$NR$^{b1}$R$^{b2}$, C$_{3-12}$cycloalkyl, C$_{6-10}$aryl, 5-6 membered heteroaryl, and 3-12 membered heterocyclyl;

wherein each C$_{1-6}$alkyl, C$_{2-6}$alkenyl, C$_{2-6}$alkynyl, C$_{1-6}$alkoxyl, C$_{1-8}$haloalkyl, and C$_{1-8}$haloalkoxyl of R$^2$, R$^3$, R$^4$, R$^5$, and R$^6$ is optionally substituted with one to two R$^c$; wherein each R$^c$ is independently selected from azido, oxo, cyano, halo, hydroxyl, —NR$^{a1}$R$^{a2}$, C$_{1-4}$alkoxyl, C$_{3-8}$cycloalkyl, C$_{6-10}$aryl, 5-6 membered heteroaryl, and 4-6 membered heterocyclyl; wherein each C$_{3-8}$cycloalkyl, C$_{6-10}$aryl, 5-6 membered heteroaryl, and 4-6 membered heterocyclyl of R$^c$ is optionally substituted with one to three groups independently selected from halo, cyano, hydroxyl, —NR$^{a1}$R$^{a2}$, C$_{1-4}$ alkyl, C$_{1-6}$haloalkyl, C$_{1-4}$alkoxyl, and C$_{3-6}$cycloalkyl;

wherein each C$_{6-10}$aryl, and 5-6 membered heteroaryl of R$^2$, R$^3$, R$^4$, R$^5$, and R$^6$ is independently optionally substituted with one to five R$^b$; and wherein each C$_{3-12}$cycloalkyl, and 3-12 membered heterocyclyl of R$^2$, R$^3$, R$^4$, R$^5$, and R$^6$ is independently optionally substituted with one to six groups independently selected from =CR$^{b1}$R$^{b2}$ and R$^b$;

wherein each R$^b$ is independently selected from azido, cyano, halo, hydroxyl, —NR$^{a1}$R$^{a2}$, C$_{1-6}$alkyl, C$_{1-8}$haloalkyl, C$_{1-6}$alkoxyl, C$_{3-6}$cycloalkyl, C$_{6-10}$aryl, 5-6 membered heteroaryl, and 4-6 membered heterocyclyl; wherein each C$_{3-6}$cycloalkyl, C$_{6-10}$aryl, 5-6 membered heteroaryl, and 4-6 membered heterocyclyl of R$^b$ is independently optionally substituted with one to three groups independently selected from halo, cyano, hydroxyl, —NR$^{a1}$R$^{a2}$, C$_{1-4}$alkyl, C$_{1-4}$ haloalkyl, and C$_{1-4}$alkoxyl;

wherein each R$^{b1}$ and R$^{b2}$ is independently selected from H, C$_{1-8}$alkyl, C$_{1-8}$haloalkyl, C$_{3-8}$cycloalkyl, C$_{6-10}$aryl, 5-6 membered heteroaryl, and 3-8 membered heterocyclyl;

wherein each C$_{3-8}$cycloalkyl, C$_{6-10}$aryl, 5-6 membered heteroaryl, and 4-6 membered heterocyclyl of R$^{b1}$ and R$^{b2}$ is independently optionally substituted with one to three groups independently selected from halo, cyano, hydroxyl, —NR$^{a1}$R$^{a2}$, C$_{1-8}$alkyl, C$_{1-8}$haloalkyl, C$_{1-6}$alkoxyl, C$_{3-6}$cycloalkyl, C$_{6-10}$aryl, 5-6 membered heteroaryl, and 4-6 membered heterocyclyl; and wherein each C$_{1-8}$alkyl and C$_{1-8}$haloalkyl of R$^{b1}$ and R$^{b2}$ is optionally substituted with one to two R$^{b5}$;

wherein R$^{b3}$ is C$_{1-4}$alkylene;

wherein R$^{b4}$ is selected from C$_{1-4}$alkyl, C$_{1-4}$haloalkyl, C$_{3-6}$cycloalkyl, C$_{6-10}$aryl, 5-6 membered heteroaryl, and 4-6 membered heterocyclyl; wherein each C$_{1-4}$alkyl, C$_{1-4}$haloalkyl, C$_{3-8}$cycloalkyl, C$_{6-10}$aryl, 5-6 membered heteroaryl, and the 4-6 membered heterocyclyl of R$^{b4}$ is optionally substituted with one to three R$^{b6}$;

wherein each R$^{b5}$ is independently selected from cyano, hydroxyl, C$_{1-4}$ alkoxyl, C$_{3-8}$cycloalkyl, C$_{6-10}$aryl, 5-6 membered heteroaryl, and 4-6 membered heterocyclyl; and each C$_{1-4}$alkoxyl, C$_{3-8}$cycloalkyl, C$_{6-10}$aryl, 5-6 membered heteroaryl, and 4-6 membered heterocyclyl of R$^{b5}$ is optionally substituted with one to three groups independently selected from halo, cyano, hydroxyl, —NR$^{a1}$R$^{a2}$, C$_{1-4}$alkyl, C$_{1-4}$haloalkyl, C$_{1-4}$alkoxyl, and phenyl; and wherein each R$^{b6}$ is independently selected from halo, cyano, C$_{1-4}$alkyl, C$_{1-4}$haloalkyl, C$_{1-4}$alkoxyl, C$_{3-6}$cycloalkyl, phenyl, 4-6 membered heterocyclyl, and 5-6 membered heteroaryl; wherein each C$_{3-6}$cycloalkyl, 4-6 membered heterocyclyl, and 5-6 membered heteroaryl of R$^{b6}$ is independently optionally substituted with one to three groups independently selected from halo, cyano, —NR$^{a1}$R$^{a2}$, C$_{1-4}$alkyl, C$_{1-4}$haloalkyl, and C$_{1-4}$alkoxyl; or R$^2$ and R$^3$, R$^3$ and R$^4$, or R$^5$ and R$^6$ together with the atoms to which they are attached form a C$_{6-10}$aryl, 5-6 membered heteroaryl, C$_{3-6}$cycloalkyl, or 5-6 membered heterocyclyl; wherein each C$_{6-10}$aryl, 5-6 membered heteroaryl, C$_{3-6}$cycloalkyl, and 5-6 membered heterocyclyl is independently optionally substituted with one to three groups independently selected from halo, cyano, —NR$^{a1}$R$^{a2}$, C$_{1-6}$alkyl, C$_{1-6}$alkoxyl, C$_{1-6}$haloalkyl, C$_{3-8}$cycloalkyl, 3-6 membered heterocyclyl, C$_{6-10}$aryl, 5-6 membered heteroaryl, C$_{1-4}$alkylene-C$_{3-8}$cycloalkyl, C$_{1-4}$alkylene-C$_{6-10}$aryl, and C$_{1-4}$alkylene-(5-6 membered heteroaryl);

each R$^7$, R$^8$, R$^9$, R$^{10}$, R$^{11}$, and R$^{12}$ is independently selected from H, halo, hydroxyl, cyano, C$_{1-6}$alkyl, C$_{1-6}$alkoxyl, C$_{1-6}$haloalkyl, C$_{1-6}$haloalkoxyl, and —NR$^{a1}$R$^{a2}$;

R$^{13}$ is selected from H, C$_{1-4}$alkyl, and C$_{1-4}$haloalkyl; and

R$^{14}$ is selected from H, C$_{1-6}$alkyl, —C$_{1-4}$alkylene-NR$^{a1}$R$^{a2}$, —C$_{1-4}$alkylene-C(O)NR$^{a1}$R$^{a2}$, —C$_{1-4}$alkylene-O—C(O)—C$_{1-4}$alkyl, —C$_{1-4}$alkylene-O—C(O)—O—C$_{1-4}$alkyl, —C$_{1-4}$alkylene-O—C(O)—C$_{1-4}$alkylene-NR$^{a1}$R$^{a2}$, —C$_{1-4}$alkylene-O—C$_{1-4}$alkyl, C$_{3-8}$cycloalkyl, —C$_{1-4}$alkylene-C$_{3-8}$cycloalkyl, 4-6 membered heterocyclyl, and —C$_{1-4}$alkylene-(4-6 membered heterocyclyl);

wherein each C$_{3-8}$cycloalkyl, —C$_{1-4}$alkylene-C$_{3-8}$cycloalkyl, 4-6 membered heterocyclyl, and —C$_{1-4}$alkylene-(4-6 membered heterocyclyl) of R$^{14}$ is optionally substituted with one to three groups independently selected from halo, C$_{1-4}$alkyl, C$_{1-4}$alkoxyl, and C$_{1-4}$haloalkyl; or R$^{14}$ together with the N that attaches to R$^{13}$ forms a 5 membered heterocyclyl; wherein the 5 membered heterocyclyl is optionally substituted with one to two groups independently selected from halo, C$_{1-6}$alkyl, C$_{1-6}$alkoxyl, C$_{1-6}$haloalkyl, and C$_{6-10}$aryl; wherein the C$_{6-10}$aryl is optionally substituted with one to three groups independently selected from halo, C$_{1-6}$alkyl, C$_{1-6}$alkoxyl, and C$_{1-6}$haloalkyl;

each R$^{a1}$ and R$^{a2}$ is independently selected from H, C$_{1-6}$alkyl, and C$_{1-6}$haloalkyl;

m is selected from 0, 1, and 2; and n is selected from 1, and 2.

DETAILED DESCRIPTION

Definitions and General Parameters

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

The prefix "$C_{u-v}$" indicates that the following group has from u to v carbon atoms. For example, "$C_{1-8}$ alkyl" indicates that the alkyl group has from 1 to 8 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkylene" (including those which are part of other groups) refers to branched and unbranched divalent "alkyl" groups. As used herein, alkylene has 1 to 20 carbon atoms (i.e., $C_{1-20}$ alkylene), 1 to 8 carbon atoms (i.e., $C_{1-8}$ alkylene), 1 to 6 carbon atoms (i.e., $C_{1-6}$ alkylene), or 1 to 4 carbon atoms (i.e., $C_{1-4}$ alkylene). Examples include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propylene also includes 1-methylethylene and butylene includes 1-methylpropylene, 1,1-dimethylethylene, and 1,2-dimethylethylene.

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" and "alkoxyl" are used interchangeably and refer to the group "alkyl-O—". Examples of alkoxyl and alkoxy groups include methoxy, ethoxy, n-propoxy, isopropoxy, n-butoxy, tert-butoxy, sec-butoxy, n-pentoxy, n-hexoxy, and 1,2-dimethylbutoxy. "Haloalkoxyl" refers to an alkoxyl group as defined above, wherein one or more hydrogen atoms are replaced by a halogen.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 ring carbon atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Azido" refers to the group —N$_3$.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl. Cycloalkyl groups also include partially unsaturated ring systems containing one or more double bonds, including fused ring systems with one aromatic ring and one non-aromatic ring, but not fully aromatic ring systems.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

The term "fused" refers to a ring which is bound to an adjacent ring.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Spiro" also refers to a bicyclic portion, wherein the two rings are connected through a single common atom. Spiro compounds may be fully carbocyclic or heterocyclic. Examples of spiro groups include 5-oxa-8-azaspiro[3.5]nonane, 7-oxa-4-azaspiro[2.5]octane, and 5$\lambda^2$-azaspiro[2.4]heptane.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

The term "heterocyclyl" or "heterocycle" as used herein refers to a single saturated or partially unsaturated non-aromatic ring or a non-aromatic multiple ring system that has at least one heteroatom in the ring (i.e., at least one annular heteroatom selected from O, N, S, S(O), S(O)$_2$, and N-oxide groups). Unless otherwise specified, a heterocyclyl group has from 3 to about 20 annular atoms, for example from 3 to 12 annular atoms, for example from 3 to 10 annular atoms, for example from 5 to 10 annular atoms or for example from 5 to 6 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms independently selected from the group consisting of O, N, S, S(O), S(O)$_2$, and N-oxide in the ring. The rings of the multiple condensed ring (e.g. bicyclic heterocyclyl) system can be connected to each other via fused, spiro and bridged bonds when allowed by valency requirements. Heterocycles include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, N-bromopyrrolidine, N-chloropiperidine, and the like. Heterocycles include spirocycles, such as, for example, aza or oxo-spiroheptanes. Heterocyclyl groups also include partially unsaturated ring systems containing one or more double bonds, including fused ring systems with one aromatic ring and one non-aromatic ring, but not fully aromatic ring systems. Examples include dihydroquinolines, e.g. 3,4-dihydroquinoline, dihydroisoquinolines, e.g. 1,2-dihydroisoquinoline, dihydroimidazole, tetrahydroimidazole, etc., indoline, isoindoline, isoindolones (e.g. isoindolin-1-one), isatin, dihydrophthalazine, quinolinone, spiro[cyclopropane-1,1'-isoindolin]-3'-one, and the like. Additional examples of heterocycles include 3,8-diazabicyclo[3.2.1]octanyl, 2,5-diazabicyclo [2.2.1]heptanyl, 3,6-diazabicyclo[3.1.1]heptanyl, 3-oxa-7,9-diazabicyclo[3.3.1]nonanyl, and hexahydropyrazino[2,1-c][1,4]oxazinyl, for example.

"Hydroxyl" and "hydroxy" are used interchangeably and refer to —OH. "Oxo" refers to the group (=O) or (O). Where tautomeric forms of the compound exist, hydroxyl and oxo groups are interchangeable.

"Heteroaryl" refers to an aromatic group, including groups having an aromatic tautomer or resonance structure, having a single ring, multiple rings, or multiple fused rings, with at least one heteroatom in the ring, i.e., one or more ring heteroatoms independently selected from nitrogen, oxygen, and sulfur, wherein the nitrogen or sulfur may be oxidized. Thus, the term includes rings having one or more annular O, N, S, S(O), S(O)$_2$, and N-oxide groups. The term includes rings having one or more annular C(O) groups. As used herein, heteroaryl include 5 to 20 ring atoms (i.e., 5- to 20-membered heteroaryl), 5 to 12 ring atoms (i.e., 5- to 12-membered heteroaryl), or 5 to 10 ring atoms (i.e., 5- to 10-membered heteroaryl), and 1 to 5 heteroatoms independently selected from nitrogen, oxygen, and sulfur, and oxidized forms of the heteroatoms. Examples of heteroaryl groups include pyridin-2(1H)-one, pyridazin-3(2H)-one, pyrimidin-4(3H)-one, quinolin-2(1H)-one, pyrimidinyl, purinyl, pyridyl, pyridazinyl, benzothiazolyl, and pyrazolyl. Heteroaryl does not encompass or overlap with aryl as defined above.

"Sulfonyl" refers to the group —S(O)$_2$R, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidinyl, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, alkoxy, halo, oxo, and hydroxyl; "substituted heterocyclyl" refers to a heterocyclyl group having one or more substituents including alkyl, haloalkyl, heterocyclyl, cycloalkyl, aryl, heteroaryl, alkoxy, halo, oxo, and hydroxyl; "substituted aryl" refers to an aryl group having one or more substituents including halo, alkyl, haloalkyl, cycloalkyl, heterocyclyl, heteroaryl, alkoxy, and cyano; "substituted heteroaryl" refers to an heteroaryl group having one or more substituents including halo, alkyl, haloalkyl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of the present disclosure, in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of the present disclosure, when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of the present disclosure.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Salts, such as TFA salts, can be converted to the free-bases/acids or other pharmaceutically acceptable salts.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of α4β7 integrin activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of α4β7 integrin" or variants thereof refers to a decrease in activity of α4β7 integrin as a direct or indirect response to the presence of a compound of the present application relative to the activity of α4β7 integrin in the absence of the compound of the present application. "Inhibition of α4β7" refers to a decrease in α4β7 integrin activity as a direct or indirect response to the presence of a compound described herein relative to the activity of α4β7 integrin in the absence of the compound described herein. In some embodiments, the inhibition of α4β7 integrin activity may be compared in the same subject prior to treatment, or other subjects not receiving the treatment.

Compounds

Provided herein are compounds that function as inhibitors of α4β7 integrin. In one aspect, provided is a compound having structure of Formula (I), or a pharmaceutically acceptable salt thereof:

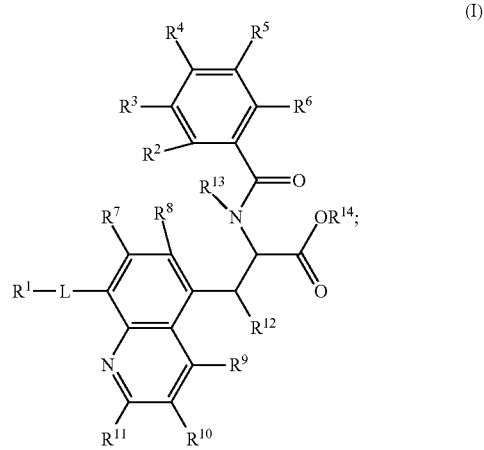

(I)

$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and L are defined as above.

In another aspect, provided are compounds of Formula (II), or pharmaceutically acceptable salts thereof:

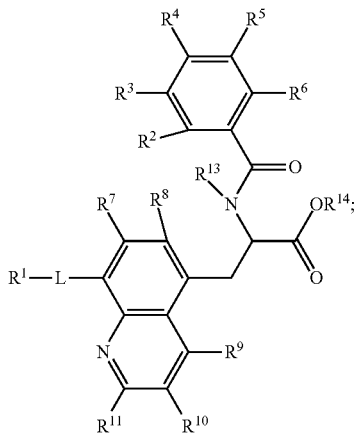

L is selected from a bond, —O—, —O—C(O)—*, —NH—, —C(O)—N(H)—*, and —N(H)—C(O)—*; wherein * indicates the point of attachment of L to $R^1$;

$R^1$ is selected from $A^1$, $A^2$, and $A^3$:
  $A^1$ is 5-10 membered heteroaryl containing one to five heteroatoms independently selected from S, N, and O; wherein $A^1$ optionally comprises one to three C(O); and wherein $A^1$ is optionally substituted with one to six $R^a$;
  $A^2$ is $C_{6-10}$aryl, optionally substituted with one to six $R^a$; and
  $A^3$ is $C_{5-10}$ cycloalkyl or 5-14 membered heterocyclyl; wherein $A^3$ is optionally substituted with one to four groups independently selected from oxo and $R^a$; and
  wherein each $R^a$ is independently selected from halo, cyano, hydroxyl, —$NR^{a1}R^{a2}$, $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —$S(O)_m$—$C_{1-6}$alkyl, $C_{3-8}$cycloalkyl, 3-6 membered heterocyclyl, $C_{6-10}$aryl, 5-6 membered heteroaryl, —O—$C_{3-8}$cycloalkyl, —O-(3-6 membered heterocyclyl), —O—$C_{1-4}$alkylene-$C_{3-8}$cycloalkyl, and —O-phenyl;
    wherein each $C_{3-8}$cycloalkyl, 3-6 membered heterocyclyl, $C_{6-10}$aryl, 5-6 membered heteroaryl, —O—$C_{3-8}$cycloalkyl, —O-(3-6 membered heterocyclyl), —O—$C_{1-4}$alkylene-$C_{3-8}$cycloalkyl, and —O-phenyl of $R^a$ is independently optionally substituted with one to three groups independently selected from halo, cyano, hydroxyl, —$NR^{a1}R^{a2}$, $C_{1-6}$alkyl, $C_{1-6}$haloalkyl, $C_{1-6}$alkoxyl, and $C_{1-6}$haloalkoxyl; and
    wherein each $C_{1-6}$alkyl, $C_{2-6}$alkenyl, $C_{2-6}$alkynyl, $C_{1-6}$alkoxyl, $C_{1-6}$ haloalkyl, $C_{1-6}$haloalkoxyl, and —$S(O)_m$—$C_{1-6}$alkyl of $R^a$ is optionally substituted with one to three $R^{a3}$, wherein each $R^{a3}$ is independently selected from halo, cyano, hydroxyl, —$NR^{a1}R^{a2}$, $C_{1-6}$alkoxyl, $C_{3-6}$cycloalkyl, and 3-6 membered heterocyclyl;
    wherein each $C_{3-8}$cycloalkyl and 3-6 membered heterocyclyl of $R^{a3}$ is optionally substituted with one to three $R^{a4}$; and each $R^{a4}$ is independently selected from halo, cyano, hydroxyl, —$NR^{a1}R^{a2}$, $C_{1-6}$alkyl, $C_{1-6}$haloalkyl, $C_{1-6}$alkoxyl, $C_{1-6}$haloalkoxyl, $C_{3-8}$cycloalkyl, and 3-6 membered heterocyclyl;

each $R^2$, $R^3$, $R^4$, $R^5$, and $R^6$ is independently selected from H, halo, cyano, hydroxyl, $C_{1-6}$alkyl, $C_{2-6}$alkenyl, $C_{2-6}$alkynyl, $C_{1-6}$alkoxyl, $C_{1-8}$haloalkyl, $C_{1-8}$haloalkoxyl, —$NR^{b1}R^{b2}$, —$R^{b3}S(O)_mR^{b4}$, —$S(O)_mR^{b4}$, —$NR^{b1}S(O)_nR^{b4}$, —$COOR^{b1}$, —$CONR^{b1}R^{b2}$, —$NR^{b1}COOR^{b2}$, —$NR^{b1}COR^{b4}$, —$R^{b3}NR^{b1}R^{b2}$, —$S(O)_nNR^{b1}R^{b2}$, $C_{3-12}$cycloalkyl, $C_{6-10}$aryl, 5-6 membered heteroaryl, and 3-12 membered heterocyclyl;
  wherein each $C_{1-6}$alkyl, $C_{2-6}$alkenyl, $C_{2-6}$alkynyl, $C_{1-6}$alkoxyl, $C_{1-8}$haloalkyl, and $C_{1-8}$haloalkoxyl of $R^2$, $R^3$, $R^4$, $R^5$, and $R^6$ is optionally substituted with one to two $R^c$; wherein each $R^c$ is independently selected from azido, oxo, cyano, halo, hydroxyl, —$NR^{a1}R^{a2}$, $C_{1-4}$alkoxyl, $C_{3-6}$cycloalkyl, $C_{6-10}$aryl, 5-6 membered heteroaryl, and 4-6 membered heterocyclyl; wherein each $C_{3-8}$cycloalkyl, $C_{6-10}$aryl, 5-6 membered heteroaryl, and 4-6 membered heterocyclyl of $R^c$ is optionally substituted with one to three groups independently selected from halo, cyano, hydroxyl, —$NR^{a1}R^{a2}$, $C_{1-4}$alkyl, $C_{1-6}$haloalkyl, $C_{1-4}$alkoxyl, and $C_{3-6}$cycloalkyl;
  wherein each $C_{6-10}$aryl, and 5-6 membered heteroaryl of $R^2$, $R^3$, $R^4$, $R^5$, and $R^6$ is independently optionally substituted with one to five $R^b$; and
  wherein each $C_{3-12}$cycloalkyl, and 3-12 membered heterocyclyl of $R^2$, $R^3$, $R^4$, $R^5$, and $R^6$ is independently optionally substituted with one to six groups independently selected from =$CR^{b1}R^{b2}$ and $R^b$;
  wherein each $R^b$ is independently selected from azido, cyano, halo, hydroxyl, —$NR^{a1}R^{a2}$, $C_{1-6}$alkyl, $C_{1-8}$haloalkyl, $C_{1-6}$alkoxyl, $C_{3-6}$cycloalkyl, $C_{6-10}$aryl, 5-6 membered heteroaryl, and 4-6 membered heterocyclyl; wherein each $C_{3-6}$cycloalkyl, $C_{6-10}$aryl, 5-6 membered heteroaryl, and 4-6 membered heterocyclyl of $R^b$ is independently optionally substituted with one to three groups independently selected from halo, cyano, hydroxyl, —$NR^{a1}R^{a2}$, $C_{1-4}$alkyl, $C_{1-4}$haloalkyl, and $C_{1-4}$alkoxyl;
  wherein each $R^{b1}$ and $R^{b2}$ is independently selected from H, $C_{1-8}$alkyl, $C_{1-8}$haloalkyl, $C_{3-6}$cycloalkyl, $C_{6-10}$aryl, 5-6 membered heteroaryl, and 3-8 membered heterocyclyl;
  wherein each $C_{3-8}$cycloalkyl, $C_{6-10}$aryl, 5-6 membered heteroaryl, and 4-6 membered heterocyclyl of $R^{b1}$ and $R^{b2}$ is independently optionally substituted with one to three groups independently selected from halo, cyano, hydroxyl, —$NR^{a1}R^{a2}$, $C_{1-8}$alkyl, $C_{1-8}$haloalkyl, $C_{1-6}$alkoxyl, $C_{3-6}$cycloalkyl, $C_{6-10}$aryl, 5-6 membered heteroaryl, and 4-6 membered heterocyclyl; and
  wherein each $C_{1-8}$-alkyl and $C_{1-8}$-haloalkyl of $R^{b1}$ and $R^{b2}$ is optionally substituted with one to two $R^{b5}$;
  wherein $R^{b3}$ is $C_{1-4}$alkylene;
  wherein $R^{b4}$ is selected from $C_{1-4}$alkyl, $C_{1-4}$haloalkyl, $C_{3-6}$cycloalkyl, $C_{6-10}$aryl, 5-6 membered heteroaryl, and 4-6 membered heterocyclyl; wherein each $C_{1-4}$alkyl, $C_{1-4}$haloalkyl, $C_{3-8}$cycloalkyl, $C_{6-10}$aryl, 5-6 membered heteroaryl, and the 4-6 membered heterocyclyl of $R^{b4}$ is optionally substituted with one to three $R^{b6}$;
  wherein each $R^{b5}$ is independently selected from cyano, hydroxyl, $C_{1-4}$alkoxyl, $C_{3-8}$cycloalkyl, $C_{6-10}$aryl, 5-6 membered heteroaryl, and 4-6 membered heterocyclyl; and each $C_{1-4}$alkoxyl, $C_{3-8}$cycloalkyl, $C_{6-10}$aryl, 5-6 membered heteroaryl, and 4-6 membered heterocyclyl of $R^{b5}$ is optionally substituted with one to three groups independently selected from halo, cyano, hydroxyl, —$NR^{a1}R^{a2}$, $C_{1-4}$alkyl, $C_{1-4}$haloalkyl, $C_{1-4}$alkoxyl, and phenyl; and wherein each $R^{b6}$ is independently selected from halo, cyano, $C_{1-4}$alkyl, $C_{1-4}$haloalkyl, $C_{1-4}$alkoxyl, $C_{3-6}$cycloalkyl, phenyl, 4-6 membered heterocyclyl, and 5-6 membered heteroaryl; wherein each $C_{3-6}$cycloalkyl, 4-6 membered heterocyclyl, and 5-6 membered heteroaryl of $R^{b6}$ is independently optionally substituted with one to three groups independently selected from halo, cyano, —$NR^{a1}R^{a2}$, $C_{1-4}$alkyl, $C_{1-4}$haloalkyl, and $C_{1-4}$alkoxyl; or $R^2$ and $R^3$, $R^3$ and $R^4$, or $R^5$ and $R^6$ together with the atoms to which they are attached form a $C_{6-10}$aryl, 5-6 membered heteroaryl, $C_{3-6}$cycloalkyl, or 5-6 membered heterocyclyl; wherein each $C_{6-10}$aryl, 5-6 membered heteroaryl, $C_{3-6}$cycloalkyl, and 5-6 membered heterocyclyl is independently optionally substituted with one to three groups independently selected from halo, cyano, —$NR^{a1}R^{a2}$, $C_{1-6}$alkyl, $C_{1-6}$alkoxyl, $C_{1-6}$haloalkyl, $C_{3-8}$cycloalkyl, 3-6 membered heterocyclyl, $C_{6-10}$aryl, 5-6 membered heteroaryl, $C_{1-4}$alkylene-$C_{3-8}$cycloalkyl, $C_{1-4}$alkylene-$C_{6-10}$aryl, and $C_{1-4}$alkylene-(5-6 membered heteroaryl);

each $R^7$, $R^8$, $R^9$, $R^{10}$, and $R^{11}$ is independently selected from H, halo, hydroxyl, cyano, $C_{1-6}$alkyl, $C_{1-6}$alkoxyl, $C_{1-6}$haloalkyl, $C_{1-6}$haloalkoxyl, and —$NR^{a1}R^{a2}$;

$R^{13}$ is selected from H, $C_{1-4}$alkyl, and $C_{1-4}$haloalkyl; and $R^{14}$ is selected from H, $C_{1-6}$alkyl, —$C_{1-4}$alkylene-$NR^{a1}R^{a2}$, —$C_{1-4}$alkylene-$C(O)NR^{a1}R^{a2}$, —$C_{1-4}$alkylene-O—C(O)—$C_{1-4}$alkyl, —$C_{1-4}$alkylene-O—C(O)—O—$C_{1-4}$alkyl, —$C_{1-4}$alkylene-O—C(O)—$C_{1-4}$alkylene-$NR^{a1}R^{a2}$, —$C_{1-4}$alkylene-O—$C_{1-4}$alkyl, $C_{3-8}$cycloalkyl, —$C_{1-4}$alkylene-$C_{3-8}$cycloalkyl, 4-6 membered heterocyclyl, and —$C_{1-4}$alkylene-(4-6 membered heterocyclyl);

wherein $C_{3-8}$cycloalkyl, —$C_{1-4}$alkylene-$C_{3-8}$cycloalkyl, 4-6 membered heterocyclyl, and —$C_{1-4}$alkylene-(4-6 membered heterocyclyl) of $R^{14}$ is optionally substituted with one to three groups independently selected from halo, $C_{1-4}$alkyl, $C_{1-4}$alkoxyl, and $C_{1-4}$haloalkyl; or $R^{14}$ together with the N that attaches to $R^{13}$ forms a 5 membered heterocyclyl; wherein the 5 membered heterocyclyl is optionally substituted with one to two groups independently selected from halo, $C_{1-6}$alkyl, $C_{1-6}$alkoxyl, $C_{1-6}$haloalkyl, and $C_{6-10}$aryl; wherein the $C_{6-10}$aryl is optionally substituted with one to three groups independently selected from halo, $C_{1-6}$alkyl, $C_{1-6}$alkoxyl, and $C_{1-6}$haloalkyl;

each $R^{a1}$ and $R^{a2}$ is independently selected from H, $C_{1-6}$alkyl, and $C_{1-6}$haloalkyl;

m is selected from 0, 1, and 2; and n is selected from 1, and 2.

In another aspect, provided are compounds of Formula (IIa), or pharmaceutically acceptable salts thereof:

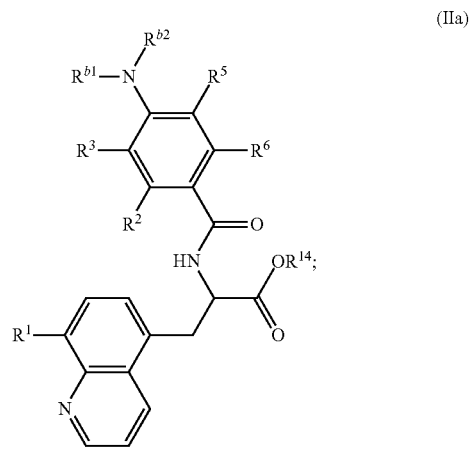

(IIa)

wherein $R^1$, $R^2$, $R^3$, $R^5$, $R^6$, $R^{14}$, $R^{b1}$, and $R^{b2}$ are as defined above in formula (I), (II), or elsewhere in this disclosure.

In another aspect, provided are compounds of Formula (IIb), or pharmaceutically acceptable salts thereof:

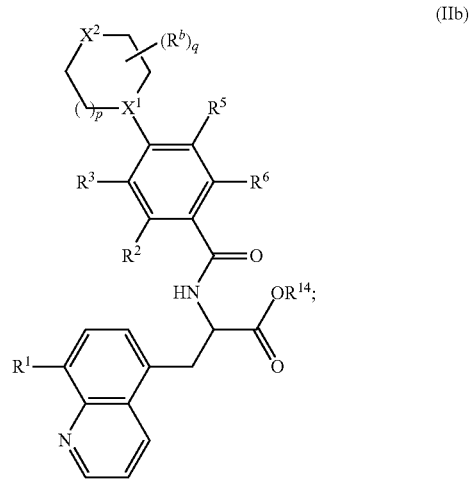

(IIb)

wherein $R^1$, $R^2$, $R^3$, $R^5$, $R^6$, $R^{14}$, and $R^b$ are as defined above in formula (I), (II), or elsewhere in this disclosure. $X^1$ is selected from $CR^{x1}$, and N; and $X^2$ is selected from $CR^{x1}R^{x2}$, $NR^{x2}$, O, and $S(O)_2$. $R^{x1}$ is selected from H, and $R^b$; and $R^{x2}$ is selected from H, $C_{1-4}$alkyl, and $C_{1-4}$haloalkyl. p is selected from 0, 1, and 2. q is selected from 0, 1, 2, 3, and 4.

In another aspect, provided are compounds of Formula (IIc), or pharmaceutically acceptable salts thereof:

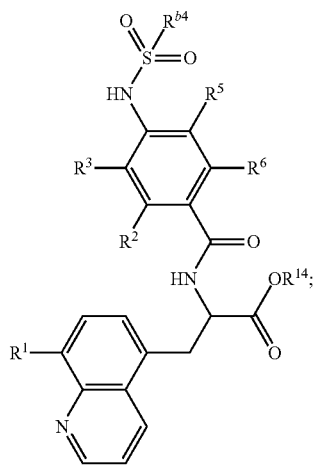
(IIc)

wherein $R^1$, $R^2$, $R^3$, $R^5$, $R^6$, $R^{14}$, and $R^{b4}$ are as defined above in formula (I), (II), or elsewhere in this disclosure.

In another aspect, provided are compounds of Formula (IId), or pharmaceutically acceptable salts thereof:

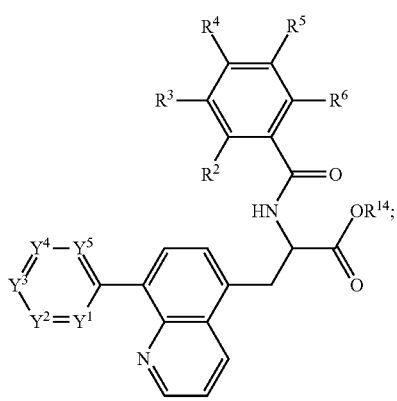
(IId)

Each $Y^1$, $Y^2$, $Y^3$, $Y^4$, and $Y^5$ is independently selected from CRY, and N. $R^y$ is selected from H, and $R^a$. $R^a$, $R^2$, $R^3$, $R^4$, $R^5$, $R^6$, and $R^{14}$ are as defined above in formula (I), (II), or elsewhere in this disclosure.

In another aspect, provided are compounds of Formula (IIe), or pharmaceutically acceptable salts thereof:

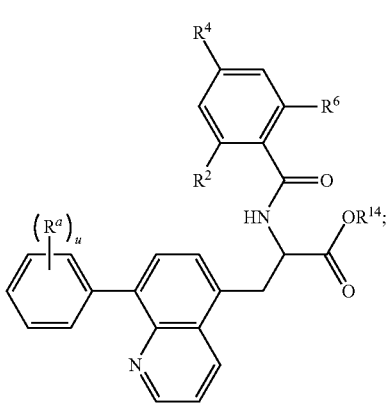
(IIe)

wherein $R^a$, $R^2$, $R^4$, $R^6$, and $R^{14}$ are as defined above in formula (I), (II), or elsewhere in this disclosure. u is selected from 0, 1, 2, 3, 4, and 5.

In another aspect, provided are compounds of Formula (IIf), or pharmaceutically acceptable salts thereof:

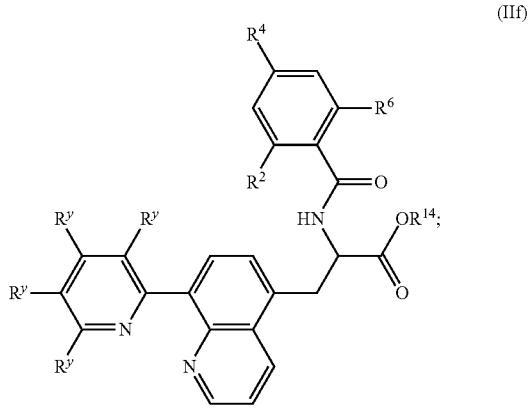
(IIf)

wherein $R^y$ is independently selected from H, and $R^a$. $R^a$, $R^2$, $R^4$, $R^6$, and $R^{14}$ are as defined above in formula (I), (II), or elsewhere in this disclosure.

In another aspect, provided are compounds of Formula (IIg), or pharmaceutically acceptable salts thereof:

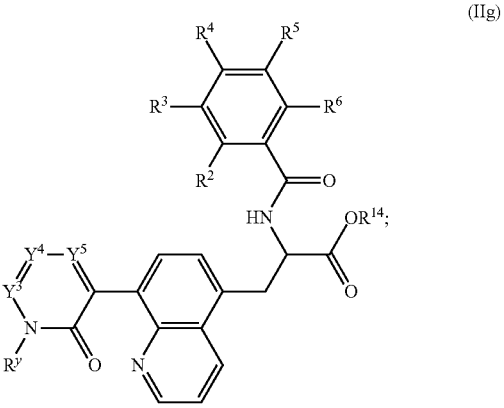
(IIg)

wherein $R^a$, $R^2$, $R^3$, $R^4$, $R^5$, $R^6$, and $R^{14}$ are as defined above in formula (I), (II), or elsewhere in this disclosure. $Y^3$, $Y^4$, and $Y^5$ are as defined above in formula (IId), or elsewhere in this disclosure. Each Ry is independently selected from H, and $R^a$.

In another aspect, provided are compounds of Formula (IIh), or pharmaceutically acceptable salts thereof:

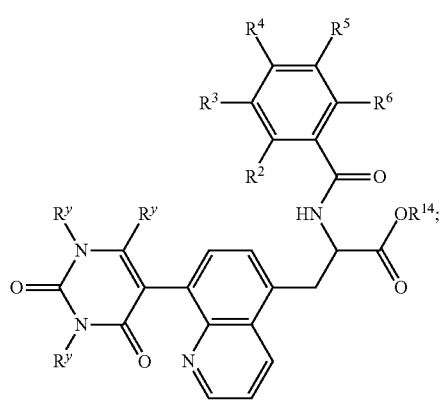

(IIh)

wherein $R^2$, $R^3$, $R^4$, $R^5$, $R^6$, and $R^{14}$ are as defined above in formula (I), (II), or elsewhere in this disclosure. Each $R^y$ is independently as defined above in formula (IId), or elsewhere in this disclosure.

In another aspect, provided are compounds of Formula (IIi), or pharmaceutically acceptable salts thereof:

(IIi)

wherein $R^a$, $R^2$, $R^3$, $R^4$, $R^5$, $R^6$, and $R^{14}$ are as defined above in formula (I), (II), or elsewhere in this disclosure. r is selected from 0, 1, 2, 3, 4, 5, and 6.

In some embodiments of formula (I), or (II), L is a bond. In some embodiments, L is —O—. In some embodiments, L is —C(O)—N(H)—*.

In some embodiments of formula (I), (II), (IIa), (IIb), or (IIc), $R^1$ is selected from phenyl, naphthyl, pyridinyl, pyridazinyl, pyrazinyl, pyrimidinyl, quinolinyl, isoquinolinyl, isoxazolyl, triazolyl, pyrazolyl, benzothiazolyl, pyridinonyl, quinolinonyl, isoquinolinonyl, quinazolinedionyl, pyrazinonyl, pyrimidinonyl, pyrimidinedionyl, pyridazinonyl, quinazolinonyl, benzofuranyl, tetrahydrocyclopenta[b]pyridinonyl, naphthyridinonyl, chromanyl, isochromanyl, and chromenonyl. Each $R^1$ is independently optionally substituted with one to four $R^a$. In some embodiments, $R^1$ is selected from phenyl, naphthyl, pyridinyl, pyrimidinyl, quinolinyl, isoxazolyl, pyridinonyl, quinolinonyl, quinazolin-edionyl, pyrazinonyl, pyrimidinonyl, pyridazinonyl, quinazolinonyl, benzofuranyl, and chromenonyl, and each $R^1$ is independently optionally substituted with one to four $R^a$.

In some embodiments of formula (I), or (II), "$R^1$-L-" is selected from

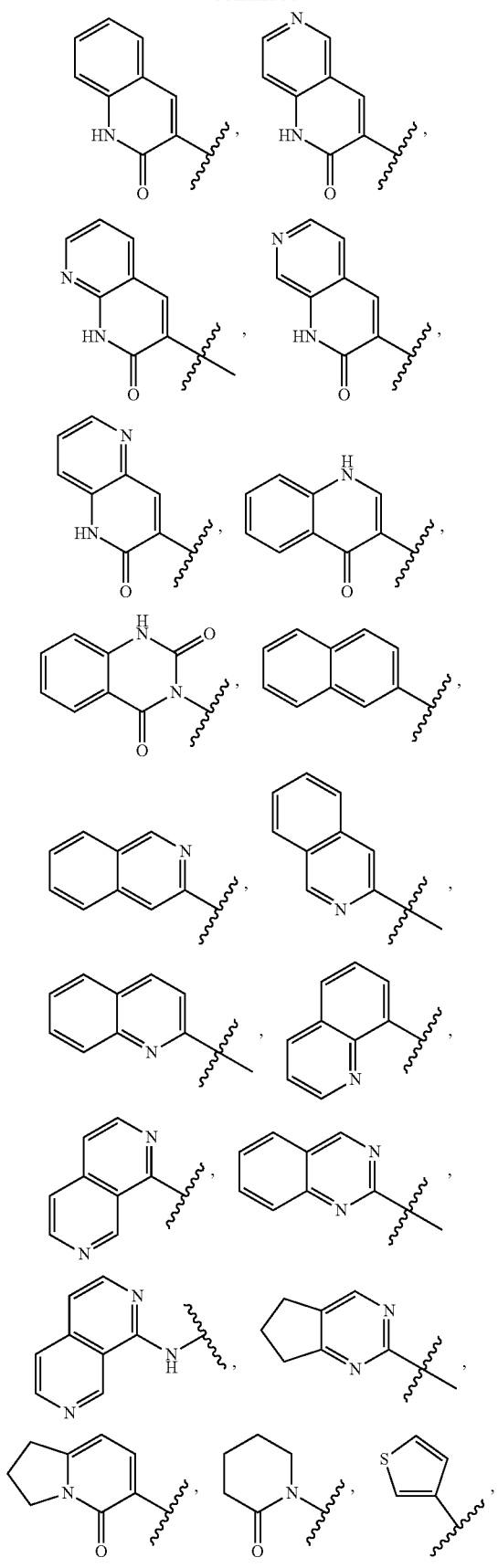

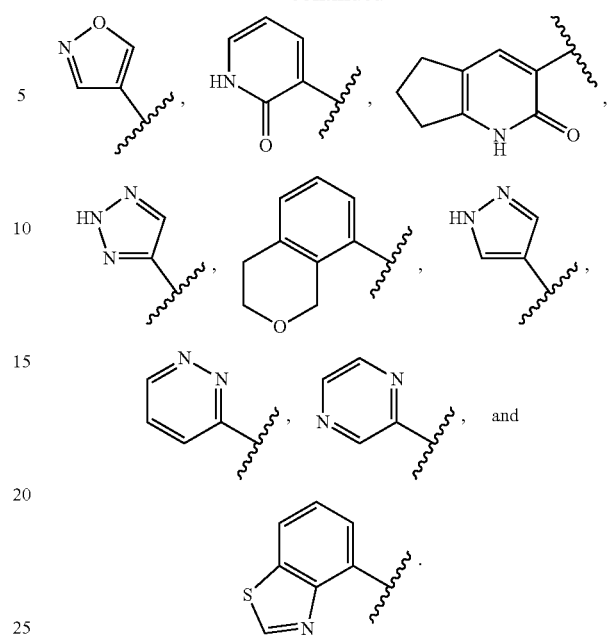

Each "R¹-L-" is optionally substituted with one to four $R^a$. In some embodiments, each $R^a$ is independently selected from halo, cyano, hydroxyl, $NR^{a1}R^{a2}$, $C_{1-4}$alkyl, $C_{1-4}$alkoxyl, $C_{1-4}$haloalkyl, $C_{1-4}$haloalkoxyl, $C_{3-6}$cycloalkyl, —O—$C_{3-6}$cycloalkyl, 3-6 membered heterocyclyl, —O-(3-6 membered heterocyclyl), and phenyl. In some embodiments, each $R^a$ is independently selected from F, Cl, ON, OH, —$NH_2$, —$CH_3$, —$CH_2F$, —$CHF_2$, —$CF_3$, —$OCH_3$, and —$OCF_3$.

In some embodiments of formula (I), or (II), "R¹-L-" is selected from

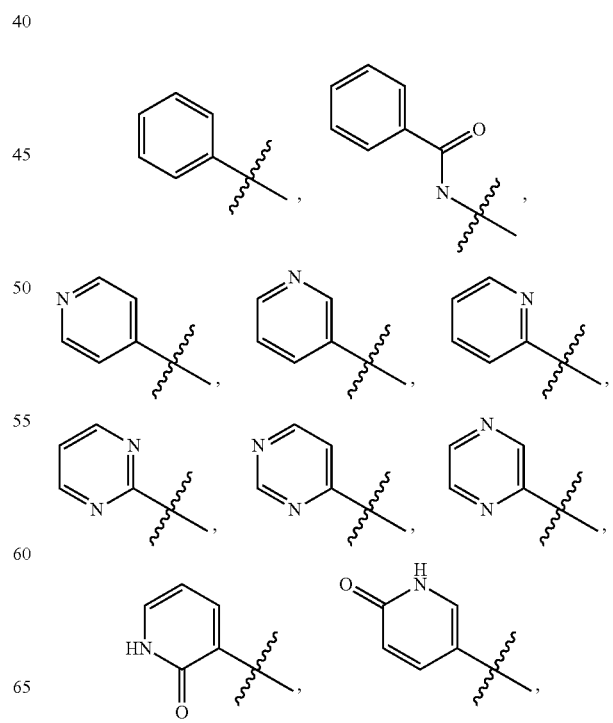

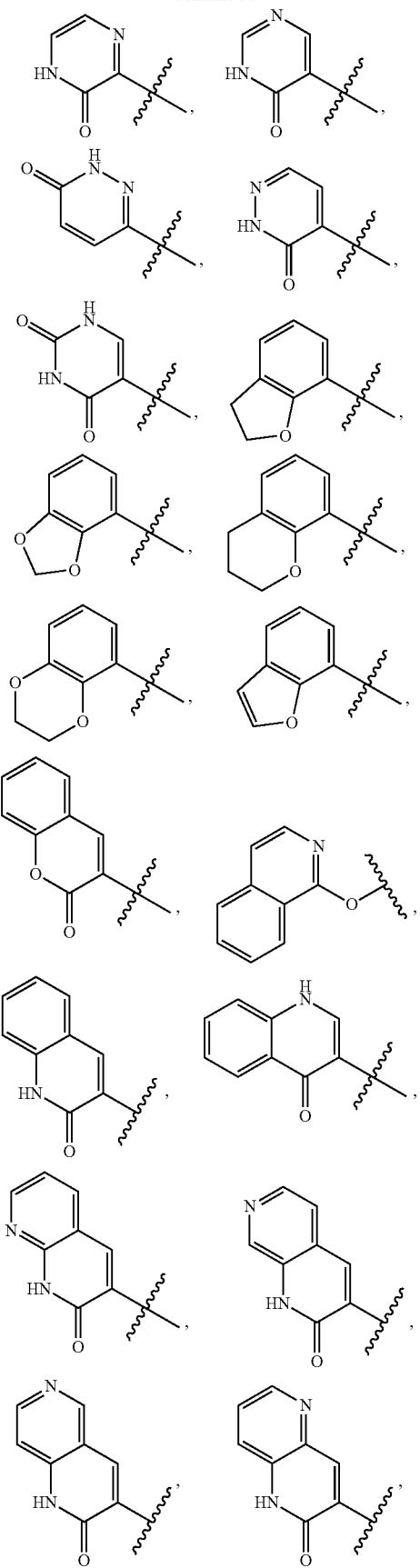
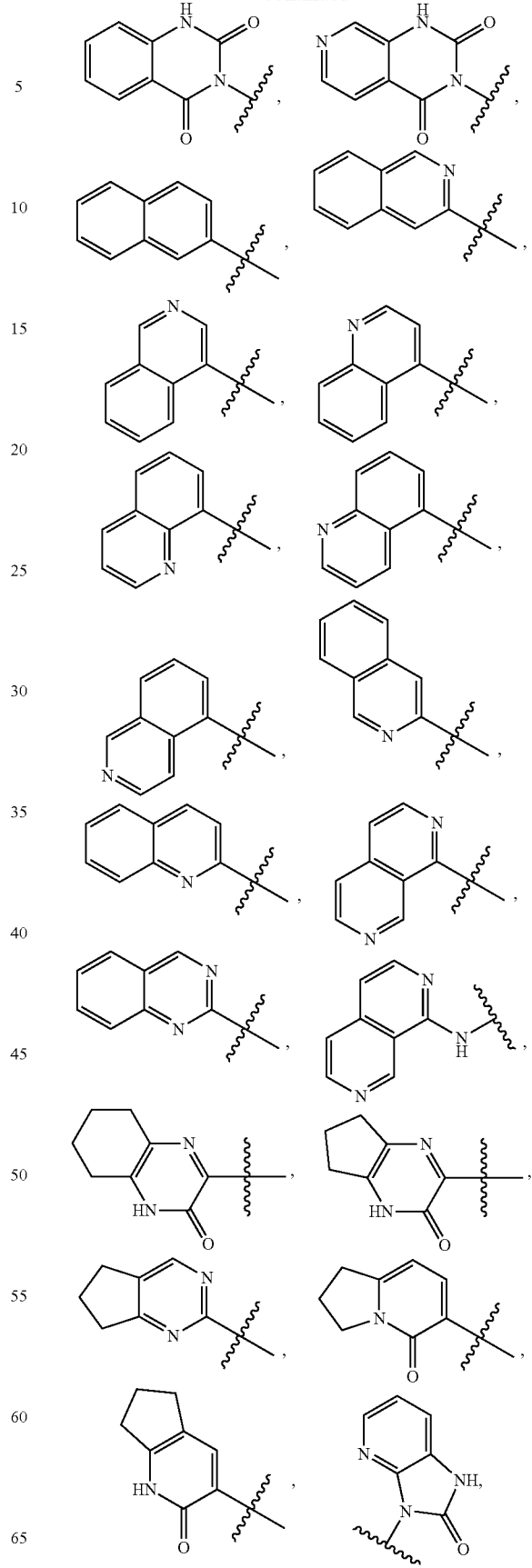

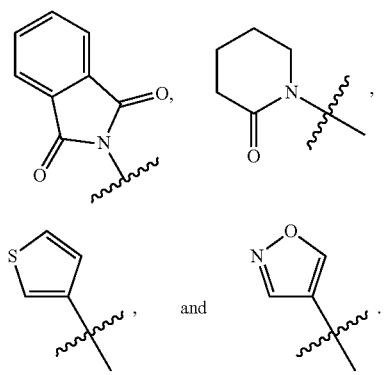

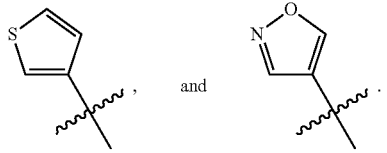 [SMILES: *c1ccsc1 ; *c1cnoc1]

Each "R¹-L-" is optionally substituted with one to four $R^a$. In some embodiments, each $R^a$ is independently selected from halo, cyano, hydroxyl, $NR^{a1}R^{a2}$, $C_{1-4}$alkyl, $C_{1-4}$alkoxyl, $C_{1-4}$haloalkyl, $C_{1-4}$haloalkoxyl, $C_{3-6}$cycloalkyl, —O—$C_{3-6}$cycloalkyl, and phenyl. In some embodiments, each $R^a$ is independently selected from F, Cl, ON, OH, —NH₂, —CH₃, —CH₂F, —CHF₂, —CF₃, —OCH₃, and —OCF₃.

In some embodiments of formula (I), (II), (IIa), (IIb), or (IIc), $R^1$ is selected from

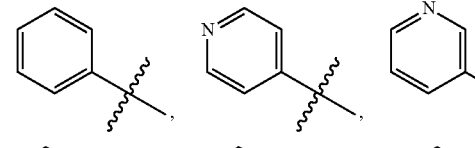

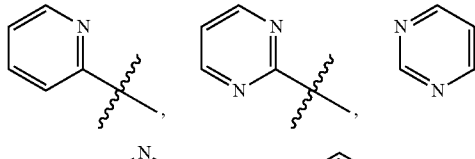

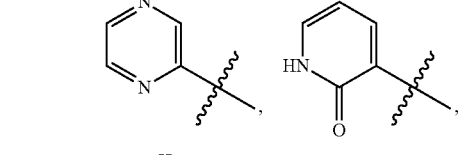

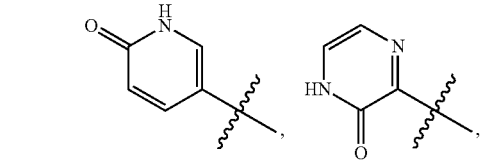

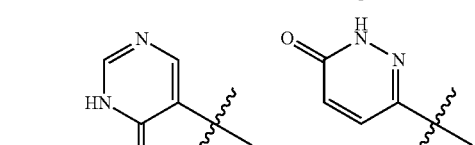

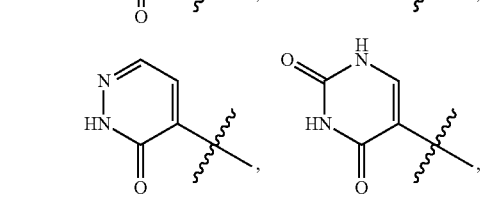

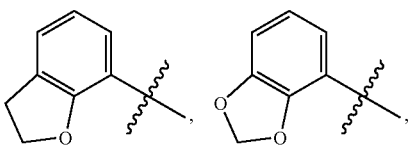

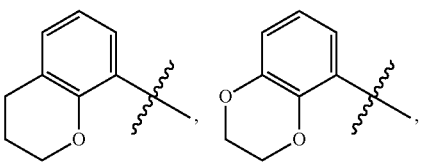

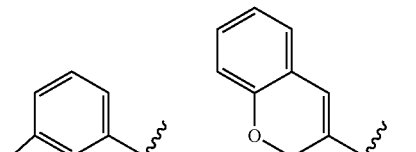

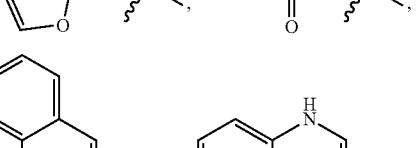

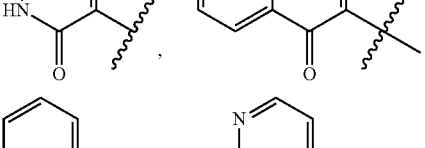

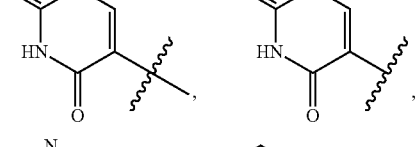

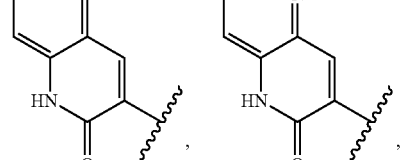

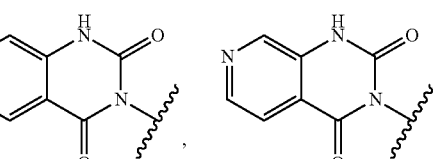

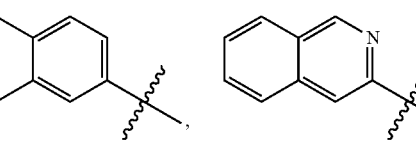

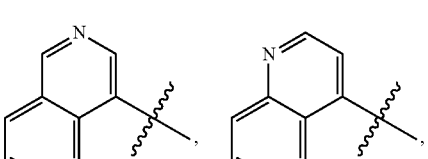

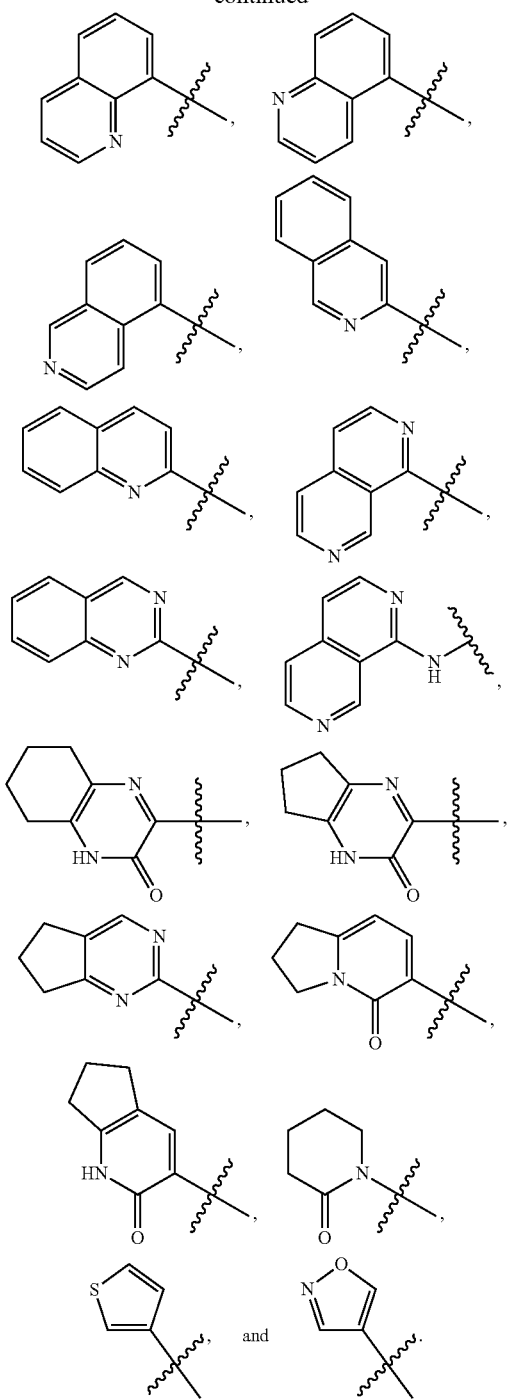
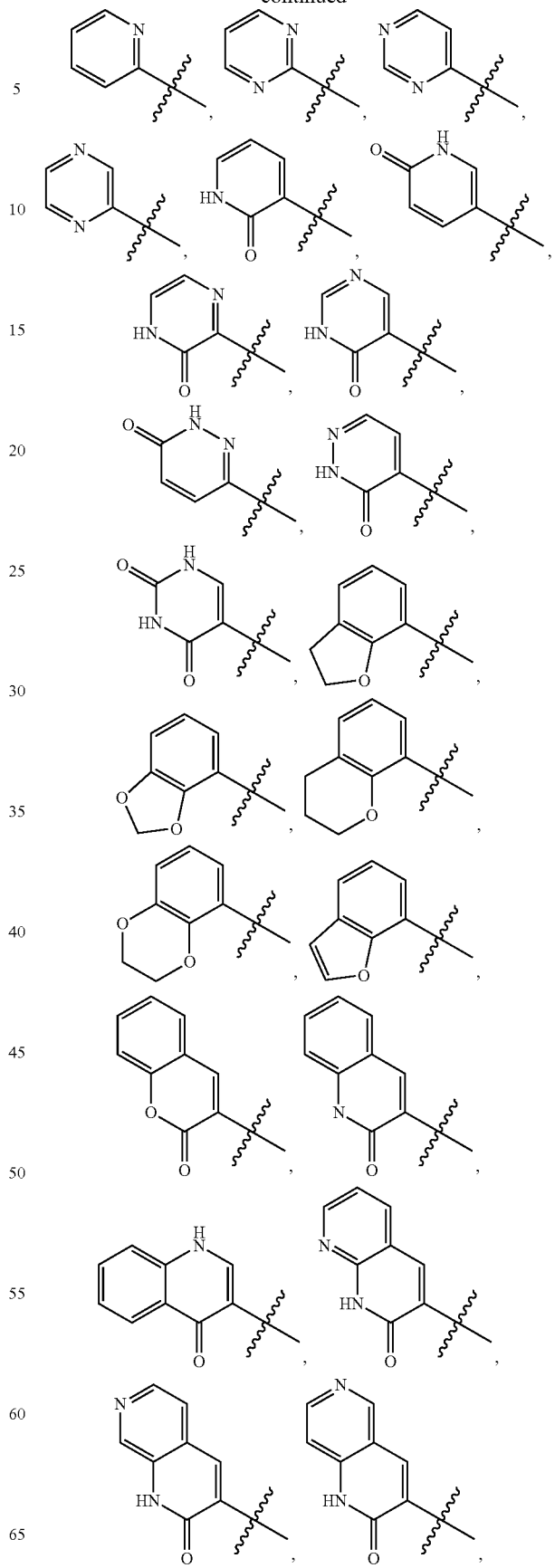
Each R[1] is optionally substituted with one to four R[a].
In some embodiments of formula (I), (II), (IIa), (IIb), or (IIc), R[1] is selected from

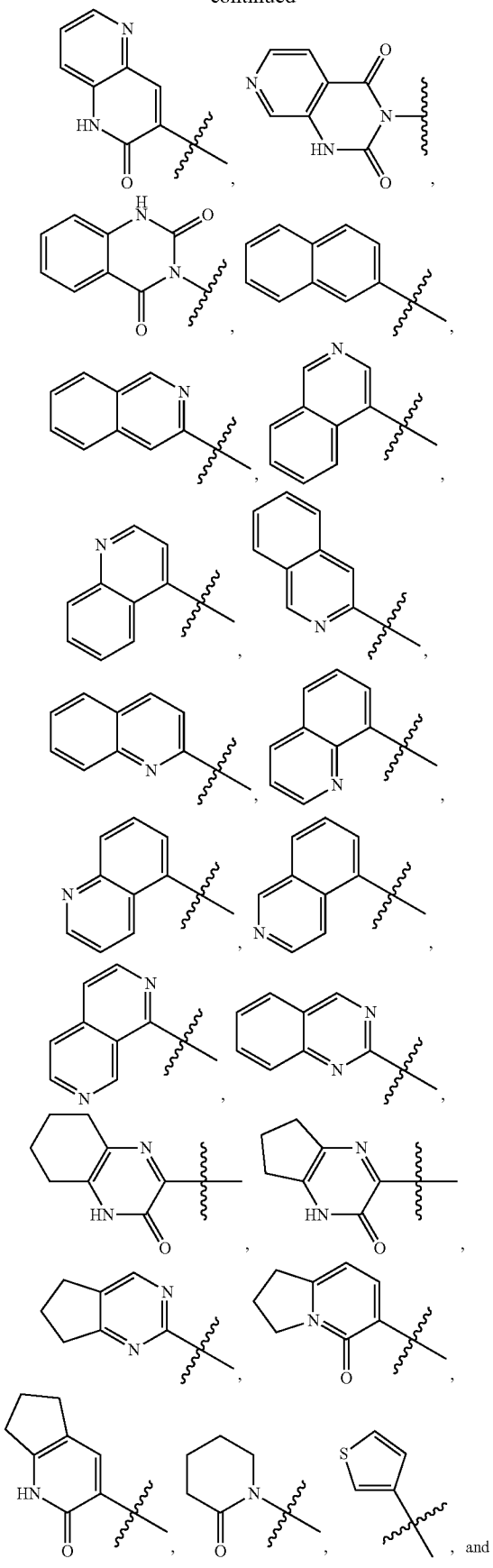

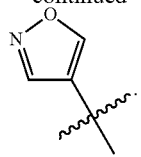

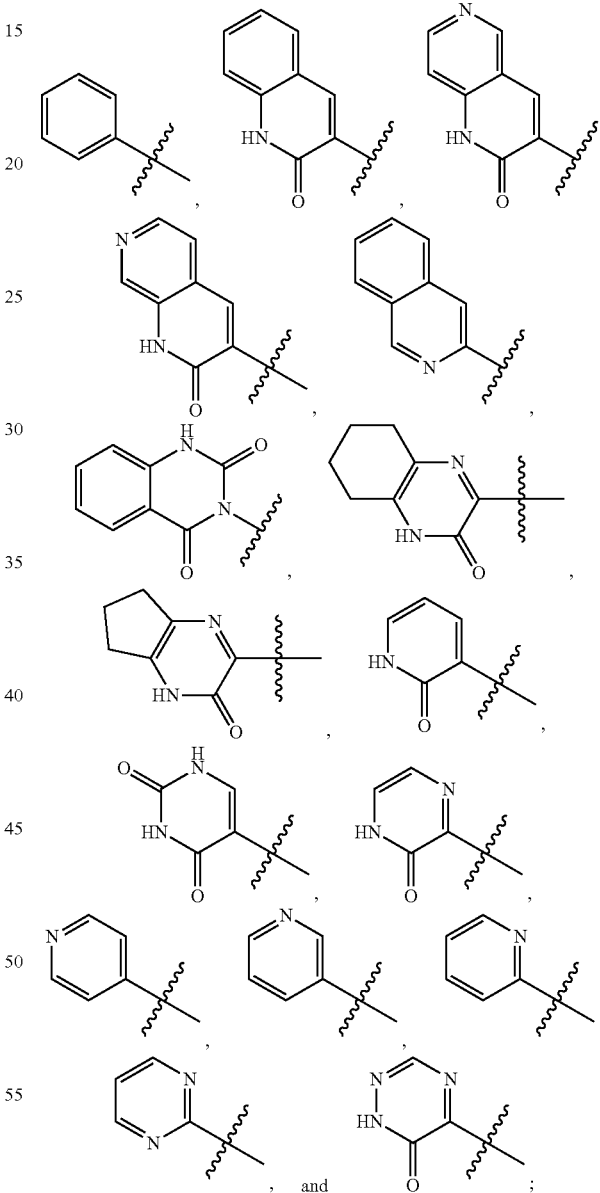

Each $R^1$ is optionally substituted with one to four $R^a$.

In some embodiments of formula (I), (II), (IIa), (IIb), or (IIc), $R^1$ is selected from each $R^1$ is optionally substituted with one to four $R^a$. In some embodiments, each $R^a$ is independently selected from halo, CN, —OH, $NR^{a1}R^{a2}$, $C_{1-4}$alkyl, $C_{1-4}$alkoxyl, $C_{1-4}$haloalkyl, $C_{1-4}$haloalkoxyl, $C_{3-6}$cycloalkyl, —O—$C_{3-6}$cycloalkyl, and phenyl. In some embodiments, each $R^a$ is independently selected from F, Cl, OH, CN, —NH$_2$, —CH$_3$, —CH$_2$F, —CHF$_2$, —CF$_3$, —OCH$_3$, and —OCF$_3$.

In some embodiments of formula (I), (I), IIa, (IIb), or (IIc), $R^1$ is selected from

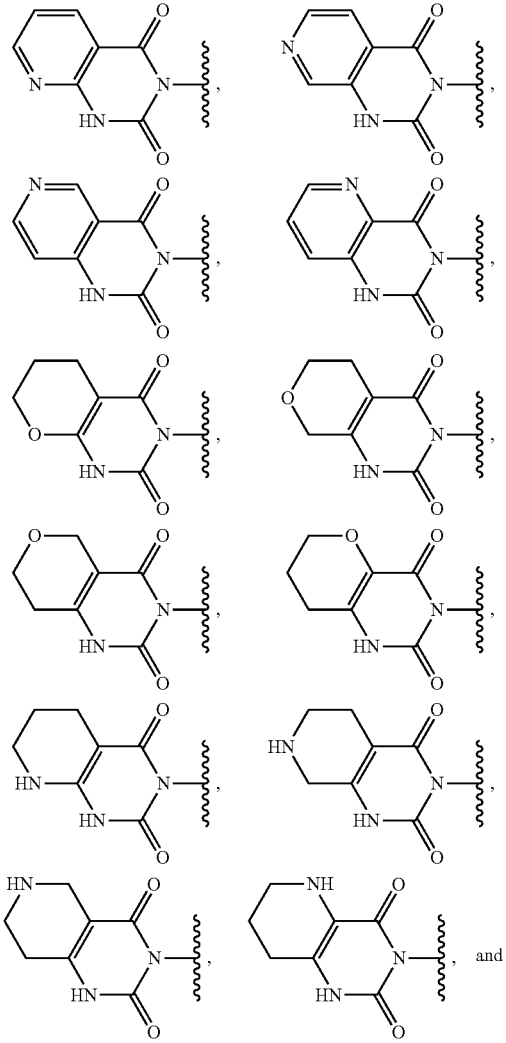

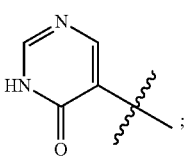

each $R^1$ is optionally substituted with one to four $R^a$. In some embodiments, each $R^a$ is independently selected from halo, CN, —OH, $NR^{a1}R^{a2}$, $C_{1-4}$alkyl, $C_{1-4}$ alkoxyl, $C_{1-4}$haloalkyl, $C_{1-4}$haloalkoxyl, $C_{3-6}$cycloalkyl, —O—$C_{3-6}$cycloalkyl, and phenyl. In some embodiments, each $R^a$ is independently selected from F, Cl, OH, CN, —NH$_2$, —NH(CH$_3$), —N(CH$_3$)$_2$, —CH$_3$, —CH$_2$F, —CHF$_2$, —CF$_3$, —OCH$_3$, and —OCF$_3$. In some embodiments, each $R^a$ is independently selected from F, Cl, —N(CH$_3$)$_2$, —CH$_3$, —OCH$_3$, and —CF$_3$.

In some embodiments of formula (I), (II), (IIa), (IIb), or (IIc), $R^1$ is

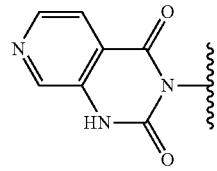

optionally substituted with one to three $R^a$. In some embodiments, each $R^a$ is independently selected from F, Cl, —N(CH$_3$)$_2$, —CH$_3$, —OCH$_3$, and —CF$_3$. In some embodiments, $R^1$ is substituted with —CH$_3$.

In some embodiments of formula (I), (II), (IIa), (IIb), or (IIc), $R^1$ is substituted with one to three $R^a$ independently selected from halo, CN, OH, $NR^{a1}R^{a2}$, $C_{1-4}$alkyl, $C_{1-4}$alkoxyl, $C_{1-4}$haloalkyl, $C_{1-4}$haloalkoxyl, and $C_{3-6}$cycloalkyl. In some embodiments, each $R^a$ is independently selected from F, Cl, CN, OH, —NH$_2$, —N(CH$_3$)$_2$, —CH$_3$, —CH$_2$CH$_3$, —CH(CH$_3$)$_2$, —C(CH$_3$)$_3$, —CH$_2$CN, —CH$_2$CH$_2$CN, —CH$_2$OH, —CH$_2$CH$_2$OH, —OCH$_3$, —OCH$_2$CH$_3$, —OCH(CH$_3$)$_2$, —OC(CH$_3$)$_3$, —CH$_2$OCH$_3$, —CH$_2$OCH$_2$CH$_3$, —CH$_2$OCH(CH$_3$)$_2$, —CH$_2$F, —CHF$_2$, —CF$_3$, —CH$_2$CH$_2$F, —CH$_2$CHF$_2$, —CH$_2$CF$_3$, —OCH$_2$F, —OCHF$_2$, —OCF$_3$, —OCH$_2$CH$_2$F, —OCH$_2$CHF$_2$, —OCH$_2$CF$_3$, —SO$_2$CH$_3$, —SO$_2$CH$_2$CH$_3$,

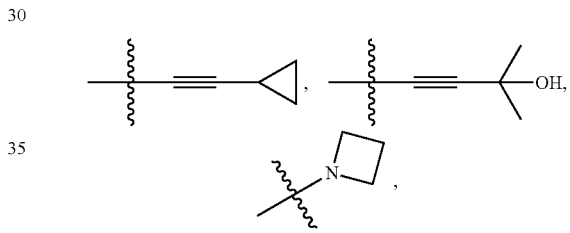

cyclopropyl, cyclobutyl, cyclopentyl, cyclohexyl, phenyl, —O— cyclopropyl, —O—CH$_2$-cyclopropyl, —O-cyclobutyl, —O—CH$_2$cyclobutyl, —O-cyclopentyl, —O—CH$_2$cyclopentyl, —O-cyclohexyl, —O—CH$_2$cyclohexyl, and —O-phenyl. In some embodiments, each $R^a$ is independently selected from F, C, CN, —NH$_2$, —CH$_3$, —CH$_2$F, —CHF$_2$, —CF$_3$, —OCH$_3$, —CH$_2$OCH$_2$CH$_3$, and —OCF$_3$.

In some embodiments of formula (I), (II), (IIa), (IIb), or (IIc), $R^1$ is selected from:

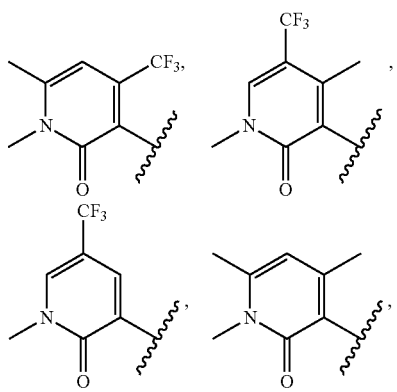

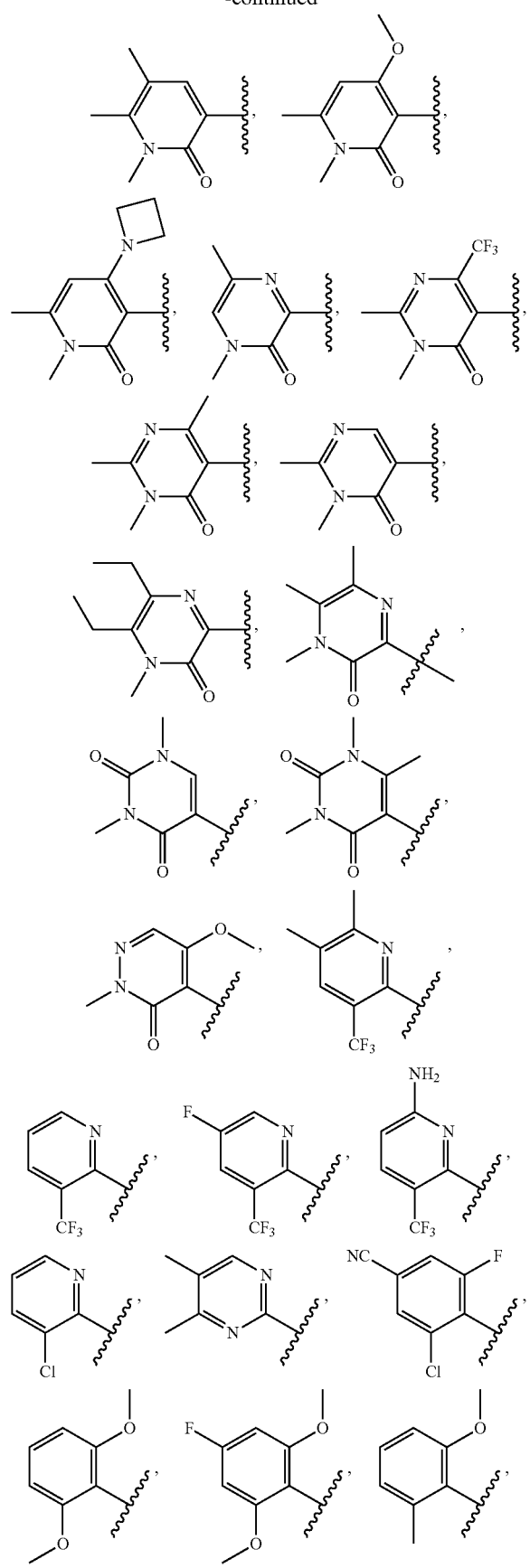
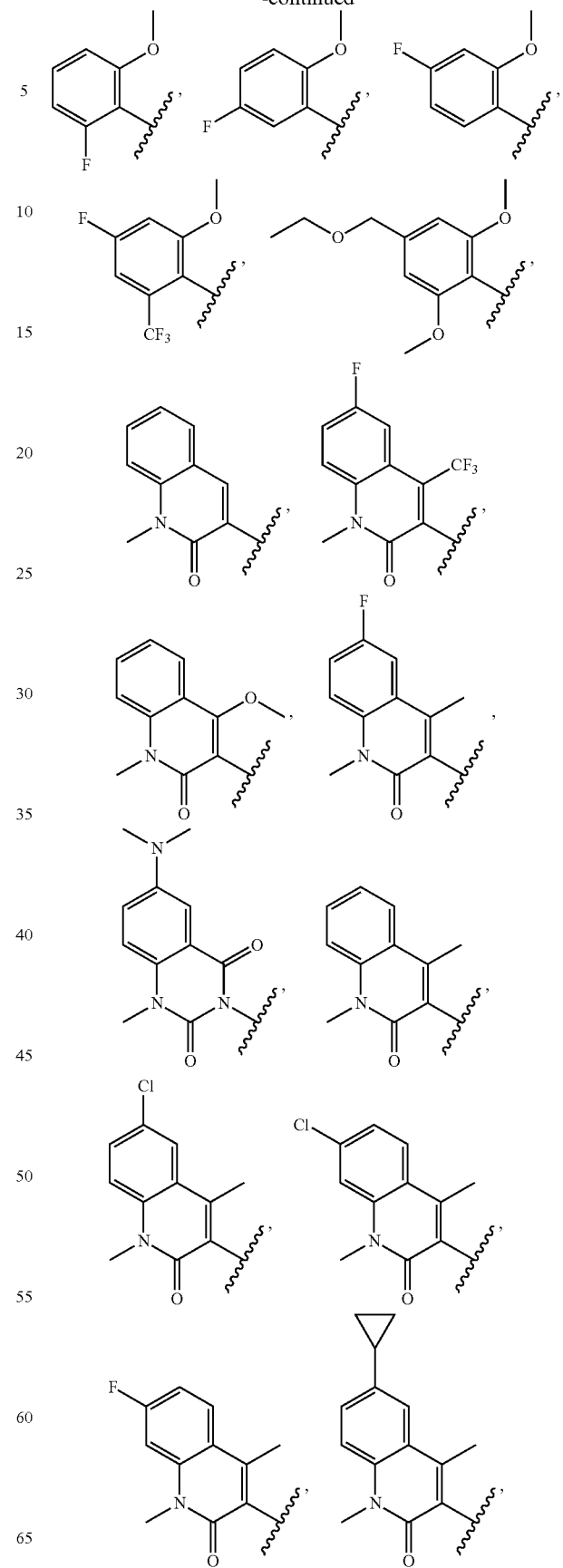

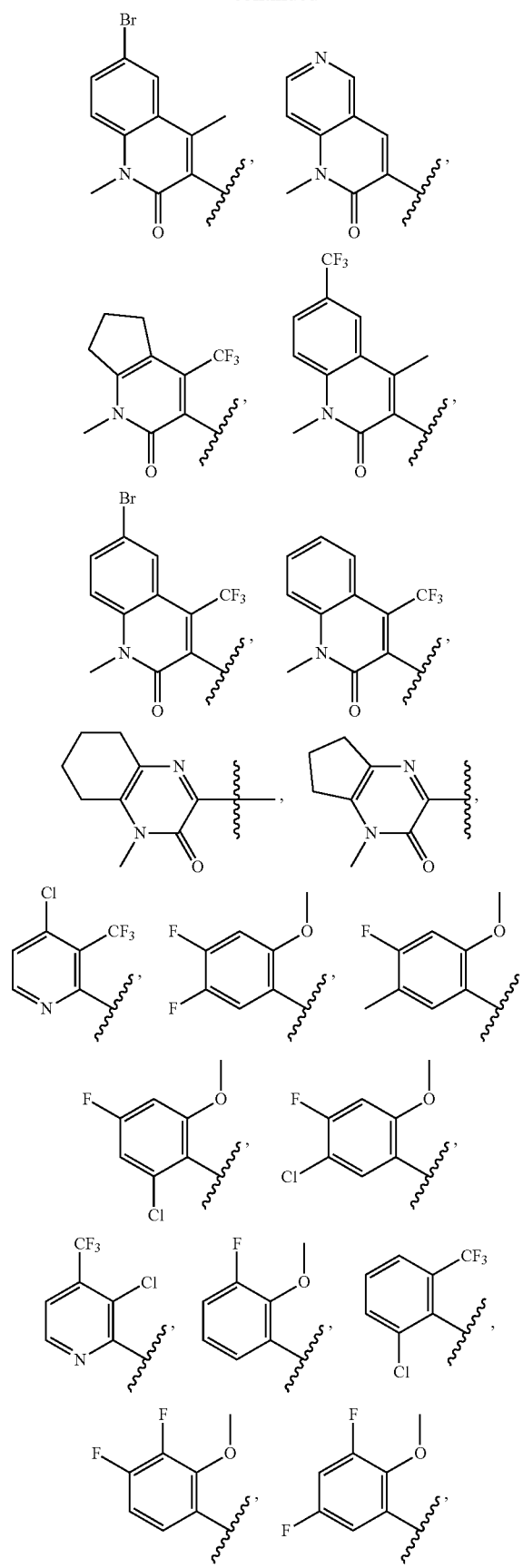
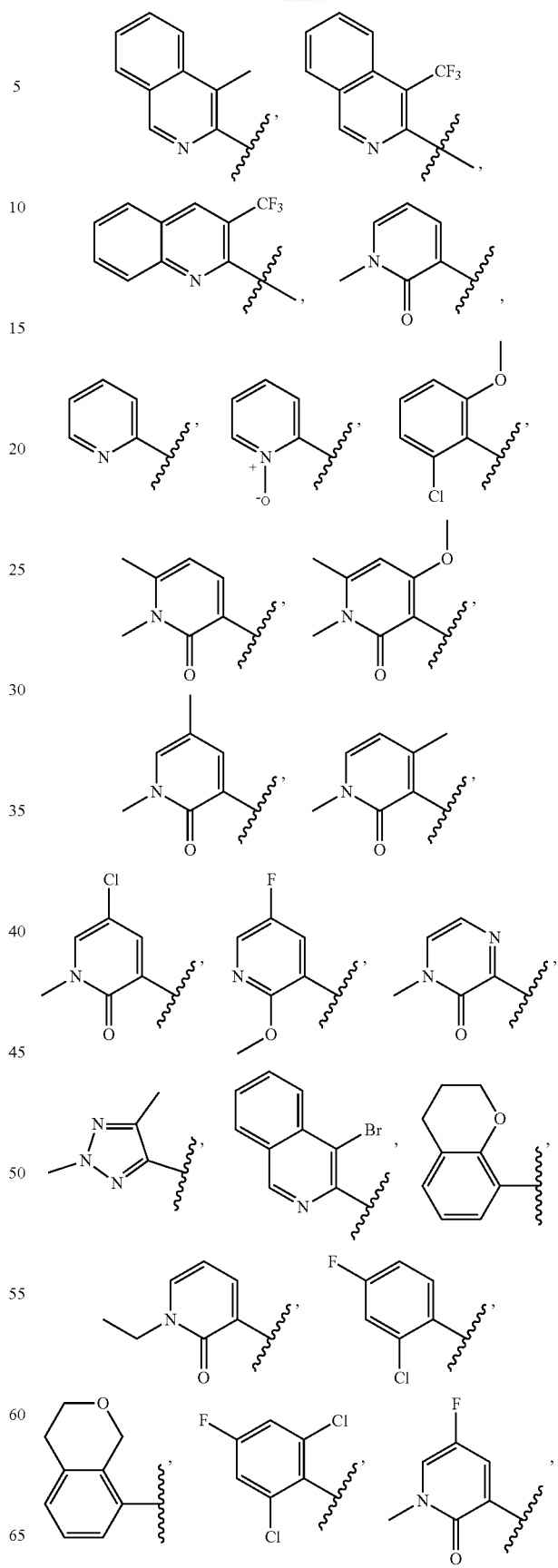

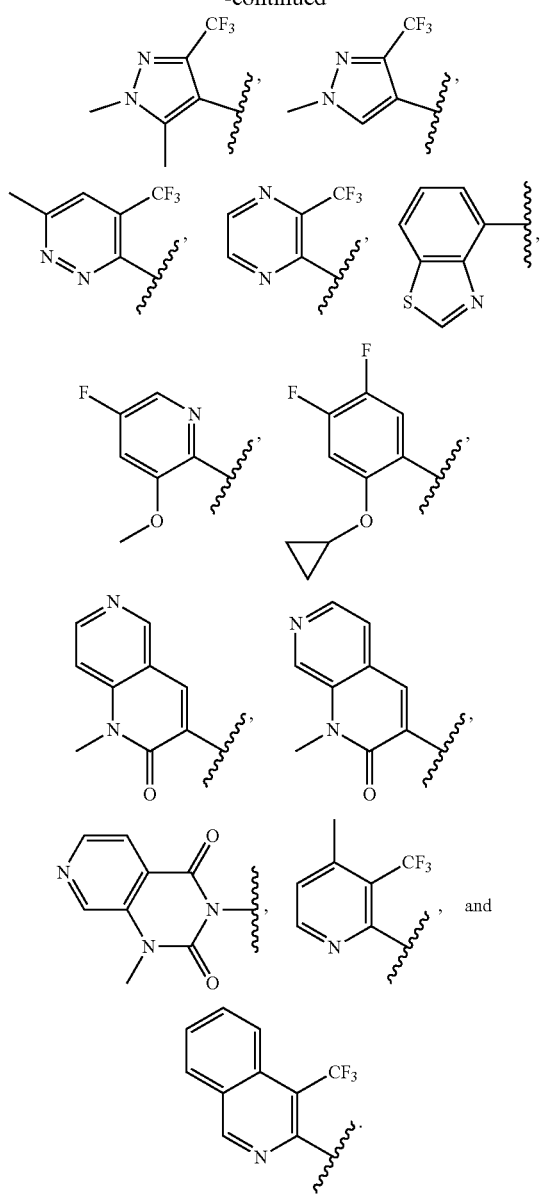
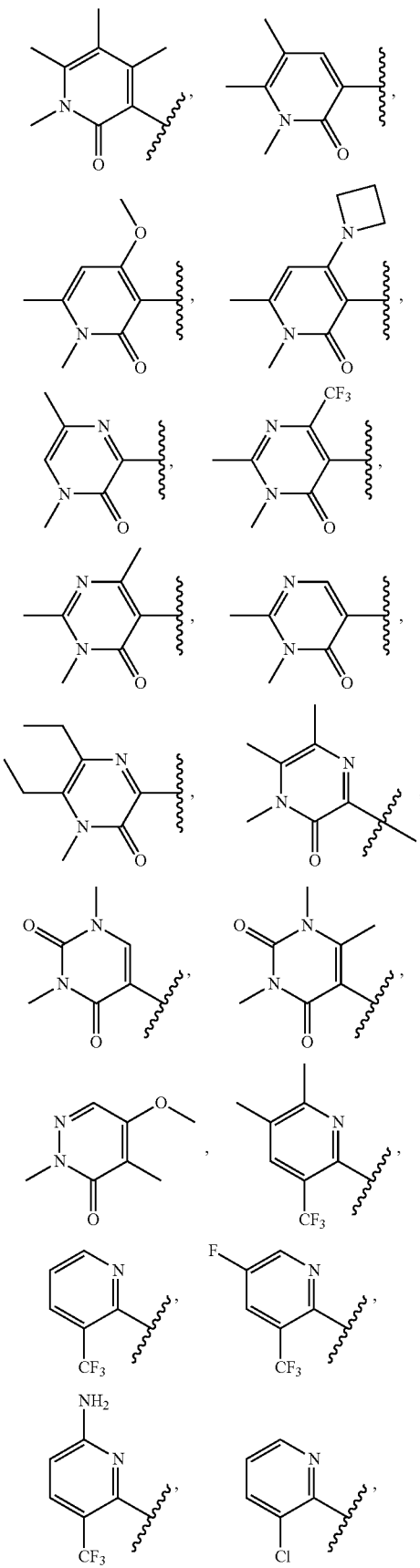
In some embodiments of formula (I), (II), (IIa), (IIb), or (IIc), $R^1$ is selected from:
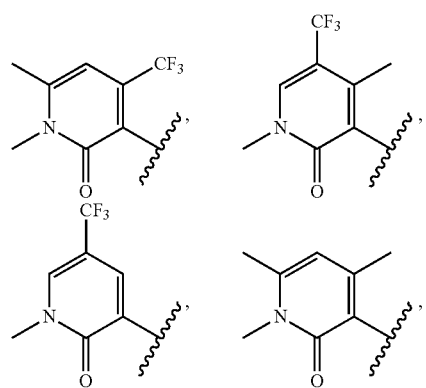

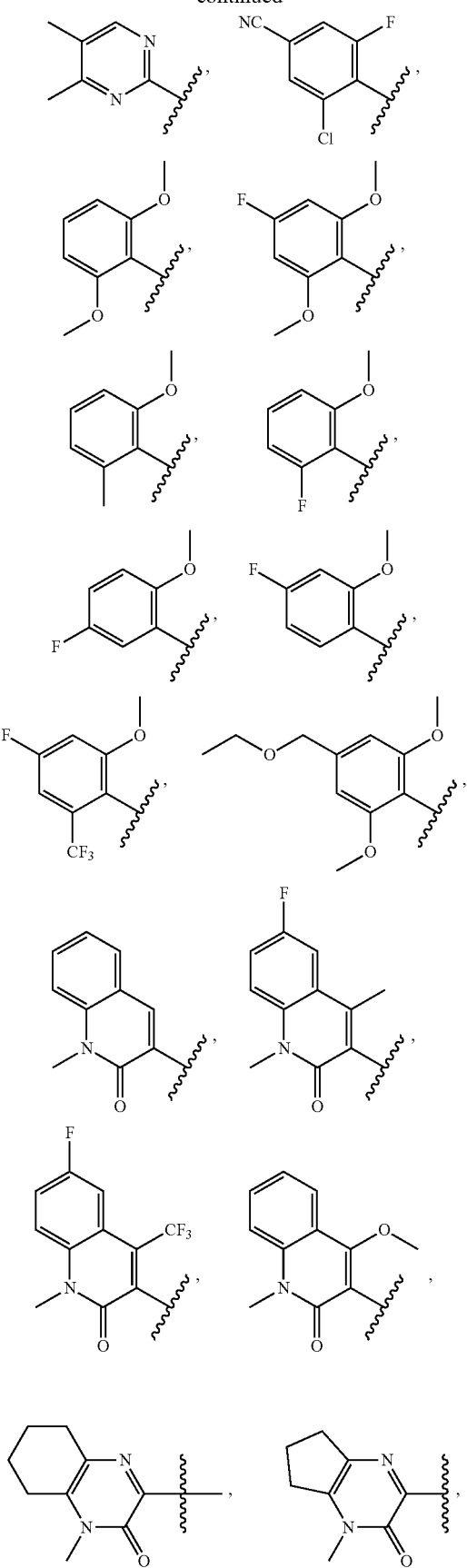
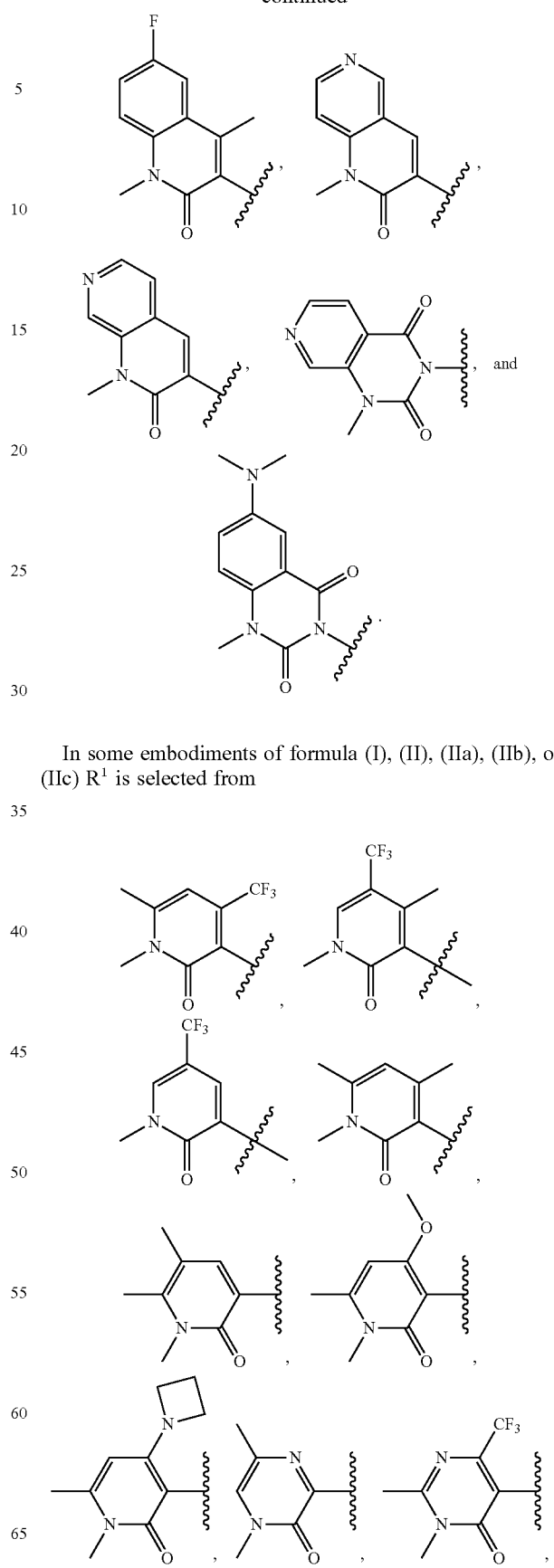
In some embodiments of formula (I), (II), (IIa), (IIb), or (IIc) R[1] is selected from

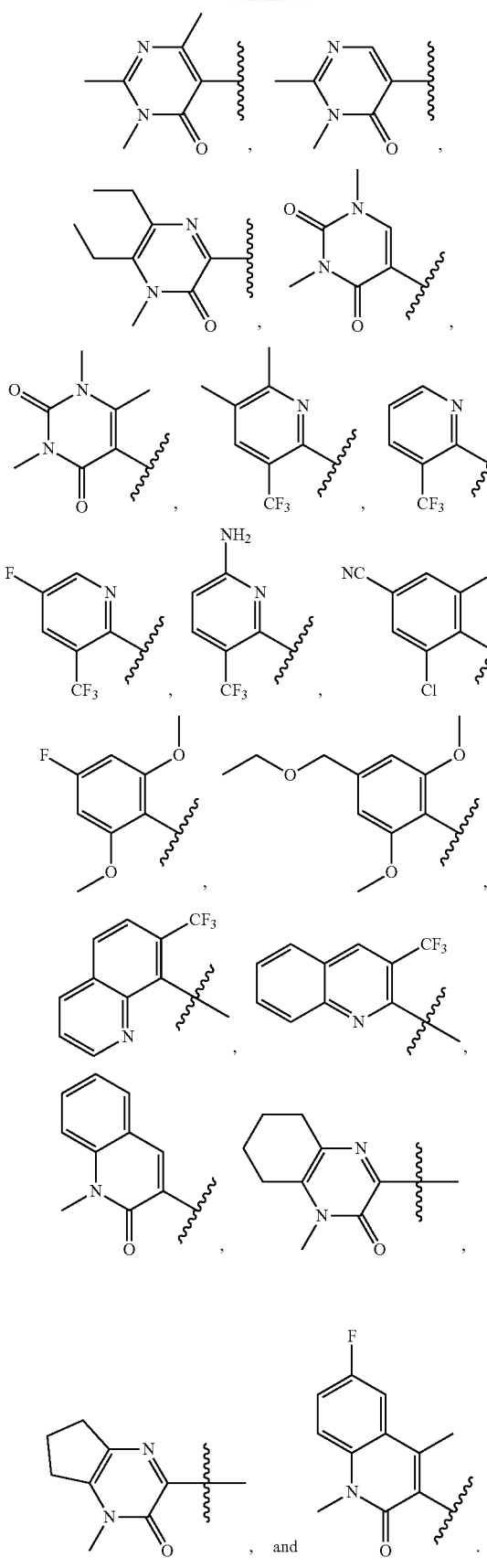
In some embodiments of formula (I), (II), (IIa), (IIb), or (IIc), $R^1$ is selected from
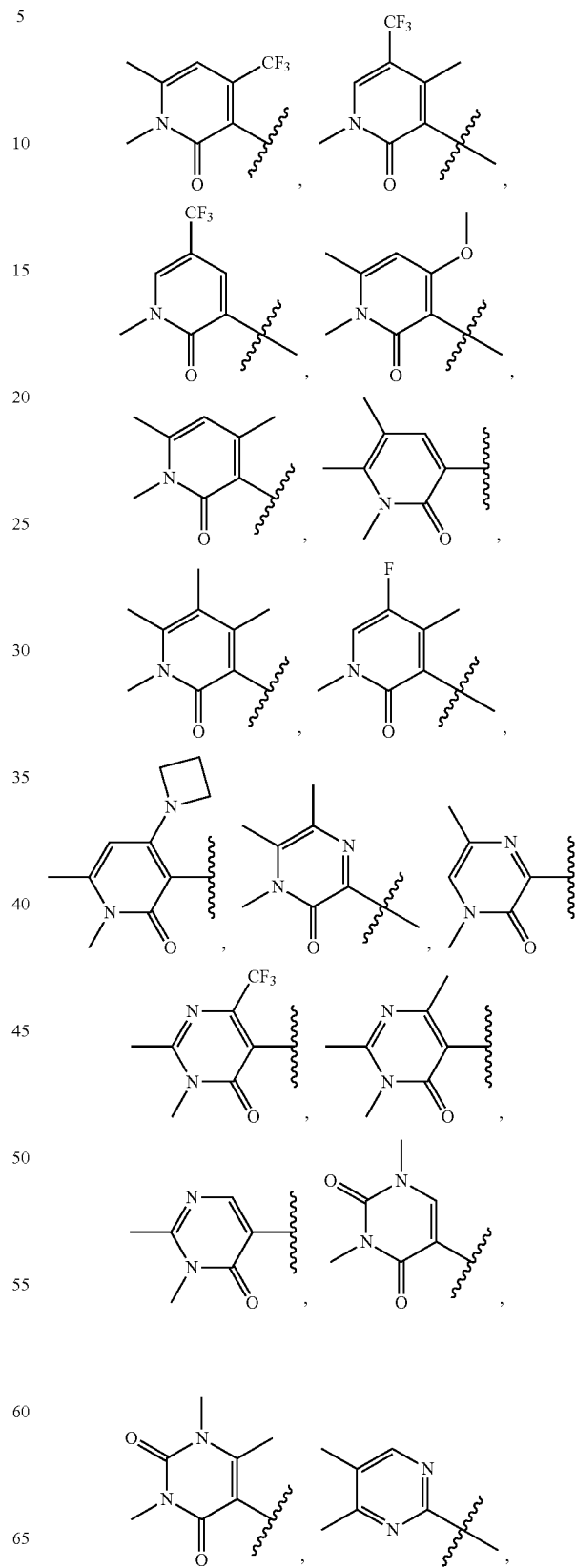

-continued

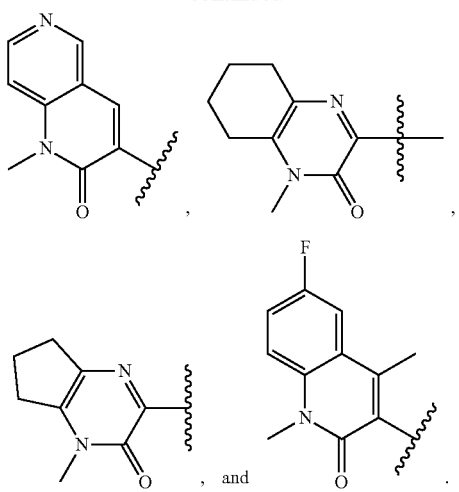

In some embodiments of formula (I), (II), (IIa), (IIb), or (IIc), $R^1$ is selected from:

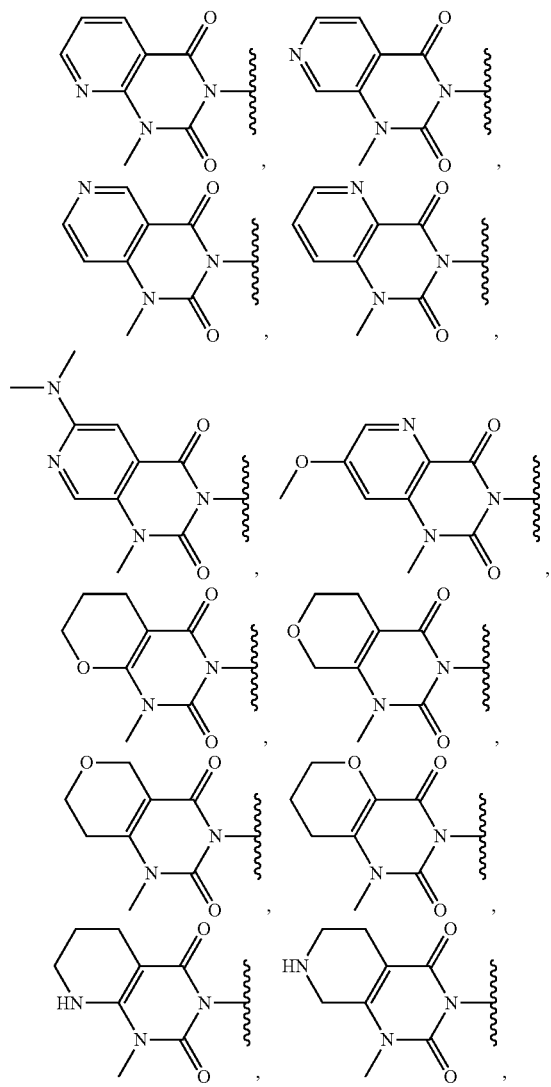

-continued

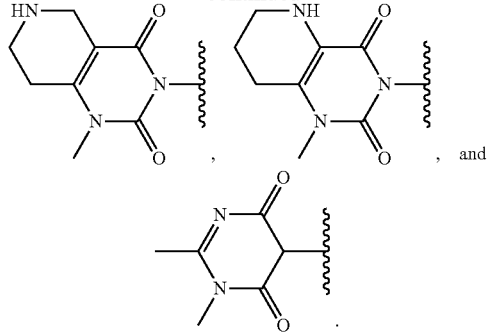

In some embodiments, $R^1$ is

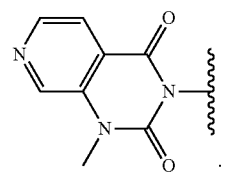

In some embodiments of formula (I), (II), (IIa), (IIb), or (IIc), "$R^1$-L-" is —O—C(O)—N $R^{a1}R^{a2}$. In some embodiments, each $R^{a1}$ and $R^{a2}$ is independently selected from H, and $C_{1-4}$alkyl. In some embodiments, each $R^{a1}$ and $R^{a2}$ is independently selected from H, $CH_3$, —$CH_2CH_3$, —CH$(CH_3)_2$, and —$C(CH_3)_3$. In some embodiments, each $R^{a1}$ and $R^{a2}$ is independently selected from H, $CH_3$, and —$CH_2CH_3$. In some embodiments, both $R^{a1}$ and $R^{a2}$ are $CH_3$. In some embodiments, "$R^1$-L-" is —O—C(O)—N$(CH_3)_2$.

In some embodiments of formula (I), or (II), $R^2$ and $R^3$ form a $C_{3-6}$cycloalkyl, 5-6 membered heterocyclyl, phenyl, or 5-6 membered heteroaryl. In some embodiments, the 5-6 membered heterocyclyl or 5-6 membered heteroaryl comprises one or two N. In some embodiments, $C_{3-6}$cycloalkyl, 5-6 membered heterocyclyl, phenyl, or 5-6 membered heteroaryl is substituted with one or two groups independently selected from halo, $C_{1-6}$alkyl, $C_{1-6}$haloalkyl, $C_{3-6}$cycloalkyl, and $C_{1-4}$alkylene-phenyl. In some embodiments, $C_{3-6}$cycloalkyl, 5-6 membered heterocyclyl, phenyl, or 5-6 membered heteroaryl is substituted with one or two groups independently selected from Cl, —$CH_3$, cyclopropyl, and —$CH_2$-phenyl.

In some embodiments of formula (I), or (II), $R^3$ and $R^4$ form a $C_{3-6}$cycloalkyl, 5-6 membered heterocyclyl, phenyl, or 5-6 membered heteroaryl. In some embodiments, the 5-6 membered heterocyclyl or 5-6 membered heteroaryl comprises one or two N. In some embodiments, $C_{3-6}$cycloalkyl, 5-6 membered heterocyclyl, phenyl, or 5-6 membered heteroaryl is substituted with one or two groups independently selected from halo, $C_{1-6}$alkyl, $C_{1-6}$haloalkyl, $C_{3-6}$cycloalkyl, and $C_{1-4}$alkylene-phenyl. In some embodiments, $C_{3-6}$cycloalkyl, 5-6 membered heterocyclyl, phenyl, or 5-6 membered heteroaryl is substituted with one or two groups independently selected from C, —$CH_3$, cyclopropyl, and —$CH_2$-phenyl.

In some embodiments of formula (I), (II), (IIa), (IIb), (IIc), (IId), (IIg), (IIh), or (IIi), each $R^2$, $R^3$, $R^4$, $R^5$, and $R^6$ is independently selected from H, halo, CN, OH, —$NR^{b1}R^{b2}$, $C_{1-6}$alkyl, $C_{1-6}$alkoxyl, $C_{1-6}$haloalkyl, and $C_{1-6}$haloalkoxyl. In some embodiments, each $R^2$, $R^3$, $R^4$, $R^5$, and $R^6$ is independently selected from H, halo, CN, OH, $-NR^{b1}R^{b2}$, $C_{1-4}$alkyl, $C_{1-4}$alkoxyl, $C_{1-4}$ haloalkyl, and $C_{1-4}$haloalkoxyl. In some embodiments, each $R^2$, $R^3$, $R^4$, $R^5$, and $R^6$ is independently selected from H, F, C, CN, OH, $-NH_2$, $-N(CH_3)_2$, $-CH_3$, $CD_3$, $-CH_2F$, $-CHF_2$, $-CF_3$, $-OCH_3$, and $-OCF_3$. In some embodiments, each $R^2$ and $R^6$ is independently selected from H, halo, CN, OH, $-NR^{b1}R^{b2}$, $C_{1-4}$alkyl, $C_{1-4}$alkoxyl, $C_{1-4}$haloalkyl, and $C_{1-4}$haloalkoxyl. In some embodiments, each $R^2$ and $R^6$ is independently selected from F, Cl, CN, OH, $-NH_2$, $-N(CH_3)_2$, $-CH_3$, $-CH_2F$, $-CHF_2$, $-CF_3$, $-OCH_3$, and $-OCF_3$. In some embodiments, both $R^2$ and $R^6$ are F. In some embodiments, $R^6$ is $-CH_3$. In some embodiments, each $R^3$ and $R^5$ is independently selected from H, $C_{1-6}$alkyl, $C_{1-6}$alkoxyl, $C_{1-6}$haloalkyl, $C_{1-6}$haloalkoxyl, and $C_{3-6}$cycloalkyl. In some embodiments, each $R^3$ and $R^5$ is independently selected from H, $C_{1-4}$alkyl, $C_{1-4}$alkoxyl, $C_{1-4}$ haloalkyl, and $C_{1-4}$haloalkoxyl. In some embodiments, each $R^3$ and $R^5$ is independently selected from H, F, $-NH_2$, $-CH_3$, $-CH_2F$, $-CHF_2$, $-CF_3$, and $-OCH_3$. In some embodiments, both $R^3$ and $R^5$ are H.

In some embodiments of formula (I), (II), (IIa), (IIb), (IIc), (IId), (IIg), (IIh), or (IIi), $R^2$ is F, and $R^6$ is $-CH_3$.

In some embodiments of formula (I), (II), (IId), (IIe), (IIf), (IIg), (IIh), or (IIi), $R^4$ is selected from H, $-NR^{b1}R^{b2}$, $-NR^{b1}S(O)_nR^{b4}$, and 3-8 membered heterocyclyl. In some embodiments, the 3-8 membered heterocyclyl of $R^4$ contains one to two heteroatoms or groups independently selected from S, N, O, and $S(O)_2$.

In some embodiments of formula (I), (II), (IId), (IIe), (IIf), (IIg), (IIh), or (IIi), $R^4$ is $-NR^{b1}R^{b2}$. In some embodiments, each $R^{b1}$ and $R^{b2}$ is independently selected from H, $C_{1-8}$alkyl, $C_{1-8}$haloalkyl, $C_{3-6}$cycloalkyl, phenyl, and 3-8 membered heterocyclyl. In some embodiments, 3-8 membered heterocyclyl contains one to two atoms independently selected from N and O. In some embodiments, $R^{b2}$ is selected from H, $C_{1-4}$alkyl, and $C_{1-6}$haloalkyl. In some embodiments, $R^{b1}$ is selected from H, and $CH_3$. In some embodiments, $R^{b2}$ is selected from $C_{1-6}$alkyl, $C_{1-8}$haloalkyl, $C_{3-6}$cycloalkyl, $C_{3-6}$cycloalkyl, and 4-6 membered heterocyclyl. In some embodiments, $R^{b2}$ is selected from $C_{1-6}$alkyl, $C_{1-6}$haloalkyl, $C_{3-6}$cycloalkyl, and 4-6 membered heterocyclyl. In some embodiments, $R^{b1}$ is H, and $R^{b2}$ is selected from $C_{1-6}$alkyl, $C_{1-8}$haloalkyl, $C_{3-6}$cycloalkyl, and 5-6 membered heterocyclyl. In some embodiments, $R^{b1}$ is H, and $R^{b2}$ is $C_{1-6}$ haloalkyl. In some embodiments, $R^{b2}$ is $-C_{1-5}$alkylene-$CF_3$. In some embodiments, $R^{b2}$ is selected from -methylene-$CF_3$, -ethylene-$CF_3$, -propylene-$CF_3$, -butylene-$CF_3$, and -pentylene-$CF_3$. In some embodiments, $R^{b2}$ is $-C_{1-5}$alkylene-$CF_3$ substituted with one or two $R^{b5}$. In some embodiments, each $R^{b5}$ is independently selected from hydroxyl, $C_{1-4}$alkoxyl, $C_{3-6}$cycloalkyl, phenyl, and 4-6 membered heterocyclyl. In some embodiments, each $R^{b5}$ is independently selected from $C_{3-6}$cycloalkyl, 4-6 membered heterocyclyl, and phenyl. Each $C_{3-6}$cycloalkyl, 4-6 membered heterocyclyl, and phenyl of $R^{b5}$ is independently optionally substituted with one or three groups independently selected from halo, hydroxyl, cyano, $-NR^{b1}R^{b2}$, $C_{1-4}$alkyl, $C_{1-4}$alkoxyl, and $C_{1-4}$haloalkyl. In some embodiments, $R^{b5}$ is selected from cyclopropyl, cyclobutyl, cylcopentyl, tetrahydropyranyl, tetrahydrofuranyl, and phenyl; and each $R^{b5}$ is optionally substituted with one group selected from F, Cl, CN, $-CH_3$, $-CH_2F$, $-CHF_2$, and $-CF_3$. In some embodiments, $R^{b5}$ is phenyl. In some embodiments, $R^{b5}$ is phenyl substituted with one or two groups independently selected from F, Cl, CN, $-CH_3$, $-CH_2F$, $-CHF_2$, and $-CF_3$. In some embodiments, $R^{b5}$ is phenyl substituted with one or two groups independently selected from F, Cl, CN, and $-CF_3$. In some embodiments, $R^{b5}$ is unsubstituted phenyl.

In some embodiments of formula (I), (II), (IId), (IIe), (IIf), (IIg), (IIh), or (IIi), $R^4$ is selected from

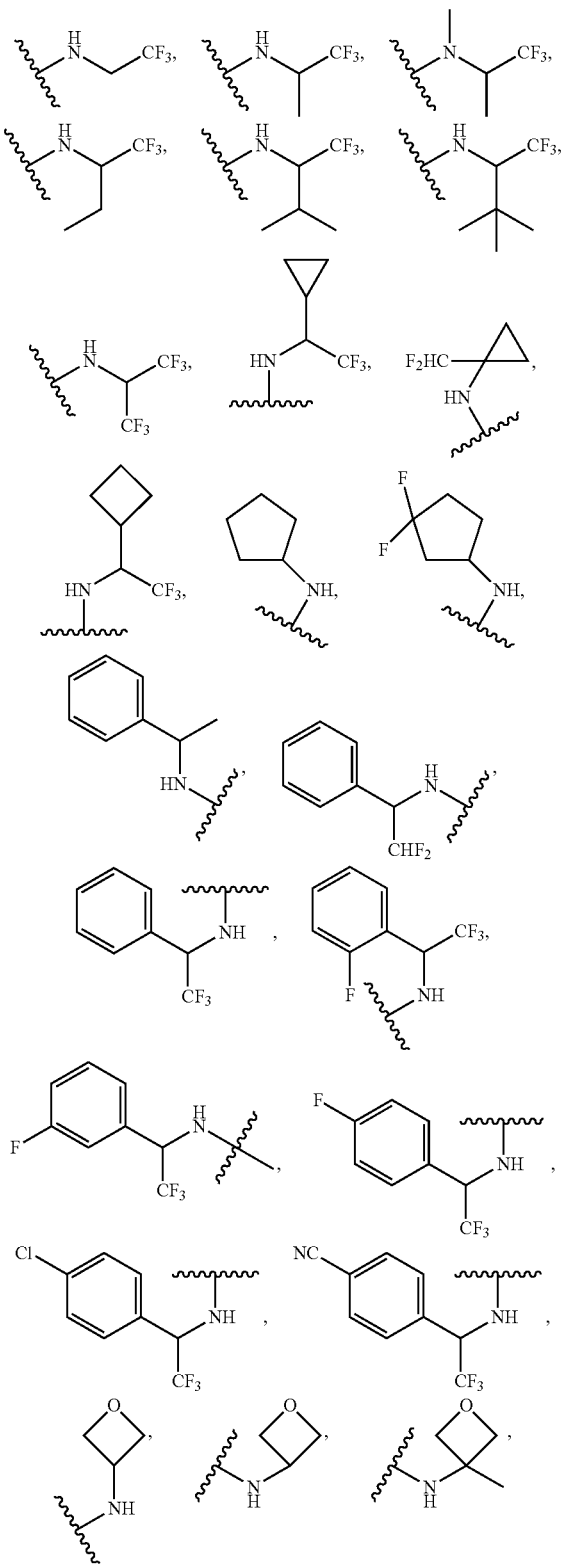

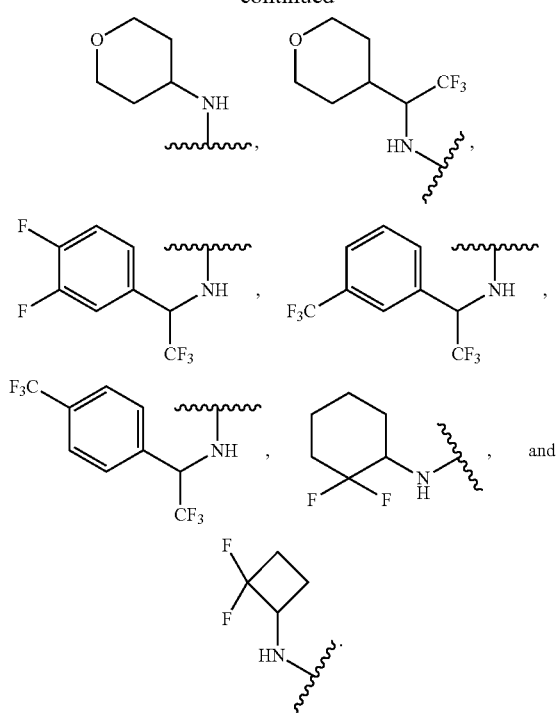
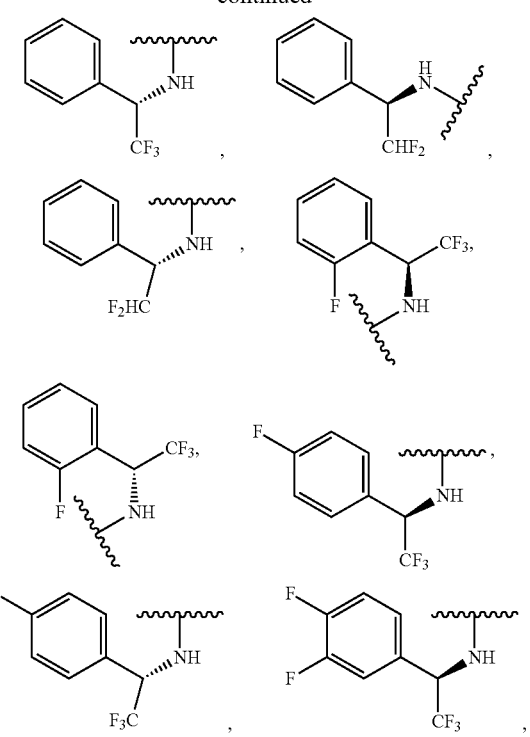
In some embodiments of formula (I), (II), (IId), (IIe), (IIf), (IIg), (IIh), or (IIi), $R^4$ is selected from
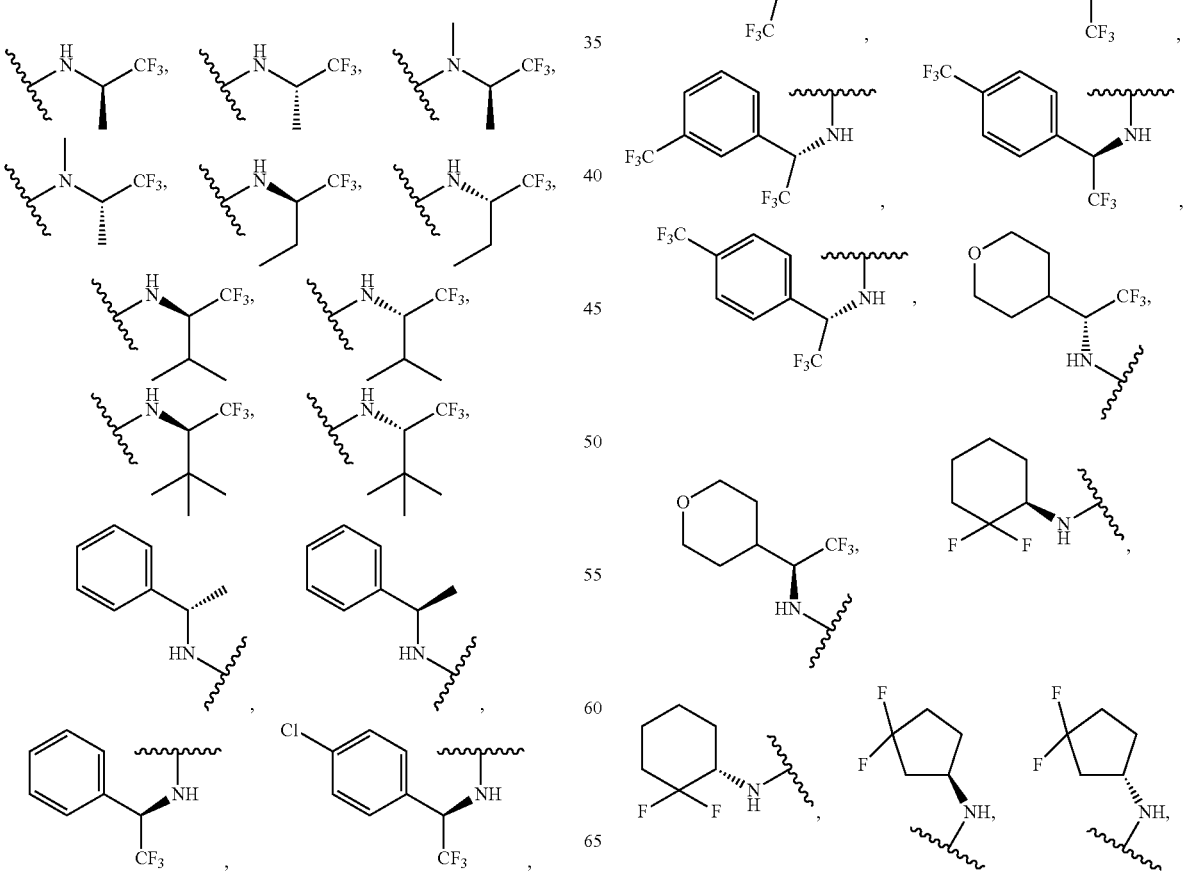

-continued

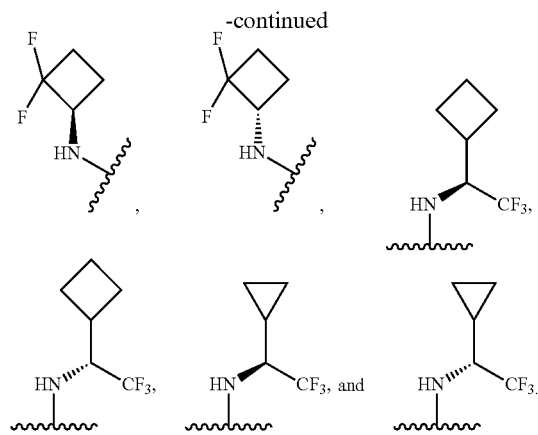

In some embodiments formula (I), (II), (IId), (IIe), (IIf), (IIg), (IIh), or (IIi), $R^4$ is

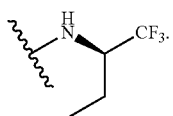

In some embodiments of formula (I), (II), (IId), (IIe), (IIf), (IIg), (IIh), or (IIi), $R^4$ is 3-8 membered heterocyclyl optionally substituted with one to three $R^b$; and each $R^b$ is independently selected from halo, hydroxyl, cyano, —$NR^{a1}R^{a2}$, $C_{1-4}$alkyl, $C_{1-4}$alkoxyl, and $C_{1-4}$ haloalkyl. In some embodiments, each $R^4$ is optionally substituted with one to two groups independently selected from F, Cl, CN, —OH, —$CH_3$, —$CH(CH_3)_2$, and —$CF_3$.

In some embodiments of formula (I), (II), (IId), (IIe), (IIf), (IIg), (IIh), or (IIi), $R^4$ is 3-8 membered spiro, fused or bridged heterocyclyl. In some embodiments, $R^4$ is selected from azetidinyl, aziridinyl, imidazolidinyl, morpholinyl, oxetanyl, piperazinyl, piperidinyl, pyrazolidinyl, piperidinyl, pyrrolidinyl, pyrrolidinonyl, tetrahydrofuranyl, tetrahydrothiophenyl, dihydropyridinyl, tetrahydropyridinyl, 1,1-dioxide-thiomorpholinyl, and quinuclidinyl; and each $R^4$ is optionally substituted with one to three $R^b$. In some embodiments, $R^4$ is selected from morpholinyl, piperidinyl, tetrahydropyranyl, and pyrrolidinyl; each $R^4$ is optionally substituted with one to three $R^b$. In some embodiments, each $R^b$ is independently selected from halo, hydroxyl, cyano, —$NR^{a1}R^{a2}$, $C_{1-4}$alkyl, $C_{1-4}$alkoxyl, and $C_{1-4}$haloalkyl. In some embodiments, each $R^b$ is independently selected from F, C, CN, —OH, —$CH_3$, —$CH(CH_3)_2$, and —$CF_3$.

In some embodiments of formula (I), (II), (IId), (IIe), (IIf), (IIg), (IIh), or (IIi), $R^4$ is a spirocyclyl optionally substituted with one to three $R^b$. In some embodiments, $R^4$ is aza spiroheptanyl. In some embodiments, $R^4$ is azaspiro[3.3] heptanyl. In some embodiments, $R^4$ is azaspiro[2.4]heptanyl. In some embodiments, each $R^b$ is independently selected from halo, hydroxyl, cyano, —$NR^{a1}R^{a2}$, $C_{1-4}$alkyl, $C_{1-4}$alkoxyl, and $C_{1-4}$haloalkyl. In some embodiments, each $R^b$ is independently selected from F, Cl, CN, —OH, —$CH_3$, —$CH(CH_3)_2$, and —$CF_3$.

In some embodiments of formula (I), (II), (IId), (IIe), (IIf), (IIg), (IIh), or (IIi), $R^4$ is a fused or bridged heterocyclyl optionally substituted with one to three $R^b$. In some embodiments, each $R^4$ is independently selected from azabyicyclo[3.1.0]hexanyl, azabyicyclo[3.2.1]octanyl, azabyicyclo[2.2.2]octanyl, and oxa-azabicyclo[2.2.2]octanyl; each $R^4$ is optionally substituted with one to three $R^b$. Each $R^b$ is independently selected from halo, hydroxyl, cyano, —$NR^{a1}R^{a2}$, $C_{1-4}$alkyl, $C_{1-4}$alkoxyl, and $C_{1-4}$haloalkyl. In some embodiments, each $R^b$ is independently selected from F, Cl, CN, —OH, —$CH_3$, —$CH(CH_3)_2$, and —$CF_3$.

In some embodiments of formula (I), (II), (IId), (IIe), (IIf), (IIg), (IIh), or (IIi), $R^4$ is selected from

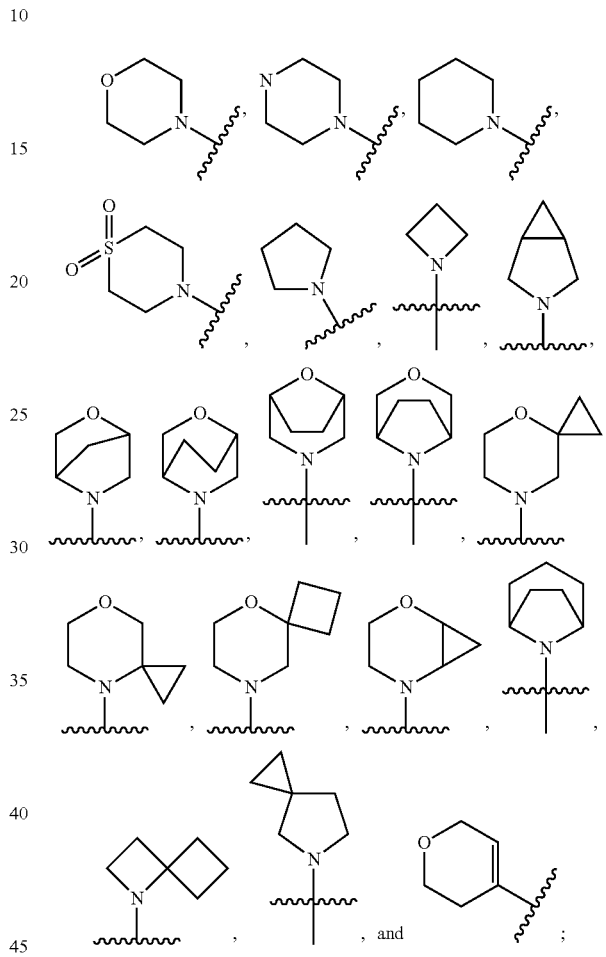

and each $R^4$ is optionally substituted with one to three groups independently selected from halo, OH, CN, —$NR^{a1}R^{a2}$, $C_{1-4}$alkyl, $C_{1-4}$alkoxyl, and $C_{1-4}$haloalkyl.

In some embodiments of formula (I), (II), (IId), (IIe), (IIf), (IIg), (IIh), or (IIi), $R^4$ is selected from

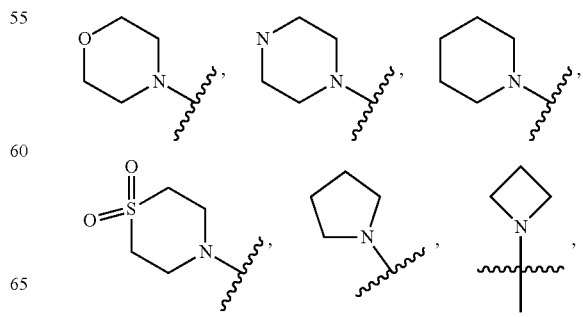

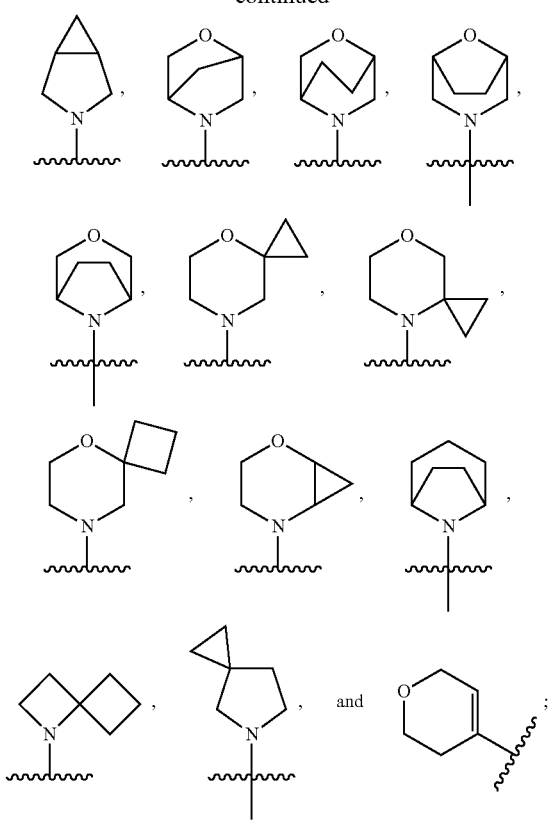
and each R[4] is optionally substituted with one to three groups independently selected from F, Cl, OH, CN, $NH_2$, $—CH_3$, $—CH(CH_3)_2$, $—CH_2F$, $—CHF_2$, $—CF_3$, $—CH_2CH_2F$, $—CH_2CHF_2$, $—CH_2CF_3$, $C_{3-6}$cycloalkyl, and $—CH_2C_{3-6}$cycloalkyl.
In some embodiments of formula (I), (II), (IId), (IIe), (IIf), (IIg), (IIh), or (IIi), R[4] is selected from
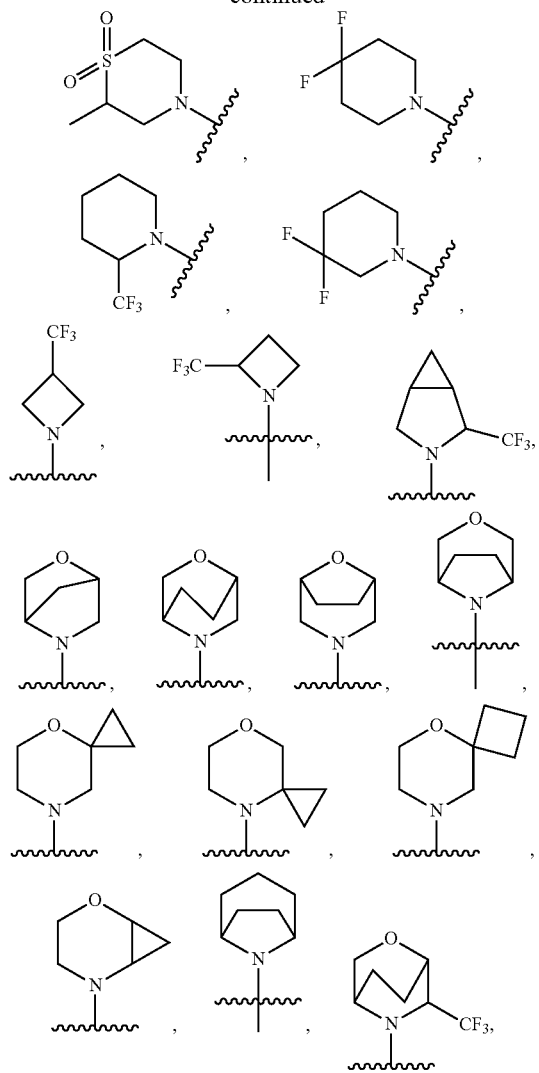
In some embodiments of formula (I), (II), (IId), (IIe), (IIf), (IIg), (IIh), or (IIi), R[4] is selected from
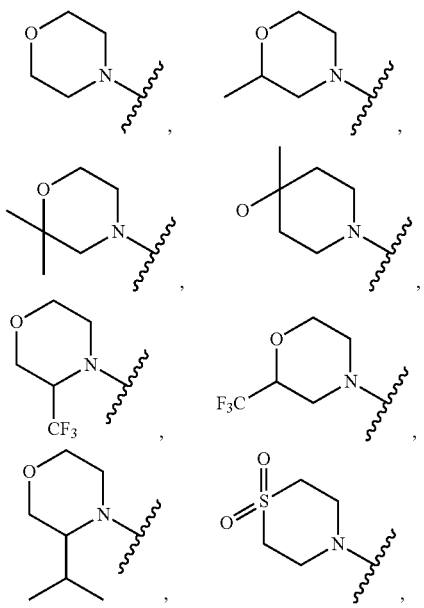

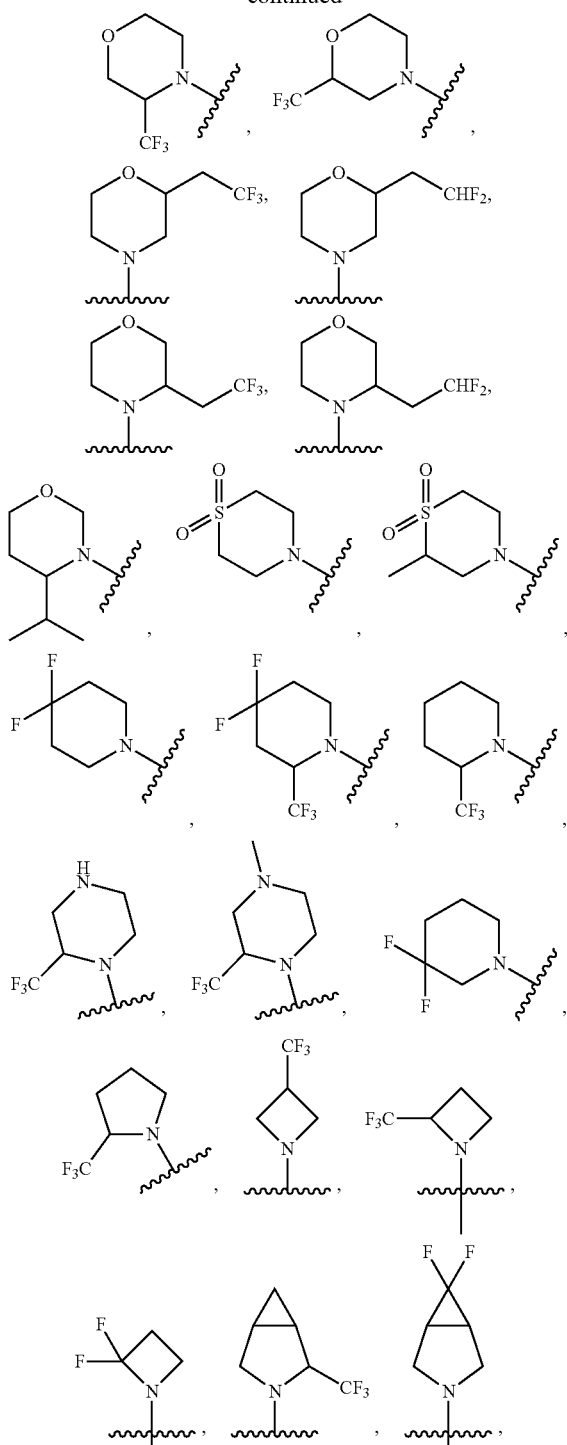
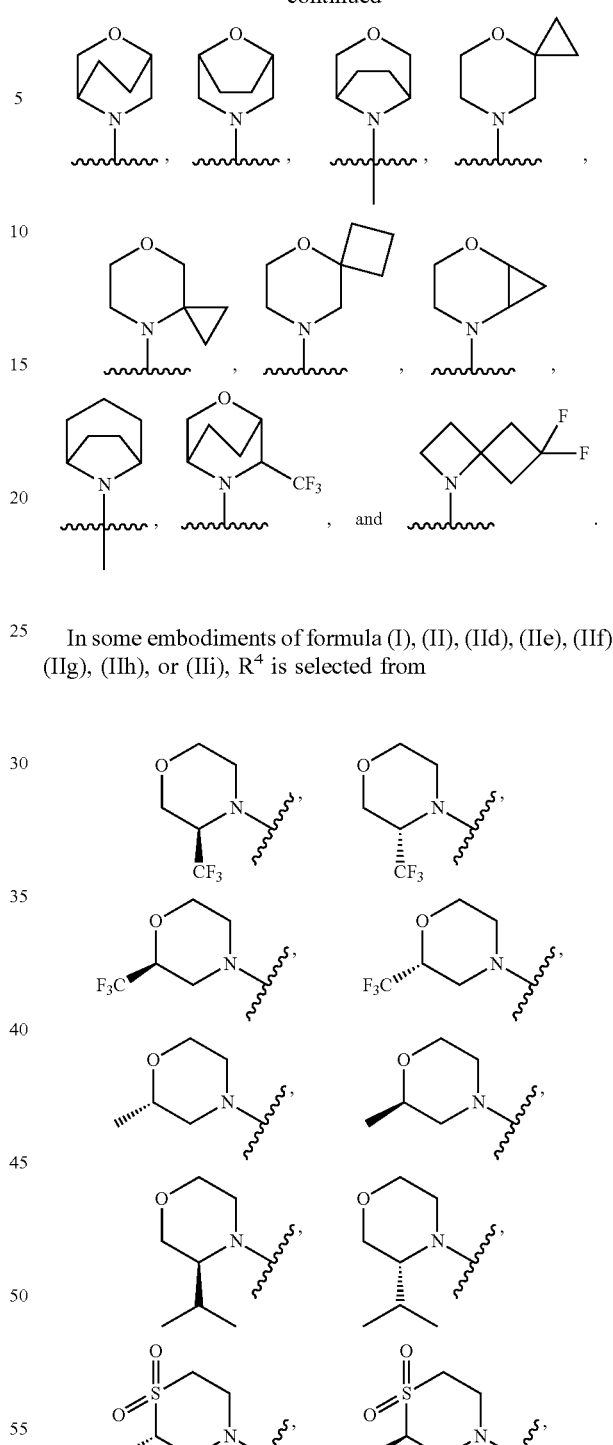
In some embodiments of formula (I), (II), (IId), (IIe), (IIf), (IIg), (IIh), or (IIi), $R^4$ is selected from -continued

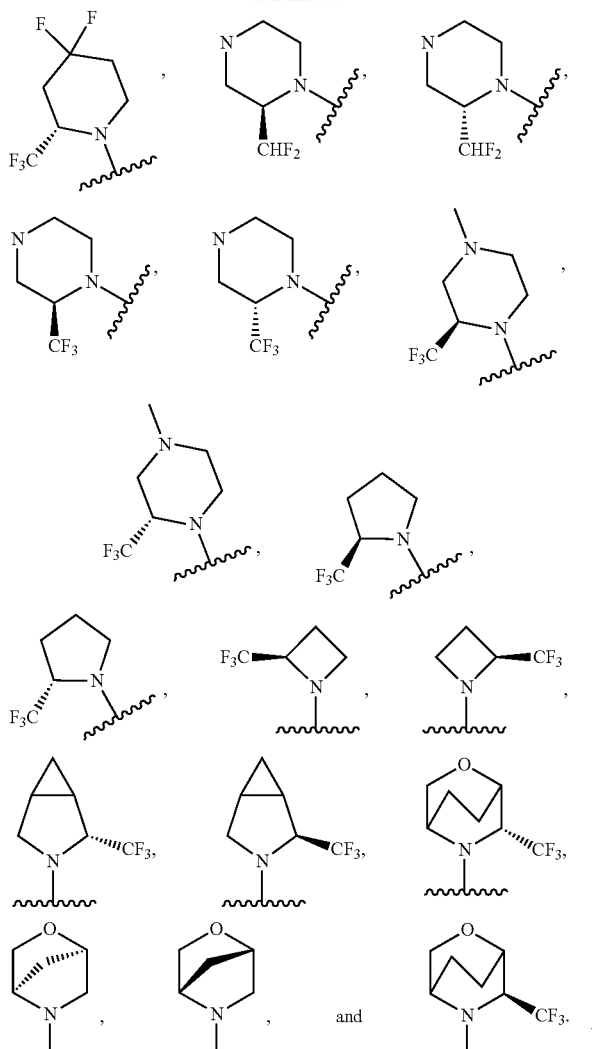

In some embodiments, R⁴ is

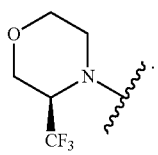

In some embodiments of formula (I), (II), (IId), (IIe), (IIf), (IIg), (IIh), or (IIi), R⁴ is —NHS(O)₂R$^{b4}$. In some embodiments, R$^{b4}$ is selected from C$_{1-4}$alkyl, C$_{1-4}$haloalkyl, C$_{3-6}$cycloalkyl, and phenyl. In some embodiments, R$^{b4}$ is selected from —CH₃, —CH₂F, —CHF₂, —CF₃, and phenyl. In some embodiments, phenyl is optionally substituted with pyridinyl that is optionally substituted with one or two groups independently selected from halo, and C$_{1-4}$alkyl. In some embodiments, the pyridinyl is optionally substituted with one or two groups independently selected from F, and —CH₃.

In some embodiments of formula (I), (II), (IId), (IIe), (IIf), (IIg), (IIh), or (IIi), R⁴ is selected from

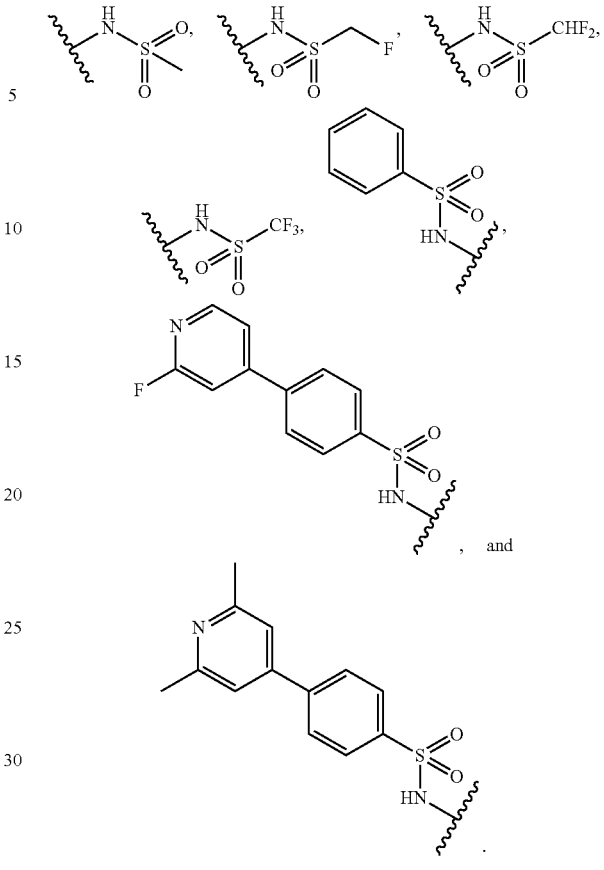

In some embodiments of formula (IIb), X¹ is CH or N. In some embodiments, X¹ is N. In some embodiments, X² is selected from CH₂, NR$^{x2}$, O, and S(O)₂. In some embodiments, X¹ is N, and X² is O. In some embodiments, X¹ is N, and X² is CH₂. In some embodiments, X¹ is N, and X² is S(O)₂. In some embodiments, each R$^b$ is independently selected from F, OH, —CH₃, —CH(CH₃)₂, —CH₂F, —CHF₂, and —CF₃.

In some embodiments of formula (IIb), p is 0. In some embodiments, p is 1. In some embodiments, p is 2. In some embodiments, q is 1. In some embodiments, q is 2.

In some embodiments of formula (IId), Y¹, Y², Y³, Y⁴, and Y⁵ are CR$^y$. In some embodiments, at least one of Y¹, Y², Y³, Y⁴, and Y⁵ is N. In some embodiments, Y¹ is N; and Y², Y³, Y⁴, and Y⁵ are CR$^y$. In some embodiments, Y² is N; and Y¹, Y³, Y⁴, and Y⁵ are CR$^y$. In some embodiments, Y³ is N; and Y¹, Y², Y⁴, and Y⁵ are CR$^y$. In some embodiments, Y¹ and Y⁵ are N; and Y¹, Y², and Y³ are CR$^y$.

In some embodiments of formula (IId), (IIf), (IIg), or (IIh), each R$^y$ is independently selected from H, halo, hydroxyl, CN, —NR$^{a1}$R$^{a2}$, C$_{1-4}$alkyl, C$_{1-4}$alkoxyl, and C$_{1-4}$haloalkyl. In some embodiments, each R$^y$ is independently selected from H, F, Cl, CN, OH, —NH₂, —N(CH₃)₂, —CH₃, —CH₂CH₃, —CH(CH₃)₂, —C(CH₃)₃, —CH₂CN, —CH₂CH₂CN, —CH₂OH, —CH₂CH₂OH, —OCH₃, —OCH₂CH₃, —OCH(CH₃)₂, —OC(CH₃)₃, —CH₂OCH₃, —CH₂OCH₂CH₃, —CH₂OCH(CH₃)₂, —CHF₂, —CHF₂, —CF₃, —CH₂CH₂F, —CH₂CHF₂, —CH₂CF₃, —OCH₂F, —OCHF₂, —OCF₃, —OCH₂CH₂F, —OCH₂CHF₂, —OCH₂CF₃, —SO₂CH₃, —SO₂CH₂CH₃,

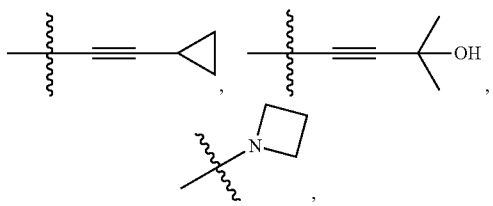

cyclopropyl, cyclobutyl, cyclopentyl, cyclohexyl, phenyl, —O-cyclopropyl, —O—CH$_2$-cyclopropyl, —O—cyclobutyl, —O—CH$_2$cyclobutyl, —O-cyclopentyl, —O—CH$_2$cyclopentyl, —O-cyclohexyl, —O—CH$_2$cyclohexyl, and —O-phenyl. In some embodiments, each R$^y$ is independently selected from H, F, Cl, OH, CN, —NH$_2$, —CH$_3$, —CH$_2$F, —CHF$_2$, —CF$_3$, —OCH$_3$, —CH$_2$OCH$_2$CH$_3$, and —OCF$_3$. In some embodiments, each R$^y$ is independently selected from H, F, —CH$_3$, —CH$_2$F, —CHF$_2$, —CF$_3$, —OCH$_3$, —CH$_2$OCH$_2$CH$_3$, and —OCF$_3$.

In some embodiments of formula (IIe), u is selected from 1, 2, and 3. In some embodiments, u is 3.

In some embodiments of formula (IIg), Y$^3$, Y$^4$, and Y$^5$ is independently selected from CRY, and N; wherein R$^y$ is selected from H, and R$^a$. In some embodiments, Y$^3$ is N; and Y$^4$ and Y$^5$ are CR$^y$. In some embodiments, Y$^5$ is N; and Y$^3$, and Y$^4$ are CR$^y$. In some embodiments, each R$^y$ is independently selected from H, F, C, CN, —NH$_2$, —N(CH$_3$)$_2$, —CH$_3$, —CH$_2$F, —CHF$_2$, —CF$_3$, and —OCH$_3$. In some embodiments, each R$^{x1}$ is independently selected from H, F, C, —NH$_2$, —N(CH$_3$)$_2$, —CH$_3$, —CF$_3$, —OCH$_3$, and —OCF$_3$.

In some embodiments of formula (Ili), r is selected from 1, 2, and 3. In some embodiments, r is 3.

In some embodiments of formula (I) or (II), each R$^7$, R$^8$, R$^9$, R$^{10}$, and R$^{11}$ is independently selected from H, F, C, CN, —NH$_2$, —N(CH$_3$)$_2$, —CH$_3$, —CH$_2$F, —CHF$_2$, —CF$_3$, —OCH$_3$, and —OCF$_3$. In some embodiments, each R$^7$, R$^8$, R$^9$, R$^{10}$, and R$^{11}$ is independently selected from H, F, CN, —N(CH$_3$)$_2$, —CH$_3$, and —CF$_3$. In some embodiments, each R$^7$ to R$^{11}$ is selected from H, F, and —N(CH$_3$)$_2$. In some embodiments, R$^7$ to R$^{11}$ are H. In some embodiments, R$^7$ is selected from H, F, CN, —N(CH$_3$)$_2$, —CH$_3$, and —CF$_3$. In some embodiments, R$^7$ is F. In some embodiments, R$^8$ is selected from H, F, CN, —N(CH$_3$)$_2$, —CH$_3$, and —CF$_3$. In some embodiments, R$^8$ is F. In some embodiments, R$^{10}$ is selected from H, F, CN, —N(CH$_3$)$_2$, —CH$_3$, and —CF$_3$. In some embodiments, R$^{10}$ is F, or —N(CH$_3$)$_2$. In some embodiments, R$^{11}$ is —CH$_3$.

In some embodiments of formula (I), R$^{12}$ is H. In some embodiments, R$^{12}$ is —CH$_3$.

In some embodiments of formula (I), R$^{13}$ is H. In some embodiment, R$^{13}$ is —CH$_3$.

In some embodiments of formula (I), each R$^7$, R$^8$, R$^9$, R$^{10}$, R$^{11}$, R$^{12}$, and R$^{13}$ is H.

In some embodiments of formula (I), (II), (IIa), (IIb), (IIc), (IId), (IIe), (IIf), (IIg), (IIh), or (IIi), R$^{14}$ is selected from C$_{1-6}$alkyl, C$_{3-8}$cycloalkyl, and 4-6 membered heterocyclyl. In some embodiments, each C$_{3-8}$cycloalkyl and 4-6 membered heterocyclyl of R$^{14}$ is optionally substituted with one to three groups independently selected from halo, C$_{1-4}$alkyl, and C$_{1-4}$haloalkyl. In some embodiments, R$^{14}$ is selected from —C$_{1-4}$alkylene-NR$^{a1}$R$^{a2}$, —C$_{1-4}$alkylene-C(O)NR$^{a1}$R$^{a2}$, —C$_{1-4}$alkylene-O—C(O)—C$_{1-4}$alkyl, —C$_{1-4}$alkylene-O—C(O)—O—C$_{1-4}$alkyl, —C$_{1-4}$alkylene-O—C(O)—O—C$_{1-4}$alkylene-NR$^{a1}$R$^{a2}$, and —C$_{1-4}$alkylene-O—C$_{1-4}$alkyl. In some embodiments, when administered to a biological system, provided esters generate active ingredients where R$^{14}$ is hydrogen, as a result of chemical reaction(s), enzyme catalyzed chemical reaction(s), and/or metabolic chemical reaction(s).

In some embodiments of formula (I), (II), (IIa), (IIb), (IIc), (IId), (IIe), (IIf), (IIg), (IIh), or (IIi), R$^{14}$ is selected from H, methyl, ethyl, propyl, butyl, —CH$_2$C(O)N(CH$_3$)$_2$, —(CH$_2$)$_2$N(CH$_2$CH$_3$)$_2$, —CH$_2$—O—C(O)CH$_3$, —(CH$_2$)$_2$—O—C(O)CH$_3$, —CH$_2$—O—C(O)C(CH$_3$)$_3$, —(CH$_2$)$_2$—O—C(O)C(CH$_3$)$_3$, —CH$_2$—O—C(O)—O—CH$_3$, —CH(CH$_3$)—O—C(O)—O—CH$_3$, —CH$_2$—O—C(O)—O—CH$_2$CH$_3$, —CH$_2$—O—C(O)—O—CH(CH$_3$)$_2$, —CH$_2$—O—C(O)—O—C(CH$_3$)$_3$, —(CH$_2$)$_2$C(O)CH$_3$,

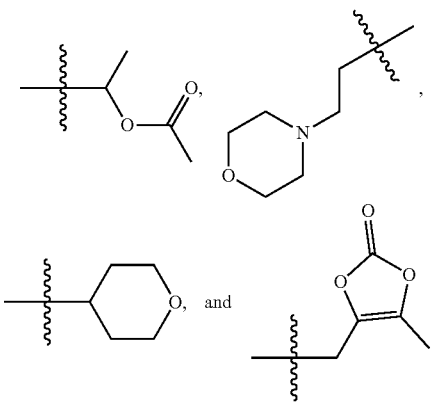

In some embodiments, R$^{14}$ is selected from H, —CH$_2$—O—C(O)C(CH$_3$)$_3$, —CH(CH$_3$)—O—C(O)—O—CH$_3$,

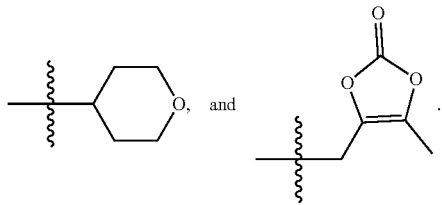

In some embodiments, R$^{14}$ together with the N that attaches to R$^{13}$ forms a 5 membered heterocyclyl. In some embodiments, the 5 membered heterocyclyl is substituted with one to two groups independently selected from C$_{1-6}$alkyl, C$_{1-6}$alkoxyl, C$_{1-6}$haloalkyl, and C$_{6-10}$aryl. In some embodiments, the 5 membered heterocyclyl is substituted with one to two groups independently selected from CH$_3$, CH$_2$CH$_3$, —OCH$_3$, —OCH$_2$CH$_3$, and phenyl. In some embodiments, the 5 membered heterocyclyl is substituted with phenyl, and phenyl is optionally substituted with one to three groups independently selected from halo, C$_{1-6}$alkyl, C$_{1-6}$alkoxyl, and C$_{1-6}$haloalkyl.

In some embodiments, R$^{14}$ is H.

In some embodiments, R$^{14}$ is CH$_3$, or CH$_2$CH$_3$. In some embodiments, R$^{14}$ is CH$_3$. In some embodiments, R$^{14}$ is CH$_2$CH$_3$.

In some embodiments, the compound of the present disclosure is selected from examples 1-354.

In some embodiments, the compound of the present disclosure is selected from examples 355-406. In some embodiments, the compound of the present disclosure is selected from examples 407-496.
In some embodiments, the compound of the present disclosure is selected from:
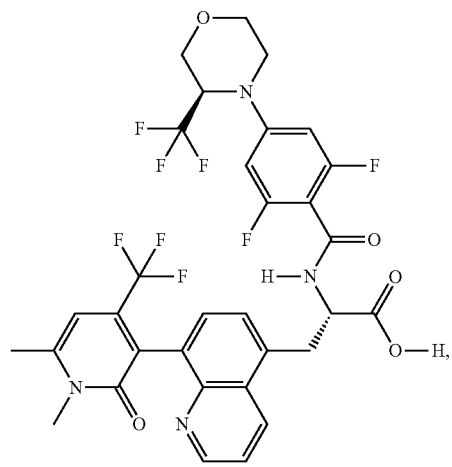
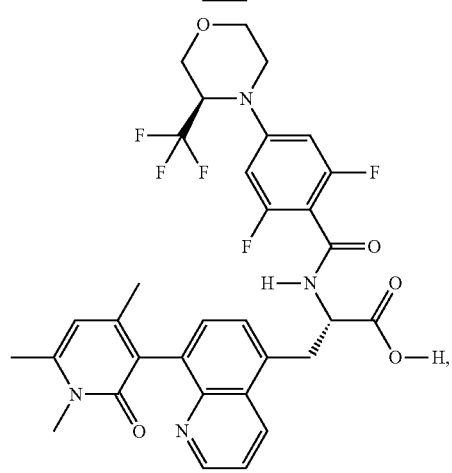
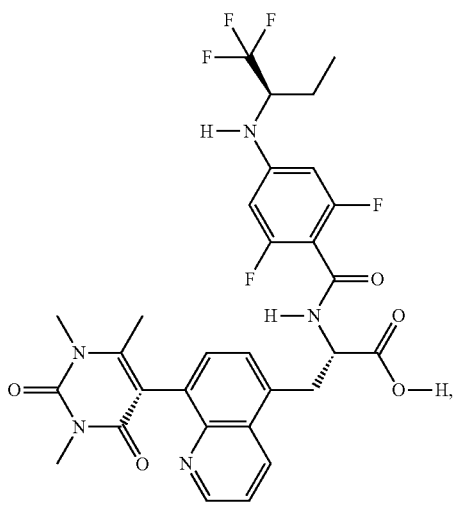
-continued
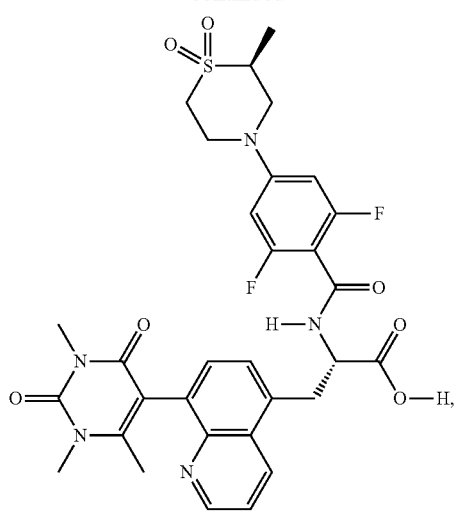
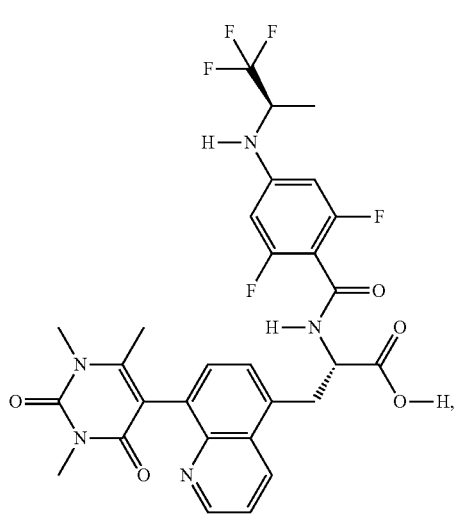
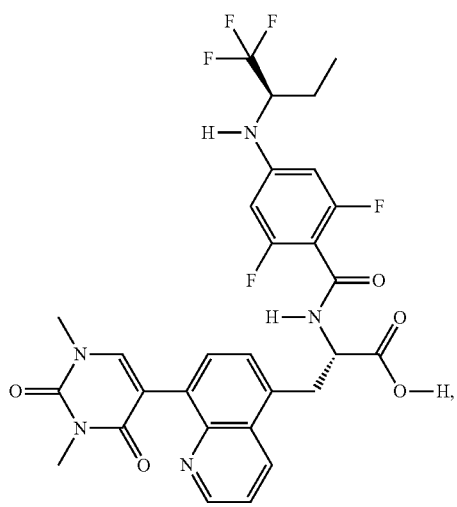

61
-continued
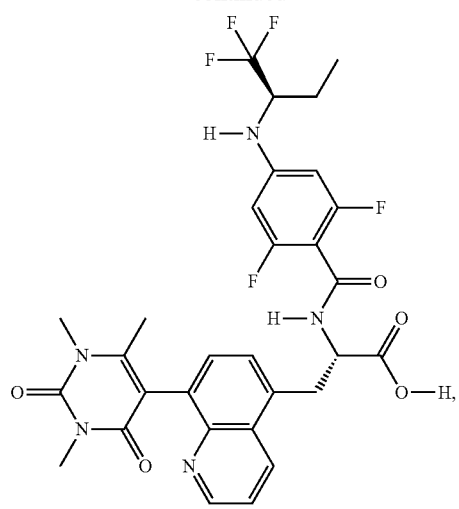
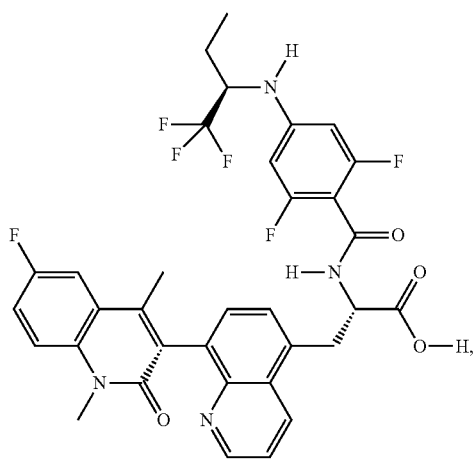
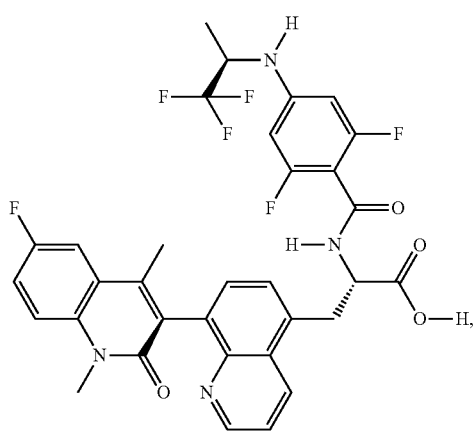
62
-continued
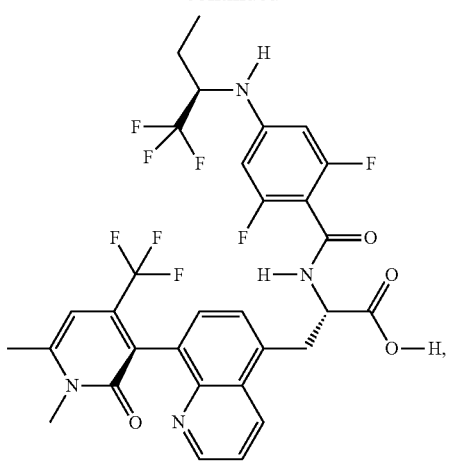
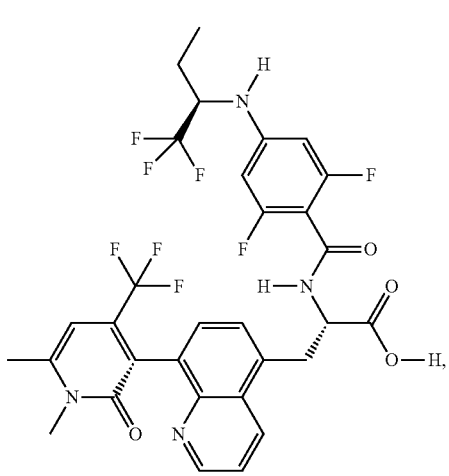
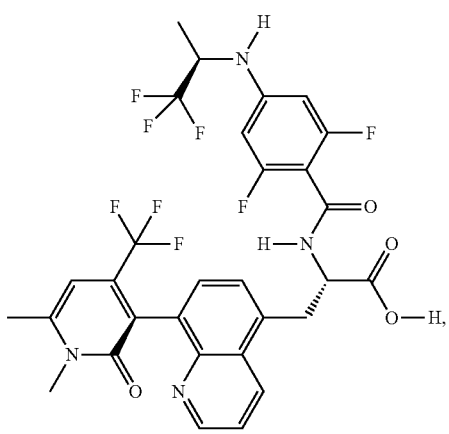

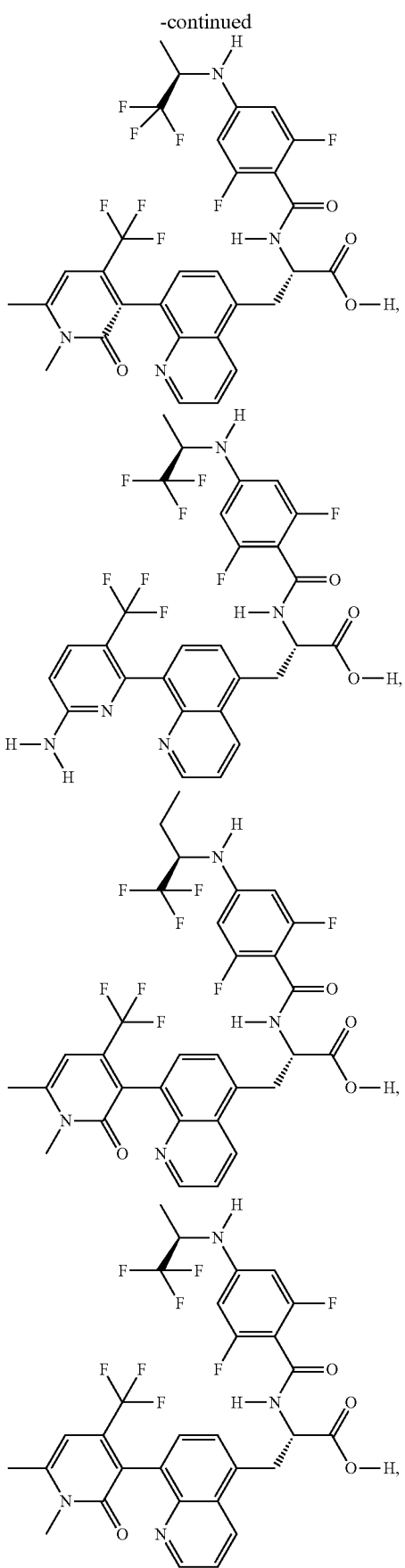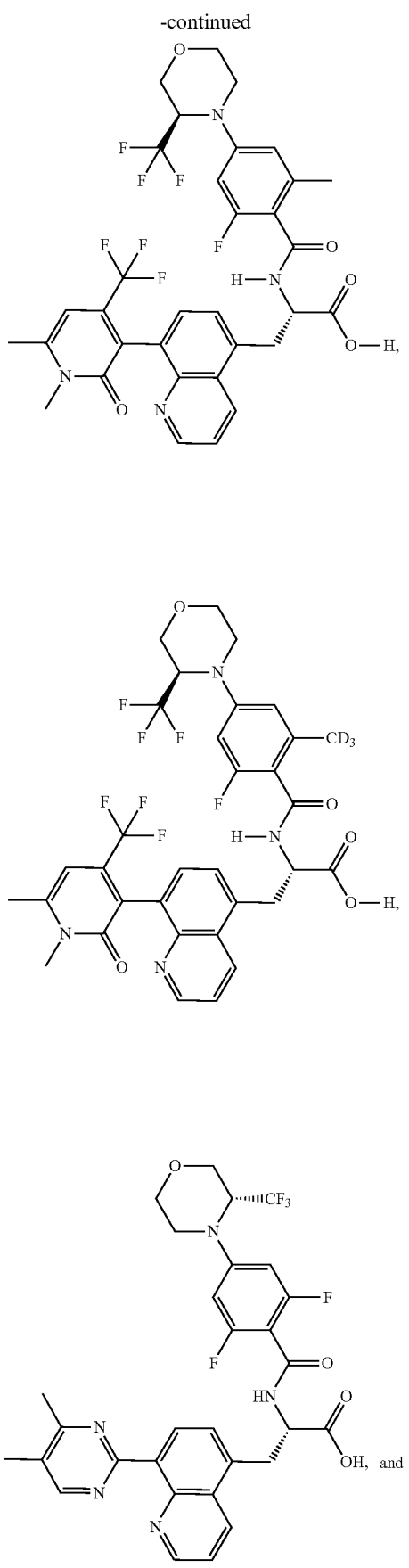

-continued

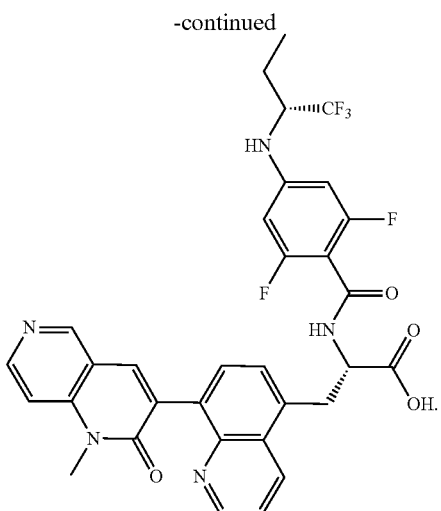

In another aspect, provided are compounds of Formula (J), or pharmaceutically acceptable salts thereof:

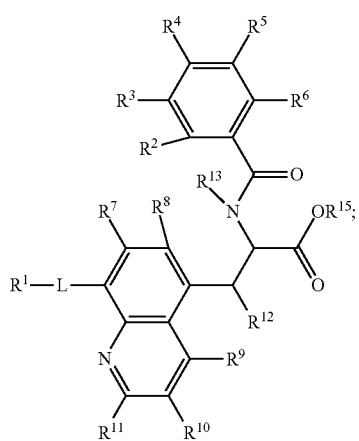

(J)

or a pharmaceutically acceptable salt thereof, wherein:
L is selected from a bond, —O—, —O—C(O)—*, —NH—, —C(O)—N(H)—*, and —N(H)—C(O)—*; wherein * indicates the point of attachment of L to $R^1$;
$R^1$ is selected from $A^1$, $A^2$, $A^3$, and $A^4$;
  $A^1$ is 5-10 membered heteroaryl containing one to five heteroatoms independently selected from S, N, and O; wherein $A^1$ optionally comprises one to three C(O); and wherein $A^1$ is optionally substituted with one to six $R^a$;
  $A^2$ is $C_{6-10}$aryl, optionally substituted with one to six $R^a$;
  $A^3$ is $C_{5-10}$cycloalkyl or 5-14 membered heterocyclyl; wherein $A^3$ is optionally substituted with one to four groups independently selected from oxo and $R^a$; and
  $A^4$ is —$NR^{a1}R^{a2}$
    wherein each $R^a$ is independently selected from halo, cyano, hydroxyl, —$NR^{a1}R^{a2}$, $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —$S(O)_m$—$C_{1-6}$alkyl, $C_{3-8}$cycloalkyl, 3-6 membered heterocyclyl, $C_{6-10}$aryl, 5-6 membered heteroaryl, —O—$C_{3-8}$cycloalkyl, —O-(3-6 membered heterocyclyl), —O—$C_{1-4}$alkylene-$C_{3-8}$cycloalkyl, and —O-phenyl;
    wherein each $C_{3-8}$cycloalkyl, 3-6 membered heterocyclyl, $C_{6-10}$aryl, 5-6 membered heteroaryl, —O—$C_{3-8}$cycloalkyl, —O-(3-6 membered heterocyclyl), —O—$C_{1-4}$alkylene-$C_{3-8}$cycloalkyl, and —O-phenyl of $R^a$ is independently optionally substituted with one to three groups independently selected from halo, cyano, hydroxyl, —$NR^{a1}R^{a2}$, $C_{1-6}$alkyl, $C_{1-6}$haloalkyl, $C_{1-6}$alkoxyl, and $C_{1-6}$haloalkoxyl; and
    wherein each $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, and —$S(O)_m$—$C_{1-6}$alkyl of $R^a$ is optionally substituted with one to three $R^{a3}$, wherein each $R^{a3}$ is independently selected from halo, cyano, hydroxyl, —$NR^{a1}R^{a2}$, $C_{1-6}$alkoxyl, $C_{3-8}$cycloalkyl, and 3-6 membered heterocyclyl;
    wherein each $C_{3-8}$cycloalkyl and 3-6 membered heterocyclyl of $R^{a3}$ is optionally substituted with one to three $R^{a4}$; and each $R^{a4}$ is independently selected from halo, cyano, hydroxyl, —$NR^{a1}R^{a2}$, $C_{1-6}$alkyl, $C_{1-6}$haloalkyl, $C_{1-6}$alkoxyl, $C_{1-6}$haloalkoxyl, $C_{3-8}$cycloalkyl, and 3-6 membered heterocyclyl;
each $R^2$, $R^3$, $R^4$, $R^5$, and $R^6$ is independently selected from H, halo, cyano, hydroxyl, $C_{1-6}$ alkyl, $C_{2-6}$alkenyl, $C_{2-6}$alkynyl, $C_{1-6}$alkoxyl, $C_{1-8}$haloalkyl, $C_{1-8}$haloalkoxyl, —$NR^{b1}R^{b2}$, —$R^{b3}S(O)_mR^{b4}$, —$S(O)_mR^{b4}$, —$NR^{b1}S(O)_nR^{b4}$, —$COOR^{b1}$, —$CONR^{b1}R^{b2}$, —$NR^{b1}COOR^{b2}$, —$NR^{b1}COR^{b4}$, —$R^{b3}NR^{b1}R^{b2}$, —$S(O)_nNR^{b1}R^{b2}$, $C_{3-12}$cycloalkyl, $C_{6-10}$aryl, 5-6 membered heteroaryl, and 3-12 membered heterocyclyl;
  wherein each $C_{1-6}$alkyl, $C_{2-6}$alkenyl, $C_{2-6}$alkynyl, $C_{1-6}$alkoxyl, $C_{1-8}$haloalkyl, and $C_{1-8}$haloalkoxyl of $R^2$, $R^3$, $R^4$, $R^5$, and $R^6$ is optionally substituted with one to two $R^c$; wherein each $R^c$ is independently selected from azido, oxo, cyano, halo, hydroxyl, —$NR^{a1}R^{a2}$, $C_{1-6}$alkoxyl, $C_{3-8}$cycloalkyl, $C_{6-10}$aryl, 5-6 membered heteroaryl, and 4-6 membered heterocyclyl; wherein each $C_{3-8}$cycloalkyl, $C_{6-10}$aryl, 5-6 membered heteroaryl, and 4-6 membered heterocyclyl of $R^c$ is optionally substituted with one to three groups independently selected from halo, cyano, hydroxyl, —$NR^{a1}R^{a2}$, $C_{1-4}$alkyl, $C_{1-6}$haloalkyl, $C_{1-4}$alkoxyl, and $C_{3-6}$cycloalkyl;
  wherein each $C_{6-10}$aryl, and 5-6 membered heteroaryl of $R^2$, $R^3$, $R^4$, $R^5$, and $R^6$ is independently optionally substituted with one to five $R^b$; and
  wherein each $C_{3-12}$cycloalkyl, and 3-12 membered heterocyclyl of $R^2$, $R^3$, $R^4$, $R^5$, and $R^6$ is independently optionally substituted with one to six groups independently selected from =$CR^{b1}R^{b2}$ and $R^b$;
    wherein each $R^b$ is independently selected from azido, cyano, halo, hydroxyl, —$NR^{a1}R^{a2}$, $C_{1-6}$alkyl, $C_{1-8}$haloalkyl, $C_{1-6}$alkoxyl, $C_{3-6}$cycloalkyl, $C_{6-10}$aryl, 5-6 membered heteroaryl, and 4-6 membered heterocyclyl; wherein each $C_{3-6}$cycloalkyl, $C_{6-10}$aryl, 5-6 membered heteroaryl, and 4-6 membered heterocyclyl of $R^b$ is independently optionally substituted with one to three groups independently selected from halo, cyano, hydroxyl, —$NR^{a1}R^{a2}$, $C_{1-4}$alkyl, $C_{1-4}$haloalkyl, and $C_{1-4}$alkoxyl;
    wherein each $R^{b1}$ and $R^{b2}$ is independently selected from H, $C_{1-8}$alkyl, $C_{1-8}$haloalkyl, $C_{3-8}$cycloalkyl, $C_{6-10}$aryl, 5-6 membered heteroaryl, and 3-8 membered heterocyclyl;

wherein each $C_{3-8}$cycloalkyl, $C_{6-10}$aryl, 5-6 membered heteroaryl, and 4-6 membered heterocyclyl of $R^{b1}$ and $R^{b2}$ is independently optionally substituted with one to three groups independently selected from halo, cyano, hydroxyl, —$NR^{a1}R^{a2}$, $C_{1-8}$alkyl, $C_{1-8}$haloalkyl, $C_{1-6}$alkoxyl, $C_{3-6}$cycloalkyl, $C_{6-10}$aryl, 5-6 membered heteroaryl, and 4-6 membered heterocyclyl; and wherein each $C_{1-8}$alkyl and $C_{1-8}$haloalkyl of $R^{b1}$ and $R^{b2}$ is optionally substituted with one to two $R^{b5}$;

wherein $R^{b3}$ is $C_{1-4}$alkylene;

wherein $R^{b4}$ is selected from $C_{1-4}$alkyl, $C_{1-4}$haloalkyl, $C_{3-6}$cycloalkyl, $C_{6-10}$aryl, 5-6 membered heteroaryl, and 4-6 membered heterocyclyl; wherein each $C_{1-4}$alkyl, $C_{1-4}$haloalkyl, $C_{3-8}$cycloalkyl, $C_{6-10}$aryl, 5-6 membered heteroaryl, and the 4-6 membered heterocyclyl of $R^{b4}$ is optionally substituted with one to three $R^{b6}$;

wherein each $R^{b5}$ is independently selected from cyano, hydroxyl, $C_{1-4}$alkoxyl, $C_{3-8}$cycloalkyl, $C_{6-10}$aryl, 5-6 membered heteroaryl, and 4-6 membered heterocyclyl; and each $C_{1-4}$alkoxyl, $C_{3-8}$cycloalkyl, $C_{6-10}$aryl, 5-6 membered heteroaryl, and 4-6 membered heterocyclyl of $R^{b5}$ is optionally substituted with one to three groups independently selected from halo, cyano, hydroxyl, —$NR^{a1}R^{a2}$, $C_{1-4}$alkyl, $C_{1-4}$haloalkyl, $C_{1-4}$alkoxyl, and phenyl; and wherein each $R^{b6}$ is independently selected from halo, cyano, $C_{1-4}$alkyl, $C_{1-4}$haloalkyl, $C_{1-4}$alkoxyl, $C_{3-6}$cycloalkyl, phenyl, 4-6 membered heterocyclyl, and 5-6 membered heteroaryl; wherein each $C_{3-6}$cycloalkyl, 4-6 membered heterocyclyl, and 5-6 membered heteroaryl of $R^{b6}$ is independently optionally substituted with one to three groups independently selected from halo, cyano, —$NR^{a1}R^{a2}$, $C_{1-4}$alkyl, $C_{1-4}$haloalkyl, and $C_{1-4}$alkoxyl; or $R^2$ and $R^3$, $R^3$ and $R^4$, or $R^5$ and $R^6$ together with the atoms to which they are attached form a $C_{6-10}$aryl, 5-6 membered heteroaryl, $C_{3-6}$cycloalkyl, or 5-6 membered heterocyclyl; wherein each $C_{6-10}$aryl, 5-6 membered heteroaryl, $C_{3-6}$cycloalkyl, and 5-6 membered heterocyclyl is independently optionally substituted with one to three groups independently selected from halo, cyano, —$NR^{a1}R^{a2}$, $C_{1-6}$alkyl, $C_{1-6}$alkoxyl, $C_{1-6}$haloalkyl, $C_{3-8}$cycloalkyl, 3-6 membered heterocyclyl, $C_{6-10}$aryl, 5-6 membered heteroaryl, $C_{1-4}$alkylene-$C_{3-8}$cycloalkyl, $C_{1-4}$alkylene-$C_{6-10}$aryl, and $C_{1-4}$alkylene-(5-6 membered heteroaryl);

each $R^7$, $R^8$, $R^9$, $R^{10}$, $R^{11}$, and $R^{12}$ is independently selected from H, halo, hydroxyl, cyano, $C_{1-6}$alkyl, $C_{1-6}$alkoxyl, $C_{1-6}$haloalkyl, $C_{1-6}$haloalkoxyl, and —$NR^{a1}R^{a2}$;

$R^{13}$ is selected from H, $C_{1-4}$alkyl, and $C_{1-4}$haloalkyl;

$R^{15}$ is selected from H, $C_{1-10}$alkyl, $C_{1-10}$haloalkyl, $C_{3-10}$cycloalkyl, 3-14 membered heterocyclyl, $C_{6-10}$aryl, 5-10 membered heteroaryl, —$C_{1-4}$alkylene-$NR^{a1}R^{a2}$, —$C_{1-4}$alkylene-C(O)$NR^{a1}R^{a2}$, and -$L^1$-$R^{16}$;

wherein $L^1$ is selected from —$C_{1-4}$alkylene-, —$C_{1-4}$alkylene-O—, —$C_{1-4}$alkylene-C(O)—, —$C_{1-4}$alkylene-O—C(O)—, —$C_{1-4}$alkylene-O—C(O)—$C_{1-4}$alkylene-, —$C_{1-4}$alkylene-C(O)—O—, —$C_{1-4}$alkylene-C(O)—O—$C_{1-4}$alkylene, —$C_{1-4}$alkylene-O—C(O)—O—, —$C_{1-4}$alkylene-O—C(O)—O—$C_{1-4}$alkylene-, —$C_{1-4}$alkylene-$NR^{a1}$C(O)—O—, and —$C_{1-4}$alkylene-O—C(O)—$NR^{a1}$—; and wherein $R^{16}$ is selected from $C_{1-6}$alkyl, $C_{1-6}$haloalkyl, $C_{3-10}$cycloalkyl, 3-14 membered heterocyclyl, $C_{6-10}$aryl, and 5-10 membered heteroaryl;

wherein each $C_{3-10}$cycloalkyl, 3-14 membered heterocyclyl, $C_{6-10}$aryl, and 5-10 membered heteroaryl of $R^{15}$ and $R^{16}$ is optionally substituted with one to four groups independently selected from halo, hydroxyl, —$COOR^{b7}$, —$NR^{a1}R^{a2}$, —$S(O)_2R^{a5}$, $C_{1-4}$alkyl, $C_{1-4}$alkoxyl, $C_{1-4}$haloalkyl, $C_{1-4}$haloalkoxyl, and —$C_{1-4}$alkylene-$NR^{a1}R^{a2}$;

each $R^{a1}$ and $R^{a2}$ is independently selected from H, $C_{1-6}$alkyl, and $C_{1-6}$haloalkyl;

$R^{a5}$ is $C_{1-6}$alkyl;

$R^{b7}$ is independently selected from H and $C_{1-6}$alkyl;

m is selected from 0, 1, and 2; and n is selected from 1, and 2.

In some embodiments of formula (J), or a pharmaceutically acceptable salt thereof, wherein the compound is of formula (Ja):

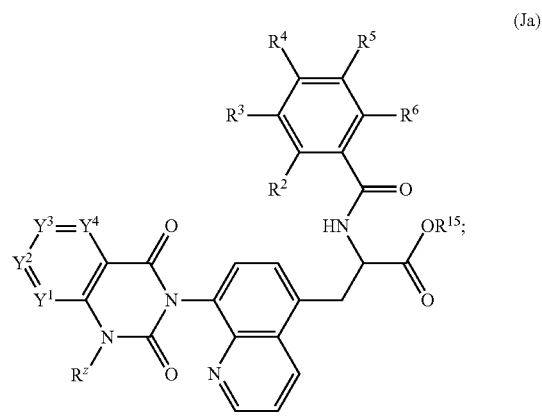

(Ja)

wherein each $Y^1$, $Y^2$, $Y^3$, and $Y^4$ is independently selected from CRY, and N; wherein each $R^y$ is independently selected from H and $R^a$; and wherein $R^z$ is selected from H, $C_{1-6}$alkyl, $C_{2-6}$alkenyl, $C_{2-6}$alkynyl, $C_{1-6}$haloalkyl, $C_{3-8}$cycloalkyl, and 3-6 membered heterocyclyl.

In some embodiments of formula (J) or (Ja), or a pharmaceutically acceptable salt thereof, wherein the compound is of formula (Jb):

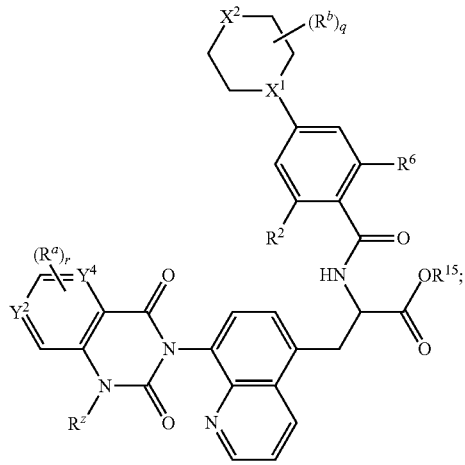

(Jb)

wherein each $Y^2$ and $Y^4$ is independently selected from $CR^y$, and N. Each $R^y$ is independently selected from H and $R^a$. $R^z$ is selected from H, $C_{1-6}$alkyl, $C_{2-6}$alkenyl, $C_{2-6}$alkynyl, $C_{1-6}$haloalkyl, $C_{3-8}$cycloalkyl, and 3-6 membered heterocyclyl. $X^1$ is selected from $CR^{x1}$, and N. $X^2$ is selected from $CR^{x1}R^{x2}$, $NR^{x2}$, O, and $S(O)_2$. $R^{x1}$ is selected from H, and $R^b$; and $R^{x2}$ is selected from H, $C_{1-4}$alkyl, and $C_{1-4}$haloalkyl. q is selected from 0, 1, 2, and 3; and r is selected from 0, 1, and 2.

In some embodiments of formula (J) or (Ja), or a pharmaceutically acceptable salt thereof, wherein the compound is of formula (Jc):

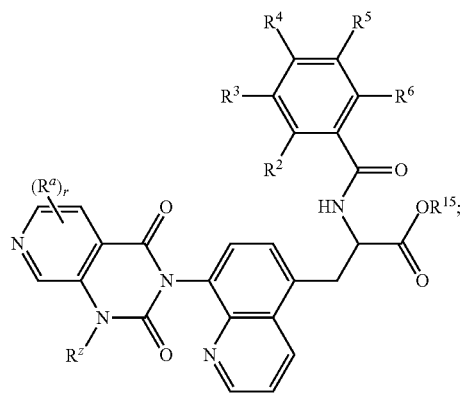

(Jc)

wherein $R^z$ is selected from H, $C_{1-6}$alkyl, $C_{2-6}$alkenyl, $C_{2-6}$alkynyl, $C_{1-6}$haloalkyl, $C_{3-8}$cycloalkyl, and 3-6 membered heterocyclyl; and wherein r is selected from 0, 1, 2, and 3.

In some embodiments of formula (J), (Ja), (Jb), or (Jc), or a pharmaceutically acceptable salt thereof, wherein the compound is of formula (Jd):

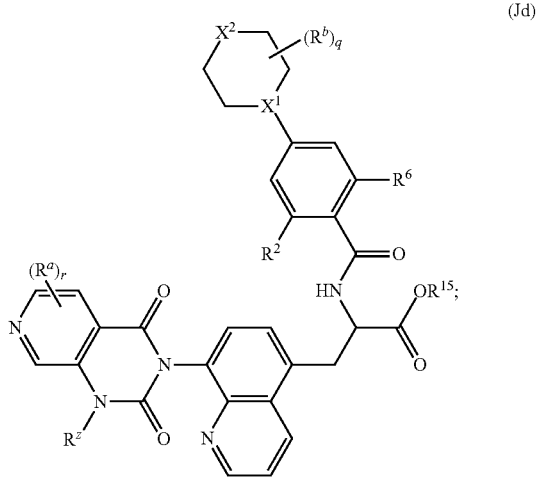

(Jd)

wherein $R^z$ is selected from H, —$CH_3$, —$CD_3$-$CH_2$F, —$CHF_2$, —$CF_3$, and —$CH_2CH_3$; $X^1$ is selected from $CR^{x1}$, and N. $X^2$ is selected from $CR^{x1}R^{x2}$, $NR^{x2}$, O, and $S(O)_2$. $R^{x1}$ is selected from H, and $R^b$; and $R^{x2}$ is selected from H, $C_{1-4}$alkyl, and $C_{1-4}$haloalkyl. q is selected from 0, 1, 2, and 3; and r is selected from 0, 1, 2, and 3.

In some embodiments of formula (J), (Ja), (Jb), (Jc), or (Jd), or a pharmaceutically acceptable salt thereof, wherein the compound is of formula (Je):

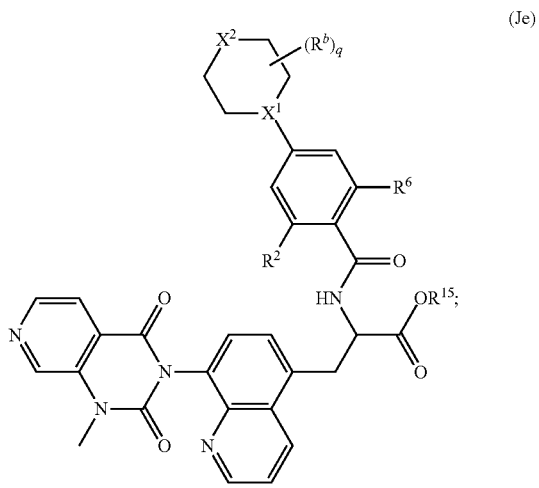

(Je)

wherein $X^1$ is selected from $CR^{x1}$, and N. $X^2$ is selected from $CR^{x1}R^{x2}$, $NR^{x2}$, O, and $S(O)_2$. $R^{x1}$ is selected from H, and $R^b$; and $R^{x2}$ is selected from H, $C_{1-4}$alkyl, and $C_{1-4}$haloalkyl. q is selected from 0, 1, 2, and 3.

In some embodiments of formula (J), or (Ja), or a pharmaceutically acceptable salt thereof, wherein the compound is of formula (Jf):

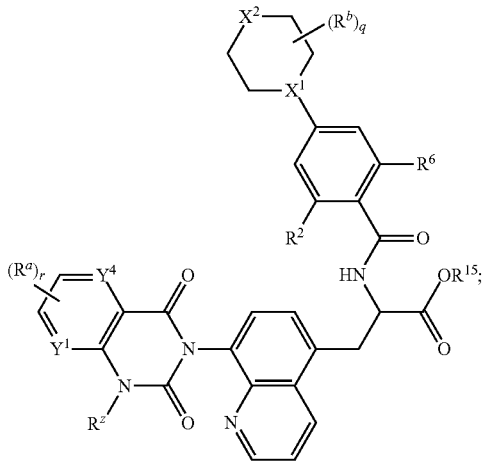

wherein each $Y^1$ and $Y^4$ is independently selected from CRY, and N. Each $R^y$ is independently selected from H and $R^a$. $R^z$ is selected from H, —$CH_3$, —$CD_3$-$CH_2F$, —$CHF_2$, —$CF_3$, and —$CH_2CH_3$. $X^1$ is selected from $CR^{x1}$, and N. $X^2$ is selected from $CR^{x1}R^{x2}$, $NR^{x2}$, O, and $S(O)_2$. $R^{x1}$ is selected from H, and $R^b$; and $R^{x2}$ is selected from H, $C_{1-4}$alkyl, and $C_{1-4}$haloalkyl. q is selected from 0, 1, 2, and 3; and r is selected from 0, 1, and 2.

In some embodiments of formula (J), or a pharmaceutically acceptable salt thereof, wherein the compound is of formula (Jg):

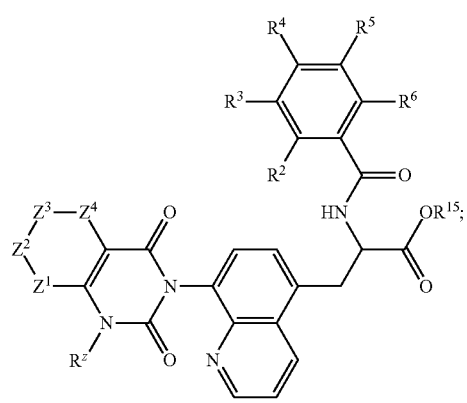

wherein each $Z^1$, $Z^2$, $Z^3$, and $Z^4$ is independently selected from $CR^{y1}R^{y2}$, $NR^{z1}$, and O; wherein each $R^{y1}$ and $R^{y2}$ is independently selected from H and $R^a$; and wherein each $R^z$ and $R^{z1}$ is independently selected from H, $C_{1-6}$alkyl, $C_{2-6}$alkenyl, $C_{2-6}$alkynyl, $C_{1-6}$haloalkyl, $C_{3-8}$cycloalkyl, and 3-6 membered heterocyclyl.

In some embodiments of formula (I), or (J), or a pharmaceutically acceptable salt thereof, $R^1$ is selected from

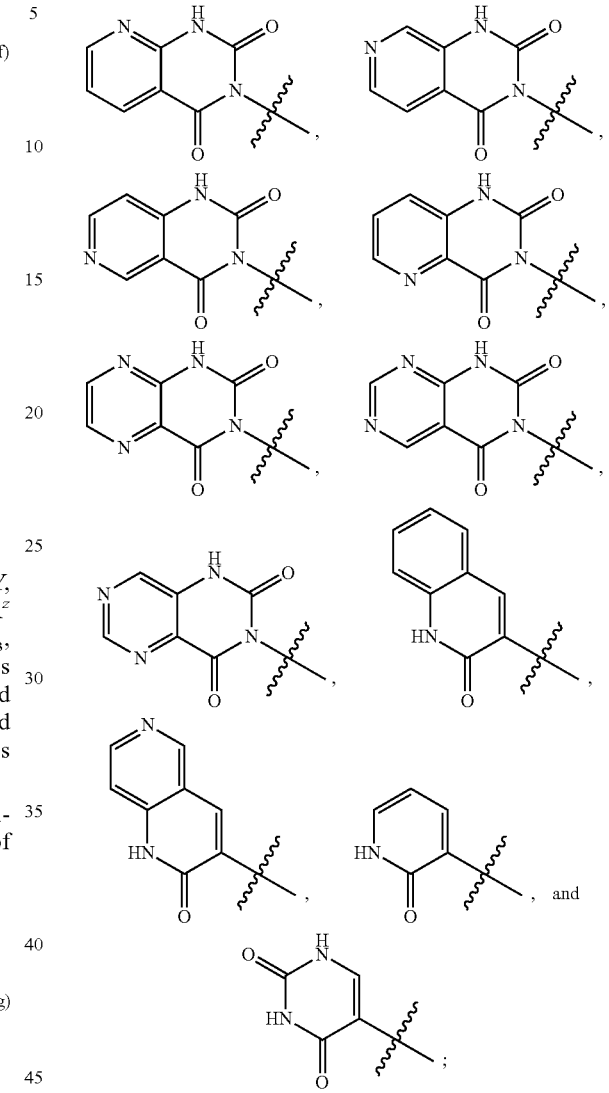

wherein each $R^1$ is substituted with one to four $R^a$. In some embodiments, $R^a$ is $C_{1-4}$alkyl. In some embodiments, $R^a$ is —$CH_3$. In some embodiments, $R^1$ is selected from

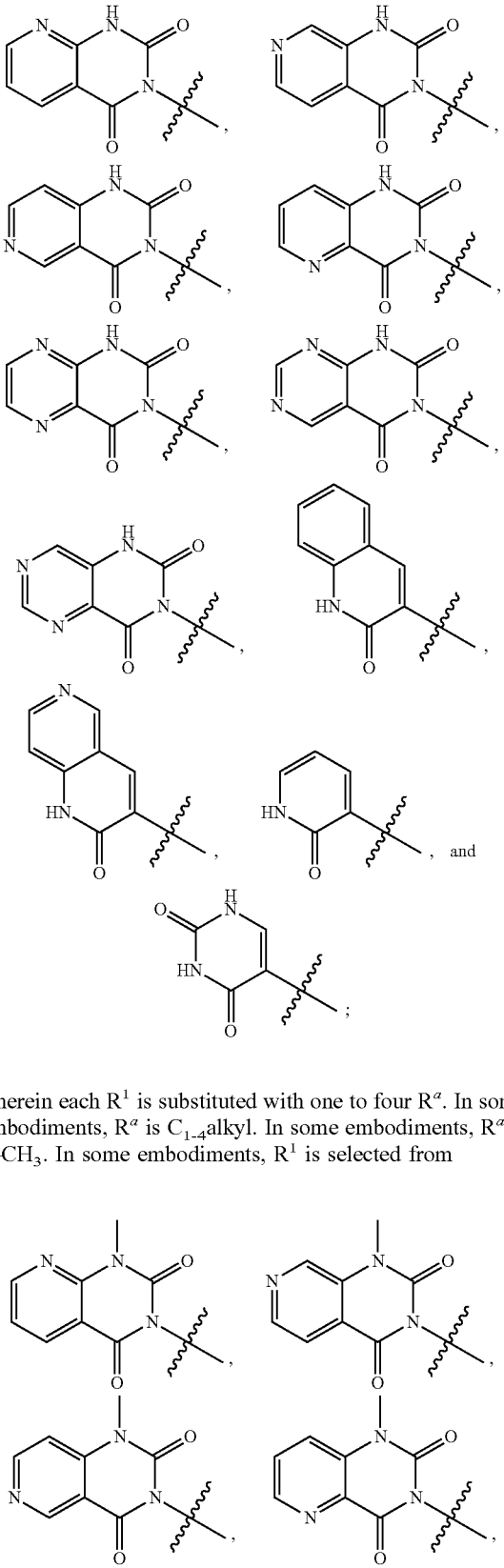

-continued

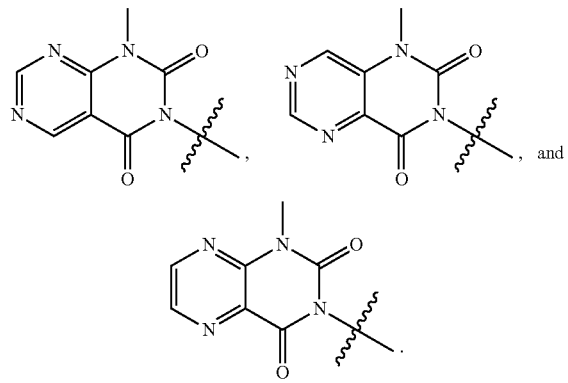

In some embodiments of formula (I) or (J), or a pharmaceutically acceptable salt thereof, R¹ is selected from

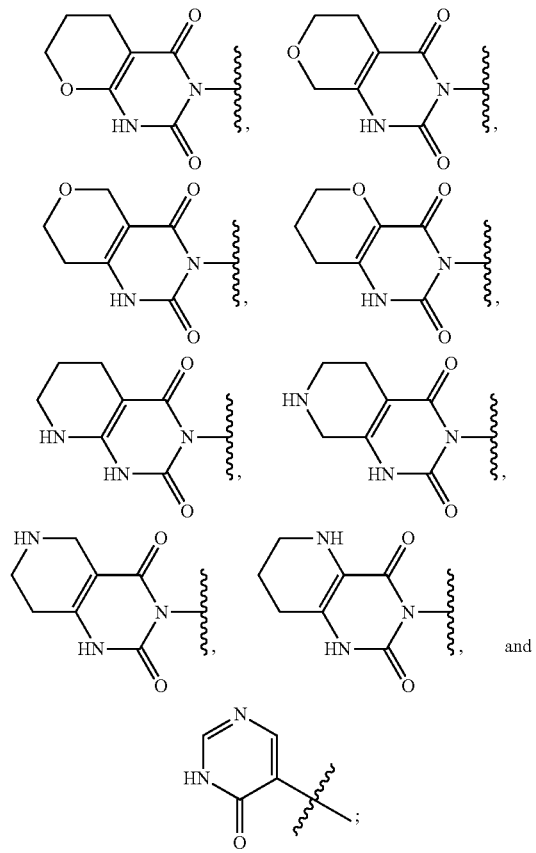

In some embodiments of formula (I), or (J), R¹ is selected from:

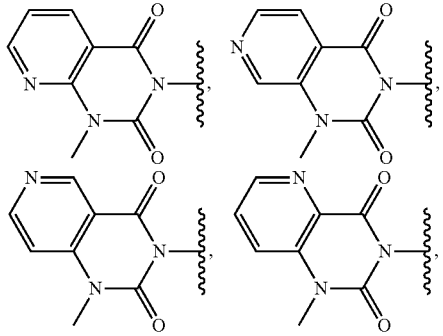

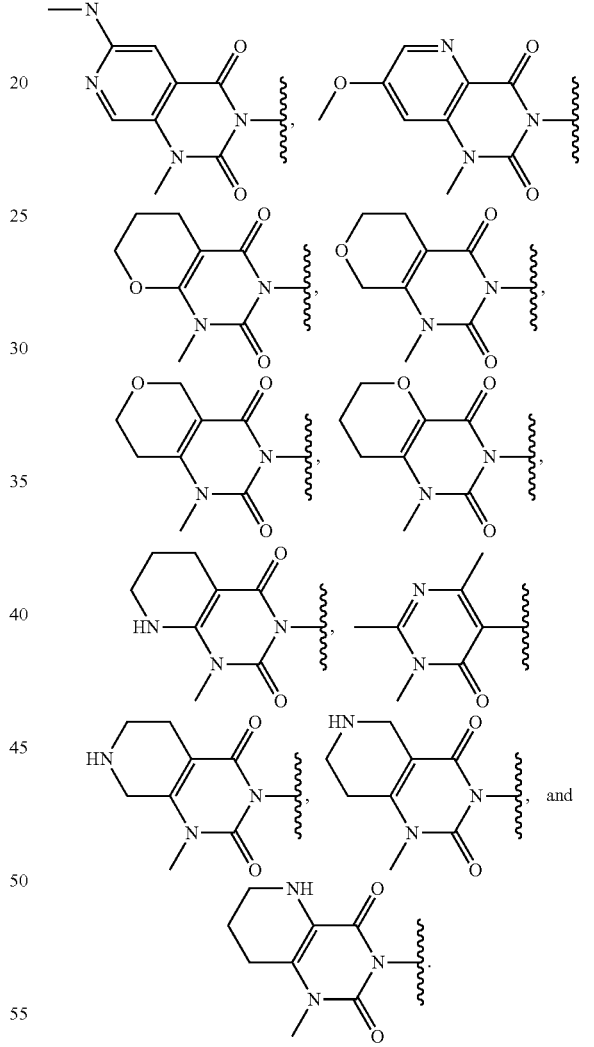

In some embodiments, R¹ is

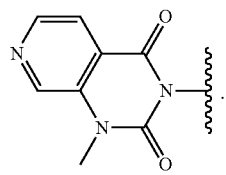

each R¹ is optionally substituted with one to four $R^a$. In some embodiments, each $R^a$ is independently selected from halo, CN, —OH, $NR^{a1}R^{a2}$, $C_{1-4}$alkyl, $C_{1-4}$alkoxyl, $C_{1-4}$haloalkyl, $C_{1-4}$haloalkoxyl, $C_{3-6}$cycloalkyl, —O—$C_{3-6}$cycloalkyl, and phenyl. In some embodiments, each $R^a$ is independently selected from F, Cl, OH, CN, —NH₂, —NH(CH₃), —N(CH₃)₂, —CH₃, —CH₂F, —CHF₂, —CF₃, —OCH₃, and —OCF₃. In some embodiments, each $R^a$ is independently selected from —N(CH₃)₂, —CH₃, —OCH₃, and —CF₃.

In some embodiments of formula (I), or (J), or a pharmaceutically acceptable salt thereof, $R^1$ is

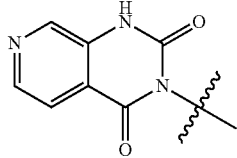 [SMILES: *n1c(=O)[nH]c2cnccc2c1=O]

substituted with one to two $R^a$. Each $R^a$ is independently selected from $C_{1-4}$alkyl, $C_{1-4}$haloalkyl, $C_{1-4}$alkoxyl, and $C_{3-6}$cycloalkyl. In some embodiments, $R^1$ is

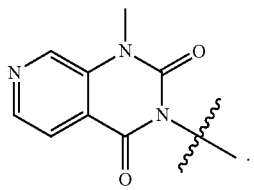 [SMILES: *n1c(=O)c2ccncc2n(C)c1=O]

In some embodiments of formula (J), (Ja), or (Jc), or a pharmaceutically acceptable salt thereof, $R^3$ and $R^5$ are H.

In some embodiments of formula (J), (Ja), (Jb), (Jc), (Jd), (Je), or (Jf), or a pharmaceutically acceptable salt thereof, each $R^2$ and $R^6$ is independently selected from H, halo, $C_{1-4}$alkyl, $C_{1-4}$alkoxyl, $C_{1-4}$haloalkyl, $C_{1-4}$haloalkoxyl, $C_{3-6}$cycloalkyl, and 3-7 membered heterocyclyl. In some embodiments, each $R^2$ and $R^6$ is independently selected from F, Cl, —$CH_3$, —$CD_3$, —$CH_2CH_3$, —$OCH_3$, —$OCH_2CH_3$, —$CH_2F$, —$CHF_2$, —$CF_3$, —$CH_2CH_2F$, —$CH_2CHF_2$, —$CH_2CF_3$, —$NH_2$, and —$N(CH_3)_2$. In some embodiments, each $R^2$ and $R^6$ is independently selected from F, Cl, and —$CH_3$. In some embodiments, $R^2$ is F, and $R^6$ is —$CH_3$. In some embodiments, each $R^2$ and $R^6$ is independently selected from F, and Cl. In some embodiments, $R^2$ and $R^6$ are F.

In some embodiments of formula (J), (Ja), (Jb), (Jc), (Jd), (Je), or (Jf), or a pharmaceutically acceptable salt thereof, $R^4$ is

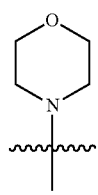

substituted with one to three $R^b$. In some embodiments, each $R^b$ is independently selected from $C_{1-4}$alkyl, $C_{1-4}$alkoxyl, $C_{1-4}$haloalkyl, and $C_{1-4}$haloalkoxyl. In some embodiments, $R^b$ is independently selected from —$CH_3$, —$CF_3$, and —$OCF_3$. In some embodiments, $R^b$ is —$CF_3$. In some embodiments, $R^4$ is

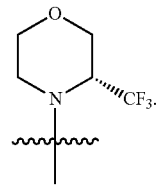

In some embodiments of formula (Ja) or (Jb), $Y^2$ is N. In some embodiments of formula (Ja) or (Jb), $Y^2$ is N, and $Y^4$ is CH. In some embodiments of formula (Ja), $Y^1$, $Y^3$, and $Y^4$ are $CR^y$. In some embodiments of (Ja), at least one of $Y^1$, $Y^2$, $Y^3$, and $Y^4$ is N. In some embodiments, $Y^4$ is CH. In some embodiments of (Ja), $Y^1$, $Y^2$, $Y^3$, and $Y^4$ are $CR^y$.

In some embodiments of formula (Jf), $Y^1$ is N. In some embodiments, $Y^4$ is N. In some embodiments, both $Y^1$ and $Y^4$ are N.

In some embodiments of formula (Ja), (Jb), (Jc), (Jd), or (Jf), or a pharmaceutically acceptable salt thereof, $R^z$ is —$CH_3$.

In some embodiments of formula (Jb), (Jd), (Je), or (Jf), or a pharmaceutically acceptable salt thereof, $X^1$ is N.

In some embodiments of formula (Jb), (Jd), (Je), or (Jf), or a pharmaceutically acceptable salt thereof, $X^2$ is O. In some embodiments, $X^1$ is N, and $X^2$ is O.

In some embodiments of formula (Jb), (Jd), (Je), or (Jf), or a pharmaceutically acceptable salt thereof, q is 1.

In some embodiments of formula (Jb), (Jd), (Je), or (Jf), each $R^b$ is independently selected from $C_{1-4}$alkyl, $C_{1-4}$alkoxyl, $C_{1-4}$haloalkyl, and $C_{1-4}$haloalkoxyl. In some embodiments, $R^b$ is $C_{1-4}$haloalkyl. In some embodiments, $R^b$ is independently selected from —$CH_2F$, —$CHF_2$, and —$CF_3$. In some embodiments, $R^b$ is $CF_3$.

In some embodiments of formula (J), (Ja), (Jb), (Jc), (Jd), (Je), or (Jf), or a pharmaceutically acceptable salt thereof, $R^{15}$ is selected from H, $C_{1-6}$alkyl, $C_{1-6}$haloalkyl, $C_{3-8}$cycloalkyl, 4-10 membered heterocyclyl, and $C_{6-10}$aryl. In some embodiments, $R^{15}$ is selected from H, $C_{1-6}$alkyl, and phenyl; and phenyl is optionally substituted with one to three groups independently selected from halo, $C_{1-4}$alkyl, $C_{1-4}$alkoxyl, $C_{1-4}$haloalkyl, and $C_{1-4}$haloalkoxyl. In some embodiments, $R^{15}$ is selected from H, methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl, and phenyl. In some embodiments, $R^{15}$ is selected from H, methyl, ethyl, and phenyl. In some embodiments, $R^{15}$ is H. In some embodiments, $R^{15}$ is methyl. In some embodiments, $R^{15}$ is ethyl. In some embodiments, $R^{15}$ is phenyl. In some embodiments, $R^{15}$ is phenyl substituted with one group selected from F, —$CH_3$, —$CF_3$, —$OCF_3$, and —$(CH_2)_2N(CH_2CH_3)_2$. In some embodiments, $R^{15}$ is —$CH_2CH_2N(CH_2CH_3)_2$.

In some embodiments of formula (J), (Ja), (Jb), (Jc), (Jd), (Je), or (Jf), or a pharmaceutically acceptable salt thereof, $R^{15}$ is -$L^1$-$R^{16}$. In some embodiments, $L^1$ is selected from —$CH_2$—, —$CH_2CH_2$—, —$CH(CH_3)$—, —$CH_2$—O—C(O)—$C_{1-4}$alkyl, and —$CH_2$—O—C(O)—O—$C_{1-4}$alkyl. In some embodiments, $R^{16}$ is selected from —$CH_2CH_3$, —$CH(CH_3)_2$, —$C(CH_3)_3$, —$CH_2CH_2CH_3$, phenyl, pyridinyl, imidazolyl, tetrahydrofuranyl, morpholinyl, and tetrahydropyranyl. Each phenyl, pyridinyl, imidazolyl, tetrahydrofuranyl, morpholinyl, and tetrahydropyranyl of $R^{16}$ is optionally substituted with one to two groups independently selected from F, —$CH_3$, —$CH_2CH_3$, hydroxyl, and —COOH.

In some embodiments of formula (J), (Ja), (Jb), (Jc), (Jd), (Je), or (Jf), or a pharmaceutically acceptable salt thereof, $R^{15}$ is selected from H, —CH$_3$, —CH$_2$CH$_3$,
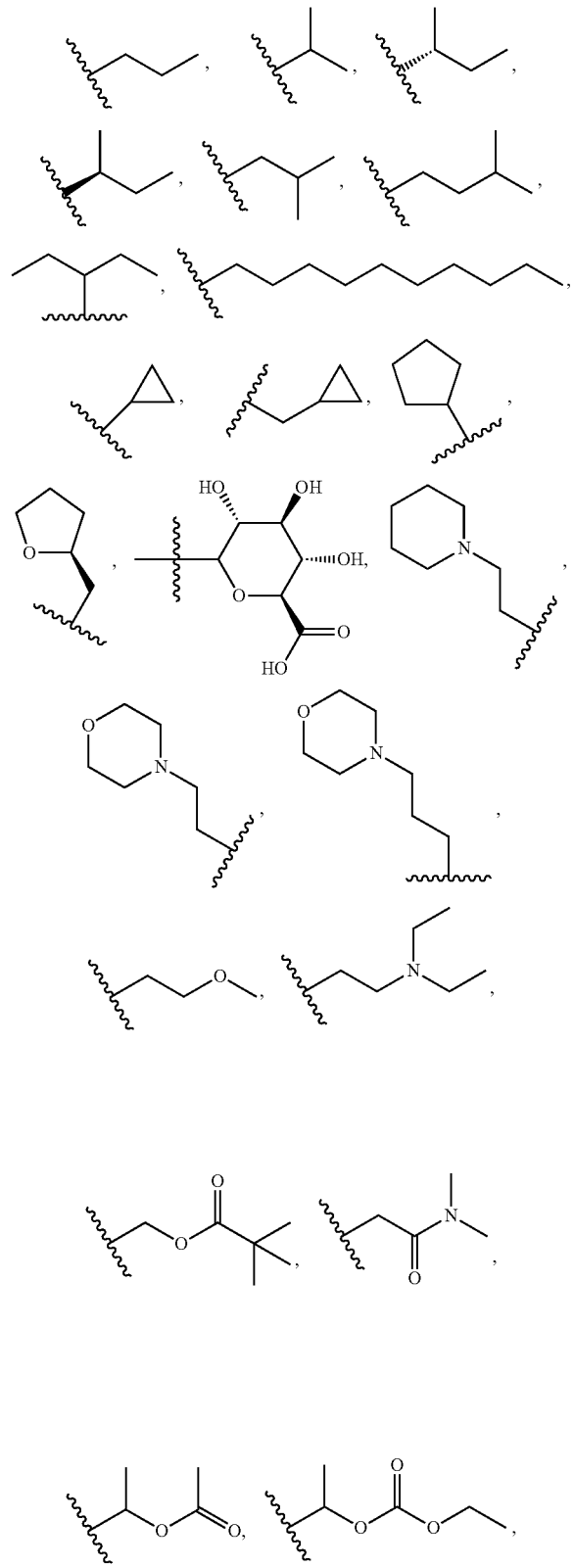
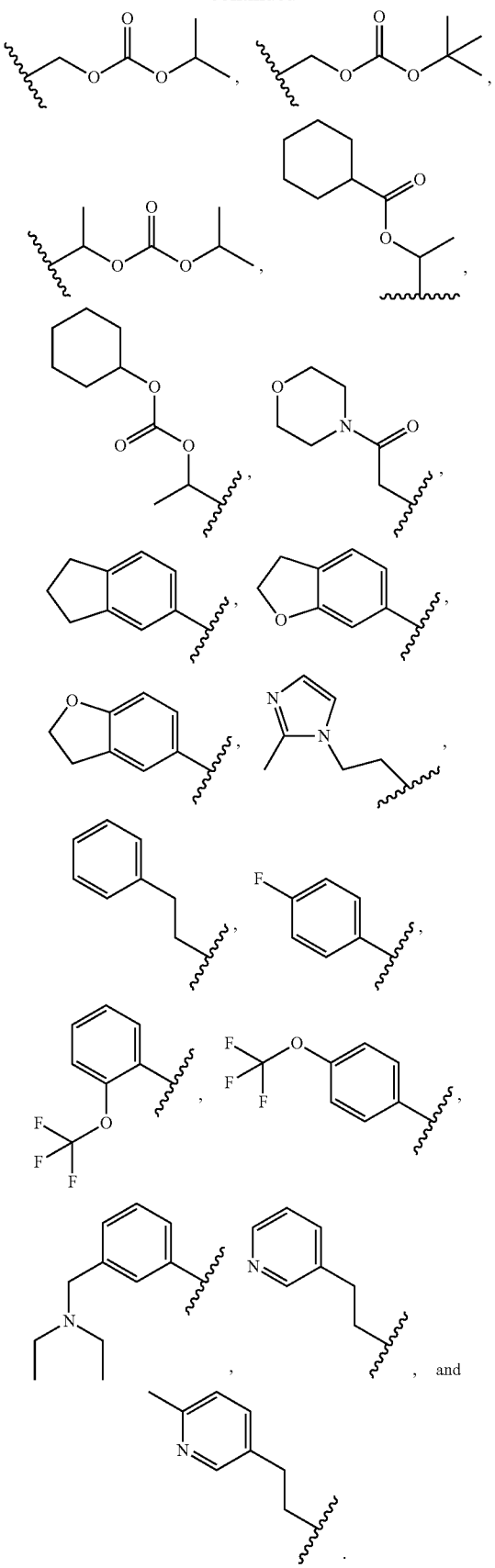

In some embodiments of formula (J), (Ja), (Jb), (Jc), (Jd), (Je), or (Jf), or a pharmaceutically acceptable salt thereof, $R^{15}$ is selected from H, —$CH_3$, and —$CH_2CH_3$. In some embodiments, $R^{15}$ is H. In some embodiments, $R^{15}$ is —$CH_2CH_3$.

In some embodiments of formula (Jg), or a pharmaceutically acceptable salt thereof, $Z^1$ is O. In some embodiments, $Z^2$ is O. In some embodiments, $Z^3$ is O. In some embodiments, $Z^4$ is O. In some embodiments, $Z^1$ is $NR^{z1}$. In some embodiments, $Z^2$ is $NR^{z1}$. In some embodiments, $Z^3$ is $NR^{z1}$. In some embodiments, $Z^4$ is $NR^{z1}$. In some embodiments, $R^{z1}$ is selected from H, —$CH_3$, and —$CH_2CH_3$. In some embodiments, $R^{z1}$ is H.

In some embodiments of formula (Jg), or a pharmaceutically acceptable salt thereof, $R^z$ is —$CH_3$.

In some embodiments of formula (Jg), or a pharmaceutically acceptable salt thereof, $R^3$ and $R^5$ are H.

In some embodiments of formula (Jg), or a pharmaceutically acceptable salt thereof, each $R^2$ and $R^6$ is independently selected from H, halo, $C_{1-4}$alkyl, $C_{1-4}$alkoxyl, $C_{1-4}$haloalkyl, $C_{1-4}$haloalkoxyl, $C_{3-6}$cycloalkyl, and 3-7 membered heterocyclyl. In some embodiments, each $R^2$ and $R^6$ is independently selected from F, Cl, —$CH_3$, —$CD_3$, —$CH_2CH_3$, —$OCH_3$, —$OCH_2CH_3$, —$CH_2F$, —$CHF_2$, —$CF_3$, —$CH_2CH_2F$, —$CH_2CHF_2$, —$CH_2CF_3$, —$NH_2$, and —$N(CH_3)_2$. In some embodiments, each $R^2$ and $R^6$ is independently selected from F, Cl, and —$CH_3$. In some embodiments, $R^2$ is F, and $R^6$ is —$CH_3$. In some embodiments, each $R^2$ and $R^6$ is independently selected from F, and Cl. In some embodiments, $R^2$ and $R^6$ are F.

In some embodiments of formula (Jg), or a pharmaceutically acceptable salt thereof, $R^4$ is

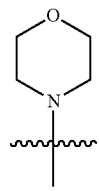

substituted with one to three $R^b$. In some embodiments, each $R^b$ is independently selected from $C_{1-4}$alkyl, $C_{1-4}$alkoxyl, $C_{1-4}$haloalkyl, and $C_{1-4}$haloalkoxyl. In some embodiments, $R^b$ is independently selected from —$CH_3$, —$CF_3$, and —$OCF_3$. In some embodiments, $R^b$ is —$CF_3$. In some embodiments, $R^4$ is

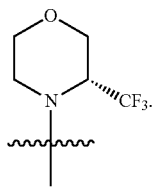 [SMILES: *N1CCOC[C@@H]1C(F)(F)F]

In some embodiments of formula (Jg), or a pharmaceutically acceptable salt thereof, $R^{15}$ is selected from H, —$CH_3$, —$CH_2CH_3$, and —$CH_2CH_2CH_3$. In some embodiments, $R^{15}$ is H. In some embodiments, $R^{15}$ is —$CH_3$. In some embodiments, $R^{15}$ is —$CH_2CH_3$. In some embodiments, $R^{15}$ is —$CH_2CH_2CH_3$.

In some embodiments, the compound of the present disclosure is selected from:

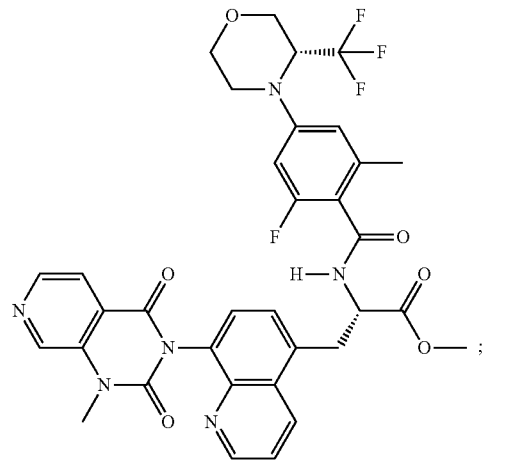

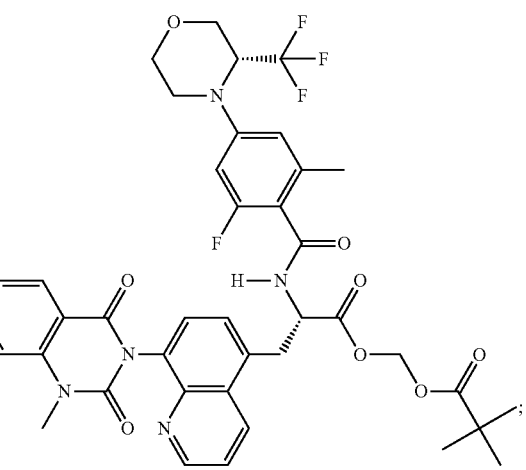

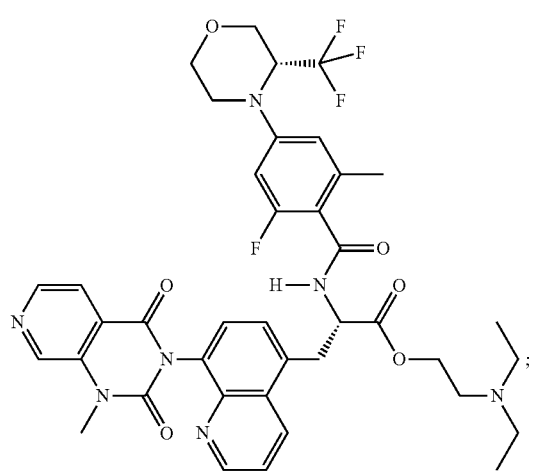

81
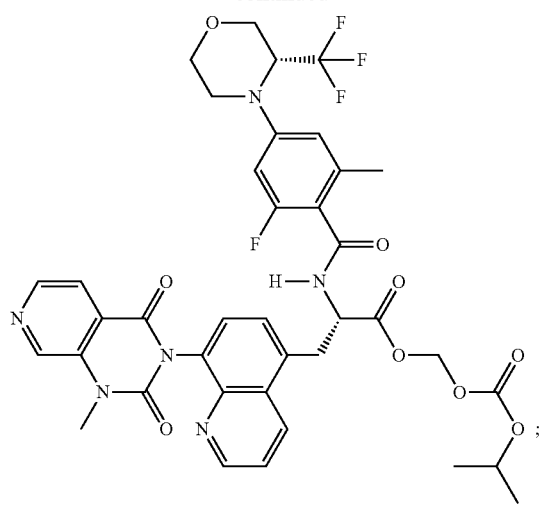
82
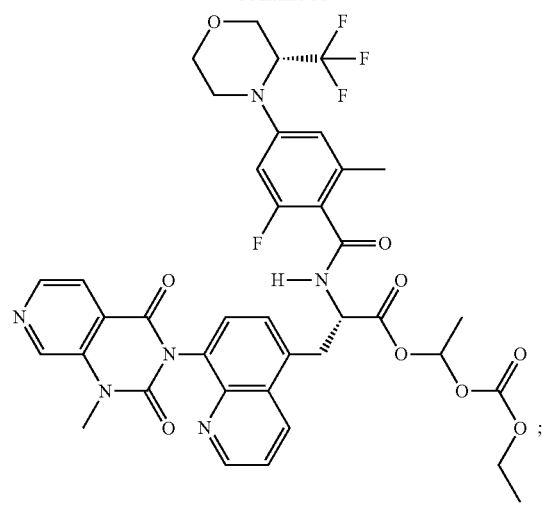
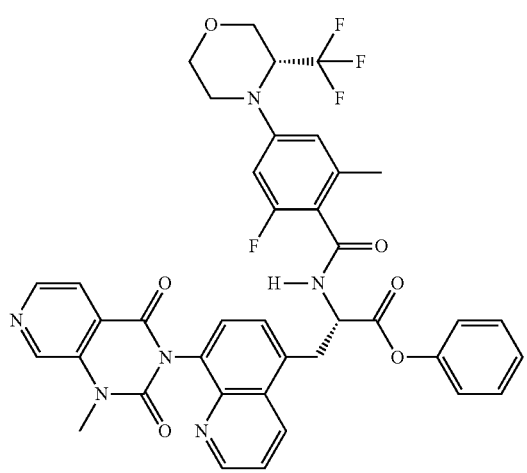
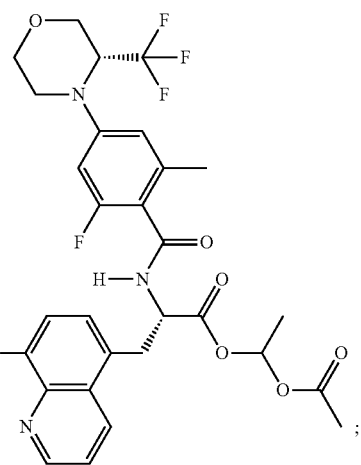
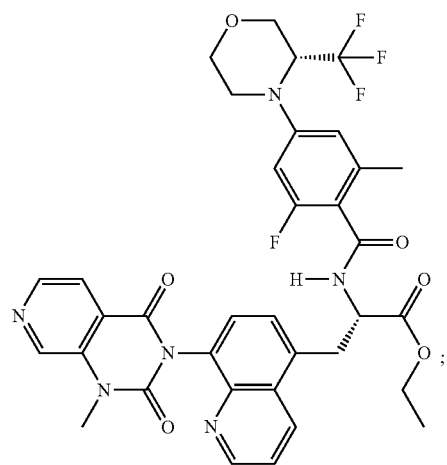
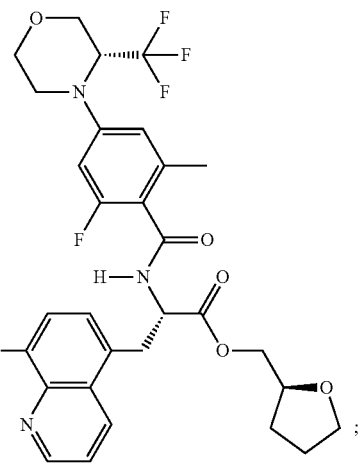

83
-continued
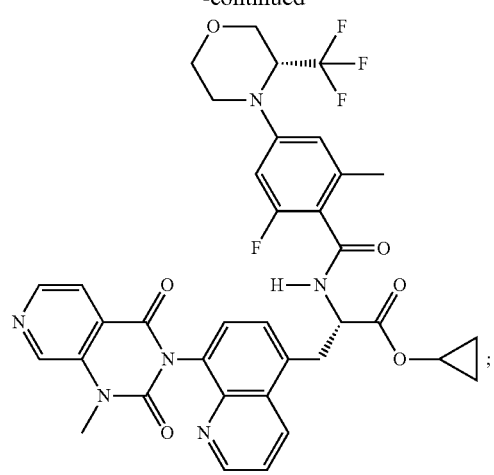
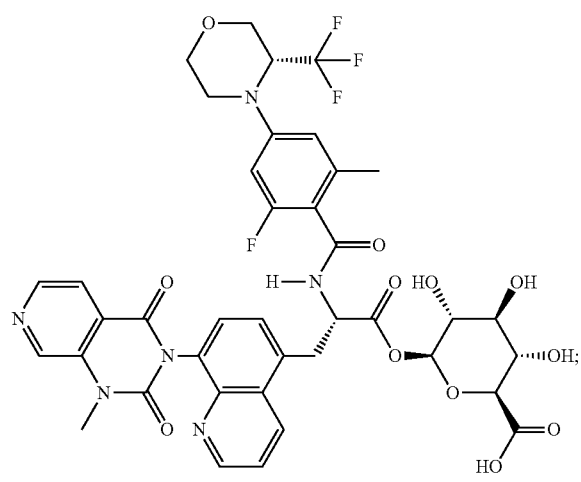
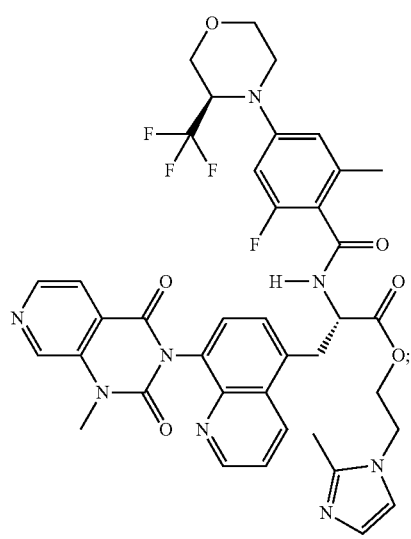
84
-continued
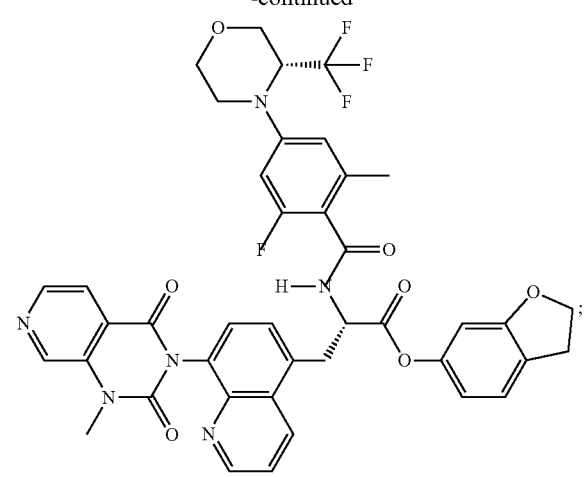
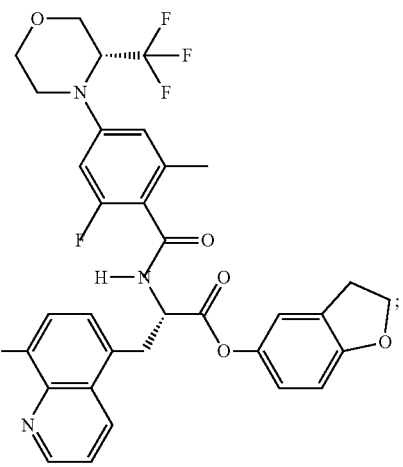

85
-continued
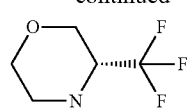
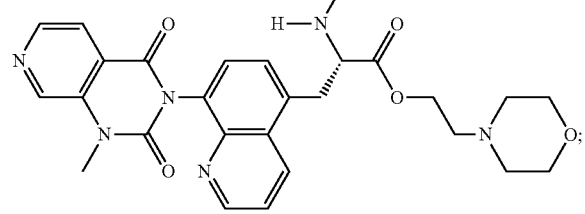
86
-continued
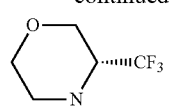
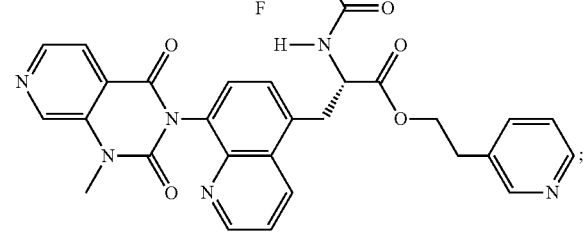
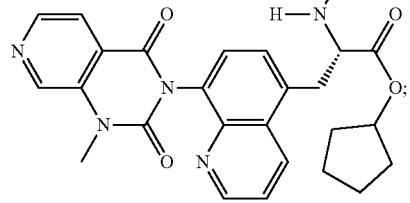
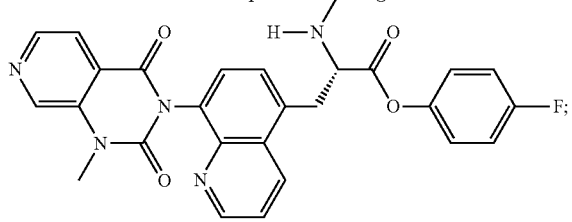
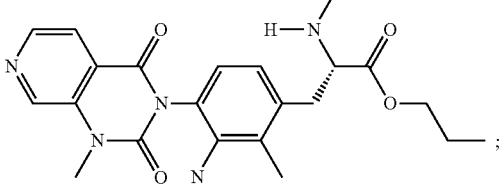

87
-continued
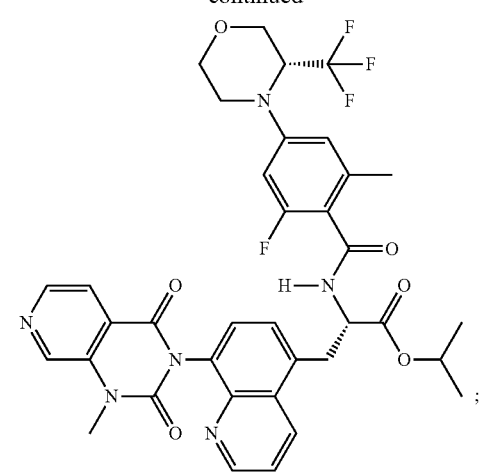
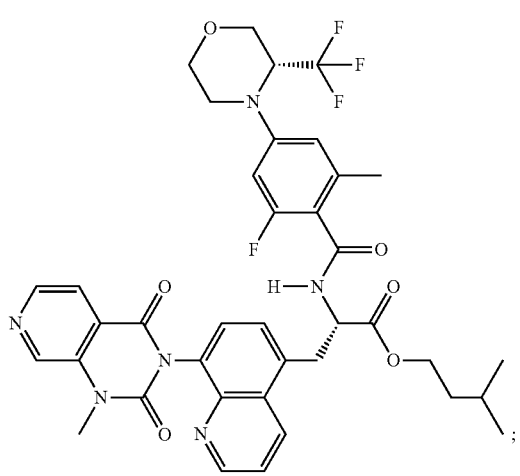
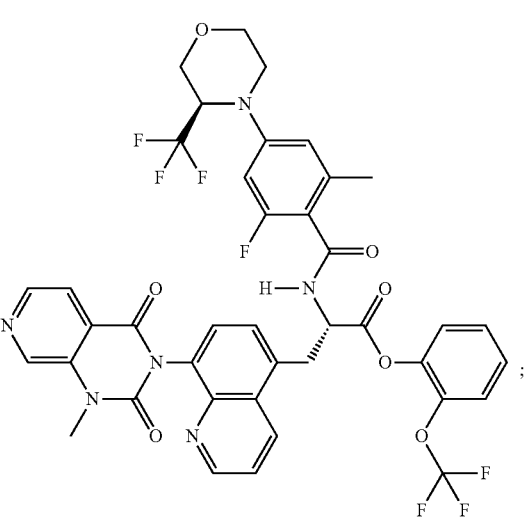
88
-continued
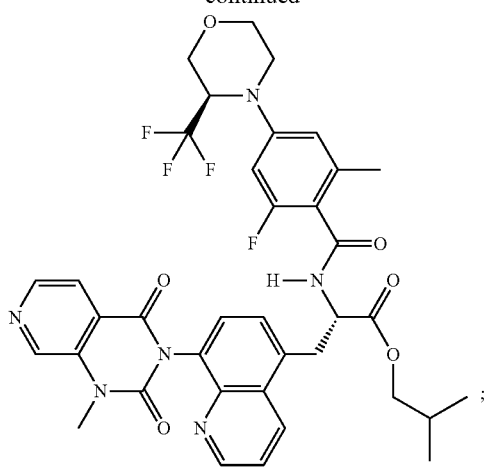
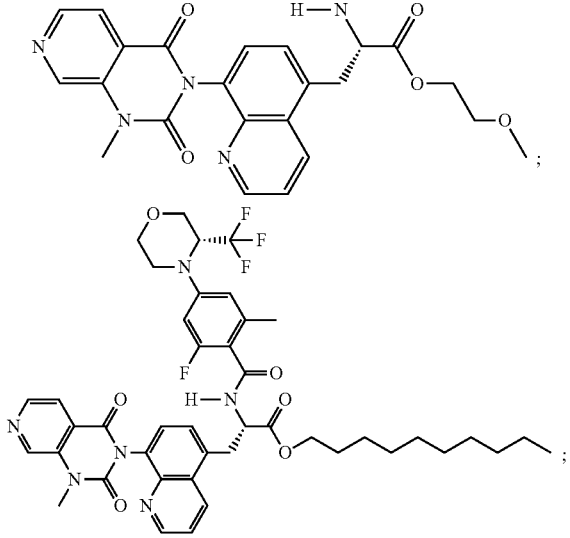

89
-continued
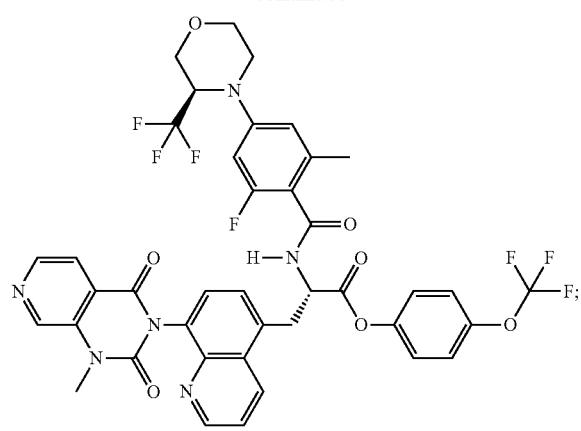
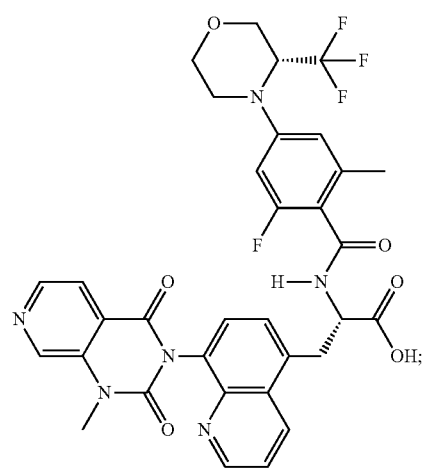
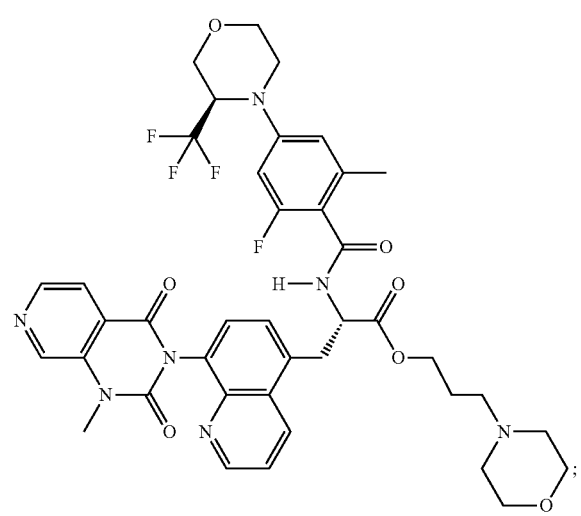
90
-continued
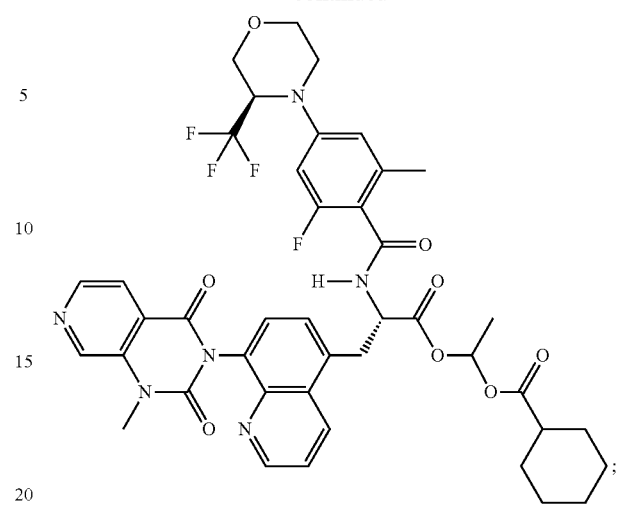
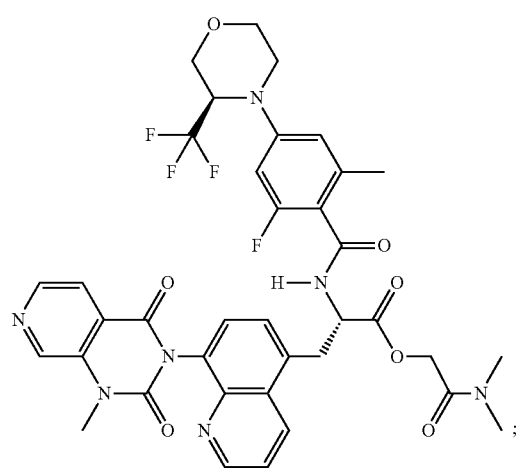
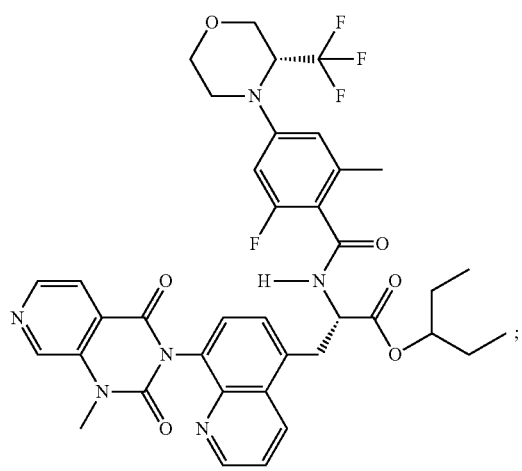

91
-continued
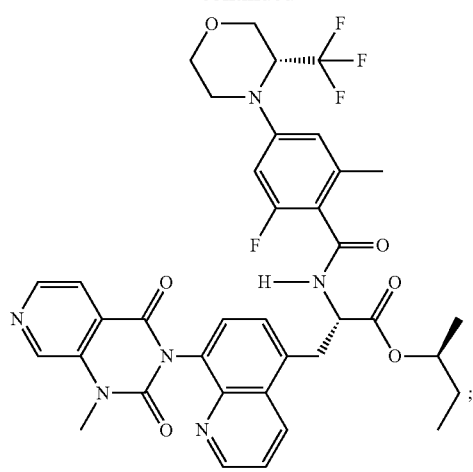
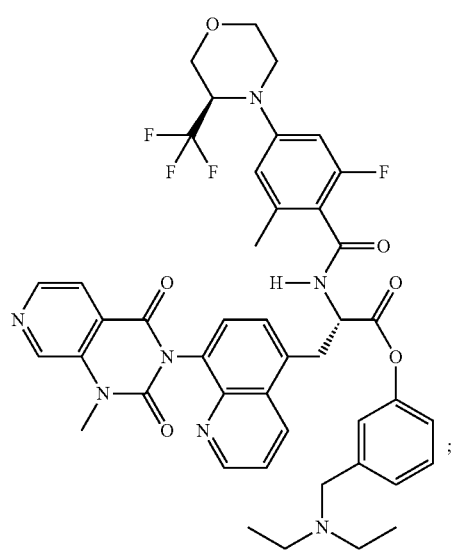
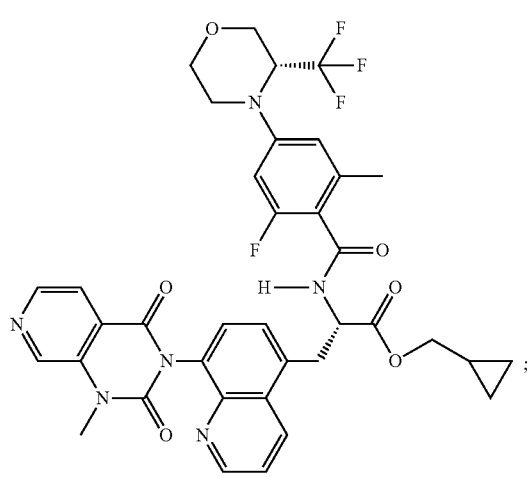
92
-continued
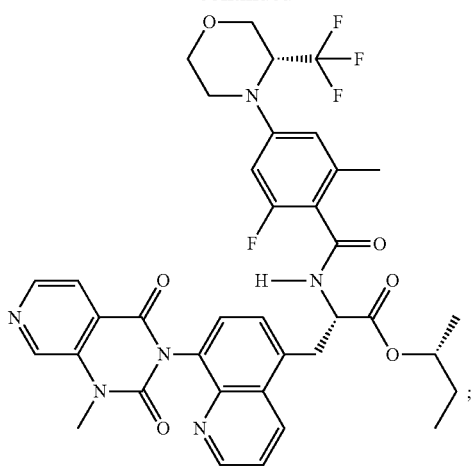
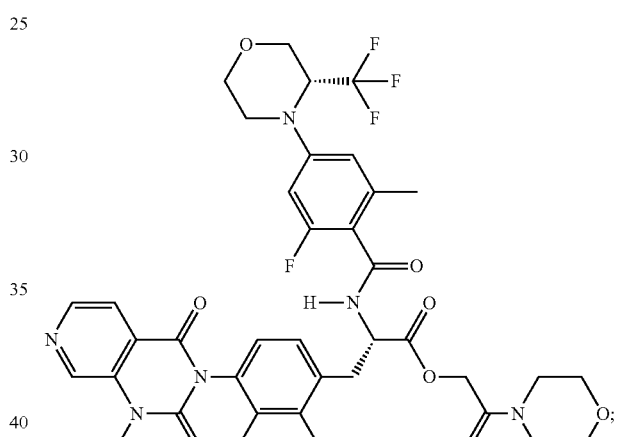
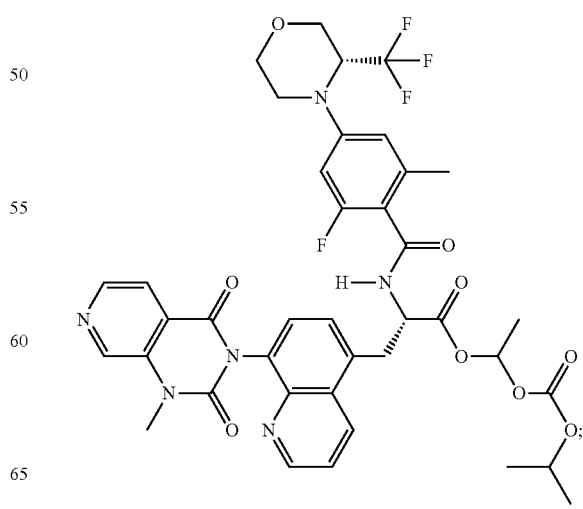

93
-continued
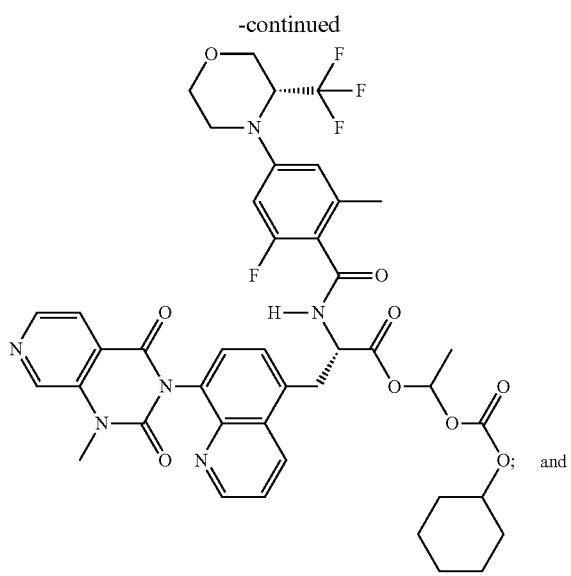
and
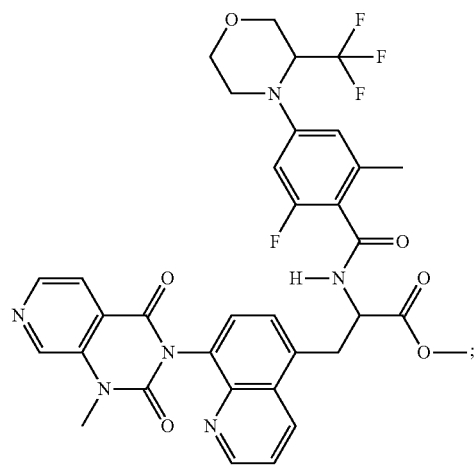
94
-continued
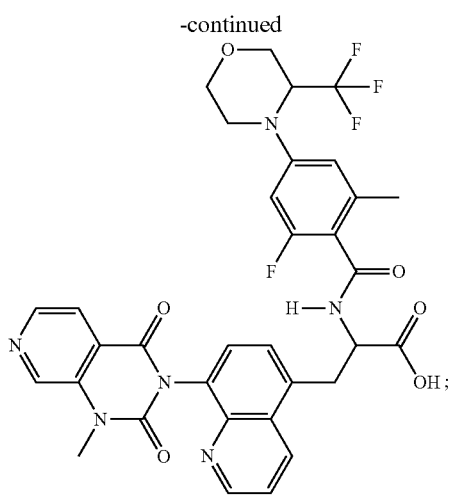
In some embodiments, the compound of the present disclosure is selected from:
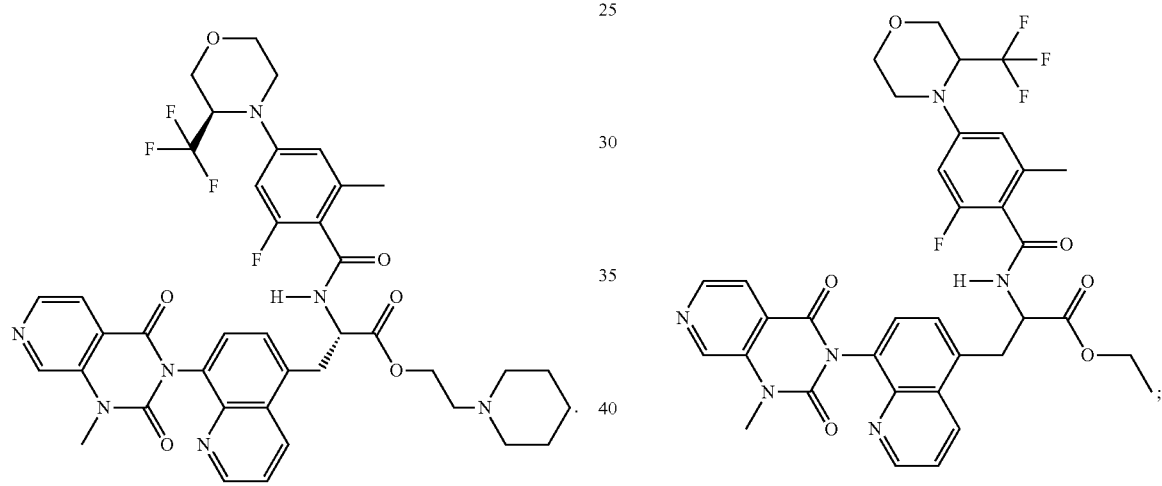
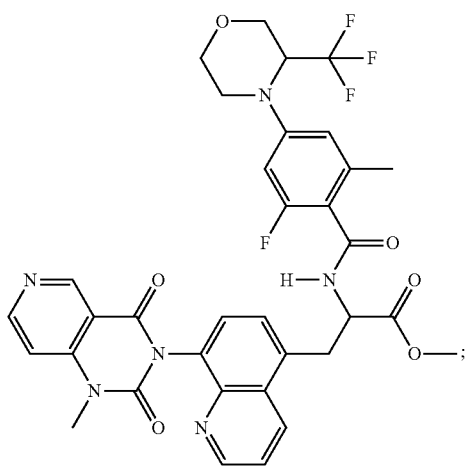

-continued

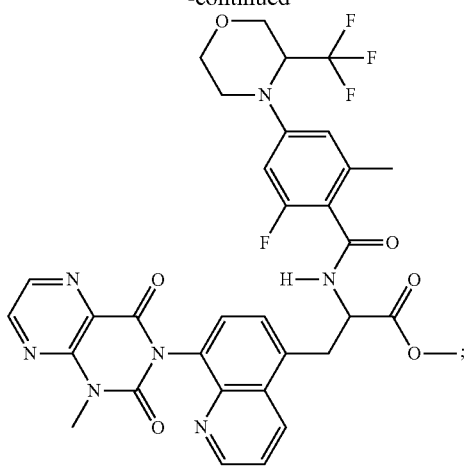

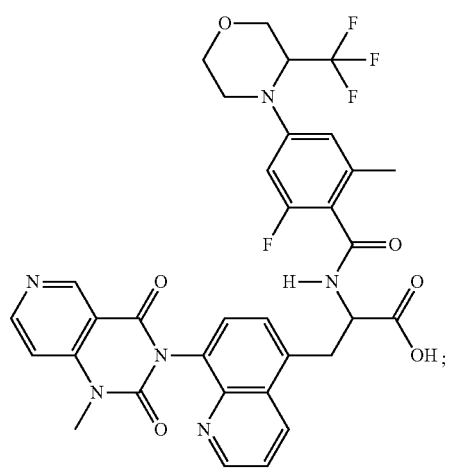

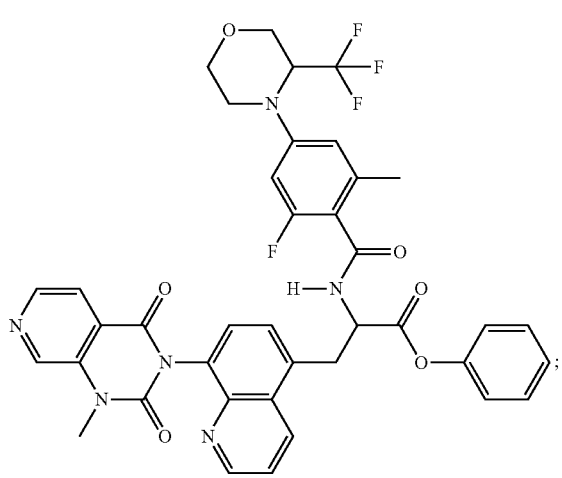

-continued
and

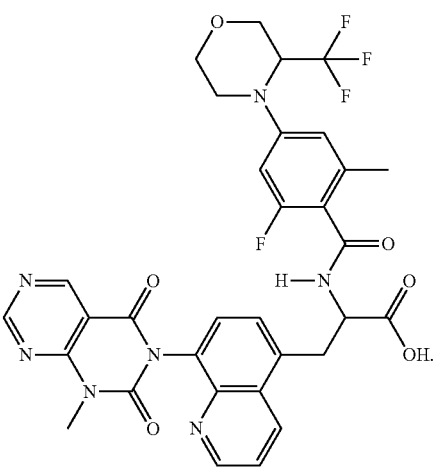

Provided are also compounds described herein or pharmaceutically acceptable salts, isomer, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

In some embodiments, the compound of the present disclosure contains one to six deuterium ($^2$H, or D). In some embodiments, one of $R^2$, $R^3$, $R^4$, $R^5$, and $R^6$ contains one to six D. In some embodiments, $R^6$ contains one to six D. In some embodiments, $R^6$ is $CD_3$.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

A "solvate" is formed by the interaction of a solvent and a compound. Solvates of salts of the compounds described herein are also provided. Hydrates of the compounds described herein are also provided.

A "prodrug" is a biologically inactive derivative of a drug that upon administration to the human body is converted to the biologically active parent drug according to some chemical or enzymatic pathway.

In certain embodiments, provided are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution of the racemate. Resolution of racemates can be accomplished, for example, by conventional methods such as crystallization in the presence of a resolving agent, or chromatography, using, for example a chiral high pressure liquid chromatography (HPLC) column. In addition, provided are also Z- and E-forms (or cis- and trans-forms) of the hydroxyamidine compounds described herein. Specifically, Z- and E-forms are included even if only one designation is named for both carbon-carbon double bonds as well as the hydroxyamidine bond.

Where chirality is not specified but is present, it is understood that the embodiment is directed to either the specific diastereomerically or enantiomerically enriched form; or a racemic or scalemic mixture of such compound(s).

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

"Atropisomers" are stereoisomers arising due to hindered rotation about a single bond, where the barrier to rotation about the bond is high enough to allow for isolation of individual stereoisomers.

In certain embodiments, provided are atropisomers thereof of the compounds described herein or pharmaceutically acceptable salts.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

In certain embodiments, provided are also chelates, non-covalent complexes, and mixtures thereof, of the compounds described herein or pharmaceutically acceptable salts, isomer, or a mixture thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Therapeutic Uses of the Compounds

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo to determine the optimal schedule and/or dosing of administration of an α4β7 integrin inhibitor for a given indication, cell type, individual, and other parameters. Information gleaned from such use may be used for experimental purposes or in the clinic to set protocols for in vivo treatment. Other ex vivo uses for which the invention may be suited are described below or will become apparent to those skilled in the art. The selected compounds may be further characterized to examine the safety or tolerance dosage in human or non-human subjects. Such properties may be examined using commonly known methods to those skilled in the art.

In some embodiments, compounds described herein, for example, compounds of formula (I), (II), (IIa), (IIb), (IIc), (IId), (IIe), (IIf), (IIg), (IIh), or (IIi), or a pharmaceutically acceptable salt, stereoisomer, mixture of stereoisomers, tautomer, or deuterated analog thereof, may be used to treat subjects who have or are suspected of having disease states, disorders, and conditions (also collectively referred to as "indications") responsive or believed to be responsive to the inhibition of α4β7 integrin activity. In some embodiments, the compounds described herein may be used to inhibit the activity of α4β7 integrin. In some embodiments, the compounds described herein may be used to inhibit excessive or destructive immune reactions or growth or a proliferation of a cell, such as a cancer cell, or inhibit immunosuppression.

In some embodiments, compounds described herein, for example, compounds of formula (J), (Ja), (Jb), (Jc), (Jd), (Je), or (Jf), or a pharmaceutically acceptable salt, stereoisomer, mixture of stereoisomers, tautomer, or deuterated analog thereof, may be used to treat subjects who have or are suspected of having disease states, disorders, and conditions (also collectively referred to as "indications") responsive or believed to be responsive to the inhibition of α4β7 integrin activity. In some embodiments, the compounds described herein may be used to inhibit the activity of α4β7 integrin. In some embodiments, the compounds described herein may be used to inhibit excessive or destructive immune reactions or growth or a proliferation of a cell, such as a cancer cell, or inhibit immunosuppression.

Methods

In some embodiments, the present disclosure provides a compound described herein useful as an inhibitor of α4β7 integrin. In some embodiments, the present disclosure provides a method of treating an inflammatory disease or condition comprising administering a compound described herein.

In some embodiments, the present disclosure provides a pharmaceutical composition comprising a compound described herein and a pharmaceutically acceptable carrier.

In some embodiments, the present disclosure provides a pharmaceutical composition comprising a compound described herein and at least one additional therapeutic agent and at least one pharmaceutically acceptable excipient.

The present disclosure provides a compound described herein for use in therapy.

In another embodiment, the present disclosure provides a compound described herein for use in the manufacture of a medicament for treating a disease or condition provided herein.

In some embodiments, provided is a compound described herein useful for the treatment of a disease or condition in a patient that is amenable to treatment by inhibiting α4β7 integrin. Diseases or conditions that may be treated with the compounds described herein include a solid tumor, diabetes, an inflammatory disease, graft versus host disease, primary sclerosing cholangitis, HIV, an autoimmune disease, inflammatory bowel disease (IBD), alcoholic hepatitis, systemic lupus erythematosus (SLE), and lupus nephritis.

In some embodiments, provided is a compound described herein useful for the treatment of an inflammatory disease or condition in a patient that is mediated, at least in part, by α4β7 integrin.

"Administering" or "administration" refers to the delivery of one or more therapeutic agents to a patient. In some embodiments, the administration is a monotherapy wherein a compound described herein is the only active ingredient administered to the patient in need of therapy. In another embodiment, the administration is co-administration such that two or more therapeutic agents are delivered together during the course of the treatment. In some embodiments, two or more therapeutic agents may be co-formulated into a single dosage form or "combined dosage unit", or formulated separately and subsequently combined into a combined dosage unit, as is typically for intravenous administration or oral administration as a mono or bilayer tablet or capsule.

In some embodiments, the compound described herein is administered to a human patient in need thereof in an effective amount, such as, from about 0.1 mg to about 1000 mg per dose of said compound. In some embodiments, the effective amount is from about 0.1 mg to about 400 mg per dose. In some embodiments, the effective amount is from about 0.1 mg to about 300 mg per dose. In some embodiments, the effective amount is from about 0.1 mg to about 200 mg per dose. In some embodiments, the effective amount is from about 1 mg to about 100 mg per dose. In other embodiments, the effective amount is about 1 mg, about 3 mg, about 5 mg, about 10 mg, about 15 mg, about 18 mg, about 20 mg, about 30 mg, about 40 mg, about 60 mg, about 80 mg, about 100 mg, about 200 mg, or about 300 mg per dose.

In some embodiments, the compound described herein and at least one additional therapeutic agent is administered to a human patient in need thereof in an effective amount of each agent, independently from about 0.1 mg to about 1000 mg per dose of a compound or formulation per dose per compound. In some embodiments, the effective amount of the combination treatment of a compound described herein and an additional compound is independently from about 0.1 mg to about 200 mg per compound per dose. In some embodiments, the effective amount of the combination treatment of a compound described herein and an additional compound is independently from about 1 mg to about 100 mg per compound per dose. In other embodiments, the effective amount of the combination treatment of a compound described herein and an additional compound is for each component, about 1 mg, about 3 mg, about 5 mg, about 10 mg, about 15 mg, about 18 mg, about 20 mg, about 30 mg, about 40 mg, about 60 mg, about 80 mg, about 100 mg, about 200 mg, or about 500 mg each per dose.

In some embodiments, the dose of a compound described herein and/or a combination of the dose of the compound described herein and/or the dose of an additional therapeutic agent is administered once per day, twice per day, or thrice per day. In yet another embodiment, the dose of a compound described herein and/or the dose of an additional therapeutic agent is administered as a loading dose of from about 0.1 mg to about 1000 mg per compound on the first day and each day or on alternate days or weekly for up to a month followed by a regular regimen of a compound described herein and/or one or more additional therapeutic agents or therapies. The maintenance dose may be about 0.1 mg to about 1000 mg once per day, twice per day, thrice per day, or weekly, for each component of a multi component drug regimen. A qualified care giver or treating physician is aware of what dose regimen is best for a particular patient or particular presenting conditions and will make appropriate treating regimen decisions for that patient. Thus, in another embodiment, the qualified caregiver is able to tailor a dose regimen of the compound described herein and/or an additional therapeutic agent(s) as disclosed herein to fit with the particular needs of the patient. Thus, it will be understood that the amount of the dose of a compound described herein and the amount of the dose of an additional therapeutic agent actually administered will usually be determined by a physician, in light of the relevant circumstances, including the condition(s) to be treated, the chosen route of administration, the actual compound (e.g., salt or free base) administered and its relative activity, the age, weight, and response of the individual patient, the severity of the patient's symptoms, and the like.

Co-administration may also include administering component drugs e.g., one on more compounds described herein and one or more additional (e.g., a second, third, fourth or fifth) therapeutic agent(s). Such combination of one on more compounds described herein and one or more additional therapeutic agent(s) may be administered simultaneously or in sequence (one after the other) within a reasonable period of time of each administration (e.g., about 1 minute to 24 hours) depending on the pharmacokinetic and/or pharmacodynamics properties of each agent or the combination. Co-administration may also involve treatment with a fixed combination wherein agents of the treatment regimen are combinable in a fixed dosage or combined dosage medium e.g., solid, liquid or aerosol. In some embodiments, a kit may be used to administer the drug or drug components.

Thus, some embodiments of the present disclosure is a method of treating a disease or condition mediated, at least in part, by α4β7 integrin, comprising administering therapeutically effective amounts of formulations of one on more compounds described herein and one or more additional therapeutic agents, including for example, via a kit to a patient in need thereof. It will be understood that a qualified care giver will administer or direct the administration of a therapeutically effective amount of any of the compound(s) or combinations of compounds of the present disclosure.

"Intravenous administration" is the administration of substances directly into a vein, or "intravenously." Compared with other routes of administration, the intravenous (IV) route is a faster way to deliver fluids and medications throughout the body. An infusion pump can allow precise control over the flow rate and total amount of medication delivered. However, in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, as a "flush", following the injection to push the medicine into the bloodstream more quickly. Thus, in some embodiments, compound(s) or combination of compounds described herein may be administered by IV administration alone or in combination with administration of certain components of the treatment regimen by oral or parenteral routes.

"Oral administration" is a route of administration where a substance is taken through the mouth, and includes buccal, sub labial, and sublingual administration, as well as enteral administration and that through the respiratory tract, unless made through e.g., tubing so the medication is not in direct contact with any of the oral mucosa. Typical form for the oral administration of therapeutic agents includes the use of tablets or capsules. Thus, in some embodiments, compound(s) or combination of compounds described herein may be administered by oral route alone or in combination with administration of certain components of the treatment regimen by IV or parenteral routes.

Pharmaceutical Formulations

The compounds described herein may be administered in a pharmaceutical formulation. Pharmaceutical formulations/compositions contemplated by the present disclosure comprise, in addition to a carrier, the compound described herein or a combination of compounds described herein optionally in combination with an additional therapeutic agent.

Pharmaceutical formulations/compositions contemplated by the present disclosure may also be intended for administration by injection and include aqueous solutions, oil suspensions, emulsions (with sesame oil, corn oil, cottonseed oil, or peanut oil) as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component compound(s) in the required amount in the appropriate solvent with various other ingredients as enumerated above or as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient(s) plus any additional desired ingredient from a previously sterile-filtered solution thereof.

In making pharmaceutical compositions that comprise compound described herein optionally in combination with an additional agent/therapy useful for the purpose or pharmaceutically acceptable salt thereof, the active ingredient is usually diluted by an excipient or carrier and/or enclosed or mixed with such a carrier that may be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 20% by weight of the active compounds, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the disclosure may be formulated so as to provide quick, sustained or delayed release of the active ingredient after administration to the patient by employing procedures known in the art. In some embodiments, sustained release formulations are used. Controlled release drug delivery systems for oral administration include osmotic pump systems and dissolutional systems containing polymer-coated reservoirs or drug-polymer matrix formulations.

Certain compositions are preferably formulated in a unit dosage form. The term "unit dosage forms" or "combined dosage unit" refers to physically discrete units suitable as unitary dosages for human subjects and other mammals, each unit containing a predetermined quantity of one or more of the active materials (e.g., a compound described herein, optionally in combination with an additional therapeutic agent calculated to produce the desired effect, in association with a suitable pharmaceutical excipient in for example, a tablet, capsule, ampoule or vial for injection. It will be understood, however, that the amount of each active agent actually administered will be determined by a physician, in the light of the relevant circumstances, including the condition to be treated, the chosen route of administration, the actual compounds administered and their relative activity, the age, weight, and response of the individual patient, the severity of the patient's symptoms, and the like.

For preparing solid compositions such as tablets, the principal active ingredient(s) is/are mixed with a pharmaceutical excipient to form a solid pre-formulation composition containing a homogeneous mixture of a compound of the present disclosure. When referring to these pre-formulation compositions as homogeneous, it is meant that the active ingredient(s) are dispersed evenly throughout the composition so that the composition may be readily subdivided into equally effective unit dosage forms such as tablets, pills and capsules.

The tablets or pills comprising compound described herein of the present disclosure optionally in combination with the second agent may be coated or otherwise compounded to provide a dosage form affording the advantage of prolonged action, or to protect from the acidic conditions of the stomach. For example, the tablet or pill can comprise an inner dosage and an outer dosage element, the latter being in the form of an envelope over the former. In some embodiments, the inner dosage element may comprise the compound described herein and the outer dosage element may comprise the second or additional therapeutic agent or vice versa. Alternatively, the combined dosage unit may be side by side configuration as in a capsule or tablet where one portion or half of the tablet or capsule is filled with a formulation of the compound described herein while the other portion or half of the table or capsule comprises the additional therapeutic agent.

A variety of materials may be used for such enteric layers or coatings, such materials including a number of polymeric acids and mixtures of polymeric acids with such materials as shellac, cetyl alcohol, and cellulose acetate. One of ordinary skill in the art is aware of techniques and materials used in the manufacture of dosages of formulations disclosed herein.

A "sustained release formulation" or "extended release formulation" is a formulation which is designed to slowly release a therapeutic agent into the body over an extended period of time, whereas an "immediate release formulation" is a formulation which is designed to quickly release a therapeutic agent into the body over a shortened period of time. In some cases, the immediate release formulation may be coated such that the therapeutic agent is only released once it reaches the desired target in the body (e.g., the stomach). One of ordinary skill in the art is able to develop sustained release formulations of the presently disclosed compounds without undue experimentation. Thus, in some embodiments, compound(s) or combination of compounds described herein may be delivered via sustained released formulations alone or in combination with administration of certain components of the treatment regimen by oral, IV or parenteral routes.

A lyophilized formulation may also be used to administer a compound described herein singly or in combination with an additional therapeutic agent. One of skill in the art is aware of how to make and use lyophilized formulations of drug substances amenable to lyophilization.

Spray-dried formulation may also be used to administer a compound described herein singly or in combination with an additional therapeutic agent. One of skill in the art is aware of how to make and use spray-dried formulations of drug substances amenable to spray-drying. Other known formulation techniques may also be employed to formulate a compound or combination of compounds disclosed herein.

The compounds disclosed herein are useful for the treatment of diseases or conditions mediated, at least in part, by $\alpha 4\beta 7$ integrin. Non-limiting examples of diseases or conditions mediated, at least in part, by $\alpha 4\beta 7$ integrin include, without limitation, acne, acid-induced lung injury, Addison's disease, adrenal hyperplasia, adrenocortical insufficiency, adult-onset Still's disease, adult respiratory distress syndrome (ARDS), age-related macular degeneration, aging, alcoholic hepatitis, alcoholic liver disease, allergen-induced asthma, allergic bronchopulmonary, allergic conjunctivitis, allergic contact dermatitis, allergies, allergic encephalomyelitis, allergic neuritis, allograft rejection, alopecia, alopecia areata, Alzheimer's disease, amyloidosis, amyotrophic lateral sclerosis, angina pectoris, angioedema, angiofibroma, anhidrotic ectodermal dysplasia-ill, anti-glomerular basement membrane disease, antigen-antibody complex mediated diseases, ankylosing spondylitis, antiphospholipid syndrome, aphthous stomatitis, appendicitis, arthritis, ascites, aspergillosis, asthma, atherosclerosis, atherosclerotic plaques, atopic dermatitis, atrophic thyroiditis, autoimmune diseases, autoimmune hemolytic anemia (immune pancytopenia, paroxysmal nocturnal hemoglobinuria), autoimmune polyendocrinopathies, autoimmune thrombocytopenia (idiopathic thrombocytopenic purpura, immune-mediated thrombocytopenia), autoimmune hepatitis, autoimmune thyroid disorders, autoinflammatory diseases, back pain, *Bacillus anthracis* infection, Bechet's disease, bee sting-induced inflammation, Behçet's syndrome, Bell's palsy, berylliosis, Blau syndrome, bone pain, bronchiolitis, bullous pemphigoid (BP) asthma, burns, bursitis, cardiac hypertrophy, carpal tunnel syndrome, Castleman's disease, catabolic disorders, cataracts, Celiac disease, cerebral aneurysm, chemical irritant-induced inflammation, chorioretinitis, chronic atypical neutrophilic dermatosis with lipodystrophy and elevated temperature (CANDLE) syndrome, chronic heart failure, chronic lung disease of prematurity, chronic obstructive pulmonary disease (COPD), chronic pancreatitis, chronic prostatitis, chronic recurrent multifocal osteomyelitis, cicatricial alopecia, colitis, complex regional pain syndrome, complications of organ transplantation, conjunctivitis, connective tissue disease, contact dermatitis, corneal graft neovascularization, corneal ulcer, Crohn's disease, cryopyrin-associated periodic syndromes, cutaneous lupus erythematosus (CLE), cryptococcosis, cystic fibrosis, deficiency of the interleukin-1 receptor antagonist (DIRA), dermatitis, dermatitis endotoxemia, dermatomyositis, diabetic macular edema, diverticulitis, eczema, encephalitis, endometriosis, endotoxemia, eosinophilic pneumonias, epicondylitis, epidermolysis bullosa, erythema multiforme, erythroblastopenia, esophagitis, familial amyloidotic polyneuropathy, familial cold urticarial, familial Mediterranean fever, fetal growth retardation, fibromyalgia, fistulizing Crohn's disease, food allergies, giant cell arteritis, glaucoma, glioblastoma, glomerular disease, glomerular nephritis, glomerulonephritis, gluten-sensitive enteropathy, gout, gouty arthritis, graft-versus-host disease (GVHD), granulomatous hepatitis, Graves' disease, growth plate injuries, Guillain-Barre syndrome, gut diseases, hair loss, Hashimoto's thyroiditis, head injury, headache, hearing loss, heart disease, hemangioma, hemolytic anemia, hemophilic joints, Henoch-Scholein purpura, hepatitis, hereditary periodic fever syndrome, heritable disorders of connective tissue, herpes zoster and simplex, hidradenitis suppurativa (HS), hip replacement, Hodgkin's disease, Huntington's disease, hyaline membrane disease, hyperactive inflammatory response, hyperammonemia, hypercalcemia, hypercholesterolemia, hypereosinophilic syndrome (HES), hyperimmunoglobulinemia D with recurrent fever (HIDS), hypersensitivity pneumonitis, hypertropic bone formation, hypoplastic and other anemias, hypoplastic anemia, ichthyosis, idiopathic demyelinating polyneuropathy, Idiopathic inflammatory myopathies (dermatomyositis, polymyositis), idiopathic pulmonary fibrosis, idiopathic thrombocytopenic purpura, immunoglobulin nephropathies, immune complex nephritis, immune thrombocytopenic purpura (ITP), incontinentia pigmenti (IP, Bloch-Siemens syndrome), infectious mononucleosis, infectious diseases including viral diseases such as AIDS (HIV infection), hepatitis A, B, C, D, and E, herpes; inflammation, inflammation of the CNS, inflammatory bowel disease (IBD), inflammatory disease of the lower respiratory tract including bronchitis or chronic obstructive pulmonary diseases, inflammatory disease of the upper respiratory tract including the nose and sinuses such as rhinitis or sinusitis, inflammatory diseases of the respiratory tract, inflammatory ischemic event such as stroke or cardiac arrest, inflammatory lung disease, inflammatory myopathy such as myocarditis, inflammatory liver disease, inflammatory neuropathy, inflammatory pain, insect bite-induced inflammation, interstitial cystitis, interstitial lung disease, iritis, irritant-induced inflammation, ischemia/reperfusion, joint replacement, juvenile arthritis, juvenile rheumatoid arthritis, keratitis, kidney injury caused by parasitic infections, kidney transplant rejection, leptospirosis, leukocyte adhesion deficiency, lichen sclerosus (LS), Lambert-Eaton myasthenic syndrome, Loeffler's syndrome, lupus, lupus nephritis, Lyme disease, Marfan syndrome (MFS), mast cell activation syndrome, mastocytosis, meningitis, meningioma, mesothelioma, mixed connective tissue disease, Muckle-Wells syndrome (urticaria deafness amyloidosis), mucositis, multiple organ injury syndrome, multiple sclerosis, muscle wasting, muscular dystrophy, myasthenia gravis (MG), myelodysplastic syndrome, myocarditis, myositis, nasal sinusitis, necrotizing enterocolitis, neonatal onset multisystem inflammatory disease (NOMID), neovascular glaucoma, nephrotic syndrome, neuritis, neuropathological diseases, non-allergen induced asthma, obesity, ocular allergy, optic neuritis, organ transplant rejection, Osier-Weber syndrome, osteoarthritis, osteogenesis imperfecta, osteonecrosis, osteoporosis, osterarthritis, otitis, pachyonychia congenita, Paget's disease, Paget's disease of bone, pancreatitis, Parkinson's disease, pediatric rheumatology, pelvic inflammatory disease, pemphigus, pemphigus vulgaris (PV), bullous pemphigoid (BP), pericarditis, periodic fever, periodontitis, peritoneal endometriosis, pernicious anemia (Addison's disease), pertussis, PFAPA (periodic fever aphthous pharyngitis and cervical adenopathy), pharyngitis and adenitis (PFAPA syndrome), plant irritant-induced inflammation, pneumocystis infection, pneumonia, pneumonitis, poison ivy/urushiol oil-induced inflammation, polyarthritis nodosa, polychondritis, polycystic kidney disease, polymyalgia rheumatic, giant cell arteritis, polymyositis, pouchitis, reperfusion injury and transplant rejection, primary biliary cirrhosis, primary pulmonary hypertension, primary sclerosing cholangitis (PSC), proctitis, psoriasis, psoriasis vulgaris, psoriatic arthritis, psoriatic epidermis, psychosocial stress diseases, pulmonary disease, pulmonary fibrosis, pulmonary hypertension, pyoderma gangrenosum, pyogenic granuloma retrolental fibroplasias, pyogenic sterile arthritis, Raynaud's syndrome, Reiter's disease, reactive arthritis, renal disease, renal graft rejection, reperfusion injury, respiratory distress syndrome, retinal disease, retrolental fibroplasia, Reynaud's syndrome, rheumatic carditis, rheumatic diseases, rheumatic fever, rheumatoid arthritis, rhinitis, rhinitis psoriasis, rosacea, sarcoidosis, Schnitzler syndrome, scleritis, sclerosis, scleroderma, scoliosis, seborrhea, sepsis, septic shock, severe pain, Sézary syndrome, sickle cell anemia, silica-induced disease (Silicosis), Sjogren's syndrome, skin diseases, skin irritation, skin rash, skin sensitization (contact dermatitis or allergic contact dermatitis), sleep apnea, spinal cord injury, spinal stenosis, spondyloarthropathies, sports injuries, sprains and strains, Stevens-Johnson syndrome (SJS), stroke, subarachnoid hemorrhage, sunburn, synovial inflammation, systemic inflammatory response syndrome (SIRS), systemic lupus erythematosus, systemic mast cell disease (SMCD), systemic vasculitis, systemic-onset juvenile idiopathic arthritis, temporal arteritis, tendinitis, tenosynovitis, thrombocytopenia, thyroditis, thyroiditis, tissue transplant, toxoplasmosis, trachoma, transplantation rejection, traumatic brain injury, tuberculosis, tubulointerstitial nephritis, tumor necrosis factor (TNF) receptor associated periodic syndrome (TRAPS), type 1 diabetes, type 2 diabetes, complications from type 1 or type 2 diabetes, ulcerative colitis, urticaria, uterine fibroids, uveitis, uveoretinitis, vascular restenosis, vasculitis, vasculitis (NHLBI), vitiligo, Wegener's granulomatosis, and Whipple's disease.

In further embodiments, the methods are provided for alleviating a symptom of a disease or disorder mediated, at least in part, by α4β7 integrin. In some embodiments, the methods include identifying a mammal having a symptom of a disease or disorder mediated, at least in part, by α4β7 integrin, and providing to the mammal an amount of a compound as described herein effective to ameliorate (i.e., lessen the severity of) the symptom.

In some embodiments, the disease or condition mediated, at least in part, by α4β7 integrin is an inflammatory disease or LPS induced endotoxin shock. In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), inflammatory bowel disease (IBD), sepsis, psoriasis, Sjoegren's syndrome, autoimmune hemolytic anemia, asthma, or chronic obstructive pulmonary disease (COPD), ankylosing spondylitis, acute gout and ankylosing spondylitis, reactive arthritis, monoarticular arthritis, osteoarthritis, gouty arthritis, juvenile arthritis, juvenile onset rheumatoid arthritis, juvenile rheumatoid arthritis or psoriatic arthritis. In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

In some embodiments, the disease or condition mediated, at least in part, by α4β7 integrin is inflammatory bowel disease (IBD). The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the presently disclosed compounds, compositions and methods include diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

Treating or preventing IBD also includes ameliorating or reducing one or more symptoms of IBD. As used herein, the term "symptoms of IBD" refers to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The term "wherein said symptoms are reduced" refers to a qualitative or quantitative reduction in detectable symptoms, including but not limited to a detectable impact on the rate of recovery from disease (e.g. rate of weight gain). The diagnosis is typically determined by way of an endoscopic observation of the mucosa, and pathologic examination of endoscopic biopsy specimens.

The course of IBD varies, and is often associated with intermittent periods of disease remission and disease exacerbation. Various methods have been described for characterizing disease activity and severity of IBD as well as response to treatment in subjects having IBD. Treatment according to the present methods is generally applicable to a subject having IBD of any level or degree of disease activity.

In some embodiments, the disease or condition treated by the administration of a compound of composition described herein includes acute gout and ankylosing spondylitis, allergic disorders, Alzheimer's disease, Amyotrophic lateral sclerosis (ALS), Amyotrophic lateral sclerosis and multiple sclerosis, atherosclerosis, bacterial infections, bone cancer pain and pain due to endometriosis, BRAF resistant melanoma, brain stem glioma or pituitary adenomas, burns, bursitis, cancer of the anal region, cancer of the endocrine system, cancer of the kidney or ureter (e.g. renal cell carcinoma, and carcinoma of the renal pelvis), cancer of the penis, cancer of the small intestine, cancer of the thyroid, cancer of the urethra, cancers of the blood such as acute myeloid leukemia, cancers of the tongue, carcinoma of the cervix, carcinoma of the endometrium, carcinoma of the fallopian tubes, carcinoma of the renal pelvis, carcinoma of the vagina or carcinoma of the vulva, chronic myeloid leukemia, chronic or acute leukemia, chronic pain, classic Bartter syndrome, common cold conjunctivitis, coronary heart disease, cutaneous or intraocular melanoma, dermatitis, dysmenorrhea, eczema, endometriosis, familial adenomatous polyposis, fibromyalgia, fungal infections, gout, gynecologic tumors, uterine sarcomas, carcinoma of the fallopian tubes, headache, hemophilic arthropathy, Parkinson's disease, AIDS, herpes zoster, Hodgkin's disease, Huntington's, hyperprostaglandin E syndrome, influenza, iritis, juvenile arthritis, juvenile onset rheumatoid arthritis, juvenile rheumatoid arthritis, low back and neck pain, lymphocytic lymphomas, myofascial disorders, myositis, neuralgia, neurodegenerative disorders such as Alzheimer's disease, neuroinflammatory disorders, neuropathic pain, carcinoma of the vulva, Parkinson's disease, pediatric malignancy, pulmonary fibrosis rectal cancer, rhinitis, sarcoidosis, sarcomas of soft tissues, scleritis, skin cancer, solid tumors of childhood, spinal axis tumors, sprains and strains, stomach cancer, stroke, subacute and chronic musculoskeletal pain syndromes such as bursitis, surgical or dental procedures, symptoms associated with influenza or other viral infections, synovitis, toothache, ulcers, uterine cancer, uterine sarcomas, uveitis, vasculitis, viral infections, viral infections {e.g. influenza) and wound healing.

Criteria useful for assessment of disease activity in subjects with ulcerative colitis can be found in, e.g., Truelove et al. (1955) Br Med J 2:1041-1048.) Using these criteria, disease activity can be characterized in a subject having IBD as mild disease activity or severe disease activity. Subjects who do not meet all the criteria for severe disease activity, and who exceed the criteria for mild disease activity are classified as having moderate disease activity.

The presently disclosed treatment methods can also be applied at any point in the course of the disease. In some embodiments, the methods are applied to a subject having IBD during a time period of remission (i.e., inactive disease). In such embodiments, the present methods provide benefit by extending the time period of remission (e.g., extending the period of inactive disease) or by preventing, reducing, or delaying the onset of active disease. In other embodiments, methods may be applied to a subject having IBD during a period of active disease. Such methods provide benefit by reducing the duration of the period of active disease, reducing or ameliorating one or more symptoms of IBD, or treating IBD.

Measures for determining efficacy of treatment of IBD in clinical practice have been described and include, for example, the following: symptom control; fistula closure; extent of corticosteroid therapy required; and, improvement in quality of life. Heath-related quality of life (HRQL) can be assessed using the Inflammatory Bowel Disease Questionnaire (IBDQ), which is extensively used in clinical practice to assess quality of life in a subject with IBD. (See Guyatt et al. (1989) Gastroenterology 96:804-810.) In some embodiments, the disease or condition is immune-mediated liver injury, disease or condition.

In some embodiments, the disease or condition mediated, at least in part, by $\alpha 4\beta 7$ integrin is alcoholic hepatitis. Alcoholic hepatitis is a clinical syndrome characterized by jaundice and liver failure that develops in subjects with chronic and active alcohol abuse. (See Akriviadis E. et. al, Ann Gastroenterol. 2016 April-June; 29(2): 236-237). Alcoholic hepatitis can cause cirrhosis and fibrosis of the liver cells. Glucocorticoids, (e.g. prednisolone) and phosophodiesterase inhibitors (e.g. pentoxifylline) can be used to treat alcoholic hepatitis. The compounds herein can be used as stand-alone treatments or in combination with the current treatments for alcoholic hepatitis.

In one aspect, the present disclosure provides methods of treating or preventing a human immunodeficiency virus (HIV) infection in a subject in need thereof, comprising administering to the subject a therapeutically effective amount of a compound provided herein, or a pharmaceutically acceptable salt thereof, or a pharmaceutical composition provided herein.

In some embodiments, the disease or condition mediated, at least in part, by $\alpha 4\beta 7$ integrin is systemic lupus erythematosus (SLE), lupus nephritis, lupus-related, or other autoimmune disorders or a symptom of SLE. Symptoms of systemic lupus erythematosus include joint pain, joint swelling, arthritis, fatigue, hair loss, mouth sores, swollen lymph nodes, sensitivity to sunlight, skin rash, headaches, numbness, tingling, seizures, vision problems, personality changes, abdominal pain, nausea, vomiting, abnormal heart rhythms, coughing up blood and difficulty breathing, patchy skin color and Raynaud's phenomenon.

Combination Therapy

Also provided are methods of treatment in which a compound described herein is given to a patient in combination with one or more additional active agents or therapy.

Thus in some embodiments, a method of treating diseases or conditions mediated, at least in part, by $\alpha 4\beta 7$ integrin and/or diseases or symptoms that co-present or are exacerbated or triggered by the diseases or conditions mediated, at least in part, by $\alpha 4\beta 7$ integrin, e.g., an allergic disorder and/or an autoimmune and/or inflammatory disease, and/or an acute inflammatory reaction, comprises administering to a patient in need thereof an effective amount of a compound described herein optionally in combination with an additional agent (e.g., a second, third, fourth or fifth active agent) which can be useful for treating diseases or conditions mediated, at least in part, by α4β7, an allergic disorder and/or an autoimmune and/or inflammatory disease, and/or an acute inflammatory reaction incident to or co-presenting with diseases or conditions mediated, at least in part, by α4β7 integrin. Treatment with the second, third, fourth or fifth active agent may be prior to, concomitant with, or following treatment with a compound described herein. In some embodiments, a compound described herein is combined with another active agent in a single dosage form. Suitable therapeutics that may be used in combination with a compound described herein include, but are not limited to, therapeutic agents provided herein, or a combination comprising at least one therapeutic agent provided herein.

Included herein are methods of treatment in which a compound described herein is administered in combination with an agent for treatment of an inflammatory disease or condition. Examples of agents for treatment of an inflammatory disease or condition that can be used in combination with compounds described herein, include alpha-fetoprotein modulators; adenosine A3 receptor antagonist; adrenomedullin ligands; AKT1 gene inhibitors; antibiotics; antifungals; ASK1 inhibitors; ATPase inhibitors; beta adrenoceptor antagonists; BTK inhibitors; calcineurin inhibitors; carbohydrate metabolism modulators; cathepsin S inhibitors; CCR9 chemokine antagonists; CD233 modulators; CD29 modulators; CD3 antagonists; CD40 ligand inhibitors; CD40 ligand receptor antagonists; chemokine CXC ligand inhibitors; CHST15 gene inhibitors; collagen modulators; CSF-1 antagonists; CX3CR1 chemokine modulators; ecobiotics; eotaxin ligand inhibitors; EP4 prostanoid receptor agonists; F1F0 ATP synthase modulators; farnesoid X receptor (FXR and NR1H4) agonists or modulators; fecal microbiota transplantation (FMT); fractalkine ligand inhibitors; free fatty acid receptor 2 antagonists; GATA 3 transcription factor inhibitors; glucagon-like peptide 2 agonists; glucocorticoid agonists; Glucocorticoid receptor modulators; guanylate cyclase receptor agonists; HIF prolyl hydroxylase inhibitors; histone deacetylase inhibitors; HLA class II antigen modulators; hypoxia inducible factor-1 stimulator; ICAM1 gene inhibitors; IL-1 beta ligand modulators; IL-12 antagonists; IL-13 antagonists; IL-18 antagonists; IL-22 agonists; IL-23 antagonists; IL-23A inhibitors; IL-6 antagonists; IL-7 receptor antagonists; IL-8 receptor antagonists; integrin alpha-4/beta-1 antagonists; integrin alpha-4/beta-7 antagonists; integrin antagonists; interleukin ligand inhibitors; interleukin receptor 17A antagonists; interleukin-1 beta ligands; interleukin 1 like receptor 2 inhibitors; IL-6 receptor modulators; JAK tyrosine kinase inhibitors; Jak1 tyrosine kinase inhibitors; Jak3 tyrosine kinase inhibitors; lactoferrin stimulators; LanC like protein 2 modulators; leukocyte elastate inhibitors; leukocyte proteinase-3 inhibitors; MAdCAM inhibitors; melanin concentrating hormone (MCH-1) antagonist; melanocortin agonists; metalloprotease-9 inhibitors; microbiome-targeting therapeutics; natriuretic peptide receptor C agonists; neuregulin-4 ligands; NLPR3 inhibitors; NKG2 D activating NK receptor antagonists; nuclear factor kappa B inhibitors; opioid receptor antagonists; OX40 ligand inhibitors; oxidoreductase inhibitors; P2X7 purinoceptor modulators; PDE 4 inhibitors; Pellino homolog 1 inhibitors; PPAR alpha/delta agonists; PPAR gamma agonists; protein fimH inhibitors; P-selectin glycoprotein ligand-1 inhibitors; Ret tyrosine kinase receptor inhibitors; RIP-1 kinase inhibitors; RIP-2 kinase inhibitors; RNA polymerase inhibitors; sphingosine 1 phosphate phosphatase 1 stimulators; sphingosine-1-phosphate receptor-1 agonists; sphingosine-1-phosphate receptor-5 agonists; sphingosine-1-phosphate receptor-1 antagonists; sphingosine-1-phosphate receptor-1 modulators; stem cell antigen-1 inhibitors; superoxide dismutase modulators; SYK inhibitors; tissue transglutaminase inhibitor; TLR-3 antagonists; TLR-4 antagonists; Toll-like receptor 8 (TLR8) inhibitors; TLR-9 agonists; TNF alpha ligand inhibitors; TNF ligand inhibitors; TNF alpha ligand modulators; TNF antagonists; TPL-2 inhibitors; tumor necrosis factor 14 ligand modulators; tumor necrosis factor 15 ligand inhibitors; Tyk2 tyrosine kinase inhibitors; type I IL-1 receptor antagonists; vanilloid VR1 agonists; and zonulin inhibitors, and combinations thereof.

Adenosine A3 receptor antagonists include PBF-677.

Adrenomedullin ligands include adrenomedullin.

Antibiotics include ciprofloxacin, clarithromycin, metronidazole, vancomycin, rifamycin, rifaximin, and tosufloxacin.

ASK1 inhibitors include GS-4997.

Alpha-fetoprotein modulators include ACT-101.

Anti-CD28 inhibitors include JNJ-3133 and abatacept.

Beta adrenoceptor antagonists include NM-001.

BTK inhibitors include GS-4059.

Calcineurin inhibitors: include tacrolimus, and ciclosporin.

Carbohydrate metabolism modulators include ASD-003.

Cathepsin S inhibitors include VBY-129.

CCR9 chemokine antagonists include CCX-507.

CD233 modulators include GSK-2831781.

CD29 modulators include PF-06687234.

CD3 antagonists include NI-0401.

CD4 antagonists include IT-1208.

CD40 ligand inhibitors include SAR-441344, and letolizumab.

CD40 gene inhibitors include NJA-730.

CD40 ligand receptor antagonists include FFP-104, BI-655064.

Chaperonin binding immunoglobulin protein includes IRL-201805.

Chemokine CXC ligand inhibitors include LY-3041658.

CHST15 gene inhibitors include STNM-01.

Collagen modulators include ECCS-50 (DCCT-10).

COT protein kinase inhibitors include GS-4875.

CSF-1 antagonists include JNJ-40346527 (PRV-6527), and SNDX-6352.

CX3CR1 chemokine modulators include E-6130.

Ecobiotics include SER-287.

Eotaxin ligand inhibitors include bertilimumab.

EP4 prostanoid receptor agonists include KAG-308.

F1F0 ATP synthase modulators include LYC-30937 EC.

Fractalkine ligand inhibitors include quetmolimab (E-6011).

Free fatty acid receptor 2 antagonists include GLPG-0974.

GATA 3 transcription factor inhibitors include SB-012.

Glucagon-like peptide 2 agonists include teduglutide, and apraglutide.

Glucocorticoid receptor agonists include budesonide, beclomethasone dipropionate, and dexamethasone sodium phosphate.

Glucocorticoid receptor modulators/TNF ligand inhibitors include ABBV-3373.

Guanylate cyclase receptor agonists include dolcanatide.

HIF prolyl hydroxylase inhibitors include DS-1093, and AKB-4924.

HIF prolyl hydroxylase-2 inhibitors/hypoxia inducible factor-1 stimulators include GB-004.

Histone deacetylase inhibitors include givinostat.

Histone deacetylase-6 inhibitors include CKD-506.

HLA class II antigen modulators include HLA class II protein modulators.

ICAM1 gene inhibitors include alicaforsen.

IL-12 antagonists include ustekinumab (IL12/IL23).

IL-13 antagonists include tralokinumab.

IL-18 antagonists include GSK-1070806

IL-22 agonists include RG-7880.

IL-23 antagonists include tildrakizumab, risankizumab (BI-655066), mirikizumab (LY-3074828), brazikumab (AMG-139), and PTG-200.

IL-23A inhibitors include guselkumab.

IL-6 antagonists include olokizumab.

IL-7 receptor antagonists include OSE-127.

IL-8 receptor antagonists include clotrimazole.

Integrin alpha-4/beta-1 antagonists include natalizumab.

Integrin alpha-4/beta-7 antagonists include etrolizumab (a4b7/aEb7), vedolizumab, carotegast methyl, TRK-170 (a4b7/a4b1), PN-10943, and PTG-100.

Integrin antagonists include E-6007.

Interleukin ligand inhibitors include bimekizumab (IL-17A/IL-17F).

Interleukin receptor 17A antagonists include brodalumab.

Interleukin-1 beta ligands include K(D)PT.

Interleukin 1 like receptor 2 inhibitors include BI-655130.

IL-6 receptor modulators include olamkicept.

JAK tyrosine kinase inhibitors include tofacitinib (1/3), peficitinib (1/3), TD-3504, an TD-1473. Jak1 tyrosine kinase inhibitors include a compound disclosed in WO2008/109943. Examples of other JAK inhibitors include, but are not limited to, AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), XL019, upadacitinib (ABT-494), filgotinib, GLPG-0555, SHR-0302, and brepocitinib (PF-06700841) (JAK1/Tyk2).

Jak3 tyrosine kinase inhibitors include PF-06651600.

Lactoferrin stimulators include recombinant human lactoferrin (VEN-100).

LanC like protein 2 modulators include BT-11.

Leukocyte elastase inhibitors/Leukocyte proteinase-3 inhibitors include tiprelestat.

MAdCAM inhibitors include SHP-647 (PF-547659).

Melanin concentrating hormone (MCH-1) antagonists include CSTI-100.

Melanocortin MC1 receptor agonists include ASP-3291, and PL-8177.

Metalloprotease-9 inhibitors include GS-5745.

Microbiome modulator include ABI-M201.

Natriuretic peptide receptor C agonists include plecanatide.

Neuregulin-4 ligands include NRG-4.

NKG2 D activating NK receptor antagonists include JNJ-4500.

NLPR3 inhibitors include dapansutrile, BMS-986299, SB-414, MCC-950, IFM-514, JT-194, PELA-167, and NBC-6.

Farnesoid X receptor (FXR and NR1H4) agonists or modulators include AGN-242266, cilofexortromethamine (GS-9674), EDP-305, EYP-001, GNF-5120, MET-409, nidufexor (LMB-763), obeticholic acid, TERN-101, and tropifexor.

Nuclear factor kappa B inhibitors include Thetanix.

Opioid receptor antagonists include naltrexone, and IRT-103.

OX40 ligand inhibitors include KHK-4083.

Oxidoreductase inhibitors include olsalazine.

Pellino homolog 1 inhibitors include BBT-401.

P2X7 purinoceptor modulators include SGM-1019.

PDE 4 inhibitors include apremilast.

PPAR alpha/delta agonists include elafibranor (GFT-1007).

PPAR gamma agonists include GED-0507-34-Levo.

Protein fimH inhibitors include sibofimloc (EB-8018).

P-selectin glycoprotein ligand-1 inhibitors include SEL-K2, AbGn-168H, and neihulizumab.

Ret tyrosine kinase receptor inhibitors include GSK-3179106.

RIP-1 kinase inhibitors include GSK-2982772.

RIP-2 kinase inhibitors include GSK-2983559.

Sphingosine 1 phosphate phosphatase 1 stimulators include etrasimod.

Sphingosine-1-phosphate receptor-1 agonists include ozanimod. mocravimod (KRP-203), and BMS-986166.

Sphingosine-1-phosphate receptor-1 agonists/Sphingosine-1-phosphate receptor-5 agonists include ozanimod.

Sphingosine-1-phosphate receptor-1 antagonists include amiselimod (MT-1303).

Sphingosine-1-phosphate receptor-1 modulators include OPL-002.

Stem cell antigen-1 inhibitors include Ampion (DMI-9523).

Superoxide dismutase modulators include midismase.

Syk inhibitors include GS-9876.

Tissue transglutaminase inhibitor includes zampilimab.

TLR-3 antagonists include PRV-300.

TLR-4 antagonists include JKB-122.

Toll-like receptor 8 (TLR8) inhibitors include E-6887, IMO-4200, IMO-8400, IMO-9200, MCT-465, MEDI-9197, motolimod, resiquimod, VTX-1463, and VTX-763.

TLR-9 agonists include cobitolimod, IMO-2055, IMO-2125, lefitolimod, litenimod, MGN-1601, and PUL-042.

TNF alpha ligand inhibitors include adalimumab, certolizumab pegol, infliximab, golimumab, DLX-105, Debio-0512, HMPL-004, CYT-020-TNFQb, Hemay-007. and V-565.

TNF antagonists include AVX-470, tulinercept, and etanercept.

TPL-2 inhibitors include GS-4875.

Tumor necrosis factor 14 ligand modulators include AEVI-002.

Tumor necrosis factor 15 ligand inhibitors include PF-06480605.

Tyk2 tyrosine kinase inhibitors include PF-06826647, and BMS-986165.

TrkA receptor antagonist includes SNA-125.

Type I IL-1 receptor antagonists include anakinra.

Zonulin inhibitors include larazotide acetate.

Included herein are methods of treatment in which a compound described herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, the anti-inflammatory compound is an anti-C5 monoclonal antibody (such as eculizumab or pexelizumab), a TNF antagonist, such as entanercept, or infliximab, which is an anti-TNF alpha monoclonal antibody.

Included herein are methods of treatment in which a compound described herein, is administered in combination with an immunosuppressant. In some embodiments, the immunosuppressant is methotrexate, leflunomide, cyclosporine, tacrolimus, azathioprine, or mycophenolate mofetil.

Included herein are methods of treatment in which a compound described herein, is administered in combination with a class of agent for treatment of IBD. Examples of classes of agents for treatment of IBD that can be used in combination with a compound described herein include ASK1 inhibitors, beta adrenoceptor antagonists, BTK inhibitors, beta-glucuronidase inhibitors, bradykinin receptor modulators, calcineurin inhibitors, calcium channel inhibitors, cathepsin S inhibitors, CCR3 chemokine antagonists, CD40 ligand receptor antagonists, chemokine CXC ligand inhibitors, CHST15 gene inhibitors, collagen modulators, CSF-1 antagonists, cyclooxygenase inhibitors, cytochrome P450 3A4 inhibitors, eotaxin ligand inhibitors, EP4 prostanoid receptor agonists, erythropoietin receptor agonists, fractalkine ligand inhibitors, free fatty acid receptor 2 antagonists, GATA 3 transcription factor inhibitors, glucagon-like peptide 2 agonists, glucocorticoid agonists, guanylate cyclase receptor agonists, histone deacetylase inhibitors, HLA class II antigen modulators, IL-12 antagonists, IL-13 antagonists, IL-23 antagonists, IL-6 antagonists, IL-6 receptor modulators, interleukin-7 receptor modulators, IL-7 antagonists, IL-8 antagonists, integrin alpha-4/beta-1 antagonists, integrin alpha-4/beta-7 antagonists, integrin alpha-E antagonists, integrin antagonists, integrin beta-7 antagonists, interleukin ligand inhibitors, interleukin-2 ligand, interleukin receptor 17A antagonists, interleukin-1 beta ligands, interleukin-1 beta ligand modulators, IRAK4 inhibitors, JAK tyrosine kinase inhibitors, Jak1 tyrosine kinase inhibitors, Jak3 tyrosine kinase inhibitors, LanC like protein 2 modulators, lipoxygenase modulators, MAdCAM inhibitors, matrix metalloprotease inhibitors, melanocortin agonists, metalloprotease-9 inhibitors, natriuretic peptide receptor C agonists, neuregulin-4 ligands, NKG2 D activating NK receptor antagonists, opioid receptor antagonists, opioid receptor delta antagonists, oxidoreductase inhibitors, P2X7 purinoceptor agonists, PDE 4 inhibitors, phagocytosis stimulating peptide modulators, potassium channel inhibitors, PPAR alpha agonists, PPAR delta agonists, PPAR gamma agonists, protein fimH inhibitors, P-selectin glycoprotein ligand-1 inhibitors, RNA polymerase inhibitors, sphingosine 1 phosphate phosphatase 1 stimulators, sphingosine 1 phosphate phosphatase modulators, sphingosine-1-phosphate receptor-1 agonists, sphingosine-1-phosphate receptor-1 antagonists, sphingosine-1-phosphate receptor-1 modulators, sphingosine-1-phosphate receptor-5 modulators, STAT3 gene inhibitors, stem cell antigen-1 inhibitors, superoxide dismutase modulators, superoxide dismutase stimulators, SYK inhibitors, TGF beta 1 ligand inhibitors, thymulin agonists, TLR antagonists, TLR agonists, TNF alpha ligand inhibitors, TNF antagonists, tumor necrosis factor 14 ligand modulators, type II TNF receptor modulators, Tpl 2 inhibitors, and Zonulin inhibitors.

Included herein are methods of treatment in which a compound described herein is administered in combination with an agent for treatment of IBD. Examples of agents for treatment of IBD that can be used in combination with a compound described herein, or a pharmaceutically acceptable salt, stereoisomer, mixture of stereoisomers, tautomer, or deuterated analog thereof, include those provided herein for the treatment of an inflammatory disease or condition, and ABX-464, adalimumab; alicaforsen, ALLO-ASC-CD, AMG-966, anakinra, apremilast; Alequel; AMG-139; amiselimod, ASD-003, ASP-3291, AX-1505, BBT-401, balsalazide; beclomethasone dipropionate; BI-655130, BMS-986184; budesonide; CEQ-508; certolizumab; ChAdOx2-HAV, dexamethasone sodium phosphate, DNVX-078, etanercept; cibinetide; *Clostridium butyricum*; ETX-201, golimumab; GS-4997, GS-9876, GS-4875, GS-4059, infliximab; mesalazine, HLD-400, LYC-30937 EC; IONIS-JB11-2.5Rx, JNJ-64304500, JNJ-4447, naltrexone; natalizumab; neihulizumab, olsalazine; PH-46-A, propionyl-L-carnitine; PTG-100; remestemcel-L; tacrolimus; teduglutide; tofacitinib; ASP-1002; ustekinumab; vedolizumab; AVX-470; INN-108; SGM-1019; PF-06480605; PF-06651600; PF-06687234; RBX-8225, SER-287; Thetanix; TOP-1288; VBY-129; 99mTc-annexin V-128; bertilimumab; DLX-105; dolcanatide; FFP-104; filgotinib; foralumab; GED-0507-34-Levo; givinostat; GLPG-0974; iberogast; JNJ-40346527; K(D)PT; KAG-308; KHK-4083; KRP-203; larazotide acetate; LY-3074828, midismase; olokizumab; OvaSave; P-28-GST; PF-547659; prednisolone; QBECO; RBX-2660, RG-7835; JKB-122; SB-012; STNM-01; Debio-0512; TRK-170; zucapsaicin; ABT-494; Ampion; BI-655066; carotegast methyl; cobitolimod; elafibranor; etrolizumab; GS-5745; HMPL-004; LP-02, ozanimod; peficitinib; quetmolimab (E-6011); RHB-104; rifaximin; tildrakizumab; tralokinumab; brodalumab; laquinimod; plecanatide; vidofludimus; and AZD-058.

Included herein are methods of treatment in which a compound described herein is administered in combination with an agent for treatment of graft versus host disease. Examples of agents for treatment of graft versus host disease that can be used in combination with a compound described herein include those provided herein for the treatment of an inflammatory disease or condition, and [18F]F-AraG, AM-01, Alpha 1 antitrypsin stimulator: AAT-IV and CSL-964; Allocetra, efavaleukin alfa (AMG-592), arsenic trioxide, ATIR-101, belatacept, belimumab, beta lactamase modulator: ribaxamase, bortezomib, brentuximab vedotin, brimonidine, brimonidine tartrate, cannabidiol, ciclosporin, CYP-001, um, dilanubicel, dornase alfa, DSM-9843, eculizumab, EDP-1066, everolimus, Furestem, GL-101, ibrutinib, IMSUT-CORD, IRX-4204, itolizumab, KD-025, MaaT-013, milatuzumab, mizoribine, mycophenolate mofetil, MSCTC-0010, nalotimagene carmaleucel, MET-2, nilotinib, narsoplimab (OMS-721), pacritinib, PF-05285401, ProTmune, QPI-1002, remestemcel-L, RGI-2001, saratin, SCM-CGH, sirolimus, T-allo10, telmisartan, TOP-1288, TZ-101, voclosporin; CCR5 chemokine antagonist: Ieronlimab (PRO-140); CD40 ligand receptor antagonist: iscalimab; Complement C1s subcomponent inhibitor: CE-1145, sutimlimab, Cinryze, BIVV-009; B-lymphocyte antigen CD20 inhibitor: obinutuzumab, rituximab; CASP9 gene stimulator: rivogenlecleucel; CD3 antagonist or CD7 inhibitor: T-Guard; Complement C5a factor inhibitor: olendalizumab; Dipeptidyl peptidase IV inhibitor: begelomab; JAK1/2 tyrosine kinase inhibitor: ruxolitinib; Jak1 tyrosine kinase inhibitor: itacitinib; Interleukin-2 ligand: aldesleukin; Interleukin 22 ligand: F-652; IL-2 receptor alpha subunit inhibitor: basiliximab and inolimomab; IL-6 receptor agonist: PLX-1; IL-6 receptor antagonist: clazakizumab; OX40 ligand inhibitor: KY-1005; An example of such OX40 inhibitor is a compound disclosed in U.S. Pat. No. 8,450,460, the entire contents of which are incorporated herein by reference; Signal transducer CD24 modulator: CD24-IgFc; Somatostatin receptor agonist: Thymoglobulin; and sphingosine-1-phosphate receptor-1 agonist: ponesimod.

Included herein are methods of treatment in which a compound described herein is administered in combination with an agent for treatment of primary sclerosing cholangitis. Examples of agents for treatment of primary sclerosing cholangitis that can be used in combination with compounds described herein include those provided herein for the treatment of an inflammatory disease or condition, and BTT-1023, CM-101, Doconexent, GRI-0124, HTD-1801, HTD-2802, hymecromone, IDN-7314, NGM-282, norursodeoxycholic acid, ORBCEL-C, integrin alpha-V/beta-1 and beta-6 antagonist: PLN-74809; PPAR delta agonist: seladelpar lysine; SCT-5-27, PTGS2 gene and TGF beta 1 gene inhibitor: SCT-5-27, and STP-705; Farnesoid X receptor (FXR, NR1H4) agonists or modulators: AGN-242266, cilofexor tromethamine (GS-9674), EDP-305, EYP-001, GNF-5120, MET-409, nidufexor (LMB-763), obeticholic acid, TERN-101, tropifexor; liver X receptor antagonist: DUR-928; and CCR5/CCR2 chemokine antagonist: cenicriviroc.

In some embodiments, the one or more additional therapeutic agents is selected from the group consisting of: combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In some embodiments, the one or more additional therapeutic agents is selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In some embodiments, the one or more additional therapeutic agent is an immune modulating agent, e.g., an immunostimulant or an immunosuppressant. In certain other embodiments, an immune modulating agent is an agent capable of altering the function of immune checkpoints, including the CTLA-4, LAG-3, B7-H3, B7-H4, Tim3, BTLA, KIR, A2aR, CD200 and/or PD-1 pathways. In other embodiments, the immune modulating agent is immune checkpoint modulating agents. Exemplary immune checkpoint modulating agents include anti-CTLA-4 antibody (e.g., ipilimumab), anti-LAG-3 antibody, anti-B7-H3 antibody, anti-B7-H4 antibody, anti-Tim3 antibody, anti-BTLA antibody, anti-KIR antibody, anti-A2aR antibody, anti CD200 antibody, anti-PD-1 antibody, anti-PD-L1 antibody, anti-CD28 antibody, anti-CD80 or -CD86 antibody, anti-B7RP1 antibody, anti-B7-H3 antibody, anti-HVEM antibody, anti-CD137 or -CD137L antibody, anti-OX40 or -OX40L antibody, anti-CD40 or -CD40L antibody, anti-GAL9 antibody, anti-IL-10 antibody and A2aR drug. For certain such immune pathway gene products, the use of either antagonists or agonists of such gene products is contemplated, as are small molecule modulators of such gene products. In some embodiments, immune modulating agents include those agents capable of altering the function of mediators in cytokine mediated signaling pathways.

In some embodiments, a compound as disclosed herein (e.g., a compound described herein may be combined with one or more (e.g., one, two, three, four, one or two, one to three, or one to four) additional therapeutic agents in any dosage amount of the compound described herein (e.g., from 10 mg to 1000 mg of compound).

A compound described herein may be combined with the agents provided herein in any dosage amount of the compound (e.g., from 50 mg to 500 mg of compound) the same as if each combination of dosages were specifically and individually listed.

In some embodiments, provided are kits comprising a pharmaceutical composition comprising a compound described herein or a compound described herein and at least one additional therapeutic agent, or a pharmaceutically acceptable salt thereof, and at least one pharmaceutically acceptable carrier. In some embodiments, kits comprising a compound disclosed herein, or a pharmaceutically acceptable salt, stereoisomer, mixture of stereoisomers, tautomer, or deuterated analog thereof, in combination with one or more (e.g., one, two, three, four, one or two, or one to three, or one to four) additional therapeutic agents are provided. Any pharmaceutical composition provided in the present disclosure may be used in the kits, the same as if each and every composition were specifically and individually listed for use in a kit. In some embodiments, the kit comprises instructions for use in the treatment of an inflammatory disease or condition. In some embodiments, the instructions in the kit are directed to use of the pharmaceutical composition for the treatment of IBD.

List of Abbreviations and Acronyms

Abbreviation Meaning

% Percent
° C. Degree Celsius
Ac Acetyl
AcOH Acetic acid
ACN/CH₃CN/MeCN Acetonitrile
ADME Absorption, distribution, metabolism and excretion
AIBN 2,2'-Azobis(2-methylpropionitrile)
Aq. Aqueous
ASK Apoptosis signal-regulating kinase
Bicarb Bicarbonate
Bn Benzyl
BOC/Boc Tert-butyloxycarbonyl
Bpin Pinacolborane
br Broad
CAS Chemical Abstract Service
cataCXium A Di(1 ann-tpsphine
CNS Central nervous system
COPD Chronic obstructive pulmonary disease
CREST Calcinosis, Raynaud's syndrome, esophageal dysmotility, sclerodactyly and telangiectasia
CVP Cyclophosphamide, vincristine, prednisone
d Doublet
D/d Deuterium
DAST Diethylaminosulfur trifluoride
DABCO® 1,4-Diazabicyclo[2.2.2]octane
DCC N,N'-Dicyclohexylcarbodiimide
DCE Dichloroethane
DCM Dichloromethane/methylene chloride
dd Doublet of doublets
DIEA N,N-Diisopropylethylamine
DIPEA N,N-Diisopropylethylamine
DMA N,N-Dimethylacetamide
DMAP 4-Dimethylaminopyridine
DME Dimethoxy ethane
DMF Dimethylformamide
DMPK Drug metabolism and pharmacokinetics
DMSO Dimethylsulfoxide
DPPA Diphenylphosphoryl azide
dppf 1,1'-Bis(diphenylphosphino)ferrocene
dppp 1,3-Bis(diphenylphosphino)propane
EC₅₀ The half maximal effective concentration
equiv/eq Equivalents
EA Ethyl acetate
Et Ethyl
Et₂O Diethyl ether
EtOAc/AcOEt Ethyl acetate
EtOH Ethanol
F Fahrenheit
FBS Fetal bovine serum
g Grams
Gp Glycoprotein
h/hr Hours
HATU (1-[Bis(dimethylamino)methylene]-1H-1,2,3-triazolo[4,5-b]pyridinium 3-oxid hexafluorophosphate)
hex Hexanes
HPLC High pressure liquid chromatography
Hz Hertz
IL Interleukin
IUPAC International Union of Pure and Applied Chemistry
J Coupling constant (MHz)
JAK Janus kinase
Kg/kg Kilogram
KOAc Potassium acetate
L Liter
LCMS/LC-MS Liquid chromatography-mass spectrometry
LHMDS Lithium hexamethyl disilazide
LiMg-TMP 2,2,6,6-Tetramethylpiperidinylmagnesium chloride lithium chloride complex
M Molar
m multiplet
M+ Mass peak
M+H Mass peak plus hydrogen
m-CPBA Meta-Chloroperbenzoic acid
Me Methyl
Me₂N Dimethylamine
MeI Methyl Iodide
MeOH Methanol
MeOTs Methyl Tosylate
mg Milligram
MHz Megahertz
min/m Minute
ml/mL Milliliter
mM Millimolar
mmol Millimole
mol Mole
MS Mass spectroscopy
MS Multiple sclerosis
MsCl Methanesulfonyl chloride
MTBE Methyl tert-Butyl ether
M/Z Mass/Charge
N Normal
NADH Nicotinamide adenine dinucleotide in reduced form
NaOH Sodium hydroxide
NBS N-Bromosuccinimide
ng Nanograms
NIS N-Iodosuccinimide
nM Nanomolar
NMR Nuclear magnetic resonance
ON Overnight
PEG Polyethylene glycol
PET Positron emission tomography
Ph Phenyl
PhMe Toluene
PhNO₂ Nitrobenzene
PhNTf₂ N-Phenyl triflamide
pH Expressing the acidity or alkalinity of a solution
prep Preparative
RA Rheumatoid arthritis
Rf Retention factor RPM Revolutions per minute
RT/r Room temperature
RuPhos 2-Dicyclohexylphosphino-2',6'-diisopropoxybiphenyl
s Second
s Singlet
sat. Saturated
SFC Super-critical fluid chromatography
SLE Systemic lupus erythematosus
SPECT Single-photon emission computed tomography
SPhos Pd G3 (2-Dicyclohexylphosphino-2',6'-dimethoxybiphenyl) [2-(2'-amino-1,1'-biphenyl)]palladium (II) methanesulfonate
SYK Spleen tyrosine kinase
t Triplet
TBACl Tetrabutylammonium chloride
TBS/TBDMS Tert-butyldimethylsilyl 2-(1H-benzotriazole-1-yl)-1,1,3,3-tetramethylaminium
TBTU tetrafluoroborate
tBuOH Tert-butanol
tBuBrettPhos Pd G3 [(2-Di-tert-butylphosphino-3,6-dimethoxy-2',4',6'-triisopropyl-1,1'-biphenyl)-2-(2'-amino-1,1'-biphenyl)]palladium(II) methanesulfonate
TCA Trichloroacetic acid
TEA/NEt₃ Triethylamine
temp. Temperature
TES Triethylsilane
TFA Trifluoroacetic acid
TFAA Trifluoroacetic acid anhydride
THF Tetrahydrofuran
TLC Thin-layer chromatography
TMP Tetramethyl piperidine
TMS Trimethylsilyl
Tol Toluene
TPL2 Tumor Progression Locus 2 Kinase
Trityl Triphenylmethyl
Vac Vacuum
w/v Weight/volume
w/w Weight/weight
XPhos Pd G3 (2-Dicyclohexylphosphino-2',4',6'-triisopropyl-1,1'-biphenyl)[2-(2'-amino-1,1'-biphenyl)]palladium(II) methanesulfonate
δ Chemical shift (ppm)
μg Microgram
μL/μl Microliter
μM Micromolar
μm Micrometer
μmol Micromole Synthesis The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of formula (I), e.g., compounds having structures described by one or more of formula (I), or other formulas or compounds disclosed herein, or a pharmaceutically acceptable salt, stereoisomer, mixture of stereoisomers, tautomer, or deuterated analog thereof, may be accomplished as described in the following examples.

Salts, such as TFA salts, can be converted to the free-bases/acids or other pharmaceutically acceptable salts.

General Schemes

Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

General Scheme 1

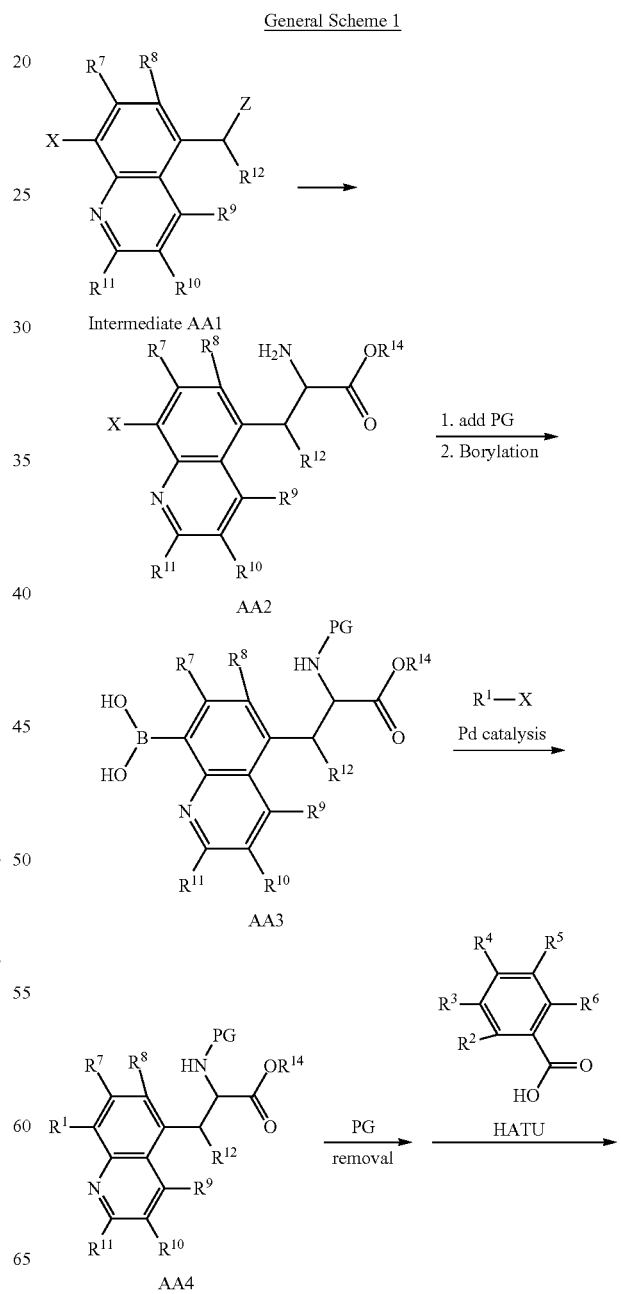

-continued

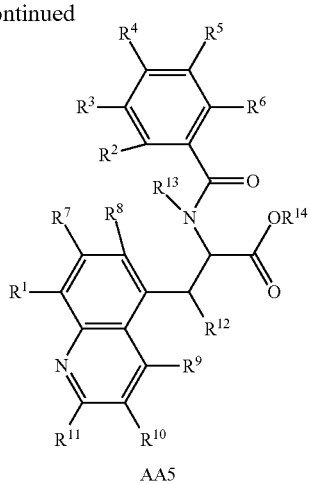

AA5

Scheme 1 describes a general route that was used to prepare some compounds of Formula (I). From Intermediate AA1 that has hydroxyl or halogen group as Z, and halogen group as X, amino acid esters (AA2) can be prepared under a variety of conditions (eg. Schollkopf, Maruoka, etc). After appropriate protection of the free amine with protecting groups (PG), eg. Trityl, Boc, etc., AA2 was converted to a boronic acid or boronic ester (AA3) under standard conditions (eg. Miyaura). $R^1$ was introduced under a variety of cross coupling conditions to give AA4. After removal of the amine protecting group (PG) under appropriate conditions, the amine was coupled with acids to provide heterocyclic compounds AA5.

General Scheme 2

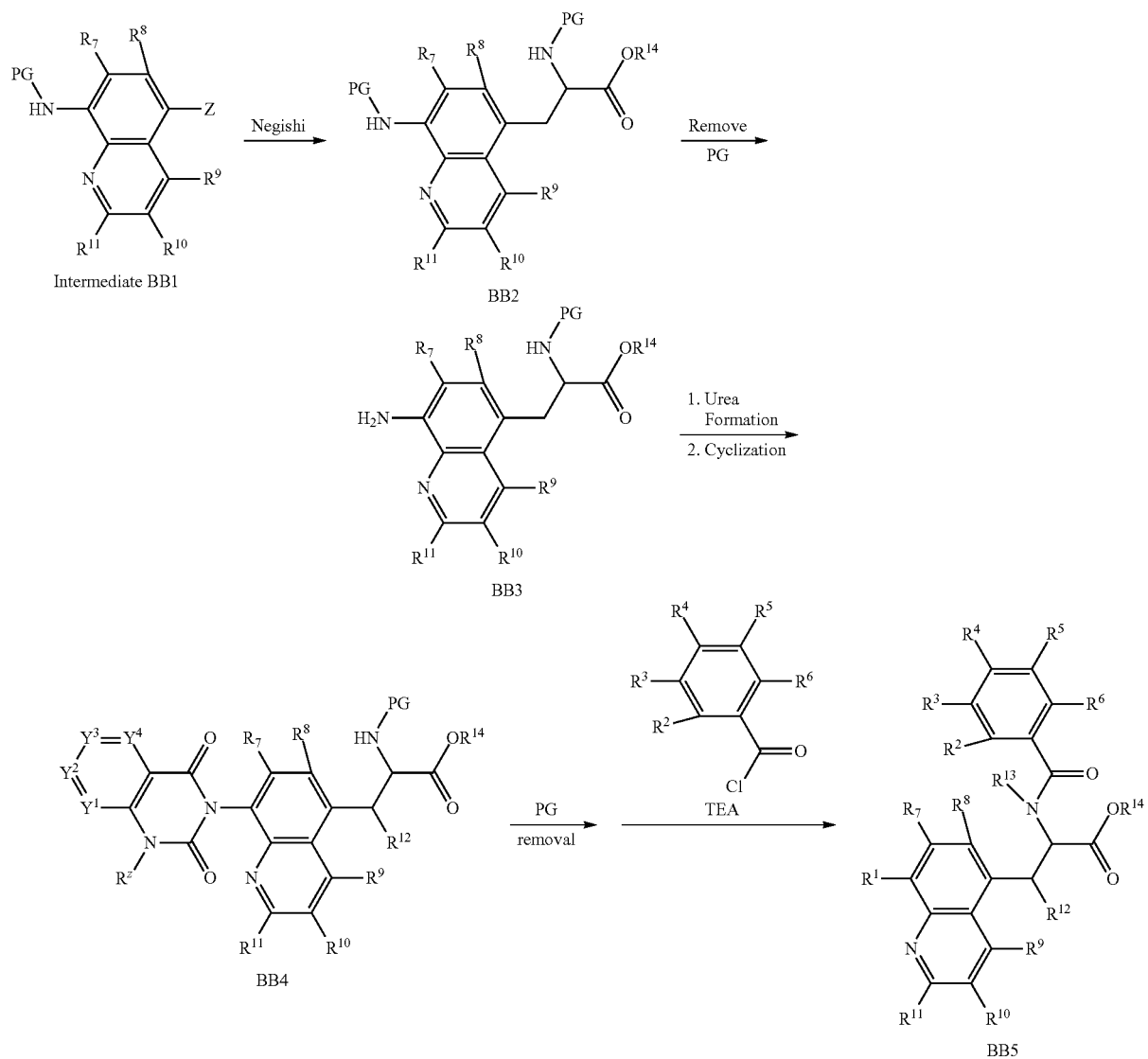

Scheme 2 describes a general route that was used to prepare some compounds of Formula (I). From Intermediate BB1 that has a halogen group as Z, amino acid esters (BB2) can be prepared under a variety of conditions (primarily by Negishi). After appropriate removal of the protecting group (eg. benzyloxycarbonyl, CBZ), BB2 was converted to the free amine (BB3) under standard conditions (eg. Pd/H$_2$). R$^1$ was introduced under a variety of urea forming conditions with appropriate carboxylic acid or amines to give BB4. After removal of the amine protecting group (PG) under appropriate conditions, the amine was coupled with carboxylic acids or acid chlorides to provide heterocyclic compounds BB5.

EXAMPLES

Example 1

Synthesis of 8-bromo-5-methylquinoline (1A): To a stirred solution of 2-bromo-5-methyl aniline (1200 g, 6.45 mol) in nitrobenzene (660 mL) and 75% H$_2$SO$_4$ (3.6 L) was added glycerol (1180 g, 6.45 mol) at RT and then slowly heated to 150° C. for 3 h. The mixture was cooled to RT and poured into ice-water while maintaining the temperature below 10° C. The pH was adjusted ~10 with aqueous 10N NaOH and the product was extracted with ethyl acetate. The combined organic layer was washed with brine, dried over anhydrous Na$_2$SO$_4$ and concentrated under vacuum to afford material that was dissolved in DCM/hexanes (5:1) and stirred for 30 minutes. The solid was filtered off and the filtrate was evaporated under reduced pressure to afford 1A.

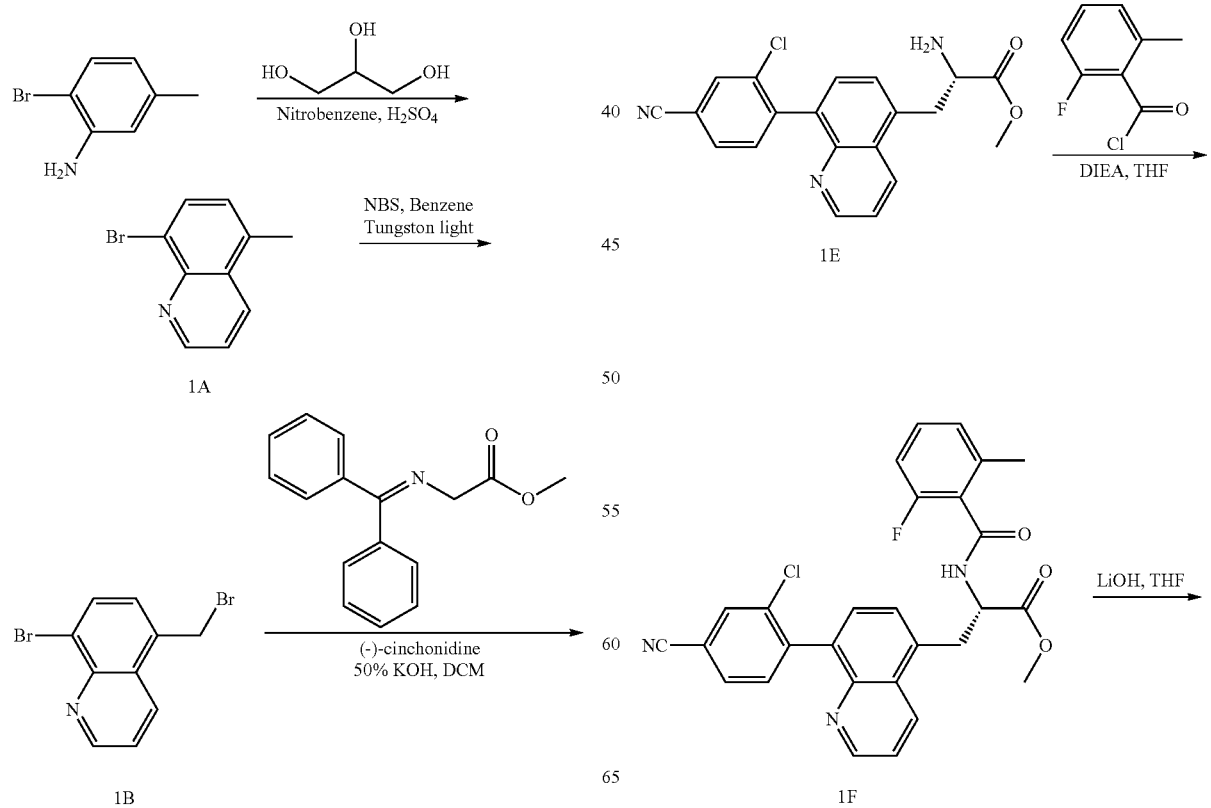

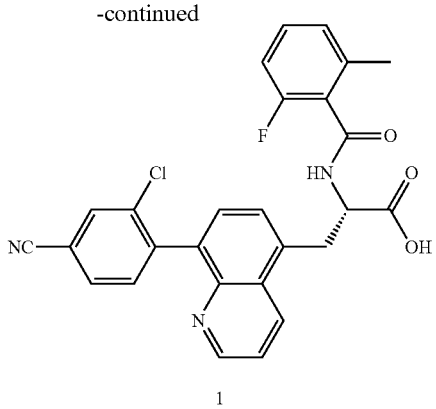

1

Synthesis of 8-bromo-5-(bromomethyl)quinoline (1B): To a stirred solution of compound 1A (500 g, 2.25 mol) in benzene (7.5 L) was added NBS (481 g, 2.7 mol) at RT. The reaction mixture was heated to 80° C. under tungsten light for 12 h. The reaction was cooled to RT, water added and extracted with ethyl acetate. The organic layer was separated, washed with water, brine, and dried over anhydrous $Na_2SO_4$ and concentrated under reduced pressure. This material was triturated with 20% ethyl acetate in hexane at RT. The material was filtered, washed with hexane and dried under reduced pressure to afford 1B.

Synthesis of methyl (S)-3-(8-bromoquinolin-5-yl)-2-((diphenylmethylene)amino) propanoate (1C): To a stirred solution of 1B (392 g, 1.3 mol) in DCM (9 L) was added (−)-cinchonidine (35 g, 0.12 mol) at RT. The reaction mixture was cooled to 10° C., KOH (2.4 L, 50% aq) was added followed by methyl 2-((diphenylmethylene)amino) acetate (300 g, 1.2 mol). The reaction mixture was allowed to stir at RT for 6 h. The reaction mixture was diluted with water and stirred for 15 minutes. DCM was added and the organic layer was washed with brine, dried over anhydrous $Na_2SO_4$, and concentrated under reduced pressure. This material was purified by 100-200 mesh silica gel column chromatography and eluted with 10-15% ethyl acetate in hexane afforded compound 1C.

Synthesis of methyl (S)-2-amino-3-(8-bromoquinolin-5-yl)propanoate (1D): To a stirred solution of 1C (400 g, 845 mmol) in methanol (2 L) was added HCl in 1,4-dioxane (2.8 L, 4N) keeping the temperature below 5° C. The reaction mixture was allowed to stir at RT for 48 h. The reaction mixture was concentrated under reduced pressure, dissolved in water, and washed with ethyl acetate. The aqueous layer was adjusted to ~pH 8 using sat. $NaHCO_3$ and extracted with DCM. The combined organic layer was washed with brine, dried over anhydrous $Na_2SO_4$, and concentrated under reduced pressure to afford a 70:30 mixture of racemic 1D. A suspension of this material in MTBE was heated to reflux for 1 h. The reaction mixture was cooled to RT, the solid was filtered off and the filtrate was evaporated under reduced pressure to obtain a solid, which was again stirred with MTBE at RT. The solid was filtered off and the filtrate was evaporated under reduced pressure to afford 1D. This material was dissolved in ethyl acetate, cooled to 0° C., followed by addition of 4N HCl and allowed to stir at RT for 1 h. The reaction mixture was concentrated under reduced pressure and triturated with MTBE to afford 1D.

Synthesis of methyl (S)-2-amino-3-(8-(2-chloro-4-cyanophenyl)quinolin-5-yl) propanoate (1E): To a microwave vial was added 1D (50 mg, 0.145 mmol), (2-chloro-4-cyanophenyl)boronic acid (45 mg, 0.246 mmol), $Pd(PPh_3)_4$ (8 mg, 0.007 mmol), and aq $Na_2CO_3$ (0.217 mL, 2M) in DME (2 mL). The reaction mixture was allowed to stir at 120° C. for 20 min. EA and water was added to the reaction mixture. The organic layer was washed with brine, dried over anhydrous $Na_2SO_4$, and concentrated under reduced pressure. The material was purified by silica gel chromatography using 0-30% MeOH in EA to afford the title compound.

Synthesis of methyl (S)-3-(8-(2-chloro-4-cyanophenyl)quinolin-5-yl)-2-(2-fluoro-6-methylbenzamido)propanoate (1F): To a stirred solution of 1E (29 mg, 0.08 mmol) in THF (2 mL) was added 2-fluoro-6-methylbenzoyl chloride (21 mg, 0.12 mmol) and DIEA (0.07 mL, 0.4 mmol). The reaction mixture was allowed to stir for 1 h, then diluted with DCM and concentrated. The material was purified on silica gel eluting with MeOH in DCM (0-30%) to give the title compound.

Synthesis of (S)-3-(8-(2-chloro-4-cyanophenyl)quinolin-5-yl)-2-(2-fluoro-6-methylbenzamido)propanoic acid (1): To a stirred solution of 1F (35 mg, 0.07 mmol) in THF (3 mL) was added aqueous LiOH (0.35 mL, 0.035 mmol). The reaction mixture was allowed to stir for 1 h then concentrated under reduced pressure. The material was purified via reverse phase HPLC to afford the title compound. MS (m/z) 488.1 $[M+H]^+$. $^1H$ NMR (400 MHz, DMSO-d6) δ 9.03 (d, J=8.4 Hz, 1H), 8.84 (dd, J=4.2, 1.6 Hz, 1H), 8.64 (dd, J=8.7, 1.7 Hz, 1H), 8.16 (d, J=1.7 Hz, 1H), 7.90 (d, J=7.9 Hz, 1H), 7.68-7.60 (m, 3H), 7.55 (d, J=7.9 Hz, 1H), 7.26 (d, J=6.1 Hz, 1H), 6.99 (d, J=6.7 Hz, 2H), 4.82 (t, J=9.9 Hz, 1H), 3.39 (d, J=12.9 Hz, 1H), 2.65 (s, 1H), 2.31 (s, 1H), 2.07 (s, 1H), 1.96 (s, 3H).

Example 2

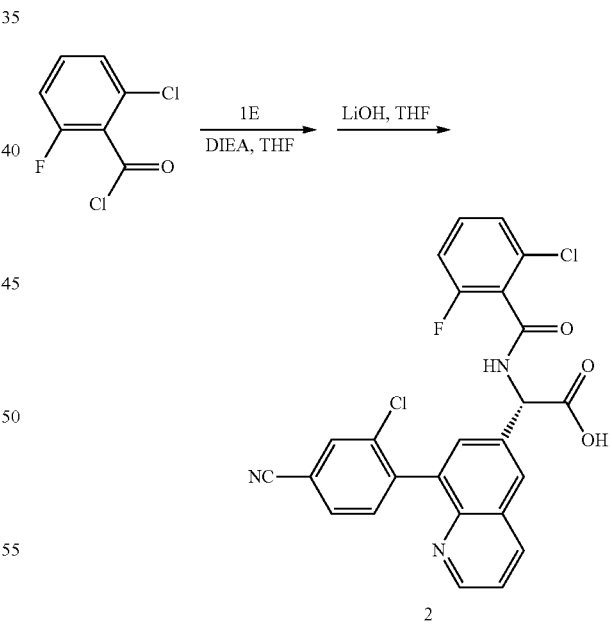

2

Synthesis of (S)-3-(8-(2-chloro-4-cyanophenyl)quinolin-5-yl)-2-(2-chloro-6-fluoro benzamido)propanoic acid (2): The title compound was prepared according to the method presented for the synthesis of compound 1F and 1 starting with 2-chloro-6-fluorobenzoyl chloride and 1E. MS (m/z) 508.1 $[M+H]^+$. $^1H$ NMR (400 MHz, DMSO-d6) δ 9.27 (d, J=8.3 Hz, 1H), 8.84 (dd, J=4.1, 1.6 Hz, 1H), 8.65 (dd, J=8.6, 1.7 Hz, 1H), 8.16 (dd, J=1.7, 0.4 Hz, 1H), 7.91 (d, J=7.9 Hz, 1H), 7.68-7.60 (m, 3H), 7.54 (d, J=7.9 Hz, 1H), 7.42 (td, J=8.3, 6.1 Hz, 1H), 7.30-7.19 (m, 2H), 4.82 (s, 1H), 3.77 (d, J=14.7 Hz, 1H), 3.38 (dd, J=14.6, 10.6 Hz, 1H).

Example 3

Synthesis of methyl (S)-3-(8-bromoquinolin-5-yl)-2-(2,6-difluorobenzamido) propanoate (3A): The title compound was prepared according to the method presented for the synthesis of compound 1F starting with 2,6-difluorobenzoyl chloride and 1D.

Synthesis of methyl (S)-3-(8-(2-chloro-4-cyanophenyl) quinolin-5-yl)-2-(2,6-difluoro benzamido)propanoate (3B): The title compound was prepared according to the method presented for the synthesis of compound 1E starting with 3A.

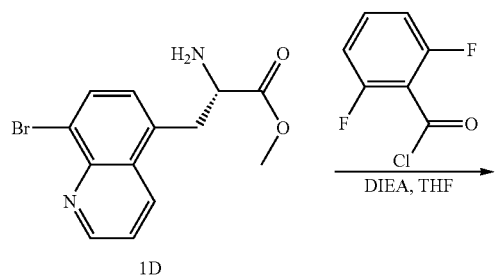

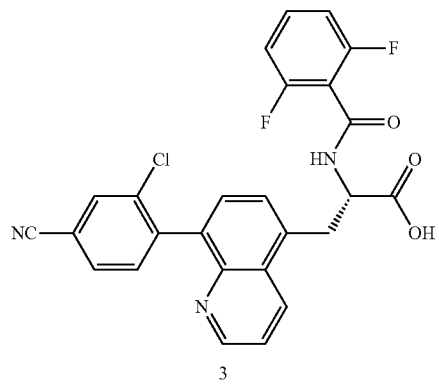

Synthesis of (S)-3-(8-(2-chloro-4-cyanophenyl)quinolin-5-yl)-2-(2,6-difluoro benzamido)propanoic acid (3): The title compound was prepared according to the method presented for the synthesis of compound 1F starting with 3B. MS (m/z) 492.1 [M+H]+. 1H NMR (400 MHz, DMSO-d6) δ 9.25 (d, J=8.1 Hz, 1H), 8.84 (dd, J=4.1, 1.6 Hz, 1H), 8.64 (dd, J=8.8, 1.7 Hz, 1H), 8.15 (d, J=1.7 Hz, 1H), 7.90 (dd, J=8.0, 1.7 Hz, 1H), 7.66-7.61 (m, 3H), 7.57 (d, J=7.9 Hz, 1H), 7.53-7.41 (m, 1H), 7.10 (t, J=8.0 Hz, 2H), 4.77 (s, 1H), 3.76 (s, 1H), 3.41 (s, 1H).

Example 4

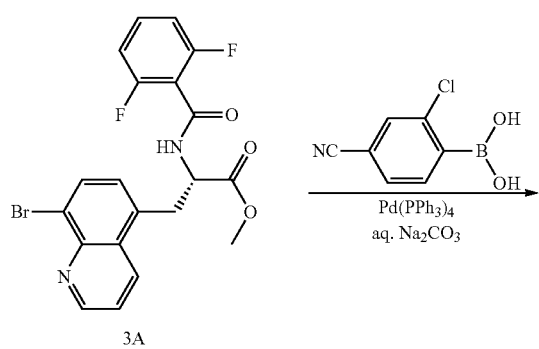

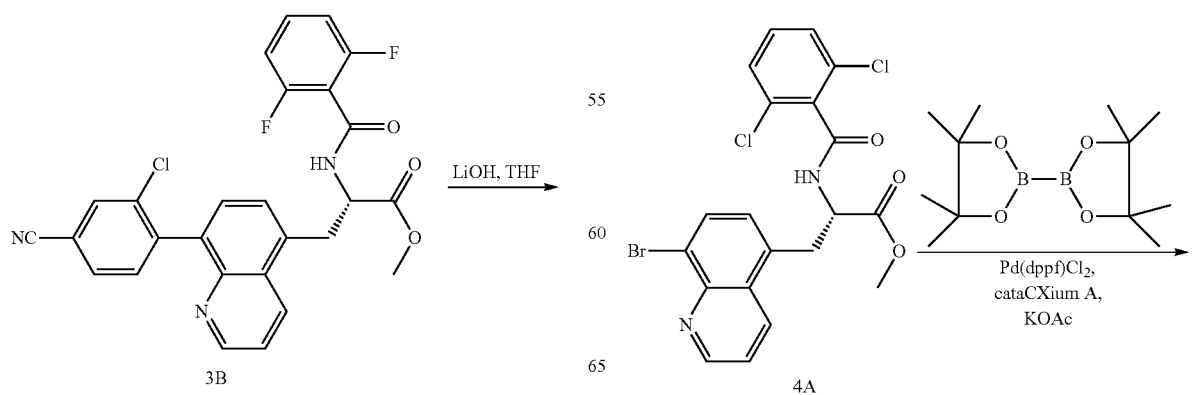

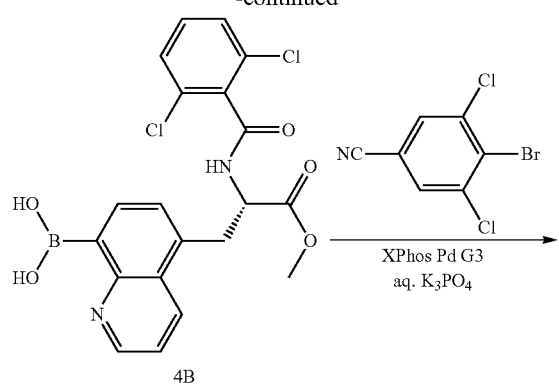

4B

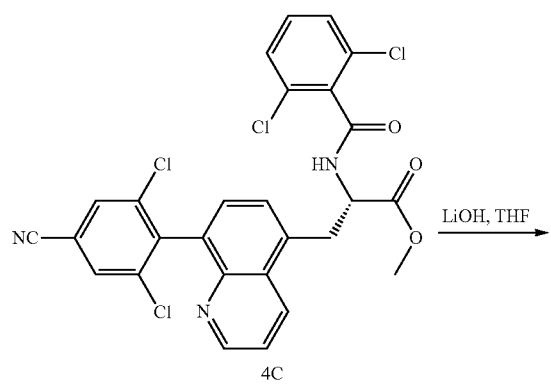

4C

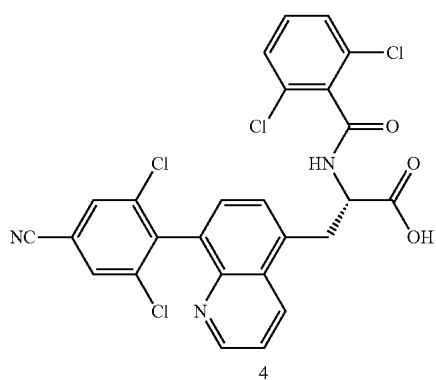

4

Synthesis of methyl (S)-3-(8-bromoquinolin-5-yl)-2-(2,6-dichlorobenzamido) propanoate (4A): The title compound was prepared according to the method presented for the synthesis of compound 3A starting with 2,6-dichlorobenzoyl chloride and 1D.

Synthesis of (S)-(5-(2-(2,6-dichlorobenzamido)-3-methoxy-3-oxopropyl)quinolin-8-yl)boronic acid (4B): To a stirred solution of 4A (0.61 g, 1.4 mmol) in dioxane was added bis(pinacolato)diboron (0.42 g, 1.6 mmol), followed by KOAc (0.4 g, 4.1 mmol), Pd(dppf)Cl₂ (0.03 g, 0.03 mmol), and cataCXium A (0.04 g, 0.08 mmol). The reaction vessel was flushed with nitrogen then heated to 100° C. for 4 hrs. EA was added then filtered through Celite and concentrated under reduced pressure to afford the title compound that was used without further purification.

Synthesis of methyl (S)-3-(8-(2,6-dichloro-4-cyanophenyl)quinolin-5-yl)-2-(2,6-dichlorobenzamido)propanoate (4C): To a stirred solution 4B (0.08 g, 0.017 mmol) in DME was added 4-bromo-3,5-dichlorobenzonitrile (0.08 g, 0.034 mmol), XPhos Pd G3 (0.014 g, 0.0017 mmol) and aq. K₃PO₄ (0.6 mL, 1 M). The reaction was degassed with nitrogen and heated at 90° C. for 30 min. The reaction mixture was concentrated under reduced pressure to give the title compound that was used without further purification.

Synthesis of (S)-3-(8-(2,6-dichloro-4-cyanophenyl)quinolin-5-yl)-2-(2,6-dichloro benzamido)propanoic acid (4): The title compound was prepared according to the method presented for the synthesis of compound 1 starting with 4C. MS (m/z) 558.0 [M+H]⁺. ¹H NMR (400 MHz, DMSO-d6) δ 9.28 (d, J=8.4 Hz, 1H), 8.82 (dd, J=4.2, 1.6 Hz, 1H), 8.65 (dd, J=8.7, 1.6 Hz, 1H), 8.25-8.15 (m, 2H), 7.74-7.62 (m, 2H), 7.60 (d, J=7.3 Hz, 1H), 7.45-7.32 (m, 3H), 4.83 (ddd, J=11.8, 8.6, 3.7 Hz, 1H), 3.78 (dd, J=14.5, 3.8 Hz, 1H), 3.38 (dd, J=14.5, 11.0 Hz, 1H).

Example 5

Synthesis of (S)-(5-(2-(2,6-difluorobenzamido)-3-methoxy-3-oxopropyl)quinolin-8-yl)boronic acid (5A): The title compound was prepared according to the method presented for the synthesis of compound 4B of Example 4 starting with 3A.

Synthesis of methyl (S)-3-(8-(4,5-dichloro-2-methoxyphenyl)quinolin-5-yl)-2-(2,6-difluorobenzamido)propanoate (5B): To a microwave vial was added 5A (145 mg, 0.234 mmol), 1-bromo-4,5-dichloro-2-methoxybenzene (50 mg, 0.195 mmol), Pd(PPh₃)₄ (11 mg, 0.01 mmol), and aq Na₂CO₃ (0.293 mL, 2M) in DME (2 mL). The reaction mixture was allowed to stir at 120° C. for 30 min. EA and water was added to the reaction mixture. The organic layer was washed with brine, dried over anhydrous Na₂SO₄, and concentrated under reduced pressure to afford the title compound.

Synthesis of (S)-3-(8-(4,5-dichloro-2-methoxyphenyl)quinolin-5-yl)-2-(2,6-difluorobenzamido)propanoic acid (5): The title compound was prepared according to the method presented for the synthesis of compound 1 starting with 5B. MS (m/z) 530.7 [M+H]⁺. ¹H NMR (400 MHz, DMSO-d6) δ 9.27 (d, J=8.1 Hz, 1H), 8.86 (dd, J=4.3, 1.6 Hz, 1H), 8.73-8.61 (m, 1H), 7.66 (dd, J=8.6, 4.3 Hz, 1H), 7.60 (q, J=7.4 Hz, 2H), 7.52-7.43 (m, 1H), 7.40 (d, J=8.7 Hz, 2H), 7.16-7.05 (m, 2H), 4.78-4.70 (m, 1H), 3.74 (dd, J=14.5, 4.4 Hz, 1H), 3.64 (s, 3H), 3.39 (dd, J=14.6, 10.1 Hz, 1H), 1.05 (s, 1H).

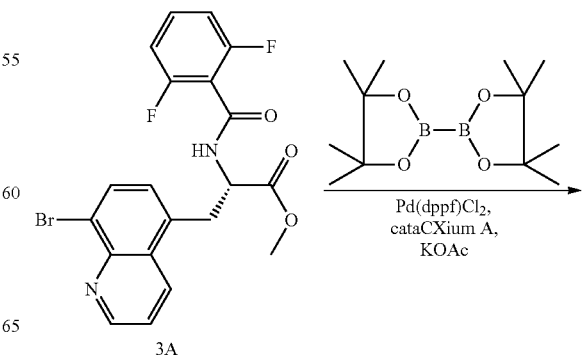

3A

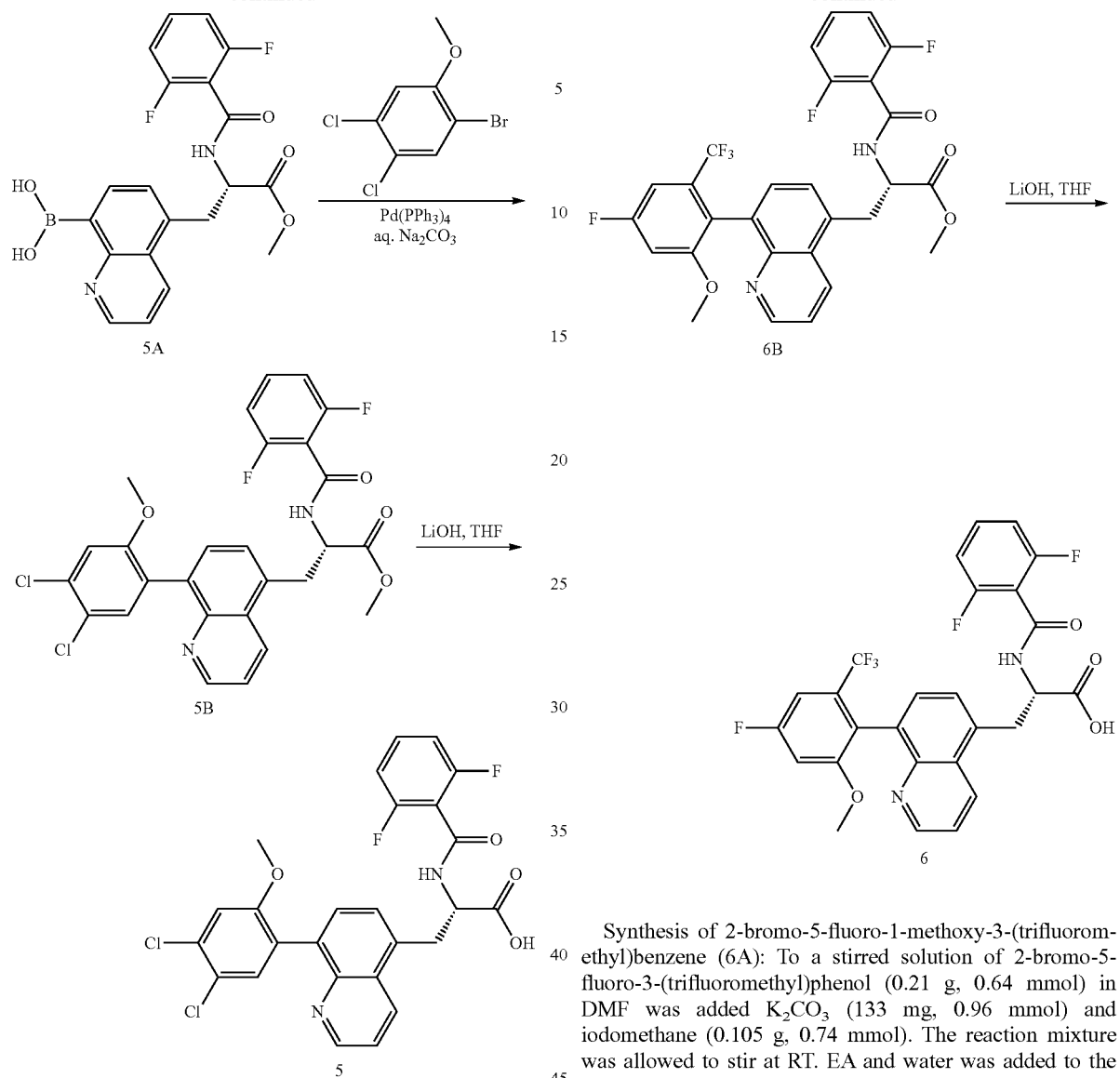

Example 6

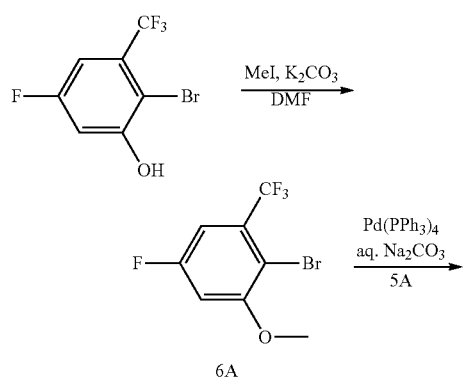

Synthesis of 2-bromo-5-fluoro-1-methoxy-3-(trifluoromethyl)benzene (6A): To a stirred solution of 2-bromo-5-fluoro-3-(trifluoromethyl)phenol (0.21 g, 0.64 mmol) in DMF was added $K_2CO_3$ (133 mg, 0.96 mmol) and iodomethane (0.105 g, 0.74 mmol). The reaction mixture was allowed to stir at RT. EA and water was added to the reaction mixture. The organic layer was washed with brine, dried over anhydrous $Na_2SO_4$, and concentrated under reduced pressure and purified by silica gel chromatography using hexanes/EA as gradient.

Synthesis of methyl (2S)-2-(2,6-difluorobenzamido)-3-(8-(4-fluoro-2-methoxy-6-(trifluoromethyl)phenyl)quinolin-5-yl)propanoate (6B): The title compound was prepared according to the method presented for the synthesis of compound 5B starting with 5A and 6A.

Synthesis of (2S)-2-(2,6-difluorobenzamido)-3-(8-(4-fluoro-2-methoxy-6-(trifluoromethyl)phenyl)quinolin-5-yl)propanoic acid (6): The title compound was prepared according to the method presented for the synthesis of compound 1 starting with 6B. MS (m/z) 549.1 $[M+H]^+$. $^1H$ NMR (400 MHz, DMSO-d6) δ 9.28 (dd, J=12.4, 8.1 Hz, 1H), 8.81 (dd, J=4.2, 1.6 Hz, 1H), 8.67 (d, J=8.7 Hz, 1H), 7.67-7.56 (m, 2H), 7.49 (dqd, J=8.2, 6.6, 1.6 Hz, 2H), 7.41-7.34 (m, 1H), 7.29 (dd, J=9.1, 2.5 Hz, 1H), 7.11 (ddd, J=8.3, 7.4, 3.8 Hz, 2H), 4.84-4.75 (m, 1H), 3.76 (dd, J=31.6, 4.3 Hz, 1H), 3.59 (d, J=5.7 Hz, 3H), 3.42 (ddd, J=21.3, 14.6, 10.4 Hz, 1H).

Examples 7 and 8

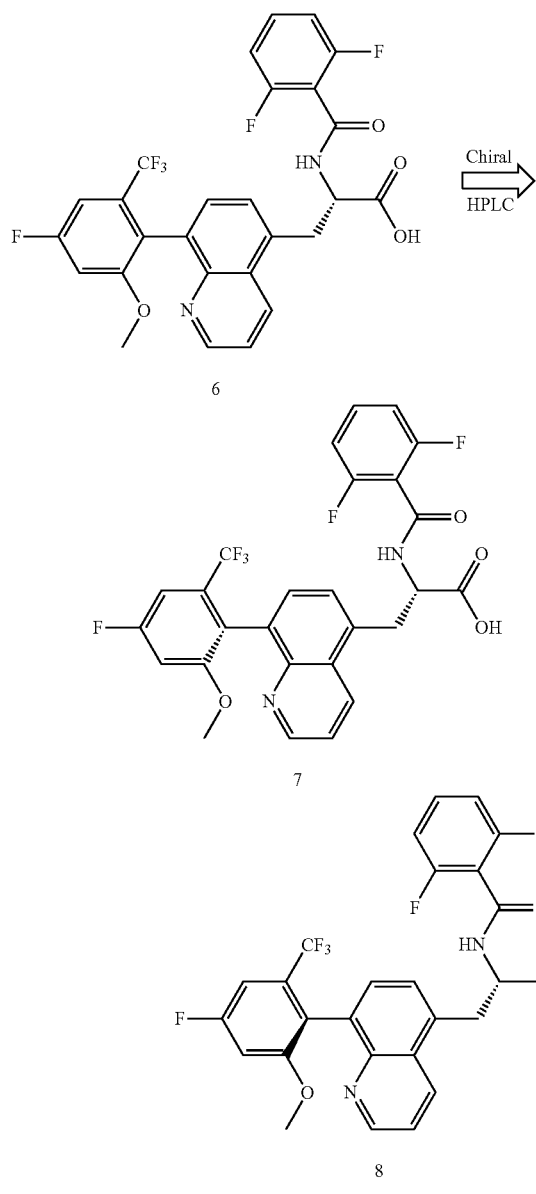

Preparation of (S)-2-(2,6-difluorobenzamido)-3-((R)-8-(4-fluoro-2-methoxy-6-(trifluoromethyl)phenyl)quinolin-5-yl)propanoic acid (7): 6 was separated into its 2 diastereomeric atropisomers by supercritical fluid chromatography using 25% EtOH/TFA co-solvent, at a flow rate of 50 mL/min, using an AD-H 5 μm 21×250 mm column. The title compound was identified as the first eluting peak. MS (m/z) 549.1 [M+H]$^+$. 1H NMR (400 MHz, Methanol-d4) δ 9.36 (dd, J=8.7, 1.6 Hz, 1H), 8.95 (dd, J=5.0, 1.5 Hz, 1H), 8.00 (dd, J=8.7, 5.0 Hz, 1H), 7.89 (d, J=7.4 Hz, 1H), 7.78 (dd, J=7.4, 0.9 Hz, 1H), 7.45 (tt, J=8.4, 6.4 Hz, 1H), 7.32 (s, 1H), 7.30 (s, 1H), 7.02-6.95 (m, 2H), 5.12 (dd, J=9.8, 5.2 Hz, 1H), 4.03 (dd, J=14.4, 5.2 Hz, 1H), 3.71-3.63 (m, 4H).

Preparation of (S)-2-(2,6-difluorobenzamido)-3-((S)-8-(4-fluoro-2-methoxy-6-(trifluoromethyl)phenyl)quinolin-5-yl)propanoic acid (8): 6 was separated into its 2 diastereomeric atropisomers by supercritical fluid chromatography using 25% EtOH/TFA cosolvent, at a flow rate of 50 mL/min, using an AD-H 5 μm 21×250 mm column. The title compound was identified as the second eluting peak. MS (m/z) 549.1 [M+H]$^+$. 1H NMR (400 MHz, Methanol-d4) δ 9.35 (dd, J=8.7, 1.5 Hz, 1H), 8.95 (dd, J=5.0, 1.5 Hz, 1H), 7.99 (dd, J=8.6, 5.0 Hz, 1H), 7.86 (d, J=7.4 Hz, 1H), 7.77 (d, J=7.4 Hz, 1H), 7.45 (tt, J=8.6, 6.4 Hz, 1H), 7.32 (s, 1H), 7.29 (s, 1H), 7.03-6.96 (m, 2H), 5.14 (dd, J=9.9, 5.0 Hz, 1H), 4.04 (dd, J=14.6, 5.1 Hz, 1H), 3.69-3.61 (m, 4H).

Example 9

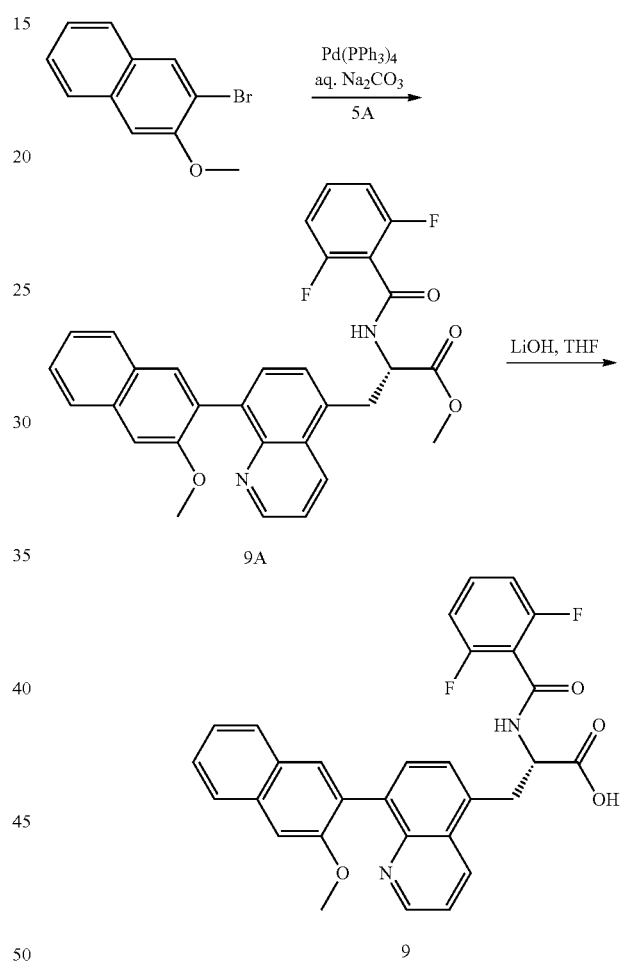

Synthesis of methyl (S)-2-(2,6-difluorobenzamido)-3-(8-(3-methoxynaphthalen-2-yl)quinolin-5-yl)propanoate (9A): The title compound was prepared according to the method presented for the synthesis of compound 5B starting with 2-bromo-3-methoxynaphthalene and 5A.

Synthesis of (S)-2-(2,6-difluorobenzamido)-3-(8-(3-methoxynaphthalen-2-yl)quinolin-5-yl)propanoic acid (9): The title compound was prepared according to the method presented for the synthesis of compound 1 starting with 9A. MS (m/z) 513.0 [M+H]$^+$. 1H NMR (400 MHz, DMSO-d6) δ 9.30 (d, J=8.2 Hz, 1H), 8.86 (d, J=4.8 Hz, 2H), 7.95-7.83 (m, 2H), 7.81-7.64 (m, 3H), 7.55-7.43 (m, 3H), 7.38 (ddd, J=8.1, 6.9, 1.2 Hz, 1H), 7.17-7.08 (m, 2H), 4.80 (ddd, J=10.1, 8.1, 4.4 Hz, 1H), 3.80 (dd, J=14.6, 4.5 Hz, 1H), 3.71 (s, 3H), 3.45 (dd, J=14.6, 10.1 Hz, 1H).

Example 10

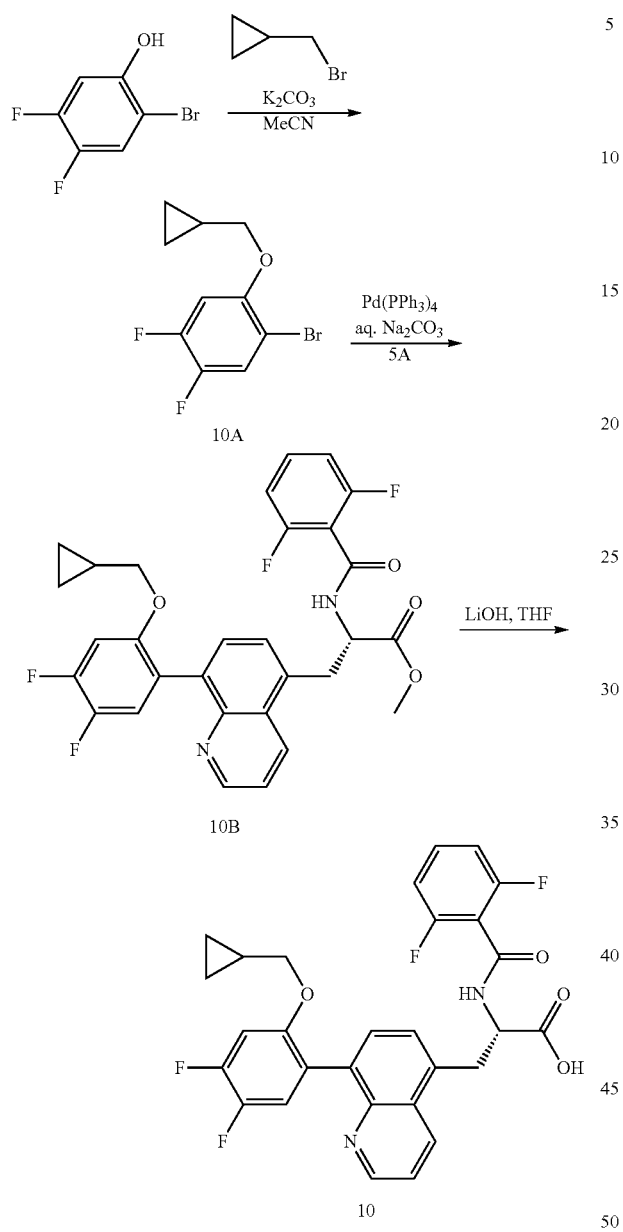

Synthesis of 1-bromo-2-(cyclopropylmethoxy)-4,5-difluorobenzene (10A): To a stirred solution of 2-bromo-4,5-difluorophenol (1.2 g, 5.5 mmol) in MeCN was added $K_2CO_3$ (2.3 g, 16.4 mmol) and (bromomethyl)cyclopropane (0.82 g, 6.0 mmol). The reaction mixture was allowed to stir for 2 hr at 70° C. EA and water was added to the reaction mixture. The organic layer was washed with brine, dried over anhydrous $Na_2SO_4$, concentrated under reduced pressure and purified by silica gel chromatography using hexanes/EA as gradient.

Synthesis of methyl (S)-3-(8-(2-(cyclopropylmethoxy)-4,5-difluorophenyl)quinolin-5-yl)-2-(2,6-difluorobenzamido)propanoate (10B): The title compound was prepared according to the method presented for the synthesis of compound 5B starting with 10A and 5A.

Synthesis of (S)-3-(8-(2-(cyclopropylmethoxy)-4,5-difluorophenyl)quinolin-5-yl)-2-(2,6-difluorobenzamido)propanoic acid (10): The title compound was prepared according to the method presented for the synthesis of compound 1 starting with 10B. MS (m/z) 538.6 [M+H]$^+$. $^1$H NMR (400 MHz, DMSO-d6) δ 12.81 (s, 1H), 9.28 (d, J=8.1 Hz, 1H), 8.89 (d, J=4.1 Hz, 1H), 8.69 (s, 2H), 7.66 (d, J=7.3 Hz, 2H), 7.60 (d, J=7.4 Hz, 1H), 7.55-7.45 (m, 1H), 7.37-7.21 (m, 2H), 7.16-7.08 (m, 2H), 4.76 (td, J=10.3, 9.2, 4.2 Hz, 1H), 3.78-3.74 (m, 2H), 3.41 (dd, J=14.6, 10.0 Hz, 1H), 3.10 (p, J=4.8 Hz, 2H), 0.81 (d, J=4.8 Hz, 1H), 0.24 (dt, J=9.0, 2.9 Hz, 2H), −0.01−−0.05 (m, 2H).

Example 11

Synthesis of methyl (S)-2-(2,6-difluorobenzamido)-3-(8-(3,5,6-trimethylpyridin-2-yl)quinolin-5-yl)propanoate (11A): The title compound was prepared according to the method presented for the synthesis of compound 4C of Example 4 starting with 2-bromo-3,5,6-trimethyl pyridine and 5A.

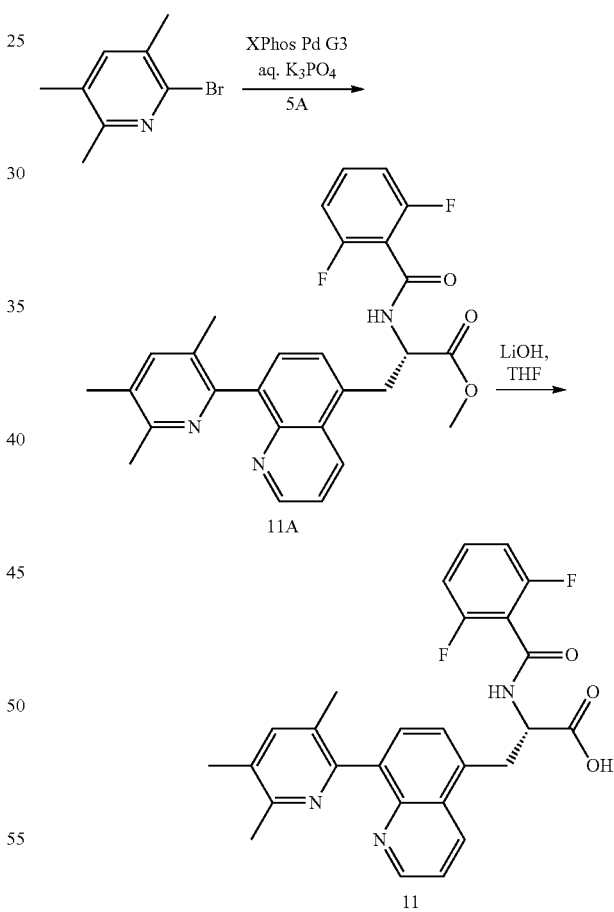

Synthesis of (S)-2-(2,6-difluorobenzamido)-3-(8-(3,5,6-trimethylpyridin-2-yl)quinolin-5-yl)propanoic acid (11): The title compound was prepared according to the method presented for the synthesis of compound 1 starting with 11A. MS (m/z) 476.2 [M+H]$^+$. $^1$H NMR (400 MHz, DMSO-d6) δ 9.33 (d, J=8.3 Hz, 1H), 8.89 (dd, J=4.2, 1.6 Hz, 1H), 8.78-8.72 (m, 1H), 8.36 (s, 1H), 7.92 (d, J=7.5 Hz, 1H), 7.78-7.69 (m, 2H), 7.49 (tt, J=8.5, 6.6 Hz, 1H), 7.11 (dd, J=8.4, 7.6 Hz, 2H), 4.84-4.74 (m, 1H), 3.85 (dd, J=14.3, 4.2 Hz, 1H), 3.43 (dd, J=14.4, 10.4 Hz, 1H), 2.64 (s, 3H), 2.46 (s, 3H), 2.05 (s, 3H).

Example 12

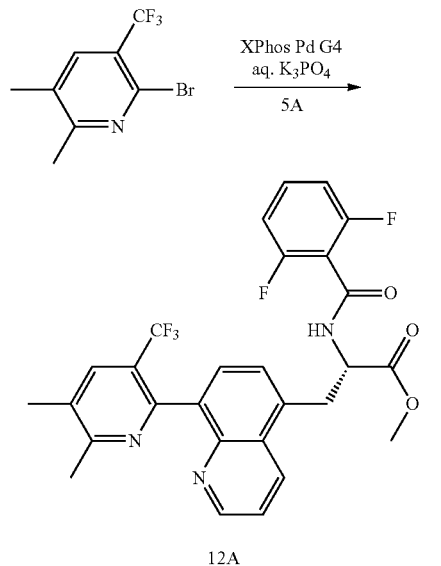

Example 13

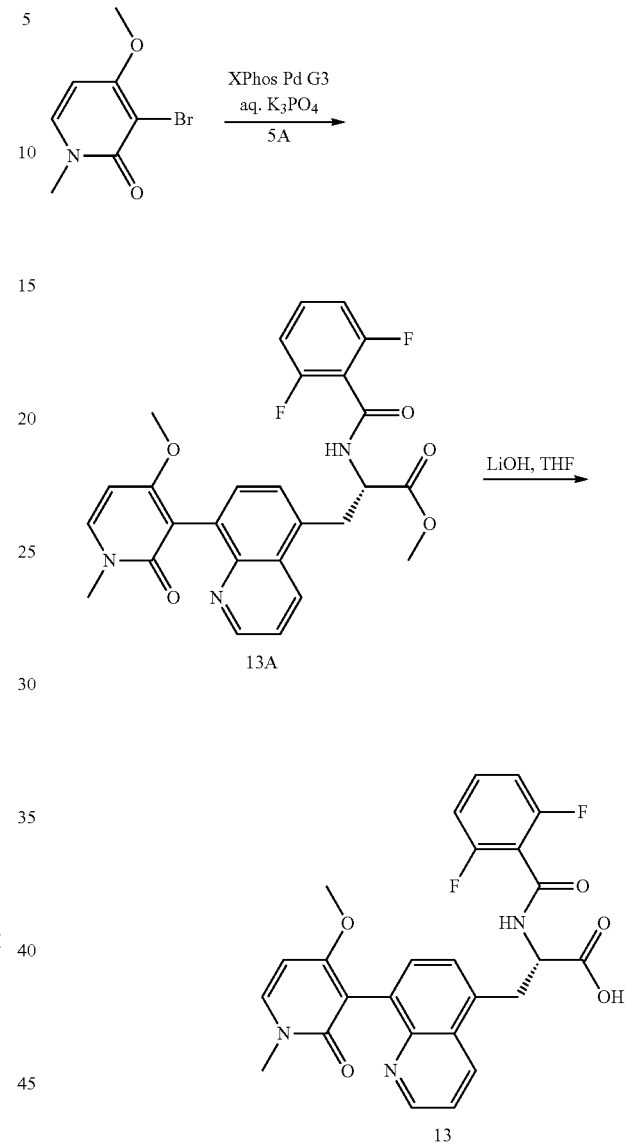

Synthesis of methyl (S)-2-(2,6-difluorobenzamido)-3-(8-(5,6-dimethyl-3-(trifluoromethyl)pyridin-2-yl)quinolin-5-yl)propanoate (12A): The title compound was prepared according to the method presented for the synthesis of compound 4C of Example 4 starting with 2-bromo-5,6-dimethyl-3-(trifluoromethyl)pyridine and 5A with Pd XPhos G4.

Synthesis of (S)-2-(2,6-difluorobenzamido)-3-(8-(5,6-dimethyl-3-(trifluoromethyl) pyridin-2-yl)quinolin-5-yl)propanoic acid (12): The title compound was prepared according to the method presented for the synthesis of compound 1 starting with 12A. MS (m/z) 530.1 [M+H]+. 1H NMR (400 MHz, DMSO-d6) δ 9.28 (d, J=8.1 Hz, 1H), 8.77 (dd, J=4.1, 1.6 Hz, 1H), 8.62 (dd, J=8.7, 1.6 Hz, 1H), 8.02 (s, 1H), 7.62-7.54 (m, 3H), 7.52-7.43 (m, 1H), 7.11 (dd, J=8.5, 7.5 Hz, 2H), 4.74 (td, J=9.0, 4.3 Hz, 1H), 3.75 (m, 1H), 3.40 (m, 1H), 2.50 (s, 3H), 2.41 (s, 3H).

Synthesis of methyl (S)-2-(2,6-difluorobenzamido)-3-(8-(4-methoxy-1-methyl-2-oxo-1,2-dihydropyridin-3-yl)quinolin-5-yl)propanoate (13A): The title compound was prepared according to the method presented for the synthesis of compound 4C of Example 4 starting with 3-bromo-4-methoxy-1-methylpyridin-2(1H)-one and 5A.

Synthesis of (S)-2-(2,6-difluorobenzamido)-3-(8-(4-methoxy-1-methyl-2-oxo-1,2-dihydropyridin-3-yl)quinolin-5-yl)propanoic acid (13): The title compound was prepared according to the method presented for the synthesis of compound 1 starting with 13A. MS (m/z) 464.1 [M+H]+. 1H NMR (400 MHz, DMSO-d6) δ 9.32 (d, J=7.9 Hz, 1H), 9.08-8.98 (m, 1H), 8.96 (d, J=4.6 Hz, 1H), 7.95 (d, J=7.7 Hz, 1H), 7.91-7.83 (m, 1H), 7.75-7.65 (m, 2H), 7.50 (tt, J=8.4, 6.5 Hz, 1H), 7.16-7.08 (m, 2H), 6.49 (dd, J=7.7, 3.5 Hz, 1H), 4.84-4.72 (m, 1H), 3.85-3.75 (m, 1H), 3.68 (d, J=7.5 Hz, 3H), 3.55-3.40 (m, 4H).

Example 14

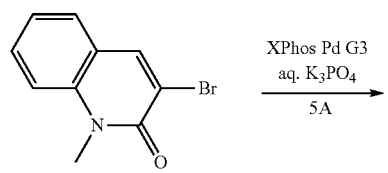

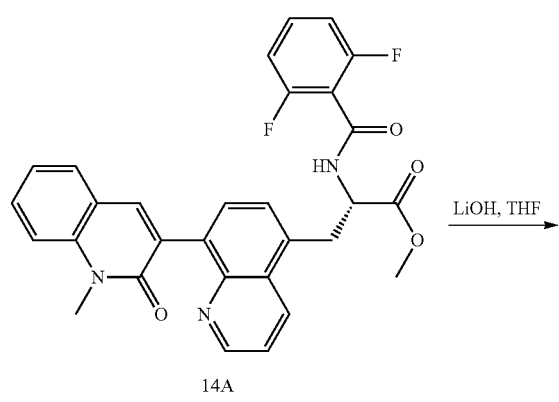

Synthesis of methyl (S)-2-(2,6-difluorobenzamido)-3-(1-methyl-2-oxo-1,2-dihydro-[3,8'-biquinolin]-5'-yl)propanoate (14A): The title compound was prepared according to the method presented for the synthesis of compound 4C of Example 4 starting with 3-bromo-1-methylquinolin-2(1H)-one and 5A.

Synthesis of (S)-2-(2,6-difluorobenzamido)-3-(1-methyl-2-oxo-1,2-dihydro-[3,8'-biquinolin]-5'-yl)propanoic acid (14): The title compound was prepared according to the method presented for the synthesis of compound 1 starting with 14A. MS (m/z) 514.1 [M+H]$^+$. 1H NMR (400 MHz, DMSO-d6) δ 9.30 (d, J=8.1 Hz, 1H), 8.88 (d, J=4.3 Hz, 1H), 8.77 (s, 1H), 7.98 (s, 1H), 7.78 (dd, J=7.8, 1.5 Hz, 1H), 7.74 (d, J=7.3 Hz, 1H), 7.70-7.56 (m, 3H), 7.49 (tt, J=8.4, 6.5 Hz, 1H), 7.35-7.27 (m, 1H), 7.18-7.08 (m, 2H), 4.75 (td, J=9.5, 4.5 Hz, 1H), 3.77 (dd, J=14.5, 4.5 Hz, 1H), 3.68 (s, 3H), 3.44 (dd, J=14.5, 9.9 Hz, 1H).

Example 15

Synthesis of methyl (S)-2-(2,6-difluorobenzamido)-3-(5'-fluoro-[8,8'-biquinolin]-5-yl)propanoate (15A): The title compound was prepared according to the method presented for the synthesis of compound 3B starting with (5-fluoroquinolin-8-yl)boronic acid and 3A.

Synthesis of (S)-2-(2,6-difluorobenzamido)-3-(5'-fluoro-[8,8'-biquinolin]-5-yl)propanoic acid (15): The title compound was prepared according to the method presented for the synthesis of compound 1 starting with 15A. MS (m/z) 502.9 [M+H]$^+$. 1 H NMR (400 MHz, DMSO-d6) δ 9.32 (d, J=8.1 Hz, 1H), 8.74 (dd, J=4.2, 1.8 Hz, 1H), 8.70 (s, 1H), 8.56 (d, J=8.7 Hz, 1H), 7.77-7.43 (m, 8H), 7.19-7.05 (m, 2H), 4.79 (m, 1H), 3.77-3.65 (m, J=1H), 3.56-3.40 (m, 1H).

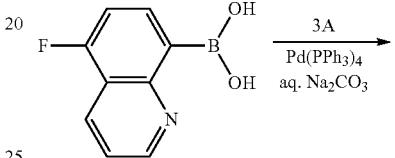

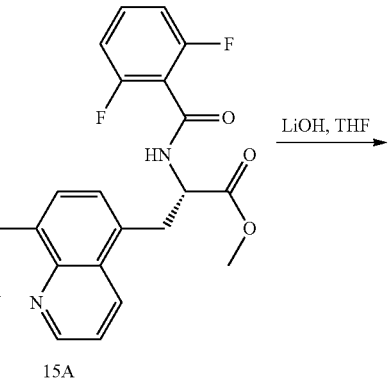

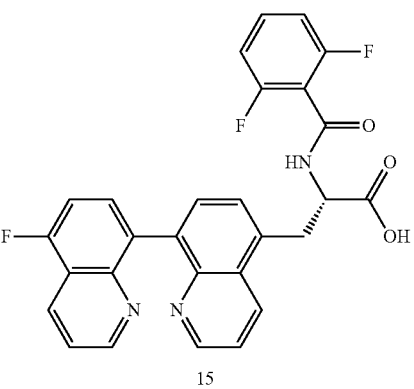

Example 16

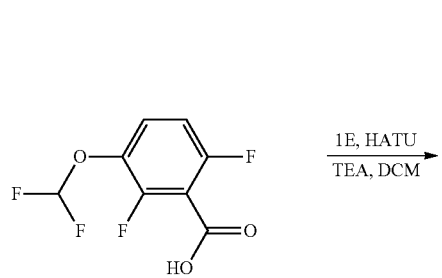

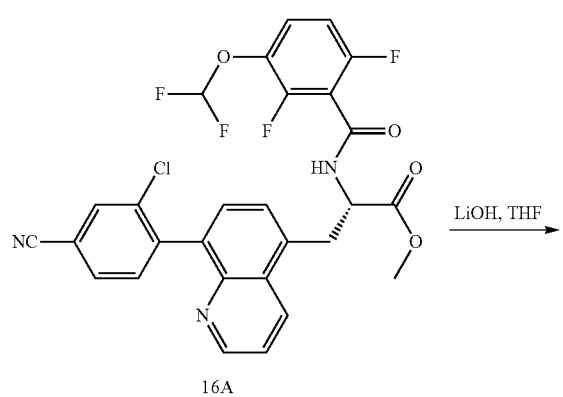

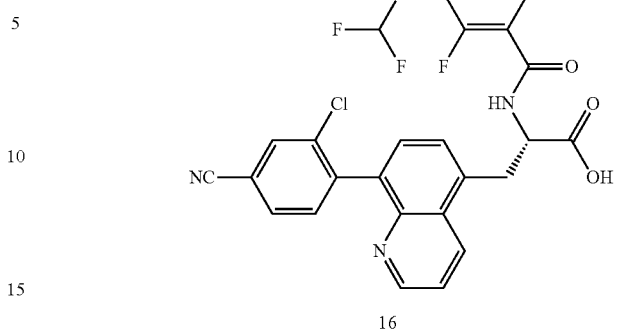

Synthesis of methyl (S)-3-(8-(2-chloro-4-cyanophenyl) quinolin-5-yl)-2-(3-(difluoro methoxy)-2,6-difluorobenzamido)propanoate (16A): To a stirred solution of 1E (0.15 g, 0.41 mmol) in DCM was added 3-(difluoromethoxy)-2, 6-difluorobenzoic acid (0.11 g, 0.49 mmol), HATU (0.187 g, 0.49 mmol) and TEA (0.36 mL, 2.1 mmol). The reaction mixture was allowed to stir for 2 hr at RT. The reaction mixture was concentrated under reduced pressure and used without further purification.

Synthesis of (S)-3-(8-(2-chloro-4-cyanophenyl)quinolin-5-yl)-2-(3-(difluoromethoxy)-2,6-difluorobenzamido)propanoic acid (16): The title compound was prepared according to the method presented for the synthesis of compound 1 starting with 16A. MS (m/z) 559.9 [M+H]⁺. 1H NMR (400 MHz, DMSO-d6) δ 8.16 (m, J=8.4 Hz, 3H), 7.67 (d, J=8.5 Hz, 2H), 7.56-7.21 (m, 6H), 4.75 (ddd, J=11.7, 8.4, 3.7 Hz, 1H), 3.10 (m, 2H) 2.99 (dd, J=14.3, 11.3 Hz, 1H).

Example 17

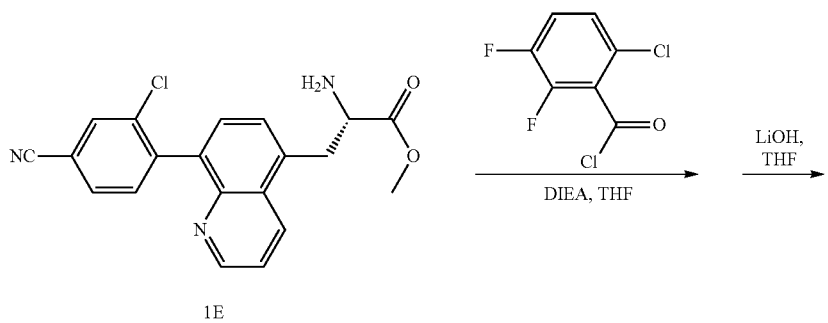

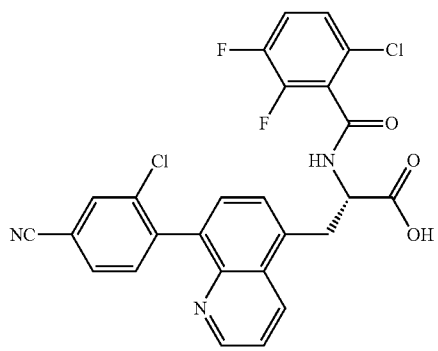

Synthesis of (S)-2-(6-chloro-2,3-difluorobenzamido)-3-(8-(2-chloro-4-cyanophenyl) quinolin-5-yl)propanoic acid (17): The title compound was prepared according to the method presented for the synthesis of compound 1F and 1 starting with 6-chloro-2,3-difluorobenzoyl chloride and 1E. MS (m/z) 559.9 [M+H]⁺. 1H NMR (400 MHz, DMSO-d6) δ 9.37 (d, J=8.4 Hz, 1H), 8.84 (dd, J=4.1, 1.6 Hz, 1H), 8.64 (dd, J=8.6, 1.6 Hz, 1H), 8.16 (dd, J=1.6, 0.4 Hz, 1H), 7.91 (d, J=7.8 Hz, 1H), 7.67-7.64 (m, 1H), 7.63 (s, 2H), 7.55 (d, J=7.9 Hz, 1H), 7.33 (td, J=8.7, 3.8 Hz, 1H), 4.83 (s, 1H), 3.84-3.74 (m, 1H), 3.38 (dd, J=14.6, 10.6 Hz, 1H).

Example 18

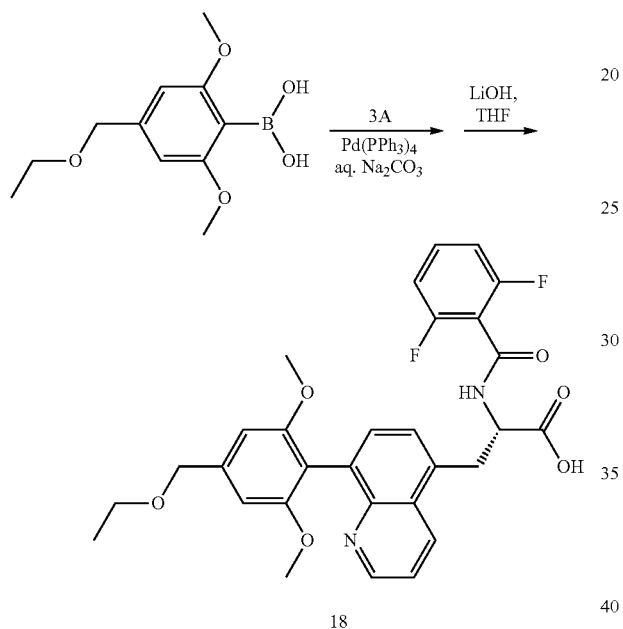

Synthesis of (S)-2-(2,6-difluorobenzamido)-3-(8-(4-(ethoxymethyl)-2,6-dimethoxy phenyl)quinolin-5-yl)propanoic acid (18): The title compound was prepared according to the method presented for the synthesis of compound 3B and 3 starting with (4-(ethoxymethyl)-2,6-dimethoxyphenyl)boronic acid and 3A. MS (m/z) 551.1 [M+H]⁺. 1H NMR (400 MHz, DMSO-d6) δ 13.09 (s, 1H), 9.30 (d, J=8.1 Hz, 1H), 9.10-8.69 (m, 2H), 7.96-7.30 (m, 4H), 7.11 (t, J=8.0 Hz, 2H), 6.75 (d, J=3.4 Hz, 2H), 4.85-4.74 (m, 1H), 4.53 (s, 2H), 3.86-3.66 (m, 1H), 3.64-3.53 (m, 8H), 3.45 (dd, J=14.7, 10.1 Hz, 1H), 1.21 (t, J=7.0 Hz, 3H).

Example 19

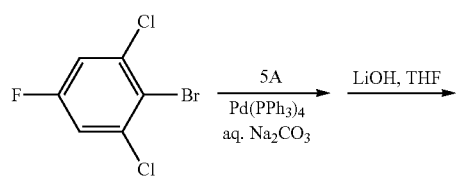

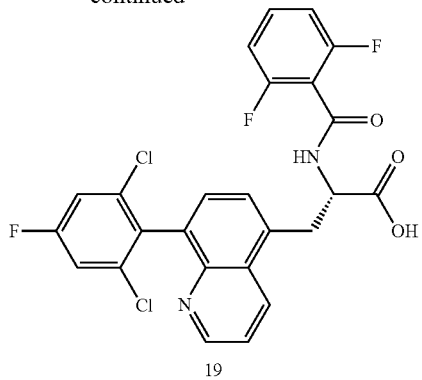

Synthesis of (S)-3-(8-(2,6-dichloro-4-fluorophenyl)quinolin-5-yl)-2-(2,6-difluoro benzamido)propanoic acid (19): The title compound was prepared according to the method presented for the synthesis of compound 5B and 5 starting with 2-bromo-1,3-dichloro-5-fluorobenzene and 5A. MS (m/z) 518.9 [M+H]⁺. 1H NMR (400 MHz, DMSO-d6) δ 13.02 (s, 1H), 9.26 (d, J=8.1 Hz, 1H), 8.82 (dd, J=4.1, 1.6 Hz, 1H), 8.68-8.58 (m, 1H), 7.70-7.59 (m, 3H), 7.57 (d, J=7.3 Hz, 1H), 7.47 (tt, J=8.5, 6.5 Hz, 1H), 7.15-7.03 (m, 2H), 4.78 (ddd, J=10.2, 8.1, 4.4 Hz, 1H), 3.76 (dd, J=14.5, 4.4 Hz, 1H), 3.41 (dd, J=14.6, 10.3 Hz, 1H).

Example 20

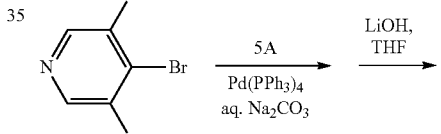

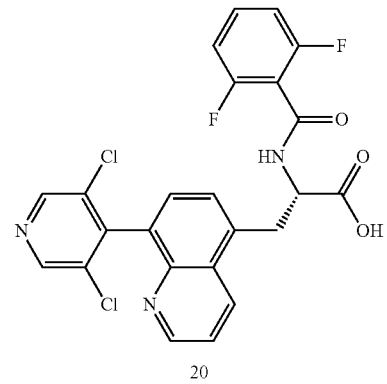

Synthesis of (S)-3-(8-(3,5-dichloropyridin-4-yl)quinolin-5-yl)-2-(2,6-difluoro benzamido)propanoic acid (20): The title compound was prepared according to the method presented for the synthesis of compound 5B and 5 starting with 4-bromo-3,5-dichloropyridine and 5A. MS (m/z) 501.9 [M+H]⁺. 1H NMR (400 MHz, DMSO-d6) δ 9.27 (d, J=8.2 Hz, 1H), 8.83 (dd, J=4.1, 1.6 Hz, 1H), 8.75 (d, J=2.4 Hz, 2H), 8.66 (dd, J=8.7, 1.7 Hz, 1H), 7.69-7.60 (m, 3H), 7.47 (tt, J=8.5, 6.5 Hz, 1H), 7.09 (dd, J=8.4, 7.5 Hz, 2H), 4.80 (ddd, J=10.4, 8.2, 4.4 Hz, 1H), 3.78 (dd, J=14.5, 4.4 Hz, 1H), 3.43 (dd, J=14.6, 10.4 Hz, 1H).

Example 21

Synthesis of (S)-3-(8-(2-chloro-4-cyanophenyl)quinolin-5-yl)-2-(2,6-difluoro-4-methoxybenzamido)propanoic acid (21): The title compound was prepared according to the method presented for the synthesis of compound 16A and 16 starting with 2,6-difluoro-4-methoxybenzoic acid and 1E. MS (m/z) 523.2 [M+H]⁺. 1H NMR (400 MHz, DMSO-d6) δ 9.41 (s, 1H), 8.62 (s, 1H), 8.30 (s, 1H), 8.15-7.98 (m, 4H), 7.11 (d, J=6.7 Hz, 3H), 6.82 (d, J=9.1 Hz, 2H), 6.67 (s, 2H), 4.47 (s, 2H), 3.62 (s, 6H), 3.53 (q, J=7.0 Hz, 2H), 3.18 (dd, J=124.4, 13.3 Hz, 2H), 1.28 (s, 3H), 1.19 (t, J=7.0 Hz, 3H).

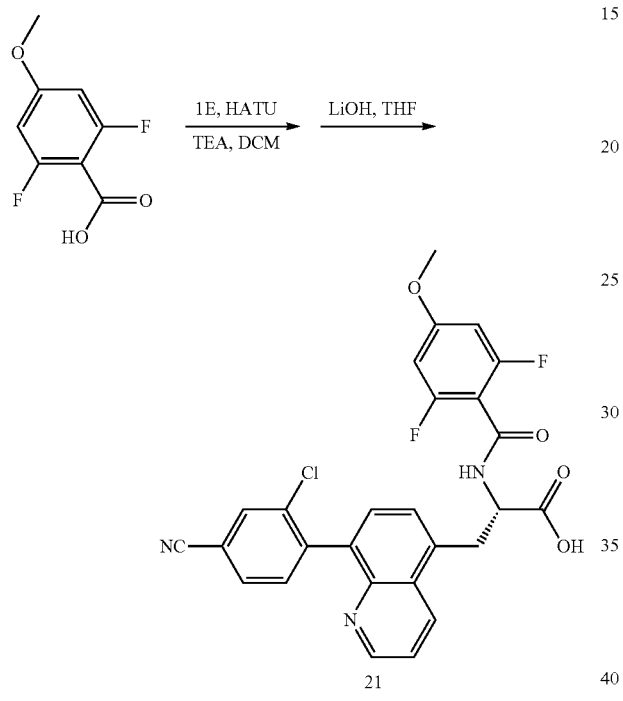

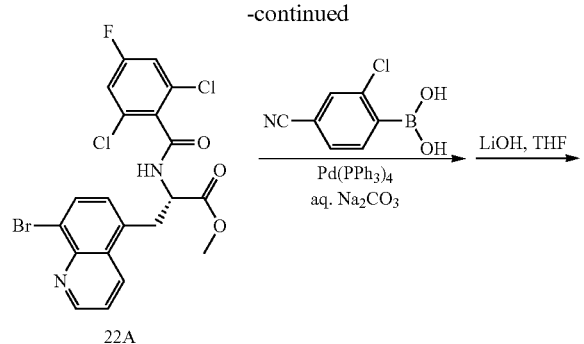

Example 22

Synthesis of (S)-3-(8-(2-chloro-4-cyanophenyl)quinolin-5-yl)-2-(2,6-dichloro-4-fluorobenzamido)propanoic acid (22): The title compound was prepared according to the method presented for the synthesis of compound 3A, 3B, and 3 starting with 2,6-dichloro-4-fluorobenzoyl chloride and 1D. MS (m/z) 541.9 [M+H]⁺. 1H NMR (400 MHz, DMSO-d6) δ 9.26 (d, J=8.5 Hz, 1H), 8.83 (dd, J=4.1, 1.6 Hz, 1H), 8.65 (dd, J=8.7, 1.7 Hz, 1H), 8.15 (dd, J=1.6, 0.4 Hz, 1H), 7.94-7.87 (m, 1H), 7.69-7.58 (m, 3H), 7.50 (d, J=8.6 Hz, 3H), 4.84 (s, 1H), 3.76 (dd, J=14.5, 4.1 Hz, 1H), 3.37 (s, 1H).

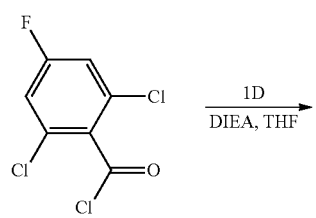

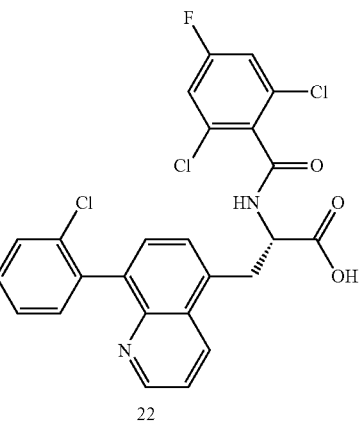

Example 23

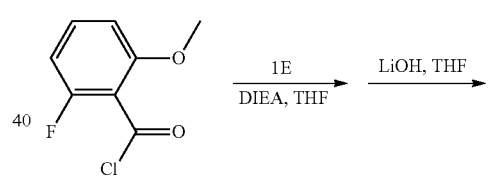

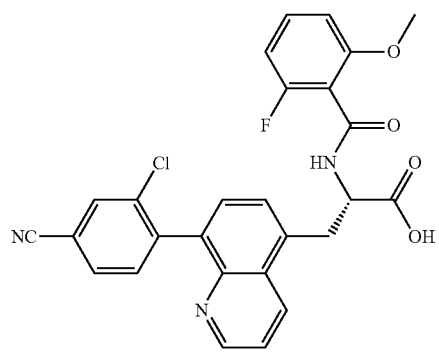

Synthesis of (S)-3-(8-(2-chloro-4-cyanophenyl)quinolin-5-yl)-2-(2-fluoro-6-methoxy benzamido)propanoic acid (23): The title compound was prepared according to the method presented for the synthesis of compound 1F and 1 starting with 2-fluoro-6-methoxy benzoyl chloride and 1E. MS (m/z) 504.2 [M+H]⁺. 1H NMR (400 MHz, DMSO-d6) δ 8.92 (d, J=8.1 Hz, 1H), 8.84 (dd, J=4.1, 1.6 Hz, 1H), 8.64 (dd, J=8.7, 1.7 Hz, 1H), 8.16 (dd, J=1.6, 0.4 Hz, 1H), 7.90 (dd, J=7.9, 1.7 Hz, 1H), 7.68-7.64 (m, 2H), 7.58 (d, J=7.6

Hz, 1H), 7.35 (td, J=8.4, 6.8 Hz, 1H), 6.84 (d, J=8.5 Hz, 1H), 6.78 (t, J=8.6 Hz, 1H), 4.80-4.68 (m, 1H), 3.69-3.65 (m, 1H), 3.63 (s, 3H), 3.50-3.40 (m, 1H).

Example 24

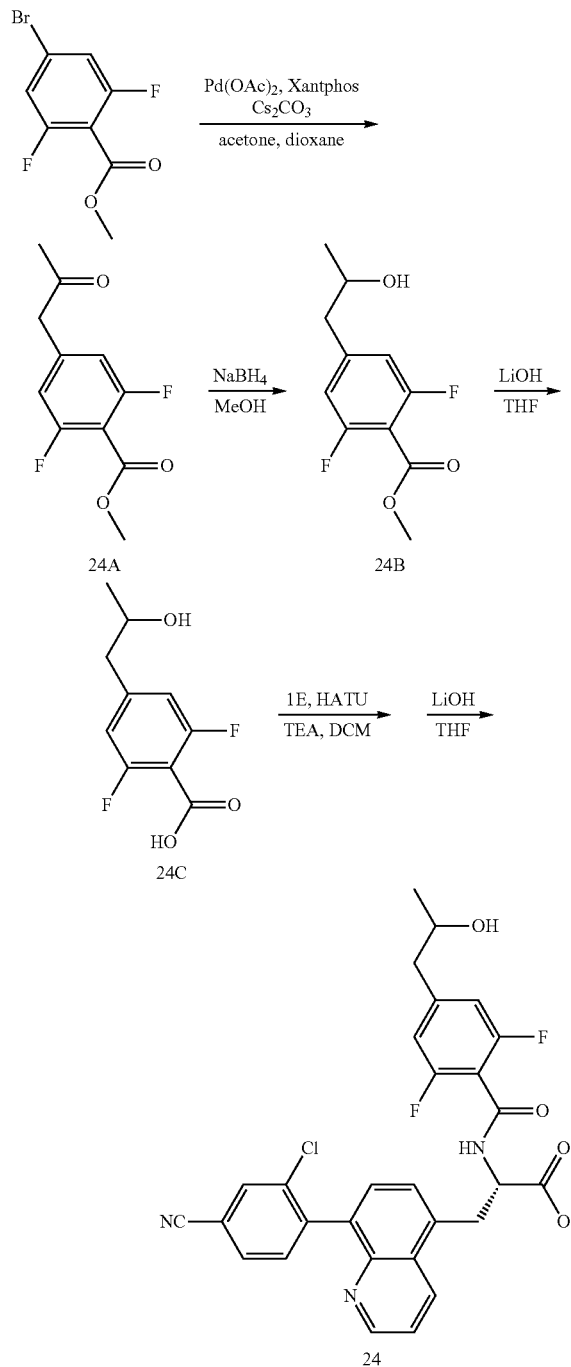

Synthesis of methyl 2,6-difluoro-4-(2-oxopropyl)benzoate (24A): To a stirred solution of methyl 4-bromo-2,6-difluorobenzoate (0.15 g, 0.41 mmol) in 1,4-dioxane was added acetone (1.8 mL), Pd(OAc)$_2$ (18 mg, 0.081 mmol), Cs$_2$CO$_3$ (1.05 g, 3.2 mmol), and 4,5-bis(diphenyl phosphino)-9,9-dimethylxanthene (93.98 mg, 0.16 mmol). This mixture was flushed with N$_2$ for 5 min, then heated to 100° C. for 2.5 hours. The reaction mixture was filtered through celite, rinsed with EA and purified by silica gel chromatography using EA in hexanes as eluent to give the title compound.

Synthesis of methyl 2,6-difluoro-4-(2-hydroxypropyl)benzoate (24B): To a stirred solution of 24A (306.4 mg, 1.34 mmol) in MeOH was added ammonium acetate (1.04 g, 13.43 mmol). NaBH$_4$ (83.81 mg, 2.22 mmol) was then slowly added to prevent major exotherm. The reaction mixture was stirred for 2 hours at RT followed by addition of NaOH (1M) and DCM. The organic layer was washed with brine, dried, and concentrated under reduced pressure. The material was purified by silica gel chromatography using EA and hexanes as eluent to afford the title compound.

Synthesis of 2,6-difluoro-4-(2-hydroxypropyl)benzoic acid (24C): To a stirred solution of 24B (87.3 mg, 0.38 mmol) in THF was added LiOH (79.56 mg, 1.9 mmol). The reaction mixture was stirred at RT for 3 hours then HCl (1 M) and EA was added. The organic layer was washed with brine, dried, and concentrated under reduced pressure to give the title compound which was used without further purification.

(2S)-3-(8-(2-chloro-4-cyanophenyl)quinolin-5-yl)-2-(2,6-difluoro-4-(2-hydroxypropyl) benzamido)propanoic acid (24): The title compound was prepared according to the method presented for the synthesis of compound 16A and 16 starting with 1E and 24C. MS (m/z) 550.2 [M+H]$^+$. 1H NMR (400 MHz, DMSO-d6) δ 9.18 (d, J=8.1 Hz, 1H), 8.84 (dd, J=4.2, 1.6 Hz, 1H), 8.64 (dd, J=8.6, 1.6 Hz, 1H), 8.16 (d, J=1.6 Hz, 1H), 7.90 (dd, J=7.9, 1.6 Hz, 1H), 7.68-7.59 (m, 3H), 7.57 (d, J=7.9 Hz, 1H), 6.94 (d, J=8.8 Hz, 2H), 4.80-4.69 (m, 1H), 3.80 (pd, J=8.9, 7.6, 3.0 Hz, 2H), 3.40 (s, 1H), 2.62 (d, J=6.2 Hz, 2H), 1.02 (d, J=6.1 Hz, 3H).

Example 25

Synthesis of tert-butyl (S)-4-((3-(8-(2-chloro-4-cyanophenyl)quinolin-5-yl)-1-methoxy-1-oxopropan-2-yl)carbamoyl)-3,5-difluorobenzoate (25A): The title compound was prepared according to the method presented for the synthesis of compound 16A starting with 4-(tert-butoxycarbonyl)-2,6-difluorobenzoic acid and 1E.

Synthesis of (S)-4-((3-(8-(2-chloro-4-cyanophenyl)quinolin-5-yl)-1-methoxy-1-oxopropan-2-yl)carbamoyl)-3,5-difluorobenzoic acid (25B): To a stirred solution of 25A (150 mg, 0.25 mmol) in DCM was added TFA (1.5 mL). The reaction mixture was stirred for 2 hours at RT, concentrated under reduced pressure, and then purified by silica gel chromatography using DCM and MeOH as the eluent to afford the title compound.

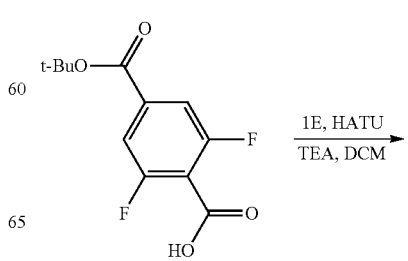

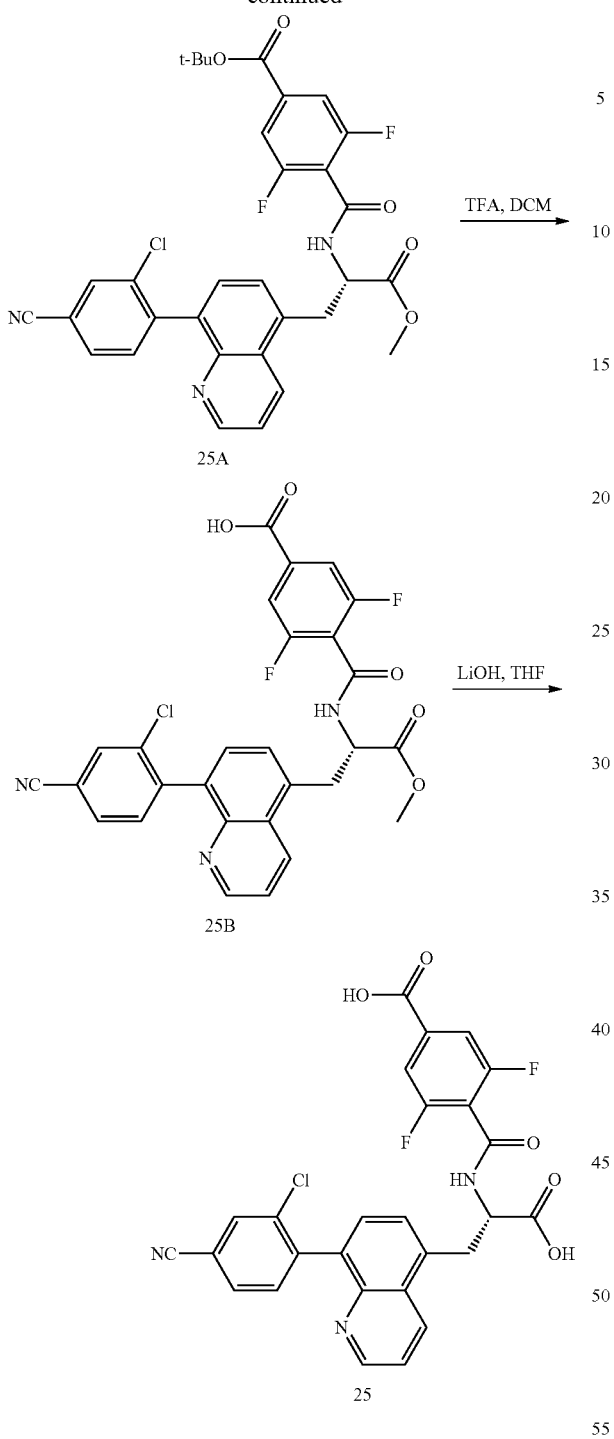
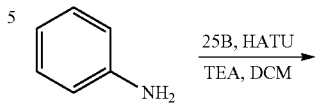
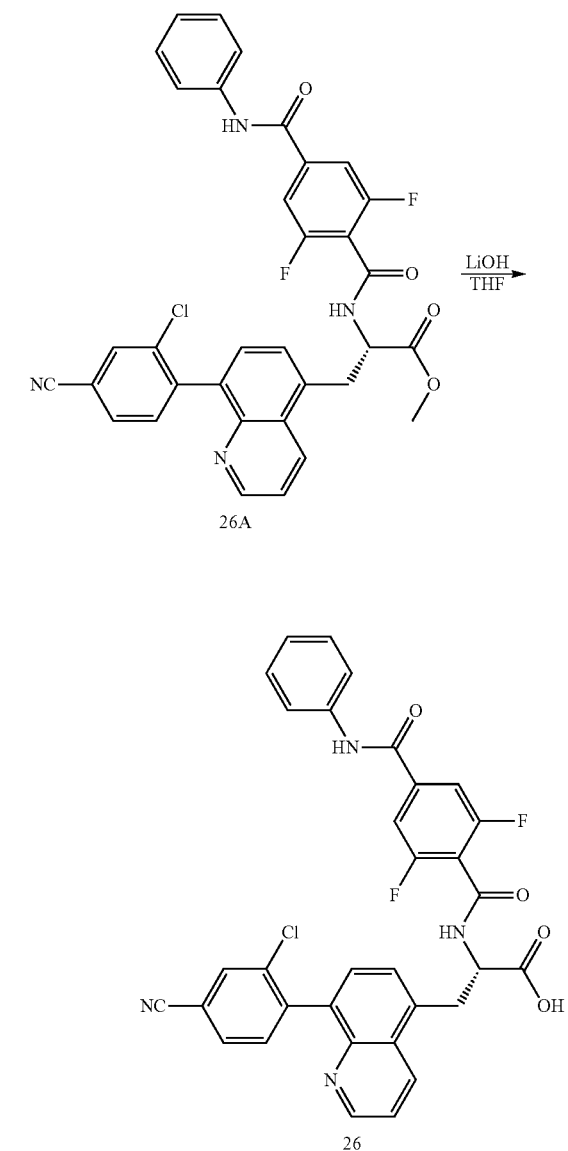

Example 26

(S)-4-((1-carboxy-2-(8-(2-chloro-4-cyanophenyl)quinolin-5-yl)ethyl)carbamoyl)-3,5-difluorobenzoic acid (25): The title compound was prepared according to the method presented for the synthesis of compound 1 starting with 25B. MS (m/z) 535.8 [M+H]$^+$. 1 H NMR (400 MHz, DMSO-d6) δ 9.40 (d, J=8.2 Hz, 1H), 8.84 (dd, J=4.1, 1.6 Hz, 1H), 8.64 (dd, J=8.7, 1.7 Hz, 1H), 8.16 (d, J=1.6 Hz, 1H), 7.95-7.86 (m, 1H), 7.64 (t, J=4.3 Hz, 1H), 7.61 (d, J=5.1 Hz, 1H), 7.57 (dd, J=7.7, 6.0 Hz, 2H), 4.80 (t, J=11.5 Hz, 1H), 3.79 (s, 1H), 3.41 (s, 1H).

(S)-3-(8-(2-chloro-4-cyanophenyl)quinolin-5-yl)-2-(2,6-difluoro-4-(phenylcarbamoyl) benzamido)propanoic acid (26): The title compound was prepared according to the method presented for the synthesis of compound 16A and 16 starting with 25B and aniline. MS (m/z) 611.2 [M+H]$^+$. 1H NMR (400 MHz, DMSO-d6) δ 10.35 (s, 1H), 9.41 (d, J=8.3 Hz, 1H), 8.88-8.80 (m, 1H), 8.65 (d, J=8.7 Hz, 1H), 8.16 (d, J=1.6 Hz, 1H), 7.91 (d, J=8.2 Hz, 1H), 7.76-7.61 (m, 7H), 7.57 (d, J=7.9 Hz, 1H), 7.42-7.29 (m, 2H), 7.12 (t, J=7.4 Hz, 1H), 4.81 (s, 1H), 3.76 (s, 1H), 3.25-3.17 (m, 1H).

Example 27

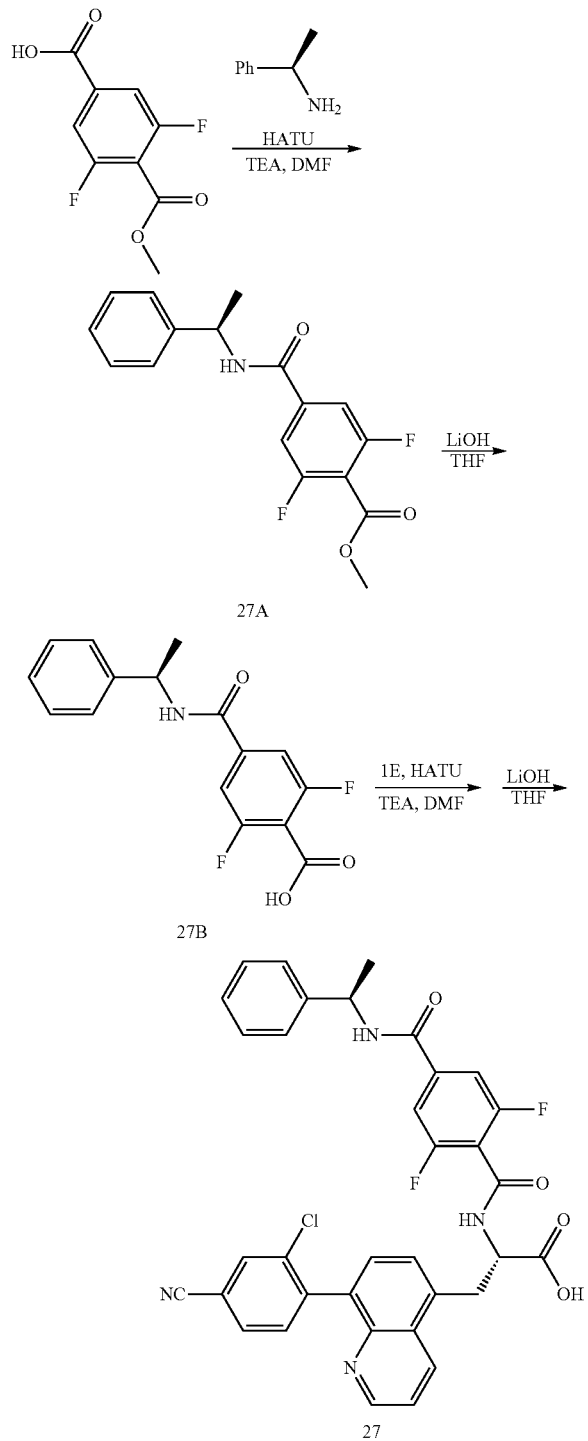

Synthesis of methyl (R)-2,6-difluoro-4-((1-phenylethyl)carbamoyl)benzoate (27A): To a stirred solution of 3,5-difluoro-4-(methoxycarbonyl)benzoic acid (20 mg, 0.093 mmol) in DMF was added (R)-1-phenylethan-1-amine (13.46 mg, 0.11 mmol), HATU (42 mg, 0.11 mmol), and TEA (0.06 mL, 0.463 mmol). The reaction was stirred for 1 h at RT, concentrated under reduced pressure, and then purified by silica gel chromatography using DCM/MeOH as eluent.

Synthesis of (R)-2,6-difluoro-4-((1-phenylethyl)carbamoyl)benzoic acid (27B): To a stirred solution of 27A (29.5 mg, 0.09 mmol) in THF was added aqueous LiOH (0.46 mL, 1 M). The mixture was allowed to stir at RT for 3 hours, concentrated under reduced pressure, and then purified by silica gel chromatography using DCM/MeOH as eluent (S)-3-(8-(2-chloro-4-cyanophenyl)quinolin-5-yl)-2-(2,6-difluoro-4-(((R)-1-phenylethyl) carbamoyl)benzamido)propanoic acid (27): The title compound was prepared according to the method presented for the synthesis of compound 16A and 16 starting with 27B. MS (m/z) 639.2 [M+H]$^+$. 1H NMR (400 MHz, DMSO-d6) δ 9.35 (d, J=8.3 Hz, 1H), 8.98 (d, J=7.9 Hz, 1H), 8.84 (dd, J=4.1, 1.6 Hz, 1H), 8.64 (d, J=7.7 Hz, 1H), 8.16 (d, J=1.6 Hz, 1H), 7.90 (d, J=7.7 Hz, 1H), 7.66-7.53 (m, 6H), 7.32 (dt, J=15.1, 7.5 Hz, 4H), 7.21 (t, J=7.1 Hz, 1H), 5.11 (t, J=7.3 Hz, 1H), 4.80 (s, 1H), 3.50-3.40 (m, 1H), 1.45 (d, J=7.0 Hz, 3H).

Example 28

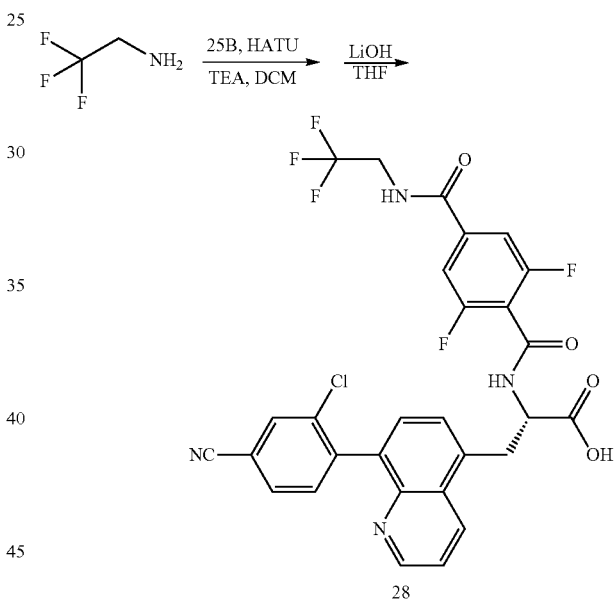

(S)-3-(8-(2-chloro-4-cyanophenyl)quinolin-5-yl)-2-(2,6-difluoro-4-((2,2,2-trifluoro ethyl)carbamoyl)benzamido) propanoic acid (28): The title compound was prepared according to the method presented for the synthesis of compound 16A and 16 starting with 25B. MS (m/z) 616.9 [M+H]$^+$. 1H NMR (400 MHz, DMSO-d6) δ 9.38 (d, J=8.3 Hz, 1H), 9.29 (t, J=6.4 Hz, 1H), 8.84 (dd, J=4.2, 1.6 Hz, 1H), 8.68-8.60 (m, 1H), 8.16 (d, J=1.6 Hz, 1H), 7.90 (d, J=8.1 Hz, 1H), 7.64 (d, J=4.6 Hz, 1H), 7.62-7.58 (m, 3H), 7.57 (d, J=7.9 Hz, 1H), 4.80 (s, 1H), 4.09 (dd, J=9.8, 6.4 Hz, 1H), 3.75-3.60 (m, 1H).

Example 29

Synthesis of ethyl (S)-3-(8-(2-chloro-4-cyanophenyl)quinolin-5-yl)-2-(2,6-dichloro-4-iodobenzamido)propanoate (29A): The title compound was prepared according to the method presented for the synthesis of compound 16A starting with 2,6-dichloro-4-iodobenzoic acid and 1E.

Synthesis of methyl (S)-3-(8-(2-chloro-4-cyanophenyl)quinolin-5-yl)-2-(2,6-dichloro-4-(3-hydroxy-3-methylbut-1-yn-1-yl)benzamido)propanoate (29B): To a stirred solution of 29A (60 mg, 0.09 mmol) in THF was added 2-methylbut-3-yn-2-ol (0.02 ml, 0.27 mmol), CuI (3.44 mg, 0.02 mmol), PdCl$_2$(PPh$_3$)$_2$ (12.71 mg, 0.02 mmol), and DIEA (0.08 ml, 0.45 mmol). The reaction mixture was allowed to stir for 1 h at 60° C. then concentrated under reduced pressure and used without further purification.

(S)-3-(8-(2-chloro-4-cyanophenyl)quinolin-5-yl)-2-(2,6-dichloro-4-(3-hydroxy-3-methylbut-1-yn-1-yl)benzamido)propanoic acid (29): The title compound was prepared according to the method presented for the synthesis of compound 1 starting with 29B. MS (m/z) 606.0 [M+H]$^+$. 1H NMR (400 MHz, DMSO-d6) δ 13.04 (s, 1H), 9.30 (d, J=7.9 Hz, 1H), 8.83 (dd, J=4.1, 1.6 Hz, 1H), 8.64 (dd, J=8.6, 1.7 Hz, 1H), 8.18-8.13 (m, 1H), 7.91 (d, J=8.2 Hz, 1H), 7.68-7.57 (m, 2H), 7.61-7.48 (m, 1H), 7.43 (s, 1H), 7.41-7.30 (m, 3H), 4.85 (s, 1H), 3.76 (dd, J=14.4, 4.2 Hz, 1H), 3.39 (t, J=12.4 Hz, 1H), 1.43 (d, J=3.7 Hz, 6H).

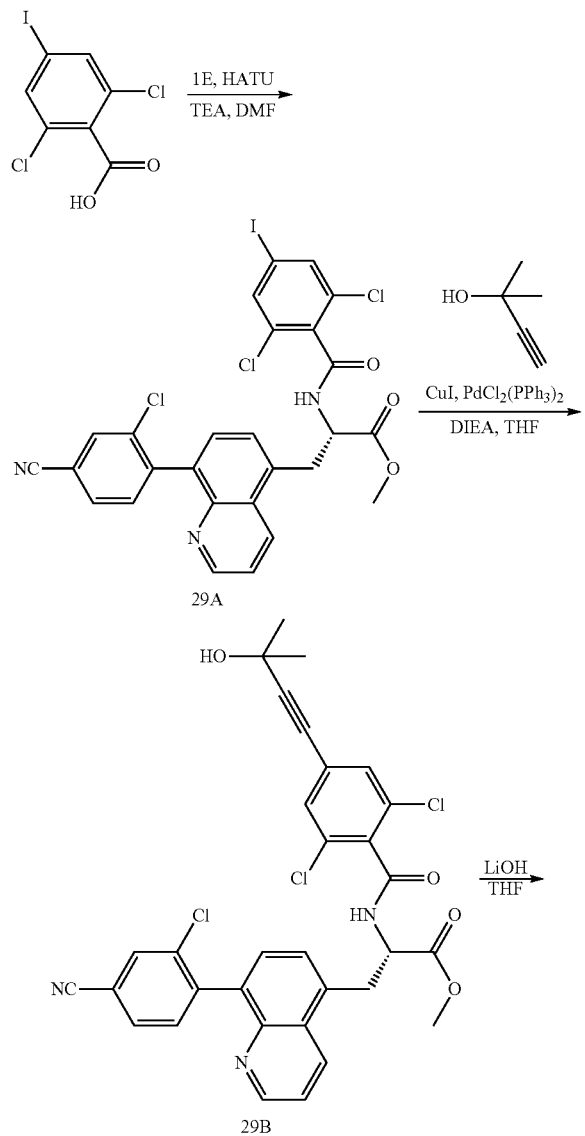

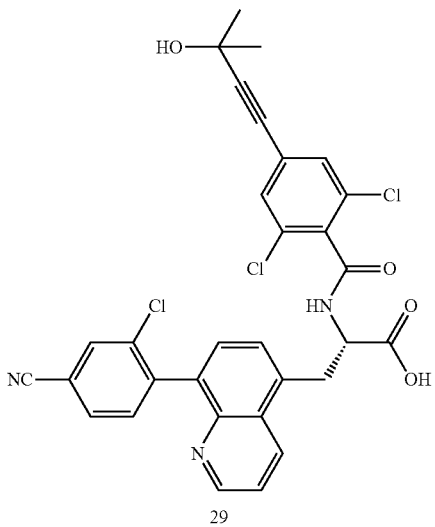

Example 30

Synthesis of methyl quinoline-5-carboxylate (30A): To a stirred solution of 3-nitrobenzoic acid (244.0 g, 1.46 mol) in conc. H$_2$SO$_4$ (750 mL) was added glycerol (1.17 L, 15.33 mol) and 3-aminobenzoic acid (500.0 g, 3.65 mol). The resulting reaction mixture was heated to 150° C. for 7 h. Then the reaction mixture was cooled to 0° C. and treated with methanol (5.0 L) and the resulting reaction mixture was heated to reflux for 12 h. The reaction mixture was cooled to 0° C. and quenched with ice water and neutralized with solid Na$_2$CO$_3$. The aqueous was extracted with EA (4 L×2), the organic layer was separated dried over Na$_2$SO$_4$ and concentrated under reduced pressure. The material was purified by column chromatography using EA/petroleum ether to obtain 30A.

Synthesis of 5-(methoxycarbonyl)quinoline 1-oxide (30C): m-CPBA (604.8 g, 2.19 mol) was added to a solution of compound 30A (205.0 g, 1.095 mol) in chloroform (4.1 L) at 0° C. The resulting reaction mixture was allowed to warm RT and stirred for 6 h. The reaction mixture was cooled to 0° C. and quenched with sat NaHCO$_3$ solution and extracted with DCM. The organic layer was separated, dried over Na$_2$SO$_4$ and concentrated under reduced pressure. The compound was purified by column chromatography using 5% MeOH/DCM as eluent to obtain 30C.

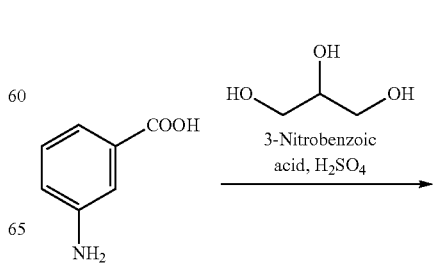

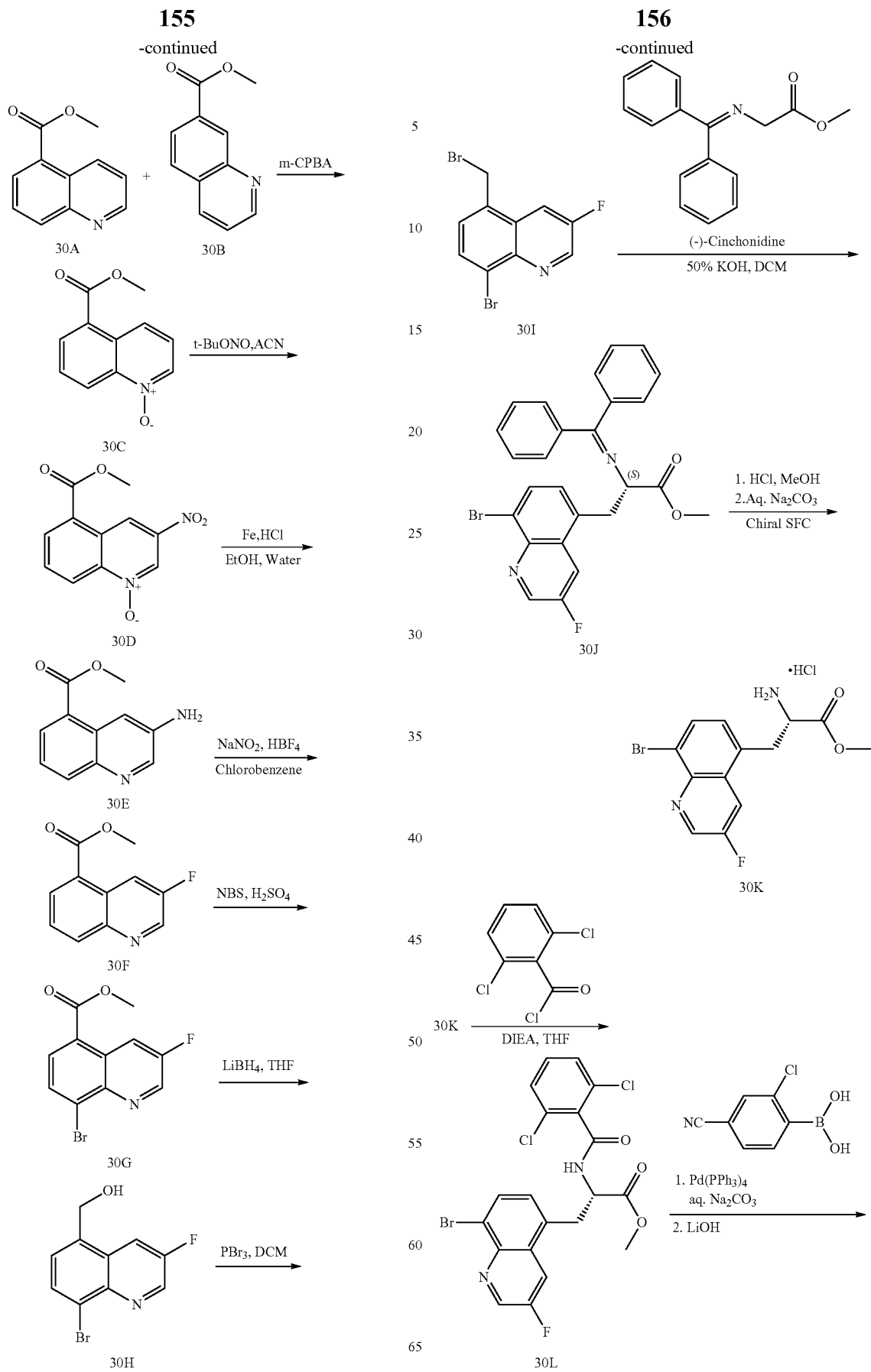

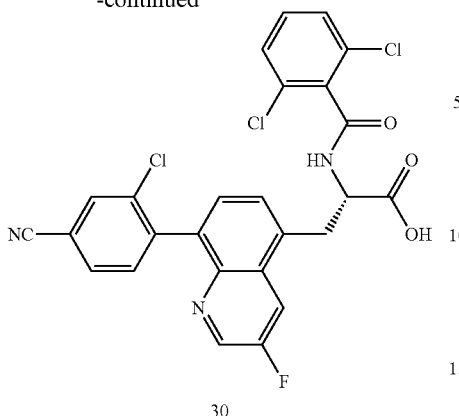

30

Synthesis of 5-(methoxycarbonyl)-3-nitroquinoline 1-oxide (30D): t-BuONO (708.1 mL, 5.9 mol) was added to a solution of compound 30C (120.0 g, 0.59 mol) in acetonitrile (6.0 L) at RT and the resulting reaction mixture was heated to 100° C. in an autoclave for 8 h. The reaction mixture was cooled to RT and concentrated under reduced pressure. The compound was washed with EA to afford compound 30D.

Synthesis of methyl 3-aminoquinoline-5-carboxylate (30E): Fe Powder (39.38 g, 0.705 mol) and conc. HCl (50.0 mL) were added to a solution of compound 30D (25.0 g, 0.1 mol) in a mixture of ethanol (500 mL) and water (500 mL) at 70° C. and the resulting reaction mixture was stirred for 18 h. The reaction mixture was cooled to RT, filtered through celite, concentrated under reduced pressure and extracted with DCM. The organic layer was separated, dried over $Na_2SO_4$ and concentrated under vacuum. The compound was purified by column chromatography using 50% EA in pet ether as eluent to obtain 30E.

Synthesis of methyl 3-fluoroquinoline-5-carboxylate (30F): A solution of sodium nitrite (13.64 g, 0.197 mol) in water (60.0 mL) was added to a solution of compound 30E (20.0 g, 0.0989 mol) in 50% $HBF_4$ (200 mL) at 0° C. The reaction mixture was allowed warm to RT and stirred for 2 h, then filtered under vacuum. The filtered compound was added to chlorobenzene, and the reaction mixture was refluxed at 125° C. for 2 h. The chlorobenzene was removed by distillation resulting in a material which was dissolved in DCM and water. The organic layer was washed with water and brine, dried over $Na_2SO_4$ and concentrated under vacuum. The compound was purified by column chromatography using 4-5% EA in petroleum ether as eluent to obtain 30F.

Synthesis of methyl 8-bromo-3-fluoroquinoline-5-carboxylate (30G): NBS (41.89 g, 0.243 mol) was added to a stirred solution of 30F (25.0 g, 0.121 mol) in $H_2SO_4$ (500.0 mL) at 0° C. and the resulting reaction mixture was allowed warm to RT and allowed to stir for 24 h. The reaction mixture was poured onto crushed ice and the solid obtained was filtered and dried under reduced pressure to afford compound 30G.

Synthesis of (8-bromo-3-fluoroquinolin-5-yl)methanol (31H): To a stirred solution of 30G (26.0 g, 0.091 mol) in THF (260 mL) was slowly added 2M $LiBH_4$ in THF (137 mL, 0.274 mol) at 0° C. The reaction mixture was heated to 40° C. for 2 h then cooled to 0° C., quenched with ice water and stirred for 30 minutes. The reaction mixture was acidified with aq. 2N HCl (pH 4-5) and heated to 40° C. for 2 h. The reaction mixture was cooled to RT and basified with sat. $NaHCO_3$ solution (pH 8-9), extracted with DCM (250 mL×2). The organic layer was separated, dried over $Na_2SO_4$, and concentrated under reduced pressure. The compound was washed with pentane to afford 31H.

Synthesis of 8-bromo-5-(bromomethyl)-3-fluoroquinoline (301): $PBr_3$ (48.5 g, 0.179 mol) was added to a stirred solution of 31H (23.0 g, 0.0897 mol) in DCM (230 mL) at 0° C., the mixture was allowed warm to RT and allowed to stir for 18 h. The reaction mixture was concentrated, cooled to 0° C. and basified with sat. $Na_2CO_3$ solution (PH 8-9) to obtain a solid that was collected by filtration and dried under vacuum to obtain 301.

Synthesis of methyl (S)-3-(8-bromo-3-fluoroquinolin-5-yl)-2-((diphenylmethylene) amino)propanoate (30J): To a stirred solution of methyl 2-((diphenylmethylene)amino) acetate (16.6 g, 0.0655 mol) in DCM (500 mL) was added (−)-cinchonidine (1.93 g, 0.0065 mol) at RT. The reaction mixture was cooled to 0° C. KOH solution (50%) (133 mL) and 301 (23.0 g, 0.0721) were added and the reaction mixture was allowed to stir at RT for 6 h. The reaction mixture was diluted with water (200 mL) and stirred for 15 minutes. After washing with water and EA, the combined organic layer was dried over anhydrous $Na_2SO_4$, filtered through Celite, washed with EA, and concentrated under reduced pressure to obtain 30J.

Synthesis of free base methyl (S)-2-amino-3-(8-bromo-3-fluoroquinolin-5-yl) propanoate (30K): 4M HCl in 1,4-dioxane (720 mL) was added to a stirred solution of 30J (60 g, 0.1221 mol) in methanol (420 mL) at 0° C. The reaction mixture was allowed to stir at RT for 36 h. The reaction mixture was concentrated under reduced pressure, dissolved in water (100 mL) and washed with EA (100 mL×2 L). The aqueous layer was separated and basified (pH-8) using Sat.$Na_2CO_3$ and extracted with DCM (500 mL×5). The combined organic layers were dried over anhydrous $Na_2SO_4$ and concentrated under reduced pressure to afford 30K.

Chiral purification of methyl (S)-2-amino-3-(8-bromo-3-fluoroquinolin-5-yl) propanoate hydrochloride (30K): 30K was enriched in the desired enantiomer by supercritical fluid chromatography using 50% (0.5% TEA in IPA) co-solvent, at a flow rate of 100 mL/min, using an Chiralpak IC (30×250 mm), 5 μm column.

Synthesis of methyl (S)-2-amino-3-(8-bromo-3-fluoroquinolin-5-yl)propanoate hydrochloride (30K): The free amine was dissolved in DCM (300 mL) and treated with 4M HCl in 1,4-dioxane (100 mL) at 0° C. and the reaction mixture was allowed to stir at RT for 30 min then concentrated under reduced pressure to afford 30K as the HCl salt.

Synthesis of methyl (S)-3-(8-bromo-3-fluoroquinolin-5-yl)-2-(2,6-dichloro benzamido)propanoate (30L): The title compound was prepared according to the method presented for the synthesis of compound 1F starting with 30K and 2,6-dichlorobenzoyl chloride.

Synthesis of (S)-3-(8-(2-chloro-4-cyanophenyl)-3-fluoroquinolin-5-yl)-2-(2,6-dichlorobenzamido)propanoic acid (30): The title compound was prepared according to the method presented for the synthesis of compound 3B and 3 starting with 30L. MS (m/z) 542.0 [M+H]⁺. 1H NMR (400 MHz, DMSO-d6) δ 9.24 (d, J=8.4 Hz, 1H), 8.90 (d, J=2.7 Hz, 1H), 8.46 (d, J=10.3 Hz, 1H), 8.16 (dd, J=1.6, 0.4 Hz, 1H), 7.92 (d, J=7.9 Hz, 1H), 7.73 (d, J=7.4 Hz, 1H), 7.62 (d, J=7.3 Hz, 1H), 7.53 (d, J=7.9 Hz, 1H), 7.43-7.24 (m, 3H), 4.87 (s, 1H), 3.69 (dd, J=14.6, 4.2 Hz, 1H), 3.45-3.35 (m, 1H).

Example 31

Synthesis of 5-bromo-8-iodo-2-methylquinoline (31A): To a stirred solution of 2-iodo-5-bromoaniline (5 g, 17 mmol) in nitrobenzene (1.7 mL) and 75% H₂SO₄ (15 mL) was added but-2-enal (2.35 g, 34 mmol) at RT and then slowly heated to 150° C. for 3 h. Caution: highly exothermic reaction. The mixture was cooled to RT and poured into ice-water while maintaining the temperature below 10° C. The pH was adjusted to ~12 with solid KOH, and the resulting material was collected. The material was washed three times with water, then were taken up in ethyl acetate and filtered. The organic solution was concentrated, then purified via flash chromatography, eluting with a linear gradient of 5-100% DCM/hexanes, to yield 31A.

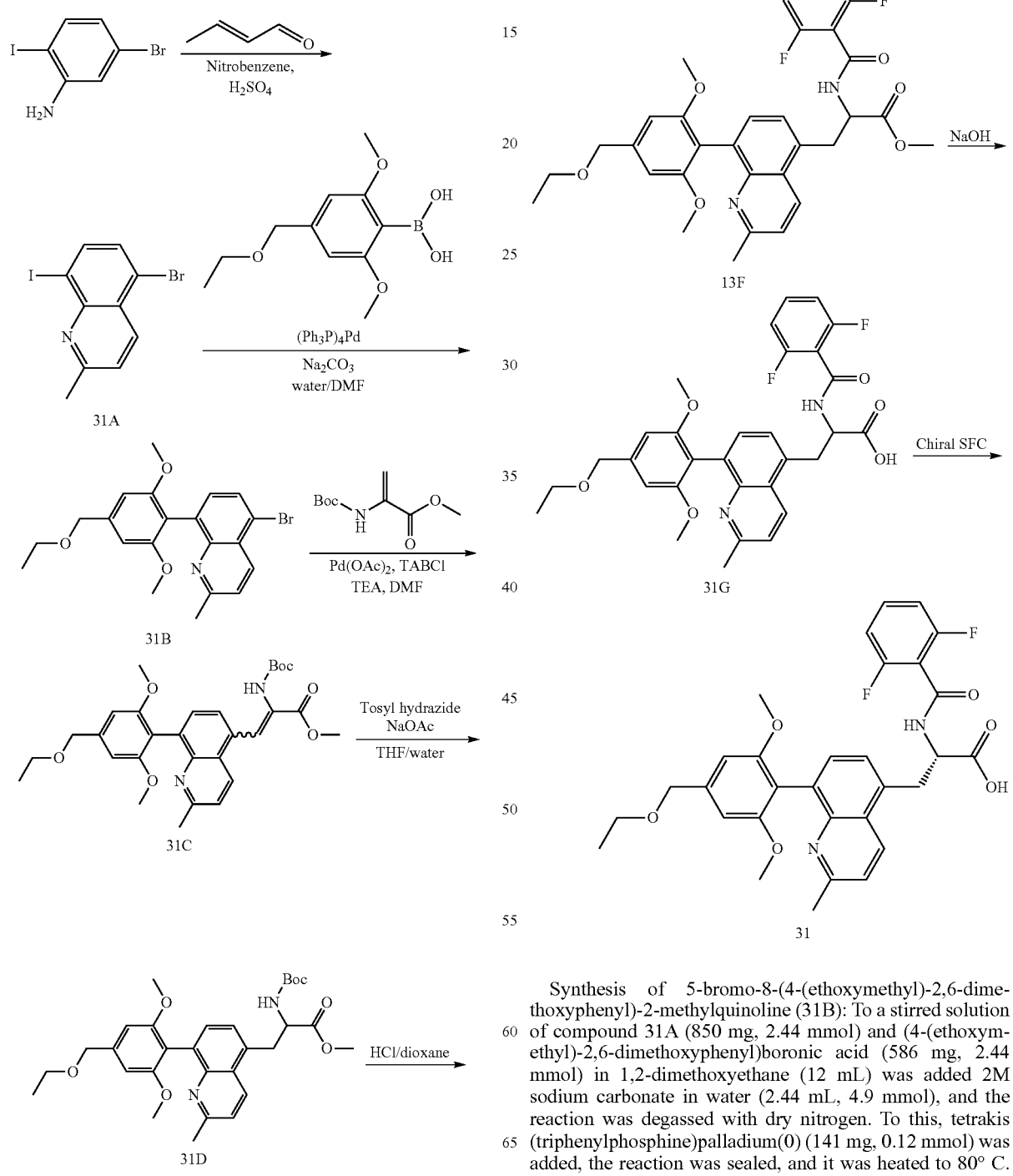

Synthesis of 5-bromo-8-(4-(ethoxymethyl)-2,6-dimethoxyphenyl)-2-methylquinoline (31B): To a stirred solution of compound 31A (850 mg, 2.44 mmol) and (4-(ethoxymethyl)-2,6-dimethoxyphenyl)boronic acid (586 mg, 2.44 mmol) in 1,2-dimethoxyethane (12 mL) was added 2M sodium carbonate in water (2.44 mL, 4.9 mmol), and the reaction was degassed with dry nitrogen. To this, tetrakis (triphenylphosphine)palladium(0) (141 mg, 0.12 mmol) was added, the reaction was sealed, and it was heated to 80° C. for 16 hours. The reaction mixture was cooled to RT, diluted with ethyl acetate, and washed with water and brine. It was then dried over anhydrous sodium sulfate, filtered, concentrated and purified via flash chromatography, eluting with a linear gradient of 5-50% ethyl acetate/hexanes, to yield 31B.

Synthesis of methyl 2-((tert-butoxycarbonyl)amino)-3-(8-(4-(ethoxymethyl)-2,6-dimethoxyphenyl)-2-methylquinolin-5-yl)acrylate (31C): To a stirred solution of 31B (190 mg, 0.46 mmol) in DMF (4.7 mL) was added palladium(II) acetate, and the reaction was degassed with nitrogen for 30 minutes. To this, methyl 2-((tert-butoxycarbonyl)amino) acrylate (230 mg, 1.1 mmol), tetrabutylammonium chloride (152 mg, 0.55 mmol), and trimethylamine (0.074 mL, 0.53 mmol) were added, and the reaction was sealed and heated to 90° C. for 3 hours. It was cooled to RT, diluted with ethyl acetate, and washed with 10% citric acid, saturated sodium bicarbonate, and saturated sodium chloride. It was dried over anhydrous sodium sulfate, filtered, and concentrated. It was purified via flash chromatography, eluting with a linear gradient of 5-100% ethyl acetate/hexanes, to yield compound 31C.

Synthesis of methyl 2-((tert-butoxycarbonyl)amino)-3-(8-(4-(ethoxymethyl)-2,6-dimethoxyphenyl)-2-methylquinolin-5-yl)propanoate (31D): To a stirred solution of 31C (150 mg, 0.28 mmol) and tosyl hydrazide (781 mg, 4 mmol) in THF (3 mL) at 60° C. was added sodium acetate (609 mg, 4 mmol) in water (3 mL) dropwise, then the reaction was heated to reflux overnight. It was partitioned between ethyl acetate and water, and then the aqueous layer was extracted twice with ethyl acetate. The combined organics were washed with saturated sodium chloride, dried over anhydrous sodium sulfate, filtered, and concentrated. The residue was twice more subjected to these conditions to yield 31D.

Synthesis of methyl 2-amino-3-(8-(4-(ethoxymethyl)-2,6-dimethoxyphenyl)-2-methyl quinolin-5-yl)propanoate dihydrochloride (31E): To a stirred solution of compound 31D (150 mg, 0.28 mmol) in ethyl acetate (2 mL) was added 4M hydrogen chloride in dioxane (0.7 mL, 1.8 mmol), and the reaction was allowed to stir overnight at RT. It was diluted with EA, and the resulting solids were collected by trituration to yield 31E.

Synthesis of methyl 2-(2,6-difluorobenzamido)-3-(8-(4-(ethoxymethyl)-2,6-dimethoxy phenyl)-2-methylquinolin-5-yl)propanoate (31F): The title compound was prepared according to the method presented for the synthesis of compound 1F starting with 31E and 2,6-difluorobenzoyl chloride.

Synthesis of 2-(2,6-difluorobenzamido)-3-(8-(4-(ethoxymethyl)-2,6-dimethoxyphenyl)-2-methylquinolin-5-yl)propanoic acid (31G): Synthesized via sodium hydroxide method to yield 31G.

Synthesis of (S)-2-(2,6-difluorobenzamido)-3-(8-(4-(ethoxymethyl)-2,6-dimethoxy phenyl)-2-methylquinolin-5-yl)propanoic acid (31): 2-(2,6-difluorobenzamido)-3-(8-(4-(ethoxy methyl)-2,6-dimethoxyphenyl)-2-methylquinolin-5-yl)propanoic acid (31G) was separated into its two enantiomers by supercritical fluid chromatography using 20% MeOH/DEA co-solvent on an IC SFC column to yield the desired enantiomer 31H as the second eluting peak. MS (m/z) 565.2 [M+H]+. 1H NMR (400 MHz, DMSO-d6) δ 8.56 (d, J=8.7 Hz, 1H), 7.51-7.41 (m, 1H), 7.38 (d, J=7.4 Hz, 1H), 7.32 (d, J=8.7 Hz, 1H), 7.26 (d, J=7.3 Hz, 1H), 7.15-7.05 (m, 2H), 6.68 (s, 2H), 4.50 (s, 2H), 4.40 (s, 1H), 3.68-3.49 (m, 9H), 3.42-3.34 (m, 1H), 2.45 (s, 3H), 1.20 (t, J=7.0 Hz, 3H).

Example 32

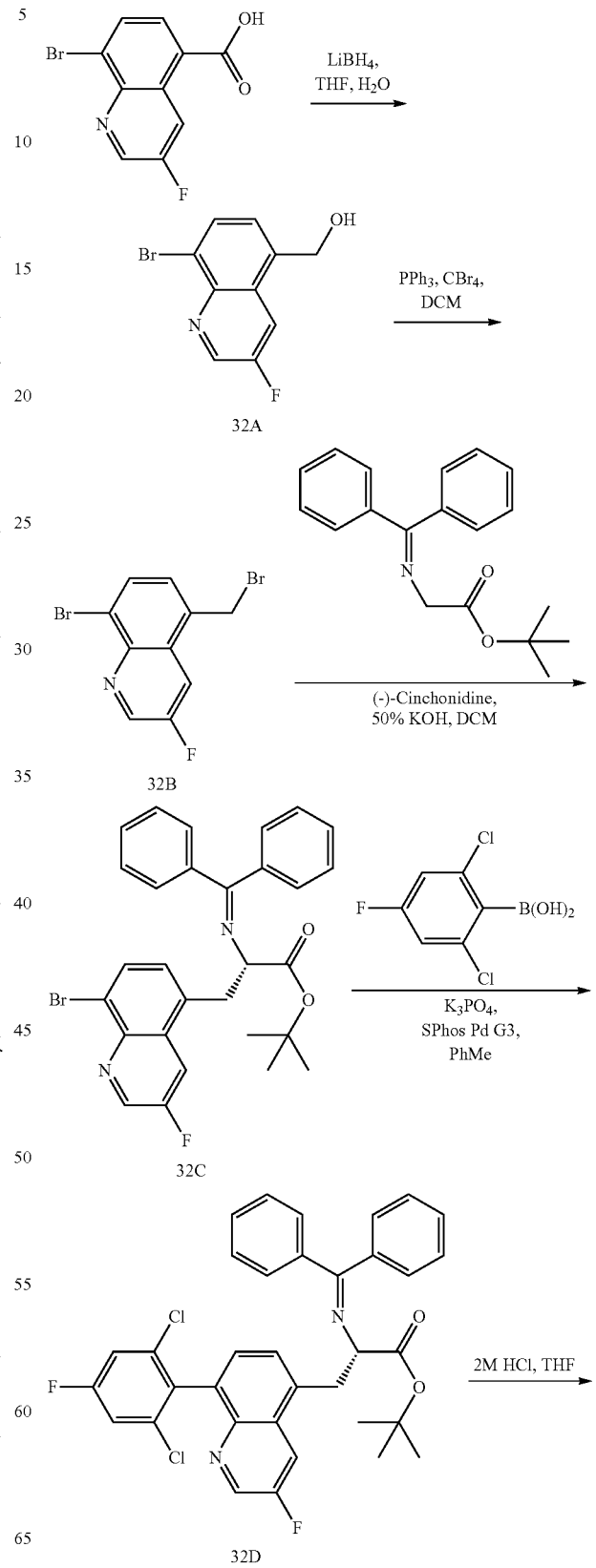

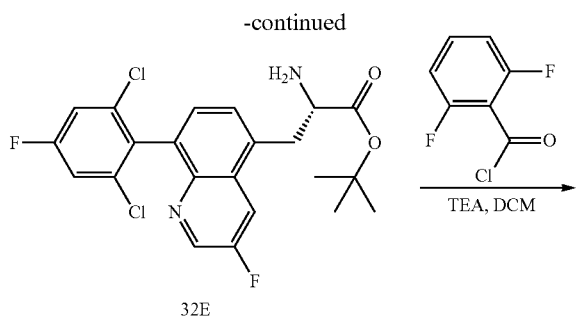

32E

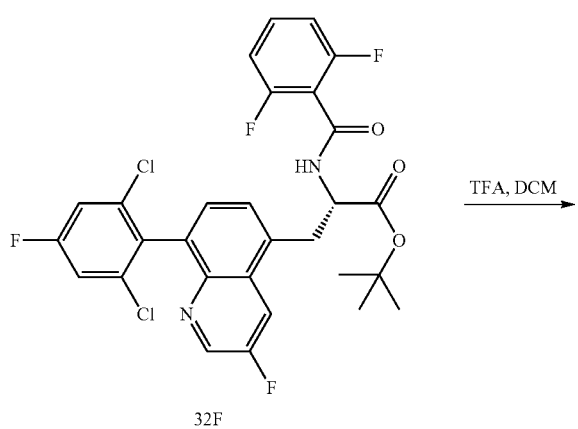

32F

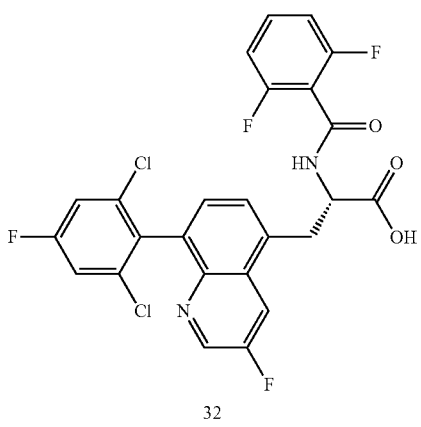

32

Synthesis of (8-bromo-3-fluoroquinolin-5-yl)methanol (32A): A flask containing methyl 8-bromo-3-fluoroquinoline-5-carboxylate (1.06 g, 3.73 mmol) in THF (19 mL) was flushed with $N_2$, and then $LiBH_4$ (813 mg, 37.3 mmol) was added in one portion. After stirring at RT for 1 h, the reaction mixture was cooled to 0° C. and water (6 mL) was added, followed by the dropwise addition of 1M HCl (84 mL). The reaction mixture was heated to 40° C. for 2.5 hours and then cooled to RT before diluting with water and EA. Aqueous was extracted and the organic layer was dried over anhydrous $MgSO_4$ and concentrated under reduced pressure. The material was purified by silica gel chromatography using 0-100% EA in hexanes to afford the title compound.

Synthesis of 8-bromo-5-(bromomethyl)-3-fluoroquinoline (32B): Triphenylphosphine (1.12 g, 4.27 mmol) and $CBr_4$ (1.42 g, 4.27 mmol) were added to a stirred solution of 32A (729 mg, 2.85 mmol) in DCM (5.7 mL) and this was stirred at RT for 20 min. The reaction mixture was then subjected to silica gel chromatography using 0-40% EA in hexanes to give the title compound.

Synthesis of tert-butyl (S)-3-(8-bromo-3-fluoroquinolin-5-yl)-2-((diphenylmethylene) amino)propanoate (32C): To a stirred solution of tert-butyl 2-((diphenylmethylene)amino) acetate (270 mg, 0.914 mmol) in DCM (7 mL) was added (−)-cinchonidine (27 mg, 0.091 mmol). The mixture was cooled to 0° C. with an ice bath before adding 50% aq KOH solution (1.8 mL), followed by 32B (321 mg, 1.01 mmol). The reaction stirred in the ice bath as it slowly warmed to RT. After 3.5 hours, the reaction was diluted with water and DCM, and aqueous was extracted. The organic layer was dried over $MgSO_4$ and concentrated under reduced pressure. The material was purified by silica gel chromatography using 0-30% EA in hexanes to afford the title compound.

Synthesis of tert-butyl (S)-3-(8-(2,6-dichloro-4-fluorophenyl)-3-fluoroquinolin-5-yl)-2-((diphenylmethylene) amino)propanoate (32D): 32C (65 mg, 0.122 mmol), (2,6-dichloro-4-fluorophenyl)boronic acid (51 mg, 0.244 mmol), $K_3PO_4$ (91 mg, 0.426 mmol), SPhos Pd G3 (95 mg, 0.122 mmol) were dissolved in toluene (2.4 mL) and heated to 100° C. for 3 hours. After cooling to RT, the reaction mixture was diluted with EA and filtered through celite. The filtrate was concentrate under reduced pressure and the resulting residue was purified by silica gel chromatography using 0-50% EA in hexanes to give the title compound.

Synthesis of tert-butyl (S)-2-amino-3-(8-(2,6-dichloro-4-fluorophenyl)-3-fluoro quinolin-5-yl)propanoate (32E): 2M HCl (0.43 mmol, 0.21 mL) was added to a stirred solution of 32D (88.2 mg, 0.14 mmol) in THF (0.84 mL). After stirring at RT for 2 hours, sat. $NaHCO_3$ and EA were added. Aqueous was extracted and the organic layer was dried over $MgSO_4$ and concentrated under reduced pressure. The material was purified by silica gel chromatography using 0-90% EA in hexanes with 1% TEA to afford the title compound.

Synthesis of tert-butyl (S)-3-(8-(2,6-dichloro-4-fluorophenyl)-3-fluoroquinolin-5-yl)-2-(2,6-difluorobenzamido) propanoate (32F): To a stirred solution of 32E (36.6 mg, 0.081 mmol) in DCM (0.54 mL) was added TEA (23 µL, 0.161 mmol). The reaction was cooled to 0° C. before adding 2,6-difluorobenzoyl chloride (15 µL, 0.121 mmol) dropwise. After stirring at RT for 1.25 hours, water and DCM were added. Aqueous layer was extracted and the organic layer was dried over $MgSO_4$ and concentrated under reduced pressure. The material was purified by silica gel chromatography using 0-40% EA in hexanes to give the title compound.

Synthesis of (S)-3-(8-(2,6-dichloro-4-fluorophenyl)-3-fluoroquinolin-5-yl)-2-(2,6-difluorobenzamido)propanoic acid (32): TFA (0.12 mL, 1.61 mmol) was added to a stirred solution of 32F (47.9 mg, 0.081 mmol) in DCM (0.40 mL). After stirring at RT for 3 hours, more TFA (0.06 mL, 0.81 mmol) was added. The reaction was stirred for another hour at RT, and then concentrated under reduced pressured. The material was purified by prep HPLC using 0-100% MeCN in water with 1% TFA to afford the title compound. MS (m/z) 537.0 [M+H]$^+$. 1 H NMR (400 MHz, DMSO-d6) δ 13.04 (s, 1H), 9.27 (d, J=8.2 Hz, 1H), 8.90 (d, J=2.7 Hz, 1H), 8.45 (dd, J=10.5, 2.8 Hz, 1H), 7.70 (d, J=7.4 Hz, 1H), 7.65 (d, J=8.6 Hz, 2H), 7.59 (d, J=7.3 Hz, 1H), 7.48 (ddd, J=8.5, 6.5, 1.9 Hz, 1H), 7.15-7.05 (m, 2H), 4.82 (ddd, J=10.2, 8.1, 4.5 Hz, 1H), 3.78-3.55 (m, 1H), 3.43 (dd, J=14.7, 10.3 Hz, 1H).

Example 33

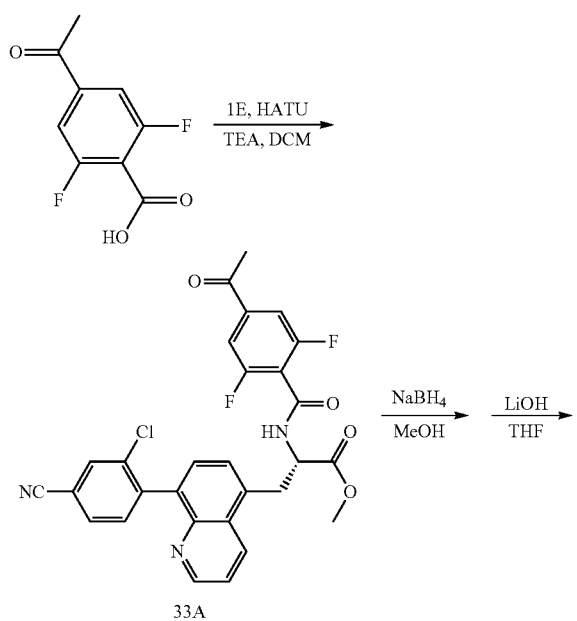

Synthesis of methyl (S)-2-(4-acetyl-2,6-difluorobenzamido)-3-(8-(2-chloro-4-cyano phenyl)quinolin-5-yl)propanoate (33A): The title compound was prepared according to the method presented for the synthesis of compound 16A starting with 1E and 4-acetyl-2,6-difluorobenzoic acid.

(2S)-3-(8-(2-chloro-4-cyanophenyl)quinolin-5-yl)-2-(2,6-difluoro-4-(1-hydroxyethyl) benzamido)propanoic acid (33): The title compound was prepared according to the method presented for the synthesis of compound 24B and 16 starting with 33A. MS (m/z) 563.2 [M+H]+. 1H NMR (400 MHz, DMSO-d6) δ 9.19 (d, J=8.2 Hz, 1H), 8.83 (dd, J=4.2, 1.6 Hz, 1H), 8.63 (dd, J=8.7, 1.6 Hz, 1H), 8.16 (dd, J=1.6, 0.4 Hz, 1H), 7.90 (d, J=7.6 Hz, 1H), 7.73-7.50 (m, 4H), 7.03 (d, J=8.8 Hz, 2H), 4.71 (d, J=6.5 Hz, 1H), 1.27 (d, J=6.5 Hz, 3H).

Example 34

Synthesis of 8-bromo-7-fluoro-5-methylquinoline (34A): the title compound was prepared according to the method presented for the synthesis of compound 1A in Example 1 starting with 2-bromo-3-fluoro-5-methylaniline. MS (m/z) 240.0 [M+H]+.

Synthesis of 8-bromo-5-(bromomethyl)-7-fluoroquinoline 34B: the title compound was prepared according to the method presented for the synthesis of compound 1B in Example 1 starting with 34A. MS (m/z) 317.9 [M+H]+.

Synthesis of 8-bromo-7-fluoro-5-(((2S,5S)-5-isopropyl-3,6-dimethoxy-2,5-dihydro pyrazin-2-yl)methyl)quinoline (34C): A solution of (R)-2-isopropyl-3,6-dimethoxy-2,5-dihydropyrazine (0.365 mL, 2.04 mmol) in THF (10 mL) was cooled to −78° C. with stirring and under positive nitrogen pressure. The mixture was treated dropwise with n-BuLi (0.98 mL, 1.6 M, 1.57 mmol). A solution of 34B (497 mg, 1.57 mmol) is then added as a THF solution (1.0 M). After 30 minutes, the reaction mixture was removed from the cooling bath, quenched with a saturated aqueous solution of NH4Cl, and allowed to warm to RT with vigorous stirring. The resulting mixture was extracted twice with EA, and the combined organic layers were concentrated under reduced pressure. The residue was purified by silica gel chromatography using 0-20% EA in hexanes to afford the title compound. MS (m/z) 422.1 [M+H]+.

Synthesis of methyl (S)-2-amino-3-(8-bromo-7-fluoroquinolin-5-yl)propanoate dihydrochloride (34D): To a stirred solution of 34C (380 mg, 0.9 mmol) in THF (3.6 mL) was added 2M aqueous hydrochloric acid (2.7 mL, 5.4 mmol). After 3 h, the reaction mixture was concentrated under reduced pressure to afford the title compound (as a mixture with valine methyl ester hydrochloride), which was advanced without further purification. MS (m/z) 327.0 [M+H]+.

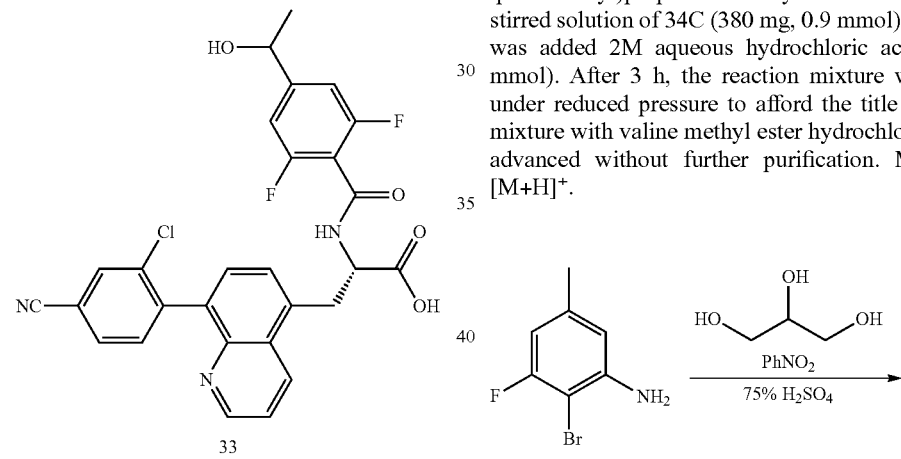

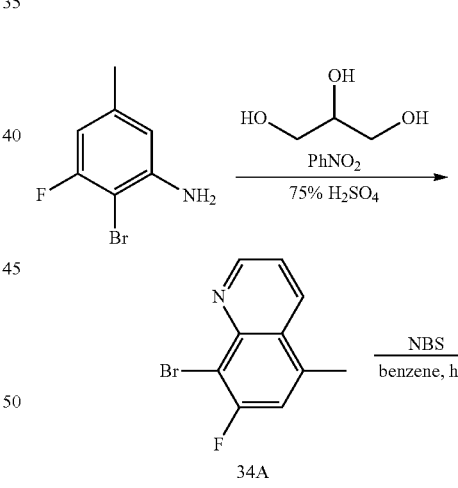

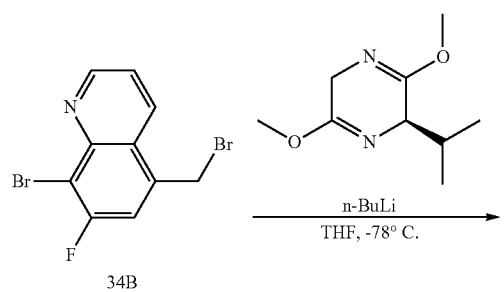

Example 35

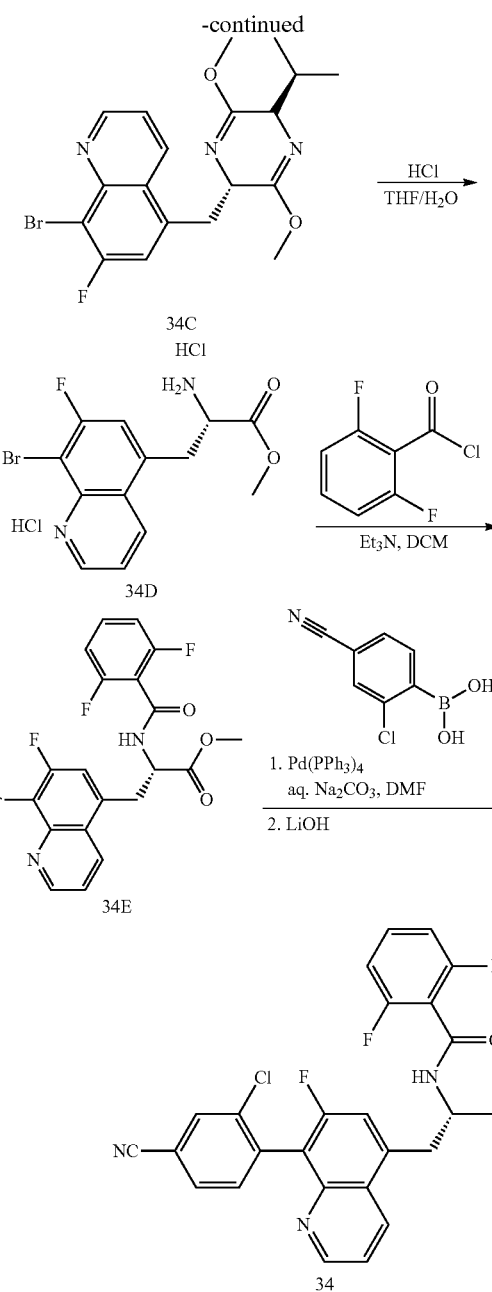

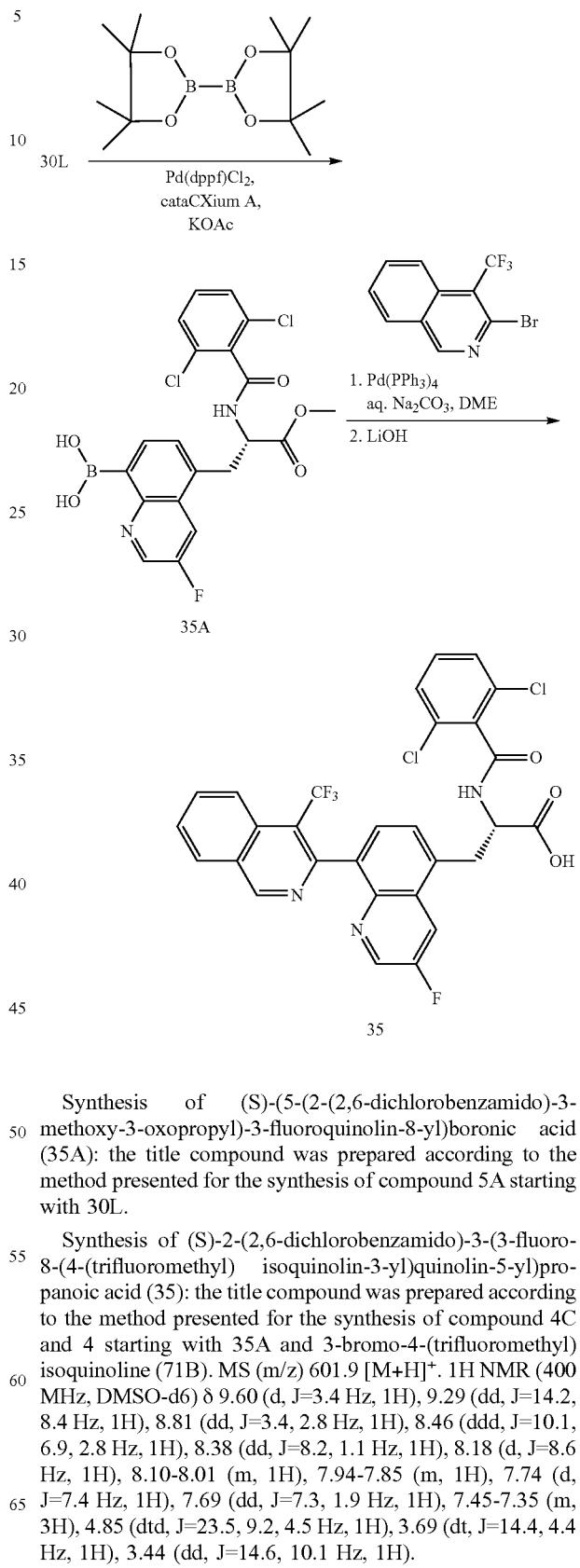

Synthesis of Methyl (S)-3-(8-bromo-7-fluoroquinolin-5-yl)-2-(2,6-difluorobenzamido) propanoate (34E): the title compound was prepared according to the method presented for the synthesis of compound 1F in Example 1 starting with 34. MS (m/z) 467.0 [M+H]$^+$.

Synthesis of (2S)-3-(8-(2-chloro-4-cyanophenyl)-7-fluoroquinolin-5-yl)-2-(2,6-difluorobenzamido)propanoic acid (34): the title compound was prepared according to the method presented for the synthesis of compound 3B and 3 starting with 34E. MS (m/z) 510.1 [M+H]$^+$. 1H NMR (400 MHz, DMSO-d6) δ 9.27 (dd, J=8.3, 1.3 Hz, 1H), 8.87 (dt, J=3.9, 1.8 Hz, 1H), 8.67 (dd, J=8.6, 1.6 Hz, 1H), 8.24 (t, J=1.9 Hz, 1H), 7.95 (ddd, J=7.9, 4.2, 1.7 Hz, 1H), 7.67-7.57 (m, 3H), 7.49 (ttd, J=8.7, 6.6, 2.3 Hz, 2H), 7.16-7.08 (m, 2H), 4.82 (dddd, J=10.8, 8.4, 4.2, 2.2 Hz, 1H), 3.85 (ddd, J=18.1, 14.5, 4.1 Hz, 1H), 3.42 (ddd, J=19.5, 14.6, 10.8 Hz, 1H).

Synthesis of (S)-(5-(2-(2,6-dichlorobenzamido)-3-methoxy-3-oxopropyl)-3-fluoroquinolin-8-yl)boronic acid (35A): the title compound was prepared according to the method presented for the synthesis of compound 5A starting with 30L.

Synthesis of (S)-2-(2,6-dichlorobenzamido)-3-(3-fluoro-8-(4-(trifluoromethyl) isoquinolin-3-yl)quinolin-5-yl)propanoic acid (35): the title compound was prepared according to the method presented for the synthesis of compound 4C and 4 starting with 35A and 3-bromo-4-(trifluoromethyl) isoquinoline (71B). MS (m/z) 601.9 [M+H]$^+$. 1H NMR (400 MHz, DMSO-d6) δ 9.60 (d, J=3.4 Hz, 1H), 9.29 (dd, J=14.2, 8.4 Hz, 1H), 8.81 (dd, J=3.4, 2.8 Hz, 1H), 8.46 (ddd, J=10.1, 6.9, 2.8 Hz, 1H), 8.38 (dd, J=8.2, 1.1 Hz, 1H), 8.18 (d, J=8.6 Hz, 1H), 8.10-8.01 (m, 1H), 7.94-7.85 (m, 1H), 7.74 (d, J=7.4 Hz, 1H), 7.69 (dd, J=7.3, 1.9 Hz, 1H), 7.45-7.35 (m, 3H), 4.85 (dtd, J=23.5, 9.2, 4.5 Hz, 1H), 3.69 (dt, J=14.4, 4.4 Hz, 1H), 3.44 (dd, J=14.6, 10.1 Hz, 1H).

Example 36

Synthesis of methyl (S)-3-(8-bromo-3-iodoquinolin-5-yl)-2-(2,6-difluorobenzamido) propanoate (36A): A solution of 3A (300 mg, 0.67 mmol) in AcOH (2.5 mL) was treated with N-iodosuccinimide (300 mg, 1.34 mmol) and stirred at 70° C. for 24 h. A second quantity of N-iodosuccinimide (300 mg, 1.34 mmol) was added, and stirring continued at 70° C. for an additional 24 h. The mixture was cooled to RT and concentrated under reduced pressure. The resulting residue was dissolved in DCM, and washed with saturated aqueous NaHCO$_3$, back-extracting the aqueous twice with DCM. The combined organic layers were adsorbed onto silica gel for purification by silica gel chromatography using 0-100% EA in hexanes to afford the title compound. MS (m/z) 575.0 [M+H]$^+$.

Synthesis of methyl (S)-3-(8-bromo-3-cyanoquinolin-5-yl)-2-(2,6-difluorobenzamido) propanoate (36B): A suspension of 36A (50 mg, 0.087 mmol) and cuprous cyanide (12 mg, 0.130 mmol) in DMF (1.5 mL) was stirred at 135° C. under microwave irradiation for 30 min. The reaction mixture was then cooled to RT, diluted with EA and saturated aqueous NaCl, and filtered through celite. The phases were separated, and the aqueous layer was further extracted twice with EA. The combined organic layers were concentrated under reduced pressure and the resulting residue purified by silica gel chromatography using 0-40% EA in hexanes to afford the title compound. MS (m/z) 474.0 [M+H]$^+$.

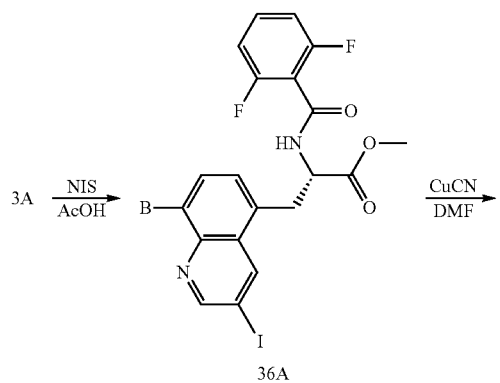

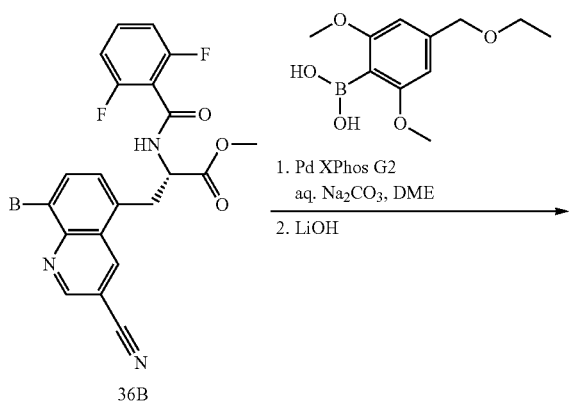

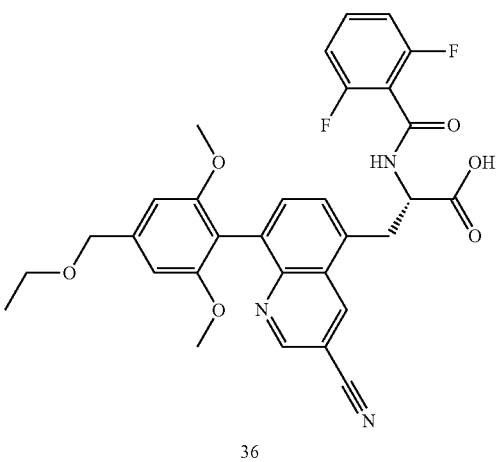

Synthesis of (S)-3-(3-cyano-8-(4-(ethoxymethyl)-2,6-dimethoxyphenyl)quinolin-5-yl)-2-(2,6-difluorobenzamido) propanoic acid (36): the title compound was prepared according to the method presented for the synthesis of compound 18 starting with 36B. MS (m/z) 576.2 [M+H]$^+$. 1H NMR (400 MHz, DMSO-d6) δ 9.27 (d, J=8.1 Hz, 1H), 9.21 (d, J=2.1 Hz, 1H), 9.02 (d, J=2.0 Hz, 1H), 7.69 (d, J=7.4 Hz, 1H), 7.63 (d, J=7.4 Hz, 1H), 7.49 (tt, J=8.4, 6.6 Hz, 1H), 7.15-7.08 (m, 2H), 6.71 (q, J=1.3 Hz, 2H), 4.82 (ddd, J=10.0, 8.2, 4.5 Hz, 1H), 4.52 (s, 2H), 3.77-3.70 (m, 1H), 3.61-3.45 (m, 9H), 1.21 (t, J=7.0 Hz, 3H).

Example 37

Synthesis of methyl (S)-3-(8-bromo-3-(trifluoromethyl)quinolin-5-yl)-2-(2,6-difluoro benzamido)propanoate (37A): A vial was charged with 36A (50 mg, 0.087 mmol) and (1,10-phenanthroline)(trifluoromethyl)copper(I) (98 mg, 0.313 mmol), sealed with a septum cap, and purged with nitrogen for 15 min. DMF (1 mL, previously degassed by sparging with nitrogen for 15 min) was added, and the mixture stirred vigorously at 50° C. for 1 h. The reaction mixture was cooled to RT, diluted with EA, and filtered through celite. The resulting filtrate was washed with saturated aqueous NaHCO$_3$, and the aqueous layer back-extracted twice with EA. The combined organic layers were adsorbed onto silica gel for silica gel chromatography using 0-50% EA in hexanes to afford the title compound. MS (m/z) 517.1 [M+H]$^+$.

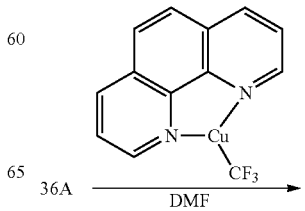

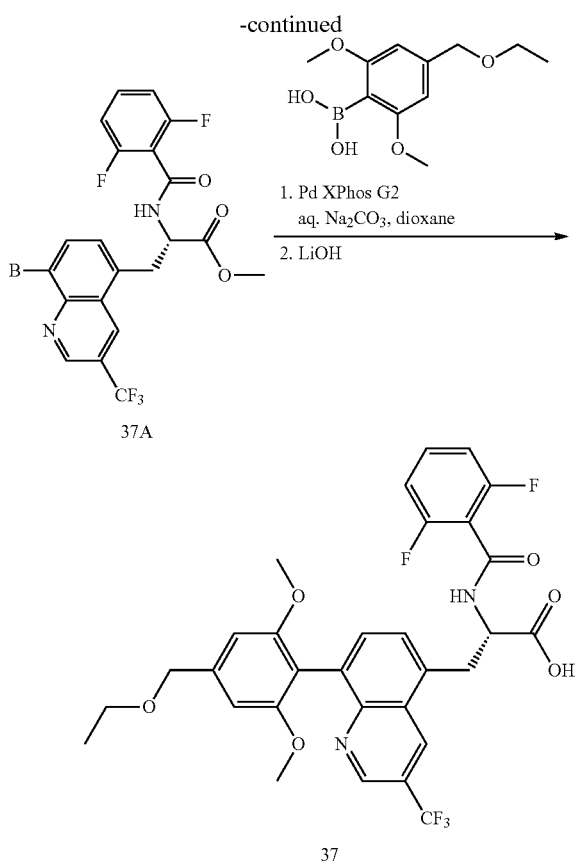

37A

37

Synthesis of (S)-2-(2,6-difluorobenzamido)-3-(8-(4-(ethoxymethyl)-2,6-dimethoxy phenyl)-3-(trifluoromethyl)quinolin-5-yl)propanoic acid (37): the title compound was prepared according to the method presented for the synthesis of compound 18 starting with 37A. MS (m/z) 619.2 [M+H]$^+$. 1H NMR (400 MHz, DMSO-d6) δ 9.31 (d, J=8.0 Hz, 1H), 9.08-9.06 (m, 1H), 8.97 (dd, J=2.3, 1.1 Hz, 1H), 7.70 (d, J=7.5 Hz, 1H), 7.63 (d, J=7.3 Hz, 1H), 7.50 (tt, J=8.5, 6.6 Hz, 1H), 7.15-7.08 (m, 2H), 6.72 (q, J=1.3 Hz, 2H), 4.78 (ddd, J=9.7, 8.0, 4.6 Hz, 1H), 4.53 (s, 2H), 3.77 (dd, J=14.8, 4.6 Hz, 1H), 3.61-3.43 (m, 9H), 1.22 (t, J=7.0 Hz, 3H).

Example 38

Synthesis of 4-((2-bromo-5-methylphenyl)amino)-1,1,1-trifluorobut-3-en-2-one (38A): To a stirred solution of 2-bromo-5-methylaniline (2.149 g, 12 mmol) and 4-(tert-butylamino)-1,1,1-trifluorobut-3-en-2-one (2.05 g, 10.5 mmol) in glacial acetic acid (4 mL) was added TFA (4 mL), and the reaction was heated to 75° C. for 16 hours. It was cooled to RT, poured onto water, and the solids were collected via filtration to yield 38A.

Synthesis of 8-bromo-5-methyl-2-(trifluoromethyl)quinoline (38B): To a stirred suspension of compound 38A (2.81 g, 9.1 mmol) in heptane (9 mL) was added POCl$_3$ (0.855 mL, 9.12 mmol), and the reaction was heated to 100° C. overnight. It was poured onto a solution of 2M sodium carbonate in water. It was extracted twice with ethyl acetate, and the combined organics were washed with saturated sodium chloride solution, dried over anhydrous sodium sulfate, filtered, and concentrated. It was purified via flash chromatography, eluting with a linear gradient of 1-20% ethyl acetate/hexanes, to yield 38B.

Synthesis of 8-bromo-5-(bromomethyl)-2-(trifluoromethyl)quinoline (38C): To a stirred solution of 38B (1.32 g, 4.6 mmol) in benzene (10 mL) was added N-bromosuccinimide (0.97 g, 5.5 mmol), and the reaction was heated to reflux under a tungsten work lamp for 16 hours. It was cooled to RT, filtered and concentrated. The residue was dissolved in ethyl acetate and washed twice with water and once with saturated sodium chloride solution. It was purified via flash chromatography, eluting with a linear gradient of 5-70% DCM/hexanes, to yield compound 38C.

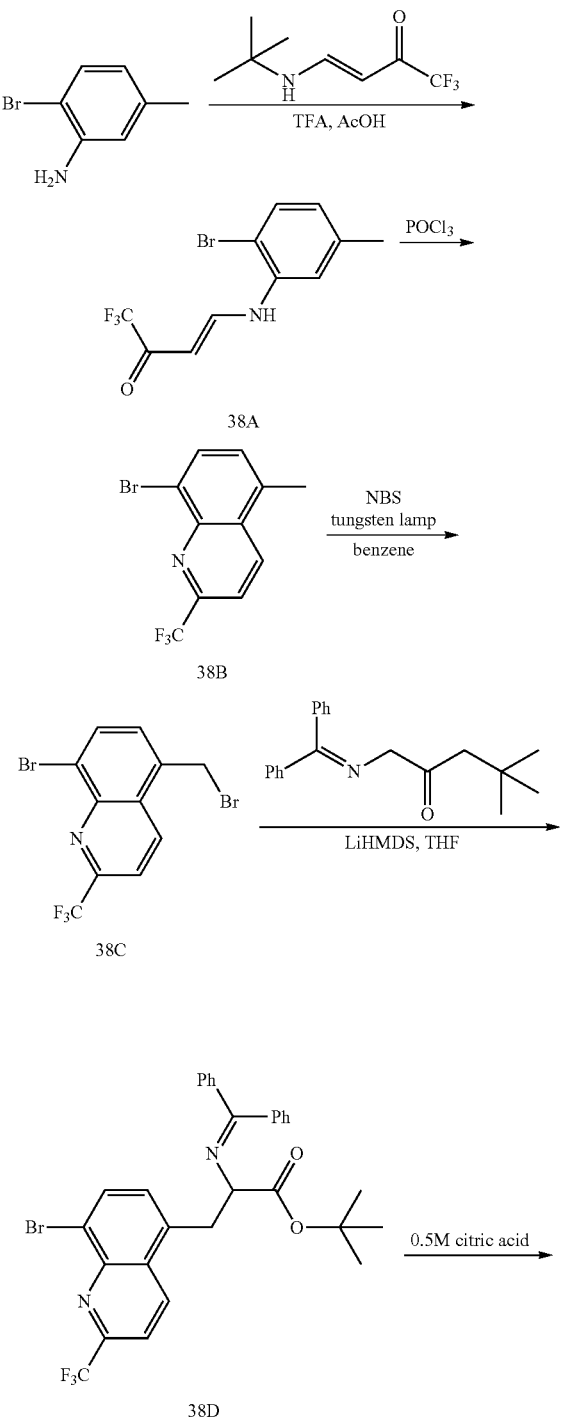

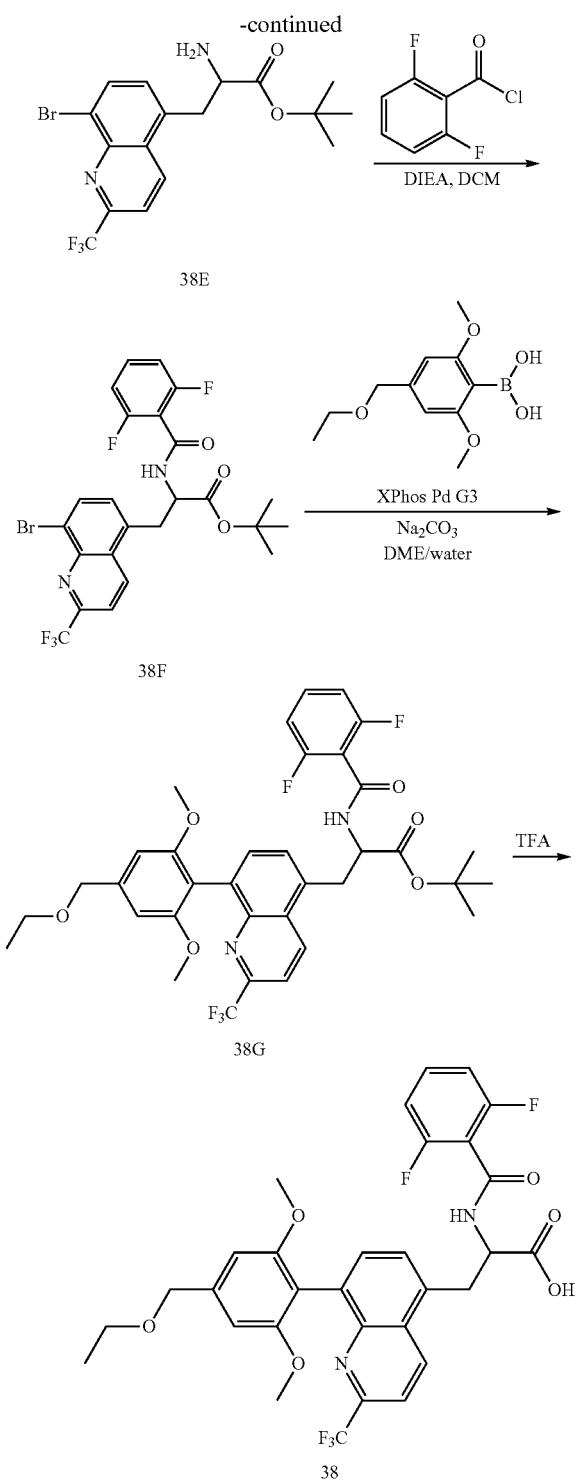

was quenched by the addition of saturated ammonium chloride, and it was partitioned between water and ethyl acetate. The aqueous was extracted with ethyl acetate, and the combined organics were washed with saturated sodium chloride, dried over anhydrous sodium sulfate, filtered, and concentrated. It was purified via flash chromatography, eluting with a linear gradient of 5-50% ethyl acetate/hexanes, to yield compound 38D.

Synthesis of tert-butyl 2-amino-3-(8-bromo-2-(trifluoromethyl)quinolin-5-yl)propanoate (38E): To a stirred solution of compound 38D (335 mg, 0.57 mmol) in tetrahydrofuran (6 mL) was added 0.5M citric acid in water (5.7 mL, 2.87 mmol), and the reaction was allowed to stir for 1 h at RT. It was diluted with water, and washed once with diethyl ether. The aqueous was treated with 1M sodium hydroxide in water until a pH of ~8 was reached, and it was extracted twice with diethyl ether. The combined extracts were washed with saturated sodium chloride solution, dried over anhydrous magnesium sulfate, filtered, and concentrated to yield 38E.

Synthesis of tert-butyl 3-(8-bromo-2-(trifluoromethyl)quinolin-5-yl)-2-(2,6-difluorobenzamido)propanoate (38F): The title compound was prepared according to the method presented for the synthesis of compound 1F starting with 38E and 2,6-difluorobenzoyl chloride.

Synthesis of tert-butyl 2-(2,6-difluorobenzamido)-3-(8-(4-(ethoxymethyl)-2,6-dimethoxyphenyl)-2-(trifluoromethyl)quinolin-5-yl)propanoate (38G): To a solution of 38F (187 mg, 0.33 mmol) and (4-(ethoxymethyl)-2,6-dimethoxyphenyl)boronic acid (104 mg, 0.44 mmol) in 1,2-dimethoxyethane (3 mL) was added 2M sodium carbonate in water (0.5 mL, 0.67 mmol), and the reaction was degassed with nitrogen. To this, XPhos Pd G3 (14 mg, 0.017 mmol) was added, the reaction was sealed, and it was heated to 85° C. for 1 h. It was cooled to RT and purified by flash chromatography, eluting with a linear gradient of 1-10% MeOH/DCM, to yield 38G.

Synthesis of 2-(2,6-difluorobenzamido)-3-(8-(4-(ethoxymethyl)-2,6-dimethoxy phenyl)-2-(trifluoromethyl)quinolin-5-yl)propanoic acid (38): To a solution of 38G (214 mg, 0.32 mmol) in DCM (1 mL) was added TFA (723 mg, 6 mmol), and the reaction was allowed to stir at RT for 4 hours. It was concentrated and purified via preparatory HPLC to yield 38. MS (m/z) 619.2 [M+H]$^+$. 1H NMR (400 MHz, DMSO-d6) δ 9.30 (d, J=8.1 Hz, 1H), 8.85 (dd, J=8.9, 0.8 Hz, 1H), 7.95 (d, J=8.8 Hz, 1H), 7.68 (d, J=7.5 Hz, 1H), 7.61 (d, J=7.3 Hz, 1H), 7.48 (tt, J=8.4, 6.5 Hz, 1H), 7.11 (dd, J=8.5, 7.5 Hz, 2H), 6.72 (q, J=1.3 Hz, 2H), 4.77 (ddd, J=10.1, 8.0, 4.5 Hz, 1H), 4.52 (d, J=0.7 Hz, 2H), 3.76 (dd, J=14.7, 4.5 Hz, 1H), 3.64-3.50 (m, 8H), 3.44 (dd, J=14.8, 10.1 Hz, 1H), 1.20 (t, J=7.0 Hz, 3H).

Example 39

Synthesis of tert-butyl 3-(8-bromo-2-(trifluoromethyl)quinolin-5-yl)-2-((diphenyl methylene)amino)propanoate (38D): A stirred solution of tert-butyl 2-((diphenylmethylene) amino)acetate (260 mg, 0.88 mmol) in tetrahydrofuran (3 mL) under dry nitrogen was cooled to −78° C. 1M Lithium hexamethyldisilazide in THF (0.968 mL, 0.968 mmol) was added dropwise, then the reaction was stirred at this temperature for 15 minutes. To this, a solution of 38C (357 mg, 0.97 mmol) in THF (2 mL) was added, and the reaction was allowed to warm to RT and stir for 16 hours. It

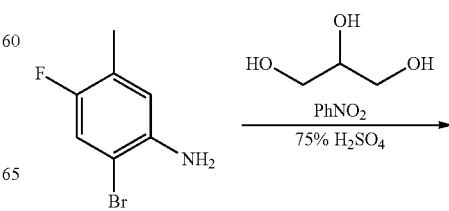

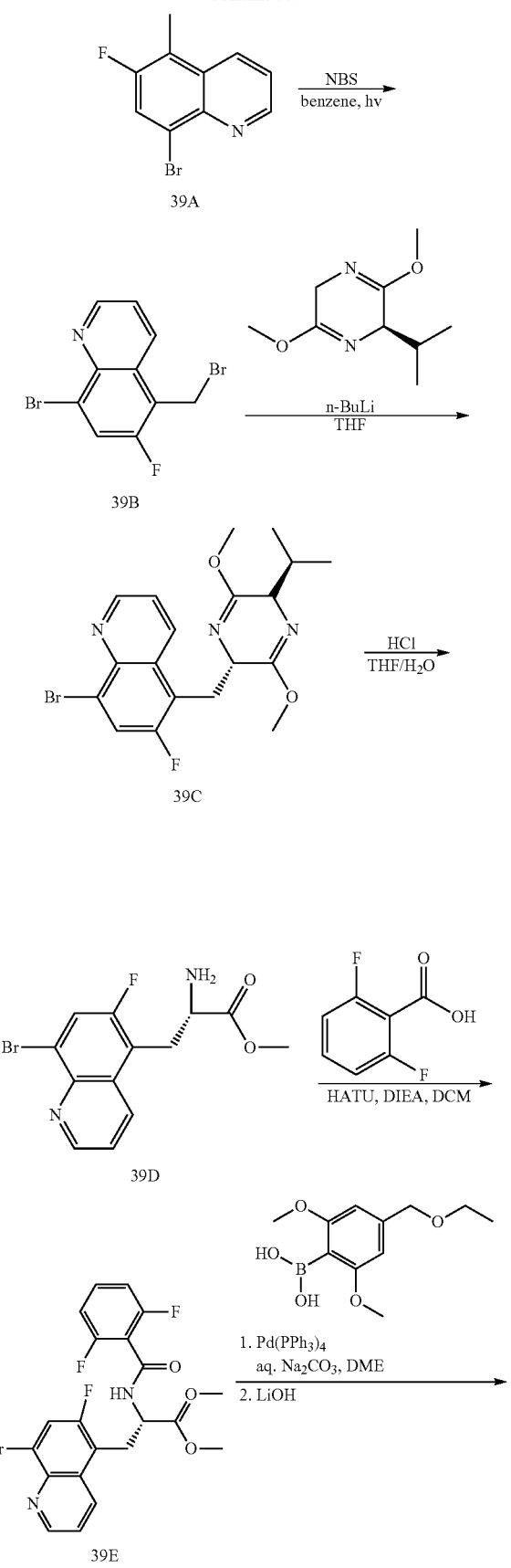

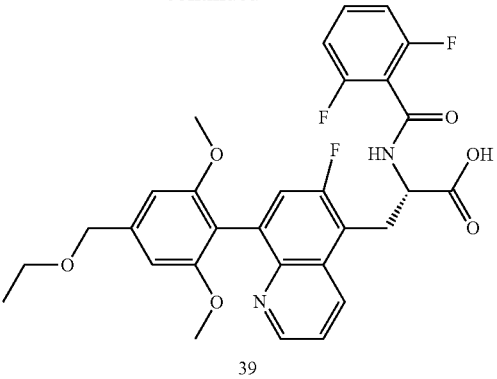 [SMILES: CCOCc1cc(OC)c(-c2cc(F)c(C[C@H](NC(=O)c3c(F)cccc3F)C(=O)O)c3cccnc23)c(OC)c1]

Synthesis of 8-bromo-6-fluoro-5-methylquinoline (39A) the title compound was prepared according to the method presented for the synthesis of compound 1A in Example 1 using 2-bromo-4-fluoro-5-methylaniline. MS (m/z) 240.0 [M+H]⁺.

Synthesis of 8-bromo-5-(bromomethyl)-6-fluoroquinoline (39B): the title compound was prepared according to the method presented for the synthesis of compound 1B in Example 1 using 39A. MS (m/z) 317.9 [M+H]⁺.

Synthesis of 8-bromo-6-fluoro-5-(((2S,5S)-5-isopropyl-3,6-dimethoxy-2,5-dihydro pyrazin-2-yl)methyl)quinoline (39C): the title compound was prepared according to the method presented for the synthesis of compound 34C4 using 39B. MS (m/z) 422.1 [M+H]⁺.

Synthesis of Methyl (S)-2-amino-3-(8-bromo-6-fluoroquinolin-5-yl)propanoate (39D): the title compound was prepared according to the method presented for the synthesis of compound 34 using 39C. MS (m/z) 327.0 [M+H]⁺.

Synthesis of Methyl (S)-3-(8-bromo-6-fluoroquinolin-5-yl)-2-(2,6-difluorobenzamido) propanoate (39E): the title compound was prepared according to the method presented for the synthesis of compound 16A in Example 16 using 39D. MS (m/z) 467.0 [M+H]⁺.

Synthesis of (S)-2-(2,6-difluorobenzamido)-3-(8-(4-(ethoxymethyl)-2,6-dimethoxy phenyl)-6-fluoroquinolin-5-yl)propanoic acid (39): the title compound was prepared according to the method presented for the synthesis of compound 18 using 39E. MS (m/z) 569.2 [M+H]⁺. 1H NMR (400 MHz, DMSO-d6) δ 9.30 (d, J=8.3 Hz, 1H), 8.83-8.70 (m, 2H), 7.68 (dd, J=8.8, 4.3 Hz, 1H), 7.55-7.44 (m, 2H), 7.11 (dd, J=8.5, 7.6 Hz, 2H), 6.75 (s, 2H), 4.77 (td, J=8.5, 6.2 Hz, 1H), 4.54 (s, 2H), 3.70-3.50 (m, 11H), 1.22 (t, J=7.0 Hz, 3H).

Example 40

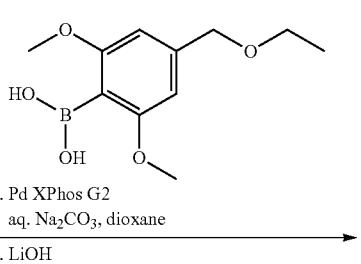

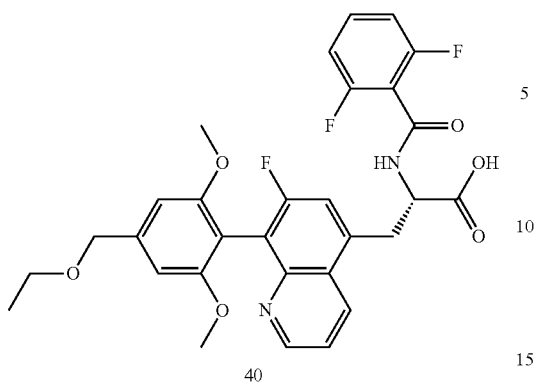

40

(S)-2-(2,6-difluorobenzamido)-3-(8-(4-(ethoxymethyl)-2,6-dimethoxyphenyl)-7-fluoroquinolin-5-yl)propanoic acid (40): the title compound was prepared according to the method presented for the synthesis of compound 18 using 34E. MS (m/z) 569.2 [M+H]$^+$. 1H NMR (400 MHz, DMSO-d6) δ 9.32 (d, J=8.1 Hz, 1H), 8.83 (dd, J=4.3, 1.5 Hz, 1H), 8.70 (d, J=5.0 Hz, 1H), 7.64 (dd, J=8.0, 3.9 Hz, 1H), 7.56-7.46 (m, 2H), 7.18-7.10 (m, 2H), 6.75 (d, J=1.7 Hz, 2H), 4.80 (ddd, J=10.6, 8.1, 4.1 Hz, 1H), 4.54 (s, 2H), 3.80 (dd, J=14.6, 4.1 Hz, 1H), 3.62-3.55 (m, 8H), 3.43 (dd, J=14.8, 10.5 Hz, 1H), 1.22 (t, J=7.0 Hz, 3H).

Example 41

Synthesis of 2,6-difluoro-4-((phenoxycarbonyl)amino)benzoic acid (41A): To a stirred solution of 4-amino-2,6-difluorobenzoic acid (504 mg, 2.16 mmol) in DCM was added phenyl chloroformate (0.41 ml, 3.24 mmol) and pyridine (0.87 ml, 10.81 mmol). The reaction mixture was allowed to stir for 3 hr at RT. The reaction mixture was concentrated under reduced pressure and purified by reverse phase preparative chromatography using aqueous 0.1% TFA/MeCN as the eluent.

Synthesis of (S)-3-(8-(2-chloro-4-cyanophenyl)quinolin-5-yl)-2-(2,6-difluoro-4-((phenoxycarbonyl)amino)benzamido)propanoic acid (41): The title compound was prepared according to the method presented for the synthesis of compound 16A and 16 starting with 41A and 1E. MS (m/z) 686.5 [M+H]$^+$. 1H NMR (400 MHz, DMSO-d6) δ 13.04 (s, 1H), 10.76 (s, 1H), 9.18 (d, J=8.0 Hz, 1H), 8.81 (s, 1H), 7.85-7.37 (m, 6H), 7.32-7.13 (m, 5H), 6.72 (s, 2H), 4.74 (s, 1H), 4.52 (s, 2H), 3.85-3.75 (m, 1H), 3.60-3.51 (m, 8H), 1.20 (t, J=7.0 Hz, 3H).

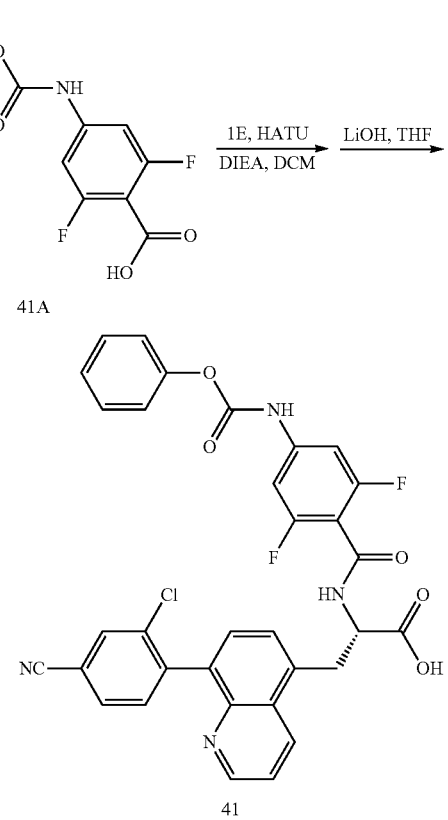

Example 42 and Example 43

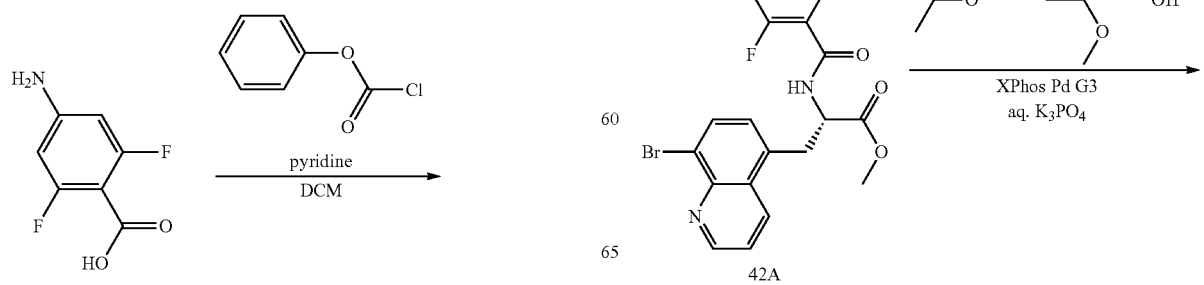

-continued

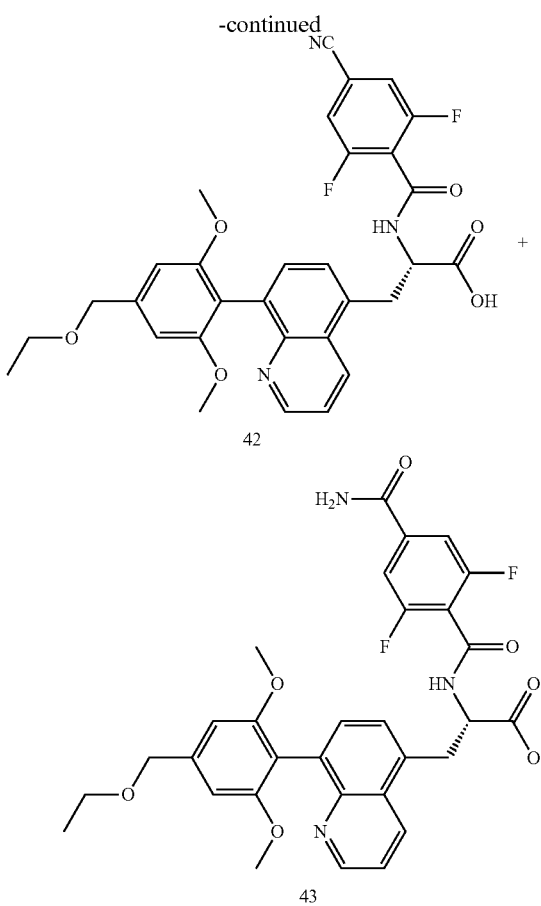

42

43

Synthesis of methyl (S)-3-(8-bromoquinolin-5-yl)-2-(4-cyano-2,6-difluoro benzamido) propanoate (42A): To a stirred solution of 4-cyano-2,6-difluorobenzoic acid (0.12 g, 0.65 mmol) in DCM was added 1D (0.2 g, 0.65 mmol), HATU (0.25 g, 0.65 mmol) and TEA (1 mL). The reaction mixture was allowed to stir ON at RT. The reaction mixture was concentrated under reduced pressure and purified by silica gel chromatography using EA in hexanes as the eluent.

(S)-2-(4-cyano-2,6-difluorobenzamido)-3-(8-(4-(ethoxymethyl)-2,6-dimethoxy phenyl)quinolin-5-yl)propanoic acid (42): To a microwave vial was added 42A (0.24 g, 0.5 mmol), (4-(ethoxymethyl)-2,6-dimethoxyphenyl)boronic acid (200 mg, 0.5 mmol), XPhos Pd G3 (0.043 g, 0.05 mmol), and $K_3PO_4$ (0.21 g, 0.15 mmol) in dioxane (2 mL). The reaction mixture was allowed to stir at 120° C. for 30 min. EA and water was added to the reaction mixture. The organic layer was washed with brine, dried over anhydrous $Na_2SO_4$, and concentrated under reduced pressure. The mixture was purified by silica gel chromatography using MeOH and DCM as eluent to afford both 42 and 43. MS (m/z) 576.2 [M+H]$^+$. 1 H NMR (400 MHz, DMSO-d6) δ 8.72 (dd, J=4.1, 1.6 Hz, 1H), 8.60 (s, 1H), 8.15 (s, 1H), 7.72 (s, 1H), 7.57 (d, J=8.1 Hz, 2H), 7.53-7.46 (m, 2H), 7.36 (d, J=7.3 Hz, 1H), 6.68 (d, J=2.3 Hz, 2H), 4.61 (s, 1H), 4.50 (s, 2H), 3.68 (dd, J=14.0, 4.7 Hz, 1H), 3.56 (d, J=7.0 Hz, 1H), 3.52 (d, J=7.1 Hz, 6H), 3.44-3.33 (m, 1H), 1.20 (t, J=7.0 Hz, 3H).

(S)-2-(4-carbamoyl-2,6-difluorobenzamido)-3-(8-(4-(ethoxymethyl)-2,6-dimethoxy phenyl)quinolin-5-yl)propanoic acid (43). MS (m/z) 595.5 [M+H]$^+$. 1H NMR (400 MHz, DMSO-d6) δ 13.15 (s, 1H), 9.48 (d, J=8.0 Hz, 1H), 8.74 (dd, J=4.1, 1.7 Hz, 1H), 8.53 (dd, J=8.7, 1.7 Hz, 1H), 8.01-7.73 (m, 2H), 7.53 (dd, J=8.6, 4.1 Hz, 1H), 7.48 (d, J=7.4 Hz, 1H), 7.38 (d, J=7.3 Hz, 1H), 6.76-6.63 (m, 2H), 4.75 (td, J=8.8, 4.4 Hz, 1H), 4.50 (s, 2H), 3.91-3.61 (m, 1H), 3.55 (t, J=7.0 Hz, 2H), 3.53 (s, 3H), 3.46-3.22 (m, 4H), 1.20 (t, J=7.0 Hz, 3H).

Example 44

Synthesis of methyl (S)-2-amino-3-(8-(4-(ethoxymethyl)-2,6-dimethoxyphenyl) quinolin-5-yl)propanoate (44A): The title compound was prepared according to the method presented for the synthesis of compound 1E starting with (4-(ethoxymethyl)-2,6-dimethoxy phenyl)boronic acid.

(S)-2-(4-amino-2,6-difluorobenzamido)-3-(8-(4-(ethoxymethyl)-2,6-dimethoxyphenyl) quinolin-5-yl)propanoic acid (44): The title compound was prepared according to the method presented for the synthesis of compound 16A and 16 starting with 44A and 4-amino-2,6-difluorobenzoic acid. MS (m/z) 567.6 [M+H]$^+$. 1H NMR (400 MHz, DMSO-d6) δ 8.84 (s, 2H), 8.67 (d, J=7.9 Hz, 1H), 7.64 (t, J=37.5 Hz, 3H), 6.74 (d, J=2.2 Hz, 2H), 6.11 (d, J=10.7 Hz, 2H), 4.75-4.62 (m, 1H), 4.53 (s, 2H), 3.81-3.65 (m, 1H), 3.58 (d, J=7.0 Hz, 2H), 3.55 (d, J=6.1 Hz, 7H), 1.20 (t, J=7.0 Hz, 3H).

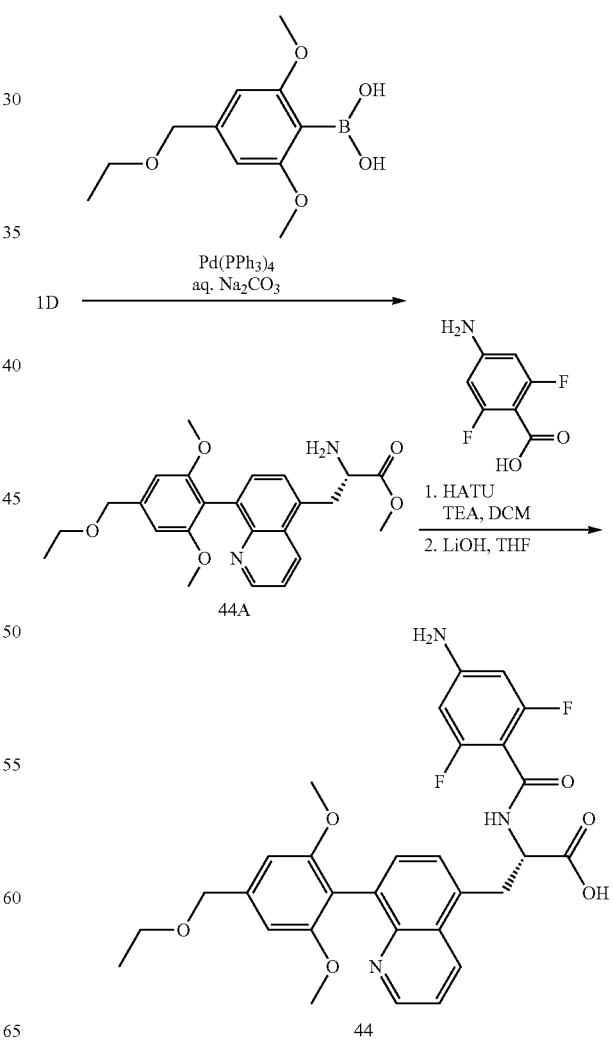

44A

44

Example 45

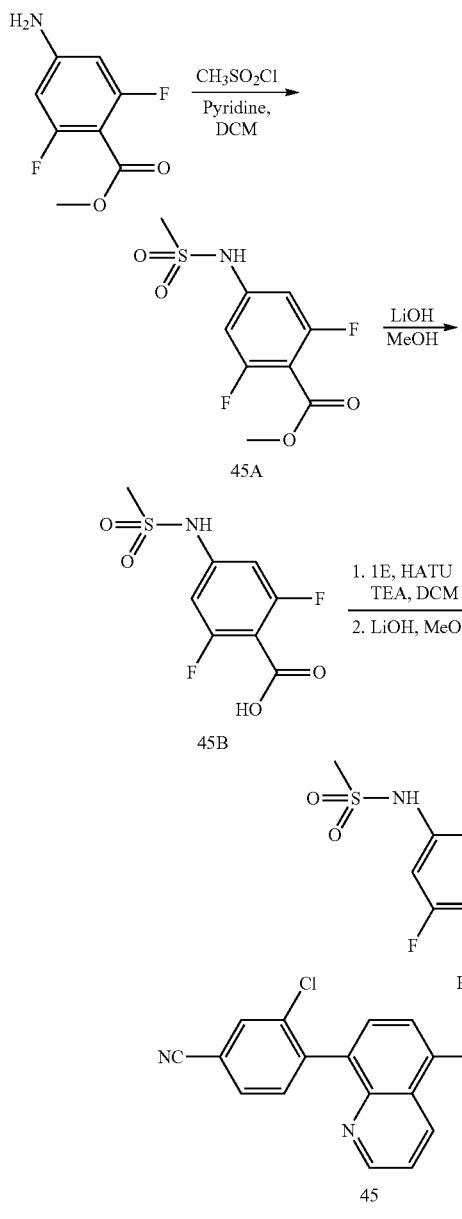

Synthesis of methyl 2,6-difluoro-4-(methylsulfonamido)benzoate (45A): To a stirred solution of methyl 4-amino-2,6-difluorobenzoate (500 mg, 0.3 mmol) in DCM was added methyl sulfonyl chloride (0.31 ml, 0.4 mmol), and pyridine (1.08 mL, 1.3 mmol). The reaction was stirred for at RT ON. The reaction mixture was diluted with EA, washed with 1 M HCl, bicarbonate, brine, and dried, filtered, and concentrated. The material was recrystallized from EA/hexanes to yield the title compound.

Synthesis of 2,6-difluoro-4-(methylsulfonamido)benzoic acid (45B): To a stirred solution of 45A (534 mg, 0.2 mmol) in THF was added aqueous LiOH (5 mL, 2 M). The mixture was allowed to stir at RT for 2 days, diluted with water and acidified with 1 M HCl. The material was extracted with DCM, dried, filtered, and concentrated under reduced pressure. The material purified by silica gel chromatography using EA/hexanes as eluent to afford the title compound.

(S)-3-(8-(2-chloro-4-cyanophenyl)quinolin-5-yl)-2-(2,6-difluoro-4-(methyl sulfonamido)benzamido)propanoic acid (45): The title compound was prepared according to the method presented for the synthesis of compound 16A and 16 starting with 45B. MS (m/z) 585.1 [M+H]+. 1H NMR (400 MHz, DMSO-d6) δ 10.46 (s, 1H), 9.15 (d, J=8.1 Hz, 1H), 8.85 (dd, J=4.1, 1.6 Hz, 1H), 8.65 (dd, J=8.7, 1.7 Hz, 1H), 8.17 (dd, J=1.6, 0.4 Hz, 1H), 7.92 (dd, J=7.9, 1.6 Hz, 1H), 7.70-7.55 (m, 4H), 6.83 (d, J=9.3 Hz, 2H), 4.83-4.68 (m, 1H), 3.87-3.66 (m, 1H), 3.51-3.33 (m, 1H), 3.14 (s, 3H).

Example 46

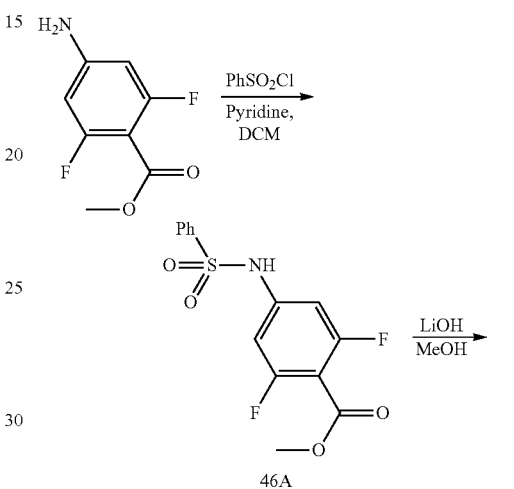

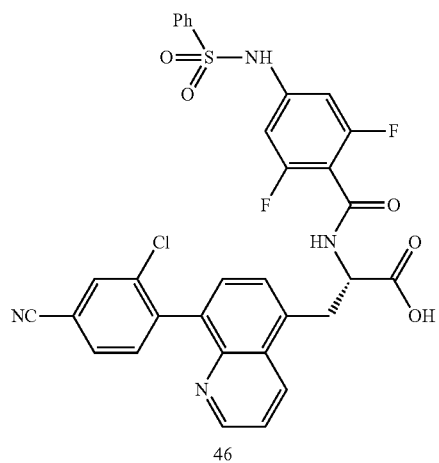

(S)-3-(8-(2-chloro-4-cyanophenyl)quinolin-5-yl)-2-(2,6-difluoro-4-(phenyl sulfonamido)benzamido)propanoic acid (46): The title compound was prepared according to the method presented for the synthesis of compounds 45A, 45B, and 45 starting with phenyl sulfonyl chloride. MS (m/z) 647.1 [M+H]+. 1H NMR (400 MHz, DMSO-d6) δ 11.09 (s, 1H), 9.12 (d, J=8.1 Hz, 1H), 8.84 (dd, J=4.2, 1.6 Hz, 1H), 8.63-8.60 (m, 1H), 8.17 (d, J=1.7 Hz, 1H), 7.92 (dd, J=7.9, 1.7 Hz, 1H), 7.89-7.82 (m, 2H), 7.73-7.53 (m, 7H), 6.75 (d, J=9.2 Hz, 2H), 4.75-4.65 (m, 1H), 3.82-3.65 (m, 1H), 3.47-3.27 (m, 1H).

Example 47

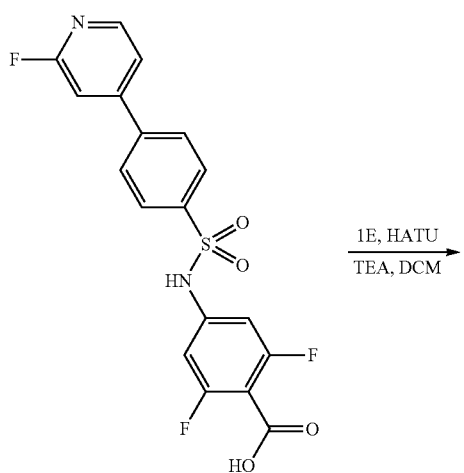

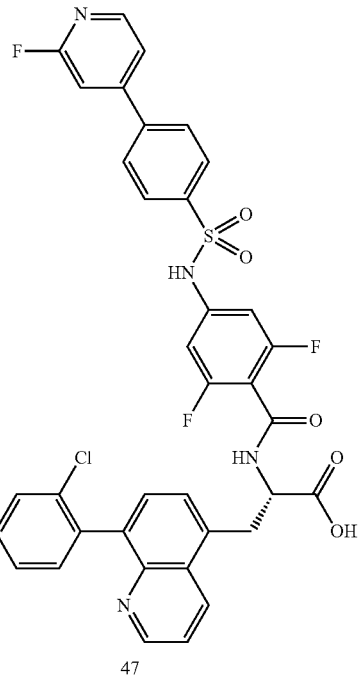

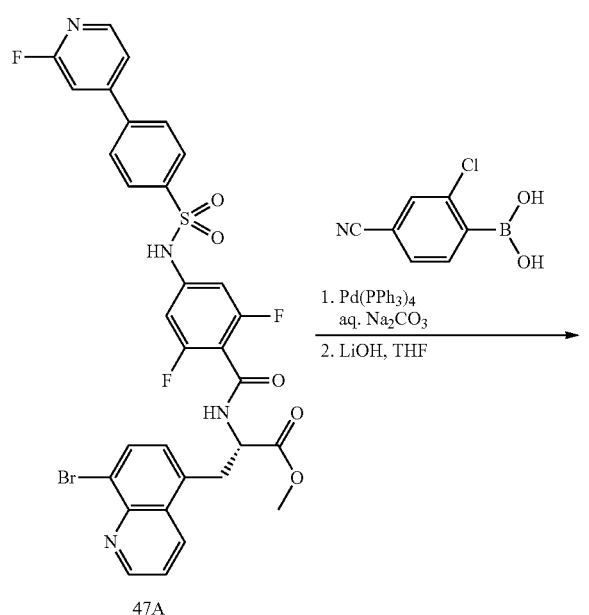

Synthesis methyl (S)-3-(8-bromoquinolin-5-yl)-2-(2,6-difluoro-4-((4-(2-fluoropyridin-4-yl)phenyl)sulfonamido)benzamido)propanoate (47A): The title compound was prepared according to the method presented for the synthesis of compound 16 of Example 16 starting with 2,6-difluoro-4-((4-(2-fluoropyridin-4-yl)phenyl)sulfonamido)benzoic acid.

Synthesis of (S)-3-(8-(2-chloro-4-cyanophenyl)quinolin-5-yl)-2-(2,6-difluoro-4-((4-(2-fluoropyridin-4-yl)phenyl)sulfonamido)benzamido)propanoic acid (47): The title compound was prepared according to the method presented for the synthesis of compound 3B and 3 starting with 47A. MS (m/z) 742.4 [M+H]+. 1H NMR (400 MHz, DMSO-d6) δ 11.21 (s, 1H), 9.11 (d, J=8.1 Hz, 1H), 8.81 (dd, J=4.1, 1.6 Hz, 1H), 8.59 (dd, J=8.6, 1.7 Hz, 1H), 8.33 (d, J=5.3 Hz, 1H), 8.14 (d, J=1.6 Hz, 1H), 8.09-8.03 (m, 2H), 8.01-7.94 (m, 2H), 7.89 (dd, J=7.9, 1.6 Hz, 1H), 7.72 (dt, J=5.4, 1.8 Hz, 1H), 7.64-7.51 (m, 5H), 6.78 (d, J=9.2 Hz, 2H), 4.83-4.59 (m, 1H), 3.71 (s, 1H), 3.34 (s, 1H).

Example 48

Synthesis of 2,6-difluoro-4-((methylsulfonyl)methyl)benzoic acid (48A): To a stirred solution of methyl 4-(bromomethyl)-2,6-difluorobenzoate (125 mg, 0.47 mmol) in DMF was added methyl sodium sulfinate (96.28 mg, 0.94 mmol). This was heated to 65° C. and stirred for 1 h. EA and water were added. The combined organics were washed with brine, dried, and concentrated. The material was then converted to the title compound according to the method presented for the synthesis of compound 1G.

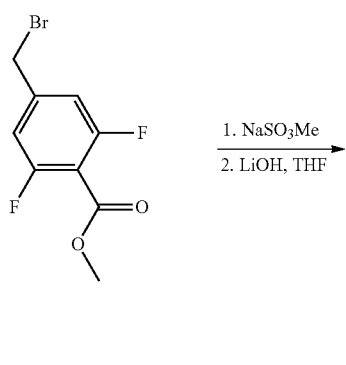
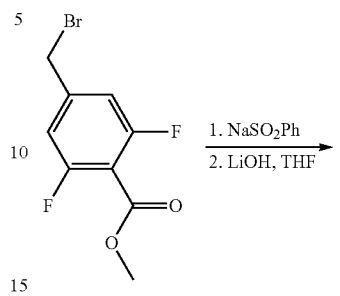
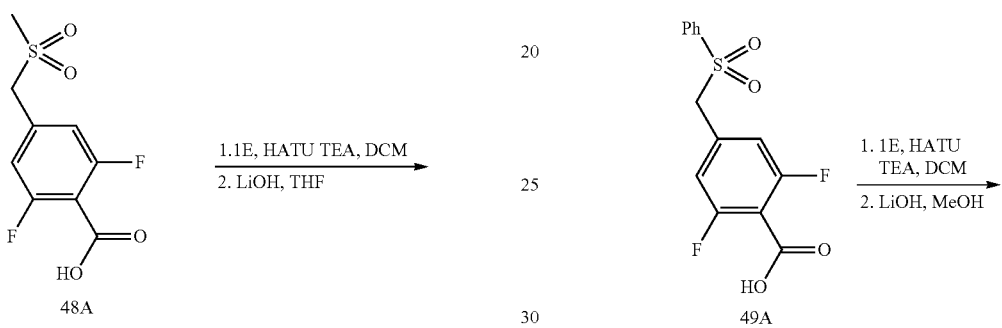
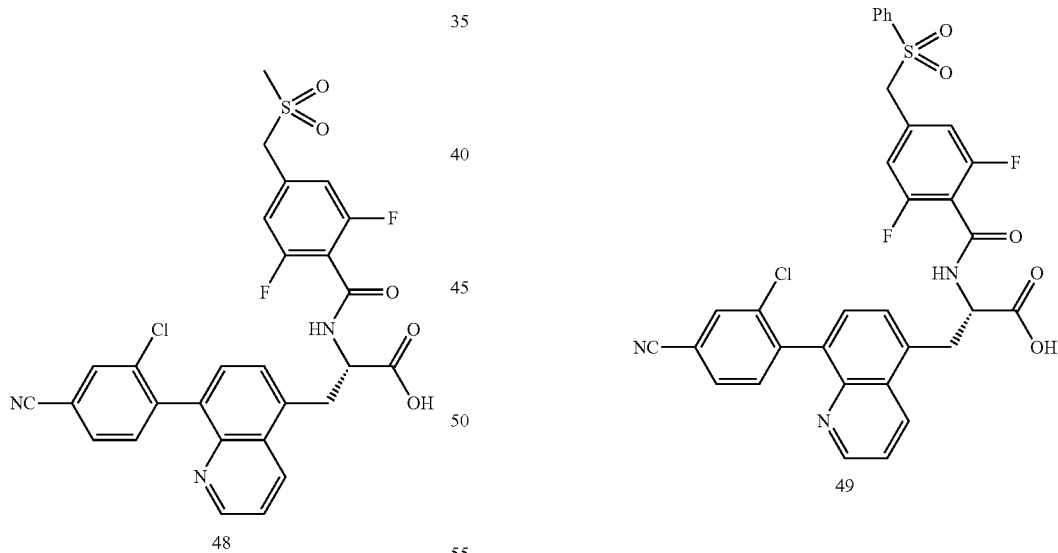

Example 49

(S)-3-(8-(2-chloro-4-cyanophenyl)quinolin-5-yl)-2-(2,6-difluoro-4-((methylsulfonyl) methyl)benzamido)propanoic acid (48): The title compound was prepared according to the method presented for the synthesis of compound 16A and 16 starting with 48A. MS (m/z) 584.2 [M+H]+. 1H NMR (400 MHz, DMSO-d6) δ 9.30 (d, J=8.2 Hz, 1H), 8.84 (dd, J=4.2, 1.6 Hz, 1H), 8.65 (dd, J=8.7, 1.6 Hz, 1H), 8.15 (d, J=1.6 Hz, 1H), 7.90 (dd, J=7.9, 1.7 Hz, 1H), 7.68-7.53 (m, 4H), 7.16 (d, J=8.1 Hz, 2H), 4.84-4.73 (m, 1H), 4.55 (s, 2H), 3.77 (s, 1H), 3.40 (s, 1H), 2.93 (s, 3H).

(S)-3-(8-(2-chloro-4-cyanophenyl)quinolin-5-yl)-2-(2,6-difluoro-4-((phenylsulfonyl) methyl)benzamido)propanoic acid (49): The title compound was prepared according to the method presented for the synthesis of compound 48A of Example 48 starting with phenyl sodium sulfinate, followed by the method presented for 16 and 16C starting with 49A. MS (m/z) 646.3 [M+H]+. 1H NMR (400 MHz, DMSO-d6) δ 9.28 (d, J=8.2 Hz, 1H), 8.83 (dd, J=4.1, 1.6 Hz, 1H), 8.64 (dd, J=8.7, 1.7 Hz, 1H), 8.15 (d, J=1.6 Hz, 1H), 7.90 (dd, J=7.9, 1.7 Hz, 1H), 7.81-7.69 (m, 3H), 7.69-7.50 (m, 6H), 6.88 (d, J=8.1 Hz, 2H), 4.82-4.73 (m, 1H), 4.77 (s, 2H), 3.76 (s, 1H), 3.40 (s, 1H).

Example 50

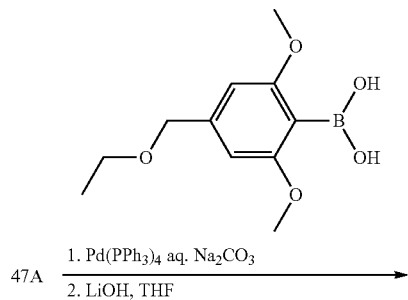

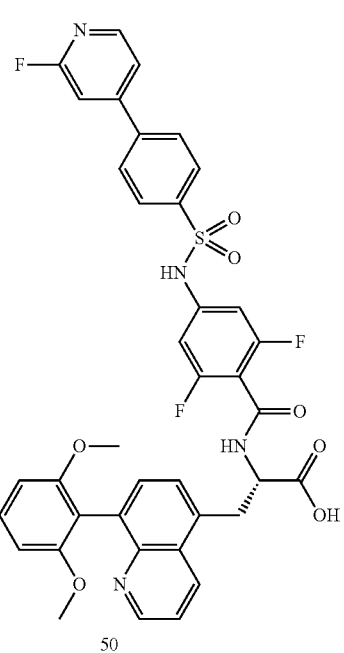

(S)-2-(2,6-difluoro-4-((4-(2-fluoropyridin-4-yl)phenyl)sulfonamido)benzamido)-3-(8-(4-(ethoxymethyl)-2,6-dimethoxyphenyl)quinolin-5-yl)propanoic acid (50): The title compound was prepared according to the method presented for the synthesis of compound 3B and 3 starting with 47A and (4-(ethoxymethyl)-2,6-dimethoxyphenyl)boronic acid. MS (m/z) 802.4 [M+H]+. 1H NMR (400 MHz, DMSO-d6) δ 11.24 (s, 1H), 9.16 (d, J=8.0 Hz, 1H), 8.83 (s, 2H), 8.35 (d, J=5.3 Hz, 1H), 8.12-8.04 (m, 2H), 8.03-7.95 (m, 2H), 7.82-7.43 (m, 5H), 6.81 (d, J=9.0 Hz, 2H), 6.74 (s, 2H), 4.72 (q, J=8.3 Hz, 1H), 4.54 (s, 2H), 3.73 (dd, J=13.3, 3.5 Hz, 1H), 3.59 (d, J=7.0 Hz, 1H), 3.54 (d, J=2.0 Hz, 6H), 3.43 (s, 1H), 1.22 (t, J=7.0 Hz, 3H).

Example 51

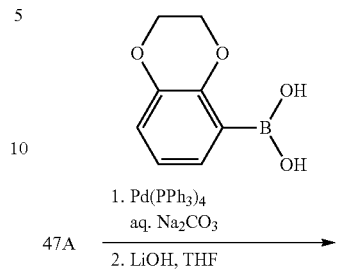

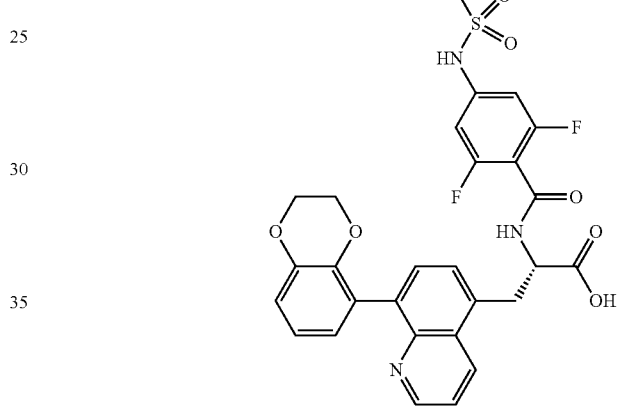

(S)-3-(8-(2-chloro-4-cyanophenyl)quinolin-5-yl)-2-(2,6-difluoro-4-((methylsulfonyl) methyl)benzamido)propanoic acid (51): The title compound was prepared according to the method presented for the synthesis of compound 3B and 3 starting with 47A and (2,3-dihydrobenzo[b][1,4]dioxin-5-yl)boronic acid. MS (m/z) 741.4 [M+H]+. 1H NMR (400 MHz, DMSO-d6) δ 11.21 (s, 1H), 9.12 (d, J=8.1 Hz, 1H), 8.87 (s, 1H), 8.71 (s, 1H), 8.38-8.26 (m, 1H), 8.10-8.02 (m, 2H), 8.02-7.93 (m, 2H), 7.78-7.47 (m, 5H), 6.90 (d, J=9.3 Hz, 2H), 6.79 (t, J=8.8 Hz, 2H), 4.67 (s, 1H), 4.20 (s, 2H), 4.05 (s, 2H), 3.71 (d, J=14.0 Hz, 1H), 3.42-3.27 (m, 1H).

Example 52

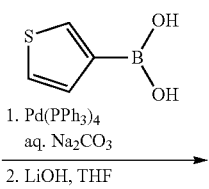

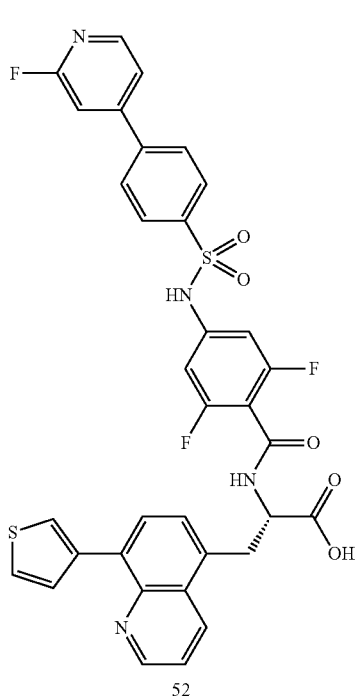

52

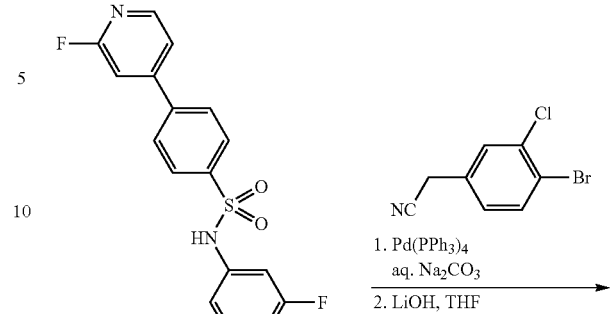

(S)-2-(2,6-difluoro-4-((4-(2-fluoropyridin-4-yl)phenyl)sulfonamido)benzamido)-3-(8-(thiophen-3-yl)quinolin-5-yl)propanoic acid (52): The title compound was prepared according to the method presented for the synthesis of compound 3B and 3 starting with 47A and thiophen-3-ylboronic acid. MS (m/z) 689.2 [M+H]+. 1H NMR (400 MHz, DMSO-d6) δ 11.23 (s, 1H), 9.11 (d, J=8.1 Hz, 1H), 8.97 (dd, J=4.1, 1.7 Hz, 1H), 8.60 (dd, J=8.6, 1.7 Hz, 1H), 8.37-8.32 (m, 1H), 8.09-8.04 (m, 3H), 8.01-7.96 (m, 2H), 7.86 (d, J=7.5 Hz, 1H), 7.74 (dt, J=5.4, 1.8 Hz, 1H), 7.69-7.59 (m, 4H), 7.51 (d, J=7.5 Hz, 1H), 6.81 (d, J=9.1 Hz, 2H), 4.66 (ddd, J=10.1, 8.1, 4.4 Hz, 1H), 3.69 (dd, J=14.3, 4.4 Hz, 1H), 3.31 (dd, J=14.5, 10.1 Hz, 1H).

Example 53

Synthesis of (S)-3-(8-boronoquinolin-5-yl)-2-(2,6-difluoro-4-((4-(2-fluoropyridin-4-yl)phenyl)sulfonamido)benzamido)propanoic acid (53A): The title compound was prepared according to the method presented for the synthesis of compound 4B starting with 47A.

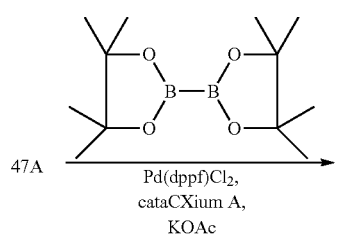

47A   Pd(dppf)Cl₂,
      cataCXium A,
      KOAc

53A

53

(S)-3-(8-(2-chloro-4-(cyanomethyl)phenyl)quinolin-5-yl)-2-(2,6-difluoro-4-((4-(2-fluoropyridin-4-yl)phenyl)sulfonamido)benzamido)propanoic acid (53): The title compound was prepared according to the method presented for the synthesis of compound 5B and 5 starting with 53A and 2-(4-bromo-3-chlorophenyl)acetonitrile. MS (m/z) 756.1 [M+H]+. 1H NMR (400 MHz, DMSO-d6) δ 11.19 (s, 1H), 9.10 (d, J=8.1 Hz, 1H), 8.81 (dd, J=4.1, 1.6 Hz, 1H), 8.58 (dd, J=8.7, 1.7 Hz, 1H), 8.33 (dt, J=5.3, 0.6 Hz, 1H), 8.09-8.02 (m, 2H), 8.01-7.94 (m, 2H), 7.72 (dt, J=5.4, 1.8 Hz, 1H), 7.62-7.49 (m, 5H), 7.43-7.32 (m, 2H), 6.79 (d, J=9.1 Hz, 2H), 4.67 (d, J=11.2 Hz, 1H), 4.14 (s, 2H), 3.36 (s, 2H).

Example 54

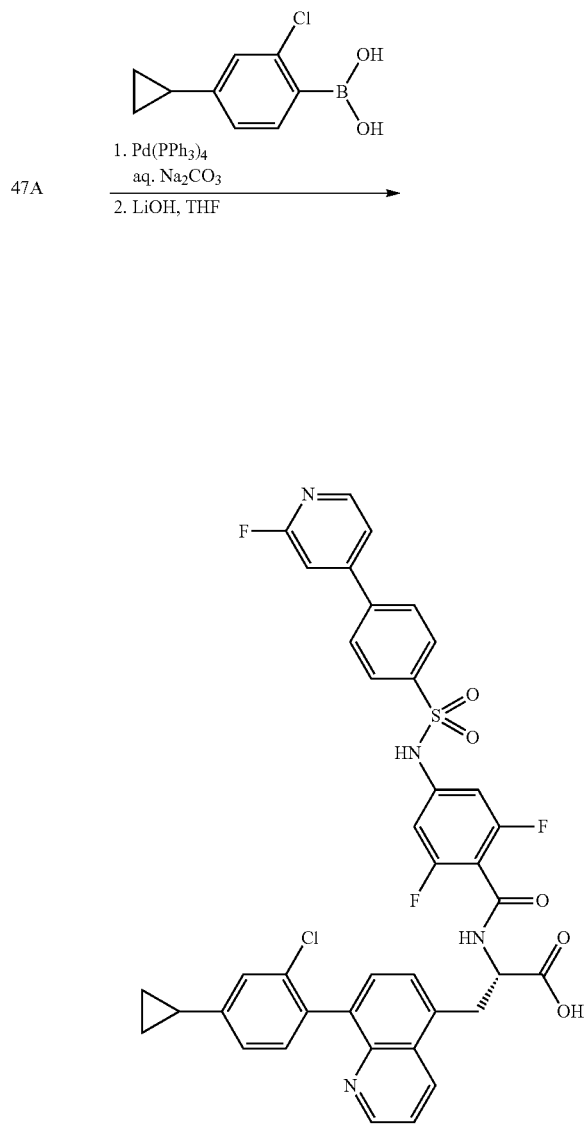

54

(S)-3-(8-(2-chloro-4-cyclopropylphenyl)quinolin-5-yl)-2-(2,6-difluoro-4-((4-(2-fluoropyridin-4-yl)phenyl)sulfonamido)benzamido)propanoic acid (54): The title compound was prepared according to the method presented for the synthesis of compound 3B and 3 starting with 47A and (2-chloro-4-cyclopropylphenyl)boronic acid. MS (m/z) 757.2 [M+H]+. 1H NMR (400 MHz, DMSO-d6) δ 11.23 (s, 1H), 9.12 (d, J=8.1 Hz, 1H), 8.82 (d, J=4.3 Hz, 1H), 8.61 (d, J=8.7 Hz, 1H), 8.35 (d, J=5.3 Hz, 1H), 8.13-8.05 (m, 2H), 8.03-7.95 (m, 2H), 7.74 (dt, J=5.3, 1.8 Hz, 1H), 7.66-7.52 (m, 4H), 7.25 (d, J=1.8 Hz, 1H), 7.21 (d, J=7.9 Hz, 1H), 7.11 (dd, J=8.1, 1.8 Hz, 1H), 6.80 (d, J=9.1 Hz, 2H), 4.76-4.64 (m, 1H), 3.82-3.62 (m, 1H), 3.45-3.25 (m, 1H), 2.02 (tt, J=8.4, 5.1 Hz, 1H), 1.07-0.99 (m, 2H), 0.84-0.73 (m, 2H).

Example 55

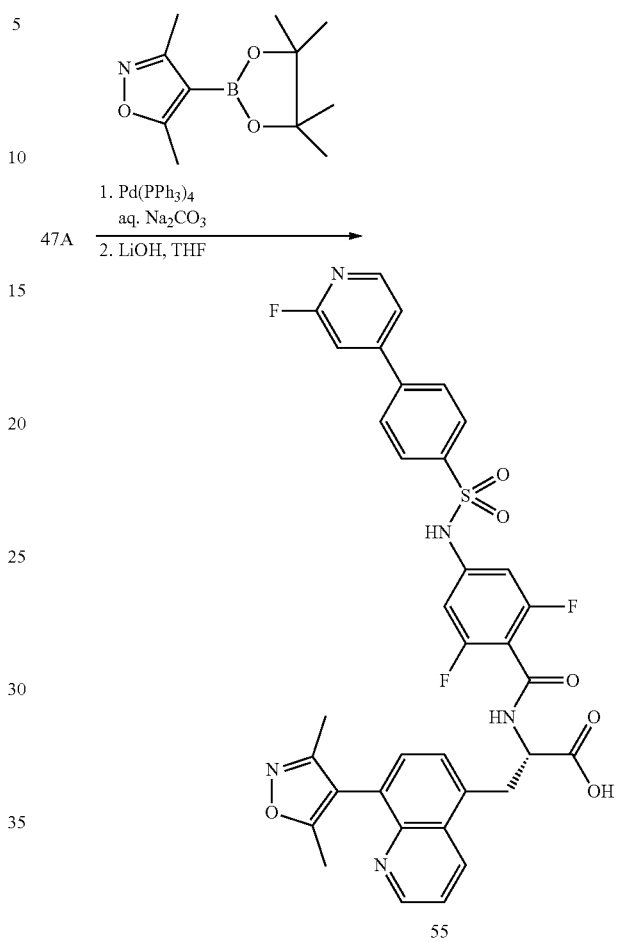

55

(S)-2-(2,6-difluoro-4-((4-(2-fluoropyridin-4-yl)phenyl)sulfonamido)benzamido)-3-(8-(3,5-dimethylisoxazol-4-yl)quinolin-5-yl)propanoic acid (55): The title compound was prepared according to the method presented for the synthesis of compound 3B and 3 starting with 47A and 3,5-dimethyl-4-(4,4,5,5-tetramethyl-1,3,2-dioxaborolan-2-yl)isoxazole. MS (m/z) 702.2 [M+H]+. 1H NMR (400 MHz, DMSO-d6) δ 11.19 (s, 1H), 9.07 (d, J=8.2 Hz, 1H), 8.88 (dd, J=4.1, 1.6 Hz, 1H), 8.58 (dd, J=8.7, 1.6 Hz, 1H), 8.33 (d, J=5.3 Hz, 1H), 8.05 (s, 1H), 8.01-7.93 (m, 2H), 7.72 (dt, J=5.4, 1.8 Hz, 1H), 7.65-7.57 (m, 3H), 7.52 (d, J=7.4 Hz, 1H), 6.77 (d, J=9.1 Hz, 2H), 4.69 (s, 1H), 3.75-3.60 (m, 1H), 3.30 (dd, J=14.4, 10.6 Hz, 1H), 2.22 (s, 3H), 2.01 (s, 3H).

Example 56

(S)-2-(2,6-difluoro-4-((4-(2-fluoropyridin-4-yl)phenyl)sulfonamido)benzamido)-3-(8-(pyrimidin-4-yl)quinolin-5-yl)propanoic acid (56): The title compound was prepared according to the method presented for the synthesis of compound 5B and 5 starting with 53A and 4-bromopyrimidine. MS (m/z) 685.4 [M+H]+. 1H NMR (400 MHz, DMSO-d6) δ 11.21 (s, 1H), 9.30 (d, J=1.4 Hz, 1H), 9.11 (d, J=8.2 Hz, 1H), 8.99 (dd, J=4.2, 1.6 Hz, 1H), 8.86 (d, J=5.4 Hz, 1H), 8.67 (dd, J=8.7, 1.7 Hz, 1H), 8.42-8.25 (m, 2H), 8.19 (d, J=7.5 Hz, 1H), 8.10-8.00 (m, 2H), 8.01-7.92 (m, 2H), 7.74-7.70 (m, 1H), 7.71-7.66 (m, 1H), 7.63 (d, J=7.6 Hz, 1H), 7.59 (d, J=1.5 Hz, 1H), 6.78 (d, J=9.1 Hz, 2H), 4.68 (ddd, J=10.3, 8.2, 4.4 Hz, 1H), 3.81-3.65 (m, 1H), 3.34 (d, J=7.0 Hz, 1H).

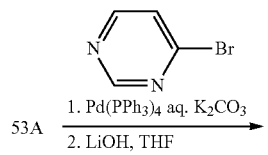

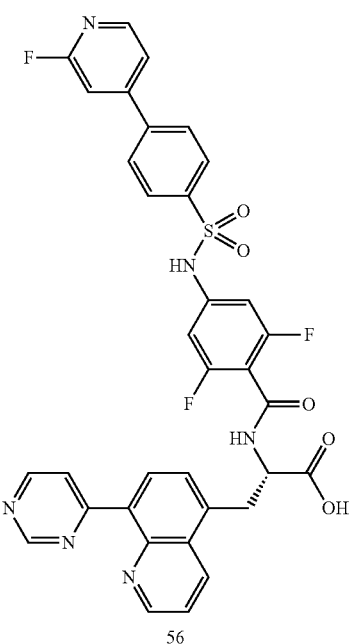

Example 57

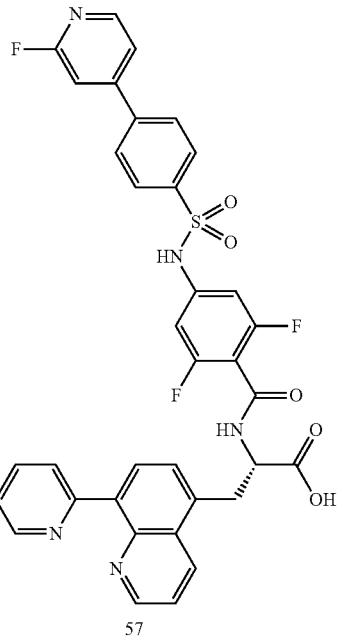

(S)-2-(2,6-difluoro-4-((4-(2-fluoropyridin-4-yl)phenyl)sulfonamido)benzamido)-3-(8-(5-(trifluoromethyl)pyridin-2-yl)quinolin-5-yl)propanoic acid (57): The title compound was prepared according to the method presented for the synthesis of compound 5B and 5 starting with 53A and 2-bromo-5-(trifluoromethyl)pyridine. MS (m/z) 752.4 [M+H]+. 1H NMR (400 MHz, DMSO-d6) δ 11.21 (s, 1H), 9.20-9.05 (m, 2H), 8.98 (dd, J=4.2, 1.6 Hz, 1H), 8.69 (dd, J=8.7, 1.7 Hz, 1H), 8.38-8.23 (m, 3H), 8.11 (d, J=7.5 Hz, 1H), 8.09-8.02 (m, 2H), 8.00-7.90 (m, 2H), 7.76-7.65 (m, 2H), 7.63 (d, J=7.5 Hz, 1H), 7.58 (d, J=1.7 Hz, 1H), 6.78 (d, J=9.1 Hz, 2H), 4.78-4.62 (m, 1H), 3.74 (dd, J=14.5, 4.4 Hz, 1H), 3.36 (dd, J=14.5, 10.2 Hz, 1H).

Example 58

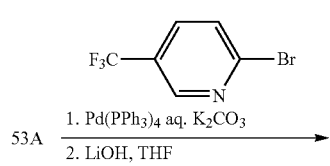

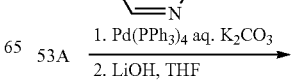

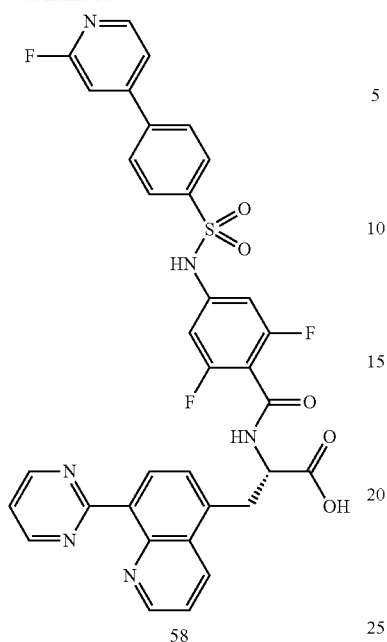

58

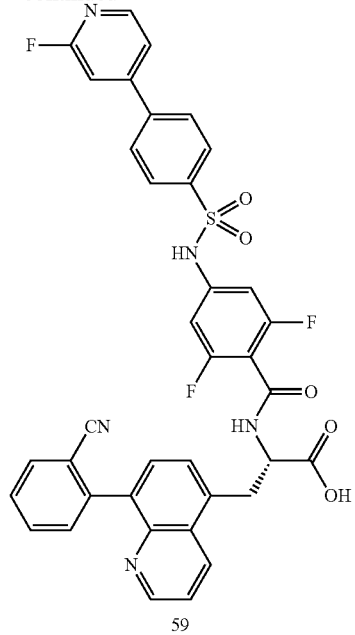

59

(S)-2-(2,6-difluoro-4-((4-(2-fluoropyridin-4-yl)phenyl) sulfonamido)benzamido)-3-(8-(pyrimidin-2-yl)quinolin-5-yl)propanoic acid (58): The title compound was prepared according to the method presented for the synthesis of compound 5B and 5 starting with 53A and 2-bromopyrimidine. MS (m/z) 685.4 [M+H]+. 1H NMR (400 MHz, DMSO-d6) δ 11.22 (s, 1H), 9.29 (d, J=4.9 Hz, 1H), 9.23 (d, J=8.7 Hz, 1H), 9.15-9.02 (m, 3H), 8.76 (s, 1H), 8.33 (dd, J=5.3, 0.6 Hz, 1H), 8.10-8.00 (m, 2H), 8.00-7.92 (m, 2H), 7.86 (d, J=7.7 Hz, 1H), 7.71 (dt, J=5.3, 1.8 Hz, 1H), 7.67 (t, J=4.9 Hz, 1H), 7.58 (p, J=0.7 Hz, 1H), 6.76 (d, J=9.1 Hz, 2H), 4.77 (ddd, J=10.4, 8.3, 4.4 Hz, 1H), 3.92-3.79 (m, 1H), 3.47 (dd, J=14.6, 10.4 Hz, 1H).

Example 59

(S)-3-(8-(2-cyanophenyl)quinolin-5-yl)-2-(2,6-difluoro-4-((4-(2-fluoropyridin-4-yl)phenyl)sulfonamido)benzamido)propanoic acid (59): The title compound was prepared according to the method presented for the synthesis of compound 5B and 5 starting with 53A and 2-bromobenzonitrile. MS (m/z) 708.2 [M+H]+. 1H NMR (400 MHz, DMSO-d6) δ 11.22 (d, J=15.6 Hz, 1H), 9.23-9.03 (m, 1H), 8.90-8.77 (m, 1H), 8.77-8.47 (m, 1H), 8.33 (dd, J=5.3, 2.2 Hz, 1H), 8.18-7.82 (m, 5H), 7.82-7.15 (m, 7H), 6.89-6.72 (m, 2H), 4.78-4.36 (m, 1H), 3.72 (d, J=10.6 Hz, 1H), 3.30 (m, 1H).

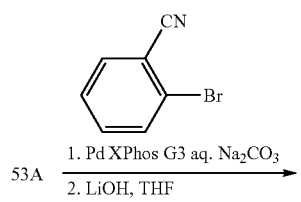

53A $\xrightarrow{\text{1. Pd XPhos G3 aq. Na}_2\text{CO}_3}{\text{2. LiOH, THF}}$ Example 60

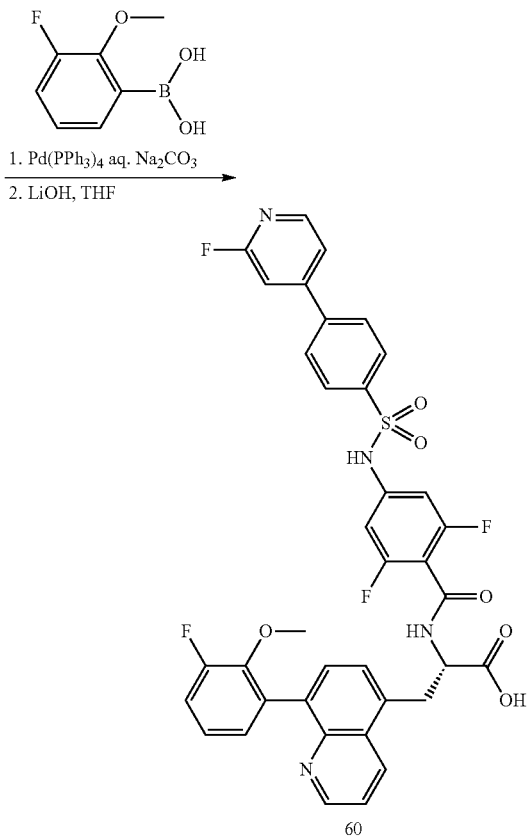

60

(S)-2-(2,6-difluoro-4-((4-(2-fluoropyridin-4-yl)phenyl) sulfonamido)benzamido)-3-(8-(3-fluoro-2-methoxyphenyl)

quinolin-5-yl)propanoic acid (60): The title compound was prepared according to the method presented for the synthesis of compound 3B and 3 starting with 47A and (3-fluoro-2-methoxyphenyl)boronic acid. MS (m/z) 731.2 [M+H]+. 1 H NMR (400 MHz, DMSO-d6) δ 11.20 (s, 1H), 9.11 (d, J=8.1 Hz, 1H), 8.85 (dd, J=4.1, 1.6 Hz, 1H), 8.61 (d, J=8.6 Hz, 1H), 8.37-8.29 (m, 1H), 8.11-8.02 (m, 2H), 8.02-7.93 (m, 2H), 7.72 (dt, J=5.3, 1.8 Hz, 1H), 7.65-7.50 (m, 4H), 7.31 (ddd, J=11.8, 8.2, 1.6 Hz, 1H), 7.15 (td, J=8.0, 5.1 Hz, 1H), 7.06-7.01 (m, 1H), 6.79 (d, J=9.1 Hz, 2H), 4.74-4.62 (m, 1H), 3.71 (dd, J=14.4, 4.4 Hz, 1H), 3.48 (d, J=1.4 Hz, 3H), 3.38-3.28 (m, 1H).

Example 61

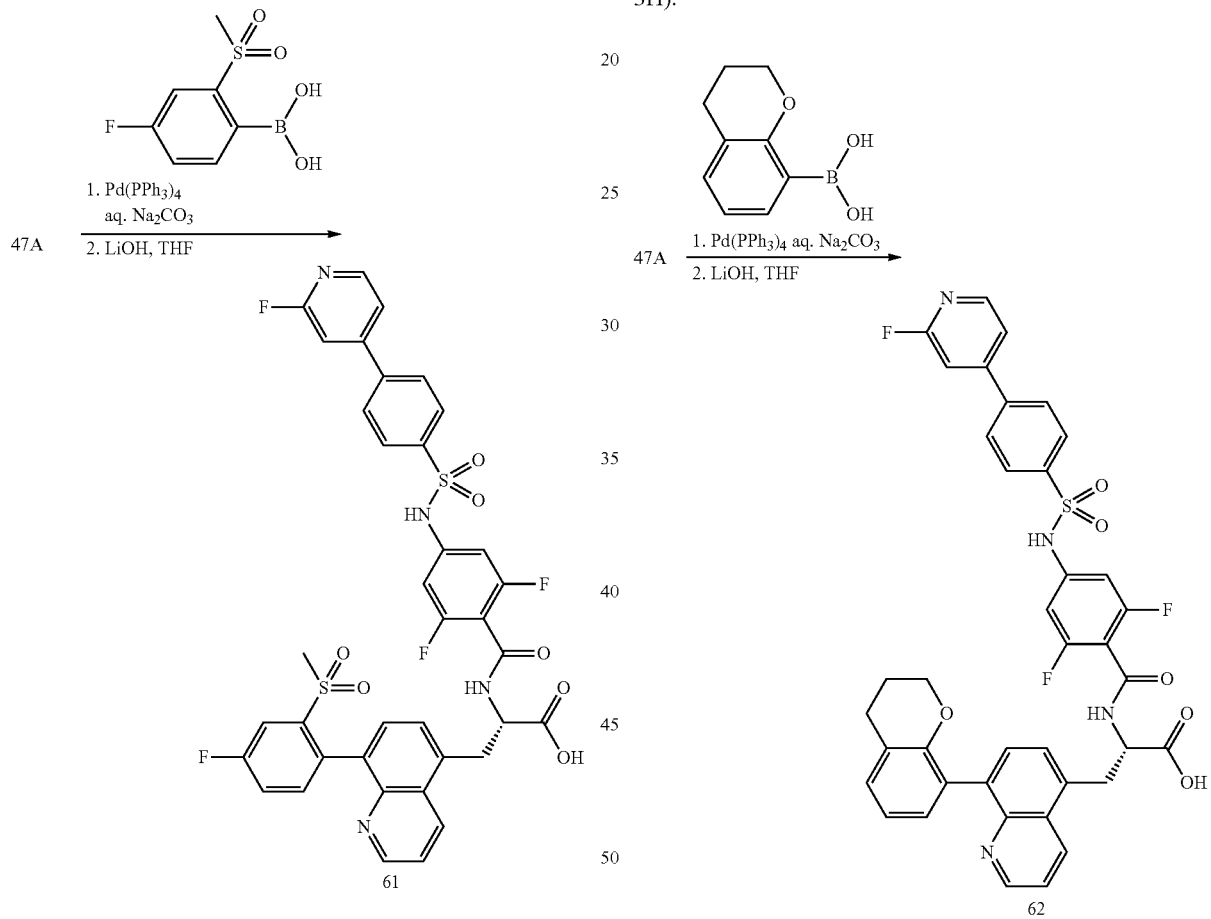

(S)-2-(2,6-difluoro-4-((4-(2-fluoropyridin-4-yl)phenyl) sulfonamido)benzamido)-3-(8-(4-fluoro-2-(methylsulfonyl) phenyl)quinolin-5-yl)propanoic acid (61): The title compound was prepared according to the method presented for the synthesis of compound 3B and 3 starting with 47A and (4-fluoro-2-(methylsulfonyl)phenyl)boronic acid. MS (m/z) 779.3 [M+H]+. 1 H NMR (400 MHz, DMSO-d6) (mixture of 50:50 diastereomers) δ 11.21 (s, 1H), 9.12 (dd, J=8.1, 3.4 Hz, 1H), 8.80 (td, J=3.8, 3.3, 1.5 Hz, 1H), 8.60 (t, J=7.4 Hz, 1H), 8.33 (d, J=5.3 Hz, 1H), 8.10-8.02 (m, 2H), 8.01-7.94 (m, 2H), 7.87 (ddd, J=8.9, 2.8, 1.2 Hz, 1H), 7.73 (dd, J=5.3, 1.7 Hz, 1H), 7.68-7.57 (m, 3H), 7.61-7.48 (m, 2H), 7.41-7.32 (m, 1H), 6.79 (dd, J=9.1, 1.9 Hz, 2H), 4.76-4.61 (m, 1H), 3.77 (dd, J=14.3, 4.0 Hz, 0.5H), 3.62 (dd, J=14.7, 5.1 Hz, 0.5H), 3.44 (dd, J=14.6, 9.6 Hz, 0.5H), 3.27 (dd, J=14.5, 10.5 Hz, 0.5H), 2.85 (s, 1.5H), 2.80 (s, 1.5H).

Example 62

(S)-3-(8-(chroman-8-yl)quinolin-5-yl)-2-(2,6-difluoro-4-((4-(2-fluoropyridin-4-yl) phenyl)sulfonamido)benzamido) propanoic acid (62): The title compound was prepared according to the method presented for the synthesis of compound 3B and 3 starting with 47A and chroman-8-ylboronic acid. MS (m/z) 739.2 [M+H]+. 1H NMR (400 MHz, DMSO-d6) δ 11.22 (s, 1H), 9.12 (d, J=8.1 Hz, 1H), 8.88 (s, 1H), 8.33 (dt, J=5.4, 0.6 Hz, 1H), 8.10-8.01 (m, 2H), 8.01-7.90 (m, 2H), 7.72 (dt, J=5.4, 1.8 Hz, 1H), 7.59 (q, J=1.1 Hz, 3H), 7.14 (d, J=7.8 Hz, 1H), 7.01 (d, J=7.3 Hz, 1H), 6.91 (t, J=7.4 Hz, 1H), 6.86-6.64 (m, 2H), 4.75-4.57 (m, 1H), 3.97-3.85 (m, 2H), 3.72 (d, J=14.3 Hz, 1H), 3.43-3.27 (m, 1H), 2.82 (t, J=6.5 Hz, 2H), 1.87 (t, J=5.6 Hz, 3H).

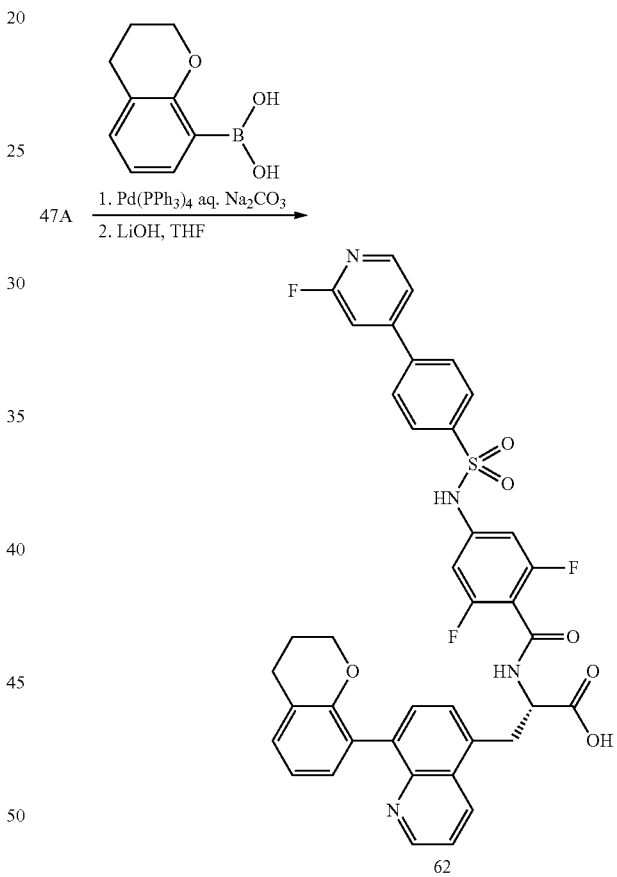

Example 63

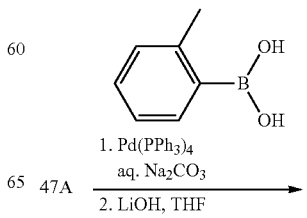

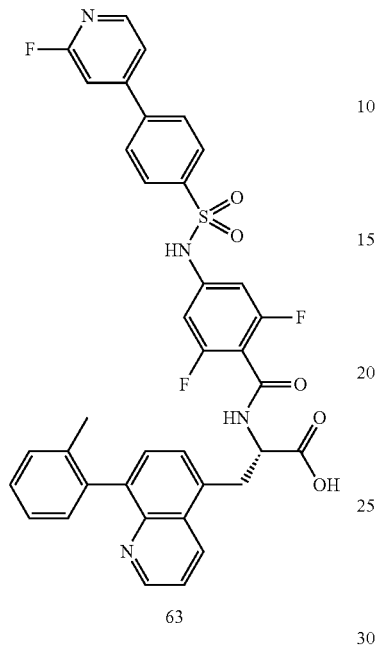

63

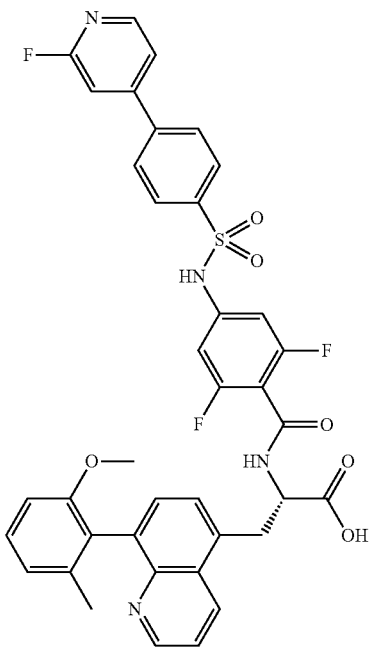

64

(S)-2-(2,6-difluoro-4-((4-(2-fluoropyridin-4-yl)phenyl)sulfonamido)benzamido)-3-(8-(o-tolyl)quinolin-5-yl)propanoic acid (63): The title compound was prepared according to the method presented for the synthesis of compound 3B and 3 starting with 47A and o-tolylboronic acid. MS (m/z) 697.2 [M+H]+. 1H NMR (400 MHz, DMSO-d6) δ 11.20 (s, 1H), 9.09 (d, J=8.2 Hz, 1H), 8.81 (dd, J=4.2, 1.6 Hz, 1H), 8.62 (d, J=8.7 Hz, 1H), 8.36-8.28 (m, 1H), 8.11-8.01 (m, 2H), 7.97 (d, J=8.4 Hz, 2H), 7.72 (dt, J=5.4, 1.8 Hz, 1H), 7.65-7.55 (m, 2H), 7.55-7.41 (m, 2H), 7.34-7.17 (m, 3H), 7.13 (d, J=7.0 Hz, 1H), 6.78 (d, J=9.5 Hz, 2H), 4.70 (s, 1H), 3.72 (dd, J=14.4, 4.4 Hz, 1H), 3.32 (dd, J=14.4, 10.3 Hz, 1H), 1.87 (s, 3H).

Example 64

(2S)-2-(2,6-difluoro-4-((4-(2-fluoropyridin-4-yl)phenyl)sulfonamido)benzamido)-3-(8-(2-methoxy-6-methylphenyl)quinolin-5-yl)propanoic acid (64): The title compound was prepared according to the method presented for the synthesis of compound 3B and 3 starting with 47A and (2-methoxy-6-methylphenyl)boronic acid. MS (m/z) 727.5 [M+H]+. 1H NMR (400 MHz, DMSO-d6) δ 13.03 (s, 1H), 11.20 (s, 1H), 9.08 (d, J=8.2 Hz, 1H), 8.73 (d, J=42.8 Hz, 2H), 8.33 (d, J=5.3 Hz, 1H), 8.13-7.89 (m, 4H), 7.72 (dt, J=5.3, 1.7 Hz, 1H), 7.69-7.37 (m, 4H), 7.28 (t, J=7.9 Hz, 1H), 6.90 (t, J=8.9 Hz, 2H), 6.83-6.71 (m, 2H), 4.79-4.66 (m, 1H), 3.77 (d, J=14.2 Hz, 1H), 3.49 (s, 3H), 3.28 (dd, J=14.4, 10.6 Hz, 1H), 1.74 (s, 3H).

Example 65

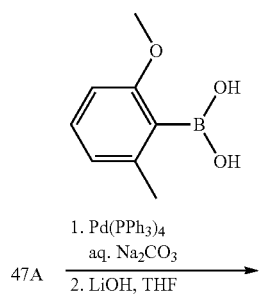

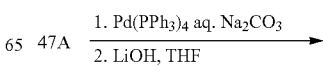

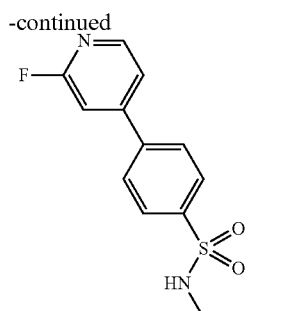

65

(S)-2-(2,6-difluoro-4-((4-(2-fluoropyridin-4-yl)phenyl)sulfonamido)benzamido)-3-(8-(2-(trifluoromethyl)phenyl)quinolin-5-yl)propanoic acid (65): The title compound was prepared according to the method presented for the synthesis of compound 3B and 3 starting with 47A and (2-(trifluoromethyl)phenyl)boronic acid. MS (m/z) 751.5 [M+H]+. 1 H NMR (400 MHz, DMSO-d6) δ 11.20 (d, J=2.3 Hz, 1H), 9.10 (dd, J=8.2, 6.2 Hz, 1H), 8.77 (dt, J=4.0, 1.9 Hz, 1H), 8.59 (d, J=8.5 Hz, 1H), 8.33 (d, J=5.3 Hz, 1H), 8.10-8.02 (m, 2H), 8.01-7.93 (m, 2H), 7.82 (dt, J=7.9, 1.9 Hz, 1H), 7.75-7.54 (m, 6H), 7.51 (d, J=1.9 Hz, 2H), 7.32 (dd, J=7.7, 4.4 Hz, 1H), 6.78 (dd, J=9.0, 3.5 Hz, 2H), 4.69 (ddd, J=10.2, 8.1, 4.6 Hz, 1H), 3.71 (ddd, J=29.9, 14.4, 4.4 Hz, 1H), 3.34 (ddd, J=25.9, 14.5, 10.2 Hz, 1H).

Example 66

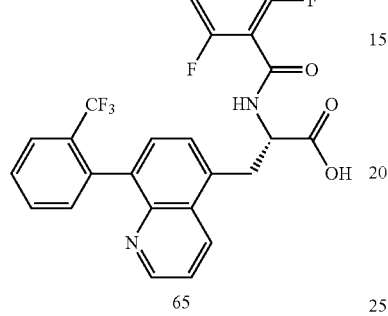

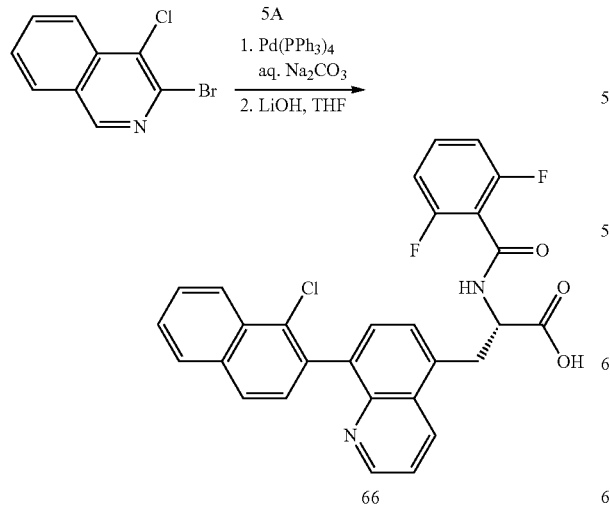

66

(S)-3-(8-(4-chloroisoquinolin-3-yl)quinolin-5-yl)-2-(2,6-difluorobenzamido)propanoic acid (66): The title compound was prepared according to the method presented for the synthesis of compound 5B and 5 starting with 5A and 3-bromo-4-chloroisoquinoline. MS (m/z) 514.1 [M+H]+. 1H NMR (400 MHz, DMSO-d6) δ 9.30 (d, J=8.1 Hz, 1H), 8.88 (d, J=4.3 Hz, 1H), 8.77 (s, 1H), 7.98 (s, 1H), 7.78 (dd, J=7.8, 1.5 Hz, 1H), 7.74 (d, J=7.3 Hz, 1H), 7.70-7.56 (m, 3H), 7.49 (tt, J=8.4, 6.5 Hz, 1H), 7.35-7.27 (m, 1H), 7.18-7.08 (m, 2H), 4.75 (td, J=9.5, 4.5 Hz, 1H), 3.77 (dd, J=14.5, 4.5 Hz, 1H), 3.68 (s, 3H), 3.44 (dd, J=14.5, 9.9 Hz, 1H).

Example 67

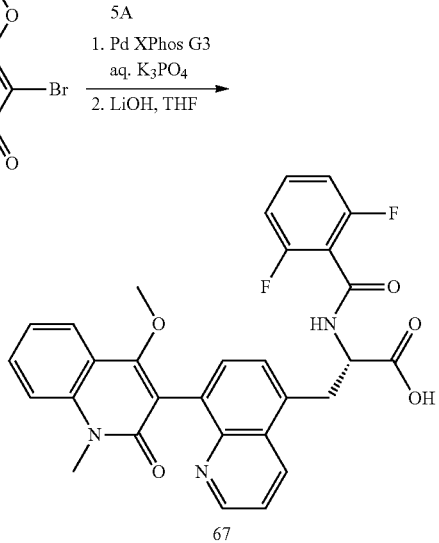

67

(S)-2-(2,6-difluorobenzamido)-3-(4-methoxy-1-methyl-2-oxo-1,2-dihydro-[3,8'-biquinolin]-5'-yl)propanoic acid (67): The title compound was prepared according to the method presented for the synthesis of compound 11A and 11 starting with 5A and 3-bromo-4-methoxy-1-methylquinolin-2(1H)-one. MS (m/z) 518.1 [M+H]+. 1H NMR (400 MHz, DMSO-d6) δ 9.41 (d, J=0.8 Hz, 1H), 9.31 (d, J=8.1 Hz, 1H), 8.81 (dd, J=4.2, 1.6 Hz, 1H), 8.72 (dd, J=8.7, 1.7 Hz, 1H), 8.38-8.29 (m, 1H), 8.24 (dq, J=8.5, 0.9 Hz, 1H), 8.02 (ddd, J=8.4, 6.9, 1.3 Hz, 1H), 7.87 (ddd, J=8.1, 7.0, 1.1 Hz, 1H), 7.78 (d, J=7.3 Hz, 1H), 7.72-7.64 (m, 2H), 7.48 (tt, J=8.5, 6.6 Hz, 1H), 7.16-7.07 (m, 2H), 4.80 (ddd, J=10.1, 8.1, 4.4 Hz, 1H), 3.81 (dd, J=14.5, 4.4 Hz, 1H), 3.46 (dd, J=14.5, 10.1 Hz, 1H).

Example 68

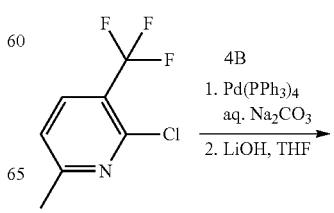

-continued

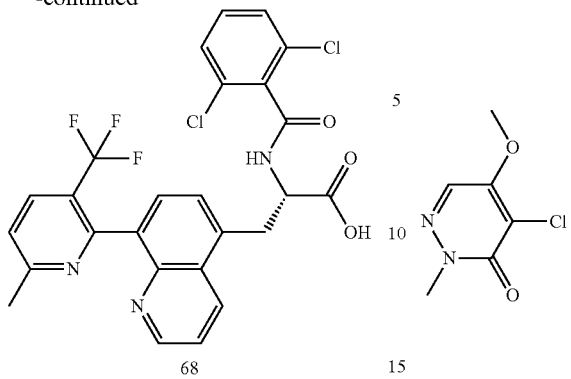

68

(S)-2-(2,6-dichlorobenzamido)-3-(8-(6-methyl-3-(trifluoromethyl)pyridin-2-yl)quinolin-5-yl)propanoic acid (68): The title compound was prepared according to the method presented for the synthesis of compound 4C and 4 starting with 4B and 2-chloro-6-methyl-3-(trifluoromethyl)pyridine. MS (m/z) 549.5 [M+H]+. 1H NMR (400 MHz, DMSO-d6) δ 9.31 (d, J=8.3 Hz, 1H), 8.81 (dd, J=4.2, 1.6 Hz, 1H), 8.69 (dd, J=8.7, 1.7 Hz, 1H), 8.20 (d, J=8.3 Hz, 1H), 7.70-7.52 (m, 4H), 7.48-7.35 (m, 3H), 4.84 (td, J=9.3, 4.3 Hz, 1H), 3.75 (dd, J=14.6, 4.4 Hz, 1H), 3.44 (dd, J=14.6, 10.1 Hz, 1H), 2.58 (s, 3H).

Example 69

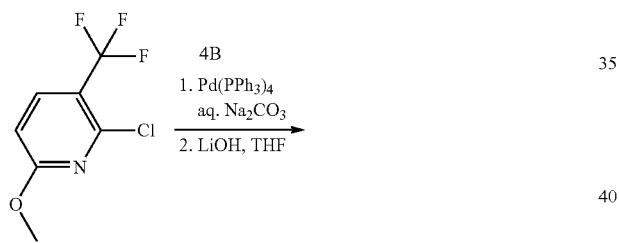

69

(S)-2-(2,6-dichlorobenzamido)-3-(8-(6-methoxy-3-(trifluoromethyl)pyridin-2-yl)quinolin-5-yl)propanoic acid (69): The title compound was prepared according to the method presented for the synthesis of compound 4C and 4 starting with 4B and 2-chloro-6-methoxy-3-(trifluoromethyl)pyridine. MS (m/z) 565.9 [M+H]+. 1H NMR (400 MHz, DMSO-d6) δ 9.28 (s, 1H), 8.83 (dd, J=4.2, 1.6 Hz, 1H), 8.68 (dd, J=8.7, 1.7 Hz, 1H), 8.16 (d, J=8.9 Hz, 1H), 7.70-7.58 (m, 3H), 7.47-7.34 (m, 3H), 7.06 (dt, J=8.7, 0.8 Hz, 1H), 4.86 (m, 1H), 3.81 (s, 3H), 3.78 (m, 1H), 3.43 (m, 1H).

Example 70

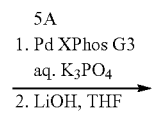

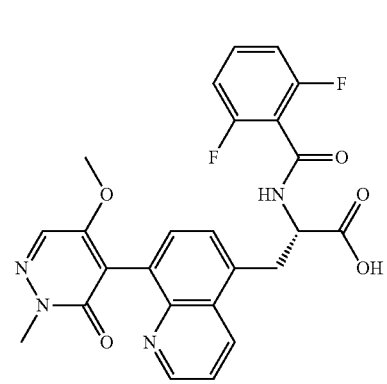

70

(S)-2-(2,6-difluorobenzamido)-3-(8-(5-methoxy-2-methyl-3-oxo-2,3-dihydropyridazin-4-yl)quinolin-5-yl)propanoic acid (70): The title compound was prepared according to the method presented for the synthesis of compound 11A and 11 starting with 5A and 4-chloro-5-methoxy-2-methylpyridazin-3(2H)-one. MS (m/z) 495.1 [M+H]+. 1H NMR (400 MHz, DMSO-d6) δ 9.30 (d, J=7.6 Hz, 1H), 8.88 (d, J=4.4 Hz, 1H), 8.75 (d, J=8.6 Hz, 1H), 8.27 (s, 1H), 7.77-7.65 (m, 1H), 7.59 (d, J=7.8 Hz, 2H), 7.48 (tt, J=8.5, 6.6 Hz, 1H), 7.12 (dd, J=8.4, 7.6 Hz, 2H), 4.74 (s, 1H), 3.86-3.63 (m, 7H), 3.43 (q, J=13.6 Hz, 1H).

Example 71

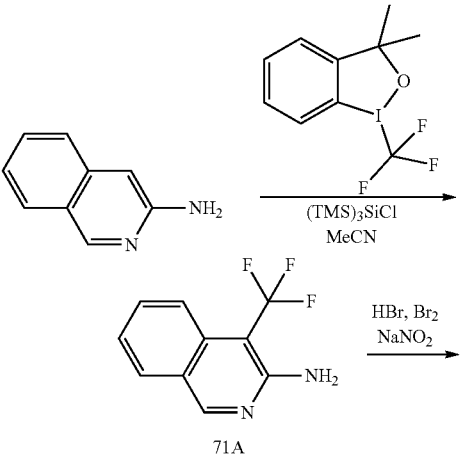

71A

-continued

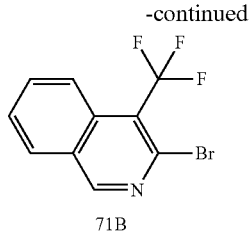

71B

Example 72

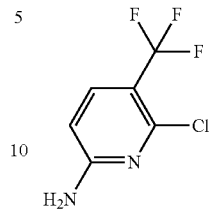

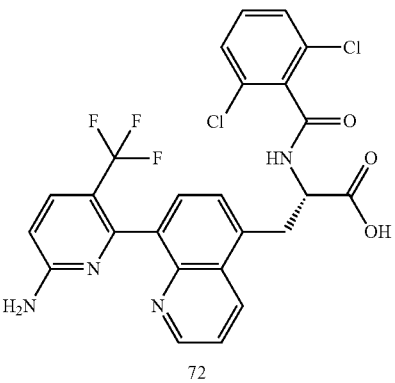

72

(S)-3-(8-(6-amino-3-(trifluoromethyl)pyridin-2-yl)quinolin-5-yl)-2-(2,6-dichloro benzamido)propanoic acid (72): The title compound was prepared according to the method presented for the synthesis of compound 4C and 4 starting with 4B and 6-chloro-5-(trifluoromethyl)pyridin-2-amine. MS (m/z) 550.4 [M+H]+. 1H NMR (400 MHz, DMSO-d6) δ 9.33 (d, J=8.3 Hz, 1H), 8.89 (dd, J=4.1, 1.6 Hz, 1H), 8.70 (dd, J=8.7, 1.6 Hz, 1H), 7.97 (d, J=9.1 Hz, 1H), 7.74-7.63 (m, 3H), 7.49-7.36 (m, 3H), 6.81 (d, J=9.1 Hz, 1H), 4.80 (td, J=9.2, 4.4 Hz, 1H), 3.74 (dd, J=14.5, 4.4 Hz, 1H), 3.43 (dd, J=14.6, 9.9 Hz, 1H).

71

Synthesis of 4-(trifluoromethyl)isoquinolin-3-amine (71A): To a stirred solution of 3-amino isoquinoline (150 mg, 1.04 mmol) in MeCN was added 3,3-dimethyl-1-(trifluoromethyl)-1,2-benziodoxole (412.1 mg, 1.25 mmol) and tris(trimethylsilyl)silyl chloride (0.35 ml, 1.25 mmol). This mixture was heated to 80° C. for 1 h. The reaction mixture was filtered through celite, rinsed with EA and purified by silica gel chromatography using EA in hexanes as eluent to give the title compound.

Synthesis of 3-bromo-4-(trifluoromethyl)isoquinoline (71B): To a stirred solution of 71A (91 mg, 0.43 mmol) in HBr (6.9 mL) was added Br$_2$ (0.13 ml, 2.57 mmol). The reaction mixture was kept at 0° C. for 10 minutes at which time NaNO$_2$ (147.96 mg, 2.14 mmol) was added as a premade solution in water (5 mL). The reaction mixture was allowed to stir at 0° C. for 30 min then allowed to warm to RT for 60 min. The reaction was quenched with sodium bicarbonate, extracted with DCM, concentrated and purified by silica gel chromatography eluting Hex/EA to give the title compound.

(S)-2-(2,6-difluorobenzamido)-3-(8-(4-(trifluoromethyl) isoquinolin-3-yl)quinolin-5-yl)propanoic acid (71): The title compound was prepared according to the method presented for the synthesis of compound 5B and 5 starting with 4B and 71B. MS (m/z) 552.2 [M+H]+. 1H NMR (400 MHz, DMSO-d6) δ 9.60 (d, J=3.3 Hz, 1H), 9.29 (t, J=7.6 Hz, 1H), 8.75 (dt, J=3.9, 1.8 Hz, 1H), 8.65 (ddd, J=8.7, 5.6, 1.7 Hz, 1H), 8.38 (d, J=8.2 Hz, 1H), 8.18 (d, J=8.7 Hz, 1H), 8.05 (ddd, J=8.6, 6.9, 1.4 Hz, 1H), 7.90 (t, J=7.6 Hz, 1H), 7.70 (dd, J=7.3, 4.7 Hz, 1H), 7.66-7.58 (m, 2H), 7.55-7.41 (m, 1H), 7.12 (q, J=8.2 Hz, 2H), 4.77 (dtd, J=18.5, 8.8, 4.4 Hz, 1H), 3.77 (ddd, J=25.7, 14.5, 4.5 Hz, 1H), 3.49-3.34 (m, 1H).

Example 73

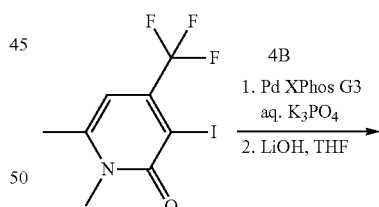

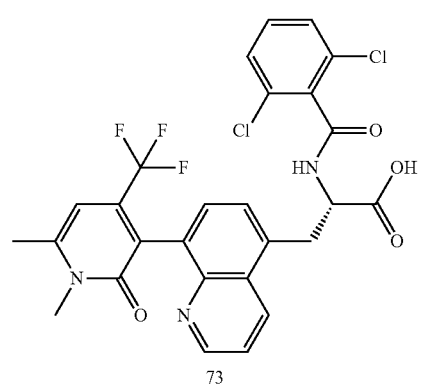

73

(S)-2-(2,6-dichlorobenzamido)-3-(8-(1,6-dimethyl-2-oxo-4-(trifluoromethyl)-1,2-dihydropyridin-3-yl)quinolin-5-yl)propanoic acid (73): The title compound was prepared according to the method presented for the synthesis of compound 11A and 11 starting with 4B and 3-iodo-1,6-dimethyl-4-(trifluoromethyl)pyridin-2(1H)-one. MS (m/z) 578.1 [M+H]+. 1H NMR (400 MHz, DMSO-d6) δ 13.00 (s, 1H), 9.27 (dd, J=27.2, 8.3 Hz, 1H), 8.83 (dt, J=4.2, 2.0 Hz, 1H), 8.69 (d, J=8.6 Hz, 1H), 7.72-7.59 (m, 2H), 7.49-7.31 (m, 4H), 6.55 (d, J=4.7 Hz, 1H), 4.90-4.71 (m, 1H), 3.73 (td, J=14.4, 4.0 Hz, 1H), 3.47 (d, J=4.2 Hz, 3H), 3.38 (ddd, J=24.5, 14.7, 10.5 Hz, 1H), 2.52 (m, 3H).

Example 74

Synthesis of tert-butyl 4-bromo-2,6-difluorobenzoate (74A): To a stirred solution of 4-bromo-2,6-difluorobenzoic acid (5 g, 21.1 mmol) in DCM (50 mL) and tert-butyl alcohol (50 mL) was added di-tert-butyl dicarbonate (9.2 g, 42.2 mol) followed by 4-dimethylaminopyridine (0.8 g, 6.3 mmol). The reaction mixture was allowed to stir at RT for 12 h. The reaction mixture was concentrated under reduced pressure, dissolved in ethyl acetate (100 mL) and washed with a 10% aqueous solution of citric acid (100 mL). The organic layer was washed with brine, dried over anhydrous $Na_2SO_4$, and concentrated under reduced pressure to afford material. This material was suspended in hexanes, the solid was filtered off and the filtrate was evaporated under reduced pressure to afford compound 74A. MS (m/z) 236.6 [M+H—$C_4H_8$]+. $^1$H NMR (400 MHz, DMSO-d6) δ 7.69-7.56 (m, 2H), 1.50 (s, 9H).

Synthesis of tert-butyl (R)-2,6-difluoro-4-((1,1,1-trifluorobutan-2-yl)amino)benzoate (74B): To a stirred suspension of tert-butyl 4-bromo-2,6-difluorobenzoate (74A) (250 mg, 0.55 mmol), (R)-1,1,1-trifluorobutan-2-amine (85 mg, 0.67 mmol), and cesium carbonate (904 mg, 2.8 mmol) in toluene (5 mL) was added XPhos Pd G3 (42 mg, 0.06 mmol). The reaction mixture was sparged with nitrogen and then heated to 90° C. for 12 h. The mixture was cooled to RT and diluted with ethyl acetate (50 mL). The resultant suspension was filtered through a pad of celite, and the filtrate was evaporated under reduced pressure to afford compound 74B. MS (m/z) 284.1 [M+H—$C_{14}H_8$]+.

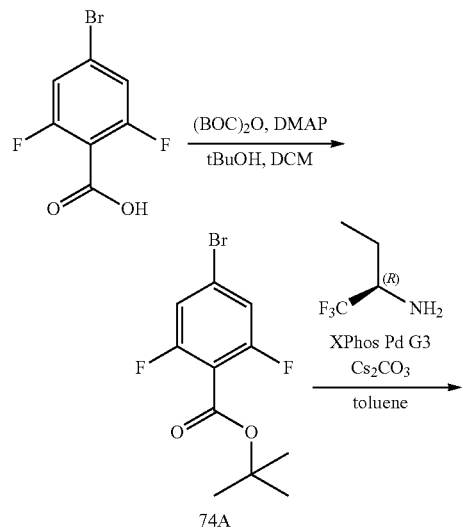

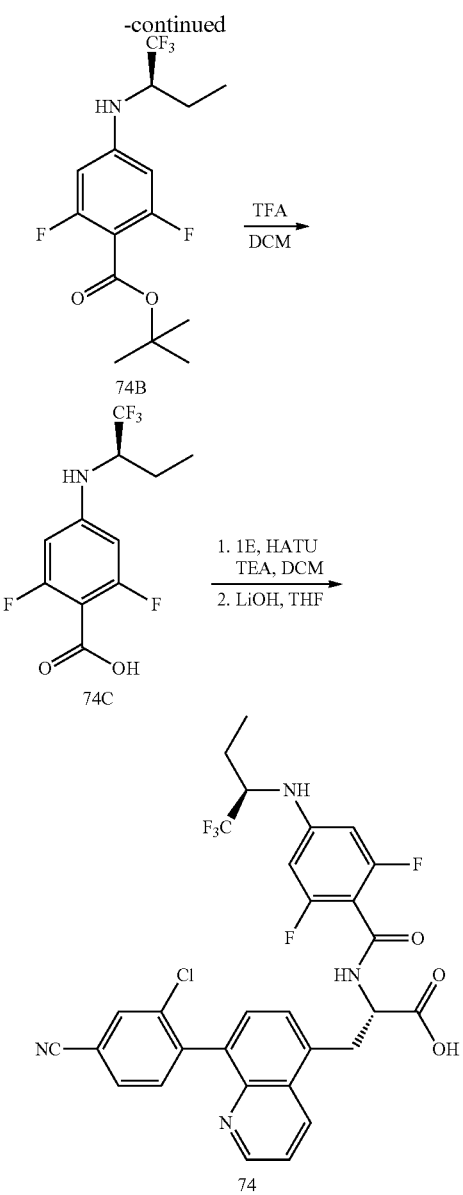

Synthesis of (R)-2,6-difluoro-4-((1,1,1-trifluorobutan-2-yl)amino)benzoic acid (74C): To a stirred solution of tert-butyl (R)-2,6-difluoro-4-((1,1,1-trifluorobutan-2-yl)amino)benzoate (74B) (188 mg, 0.55 mmol) in DCM (1 mL) was added TFA (1 mL). The reaction mixture was allowed to stir at RT for 20 mins. The reaction mixture was concentrated under reduced pressure to afford material that was purified by silica gel column chromatography and eluted by ethyl acetate in hexane to afford compound 74C. MS (m/z) 338.1 [M+H]+.

(S)-3-(8-(2-chloro-4-cyanophenyl)quinolin-5-yl)-2-(2,6-difluoro-4-(((R)-1,1,1-trifluoro butan-2-yl)amino)benzamido)propanoic acid (74): The title compound was prepared according to the method presented for the synthesis of compound 16A and 16 starting with 74C. MS (m/z) 617.2 [M+H]+. 1H NMR (400 MHz, DMSO-d6) δ 8.87-8.77 (m, 2H), 8.64 (dd, J=8.7, 1.7 Hz, 1H), 8.15 (dd, J=1.7, 0.4 Hz, 1H), 7.90 (dd, J=7.9, 1.7 Hz, 1H), 7.73-7.44 (m, 4H), 6.76 (d, J=9.4 Hz, 1H), 6.43 (d, J=11.6 Hz, 2H), 4.68 (s, 1H), 4.29 (d, J=10.2 Hz, 1H), 3.73 (s, 1H), 3.49-3.33 (m, 1H), 1.75

(ddt, J=10.1, 7.5, 3.8 Hz, 1H), 1.51 (ddt, J=17.6, 14.4, 7.3 Hz, 1H), 0.90 (t, J=7.3 Hz, 3H).

Example 75

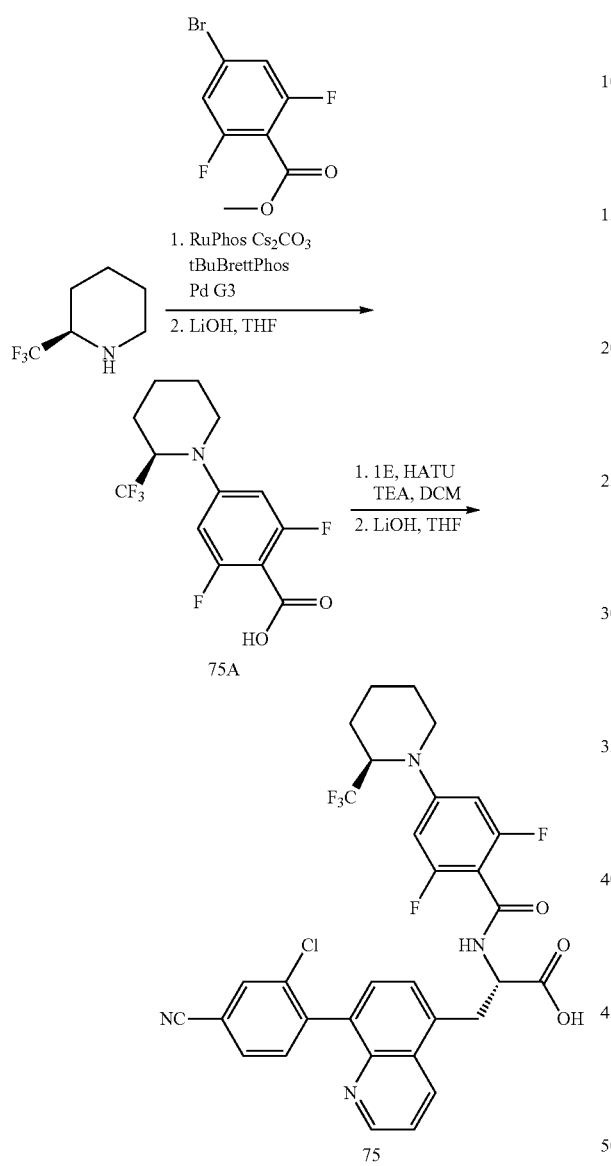

75

Synthesis of (R)-2,6-difluoro-4-(2-(trifluoromethyl)piperidin-1-yl)benzoic acid (75A): To a 150 mL pressure vessel containing a stir bar was added methyl 4-bromo-2,6-difluoro benzoate (700 mg, 1.8 mmol), RuPhos (169 mg, 0.36 mmol), tBuBrettPhos Pd G3 (155 mg, 0.18 mmol), $Cs_2CO_3$ (2.95 g, 9.1 mmol), (R)-2-(trifluoromethyl)piperidine (416 mg, 2.7 mmol) and toluene (18 mL). The reaction vessel was then sealed and heated at 90° C. overnight. The reaction mixture was cooled to RT and filtered over a pad of Celite, rinsed with EA and the filtrate was evaporated to dryness under reduced pressure. The material was purified by silica gel chromatography using EA in Hexane as eluent. To this material was added THF (6 mL) and aqueous LiOH (6.2 mL, 1.0 M). The reaction mixture was stirred at 60° C. for 20 hrs. The reaction mixture was cooled to RT and acidified with 1.0 M HCl before extracting with EA. Organic layers were combined and dried over $Na_2SO_4$. The solvent was removed under reduced pressure to afford 75A.

(S)-3-(8-(2-chloro-4-cyanophenyl)quinolin-5-yl)-2-(2,6-difluoro-4-((R)-2-(trifluoromethyl)piperidin-1-yl)benzamido)propanoic acid (75): The title compound was prepared according to the method presented for the synthesis of compound 16A and 16 starting with 75A. MS (m/z) 645.2 [M+H]+. 1H NMR (400 MHz, DMSO-d6) δ 8.90 (d, J=8.1 Hz, 1H), 8.83 (dd, J=4.2, 1.6 Hz, 1H), 8.64 (dd, J=8.6, 1.7 Hz, 1H), 8.15 (dd, J=1.7, 0.4 Hz, 1H), 7.90 (dd, J=7.9, 1.7 Hz, 1H), 7.67-7.52 (m, 4H), 6.72 (d, J=12.0 Hz, 2H), 4.93 (d, J=9.0 Hz, 1H), 4.70 (dt, J=9.7, 4.9 Hz, 1H), 3.74 (s, 1H), 3.59 (d, J=12.9 Hz, 1H), 3.41 (s, 1H), 2.99 (t, J=12.2 Hz, 1H), 1.94 (d, J=14.4 Hz, 1H), 1.85-1.67 (m, 2H), 1.67-1.42 (m, 3H).

Example 76

Synthesis of (R)-2,6-difluoro-4-(2-(trifluoromethyl)pyrrolidin-1-yl)benzoic acid (76A): The title compound was prepared according to the method presented for the synthesis of compound 75A starting with (R)-2-(trifluoromethyl)pyrrolidine.

(S)-3-(8-(2-chloro-4-cyanophenyl)quinolin-5-yl)-2-(2,6-difluoro-4-((R)-2-(trifluoro methyl)pyrrolidin-1-yl)benzamido)propanoic acid (76): The title compound was prepared according to the method presented for the synthesis of compound 16A and 16 starting with 76A. MS (m/z) 629.5 [M+H]+. 1H NMR (400 MHz, DMSO-d6) δ 8.88 (d, J=8.2 Hz, 1H), 8.83 (dd, J=4.1, 1.6 Hz, 1H), 8.65 (dd, J=8.7, 1.7 Hz, 1H), 8.15 (dd, J=1.7, 0.4 Hz, 1H), 7.96-7.83 (m, 1H), 7.66-7.58 (m, 3H), 7.56 (dt, J=7.9, 0.6 Hz, 1H), 6.48 (d, J=11.5 Hz, 2H), 4.82-4.63 (m, 2H), 3.72 (d, J=13.0 Hz, 1H), 3.56 (t, J=8.5 Hz, 1H), 3.41 (s, 1H), 3.15 (q, J=8.7 Hz, 1H), 2.16-1.91 (m, 4H).

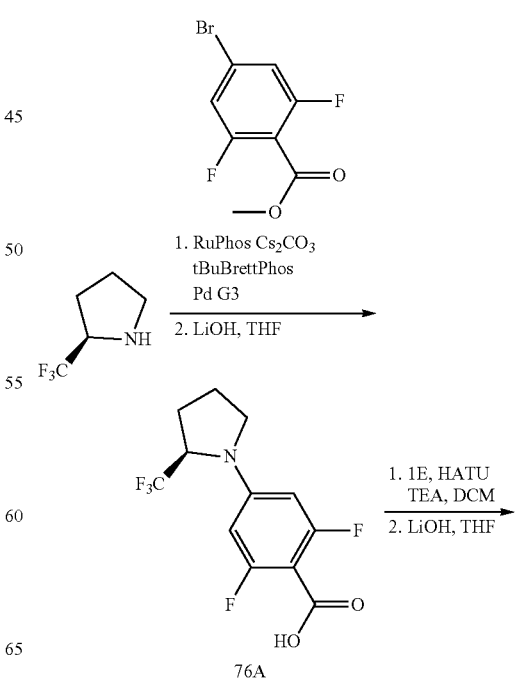

76A

211

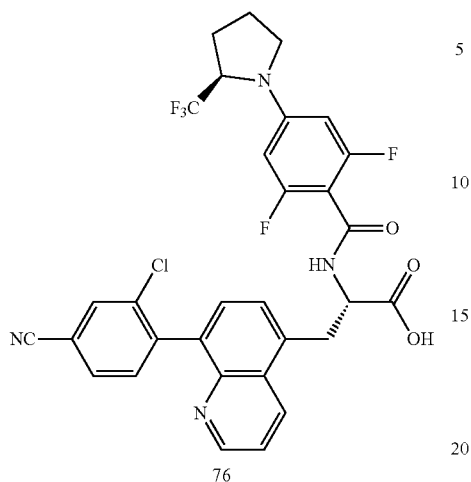

76

Example 77

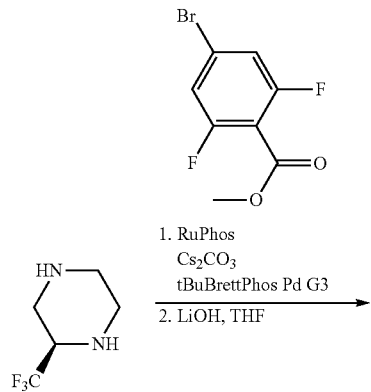

212

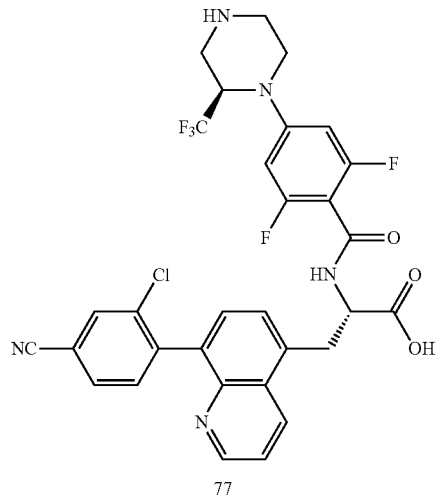

77

Synthesis of (R)-2,6-difluoro-4-(2-(trifluoromethyl)piperazin-1-yl)benzoic acid (77A): The title compound was prepared according to the method presented for the synthesis of compound 75A starting with (R)-2-(trifluoromethyl)piperazine.

(S)-3-(8-(2-chloro-4-cyanophenyl)quinolin-5-yl)-2-(2,6-difluoro-4-((R)-2-(trifluoromethyl)piperazin-1-yl)benzamido)propanoic acid (77): The title compound was prepared according to the method presented for the synthesis of compound 16A and 16 starting with 77A. MS (m/z) 644.1 [M+H]+. 1H NMR (400 MHz, DMSO-d6) δ 8.94 (d, J=8.1 Hz, 1H), 8.83 (dd, J=4.1, 1.6 Hz, 1H), 8.63 (dd, J=8.7, 1.7 Hz, 1H), 8.15 (dd, J=1.6, 0.4 Hz, 1H), 7.90 (dd, J=7.9, 1.6 Hz, 1H), 7.67-7.57 (m, 3H), 7.58-7.53 (m, 1H), 6.79 (d, J=11.5 Hz, 2H), 4.71 (td, J=9.2, 8.2, 4.3 Hz, 1H), 4.26 (br, 1H), 4.05 (d, J=13.2 Hz, 1H), 3.84 (d, J=10.9 Hz, 1H), 3.75 (s, 1H), 3.42 (s, 1H), 3.29 (d, J=10.7 Hz, 1H), 3.12-2.96 (m, 3H).

Example 78

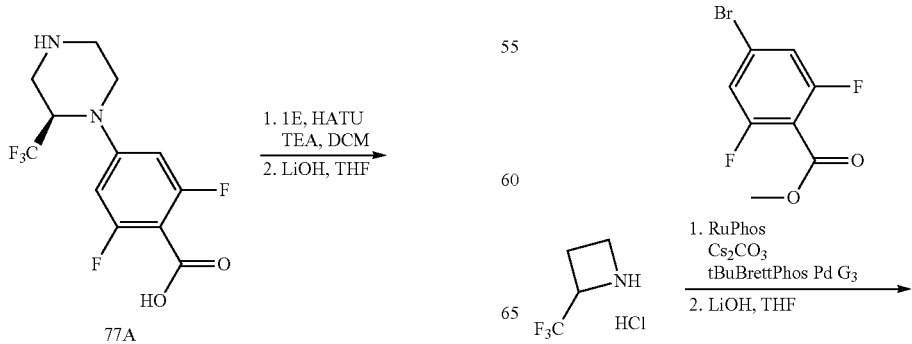

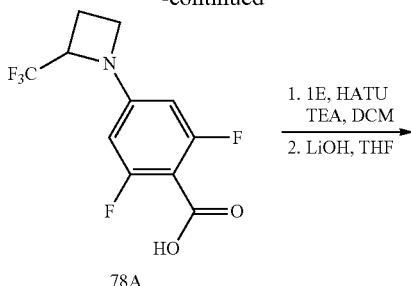

78A

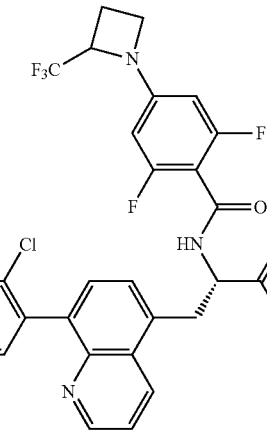

78

Synthesis of 2,6-difluoro-4-(2-(trifluoromethyl)azetidin-1-yl)benzoic acid (78A): The title compound was prepared according to the method presented for the synthesis of compound 75A starting with 2-(trifluoromethyl)azetidine hydrochloride.

(2S)-3-(8-(2-chloro-4-cyanophenyl)quinolin-5-yl)-2-(2,6-difluoro-4-(2-(trifluoromethyl) azetidin-1-yl)benzamido) propanoic acid (78): The title compound was prepared according to the method presented for the synthesis of compound 16A and 16 starting with 78A. MS (m/z) 617.1 [M+H]+. 1H NMR (400 MHz, DMSO-d6) δ 8.93 (dd, J=8.1, 3.2 Hz, 1H), 8.87-8.77 (m, 1H), 8.64 (dd, J=8.7, 1.7 Hz, 1H), 8.15 (d, J=1.7 Hz, 1H), 7.90 (dd, J=7.9, 1.6 Hz, 1H), 7.67-7.50 (m, 4H), 6.24 (d, J=9.9 Hz, 2H), 4.91 (q, J=6.3 Hz, 1H), 4.71 (d, J=9.6 Hz, 1H), 4.16-3.97 (m, 1H), 3.84-3.62 (m, 2H), 3.40 (s, 1H), 2.68-2.53 (m, 1H), 2.37 (ddd, J=11.7, 5.6, 2.6 Hz, 1H).

Example 79

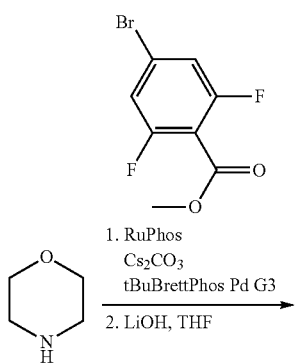

1. RuPhos
Cs$_2$CO$_3$
tBuBrettPhos Pd G3
2. LiOH, THF

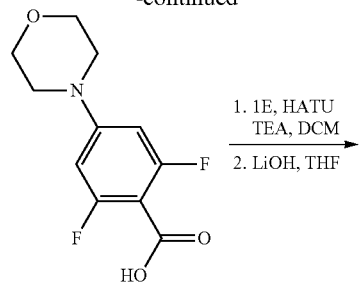

79A

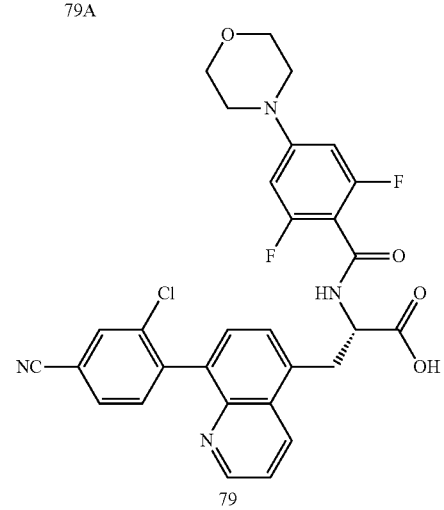

79

Synthesis of 2,6-difluoro-4-morpholinobenzoic acid (79A): The title compound was prepared according to the method presented for the synthesis of compound 75A starting with morpholine.

(S)-3-(8-(2-chloro-4-cyanophenyl)quinolin-5-yl)-2-(2,6-difluoro-4-morpholino benzamido)propanoic acid (79): The title compound was prepared according to the method presented for the synthesis of compound 16A and 16 starting with 79A. MS (m/z) 577.3 [M+H]+. 1H NMR (400 MHz, DMSO-d6) δ 8.87 (d, J=8.0 Hz, 1H), 8.83 (dd, J=4.1, 1.6 Hz, 1H), 8.64 (dd, J=8.7, 1.7 Hz, 1H), 8.15 (d, J=1.6 Hz, 1H), 7.96-7.84 (m, 1H), 7.67-7.58 (m, 3H), 7.56 (d, J=7.9 Hz, 1H), 6.61 (d, J=11.8 Hz, 2H), 4.69 (q, J=5.9, 4.3 Hz, 1H), 3.74 (s, 1H), 3.70-3.61 (m, 4H), 3.42 (s, 1H), 3.22-3.12 (m, 4H).

Example 80

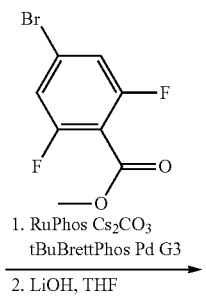

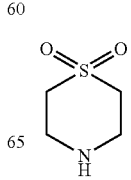

1. RuPhos Cs$_2$CO$_3$
tBuBrettPhos Pd G3
2. LiOH, THF

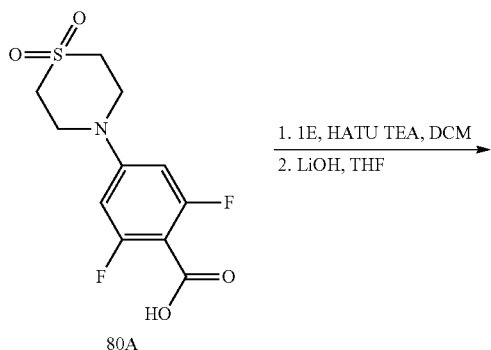

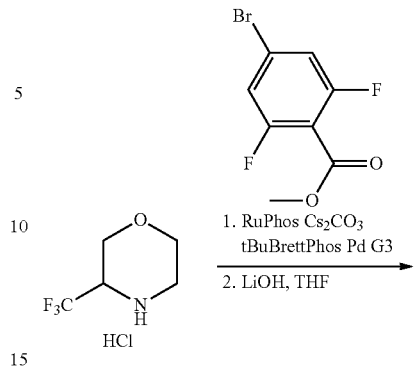

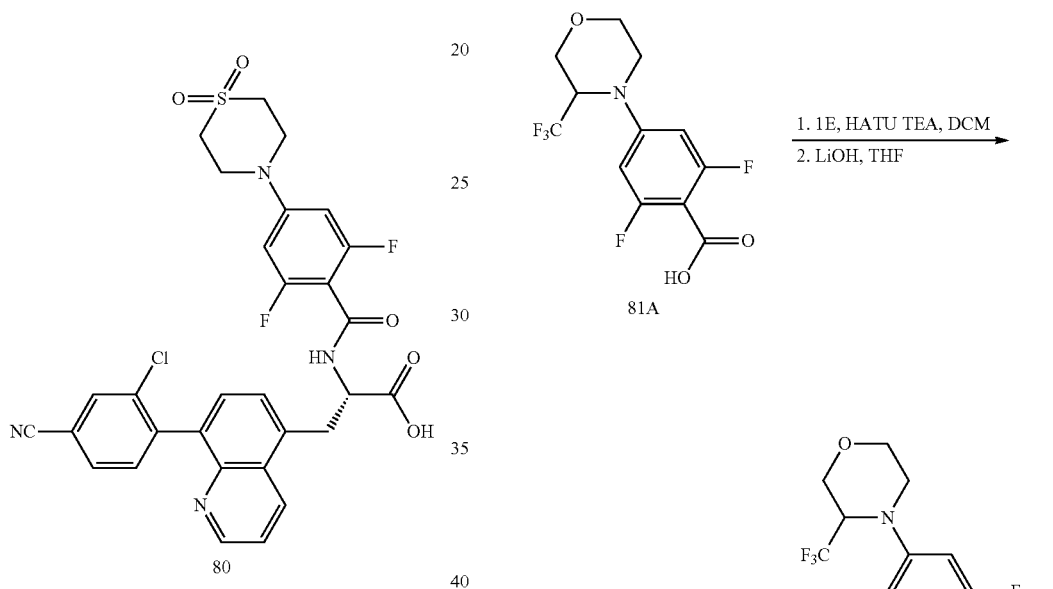

Synthesis of 4-(1,1-dioxidothiomorpholino)-2,6-difluorobenzoic acid (80A): The title compound was prepared according to the method presented for the synthesis of compound 75A starting with thiomorpholine 1,1-dioxide.

(S)-3-(8-(2-chloro-4-cyanophenyl)quinolin-5-yl)-2-(4-(1,1-dioxidothiomorpholino)-2,6-difluorobenzamido)propanoic acid (80): The title compound was prepared according to the method presented for the synthesis of compound 16A and 16 starting with 80A. MS (m/z) 625.5 [M+H]+. 1H NMR (400 MHz, DMSO-d6) δ 8.90 (d, J=8.1 Hz, 1H), 8.84 (dd, J=4.1, 1.6 Hz, 1H), 8.64 (dd, J=8.6, 1.7 Hz, 1H), 8.15 (dd, J=1.7, 0.4 Hz, 1H), 7.90 (dd, J=7.9, 1.7 Hz, 1H), 7.67-7.58 (m, 3H), 7.56 (dd, J=7.9, 0.4 Hz, 1H), 6.76 (d, J=11.7 Hz, 2H), 4.78-4.64 (m, 1H), 3.85 (s, 4H), 3.75 (s, 1H), 3.42 (s, 1H), 3.06 (s, 4H).

Example 81

Synthesis of 2,6-difluoro-4-morpholinobenzoic acid (81A): The title compound was prepared according to the method presented for the synthesis of compound 75A starting with 3-(trifluoromethyl)morpholine hydrochloride.

2,6-difluoro-4-(3-(trifluoromethyl)morpholino)benzoic acid (81): The title compound was prepared according to the method presented for the synthesis of compound 16A and 16 starting with 81A. MS (m/z) 645.1 [M+H]+. 1H NMR (400 MHz, DMSO-d6) δ 8.96 (dd, J=8.0, 2.7 Hz, 1H), 8.84 (dd, J=4.1, 1.6 Hz, 1H), 8.65 (dd, J=8.7, 1.7 Hz, 1H), 8.16 (dd, J=1.6, 0.4 Hz, 1H), 7.90 (dd, J=7.9, 1.6 Hz, 1H), 7.68-7.59 (m, 3H), 7.57 (dt, J=7.9, 0.6 Hz, 1H), 6.74 (d, J=11.7 Hz, 2H), 4.89 (dd, J=8.7, 3.6 Hz, 1H), 4.71 (d, J=6.2 Hz, 1H), 4.14 (d, J=12.7 Hz, 1H), 3.93 (dd, J=11.5, 3.8 Hz, 1H), 3.72 (d, J=13.0 Hz, 2H), 3.59-3.45 (m, 1H), 3.40 (d, J=12.7 Hz, 2H), 3.21 (t, J=12.2 Hz, 1H).

Examples 82 and 83

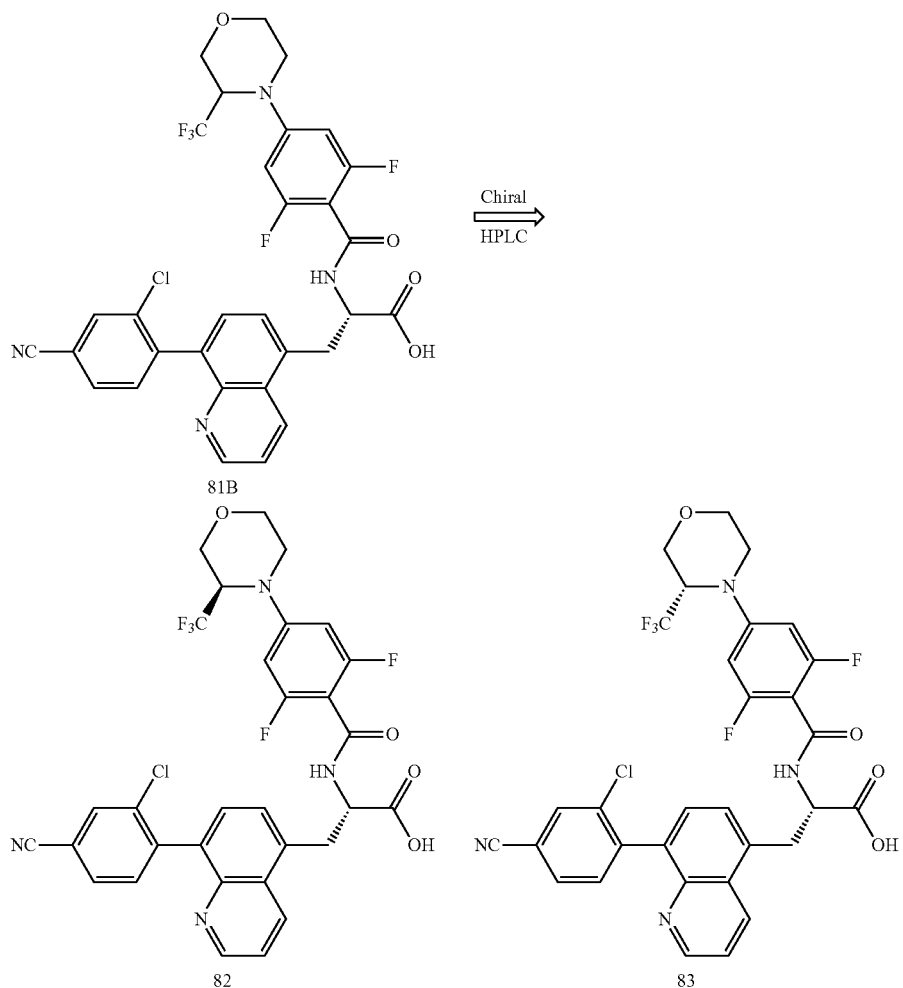

Preparation of (S)-3-(8-(2-chloro-4-cyanophenyl)quinolin-5-yl)-2-(2,6-difluoro-4-((R)-3-(trifluoromethyl)morpholino)benzamido)propanoic acid (82): 81 was separated into its 2 stereoisomers by supercritical fluid chromatography using 25% MeOH/DEA co-solvent, at a flow rate of 50 mL/min, using a Chiralpak AD-H 5 um 21×250 mm column. The title compound was identified as the first eluting peak. MS (m/z) 645.1 [M+H]+. 1H NMR (400 MHz, DMSO-d6) δ 8.78 (dd, J=4.2, 1.6 Hz, 1H), 8.74 (s, 1H), 8.14 (dd, J=1.6, 0.4 Hz, 1H), 8.0-8.4 (br, 1H), 7.88 (dd, J=7.9, 1.7 Hz, 1H), 7.61-7.49 (m, 4H), 6.74 (d, J=11.9 Hz, 2H), 4.88 (d, J=9.0 Hz, 1H), 4.43 (s, 1H), 4.14 (d, J=12.7 Hz, 1H), 3.93 (dd, J=11.5, 3.7 Hz, 1H), 3.72 (d, J=12.6 Hz, 2H), 3.60-3.48 (m, 1H), 3.41 (d, J=12.9 Hz, 1H), 3.21 (t, J=13.1 Hz, 2H).

Preparation of (S)-3-(8-(2-chloro-4-cyanophenyl)quinolin-5-yl)-2-(2,6-difluoro-4-((S)-3-(trifluoromethyl)morpholino)benzamido)propanoic acid (83): 81 was separated into its 2 stereoisomers by supercritical fluid chromatography using 25% EtOH/TFA cosolvent, at a flow rate of 50 mL/min, using a Chiralpak AD-H 5 μm 21×250 mm column. The title compound was identified as the second eluting peak. MS (m/z) 645.1 [M+H]+. 1H NMR (400 MHz, DMSO-d6) δ 8.77 (dd, J=4.1, 1.5 Hz, 2H), 8.13 (dd, J=1.7, 0.4 Hz, 1H), 8.08 (s, 1H), 7.88 (dd, J=7.9, 1.7 Hz, 1H), 7.65-7.42 (m, 4H), 6.74 (d, J=11.9 Hz, 2H), 4.88 (dt, J=9.4, 4.7 Hz, 1H), 4.40 (d, J=6.6 Hz, 1H), 4.14 (d, J=12.7 Hz, 1H), 3.93 (dd, J=11.5, 3.7 Hz, 1H), 3.71 (d, J=13.0 Hz, 2H), 3.60-3.46 (m, 1H), 3.41 (d, J=13.0 Hz, 2H), 3.23 (d, J=11.8 Hz, 1H).

Example 84

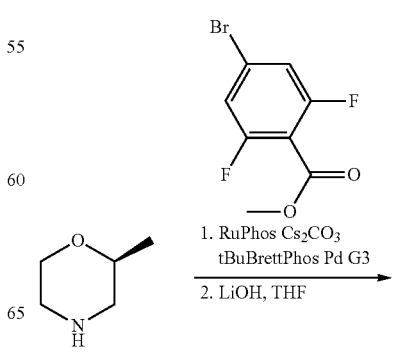

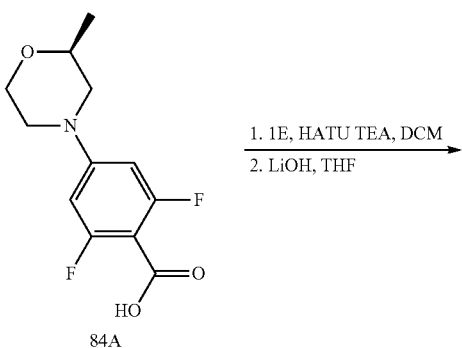

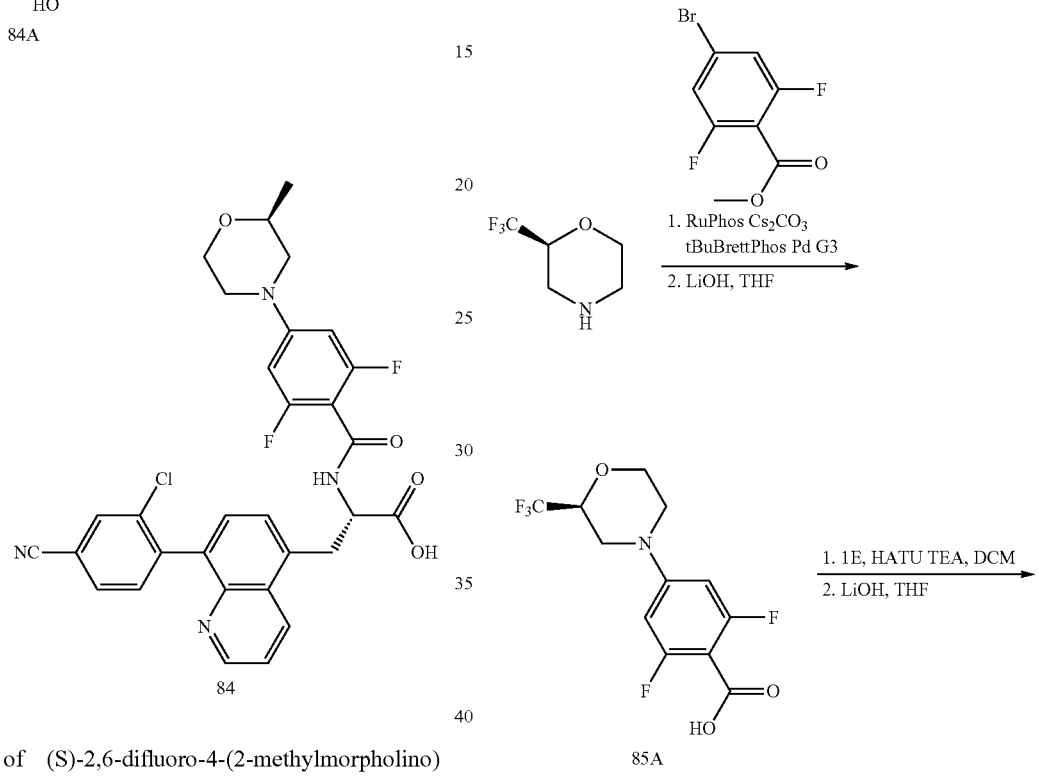

Synthesis of (S)-2,6-difluoro-4-(2-methylmorpholino)benzoic acid (84A): The title compound was prepared according to the method presented for the synthesis of compound 75A starting with (S)-2-methylmorpholine.

(S)-3-(8-(2-chloro-4-cyanophenyl)quinolin-5-yl)-2-(2,6-difluoro-4-((S)-2-methyl morpholino)benzamido)propanoic acid (84): The title compound was prepared according to the method presented for the synthesis of compound 16A and 16 starting with 84A. MS (m/z) 591.8 [M+H]+. 1H NMR (400 MHz, DMSO-d6) δ 8.88 (d, J=8.1 Hz, 1H), 8.85 (dd, J=4.2, 1.5 Hz, 1H), 8.65 (d, J=8.6 Hz, 1H), 8.17 (d, J=1.6 Hz, 1H), 7.91 (dd, J=7.9, 1.6 Hz, 1H), 7.69-7.55 (m, 4H), 6.62 (d, J=11.9 Hz, 2H), 4.71 (t, J=11.2 Hz, 1H), 3.87 (dd, J=11.2, 3.4 Hz, 1H), 3.71 (d, J=12.4 Hz, 2H), 3.66-3.50 (m, 3H), 3.44 (s, 1H), 2.70 (td, J=11.8, 3.6 Hz, 1H), 2.38 (dd, J=12.3, 10.4 Hz, 1H), 1.13 (d, J=6.2 Hz, 3H).

Example 85

Synthesis of (S)-2,6-difluoro-4-(2-methylmorpholino)benzoic acid (85A): The title compound was prepared according to the method presented for the synthesis of compound 75A starting with (S)-2-(trifluoromethyl)morpholine.

(S)-3-(8-(2-chloro-4-cyanophenyl)quinolin-5-yl)-2-(2,6-difluoro-4-((S)-2-(trifluoro methyl)morpholino)benzamido)propanoic acid (85): The title compound was prepared according to the method presented for the synthesis of compound 16A and 16 starting with 85A. MS (m/z) 645.1 [M+H]+. 1H NMR (400 MHz, DMSO-d6) δ 8.93 (d, J=8.1 Hz, 1H), 8.83 (dd, J=4.1, 1.6 Hz, 1H), 8.64 (dd, J=8.7, 1.7 Hz, 1H), 8.16 (d, J=1.6 Hz, 1H), 7.90 (dd, J=7.9, 1.7 Hz, 1H), 7.67-7.57 (m, 3H), 7.56 (d, J=7.9 Hz, 1H), 6.75 (d, J=11.6 Hz, 2H), 4.77-4.66 (m, 1H), 4.29 (dq, J=6.7, 3.3 Hz, 1H), 4.03 (dd, J=10.9, 3.3 Hz, 1H), 3.86 (d, J=12.2 Hz, 1H), 3.75 (m, 1H), 3.69 (t, J=10.4 Hz, 2H), 3.41 (s, 1H), 2.92-2.72 (m, 2H).

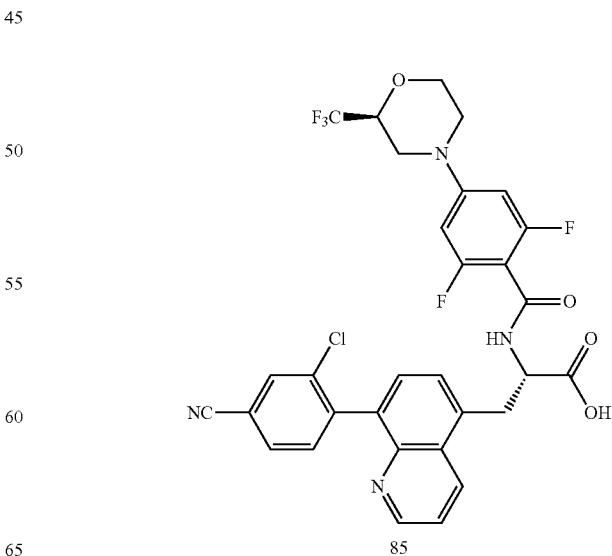

Example 86

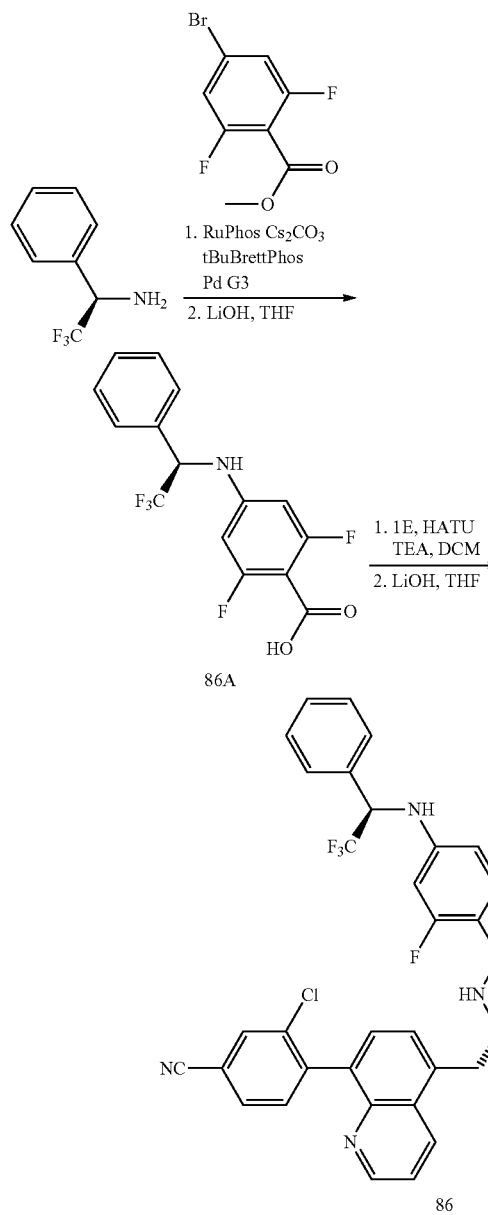

Example 87

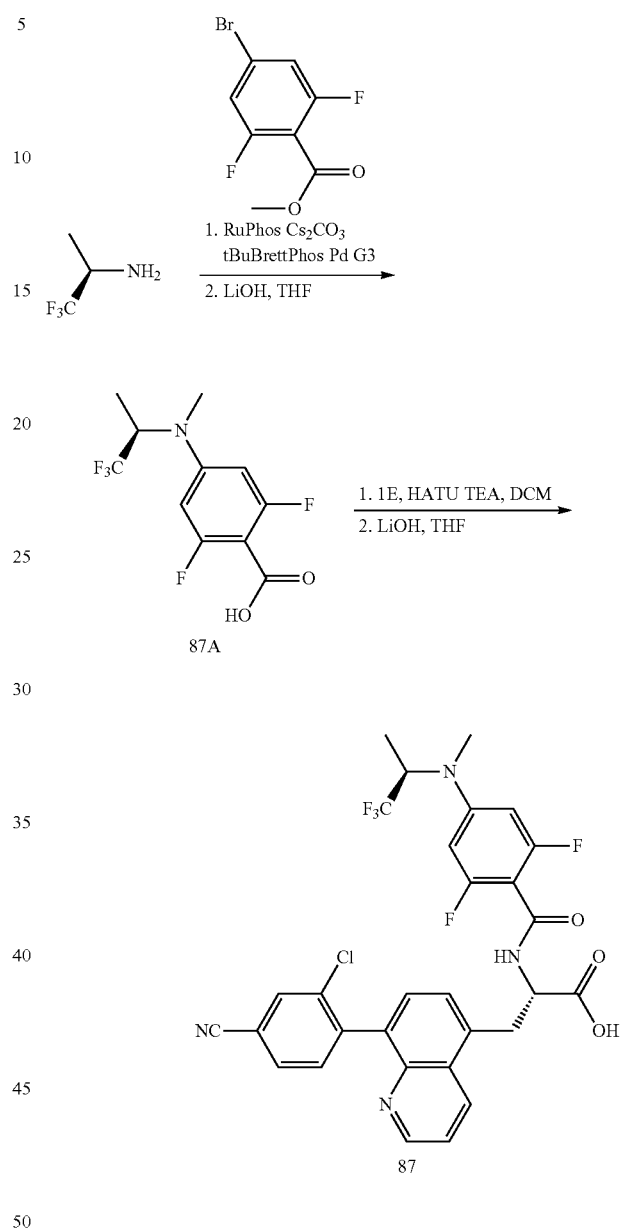

Synthesis of (R)-2,6-difluoro-4-((2,2,2-trifluoro-1-phenylethyl)amino)benzoic acid (86A): The title compound was prepared according to the method presented for the synthesis of compound 75A starting with (R)-2,2,2-trifluoro-1-phenylethan-1-amine.

(S)-3-(8-(2-chloro-4-cyanophenyl)quinolin-5-yl)-2-(2,6-difluoro-4-(((R)-2,2,2-trifluoro-1-phenylethyl)amino)benzamido)propanoic acid (86): The title compound was prepared according to the method presented for the synthesis of compound 16A and 16 starting with 86A. MS (m/z) 665.2 [M+H]+. 1 H NMR (400 MHz, DMSO-d6) δ 8.85-8.77 (m, 2H), 8.61 (dd, J=8.8, 1.7 Hz, 1H), 8.15 (dd, J=1.6, 0.4 Hz, 1H), 7.89 (dd, J=7.9, 1.6 Hz, 1H), 7.66-7.48 (m, 7H), 7.46-7.32 (m, 3H), 6.53 (d, J=11.6 Hz, 2H), 5.67 (q, J=8.7 Hz, 1H), 4.64 (d, J=11.6 Hz, 1H), 3.71 (s, 1H), 3.37 (s, 1H).

Synthesis of (R)-2,6-difluoro-4-(methyl(1,1,1-trifluoropropan-2-yl)amino)benzoic acid (87A): The title compound was prepared according to the method presented for the synthesis of compound 75A starting with (R)-1,1,1-trifluoro-N-methylpropan-2-amine.

(S)-3-(8-(2-chloro-4-cyanophenyl)quinolin-5-yl)-2-(2,6-difluoro-4-(methyl((R)-1,1,1-trifluoropropan-2-yl)amino)benzamido)propanoic acid (87): The title compound was prepared according to the method presented for the synthesis of compound 16A and 16 starting with 87A. MS (m/z) 617.2 [M+H]+. 1H NMR (400 MHz, DMSO-d6) δ 8.92-8.81 (m, 2H), 8.65 (dd, J=8.7, 1.7 Hz, 1H), 8.16 (dd, J=1.7, 0.4 Hz, 1H), 7.90 (dd, J=7.9, 1.6 Hz, 1H), 7.68-7.53 (m, 4H), 6.63 (d, J=12.0 Hz, 2H), 4.93 (p, J=7.4 Hz, 1H), 4.70 (s, 1H), 3.74 (s, 1H), 3.41 (s, 1H), 2.83-2.77 (m, 3H), 1.36 (d, J=6.8 Hz, 3H).

Example 88

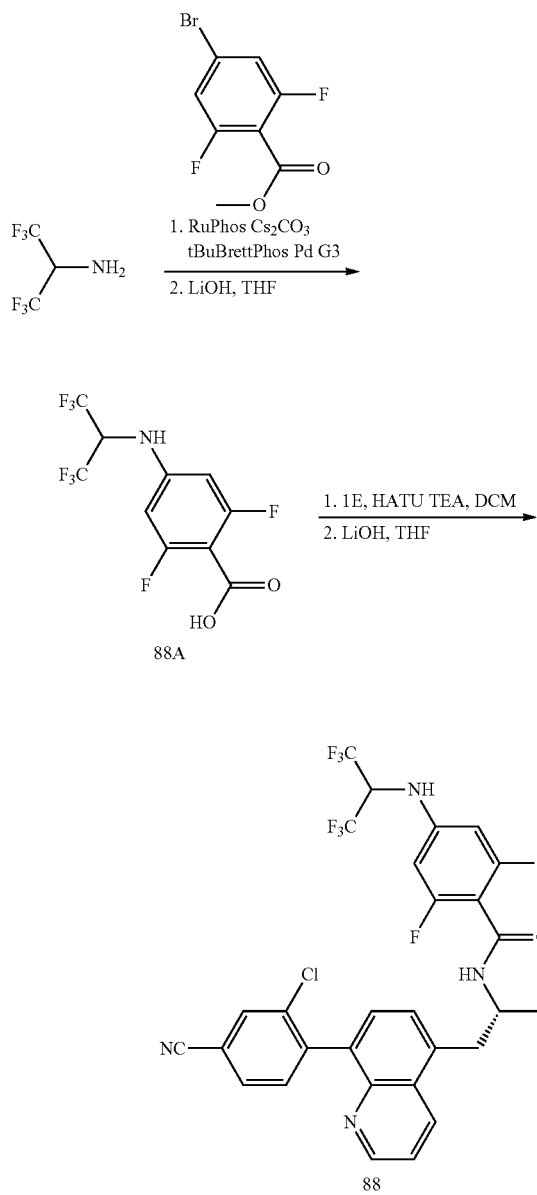

Synthesis of 2,6-difluoro-4-((1,1,1,3,3,3-hexafluoropropan-2-yl)amino)benzoic acid (88A): The title compound was prepared according to the method presented for the synthesis of compound 75A starting with 1,1,1,3,3,3-hexafluoropropan-2-amine.

(S)-3-(8-(2-chloro-4-cyanophenyl)quinolin-5-yl)-2-(2,6-difluoro-4-((1,1,1,3,3,3-hexafluoropropan-2-yl)amino)benzamido)propanoic acid (88): The title compound was prepared according to the method presented for the synthesis of compound 16A and 16 starting with 88A. MS (m/z) 657.1 [M+H]+. 1H NMR (400 MHz, DMSO-d6) δ 8.93 (d, J=8.0 Hz, 1H), 8.83 (dd, J=4.1, 1.6 Hz, 1H), 8.66-8.59 (m, 1H), 8.15 (d, J=1.7 Hz, 1H), 7.90 (dd, J=7.8, 1.6 Hz, 1H), 7.67-7.53 (m, 5H), 6.69 (d, J=11.1 Hz, 2H), 5.93 (s, 1H), 4.70 (s, 1H), 3.62 (s, 1H), 3.40 (s, 1H).

Example 89

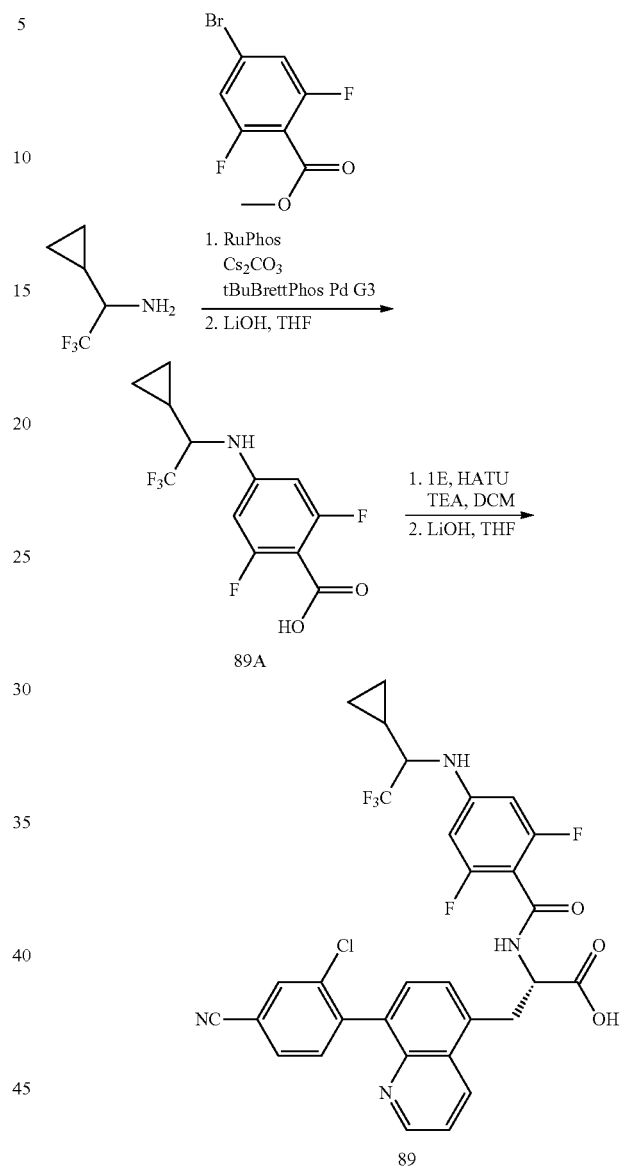

Synthesis of 4-((1-cyclopropyl-2,2,2-trifluoroethyl)amino)-2,6-difluorobenzoic acid (89A): The title compound was prepared according to the method presented for the synthesis of compound 75A starting with 1-cyclopropyl-2,2,2-trifluoroethan-1-amine.

(2S)-3-(8-(2-chloro-4-cyanophenyl)quinolin-5-yl)-2-(4-((1-cyclopropyl-2,2,2-trifluoro ethyl)amino)-2,6-difluorobenzamido)propanoic acid (89): The title compound was prepared according to the method presented for the synthesis of compound 16A and 16 starting with 89A. MS (m/z) 629.2 [M+H]+. 1 H NMR (400 MHz, DMSO-d6) δ 8.86-8.75 (m, 2H), 8.63 (dd, J=8.7, 1.6 Hz, 1H), 8.15 (dd, J=1.7, 0.4 Hz, 1H), 7.90 (dd, J=7.9, 1.6 Hz, 1H), 7.67-7.53 (m, 4H), 6.93 (d, J=9.5 Hz, 1H), 6.40 (d, J=11.8 Hz, 2H), 4.67 (s, 1H), 3.91 (q, J=8.1 Hz, 1H), 3.72 (s, 1H), 3.40 (s, 1H), 1.08-0.96 (m, 1H), 0.60 (dq, J=8.5, 4.1, 3.3 Hz, 1H), 0.49 (dd, J=11.1, 5.8 Hz, 2H), 0.34-0.23 (m, 1H).

Example 90

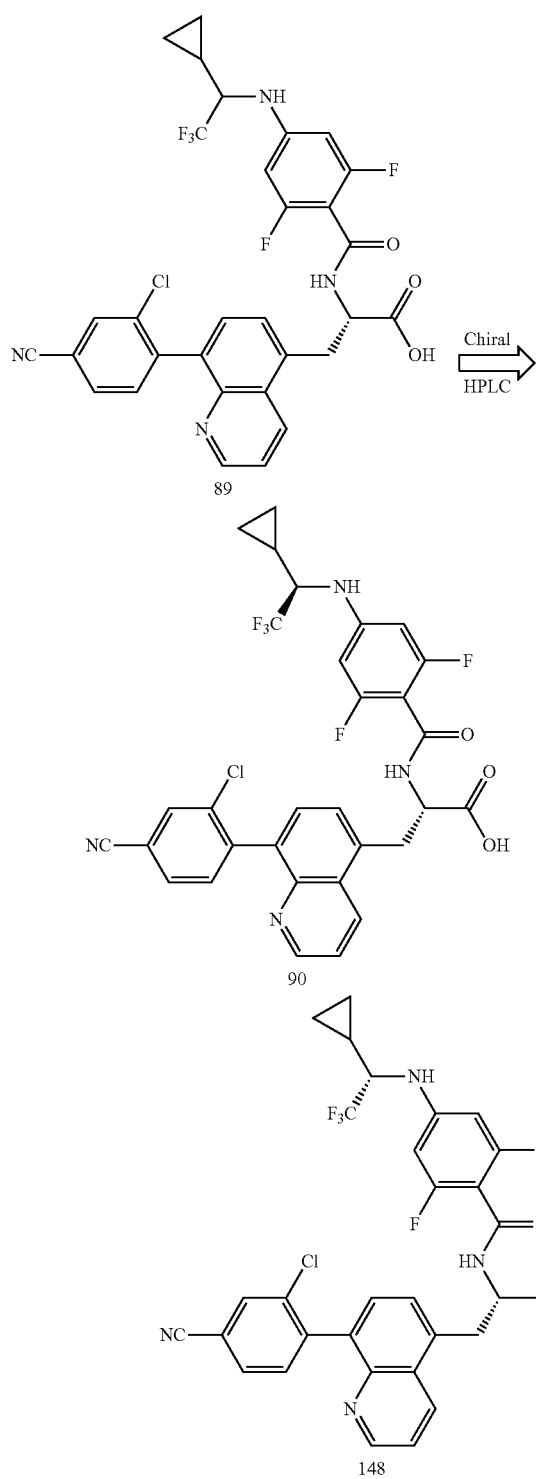

Preparation of (S)-3-(8-(2-chloro-4-cyanophenyl)quinolin-5-yl)-2-(2,6-difluoro-4-((R)-3-(trifluoromethyl)morpholino)benzamido)propanoic acid (90): 89 was separated into its 2 stereoisomers by supercritical fluid chromatography using 30% EtOH/TFA co-solvent, at a flow rate of 45 mL/min, using an IE 5 μm 21×250 mm column. The title compound was identified as the first eluting peak. MS (m/z) 629.2 [M+H]⁺. 1H NMR (400 MHz, DMSO-d6) δ 8.86-8.75 (m, 2H), 8.66-8.59 (m, 1H), 8.15 (dd, J=1.7, 0.4 Hz, 1H), 7.90 (dd, J=7.9, 1.7 Hz, 1H), 7.67-7.49 (m, 4H), 6.92 (d, J=9.5 Hz, 1H), 6.40 (d, J=11.8 Hz, 2H), 4.67 (s, 1H), 3.91 (d, J=7.8 Hz, 1H), 3.72 (s, 1H), 3.39 (s, 1H), 1.08-1.00 (m, 1H), 0.66-0.56 (m, 1H), 0.53-0.42 (m, 2H), 0.33-0.26 (m, 1H).

Example 91

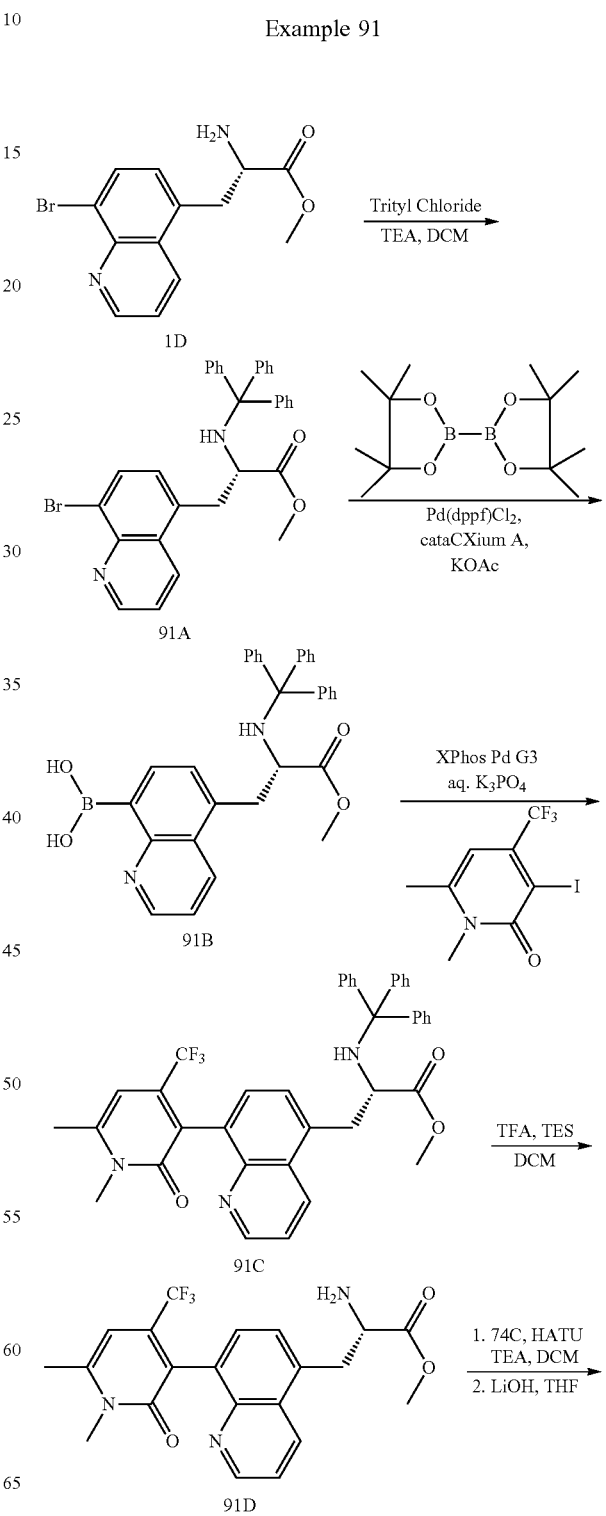

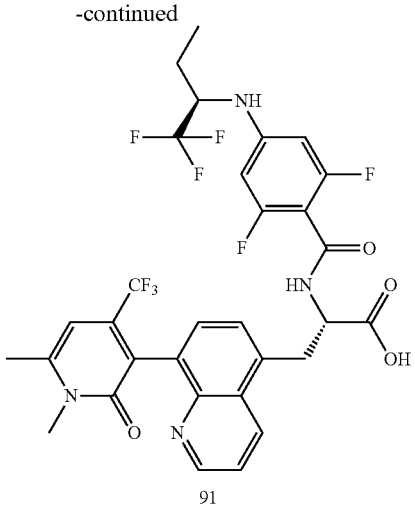

91

Synthesis of methyl (S)-3-(8-bromoquinolin-5-yl)-2-(tritylamino)propanoate (91A): To a stirred solution of 1D (15 g, 43.4 mmol) in DCM was added TEA (15.12 mL, 108.5 mmol) and trityl chloride (12.7 g, 45.57 mmol). The reaction mixture was stirred for 2 hours then filtered through celite, and washed 3× with EA. The filtrate was concentrated and purified by silica gel chromatography eluting with EA/hexanes to give the title compound.

Synthesis of (S)-(5-(3-methoxy-3-oxo-2-(tritylamino)propyl)quinolin-8-yl)boronic acid (91B): The title compound was prepared according to the method presented for the synthesis of compound 4B starting with 91A.

Synthesis of methyl (S)-3-(8-(1,6-dimethyl-2-oxo-4-(trifluoromethyl)-1,2-dihydro pyridin-3-yl)quinolin-5-yl)-2-(tritylamino)propanoate (91C): The title compound was prepared according to the method presented for the synthesis of compound 11A starting with 91B and 3-iodo-1,6-dimethyl-4-(trifluoromethyl)pyridin-2(1H)-one.

Synthesis of methyl (S)-2-amino-3-(8-(1,6-dimethyl-2-oxo-4-(trifluoromethyl)-1,2-dihydropyridin-3-yl)quinolin-5-yl)propanoate (91D): To a stirred solution of 91C (0.3 g, 0.46 mmol) in DCM was added triethylsilane (0.064 g, 0.49 mmol) and TFA (0.18 mL, 2.0 mmol). The reaction mixture was allowed to stir at RT for 1 h then concentrated under reduced pressure to give a material that was used without further purification.

(S)-2-(2,6-difluoro-4-(((R)-1,1,1-trifluorobutan-2-yl)amino)benzamido)-3-(8-(1,6-dimethyl-2-oxo-4-(trifluoromethyl)-1,2-dihydropyridin-3-yl)quinolin-5-yl)propanoic acid (91): The title compound was prepared according to the method presented for the synthesis of compound 74 starting with 91D. MS (m/z) 671.2 [M+H]+. 1H NMR (400 MHz, DMSO-d6) δ 8.84-8.70 (m, 2H), 8.62 (s, 1H), 7.55 (s, 2H), 7.42 (s, 1H), 6.75 (dd, J=9.4, 5.5 Hz, 1H), 6.54 (s, 1H), 6.42 (dd, J=11.4, 4.2 Hz, 2H), 4.66 (s, 1H), 4.29 (s, 1H), 3.66 (d, J=13.6 Hz, 1H), 3.59-3.21 (m, 5H), 2.51 (s, 2H), 1.79-1.70 (m, 1H), 1.51 (ddd, J=13.7, 10.4, 7.1 Hz, 1H), 0.91 (t, J=7.3 Hz, 3H).

Example 92

Synthesis of 2-chloro-4-methoxy-3-(trifluoromethyl)pyridine (92A): To a stirred solution of 2,4-dichloro-3-(trifluoromethyl)pyridine (157.5 mg, 0.729 mmol) in methanol at 0° C. was added sodium methoxide powder (118.19 mg, 2.188 mmol). The reaction mixture was allowed to warm to RT and was stirred for 16 hours. The solvent was removed under reduced pressure, and the resulting residue was purified by silica gel chromatography using EA in hexanes as eluent to afford the title compound.

Synthesis of methyl (S)-2-amino-3-(8-(4-methoxy-3-(trifluoromethyl)pyridin-2-yl)quinolin-5-yl)propanoate (92B): The title compound was prepared according to the method presented for the synthesis of compound 91C and 91D starting with 92A.

(S)-2-(2,6-difluoro-4-(((R)-1,1,1-trifluorobutan-2-yl)amino)benzamido)-3-(8-(4-methoxy-3-(trifluoromethyl)pyridin-2-yl)quinolin-5-yl)propanoic acid (92): The title compound was prepared according to the method presented for the synthesis of compound 74 starting with 92B. MS (m/z) 657.8 [M+H]+. 1H NMR (400 MHz, DMSO-d6) δ 8.80 (d, J=8.9 Hz, 2H), 8.73 (d, J=5.9 Hz, 1H), 8.62 (t, J=7.9 Hz, 1H), 7.60 (t, J=6.8 Hz, 3H), 7.44 (d, J=6.0 Hz, 1H), 6.76 (t, J=8.2 Hz, 1H), 6.45 (dd, J=11.7, 7.2 Hz, 2H), 4.68 (d, J=19.6 Hz, 1H), 4.30 (s, 1H), 4.07 (s, 3H), 3.74 (d, J=15.1 Hz, 1H), 3.69-3.64 (m, 1H), 1.77 (s, 1H), 1.53 (s, 1H), 0.93 (t, J=7.4 Hz, 3H).

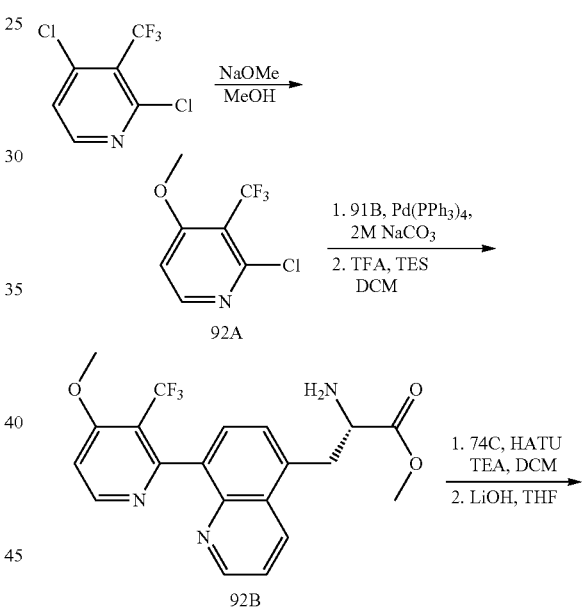

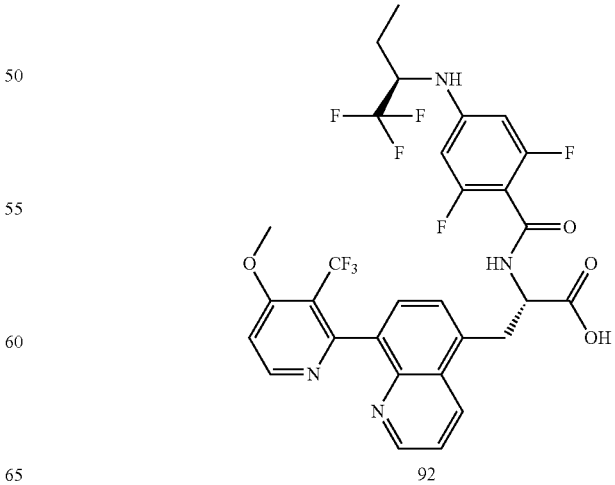

92

Example 93

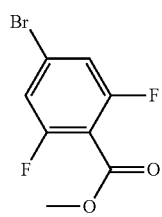

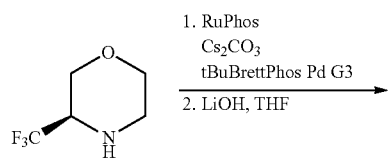

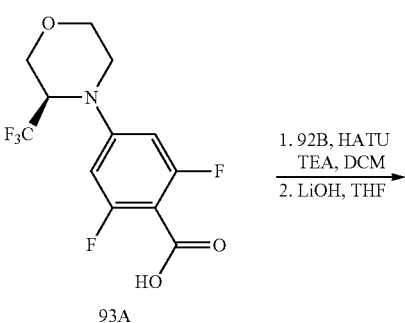

93A

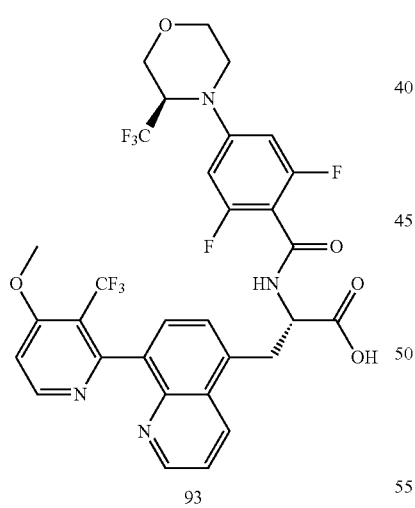

93

Synthesis of (R)-2,6-difluoro-4-(3-(trifluoromethyl)morpholino)benzoic acid (93A): The title compound was prepared according to the method presented for the synthesis of compound 75A starting with (R)-3-(trifluoromethyl)morpholine.

(S)-2-(2,6-difluoro-4-((R)-3-(trifluoromethyl)morpholino)benzamido)-3-(8-(4-methoxy-3-(trifluoromethyl)pyridin-2-yl)quinolin-5-yl)propanoic acid (93): The title compound was prepared according to the method presented for the synthesis of compound 16A and 16 starting with 92B and 93A. MS (m/z) 685.9 [M+H]+. 1H NMR (500 MHz, DMSO-d6) δ 8.95 (dd, J=11.7, 8.0 Hz, 1H), 8.80 (d, J=3.7 Hz, 1H), 8.74 (d, J=6.0 Hz, 1H), 8.63 (t, J=8.7 Hz, 1H), 7.61 (dd, J=13.0, 5.4 Hz, 3H), 7.46 (d, J=6.1 Hz, 1H), 6.76 (t, J=11.2 Hz, 2H), 4.91 (d, J=9.3 Hz, 1H), 4.77-4.64 (m, 1H), 4.19-4.13 (m, 1H), 4.08 (s, 3H), 3.95 (d, J=11.7 Hz, 1H), 3.80-3.66 (m, 2H), 3.55 (t, J=11.8 Hz, 1H), 3.51-3.36 (m, 2H), 3.23 (t, J=12.5 Hz, 1H).

Example 94

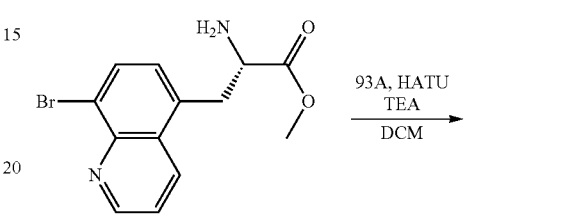

1D

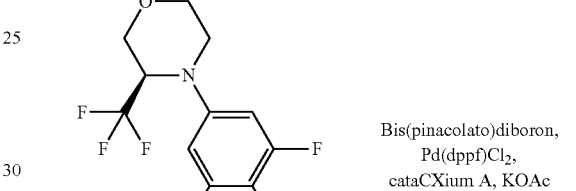

94A

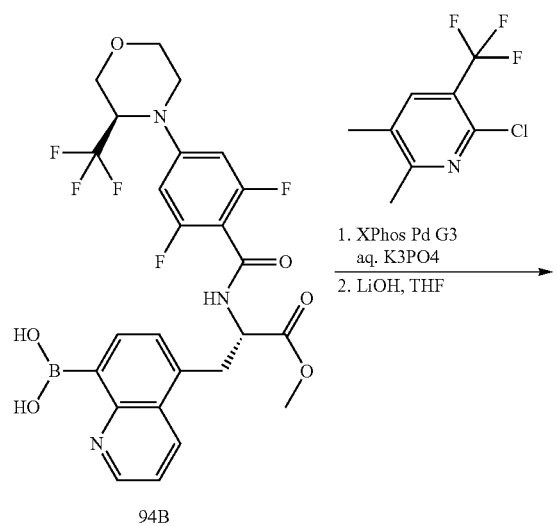

94B

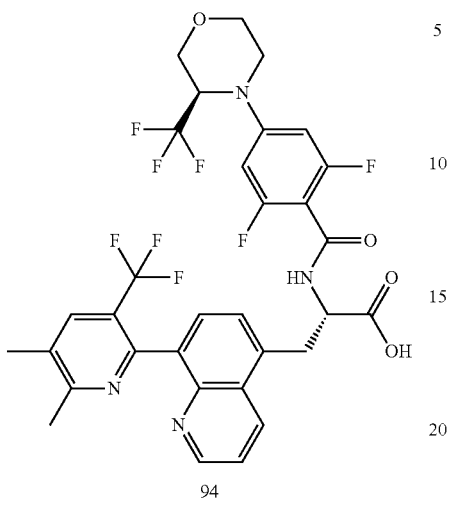

94

Synthesis of methyl (S)-3-(8-bromoquinolin-5-yl)-2-(2,6-difluoro-4-((R)-3-(trifluoromethyl)morpholino)benzamido)propanoate (94A): The title compound was prepared according to the method presented for the synthesis of compound 16A in Example 16 starting with 93A.

Synthesis of (5-((S)-2-(2,6-difluoro-4-((R)-3-(trifluoromethyl)morpholino) benzamido)-3-methoxy-3-oxopropyl)quinolin-8-yl)boronic acid (94B): The title compound was prepared according to the method presented for the synthesis of compound 4B starting with 94A.

(S)-2-(2,6-difluoro-4-((R)-3-(trifluoromethyl)morpholino)benzamido)-3-(8-(5,6-dimethyl-3-(trifluoromethyl)pyridin-2-yl)quinolin-5-yl)propanoic acid (94): The title compound was prepared according to the method presented for the synthesis of compound 11A and 11 starting with 94B and 2-chloro-5,6-dimethyl-3-(trifluoromethyl)pyridine. MS (m/z) 683.2 [M+H]+. 1H NMR (400 MHz, DMSO-d6) δ 8.96 (d, J=8.0 Hz, 1H), 8.77 (dd, J=4.0, 1.5 Hz, 1H), 8.67-8.59 (m, 1H), 8.03 (s, 1H), 7.68-7.47 (m, 3H), 6.74 (d, J=11.7 Hz, 2H), 4.95-4.84 (m, 1H), 4.72-4.61 (m, 1H), 4.14 (d, J=12.8 Hz, 1H), 3.98-3.86 (m, 1H), 3.72 (d, J=13.1 Hz, 2H), 3.58-3.30 (m, 3H), 3.21 (s, 1H), 2.50 (s, 3H), 2.41 (s, 3H).

Example 95

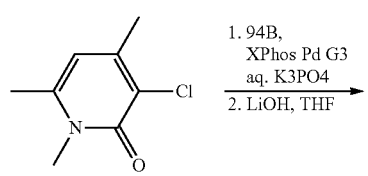

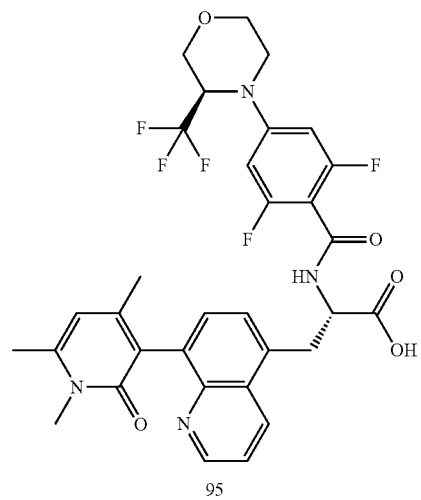

95

(S)-2-(2,6-difluoro-4-((R)-3-(trifluoromethyl)morpholino)benzamido)-3-(8-(1,4,6-trimethyl-2-oxo-1,2-dihydropyridin-3-yl)quinolin-5-yl)propanoic acid (95): The title compound was prepared according to the method presented for the synthesis of compound 11A and 11 starting with 94B and 3-chloro-1,4,6-trimethylpyridin-2(1H)-one. MS (m/z) 645.2 [M+H]+. 1H NMR (400 MHz, DMSO-d6) δ 8.99-8.81 (m, 3H), 7.76 (s, 1H), 7.65 (dd, J=13.5, 7.3 Hz, 1H), 7.53 (t, J=8.1 Hz, 1H), 6.72 (dd, J=11.5, 2.7 Hz, 2H), 6.20 (s, 1H), 4.88 (d, J=9.4 Hz, 1H), 4.74-4.69 (m, 1H), 4.14 (d, J=12.7 Hz, 1H), 3.93 (dd, J=11.5, 3.8 Hz, 1H), 3.79 (s, 1H), 3.70 (t, J=9.9 Hz, 1H), 3.51 (d, J=10.7 Hz, 2H), 3.46-3.34 (m, 4H), 3.21 (t, J=12.3 Hz, 1H), 2.40 (s, 3H), 1.73 (d, J=10.6 Hz, 3H).

Example 96

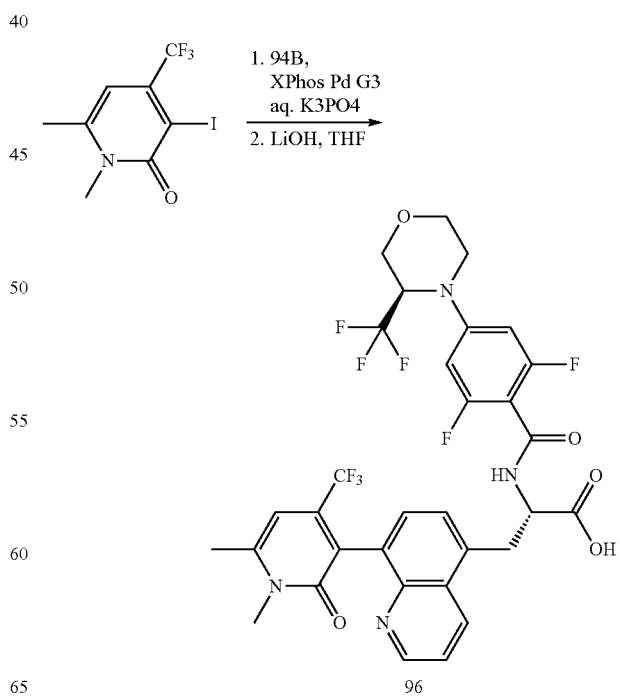

96

(S)-2-(2,6-difluoro-4-((R)-3-(trifluoromethyl)morpholino)benzamido)-3-(8-(1,6-dimethyl-2-oxo-4-(trifluoromethyl)-1,2-dihydropyridin-3-yl)quinolin-5-yl)propanoic acid (96): The title compound was prepared according to the method presented for the synthesis of compound 11A and 11 starting with 94B and 3-iodo-1,6-dimethyl-4-(trifluoromethyl)pyridin-2(1H)-one. MS (m/z) 699.2 [M+H]+. 1H NMR (400 MHz, DMSO-d6) δ 8.96 (dd, J=7.9, 4.2 Hz, 1H), 8.86-8.79 (m, 1H), 8.67 (s, 1H), 7.60 (dt, J=25.1, 8.5 Hz, 2H), 7.48-7.39 (m, 1H), 6.74 (dd, J=11.6, 4.3 Hz, 2H), 6.54 (s, 1H), 4.90 (dd, J=8.7, 3.6 Hz, 1H), 4.72-4.63 (m, 1H), 4.14 (d, J=12.7 Hz, 1H), 3.93 (dd, J=11.5, 3.8 Hz, 1H), 3.75-3.62 (m, 2H), 3.60-3.32 (m, 6H), 3.23 (d, J=12.4 Hz, 1H), 2.52 (s, 3H).

Example 97

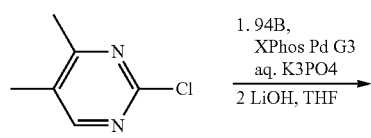

(S)-2-(2,6-difluoro-4-((R)-3-(trifluoromethyl)morpholino)benzamido)-3-(8-(4,5-dimethylpyrimidin-2-yl)quinolin-5-yl)propanoic acid (97): The title compound was prepared according to the method presented for the synthesis of compound 11A and 11 starting with 94B and 2-chloro-4,5-dimethylpyrimidine. MS (m/z) 617.0 [M+H]+. 1H NMR (400 MHz, DMSO-d6) δ 9.37 (s, 1H), 9.31 (s, 1H), 8.94 (d, J=8.3 Hz, 1H), 8.78 (s, 2H), 8.11 (s, 1H), 7.93 (d, J=7.7 Hz, 1H), 6.77 (dd, J=37.8, 12.3 Hz, 2H), 4.97-4.75 (m, 2H), 4.16 (dd, J=12.9, 8.0 Hz, 1H), 3.91 (ddd, J=25.2, 12.9, 4.2 Hz, 2H), 3.72 (d, J=13.1 Hz, 1H), 3.59-3.53 (m, 2H), 3.41-3.36 (m, 1H), 3.22 (dd, J=14.4, 11.1 Hz, 1H), 2.66 (s, 3H), 2.39 (s, 3H).

Example 98

(S)-2-(2,6-difluoro-4-((R)-3-(trifluoromethyl)morpholino)benzamido)-3-(8-(1-methyl-2-oxo-5-(trifluoromethyl)-1,2-dihydropyridin-3-yl)quinolin-5-yl)propanoic acid (98): The title compound was prepared according to the method presented for the synthesis of compound 11A and 11 starting with 94B and 3-bromo-1-methyl-5-(trifluoromethyl)pyridin-2(1H)-one. MS (m/z) 685.2 [M+H]+. 1H NMR (400 MHz, DMSO-d6) δ 12.96 (s, 1H), 8.96 (d, J=8.0 Hz, 1H), 8.89 (d, J=4.2 Hz, 1H), 8.71 (d, J=8.6 Hz, 1H), 8.50 (s, 1H), 7.73-7.64 (m, 3H), 7.61 (d, J=7.3 Hz, 1H), 6.76 (d, J=11.8 Hz, 2H), 4.91 (d, J=9.7 Hz, 1H), 4.68 (s, 1H), 4.16 (d, J=12.7 Hz, 1H), 3.95 (d, J=11.4 Hz, 1H), 3.73 (d, J=13.4 Hz, 2H), 3.57 (s, 4H), 3.44 (dd, J=14.0, 9.3 Hz, 2H), 3.24 (t, J=12.5 Hz, 1H).

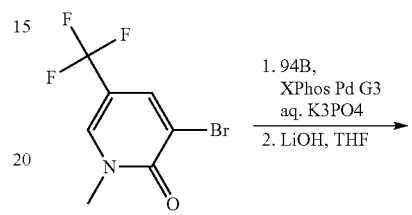

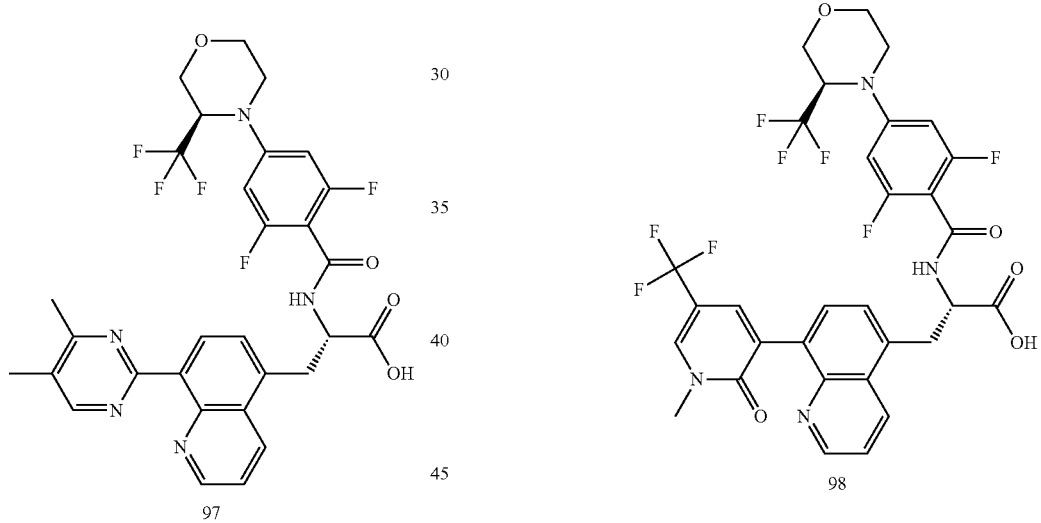

Example 99

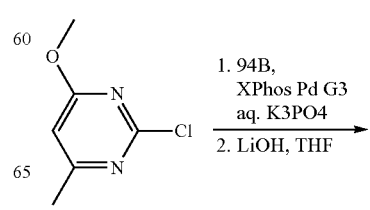

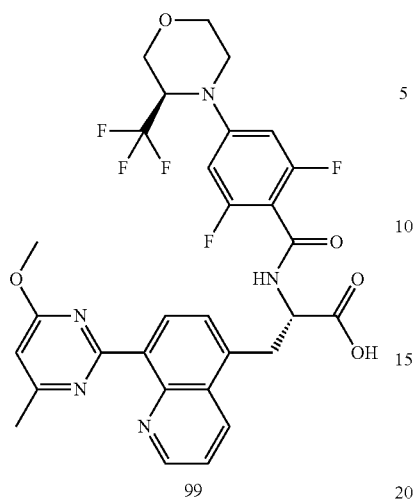

99

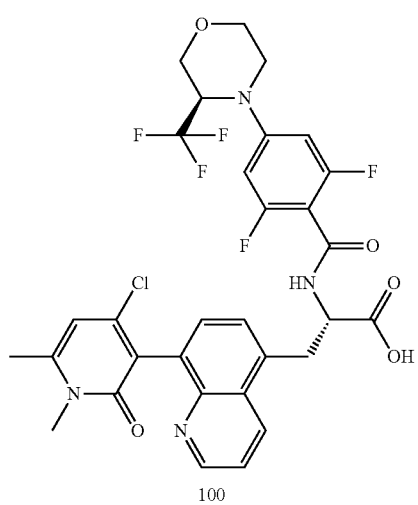

100

(S)-2-(2,6-difluoro-4-((R)-3-(trifluoromethyl)morpholino)benzamido)-3-(8-(4-methoxy-6-methylpyrimidin-2-yl)quinolin-5-yl)propanoic acid (99): The title compound was prepared according to the method presented for the synthesis of compound 11A and 11 starting with 94B and 2-chloro-4-methoxy-6-methylpyrimidine. MS (m/z) 632.2 [M+H]+. 1H NMR (400 MHz, DMSO-d6) δ 9.49 (d, J=4.9 Hz, 1H), 9.39 (d, J=8.7 Hz, 1H), 9.04 (d, J=7.5 Hz, 1H), 8.95 (d, J=8.4 Hz, 1H), 8.18 (dd, J=8.7, 5.0 Hz, 1H), 8.00 (d, J=7.8 Hz, 1H), 7.10 (s, 1H), 6.72 (d, J=12.2 Hz, 2H), 4.94-4.78 (m, 2H), 4.15 (s, 4H), 4.00-3.84 (m, 2H), 3.74 (t, J=16.0 Hz, 1H), 3.65-3.46 (m, 2H), 3.39 (d, J=12.8 Hz, 1H), 3.21 (t, J=12.5 Hz, 1H), 2.70 (s, 3H).

Example 100

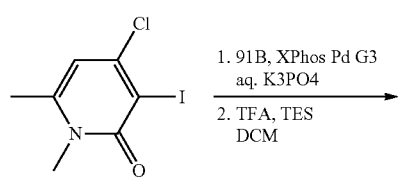

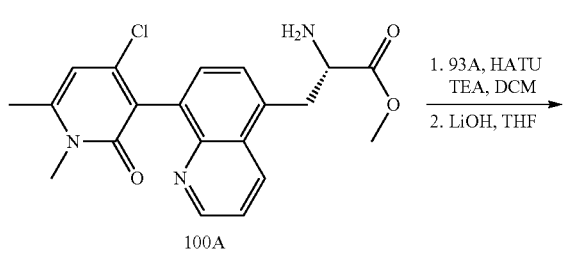

100A

Synthesis of methyl (S)-2-amino-3-(8-(4-chloro-1,6-dimethyl-2-oxo-1,2-dihydro pyridin-3-yl)quinolin-5-yl)propanoate (100A): The title compound was prepared according to the method presented for the synthesis of compound 91C and 91D starting with 4-chloro-3-iodo-1,6-dimethylpyridin-2(1H)-one.

(S)-3-(8-(4-chloro-1,6-dimethyl-2-oxo-1,2-dihydropyridin-3-yl)quinolin-5-yl)-2-(2,6-difluoro-4-((R)-3-(trifluoromethyl)morpholino)benzamido)propanoic acid (100): The title compound was prepared according to the method presented for the synthesis of compound 93 starting with 100A. MS (m/z) 665.7 [M+H]+. 1H NMR (400 MHz, DMSO-d6) δ 8.98 (d, J=7.9 Hz, 1H), 8.87 (d, J=4.3 Hz, 1H), 8.73 (s, 1H), 7.67 (d, J=9.1 Hz, 1H), 7.63 (dd, J=7.6, 4.2 Hz, 1H), 7.54 (d, J=7.3 Hz, 1H), 6.76 (dd, J=11.7, 3.9 Hz, 2H), 6.49 (d, J=2.8 Hz, 1H), 4.91 (dd, J=8.9, 3.6 Hz, 1H), 4.70 (dd, J=12.5, 7.4 Hz, 1H), 4.16 (d, J=12.7 Hz, 1H), 3.97-3.93 (m, 2H), 3.73 (dd, J=12.0, 8.5 Hz, 2H), 3.52 (d, J=22.8 Hz, 1H), 3.45 (d, J=1.9 Hz, 3H), 3.41 (d, J=3.5 Hz, 1H), 3.24 (t, J=12.4 Hz, 1H), 2.46 (s, 3H).

Example 101

Synthesis of methyl (S)-2-amino-3-(8-(3-(dimethylamino)pyridin-2-yl)quinolin-5-yl)propanoate (101A): The title compound was prepared according to the method presented for the synthesis of compound 91C and 91D starting with 2-bromo-N,N-dimethylpyridin-3-amine.

(S)-2-(2,6-difluoro-4-((R)-3-(trifluoromethyl)morpholino)benzamido)-3-(8-(3-(dimethylamino)pyridin-2-yl)quinolin-5-yl)propanoic acid (101): The title compound was prepared according to the method presented for the synthesis of compound 93 starting with 101A. MS (m/z) 630.3 [M+H]+. 1H NMR (400 MHz, DMSO-d6) δ 9.04-8.92 (m, 2H), 8.77 (dd, J=8.8, 1.6 Hz, 1H), 8.32 (d, J=5.3 Hz, 1H), 8.11 (d, J=8.8 Hz, 1H), 7.91 (t, J=7.9 Hz, 2H), 7.81-7.71 (m, 2H), 6.74 (d, J=11.8 Hz, 2H), 4.90 (dd, J=8.8, 3.5 Hz, 1H), 4.81-4.72 (m, 1H), 4.16 (d, J=12.7 Hz, 1H), 3.96 (dd, J=11.4, 3.7 Hz, 1H), 3.82 (dd, J=14.2, 4.4 Hz, 1H), 3.73 (d, J=12.8 Hz, 1H), 3.62-3.36 (m, 3H), 3.23 (t, J=12.1 Hz, 1H), 2.50 (m, 6H).

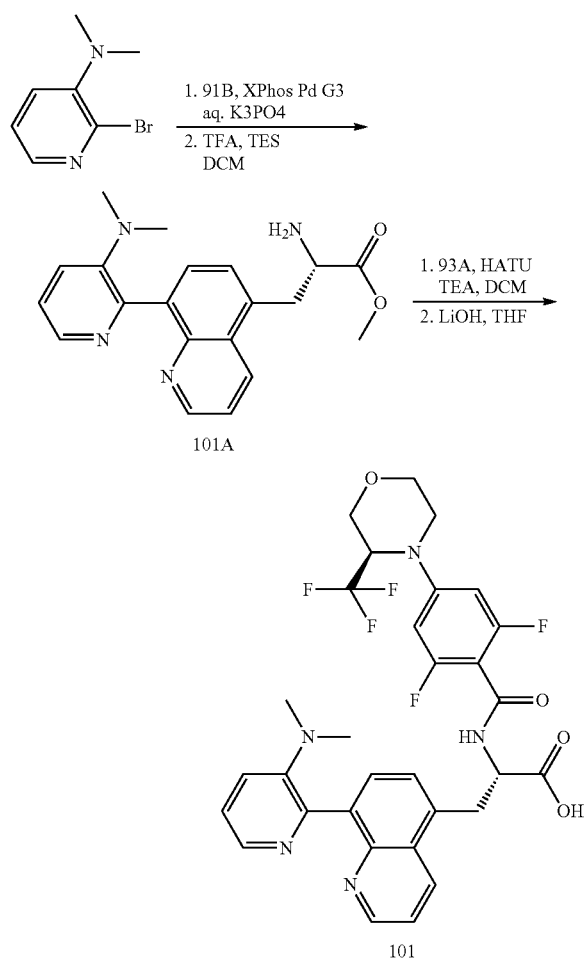

Example 102

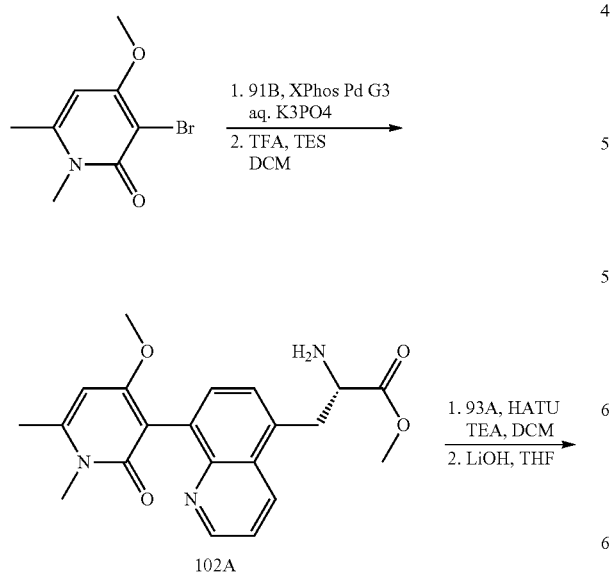

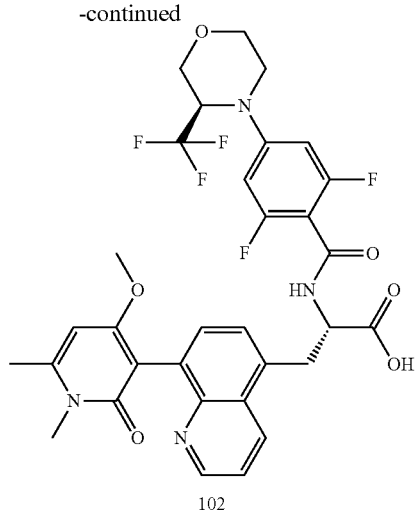

Synthesis of methyl (S)-2-amino-3-(8-(4-methoxy-1,6-dimethyl-2-oxo-1,2-dihydropyridin-3-yl)quinolin-5-yl)propanoate (102A): The title compound was prepared according to the method presented for the synthesis of compound 91C and 91D starting with 3-bromo-4-methoxy-1,6-dimethylpyridin-2(1H)-one.

(S)-2-(2,6-difluoro-4-((R)-3-(trifluoromethyl)morpholino)benzamido)-3-(8-(4-methoxy-1,6-dimethyl-2-oxo-1,2-dihydropyridin-3-yl)quinolin-5-yl)propanoic acid (102): The title compound was prepared according to the method presented for the synthesis of compound 93 starting with 102A. MS (m/z) 661.2 [M+H]+. 1H NMR (400 MHz, DMSO-d6) δ 13.02 (s, 1H), 9.09 (s, 1H), 9.04-8.93 (m, 2H), 7.91 (s, 1H), 7.71 (d, J=14.6 Hz, 2H), 6.76 (d, J=11.8 Hz, 2H), 6.46 (s, 1H), 4.92 (s, 1H), 4.72 (s, 1H), 4.16 (d, J=12.7 Hz, 1H), 4.00-3.91 (m, 1H), 3.70 (m, 5H), 3.61-3.37 (m, 6H), 3.23 (t, J=12.3 Hz, 1H).

Example 103

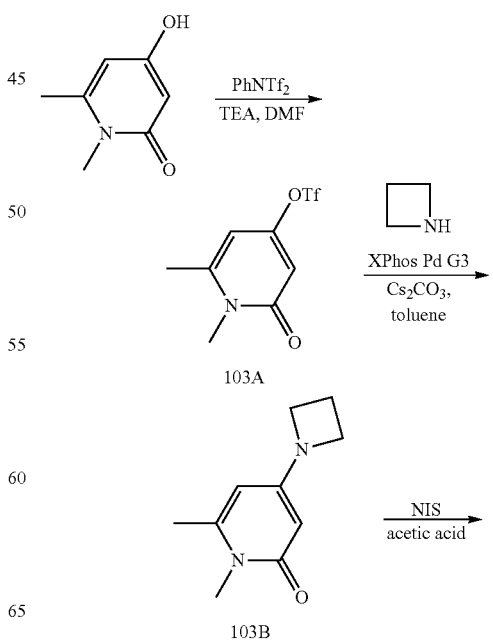

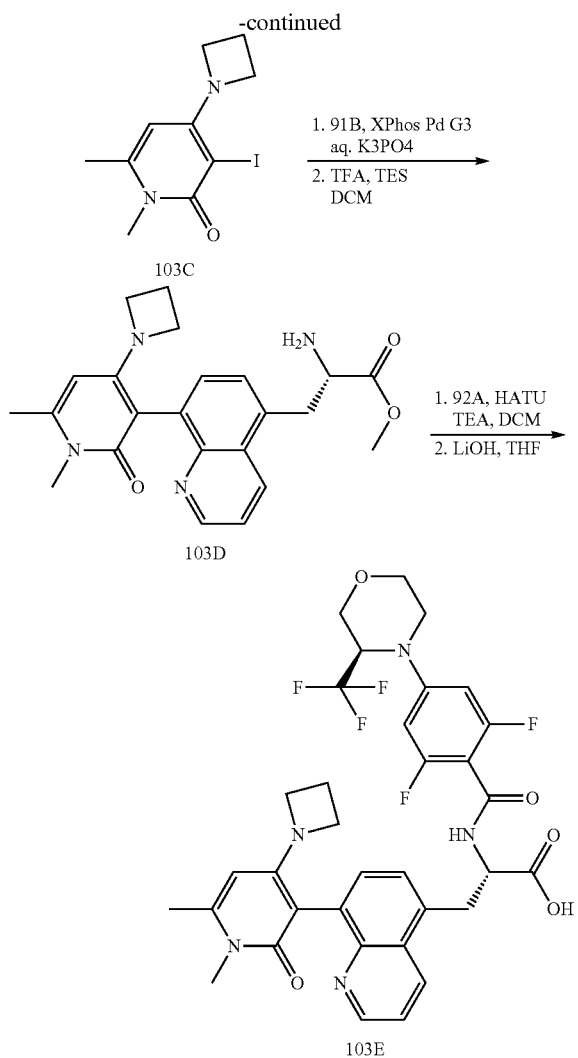

organic layer was washed with brine, dried over anhydrous Na₂SO₄, and concentrated under reduced pressure. The material was purified by silica gel chromatography using EA in hexanes to afford the title compound.

Synthesis of methyl (S)-2-amino-3-(8-(4-(azetidin-1-yl)-1,6-dimethyl-2-oxo-1,2-dihydropyridin-3-yl)quinolin-5-yl) propanoate (103D): The title compound was prepared according to the method presented for the synthesis of compound 91C and 91D starting with 103C.

(S)-3-(8-(4-(azetidin-1-yl)-1,6-dimethyl-2-oxo-1,2-dihydropyridin-3-yl)quinolin-5-yl)-2-(2,6-difluoro-4-((R)-3-(trifluoromethyl)morpholino)benzamido)propanoic acid (103E): The title compound was prepared according to the method presented for the synthesis of compound 93 starting with 103D. MS (m/z) 686.4 [M+H]+. 1H NMR (400 MHz, DMSO-d6) δ 9.20 (s, 1H), 9.05 (d, J=4.9 Hz, 1H), 8.91 (dd, J=8.3, 3.5 Hz, 1H), 7.98 (d, J=27.1 Hz, 1H), 7.84-7.55 (m, 2H), 6.73 (dd, J=17.5, 11.8 Hz, 2H), 5.74 (d, J=2.8 Hz, 1H), 4.90 (s, 1H), 4.82-4.70 (m, 1H), 4.16 (dd, J=12.6, 4.0 Hz, 1H), 4.01-3.88 (m, 1H), 3.73 (d, J=13.2 Hz, 1H), 3.68-3.48 (m, 2H), 3.35 (d, J=5.2 Hz, 4H), 3.21 (s, 3H), 2.42-2.36 (m, 3H), 1.83 (dt, J=27.5, 7.6 Hz, 1H).

Example 104

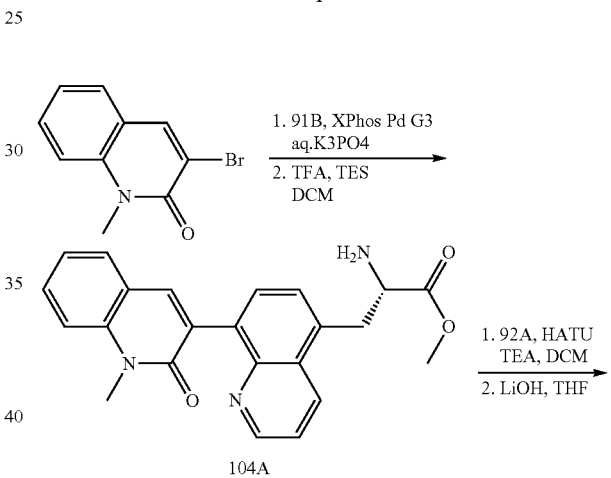

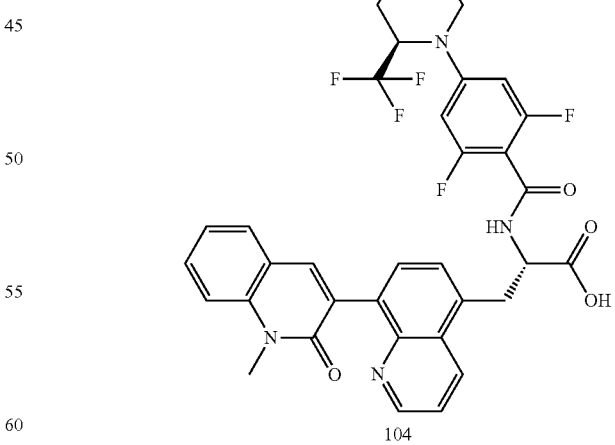

Synthesis of 1,6-dimethyl-2-oxo-1,2-dihydropyridin-4-yl 4-methylbenzenesulfonate (103A): To a stirred suspension of 4-hydroxy-1,6-dimethylpyridin-2(1H)-one (1.5 g, 10.8 mmol) in TEA (1.8 mL, 12.9 mmol) in DMF (27 mL) was added N-Ph triflimide (3.85 g, 10.8 mmol). The reaction mixture was stirred for 15 min during which the suspended solids went into solution. The solution was concentrated under reduced pressure and purified by silica gel chromatography using EA in hexanes to afford the title compound.

Synthesis of 4-(azetidin-1-yl)-1,6-dimethylpyridin-2(1H)-one (103B): To a pressure tube was added 103A (450 mg, 1.66 mmol), azetidine (0.11 mL, 1.66 mmol), XPhos Pd G3 (140 mg, 0.17 mmol), and Cs₂CO₃ (1.08 g, 3.3 mmol) in toluene (5.5 mL). After sparging with N₂, the mixture was heated at 90° C. and allowed to stir vigorously for 90 min. The reaction mixture was cooled and filtered through a pad of Celite rinsing with EA. The solution was concentrated under reduced pressure and purified by silica gel chromatography using MeOH in DCM to afford the title compound.

Synthesis of 4-(azetidin-1-yl)-3-iodo-1,6-dimethylpyridin-2(1H)-one (103C): To a stirred solution of 103B (90 mg, 0.5 mmol) in acetic acid (0.5 mL) was added N-iodosuccinimide (125 mg, 0.56 mmol). After 10 min stirred and added a 1:1 mixture of aq sat NaHCO₃ and aq sat Na₂S₂O₃. The aqueous layer was extracted with EA. The Synthesis of methyl (S)-2-amino-3-(1-methyl-2-oxo-1,2-dihydro-[3,8'-biquinolin]-5'-yl)propanoate (104A): The title compound was prepared according to the method presented for the synthesis of compound 91C and 91D starting with 3-bromo-1-methylquinolin-2(1H)-one.

(S)-2-(2,6-difluoro-4-((R)-3-(trifluoromethyl)morpholino)benzamido)-3-(1-methyl-2-oxo-1,2-dihydro-[3,8'-biquinolin]-5'-yl)propanoic acid (104): The title compound was prepared according to the method presented for the synthesis of compound 93 starting with 104A. MS (m/z) 667.2 [M+H]+. 1H NMR (400 MHz, DMSO-d6) δ 8.99 (1H, d, J=8.0 Hz), 8.90 (1H, d, J=4.2 Hz), 8.79 (1H, m), 7.99 (1H, s), 7.82-7.58 (6H, m), 7.32 (1H, t, J=7.4 Hz), 6.78 (2H, d, J=11.8 Hz), 4.95-4.88 (1H, m), 4.76-4.66 (1H, m), 4.16 (1H, d, J=12.7 Hz), 3.96 (2H, dd, J=11.4, 3.9 Hz), 3.70 (4H, m), 3.50 (3H, ddd, J=44.1, 17.5, 11.8 Hz), 3.24 (1H, t, J=12.6 Hz).

Example 105

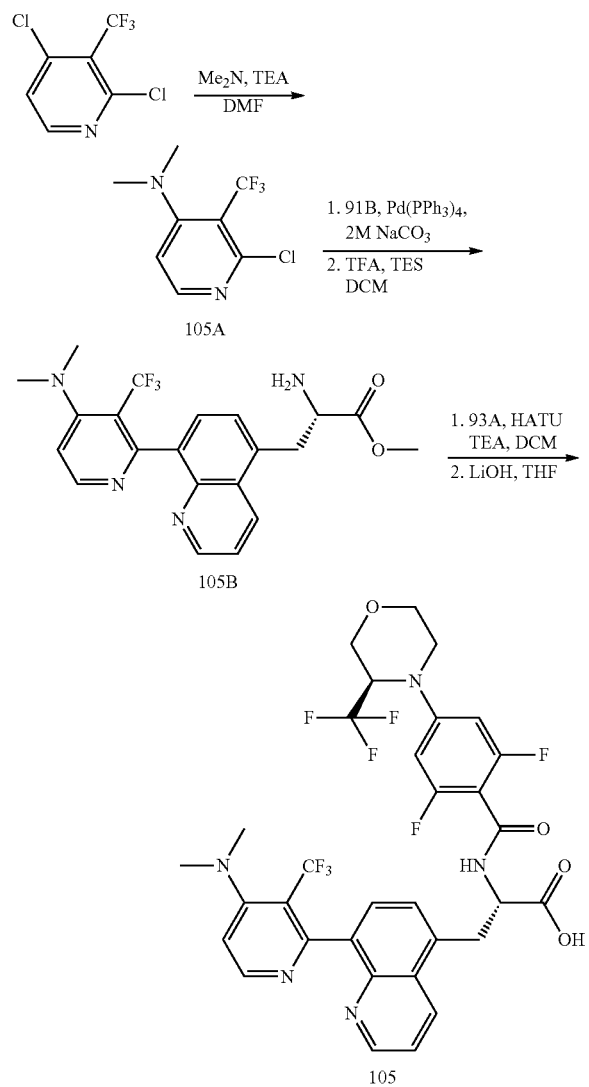

Synthesis of 2-chloro-N,N-dimethyl-3-(trifluoromethyl)pyridin-4-amine (105A): The title compound was prepared according to the method presented for the synthesis of compound 92A in Example 92 starting with dimethyl amine.

Synthesis of methyl (S)-2-amino-3-(8-(4-(dimethylamino)-3-(trifluoromethyl)pyridin-2-yl)quinolin-5-yl)propanoate (105B): The title compound was prepared according to the method presented for the synthesis of compound 91C and 91D starting with 105A.

(S)-2-(2,6-difluoro-4-((R)-3-(trifluoromethyl)morpholino)benzamido)-3-(8-(4-(dimethylamino)-3-(trifluoromethyl)pyridin-2-yl)quinolin-5-yl)propanoic acid (105): The title compound was prepared according to the method presented for the synthesis of compound 93 starting with 105B. MS (m/z) 698.3 [M+H]+. 1H NMR (400 MHz, DMSO-d6) δ 13.08 (s, 1H), 9.00 (dd, J=30.1, 6.7 Hz, 2H), 8.74 (s, 1H), 8.38 (d, J=7.5 Hz, 1H), 7.96 (s, 1H), 7.72 (d, J=21.3 Hz, 2H), 7.43 (d, J=7.4 Hz, 1H), 6.75 (d, J=11.7 Hz, 2H), 4.91 (s, 1H), 4.74 (s, 1H), 4.16 (d, J=12.7 Hz, 1H), 3.96 (dd, J=11.4, 3.8 Hz, 1H), 3.85 (d, J=14.5 Hz, 1H), 3.74 (d, J=13.0 Hz, 2H), 3.55 (t, J=12.1 Hz, 1H), 3.41 (d, J=12.5 Hz, 1H), 3.31 (s, 6H), 3.23 (s, 1H).

Example 106

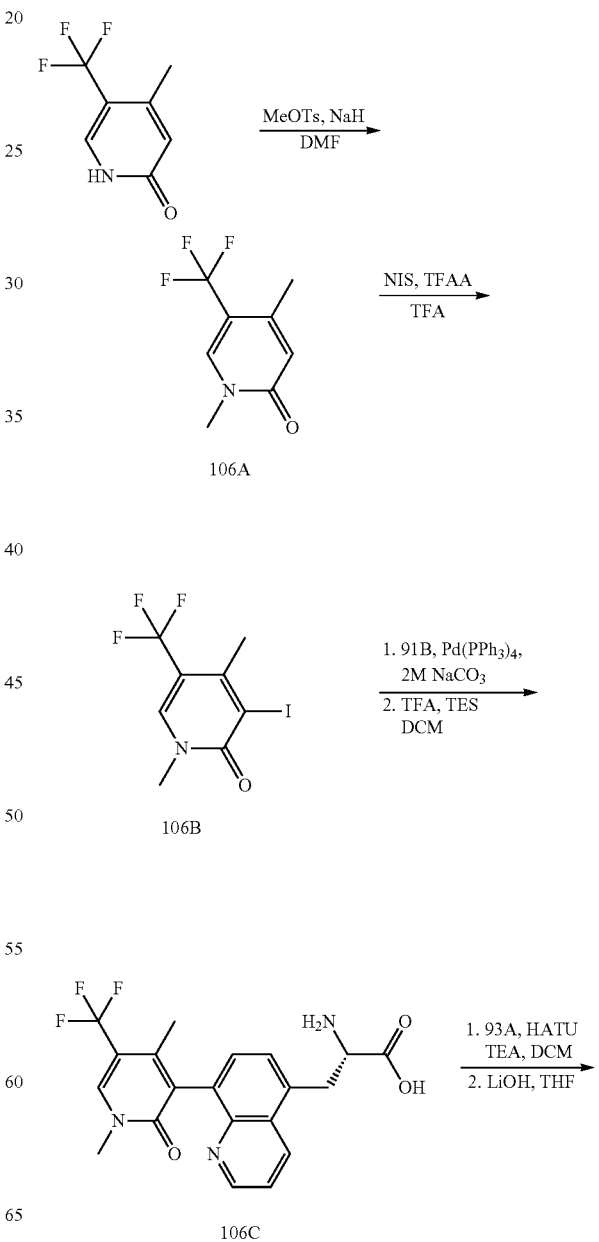

243
-continued

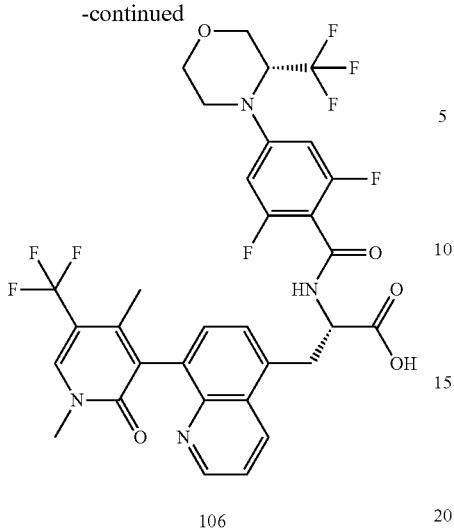

106

Synthesis of 1,4-dimethyl-5-(trifluoromethyl)pyridin-2 (1H)-one (106A): To a stirred solution of 4-methyl-5-(trifluoromethyl)pyridin-2(1H)-one (100 mg, 0.056 mmol) in DMF was added NaH (25 mg, 0.62 mmol) and the reaction mixture was allowed to stir for 30 min at which time the bubbling ceased. The reaction mixture was cooled to 0° C. and methyl p-toluene sulfonate (116 mg, 0.062 mmol) was added dropwise. After 4 hrs the reaction mixture was allowed to warm to RT, concentrated under reduced pressure, and purified on silica gel chromatography eluting with Hex/EA 0-100% to afford the title compound.

Synthesis of 3-iodo-1,4-dimethyl-5-(trifluoromethyl) pyridin-2(1H)-one (106B): To a stirred solution of 106A (0.72 g, 4 mmol) neat TFA was added TFAA (1.6 g, 8 mmol). The reaction mixture was heated to 100° C. for 5 min in a sealed vial, followed by the addition of NIS (1.08 g, 5 mmol) and further heating at 60° C. for 3 hrs. The reaction mixture was cooled and the TFA removed under reduced pressure. The residue was dissolved in EA and washed with sat. sodium bicarbonate then brine. The organic layer was filtered then concentrated to give the title compound without further purification.

Synthesis of (S)-2-amino-3-(8-(1,4-dimethyl-2-oxo-5-(trifluoromethyl)-1,2-dihydro pyridin-3-yl)quinolin-5-yl) propanoic acid (106C): The title compound was prepared according to the method presented for the synthesis of compound 91C and 91D starting with 106B.

(S)-2-(2,6-difluoro-4-((R)-3-(trifluoromethyl)morpholino)benzamido)-3-(8-(1,4-dimethyl-2-oxo-5-(trifluoromethyl)-1,2-dihydropyridin-3-yl)quinolin-5-yl)propanoic acid (106)

The title compound was prepared according to the method presented for the synthesis of compound 93 starting with 106C. MS (m/z) 699.3 [M+H]+. 1H NMR (400 MHz, DMSO-d6) δ 12.94 (s, 1H), 8.94 (t, J=7.2 Hz, 1H), 8.86 (t, J=3.0 Hz, 1H), 8.73 (d, J=8.4 Hz, 1H), 8.39 (s, 1H), 7.74-7.58 (m, 2H), 7.53 (dd, J=11.4, 7.3 Hz, 1H), 6.74 (d, J=12.3 Hz, 2H), 4.90 (d, J=9.0 Hz, 1H), 4.74 (dd, J=9.1, 5.0 Hz, 1H), 4.16 (d, J=12.7 Hz, 1H), 4.00-3.90 (m, 1H), 3.86-3.64 (m, 2H), 3.56 (d, J=13.1 Hz, 1H), 3.51 (d, J=1.7 Hz, 3H), 3.46-3.31 (m, 2H), 3.23 (t, J=12.4 Hz, 1H), 1.83 (d, J=10.2 Hz, 3H).

244
Example 107

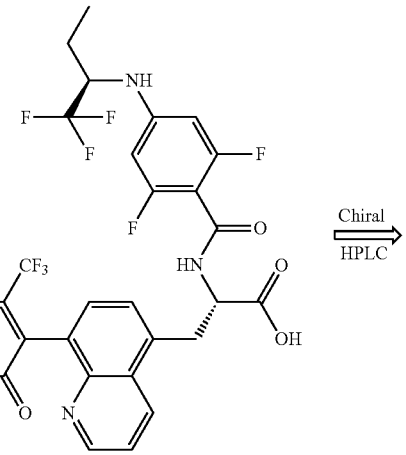

91

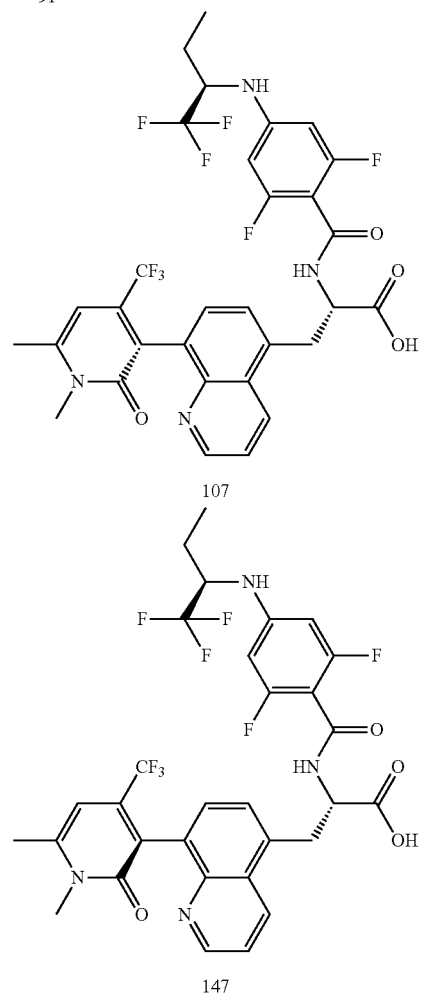

107

147

Preparation of (S)-2-(2,6-difluoro-4-(((R)-1,1,1-trifluorobutan-2-yl)amino)benzamido)-3-(8-(1,6-dimethyl-2-oxo-4-(trifluoromethyl)-1,2-dihydropyridin-3-yl)quinolin-5-yl) propanoic acid (107): 91 was separated into its 2 atropisomeric enantiomers by supercritical fluid chromatography using 30% MeOH co-solvent, at a flow rate of 60 mL/min, using an IC 5 μm 21×250 mm column. The title compound was identified as the first eluting peak. MS (m/z) 671.2 [M+H]$^+$. 1 H NMR (400 MHz, DMSO-d6) δ 8.85-8.72 (m, 2H), 8.63 (d, J=8.1 Hz, 1H), 7.67-7.60 (m, 1H), 7.54 (d, J=7.2 Hz, 1H), 7.42 (d, J=7.3 Hz, 1H), 6.74 (d, J=9.2 Hz, 1H), 6.54 (s, 1H), 6.42 (d, J=11.8 Hz, 2H), 4.66 (s, 1H), 4.29 (s, 1H), 3.75-3.66 (m, 1H), 3.41 (m, 7H), 1.75 (s, 1H), 1.58-1.46 (m, 1H), 0.91 (t, J=7.3 Hz, 3H).

Example 108

Synthesis of methyl (S)-3-(8-aminoquinolin-5-yl)-2-(tritylamino)propanoate (108A). To a stirred solution of (91A) (1.148 g, 2.08 mmol) in dioxane (5 mL) was added cesium carbonate (2.04 g, 6 mmol), benzophenone imine, (755 mg, 4.16 mmol), rac-Binap-Pd-G3 (103 mg, 0.1 mmol). The mixture was heated at 90° C. overnight, cooled to RT diluted with THF and added hydroxylamine hydrochloride (289 mg, 4.1 mmol) and sodium acetate (850 mg, 6 mmol) and methanol (1 mL) and let stir for 4 h. The mixture was diluted with ethyl acetate and washed with water. The organic extracts were dried over magnesium sulfate and chromatographed on silica gel eluting with hexanes and ethyl acetate to afford the title compound.

Synthesis of methyl (S)-3-(8-(5-(dimethylamino)-2-((ethoxycarbonyl)amino) benzamido)quinolin-5-yl)-2-(tritylamino)propanoate (108B). A stirred solution of 2-amino-5-(dimethylamino)benzoic acid (299 mg, 1.6 mmol) and acetonitrile (3 mL) was cooled to 0° C. and added pyridine (672 uL, 8.3 mmol), and ethyl chloroformate (0.635 mL, 6.645 mmol). The mixture was removed from an ice bath and let warm to RT over 30 minutes. Ethanol was then added and the mixture stirred a further 1 h. This entire mixture was then added to 108A (675 mg, 1.38 mmol) dissolved in DMF (4 mL) and left to stir for 4 h. Solvents were removed on a rotary evaporator and the product mixture was slurried with DCM and added to silica gel which was eluted with hexanes and ethyl acetate to provide the afford the title compound.

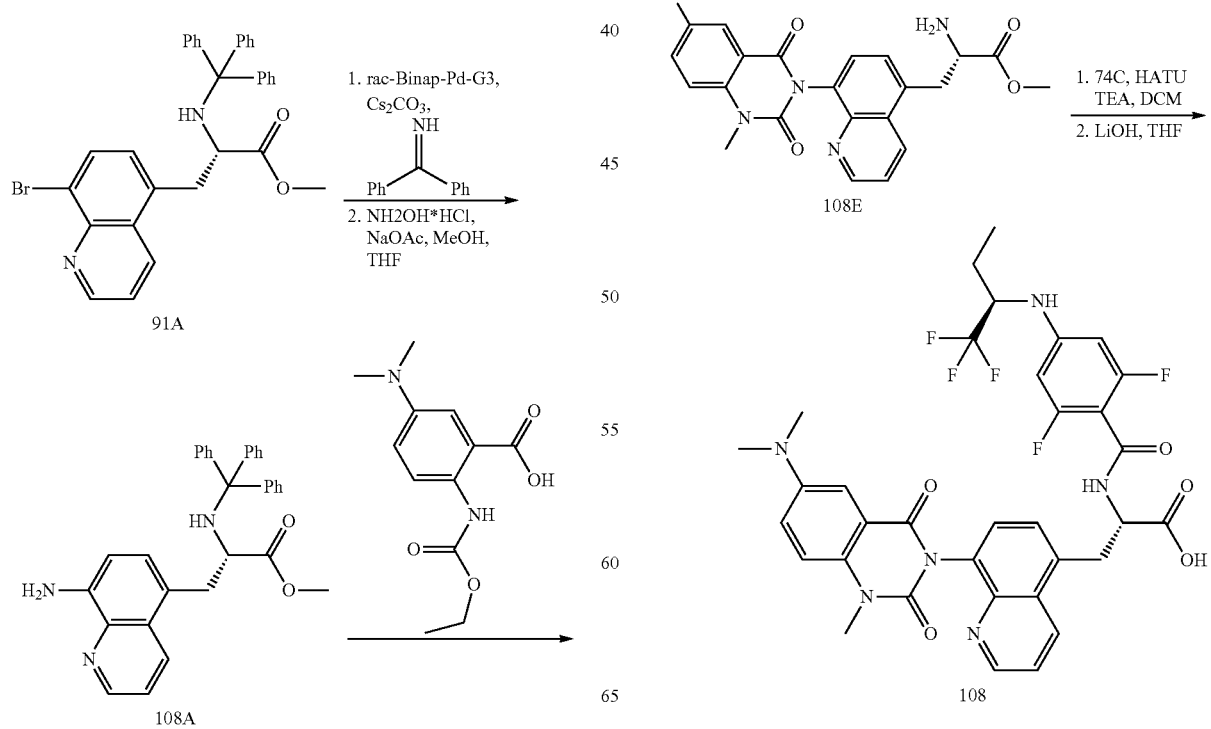

Synthesis of methyl (S)-3-(8-(6-(dimethylamino)-2,4-dioxo-1,4-dihydroquinazolin-3(2H)-yl)quinolin-5-yl)-2-(tritylamino)propanoate (108C). To a stirred solution of 108B (100 mg, 0.14 mmol) in DMF (2 mL) was added potassium carbonate (96 mg, 0.695 mmol) and methanol (1 mL). The mixture was stirred overnight and then the adsorbed directly onto silica gel and chromatographed eluting with hexanes and ethyl acetate to afford the title compound.

Synthesis of methyl (S)-3-(8-(6-(dimethylamino)-1-methyl-2,4-dioxo-1,4-dihydro quinazolin-3(2H)-yl)quinolin-5-yl)-2-(tritylamino)propanoate (108D): To a stirred solution of 108C (250 mg, 0.37 mol) in DMF (1 mL) was added potassium carbonate (51 mg, 0.37 mmol) and methyl tosylate (103 mg, 0.55 mmol). The reaction mixture was stirred overnight and concentrated under reduced pressure to afford material that was chromatographed on silica gel column eluting with EA in hexane to afford the title compound.

Synthesis of methyl (S)-2-amino-3-(8-(6-(dimethylamino)-1-methyl-2,4-dioxo-1,4-dihydroquinazolin-3(2H)-yl)quinolin-5-yl)propanoate (108E). 108D was dissolved in DCM (1 mL) and added TFA (1 mL) and let stir for 4 h. The mixture was concentrated and used without further purification.

(S)-2-(2,6-difluoro-4-(((R)-1,1,1-trifluorobutan-2-yl) amino)benzamido)-3-(8-(6-(dimethylamino)-1-methyl-2,4-dioxo-1,4-dihydroquinazolin-3(2H)-yl)quinolin-5-yl)propanoic acid (108): The title compound was prepared according to the method presented for the synthesis of compound 74 starting with 108E. MS (m/z) 699.8 [M+H]+. 1H NMR (400 MHz, DMSO-d6) δ 9.00-8.79 (m, 2H), 8.64 (d, J=8.4 Hz, 1H), 7.78-7.55 (m, 3H), 7.44 (d, J=9.1 Hz, 1H), 7.37 (dd, J=9.5, 2.9 Hz, 1H), 7.25 (s, 1H), 6.78 (d, J=9.4 Hz, 1H), 6.45 (d, J=11.7 Hz, 3H), 5.74 (s, 1H), 4.66 (s, 1H), 3.51 (d, J=1.7 Hz, 3H), 3.49-3.30 (m, 1H), 2.94 (s, 6H).

Example 109

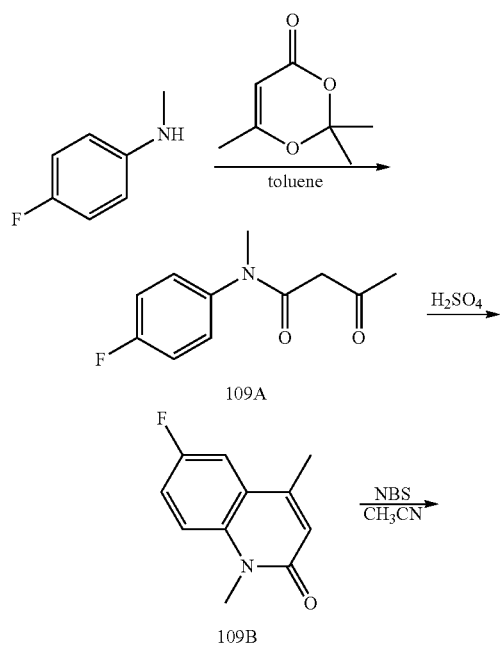

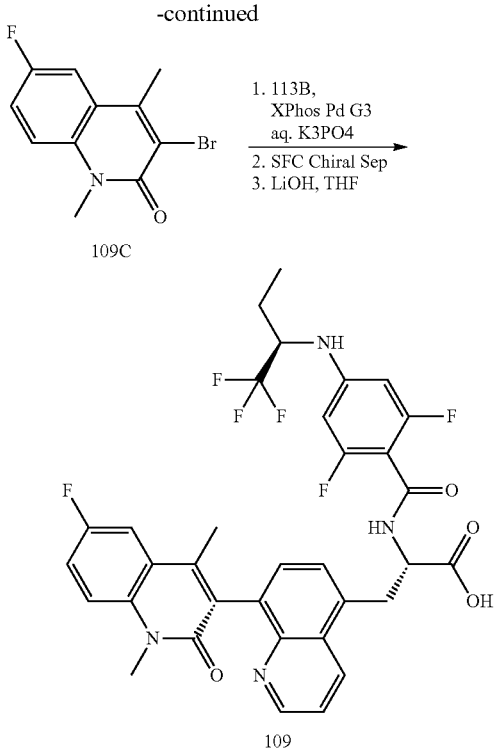

Synthesis of N-(4-fluorophenyl)-N-methyl-3-oxobutanamide (109A): To a solution of 4-fluoro-N-methylaniline (0.500 g, 4.00 mmol) in toluene (4.0 mL) at 110° C. in an open vial (to evaporate off acetone-byproduct) was added 2,2,6-trimethyl-4H-1,3-dioxin-4-one (0.568 g, 4.00 mmol) and the mixture was heated at 110° C. for 3 h. Upon completion, the solvent was evaporated off under reduced pressure. The material was purified by flash chromatography using EA in hexanes to afford the product (mixture of keto and enol form).

Synthesis of 6-fluoro-1,4-dimethylquinolin-2(1H)-one (109B): A mixture of 109A (0.250 g, 1.20 mmol) and concentrated H$_2$SO$_4$ (5.53 g, 56.4 mmol) was heated at 95° C. for 2 h. Upon completion, the reaction mixture was poured over ice. The precipitate was filtered off to afford the product that was used without further purification.

Synthesis of 6-fluoro-1,4-dimethylquinolin-2(1H)-one (109C): To a microwave vial was added 109B (0.210 g, 1.10 mmol), NBS (0.489 g, 2.75 mmol) and CH$_3$CN (11 mL), and the mixture was heated at 100° C. for 1 h. The precipitate was filtered off to afford the title compound and used without further purification.

(S)-2-(2,6-difluoro-4-(((R)-1,1,1-trifluorobutan-2-yl) amino)benzamido)-3-(6-fluoro-1,4-dimethyl-2-oxo-1,2-dihydro-[3,8'-biquinolin]-5'-yl)propanoic acid (109): The title compound was prepared according to the method presented for the synthesis of compound 113 starting with 109C. MS (m/z) 671.2 [M+H]+. 1H NMR (400 MHz, DMSO-d6) δ 8.82 (dd, J=9.8, 6.2 Hz, 3H), 7.80-7.49 (m, 6H), 6.76 (d, J=9.4 Hz, 1H), 6.49-6.38 (m, 2H), 4.72 (ddd, J=10.6, 8.3, 4.2 Hz, 1H), 4.29 (d, J=8.5 Hz, 2H), 3.81 (d, J=4.1 Hz, 3H), 3.65 (d, J=2.6 Hz, 1H), 3.35 (dd, J=14.3, 10.5 Hz, 1H), 2.06 (d, J=9.3 Hz, 3H), 1.75 (ddd, J=13.8, 7.4, 3.3 Hz, 1H), 1.51 (ddd, J=13.7, 10.4, 7.0 Hz, 1H), 0.91 (t, J=7.3 Hz, 3H).

Example 110

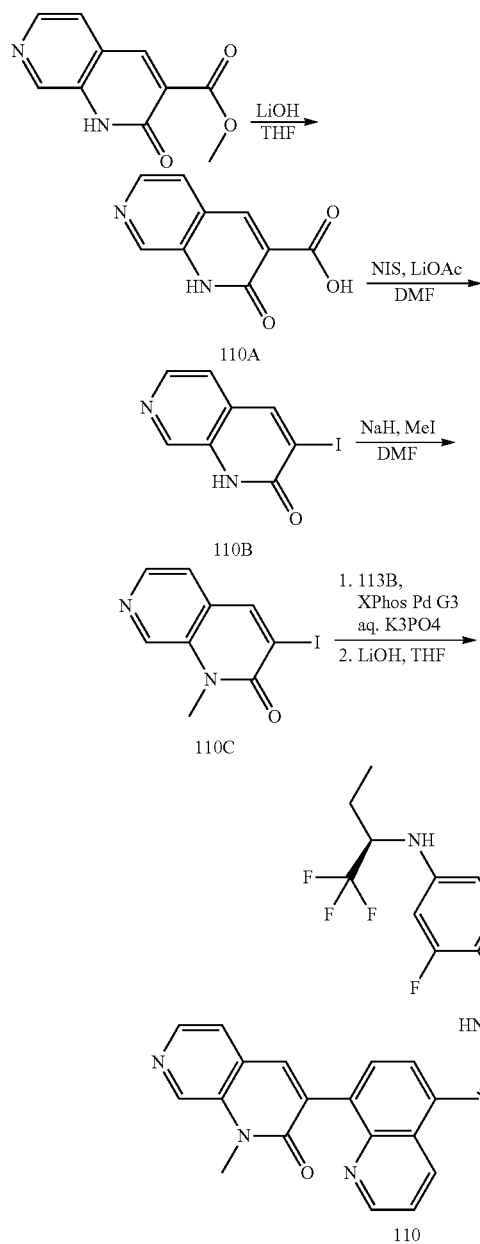

Synthesis of 2-oxo-1,2-dihydro-1,7-naphthyridine-3-carboxylic acid (110A): To a suspension of methyl 2-oxo-1,2-dihydro-1,7-naphthyridine-3-carboxylate (0.109 g, 0.534 mmol) in THF/H₂O (1:1/0.76 mL) was added LiOH (64.0 mg, 2.67 mmol), and the mixture was heated at 65° C. for 3 h. The precipitate was filtered off to afford the title compound and used without further purification.

Synthesis of 2-oxo-1,2-dihydro-1,7-naphthyridine-3-carboxylic acid (110B): To a microwave vial was added 110A (0.200 g, 1.05 mmol), NIS (0.828 g, 3.68 mmol), LiOAc (0.104 g, 1.58 mmol) and a mixture of DMF/water (9:1, 12 mL). The reaction mixture was then stirred under microwave heating at 120° C. for 1 h. The solvent was removed under reduced pressure and the material was used without further purification.

Synthesis of 2-oxo-1,2-dihydro-1,7-naphthyridine-3-carboxylic acid (110C): To a solution of 110B (0.275 g, 1.01 mmol) in DMF (5 mL) at 0° C. was added NaH (32.0 mg, 1.00 mmol). The mixture was stirred for 5 min at 0° C., followed by the addition of iodomethane (0.187 g, 1.31 mmol). The cold bath was removed, and the mixture was stirred for 45 min at RT. Upon completion, the solvent was removed under reduced pressure and the material was purified by flash chromatography using MeOH in DCM (0-25%) to afford the title compound.

(S)-2-(2,6-difluoro-4-(((R)-1,1,1-trifluorobutan-2-yl)amino)benzamido)-3-(8-(1-methyl-2-oxo-1,2-dihydro-1,7-naphthyridin-3-yl)quinolin-5-yl)propanoic acid (110): The title compound was prepared according to the method presented for the synthesis of compound 113 starting with 110C. MS (m/z) 640.2 [M+H]+. 1H NMR (400 MHz, DMSO-d6) δ 9.01 (s, 1H), 8.87-8.79 (m, 2H), 8.65 (s, 1H), 8.49 (d, J=5.1 Hz, 1H), 8.01 (s, 1H), 7.77-7.68 (m, 2H), 7.65-7.57 (m, 2H), 6.78 (d, J=9.4 Hz, 1H), 6.50-6.42 (m, 2H), 4.72-4.64 (m, 1H), 4.36-4.25 (m, 1H), 3.77 (s, 5H), 3.75-3.69 (m, 8H), 3.43 (dd, J=13.8, 9.4 Hz, 3H), 1.83-1.73 (m, 1H), 1.60-1.47 (m, 1H), 0.93 (t, J=7.4 Hz, 3H).

Example 111

Synthesis of 2-oxo-1,2-dihydro-1,7-naphthyridine-3-carboxylic acid (111A): To a suspension of methyl 2-oxo-4-(trifluoromethyl)-1,2-dihydro-1,7-naphthyridine-3-carboxylate (0.109 g, 0.534 mmol) in THF/H₂O (1:1/0.76 mL) was added LiOH (64.0 mg, 2.67 mmol), and the mixture was heated at 65° C. for 3 h. The precipitate was filtered off to afford the title compound and used without further purification.

Synthesis of 2-oxo-1,2-dihydro-1,7-naphthyridine-3-carboxylic acid (111B): To a microwave vial was added 111A (0.200 g, 1.05 mmol), NIS (0.828 g, 3.68 mmol), LiOAc (0.104 g, 1.58 mmol) and a mixture of DMF/water (9:1, 12 mL). The reaction mixture was then stirred under microwave heating at 120° C. for 1 h. The solvent was removed under reduced pressure and the material was used without further purification.

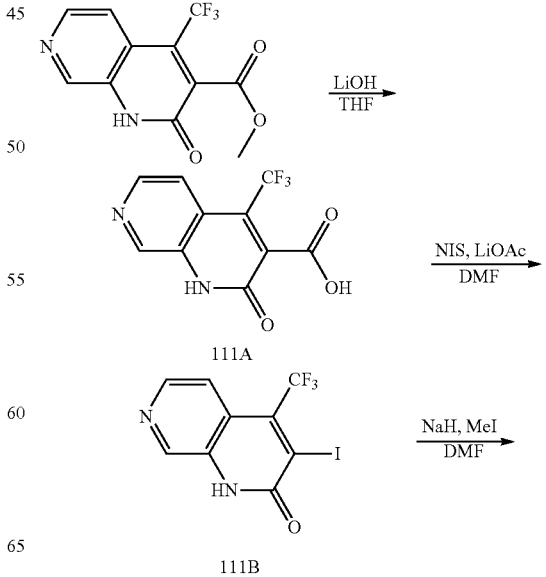

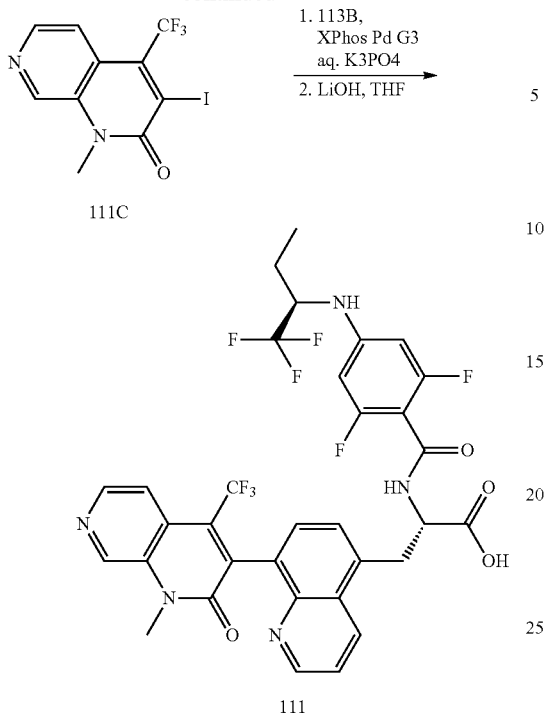

Synthesis of 2-oxo-1,2-dihydro-1,7-naphthyridine-3-carboxylic acid (111C): To a solution of 111B (0.275 g, 1.01 mmol) in DMF (5 mL) at 0° C. was added NaH (32.0 mg, 1.00 mmol). The mixture was stirred for 5 min at 0° C., followed by the addition of iodomethane (0.187 g, 1.31 mmol). The cold bath was removed, and the mixture was stirred for 45 min at RT. Upon completion, the solvent was removed under reduced pressure and the material was purified by flash chromatography using MeOH in DCM (0-25%) to afford the title compound.

(S)-2-(2,6-difluoro-4-(((R)-1,1,1-trifluorobutan-2-yl)amino)benzamido)-3-(8-(1-methyl-2-oxo-4-(trifluoromethyl)-1,2-dihydro-1,7-naphthyridin-3-yl)quinolin-5-yl)propanoic acid (111): The title compound was prepared according to the method presented for the synthesis of compound 113 starting with 111C. MS (m/z) 708.1 [M+H]+. 1H NMR (400 MHz, DMSO-d6) δ 9.15 (d, J=2.2 Hz, 1H), 8.86-8.75 (m, 2H), 8.61 (t, J=8.8 Hz, 2H), 7.76 (d, J=5.2 Hz, 1H), 7.60 (ddd, J=18.7, 8.8, 5.3 Hz, 3H), 7.24 (dd, J=36.0, 7.8 Hz, 1H), 6.76 (t, J=7.4 Hz, 1H), 6.57-6.36 (m, 2H), 4.70 (s, 1H), 4.32 (s, 1H), 3.79 (s, 3H), 3.77-3.61 (m, 1H), 2.89 (d, J=2.2 Hz, 1H), 2.81-2.65 (m, 1H), 1.77 (dd, J=14.3, 7.2 Hz, 1H), 1.61-1.44 (m, 1H), 1.24 (s, 1H), 0.93 (t, J=7.4 Hz, 3H).

Example 112

Synthesis of 2-oxo-1,2-dihydro-1,6-naphthyridine-3-carboxylic acid (112A): To a stirred solution of 4-aminonicotinaldehyde (0.15 g, 1.2 mmol) in EtOH (2 mL) was added Meldrum's acid (0.17 g, 1.2 mmol), piperidine (10 µL, 0.13 mmol), and acetic acid (20 µL, 0.36 mmol). The reaction mixture was stirred at RT for 20 min and then heated at 100° C. for 2 h. After cooling to RT, the product was filtered, washed with EtOH, and dried in vacuo to give the title compound.

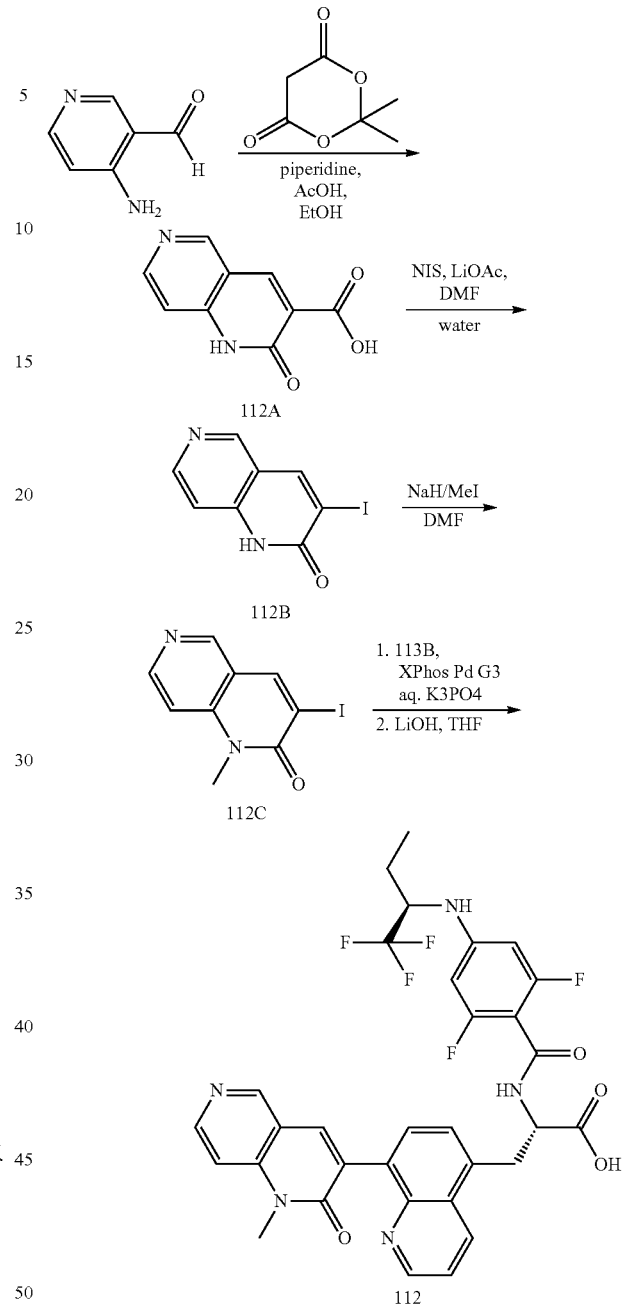

Synthesis of 3-iodo-1,6-naphthyridin-2(1H)-one (112B): In a microwave vial (10 mL) that contained a solution of compound 112A (80 mg, 0.42 mmol) in a mixture of DMF/water (9:1, 5 mL) were added NIS (331 mg, 1.47 mmol) and LiOAc (42 mg, 0.63 mmol). The vial was sealed and then heated under microwave heating at 120° C. for 30 min. After cooling, water was added, and the mixture was extracted with DCM. The organic layer was washed with brine, dried with Na₂SO₄, filtered, and concentrated under reduced pressure to give the title compound which was used without further purification.

Synthesis of 3-iodo-1-methyl-1,6-naphthyridin-2-one (112C): To a stirred solution of compound 112B (114 mg, 0.42 mmol) in DMF (4 mL) at 0° C. was added sodium hydride (60%, 20 mg, 0.5 mmol) and the mixture was stirred for 10 min at 0° C., followed by the addition of MeI (31 µL, 0.5 mmol). Ice bath was removed, and the reaction mixture was stirred at RT for 30 minutes. EA and water was added to the reaction mixture. The organic layer was washed with brine, dried over anhydrous Na$_2$SO$_4$, and concentrated under reduced pressure. The material was purified by silica gel chromatography using MeOH in DCM as eluent to afford the title compound.

(S)-2-(2,6-difluoro-4-(((R)-1,1,1-trifluorobutan-2-yl)amino)benzamido)-3-(8-(1-methyl-2-oxo-1,2-dihydro-1,6-naphthyridin-3-yl)quinolin-5-yl)propanoic acid (112): The title compound was prepared according to the method presented for the synthesis of compound 113 starting with 112C. MS (m/z) 640.3 [M+H]+. 1H NMR (400 MHz, DMSO-d6) δ 9.16 (s, 1H), 8.87-8.81 (m, 2H), 8.79 (d, J=6.6 Hz, 1H), 8.67 (d, J=8.6 Hz, 1H), 8.19 (s, 1H), 7.87 (d, J=6.6 Hz, 1H), 7.72 (d, J=7.3 Hz, 1H), 7.67 (dd, J=8.6, 4.2 Hz, 1H), 7.63 (d, J=7.4 Hz, 1H), 6.78 (d, J=9.4 Hz, 1H), 6.46 (d, J=11.6 Hz, 2H), 4.76-4.61 (m, 1H), 4.31 (d, J=8.8 Hz, 1H), 3.76 (d, J=4.6 Hz, 1H), 3.73 (s, 3H), 3.43 (dd, J=14.5, 9.9 Hz, 1H), 1.78 (ddd, J=13.7, 7.2, 3.2 Hz, 1H), 1.61-1.50 (m, 1H), 0.93 (t, J=7.3 Hz, 3H).

Example 113

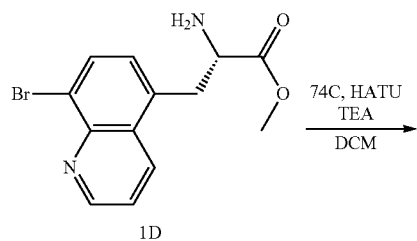

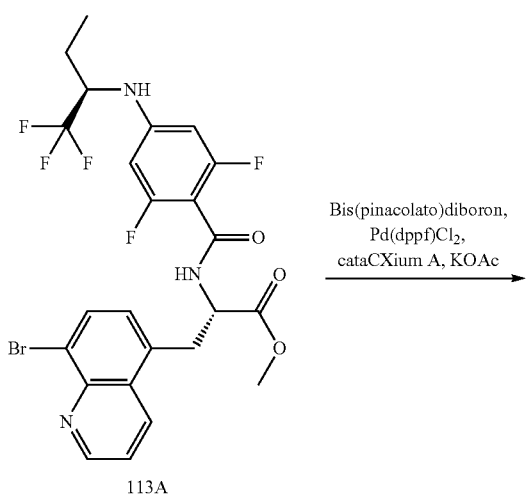

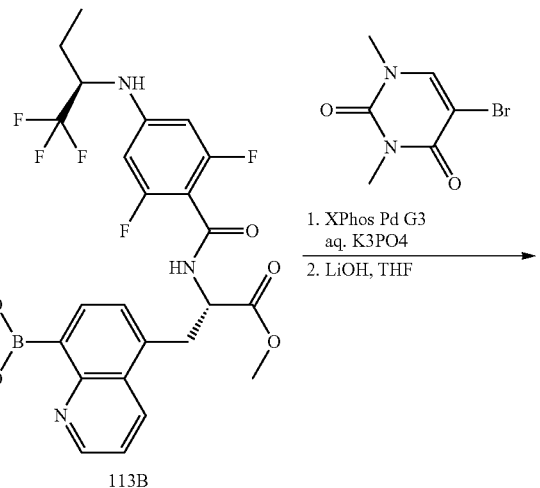

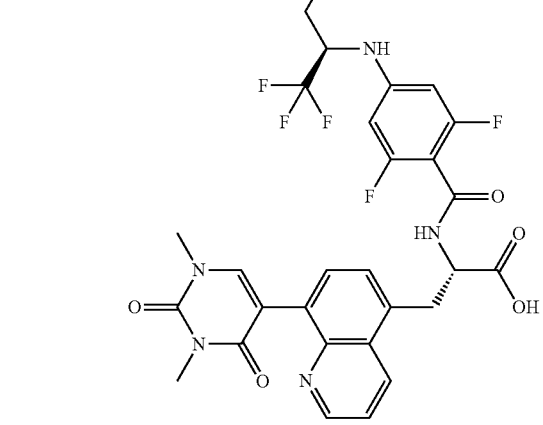

Synthesis of methyl (S)-3-(8-bromoquinolin-5-yl)-2-(2,6-difluoro-4-((R)-3-(trifluoro methyl)morpholino)benzamido)propanoate (113A): The title compound was prepared according to the method presented for the synthesis of compound 16A in Example 16 starting with 74C.

Synthesis of (5-((S)-2-(2,6-difluoro-4-((R)-3-(trifluoromethyl)morpholino)benzamido)-3-methoxy-3-oxopropyl)quinolin-8-yl)boronic acid (113B): The title compound was prepared according to the method presented for the synthesis of compound 4B starting with 113A.

(S)-2-(2,6-difluoro-4-(((R)-1,1,1-trifluorobutan-2-yl)amino)benzamido)-3-(8-(1,3-dimethyl-2,4-dioxo-1,2,3,4-tetrahydropyrimidin-5-yl)quinolin-5-yl)propanoic acid (113): The title compound was prepared according to the method presented for the synthesis of compound 11A and 11 starting with 113B and 5-bromo-1,3-dimethylpyrimidine-2,4(1H,3H)-dione. MS (m/z) 620.2 [M+H]+. 1H NMR (400 MHz, DMSO-d6) δ 8.98-8.83 (m, 1H), 8.78 (dd, J=15.0, 8.3 Hz, 2H), 7.92 (s, 1H), 7.79-7.64 (m, 2H), 7.60 (d, J=7.4 Hz, 1H), 6.84-6.69 (m, 1H), 6.43 (d, J=11.6 Hz, 2H), 4.63 (td, J=9.3, 4.5 Hz, 1H), 4.30 (d, J=10.0 Hz, 1H), 3.70 (dd, J=14.4, 4.5 Hz, 1H), 3.39 (s, 4H), 3.24 (s, 3H), 1.75 (ddt, J=15.0, 7.7, 3.9 Hz, 1H), 1.51 (ddt, J=17.8, 14.5, 7.3 Hz, 1H), 0.91 (t, J=7.3 Hz, 3H).

Example 114

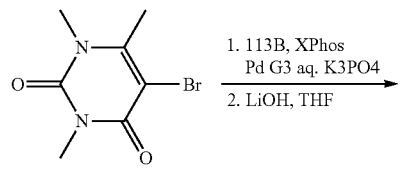

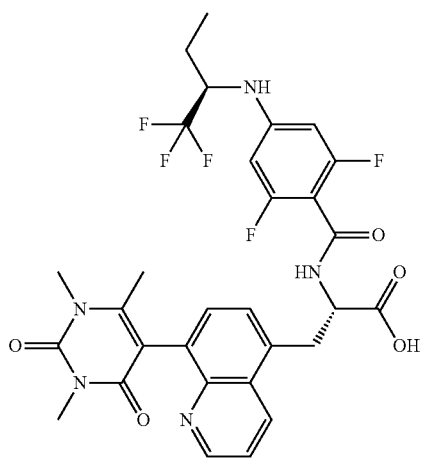

114

(S)-2-(2,6-difluoro-4-(((R)-1,1,1-trifluorobutan-2-yl)amino)benzamido)-3-(8-(1,3,6-trimethyl-2,4-dioxo-1,2,3,4-tetrahydropyrimidin-5-yl)quinolin-5-yl)propanoic acid (114): The title compound was prepared according to the method presented for the synthesis of compound 11A and 11 starting with 113B and 5-bromo-1,3,6-trimethylpyrimidine-2,4(1H,3H)-dione. MS (m/z) 634.2 [M+H]+. 1H NMR (400 MHz, DMSO-d6) δ 8.91 (d, J=4.3 Hz, 1H), 8.78 (dd, J=8.0, 2.3 Hz, 1H), 7.76-7.44 (m, 3H), 6.78-6.67 (m, 1H), 6.41 (dd, J=11.3, 3.5 Hz, 2H), 4.73-4.57 (m, 1H), 4.29 (s, 1H), 3.72 (ddd, J=56.2, 14.3, 4.5 Hz, 1H), 3.45 (d, J=1.6 Hz, 4H), 3.21 (d, J=2.4 Hz, 3H), 1.92 (d, J=10.1 Hz, 3H), 1.75 (ddd, J=13.6, 7.3, 3.2 Hz, 1H), 1.50 (ddd, J=13.7, 10.3, 7.0 Hz, 1H), 0.90 (t, J=7.3 Hz, 3H).

Example 115

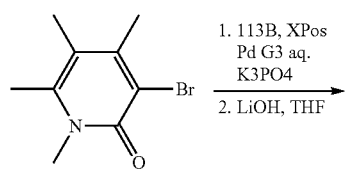

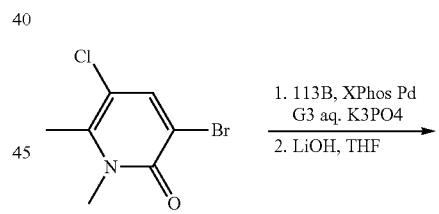

115

(S)-2-(2,6-difluoro-4-(((R)-1,1,1-trifluorobutan-2-yl)amino)benzamido)-3-(8-(1,4,5,6-tetramethyl-2-oxo-1,2-dihydropyridin-3-yl)quinolin-5-yl)propanoic acid (115): The title compound was prepared according to the method presented for the synthesis of compound 11A and 11 starting with 113B and 3-bromo-1,4,5,6-tetramethylpyridin-2(1H)-one. MS (m/z) 631.2 [M+H]+. 1H NMR (400 MHz, DMSO-d6) δ 8.91-8.86 (m, 1H), 8.79 (dd, J=7.8, 3.0 Hz, 1H), 7.80-7.71 (m, 1H), 7.66 (dd, J=11.8, 7.3 Hz, 1H), 7.50 (t, J=7.8 Hz, 1H), 6.76 (dd, J=9.2, 4.4 Hz, 1H), 6.47-6.39 (m, 2H), 4.77-4.66 (m, 1H), 4.36-4.25 (m, 1H), 3.71-3.64 (m, 2H), 3.53 (s, 1H), 3.49 (s, 3H), 3.37 (dd, J=13.8, 10.2 Hz, 1H), 2.43 (s, 3H), 2.32 (s, 1H), 2.09 (d, J=6.8 Hz, 3H), 1.75 (d, J=10.8 Hz, 3H), 1.58-1.47 (m, 1H), 0.92 (t, J=7.3 Hz, 3H).

Example 116

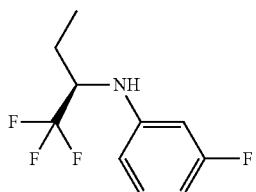

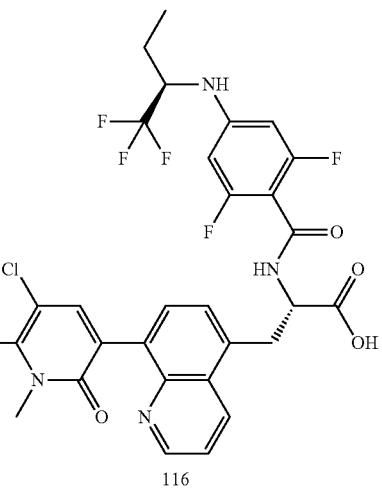

116

(S)-3-(8-(5-chloro-1,6-dimethyl-2-oxo-1,2-dihydropyridin-3-yl)quinolin-5-yl)-2-(2,6-difluoro-4-(((R)-1,1,1-trifluorobutan-2-yl)amino)benzamido)propanoic acid (116): The title compound was prepared according to the method presented for the synthesis of compound 11A and 11 starting with 113B and 3-bromo-5-chloro-1,6-dimethylpyridin-2(1H)-one. MS (m/z) 637.3 [M+H]+. 1H NMR (400 MHz, DMSO-d6) δ 8.96 (dd, J=4.5, 1.5 Hz, 1H), 8.87 (d, J=8.5 Hz, 1H), 8.81 (d, J=8.0 Hz, 1H), 7.82-7.72 (m, 2H), 7.65 (d, J=7.5 Hz, 1H), 7.58 (s, 1H), 6.78 (d, J=9.4 Hz, 1H), 6.45 (d, J=11.7 Hz, 2H), 4.72-4.62 (m, 1H), 4.37-4.23 (m, 1H), 3.74 (dd, J=14.5, 4.6 Hz, 1H), 3.56 (s, 3H), 3.44 (dd, J=14.5, 9.8 Hz, 1H), 2.58 (s, 3H), 1.84-1.70 (m, 1H), 1.60-1.45 (m, 1H), 0.93 (t, J=7.3 Hz, 3H).

Example 117

(S)-2-(2,6-difluoro-4-(((R)-1,1,1-trifluorobutan-2-yl)amino)benzamido)-3-(8-(4,5,6-trimethyl-3-oxo-3,4-dihydropyrazin-2-yl)quinolin-5-yl)propanoic acid (117): The title compound was prepared according to the method presented for the synthesis of compound 11A and 11 starting with 113B and 3-chloro-1,5,6-trimethylpyrazin-2(1H)-one. MS (m/z) 618.2 [M+H]+. 1H NMR (400 MHz, DMSO-d6) δ 8.91 (d, J=4.4 Hz, 1H), 8.80 (d, J=7.9 Hz, 2H), 7.84-7.69 (m, 2H), 7.64 (d, J=7.4 Hz, 1H), 6.78 (d, J=9.4 Hz, 1H), 6.45 (d, J=11.6 Hz, 2H), 4.68 (dt, J=8.6, 4.1 Hz, 1H), 4.36-4.29 (m, 1H), 3.73 (dd, J=14.4, 4.6 Hz, 1H), 3.53 (s, 3H), 3.45 (dd, J=14.4, 9.7 Hz, 1H), 2.42 (s, 3H), 2.34 (s, 3H), 1.77 (ddd, J=13.8, 7.2, 3.3 Hz, 1H), 1.57-1.47 (m, 1H), 0.93 (t, J=7.3 Hz, 3H).

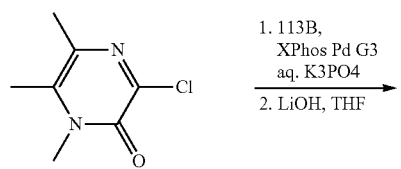

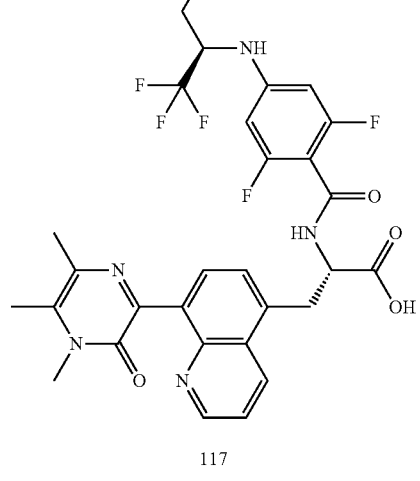

117

Example 118

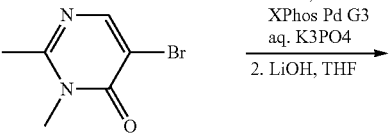

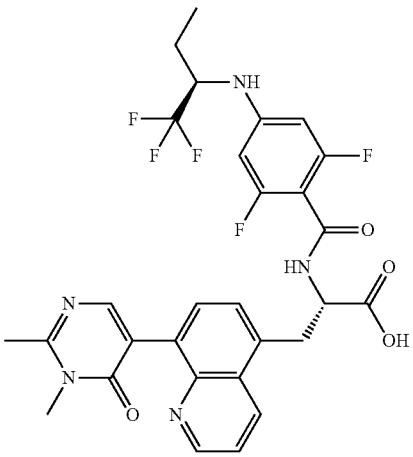

118

(S)-2-(2,6-difluoro-4-(((R)-1,1,1-trifluorobutan-2-yl)amino)benzamido)-3-(8-(1,2-dimethyl-6-oxo-1,6-dihydropyrimidin-5-yl)quinolin-5-yl)propanoic acid (118): The title compound was prepared according to the method presented for the synthesis of compound 11A and 11 starting with 113B and 5-bromo-2,3-dimethylpyrimidin-4(3H)-one. MS (m/z) 604.2 [M+H]+. 1H NMR (400 MHz, DMSO-d6) δ 8.89 (dd, J=4.3, 1.5 Hz, 1H), 8.80 (d, J=7.9 Hz, 1H), 8.70 (d, J=8.6 Hz, 1H), 7.95 (s, 1H), 7.68 (dd, J=7.9, 3.9 Hz, 2H), 7.59 (d, J=7.4 Hz, 1H), 6.77 (d, J=9.4 Hz, 1H), 6.44 (d, J=11.5 Hz, 2H), 4.70-4.55 (m, 1H), 4.30 (s, 1H), 3.70 (dd, J=14.4, 4.6 Hz, 1H), 3.53 (s, 3H), 3.41 (dd, J=14.5, 9.8 Hz, 1H), 2.62 (s, 3H), 1.77 (ddd, J=13.7, 7.3, 3.2 Hz, 1H), 1.52 (ddd, J=13.7, 10.4, 7.2 Hz, 1H), 0.92 (t, J=7.3 Hz, 3H).

Example 119

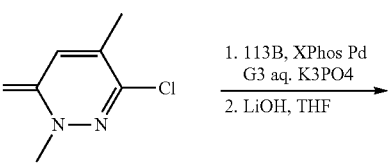

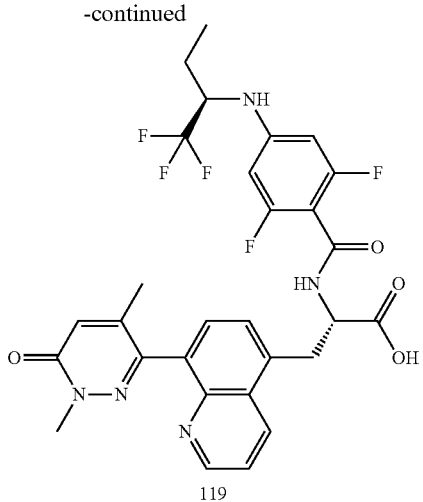

(S)-2-(2,6-difluoro-4-(((R)-1,1,1-trifluorobutan-2-yl)amino)benzamido)-3-(8-(1,4-dimethyl-6-oxo-1,6-dihydropyridazin-3-yl)quinolin-5-yl)propanoic acid (119): The title compound was prepared according to the method presented for the synthesis of compound 11A and 11 starting with 113B and 6-chloro-2,5-dimethylpyridazin-3(2H)-one. MS (m/z) 604.2 [M+H]+. 1H NMR (400 MHz, DMSO-d6) δ 8.87 (dd, J=4.2, 1.5 Hz, 1H), 8.76 (d, J=8.1 Hz, 1H), 8.64 (dd, J=8.7, 1.6 Hz, 1H), 7.70-7.56 (m, 3H), 6.86 (d, J=1.4 Hz, 1H), 6.75 (d, J=9.4 Hz, 1H), 6.42 (d, J=11.6 Hz, 2H), 4.67 (t, J=11.3 Hz, 1H), 4.29 (d, J=9.4 Hz, 1H), 3.72 (dd, J=14.3, 4.5 Hz, 1H), 3.64 (s, 3H), 3.39 (dd, J=14.3, 10.1 Hz, 1H), 1.74 (d, J=1.2 Hz, 4H), 1.50 (ddd, J=13.7, 10.4, 7.1 Hz, 1H), 0.90 (t, J=7.3 Hz, 3H).

Example 120

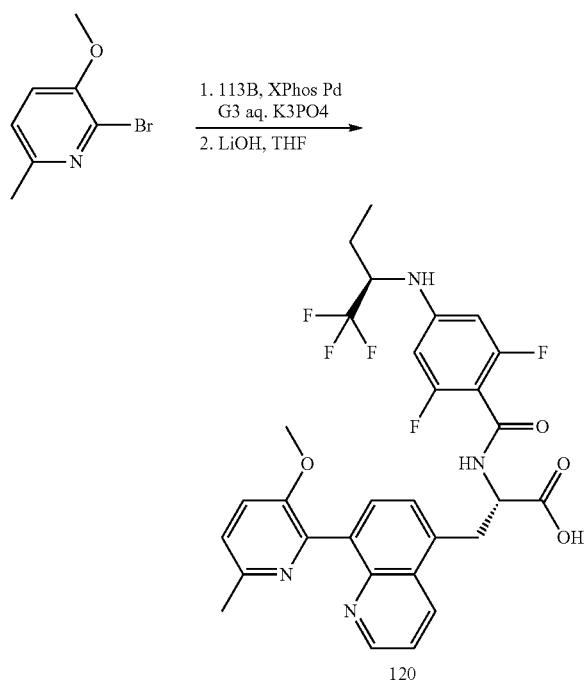

(S)-2-(2,6-difluoro-4-(((R)-1,1,1-trifluorobutan-2-yl)amino)benzamido)-3-(8-(3-methoxy-6-methylpyridin-2-yl)quinolin-5-yl)propanoic acid (120): The title compound was prepared according to the method presented for the synthesis of compound 11A and 11 starting with 113B and 2-bromo-3-methoxy-6-methylpyridine. MS (m/z) 603.2 [M+H]+. 1H NMR (400 MHz, DMSO-d6) δ 8.88 (dd, J=11.7, 5.9 Hz, 2H), 8.74 (d, J=8.6 Hz, 1H), 8.16 (s, 1H), 7.85 (d, J=24.9 Hz, 2H), 7.71 (d, J=7.1 Hz, 2H), 6.79 (d, J=9.4 Hz, 1H), 6.46 (d, J=12.0 Hz, 2H), 4.70 (s, 1H), 4.31 (d, J=10.1 Hz, 1H), 3.79 (s, 4H), 3.50-3.41 (m, 1H), 2.62 (s, 3H), 1.77 (s, 1H), 1.54 (dd, J=15.7, 7.7 Hz, 1H), 0.93 (t, J=7.0 Hz, 3H).

Example 121

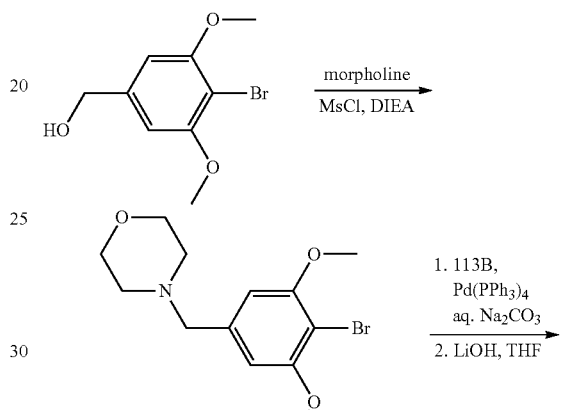

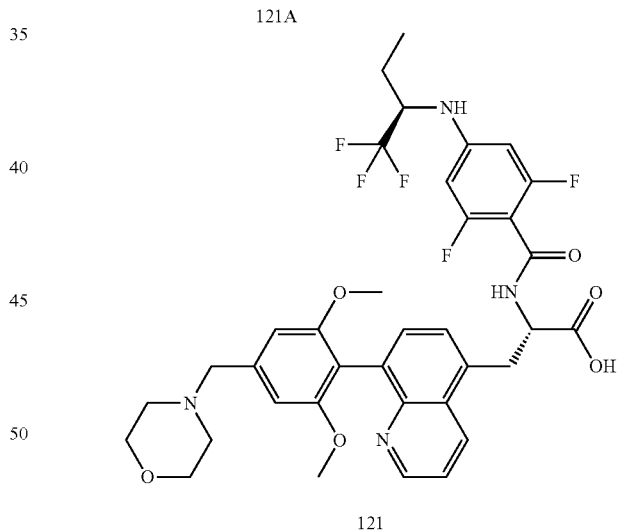

Synthesis of 4-(4-bromo-3,5-dimethoxybenzyl)morpholine (121A): To a stirred solution of (4-bromo-3,5-dimethoxyphenyl)methanol (300 mg, 1.214 mmol) in DCM (3 mL) was added N,N-diisopropylethyl amine (0.306 mL, 2.428 mmol). Methanesulfonyl chloride (0.094 mL, 1.214 mmol) was added dropwise and the reaction mixture was allowed to stir at RT for 5 min. Morpholine (0.134 mL, 3.642 mmol) was added dropwise and the reaction mixture was allowed to stir at RT for 14 hrs. The reaction mixture was concentrated under reduced pressure, dissolved in toluene (2 mL) and again concentrated under reduced pressure to afford the title compound without further purification.

(S)-2-(2,6-difluoro-4-(((R)-1,1,1-trifluorobutan-2-yl)amino)benzamido)-3-(8-(2,6-dimethoxy-4-(morpholinomethyl)phenyl)quinolin-5-yl)propanoic acid (121): The title compound was prepared according to the method presented for the synthesis of compound 5B and 5 starting with 113B and 121A. MS (m/z) 717.3 [M+H]+. 1H NMR (400 MHz, DMSO-d6) δ 12.93 (s, 1H), 10.01 (s, 1H), 8.84 (d, J=7.9 Hz, 1H), 8.75 (dd, J=4.2, 1.6 Hz, 1H), 8.60 (d, J=8.5 Hz, 1H), 7.57 (dd, J=16.9, 8.0 Hz, 2H), 7.40 (d, J=7.3 Hz, 1H), 6.91 (q, J=1.3 Hz, 2H), 6.78 (d, J=9.4 Hz, 1H), 6.44 (d, J=11.5 Hz, 2H), 4.66 (td, J=8.8, 8.1, 4.3 Hz, 1H), 4.39 (s, 2H), 4.30 (d, J=9.5 Hz, 1H), 4.02 (d, J=12.6 Hz, 2H), 3.70 (t, J=12.1 Hz, 5H), 3.58 (d, J=5.6 Hz, 6H), 3.38 (dd, J=14.2, 10.2 Hz, 3H), 3.19 (d, J=10.8 Hz, 3H), 1.76 (ddt, J=10.7, 7.3, 3.1 Hz, 1H), 1.51 (ddt, J=17.5, 14.2, 7.3 Hz, 1H), 0.91 (t, J=7.3 Hz, 3H).

Example 122

Synthesis of methyl (S)-2-amino-3-(4-methoxy-1-methyl-2-oxo-1,2-dihydro-[3,8'-biquinolin]-5'-yl)propanoate (122A): The title compound was prepared according to the method presented for the synthesis of compound 91C and 91D starting with 3-bromo-4-methoxy-1-methylquinolin-2(1H)-one.

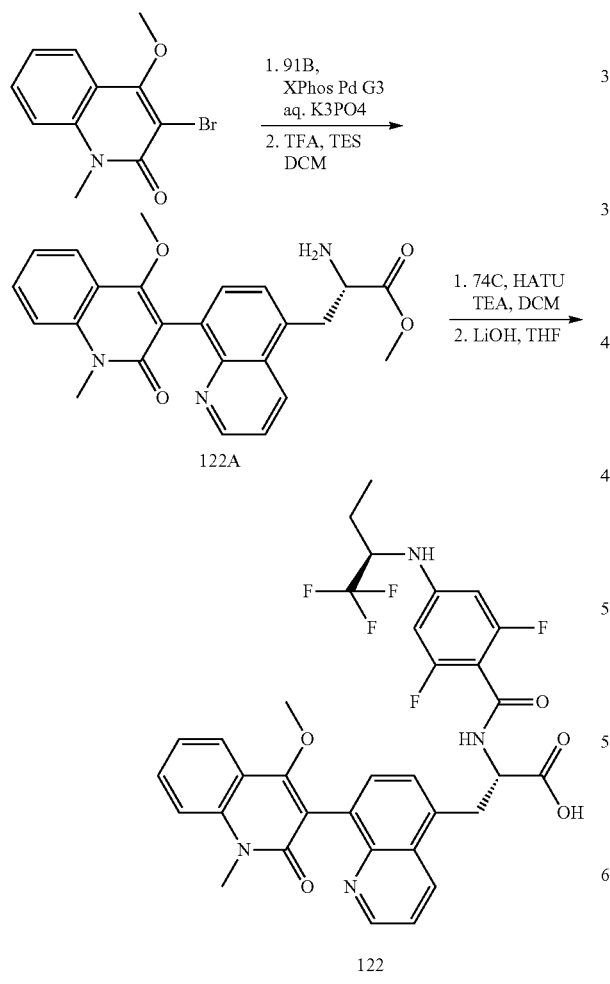

122A

122

(S)-2-(2,6-difluoro-4-(((R)-1,1,1-trifluorobutan-2-yl)amino)benzamido)-3-(4-methoxy-1-methyl-2-oxo-1,2-dihydro-[3,8'-biquinolin]-5'-yl)propanoic acid (122): The title compound was prepared according to the method presented for the synthesis of compound 74 starting with 122A. MS (m/z) 669.3 [M+H]+. 1H NMR (400 MHz, DMSO-d6) δ 8.95 (d, J=5.1 Hz, 2H), 8.81 (dd, J=8.2, 2.6 Hz, 1H), 7.97 (dt, J=8.0, 1.9 Hz, 1H), 7.89-7.66 (m, 4H), 7.68-7.59 (m, 1H), 7.42-7.32 (m, 1H), 6.77 (d, J=9.4 Hz, 1H), 6.44 (dd, J=11.5, 8.0 Hz, 2H), 4.80-4.69 (m, 1H), 4.37-4.22 (m, 1H), 3.76-3.52 (m, 4H), 3.30 (d, J=2.1 Hz, 3H), 1.84-1.70 (m, 1H), 1.61-1.44 (m, 1H), 0.92 (td, J=7.4, 2.4 Hz, 3H).

Example 123

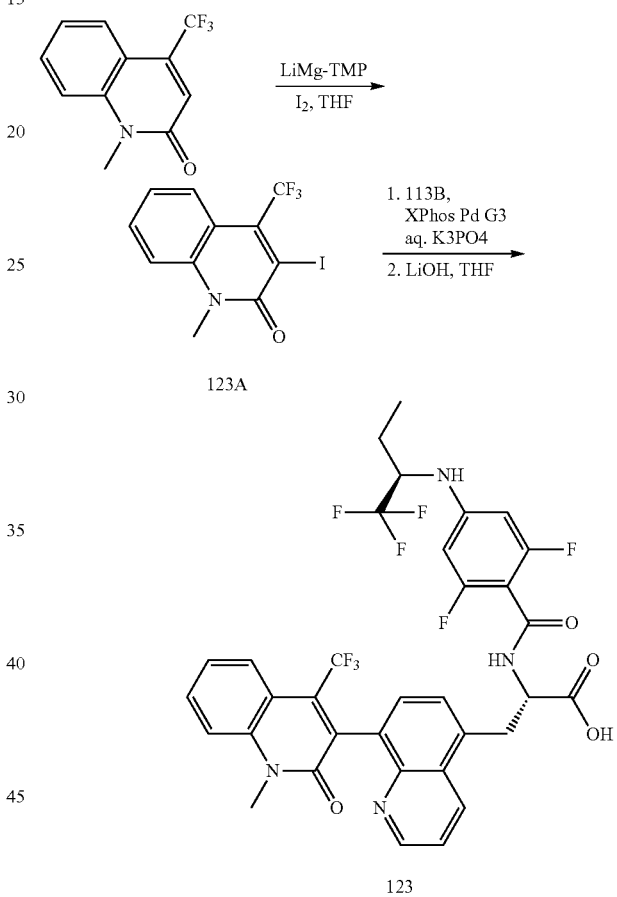

123A

123

Synthesis of 3-iodo-1-methyl-4-(trifluoromethyl)quinolin-2(1H)-one (123A): To a stirred solution of 1-methyl-4-(trifluoromethyl)quinolin-2(1H)-one (243 mg, 1.07 mmol) in THF was added LiMg-TMP (1.74 mL, 1 M) dropwise at −78° C. The reaction mixture was allowed to stir for 30 min, then a solution of iodine (488 mg, 2 mmol) in THF was then added at −78° C. The reaction mixture was allowed to warm to RT then was concentrated under reduced pressure, and purified by silica gel chromatography using EA/hexanes as the eluent to afford the title compound.

(S)-2-(2,6-difluoro-4-(((R)-1,1,1-trifluorobutan-2-yl)amino)benzamido)-3-(1-methyl-2-oxo-4-(trifluoromethyl)-1,2-dihydro-[3,8'-biquinolin]-5'-yl)propanoic acid (123): The title compound was prepared according to the method presented for the synthesis of compound 11A and 11 starting with 113B and 123A. MS (m/z) 707.2 [M+H]+. 1H NMR (400 MHz, DMSO-d6) δ 8.85-8.77 (m, 2H), 8.65 (d, J=8.6

Hz, 1H), 7.91 (d, J=8.1 Hz, 1H), 7.85-7.72 (m, 2H), 7.67-7.57 (m, 2H), 7.54 (t, J=7.3 Hz, 1H), 7.46 (t, J=7.7 Hz, 1H), 6.76 (dd, J=9.4, 5.6 Hz, 1H), 6.45 (dd, J=11.4, 3.7 Hz, 2H), 4.70 (tt, J=8.8, 4.7 Hz, 1H), 4.39-4.24 (m, 1H), 3.80-3.63 (m, 4H), 3.44 (ddd, J=35.4, 14.5, 9.8 Hz, 1H), 1.85-1.69 (m, 1H), 1.60-1.43 (m, 1H), 0.93 (t, J=7.3 Hz, 3H).

Example 124

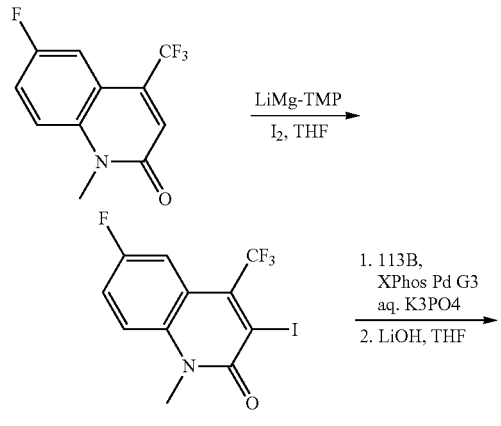

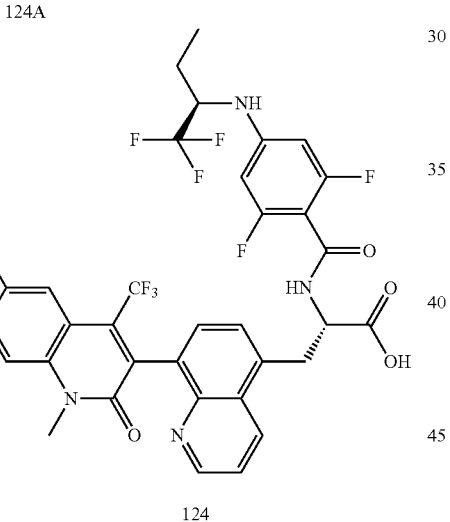

Example 125

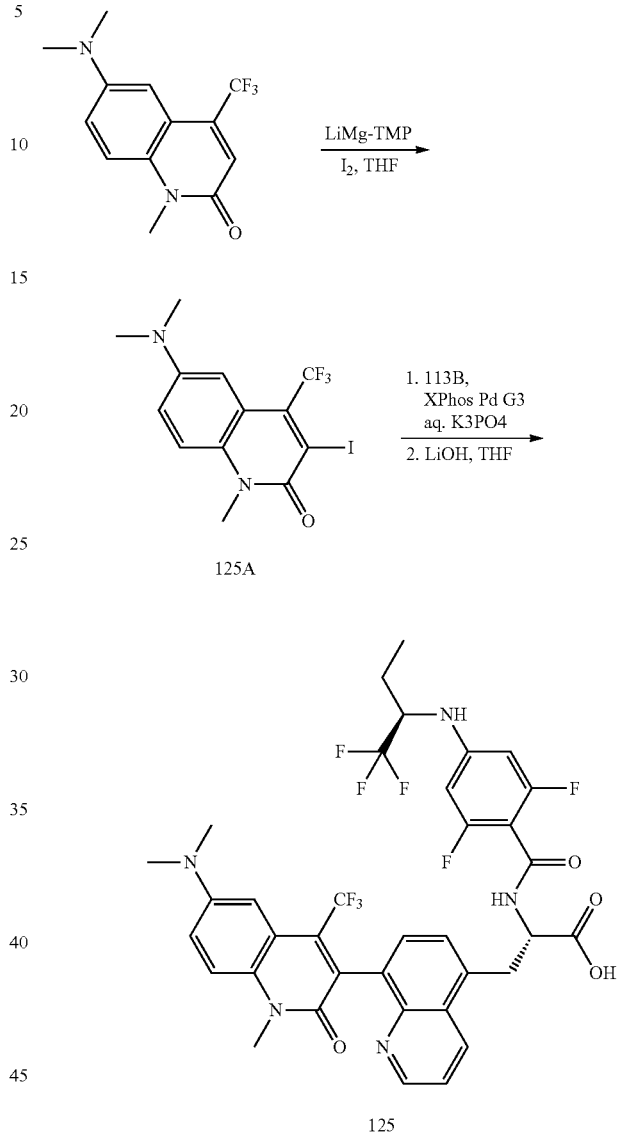

Synthesis of 3-iodo-1-methyl-4-(trifluoromethyl)quinolin-2(1H)-one (124A): The title compound was prepared according to the method presented for the synthesis of compound 123A starting with 6-fluoro-1-methyl-4-(trifluoromethyl)quinolin-2(1H)-one.

(S)-2-(2,6-difluoro-4-(((R)-1,1,1-trifluorobutan-2-yl)amino)benzamido)-3-(1-methyl-2-oxo-4-(trifluoromethyl)-1,2-dihydro-[3,8'-biquinolin]-5'-yl)propanoic acid (124): The title compound was prepared according to the method presented for the synthesis of compound 11A and 11 starting with 113B and 124A. MS (m/z) 724.9 [M+H]+. 1H NMR (400 MHz, DMSO-d6) δ 8.95-8.70 (m, 2H), 8.62 (d, J=8.6 Hz, 1H), 6.75 (dd, J=9.4, 5.6 Hz, 1H), 6.43 (dd, J=11.3, 3.7 Hz, 2H), 4.76-4.62 (m, 1H), 4.28 (s, 2H), 3.69 (d, J=2.0 Hz, 3H), 3.43 (d, J=47.0 Hz, 1H), 1.89-1.69 (m, 1H), 1.51 (dt, J=17.5, 7.4 Hz, 1H), 0.91 (t, J=7.3 Hz, 3H).

Synthesis of 3-iodo-1-methyl-4-(trifluoromethyl)quinolin-2(1H)-one (125A): The title compound was prepared according to the method presented for the synthesis of compound 123A starting with 6-(dimethylamino)-1-methyl-4-(trifluoromethyl)quinolin-2(1H)-one.

(S)-2-(2,6-difluoro-4-(((R)-1,1,1-trifluorobutan-2-yl)amino)benzamido)-3-(6-(dimethyl amino)-1-methyl-2-oxo-4-(trifluoromethyl)-1,2-dihydro-[3,8'-biquinolin]-5'-yl)propanoic acid (125): The title compound was prepared according to the method presented for the synthesis of compound 11A and 11 starting with 113B and 125A. MS (m/z) 724.9 [M+H]+. 1H NMR (400 MHz, DMSO-d6) δ 8.95-8.70 (m, 2H), 8.62 (d, J=8.6 Hz, 1H), 6.75 (dd, J=9.4, 5.6 Hz, 1H), 6.43 (dd, J=11.3, 3.7 Hz, 2H), 4.76-4.62 (m, 1H), 4.28 (s, 2H), 3.69 (d, J=2.0 Hz, 3H), 3.43 (d, J=47.0 Hz, 1H), 1.89-1.69 (m, 1H), 1.51 (dt, J=17.5, 7.4 Hz, 1H), 0.91 (t, J=7.3 Hz, 3H).

Example 126

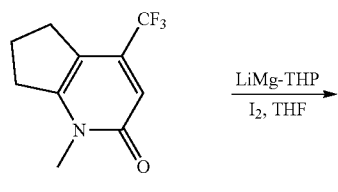

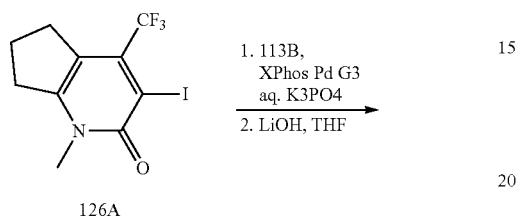

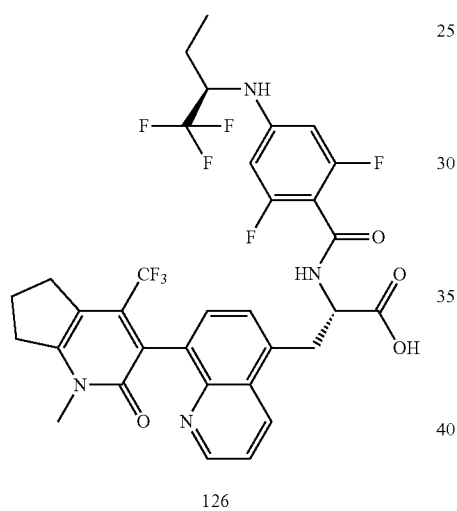

Synthesis of 3-iodo-1-methyl-4-(trifluoromethyl)-1,5,6,7-tetrahydro-2H-cyclopenta [b]pyridin-2-one (126A): The title compound was prepared according to the method presented for the synthesis of compound 123A starting with 1-methyl-4-(trifluoromethyl)-1,5,6,7-tetrahydro-2H-cyclopenta[b]pyridin-2-one.

(S)-2-(2,6-difluoro-4-(((R)-1,1,1-trifluorobutan-2-yl)amino)benzamido)-3-(8-(1-methyl-2-oxo-4-(trifluoromethyl)-2,5,6,7-tetrahydro-1H-cyclopenta[b]pyridin-3-yl)quinolin-5-yl)propanoic acid (126): The title compound was prepared according to the method presented for the synthesis of compound 11A and 11 starting with 113B and 126A. MS (m/z) 697.3 [M+H]+. 1H NMR (400 MHz, DMSO-d6) δ 8.89-8.75 (m, 2H), 8.68 (d, J=8.1 Hz, 1H), 7.65 (dt, J=8.9, 4.9 Hz, 1H), 7.58 (dd, J=7.4, 5.8 Hz, 1H), 7.43 (dd, J=7.3, 5.4 Hz, 1H), 6.76 (dd, J=9.4, 6.4 Hz, 1H), 6.56 (q, J=1.1 Hz, 1H), 6.44 (dd, J=11.4, 4.9 Hz, 2H), 4.77-4.53 (m, 1H), 4.30 (s, 1H), 3.86-3.56 (m, 1H), 3.10 (q, J=7.2, 6.8 Hz, 2H), 2.98 (dt, J=17.6, 7.4 Hz, 3H), 2.85-2.72 (m, 2H), 2.24-1.98 (m, 3H), 1.89-1.67 (m, 1H), 1.53 (ddd, J=13.7, 10.3, 7.0 Hz, 1H), 0.93 (t, J=7.3 Hz, 3H).

Example 127

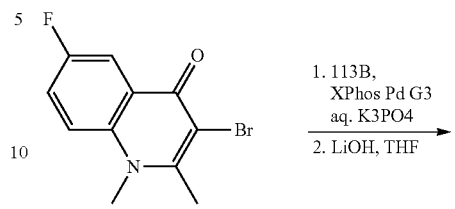

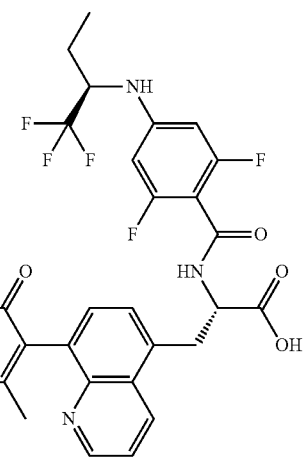

(S)-2-(2,6-difluoro-4-(((R)-1,1,1-trifluorobutan-2-yl)amino)benzamido)-3-(6-fluoro-1,2-dimethyl-4-oxo-1,4-dihydro-[3,8'-biquinolin]-5'-yl)propanoic acid (127): The title compound was prepared according to the method presented for the synthesis of compound 11A and 11 starting with 113B and 3-bromo-6-fluoro-1,2-dimethylquinolin-4(1H)-one. MS (m/z) 671.2 [M+H]+. 1H NMR (400 MHz, DMSO-d6) δ 8.87 (d, J=3.9 Hz, 2H), 8.84-8.78 (m, 1H), 8.01 (dd, J=9.6, 4.4 Hz, 1H), 7.84-7.79 (m, 1H), 7.78-7.65 (m, 3H), 7.60 (dd, J=12.7, 8.4 Hz, 1H), 6.76 (dd, J=10.0, 2.5 Hz, 1H), 6.44 (d, J=13.0 Hz, 2H), 4.78-4.68 (m, 1H), 4.35-4.25 (m, 2H), 3.90-3.88 (m, 3H), 3.84 (dd, J=14.8, 3.8 Hz, 1H), 3.71-3.66 (m, 1H), 3.58-3.51 (m, 1H), 3.38 (dd, J=14.6, 10.5 Hz, 1H), 2.16 (d, J=8.7 Hz, 3H), 1.83-1.71 (m, 1H), 1.59-1.47 (m, 1H), 0.93 (t, J=7.4 Hz, 3H).

Example 128

Synthesis of (R)-2,6-difluoro-4-((1,1,1-trifluoropropan-2-yl)amino)benzoic acid (128A): The title compound was prepared according to the method presented for the synthesis of compound 75A Example 75 starting with (R)-1,1,1-trifluoropropan-2-amine.

Example 129

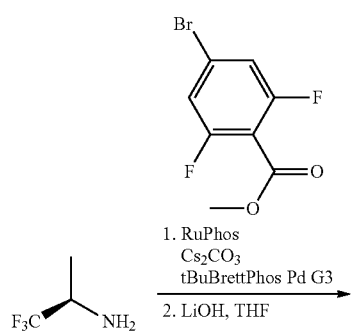

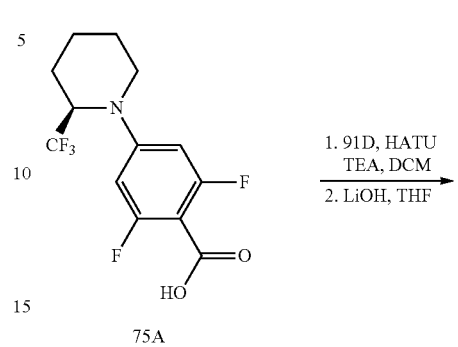

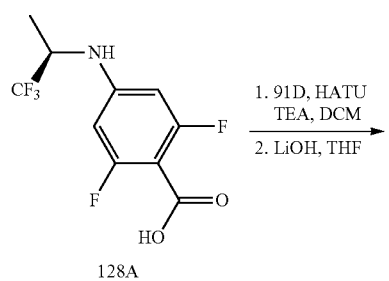

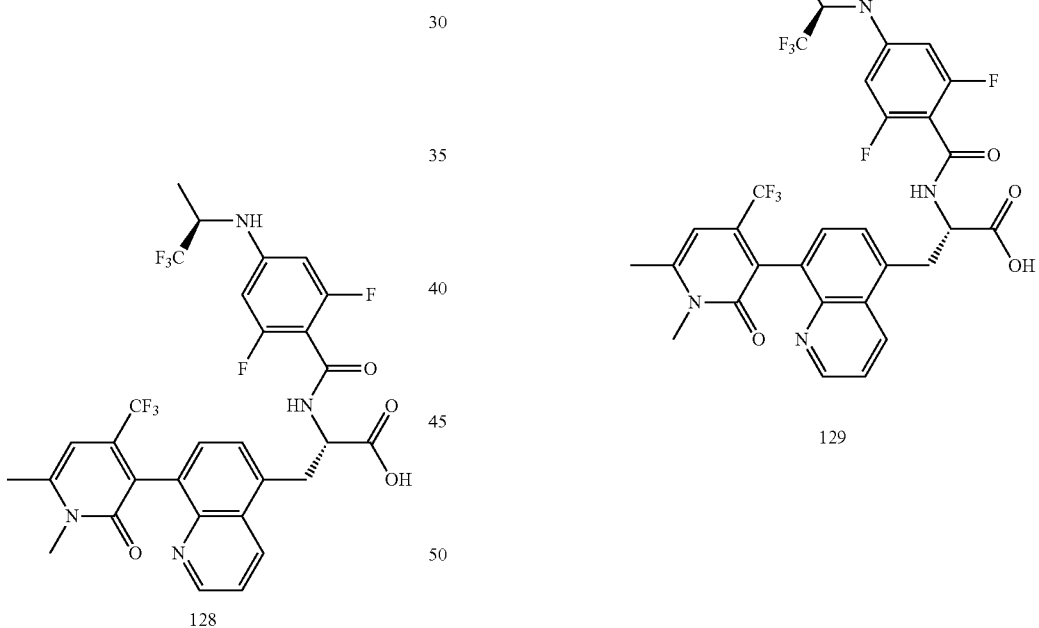

(S)-2-(2,6-difluoro-4-(((R)-1,1,1-trifluoropropan-2-yl)amino)benzamido)-3-(8-(1,6-dimethyl-2-oxo-4-(trifluoromethyl)-1,2-dihydropyridin-3-yl)quinolin-5-yl)propanoic acid (128): The title compound was prepared according to the method presented for the synthesis of compound 16A and 16 starting with 91D and 128A. MS (m/z) 657.2 [M+H]+. 1H NMR (400 MHz, DMSO-d6) δ 8.80 (t, J=6.0 Hz, 2H), 8.60 (d, J=8.7 Hz, 1H), 7.63-7.51 (m, 2H), 7.46-7.33 (m, 1H), 6.88-6.76 (m, 1H), 6.53 (s, 1H), 6.40 (dd, J=11.2, 4.3 Hz, 2H), 4.65 (dt, J=13.4, 4.7 Hz, 1H), 4.50 (dd, J=15.4, 7.7 Hz, 1H), 3.73-3.56 (m, 2H), 3.47 (d, J=2.2 Hz, 4H), 3.16-3.03 (m, 1H), 2.51 (s, 2H), 1.27-1.23 (m, 4H).

(S)-2-(2,6-difluoro-4-((R)-2-(trifluoromethyl)piperidin-1-yl)benzamido)-3-(8-(1,6-dimethyl-2-oxo-4-(trifluoromethyl)-1,2-dihydropyridin-3-yl)quinolin-5-yl)propanoic acid (129): The title compound was prepared according to the method presented for the synthesis of compound 75 starting with 91D. MS (m/z) 697.8 [M+H]+. 1H NMR (400 MHz, DMSO-d6) δ 8.92 (dd, J=7.8, 4.2 Hz, 1H), 8.86 (d, J=4.0 Hz, 1H), 8.73 (d, J=7.7 Hz, 1H), 7.74-7.64 (m, 1H), 7.61 (t, J=7.7 Hz, 1H), 7.48 (dd, J=7.1, 3.7 Hz, 1H), 6.73 (dd, J=11.9, 4.0 Hz, 2H), 6.57 (s, 1H), 5.00-4.87 (m, 1H), 4.77-4.71 (m, 1H), 3.73 (td, J=19.1, 14.5, 4.2 Hz, 1H), 3.66-3.56 (m, 1H), 3.53-3.37 (m, 4H), 3.02 (t, J=12.4 Hz, 1H), 2.54 (s, 3H), 1.97 (d, J=14.5 Hz, 1H), 1.87-1.67 (m, 2H), 1.67-1.43 (m, 3H).

Example 130

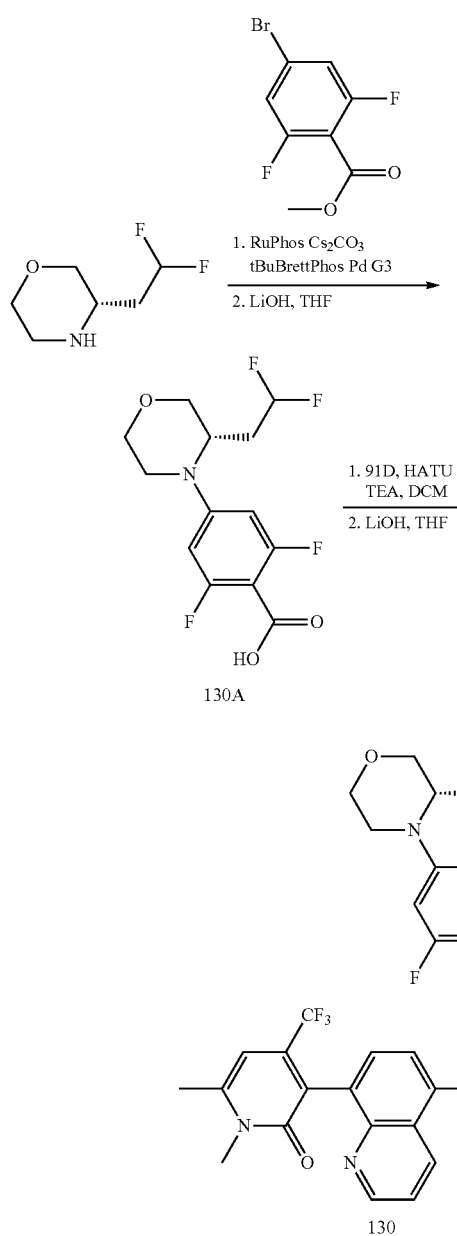

Synthesis of (S)-4-(3-(2,2-difluoroethyl)morpholino)-2,6-difluorobenzoic acid (130A): The title compound was prepared according to the method presented for the synthesis of compound 75A starting with (S)-3-(2,2-difluoroethyl)morpholine.

(S)-2-(4-((S)-3-(2,2-difluoroethyl)morpholino)-2,6-difluorobenzamido)-3-(8-(1,6-dimethyl-2-oxo-4-(trifluoromethyl)-1,2-dihydropyridin-3-yl)quinolin-5-yl)propanoic acid (130): The title compound was prepared according to the method presented for the synthesis of compound 16A and 16 starting with 91D and 130A. MS (m/z) 695.2 [M+H]+. 1H NMR (400 MHz, DMSO-d6) δ 8.85 (d, J=10.4 Hz, 2H), 8.72 (s, 1H), 7.65 (s, 1H), 7.52 (d, J=10.0 Hz, 1H), 6.78 (d, J=9.3 Hz, 1H), 6.46 (d, J=12.0 Hz, 2H), 6.40 (d, J=3.6 Hz, 1H), 4.67 (s, 1H), 4.32 (s, 1H), 3.66 (d, J=3.2 Hz, 7H), 3.44 (s, 5H), 1.77 (s, 1H), 1.55 (d, J=15.1 Hz, 1H), 0.93 (t, J=7.3 Hz, 3H).

Example 131

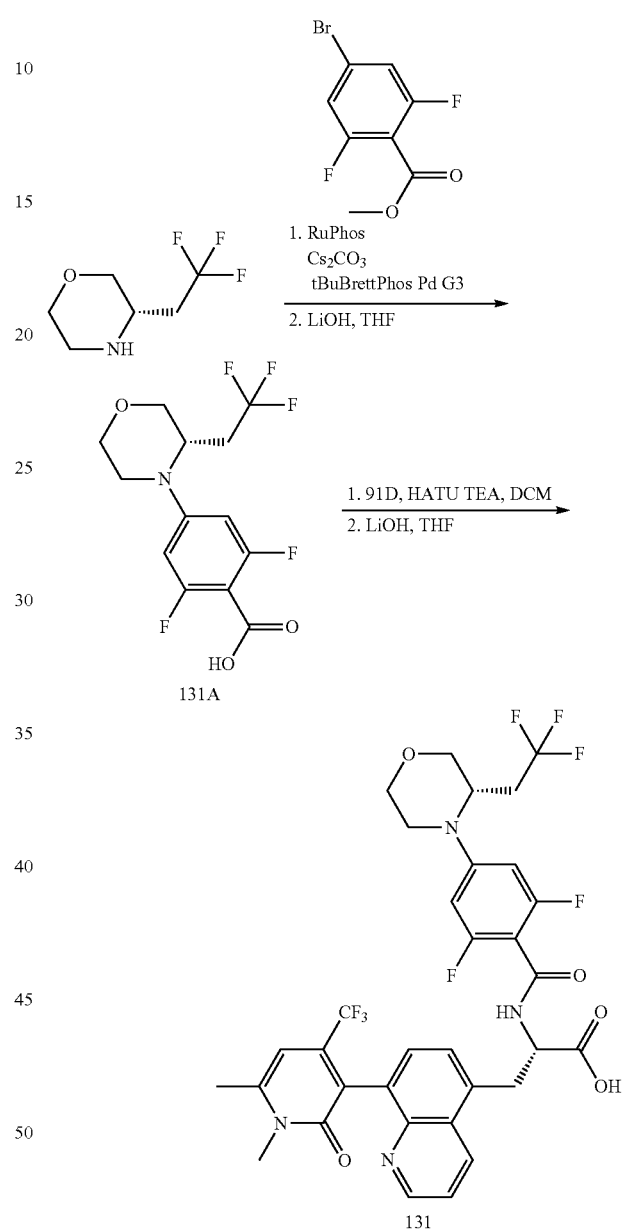

Synthesis of (S)-2,6-difluoro-4-(3-(2,2,2-trifluoroethyl)morpholino)benzoic acid (131A): The title compound was prepared according to the method presented for the synthesis of compound 75A starting with (S)-3-(2,2,2-trifluoroethyl)morpholine (S)-2-(2,6-difluoro-4-((S)-3-(2,2,2-trifluoroethyl)morpholino)benzamido)-3-(8-(1,6-dimethyl-2-oxo-4-(trifluoromethyl)-1,2-dihydropyridin-3-yl)quinolin-5-yl)propanoic acid (131): The title compound was prepared according to the method presented for the synthesis of compound 16A and 16 starting with 91D and 131A. MS (m/z) 713.2 [M+H]+. 1H NMR (400 MHz, DMSO-d6) δ 8.90 (dd, J=7.9, 4.2 Hz, 1H), 8.86-8.77 (m, 1H), 8.65 (s, 1H), 7.63 (dd, J=8.7, 4.4 Hz, 1H), 7.57 (t, J=7.1 Hz, 1H), 7.44 (dd, J=7.3, 4.5 Hz, 1H), 6.66-6.50 (m, 3H), 4.78-4.66 (m, 1H), 4.28 (s, 1H), 3.89 (dd, J=11.4, 3.6 Hz, 1H), 3.78 (d, J=11.9 Hz, 1H), 3.67 (dd, J=22.0, 13.3 Hz, 2H), 3.57-3.36 (m, 6H), 3.07 (td, J=12.6, 3.8 Hz, 1H), 2.77 (ddd, J=15.4, 11.8, 8.1 Hz, 1H), 2.53 (s, 3H), 2.39-2.20 (m, 1H).

Example 132

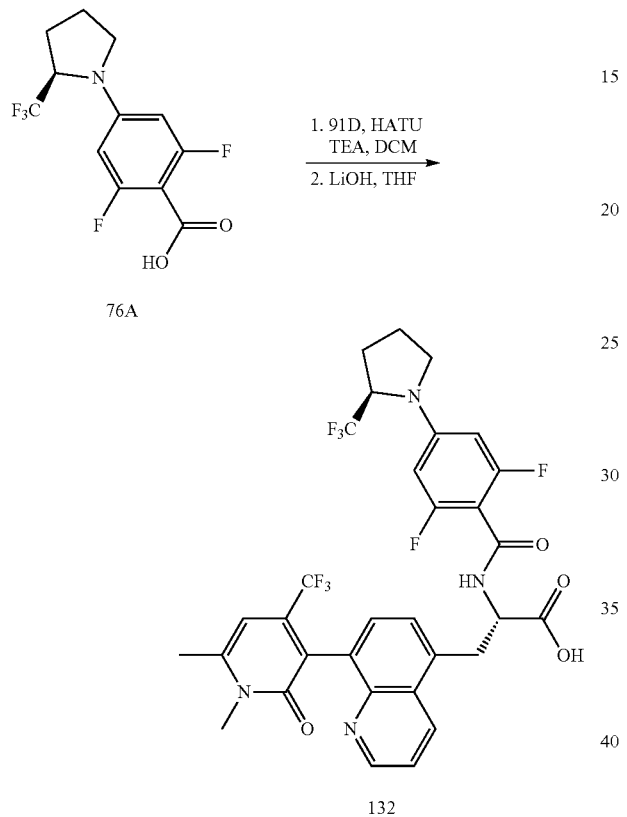

132

(S)-2-(2,6-difluoro-4-((R)-2-(trifluoromethyl)pyrrolidin-1-yl)benzamido)-3-(8-(1,6-dimethyl-2-oxo-4-(trifluoromethyl)-1,2-dihydropyridin-3-yl)quinolin-5-yl)propanoic acid (132): The title compound was prepared according to the method presented for the synthesis of compound 76 starting with 91D. MS (m/z) 683.7 [M+H]+. 1H NMR (400 MHz, DMSO-d6) δ 8.89 (dd, J=8.0, 3.8 Hz, 1H), 8.84 (dd, J=4.3, 1.5 Hz, 1H), 8.70 (t, J=7.6 Hz, 1H), 7.71-7.63 (m, 1H), 7.60 (t, J=7.5 Hz, 1H), 7.47 (dd, J=7.3, 4.1 Hz, 1H), 6.56 (t, J=1.1 Hz, 1H), 6.49 (dd, J=11.3, 4.1 Hz, 2H), 4.83-4.66 (m, 2H), 3.72 (td, J=15.5, 4.6 Hz, 1H), 3.58 (t, J=8.5 Hz, 1H), 3.53-3.36 (m, 4H), 3.18 (q, J=8.8 Hz, 1H), 2.54 (s, 3H), 2.19-1.93 (m, 4H).

Example 133

Synthesis of 2,6-difluoro-4-(propylamino)benzoic acid (133A): The title compound was prepared according to the method presented for the synthesis of compound 75A starting with propan-1-amine.

(S)-2-(2,6-difluoro-4-(propylamino)benzamido)-3-(8-(1,6-dimethyl-2-oxo-4-(trifluoromethyl)-1,2-dihydropyridin-3-yl)quinolin-5-yl)propanoic acid (133): The title compound was prepared according to the method presented for the synthesis of compound 16A and 16 starting with 91D and 133A. MS (m/z) 603.2 [M+H]+. 1H NMR (400 MHz, DMSO-d6) δ 8.82 (d, J=4.1 Hz, 1H), 8.65 (dd, J=7.8, 5.4 Hz, 2H), 7.63 (dd, J=8.4, 4.1 Hz, 1H), 7.60-7.53 (m, 1H), 7.44 (dd, J=7.3, 3.0 Hz, 1H), 6.55 (s, 1H), 6.15 (dd, J=11.6, 4.4 Hz, 2H), 4.74-4.61 (m, 1H), 3.78-3.61 (m, 1H), 3.49 (d, J=1.9 Hz, 3H), 3.47-3.36 (m, 1H), 2.97 (t, J=7.0 Hz, 2H), 2.53 (s, 3H), 1.51 (h, J=7.3 Hz, 2H), 0.91 (t, J=7.4 Hz, 3H).

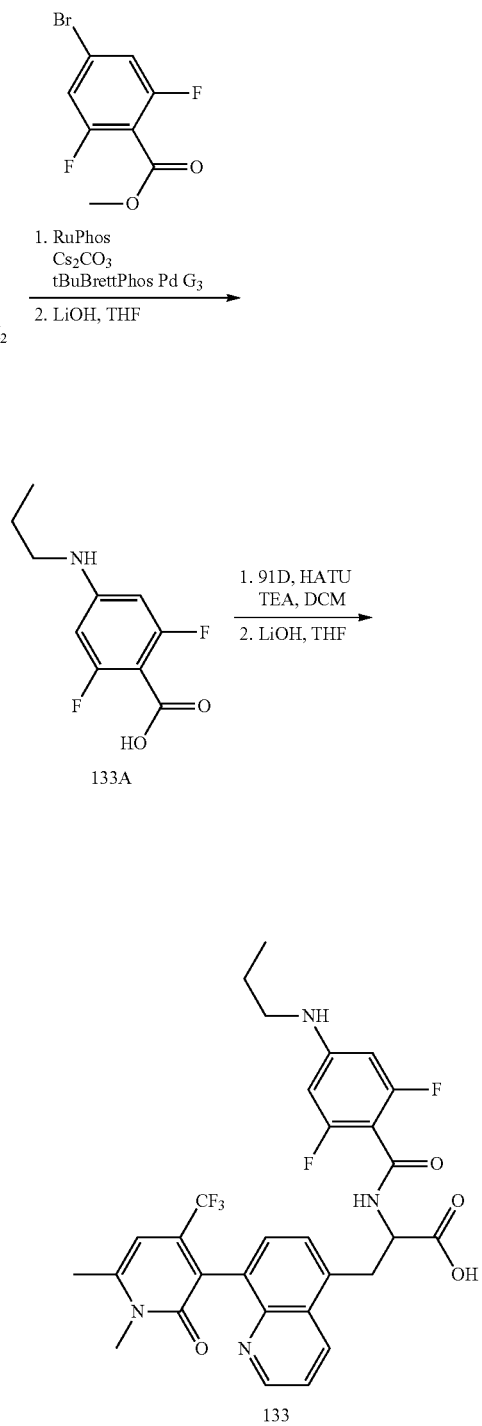

133

Example 134

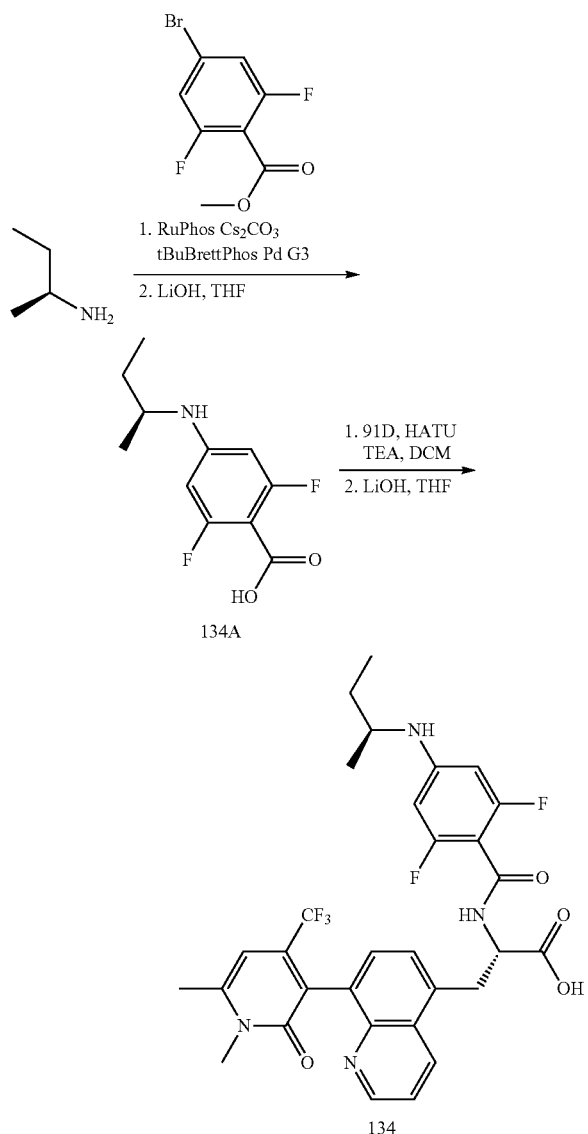

Example 135

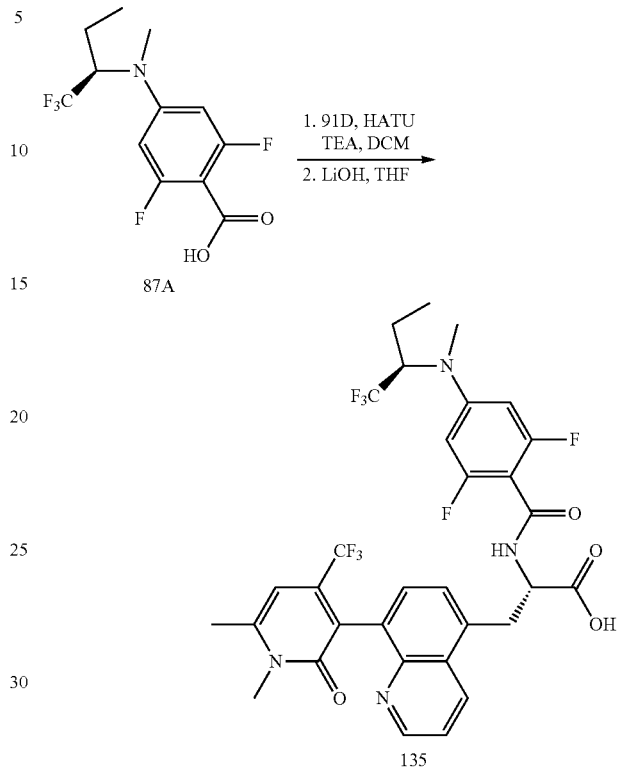

Synthesis of (S)-4-(sec-butylamino)-2,6-difluorobenzoic acid (134A): The title compound was prepared according to the method presented for the synthesis of compound 75A starting with (S)-butan-2-amine.

(S)-2-(4-(((S)-sec-butyl)amino)-2,6-difluorobenzamido)-3-(8-(1,6-dimethyl-2-oxo-4-(trifluoromethyl)-1,2-dihydropyridin-3-yl)quinolin-5-yl)propanoic acid (134): The title compound was prepared according to the method presented for the synthesis of compound 16A and 16 starting with 91D and 134A. MS (m/z) 617.2 [M+H]+. 1H NMR (400 MHz, DMSO-d6) δ 8.86-8.77 (m, 1H), 8.73-8.57 (m, 2H), 7.63 (dd, J=8.4, 4.1 Hz, 1H), 7.58 (t, J=6.4 Hz, 1H), 7.48-7.40 (m, 1H), 6.55 (s, 1H), 6.33 (s, 1H), 6.15 (dd, J=11.7, 4.4 Hz, 2H), 4.67 (dt, J=14.5, 5.6 Hz, 1H), 3.77-3.62 (m, 1H), 3.49 (d, J=2.0 Hz, 3H), 3.47-3.24 (m, 2H), 2.53 (s, 3H), 1.57-1.31 (m, 2H), 1.06 (d, J=6.3 Hz, 3H), 0.87 (t, J=7.4 Hz, 3H).

(S)-2-(2,6-difluoro-4-(methyl((R)-1,1,1-trifluorobutan-2-yl)amino)benzamido)-3-(8-(1,6-dimethyl-2-oxo-4-(trifluoromethyl)-1,2-dihydropyridin-3-yl)quinolin-5-yl)propanoic acid (135): The title compound was prepared according to the method presented for the synthesis of compound 87 starting with 91D. MS (m/z) 671.2 [M+H]+. 1H NMR (400 MHz, DMSO-d6) δ 8.89 (dd, J=7.9, 2.5 Hz, 1H), 8.84 (dd, J=4.3, 1.5 Hz, 1H), 8.69 (s, 1H), 7.72-7.54 (m, 2H), 7.46 (dd, J=7.4, 3.3 Hz, 1H), 6.64 (dd, J=12.0, 4.4 Hz, 2H), 6.56 (d, J=1.5 Hz, 1H), 5.02-4.90 (m, 1H), 4.70 (dt, J=4.7, 2.4 Hz, 1H), 3.72 (td, J=15.0, 4.5 Hz, 1H), 3.54-3.35 (m, 4H), 2.82 (s, 3H), 2.54 (s, 3H), 1.38 (d, J=6.7 Hz, 3H).

Example 136

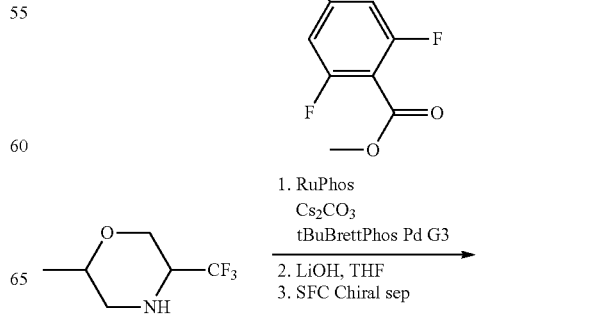

275

-continued

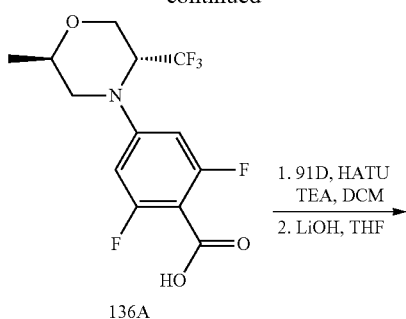

136A 1. 91D, HATU
   TEA, DCM
2. LiOH, THF

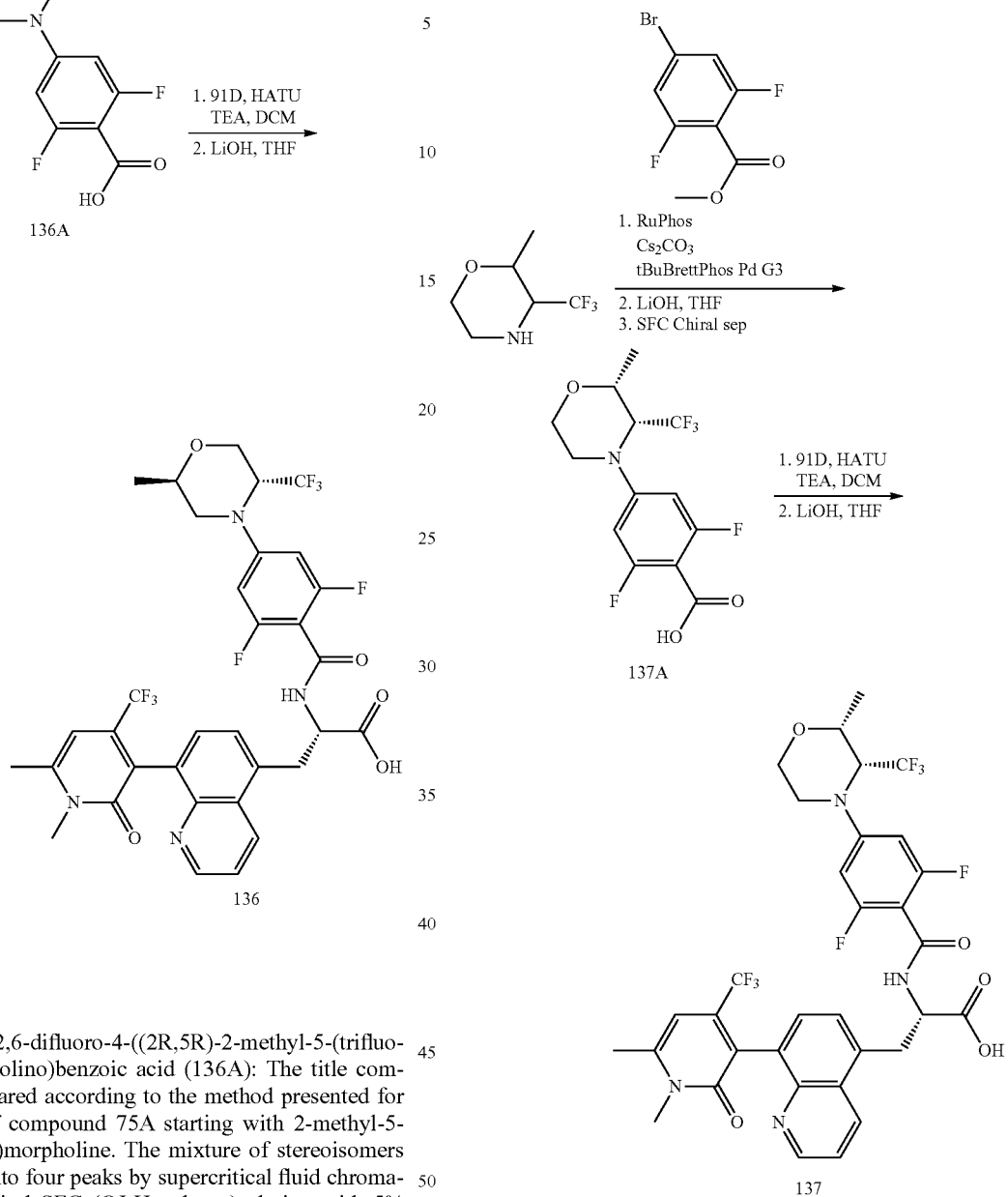

Synthesis of 2,6-difluoro-4-((2R,5R)-2-methyl-5-(trifluoromethyl)morpholino)benzoic acid (136A): The title compound was prepared according to the method presented for the synthesis of compound 75A starting with 2-methyl-5-(trifluoromethyl)morpholine. The mixture of stereoisomers was separated into four peaks by supercritical fluid chromatography via chiral SFC (OJ-H column) eluting with 5% TFA in EtOH to yield intermediate 136A. The title compound was identified as the first eluting peak.

(S)-2-(2,6-difluoro-4-((2R,5R)-2-methyl-5-(trifluoromethyl)morpholino)benzamido)-3-(8-(1,6-dimethyl-2-oxo-4-(trifluoromethyl)-1,2-dihydropyridin-3-yl)quinolin-5-yl)propanoic acid (136): The title compound was prepared according to the method presented for the synthesis of compound 16A and 16 starting with 91D and 136A. MS (m/z) 713.2 [M+H]+. 1H NMR (400 MHz, DMSO-d6) δ 8.95 (d, J=7.7 Hz, 1H), 8.80 (d, J=4.1 Hz, 1H), 8.61 (d, J=8.4 Hz, 1H), 7.66-7.51 (m, 2H), 7.47-7.35 (m, 1H), 6.75 (dd, J=11.5, 4.4 Hz, 2H), 6.54 (s, 1H), 4.85 (s, 1H), 4.70 (s, 1H), 4.10 (s, 13H), 3.87 (d, J=12.9 Hz, 1H), 3.69 (d, J=16.9 Hz, 1H), 3.49 (d, J=2.1 Hz, 3H), 3.42 (d, J=20.5 Hz, 4H), 2.53 (s, 4H), 1.20 (d, J=6.6 Hz, 3H).

276

Example 137

Synthesis of 2,6-difluoro-4-((2R,3R)-2-methyl-3-(trifluoromethyl)morpholino)benzoic acid (137A): The title compound was prepared according to the method presented for the synthesis of compound 75A starting with (cis)-2-methyl-3-(trifluoromethyl)morpholine. The mixture of stereoisomers was separated into two peaks by supercritical fluid chromatography via chiral SFC (IG-H column) eluting with 10% TFA in EtOH to yield intermediate 137A. The title compound was identified as the first eluting peak.

(S)-2-(2,6-difluoro-4-((2R,3R)-2-methyl-3-(trifluoromethyl)morpholino)benzamido)-3-(8-(1,6-dimethyl-2-oxo-4-(trifluoromethyl)-1,2-dihydropyridin-3-yl)quinolin-5-yl)propanoic acid (137): The title compound was prepared according to the method presented for the synthesis of compound 16A and 16 starting with 91D and 137A. MS (m/z) 712.7 [M+H]+. 1H NMR (400 MHz, DMSO-d6) δ 8.95 (dd, J=7.9, 3.4 Hz, 1H), 8.80 (dd, J=4.2, 1.5 Hz, 1H), 8.61 (d, J=8.7 Hz, 1H), 7.65-7.52 (m, 2H), 7.48-7.38 (m, 1H), 6.74 (dd, J=11.7, 4.5 Hz, 2H), 6.53 (s, 1H), 4.86 (d, J=6.9 Hz, 1H), 4.69 (td, J=9.1, 8.7, 4.3 Hz, 1H), 3.94 (dd, J=11.4, 3.7 Hz, 1H), 3.85 (s, 1H), 3.48 (d, J=2.0 Hz, 3H), 3.46 (s, 2H), 3.39 (dd, J=13.9, 9.6 Hz, 1H), 3.08 (dd, J=14.3, 10.6 Hz, 1H), 2.52 (s, 4H), 1.34-1.24 (m, 3H).

Example 138

Synthesis of 7-fluoro-5-(((2S,5R)-5-isopropyl-3,6-dimethoxy-2,5-dihydropyrazin-2-yl)methyl)-8-(4,4,5,5-tetramethyl-1,3,2-dioxaborolan-2-yl)quinoline (138A): To 34C (676 mg, 1.601 mmol), bis(pinacolato)diboron (813 mg, 3.202 mmol), potassium acetate (471 mg, 4.802 mmol), CataCXium A (86 mg, 0.192 mmol), and tris(dibenzylideneacetone)dipalladium(0) (46 mg, 0.080 mmol) were added dioxane (13.5 mL) and the reaction mixture was purged with N₂ for 10 min. The reaction mixture was sealed, affixed with a N₂ balloon, and allowed to stir at 105° C. for 14 hrs. The reaction mixture was cooled to RT, diluted with EA, and filtered. The filtrate was collected and concentrated under reduced pressure to afford the title compound without further purification.

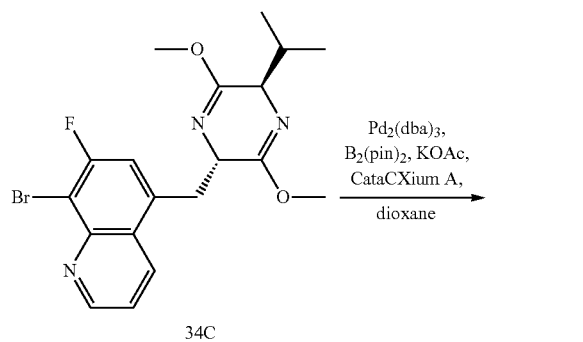

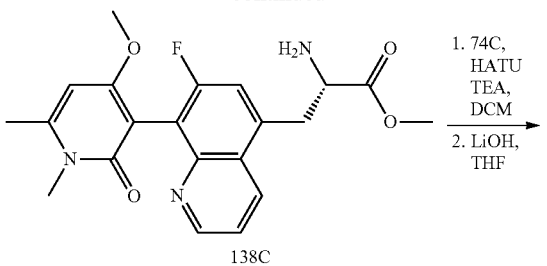

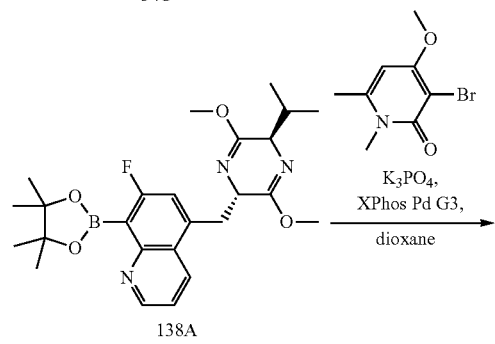

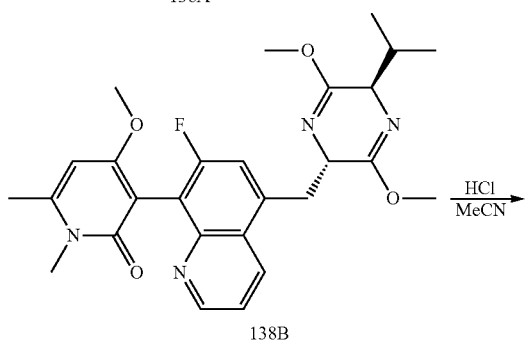

Synthesis of 3-(7-fluoro-5-(((2S,5R)-5-isopropyl-3,6-dimethoxy-2,5-dihydropyrazin-2-yl)methyl)quinolin-8-yl)-4-methoxy-1,6-dimethylpyridin-2(1H)-one (138B): To a stirred solution of 138A (325 mg, 0.277 mmol), 3-bromo-4-methoxy-1,6-dimethylpyridin-2(1H)-one (128 mg, 0.554 mmol), and XPhos Pd G3 (70 mg, 0.083 mmol), in dioxane (5 mL) were added 1M potassium phosphate (0.96 mL, 0.989 mmol). The reaction mixture was purged with N₂ for 5 min, sealed, and allowed to stir at 90° C. for 2 hrs. The reaction mixture was concentrated under reduced pressure and purified on silica gel chromatography eluting with Hex/EA 0-100% then DCM/MeOH 0-30% to afford the title compound.

Synthesis of methyl (S)-2-amino-3-(7-fluoro-8-(4-methoxy-1,6-dimethyl-2-oxo-1,2-dihydropyridin-3-yl)quinolin-5-yl)propanoate (138C): To a stirred solution of 138B (80 mg, 0.162 mmol) in acetonitrile (3.8 mL) was added 2M HCl (0.404 mL, 0.809 mmol). The reaction mixture was allowed to stir at RT for 2 hrs then concentrated under reduced pressure to yield the title compound without further purification.

(S)-2-(2,6-difluoro-4-(((R)-1,1,1-trifluorobutan-2-yl)amino)benzamido)-3-(7-fluoro-8-(4-methoxy-1,6-dimethyl-2-oxo-1,2-dihydropyridin-3-yl)quinolin-5-yl)propanoic acid (138): The title compound was prepared according to the method presented for the synthesis of compound 74 of starting with 137C. MS (m/z) 650.6 [M+H]+. 1H NMR (400 MHz, DMSO-d6) δ 8.85 (d, J=10.4 Hz, 2H), 8.72 (s, 1H), 7.65 (s, 1H), 7.52 (d, J=10.0 Hz, 1H), 6.78 (d, J=9.3 Hz, 1H), 6.46 (d, J=12.0 Hz, 2H), 6.40 (d, J=3.6 Hz, 1H), 4.67 (s, 1H), 4.32 (s, 1H), 3.66 (d, J=3.2 Hz, 7H), 3.44 (s, 5H), 1.77 (s, 1H), 1.55 (d, J=15.1 Hz, 1H), 0.93 (t, J=7.3 Hz, 3H).

Example 139

Synthesis of methyl (S)-3-(8-bromo-3-fluoroquinolin-5-yl)-2-(tritylamino)propanoate (139A): The title compound was prepared according to the method presented for the synthesis of compound 91A starting with 30K.

Synthesis of methyl (S)-3-(8-bromo-3-(dimethylamino)quinolin-5-yl)-2-(tritylamino) propanoate (139B): 139A (445 mg, 0.781 mmol) was dissolved in DMF (2.4 mL), and to this was added $K_2CO_3$ (113 mg, 0.82 mmol) and dimethylamine (4.69 mmol, 2.3 mL, 2.0M in THF). The reaction was heated to 100° C. and stirred for 21.5 hours. After cooling to RT, EA and water were added to the reaction mixture. The aqueous layer was extracted and the organic layer was dried over anhydrous $MgSO_4$, and concentrated under reduced pressure. The material was purified by silica gel chromatography using 0-50% EA in hexanes to afford the title compound.

Synthesis of (S)-(3-(dimethylamino)-5-(3-methoxy-3-oxo-2-(tritylamino)propyl) quinolin-8-yl)boronic acid (139C): The title compound was prepared according to the method presented for the synthesis of compound 4B starting with 91A.

Synthesis of methyl (S)-2-amino-3-(8-(1,6-dimethyl-2-oxo-4-(trifluoromethyl)-1,2-dihydropyridin-3-yl)-3-(dimethylamino)quinolin-5-yl)propanoate (139D): The title compound was prepared according to the method presented for the synthesis of compound 91C and 91D in starting with 139C and 3-iodo-1,6-dimethyl-4-(trifluoromethyl)pyridin-2 (1H)-one.

(S)-2-(2,6-difluoro-4-(((R)-1,1,1-trifluorobutan-2-yl)amino)benzamido)-3-(8-(1,6-dimethyl-2-oxo-4-(trifluoromethyl)-1,2-dihydropyridin-3-yl)-3-(dimethylamino)quinolin-5-yl)propanoic acid (139): The title compound was prepared according to the method presented for the synthesis of compound 74 starting with 139D. MS (m/z) 714.5 [M+H]+. 1H NMR (400 MHz, DMSO-d6) δ 8.83 (d, J=7.8 Hz, 1H), 8.62 (t, J=3.0 Hz, 1H), 7.58 (s, 1H), 7.44 (t, J=5.8 Hz, 1H), 7.12 (d, J=7.2 Hz, 1H), 6.84-6.73 (m, 1H), 6.55 (d, J=2.7 Hz, 1H), 6.45 (dd, J=11.3, 3.9 Hz, 2H), 4.67 (dt, J=13.4, 9.0 Hz, 1H), 4.31 (d, J=8.8 Hz, 1H), 3.65-3.54 (m, 1H), 3.48 (d, J=1.7 Hz, 3H), 3.39-3.26 (m, 1H), 3.10 (d, J=3.9 Hz, 6H), 2.53 (s, 3H), 1.77 (ddd, J=10.7, 7.5, 3.7 Hz, 1H), 1.61-1.46 (m, 1H), 0.93 (t, J=7.3 Hz, 3H).

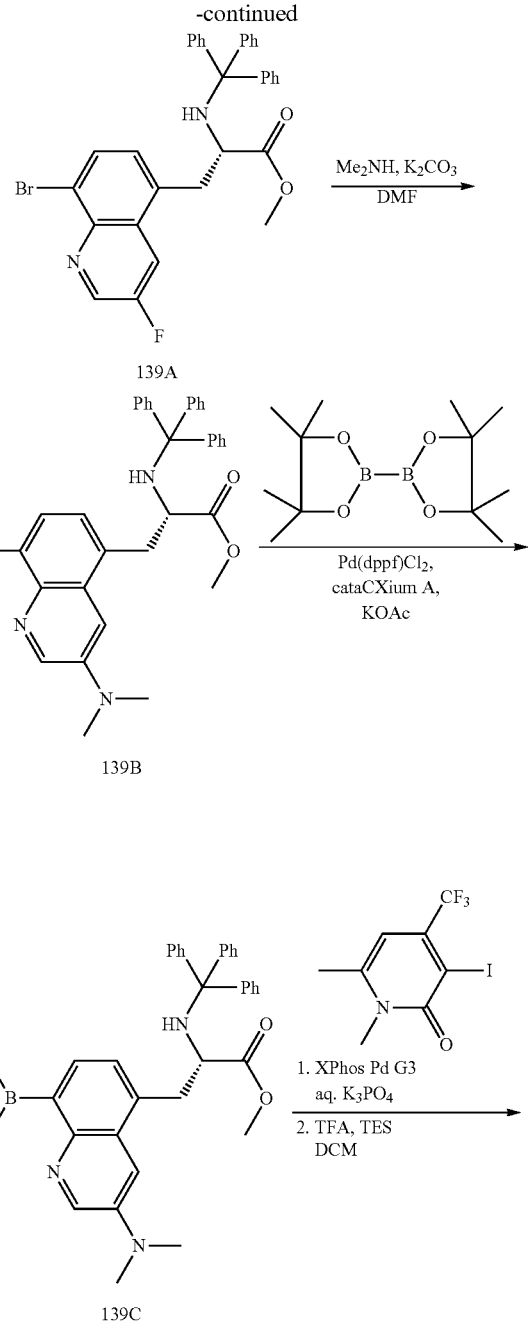

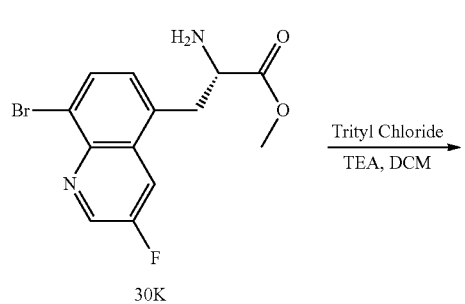

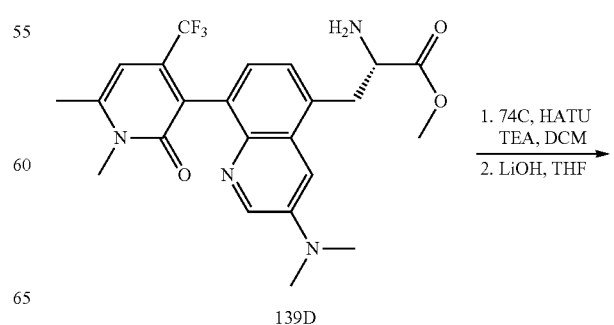

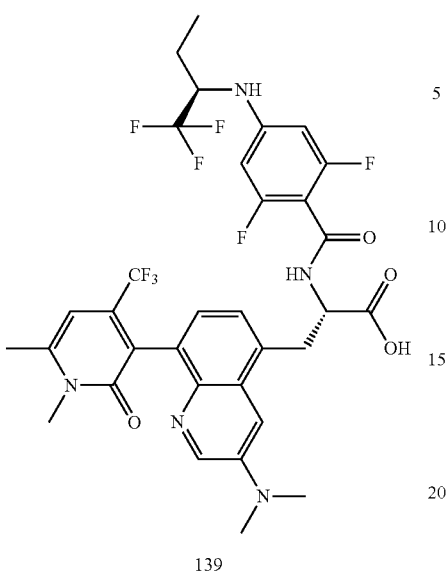

139

Example 140

Synthesis of (S)-(3-fluoro-5-(3-methoxy-3-oxo-2-(tritylamino)propyl)quinolin-8-yl)boronic acid (140A): The title compound was prepared according to the method presented for the synthesis of compound 4B starting with 139A.

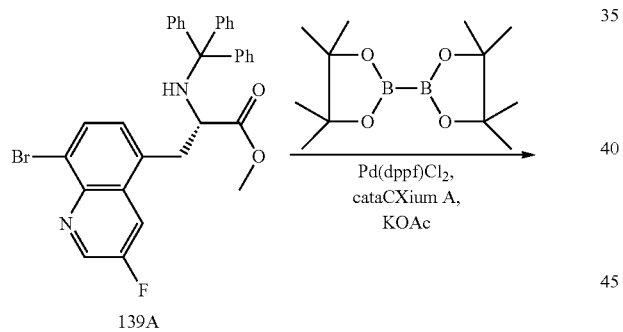

139A

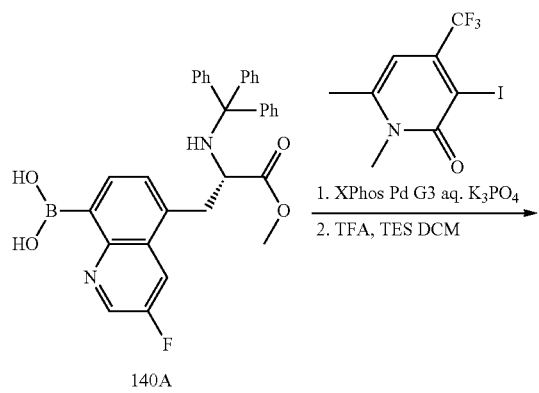

140A

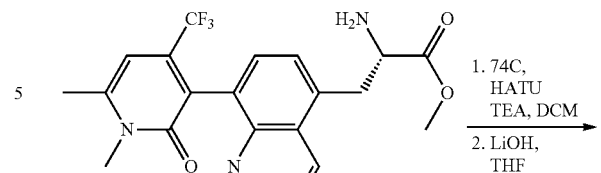

140B

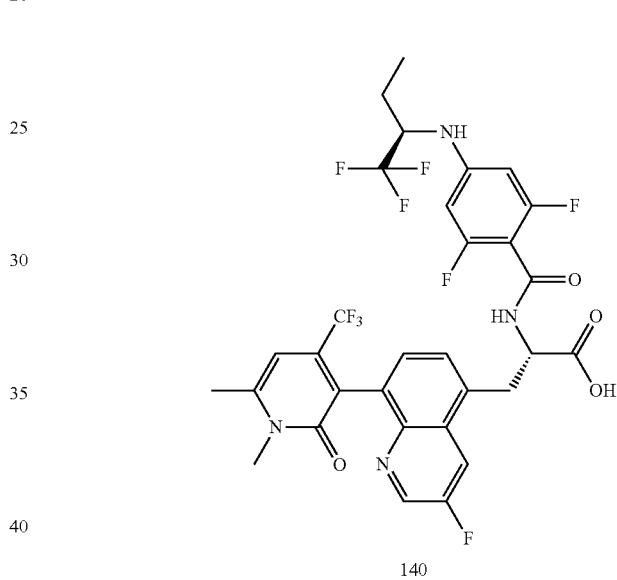

140

Synthesis of methyl (S)-2-amino-3-(8-(1,6-dimethyl-2-oxo-4-(trifluoromethyl)-1,2-dihydropyridin-3-yl)-3-fluoroquinolin-5-yl)propanoate (140B): The title compound was prepared according to the method presented for the synthesis of compound 91C and 91D in starting with 140A and 3-iodo-1,6-dimethyl-4-(trifluoromethyl)pyridin-2(1H)-one.

(S)-2-(2,6-difluoro-4-(((R)-1,1,1-trifluorobutan-2-yl)amino)benzamido)-3-(8-(1,6-dimethyl-2-oxo-4-(trifluoromethyl)-1,2-dihydropyridin-3-yl)-3-fluoroquinolin-5-yl)propanoic acid (140): The title compound was prepared according to the method presented for the synthesis of compound 74 starting with 140B. MS (m/z) 689.0 [M+H]+. 1H NMR (400 MHz, DMSO-d6) δ 8.85 (d, J=2.6 Hz, 1H), 8.81 (d, J=7.9 Hz, 1H), 8.37 (dt, J=10.6, 3.3 Hz, 1H), 7.60 (t, J=7.4 Hz, 1H), 7.41 (dd, J=7.3, 5.2 Hz, 1H), 6.77 (d, J=9.3 Hz, 1H), 6.54 (s, 1H), 6.44 (d, J=11.8 Hz, 2H), 4.68 (td, J=8.8, 4.5 Hz, 1H), 4.31 (d, J=9.1 Hz, 1H), 3.62 (td, J=14.1, 4.4 Hz, 1H), 3.48 (d, J=1.7 Hz, 3H), 3.41 (td, J=15.3, 9.9 Hz, 1H), 2.52 (s, 3H), 1.77 (ddd, J=13.9, 7.1, 3.3 Hz, 1H), 1.52 (ddd, J=13.6, 10.2, 6.9 Hz, 1H), 0.92 (t, J=7.3 Hz, 3H).

Example 141

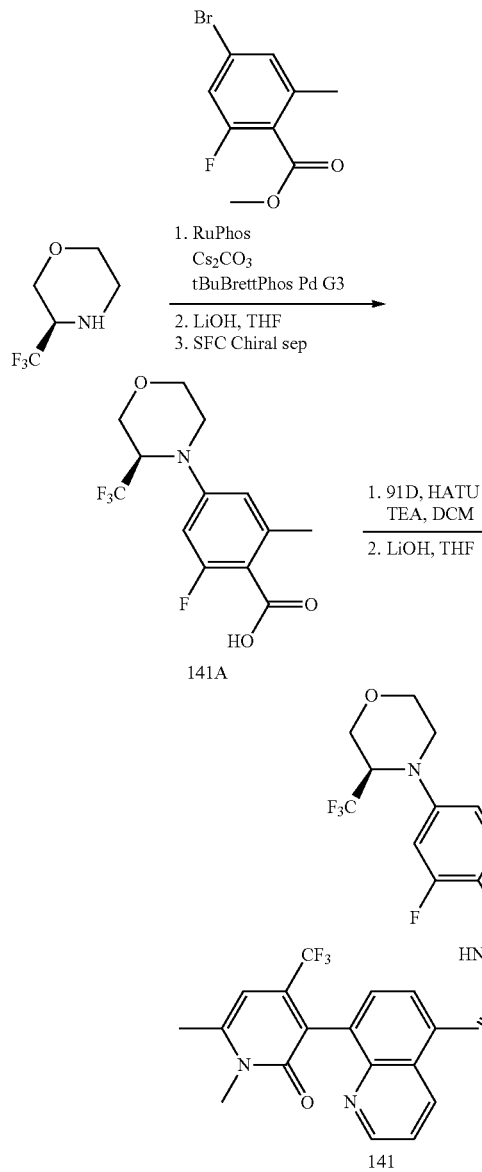

Synthesis of (R)-2-fluoro-6-methyl-4-(3-(trifluoromethyl)morpholino)benzoic acid (141A): The title compound was prepared according to the method presented for the synthesis of compound 93A starting with methyl 4-bromo-2-fluoro-6-methylbenzoate.

(S)-3-(8-(1,6-dimethyl-2-oxo-4-(trifluoromethyl)-1,2-dihydropyridin-3-yl)quinolin-5-yl)-2-(2-fluoro-6-methyl-4-((R)-3-(trifluoromethyl)morpholino)benzamido)propanoic acid (141): The title compound was prepared according to the method presented for the synthesis of compound 16A and 16 starting with 141A and 91D. MS (m/z) 695.2 [M+H]+. 1H NMR (400 MHz, DMSO-d6) δ 8.89-8.77 (m, 2H), 8.63 (d, J=8.6 Hz, 1H), 7.68-7.53 (m, 2H), 7.43 (t, J=7.2 Hz, 1H), 6.71-6.61 (m, 2H), 6.55 (d, J=3.2 Hz, 1H), 4.89-4.69 (m, 2H), 4.14 (d, J=12.6 Hz, 1H), 3.94 (d, J=9.6 Hz, 1H), 3.80-3.64 (m, 2H), 3.59-3.19 (m, 7H), 2.53 (s, 3H), 1.99-1.97 (m, 3H).

Example 142

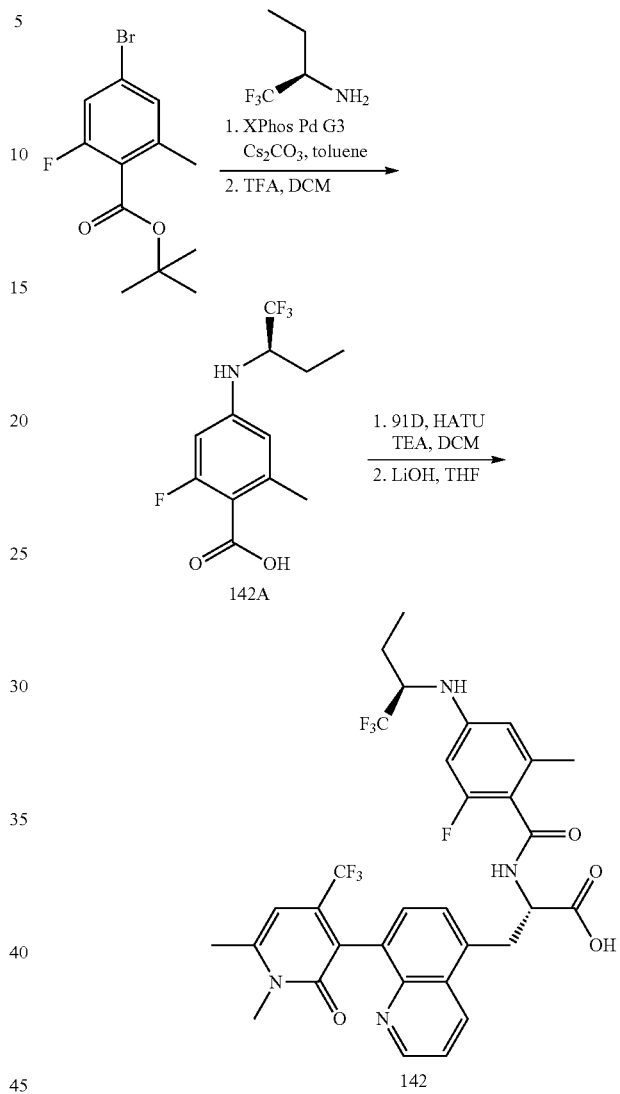

Synthesis of (R)-2-fluoro-6-methyl-4-((1,1,1-trifluorobutan-2-yl)amino)benzoic acid (142A): The title compound was prepared according to the method presented for the synthesis of compound 74B and 74C starting with methyl 4-bromo-2-fluoro-6-methylbenzoate.

(S)-3-(8-(1,6-dimethyl-2-oxo-4-(trifluoromethyl)-1,2-dihydropyridin-3-yl)quinolin-5-yl)-2-(2-fluoro-6-methyl-4-(((R)-1,1,1-trifluorobutan-2-yl)amino)benzamido)propanoic acid (142): The title compound was prepared according to the method presented for the synthesis of compound 16A and 16 starting with 142A and 91D. MS (m/z) 667.2 [M+H]+. 1H NMR (400 MHz, DMSO-d6) δ 8.81 (dt, J=3.9, 1.8 Hz, 1H), 8.71 (dd, J=9.9, 8.1 Hz, 1H), 8.63 (d, J=8.5 Hz, 1H), 7.61 (ddd, J=20.7, 9.0, 4.6 Hz, 2H), 7.43 (t, J=6.8 Hz, 1H), 6.55 (d, J=3.5 Hz, 1H), 6.41-6.34 (m, 2H), 6.28 (d, J=9.2 Hz, 1H), 4.80-4.67 (m, 1H), 4.18 (br s, 1H), 3.71 (ddd, J=28.0, 14.6, 4.0 Hz, 1H), 3.53-3.29 (m, 4H), 2.53 (s, 3H), 1.95-1.91 (m, 3H), 1.80-1.70 (m, 1H), 1.59-1.47 (m, 1H), 0.96-0.87 (m, 3H).

Example 143

Synthesis of (R)-2,6-dichloro-4-((1,1,1-trifluorobutan-2-yl)amino)benzoic acid (143A): The title compound was prepared according to the method presented for the synthesis of compound 74B and 74C starting with tert-butyl 4-bromo-2,6-dichlorobenzoate.

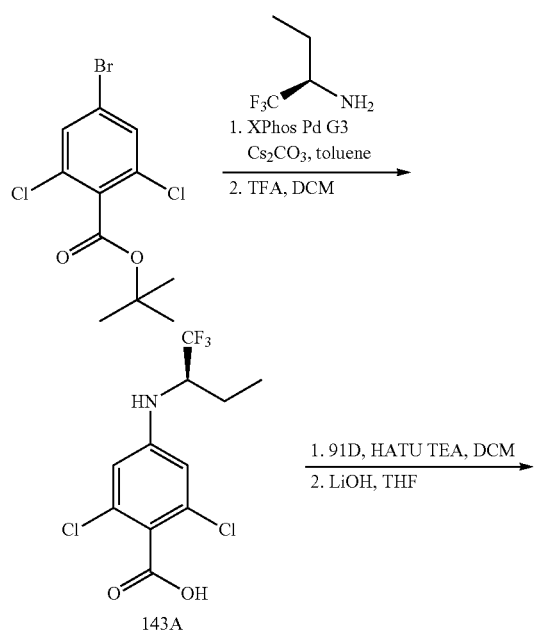

Example 144

Synthesis of (R)-2-chloro-6-fluoro-4-((1,1,1-trifluorobutan-2-yl)amino)benzoic acid (144A): The title compound was prepared according to the method presented for the synthesis of compound 74B and 74C starting with tert-butyl 4-bromo-2-chloro-6-fluorobenzoate.

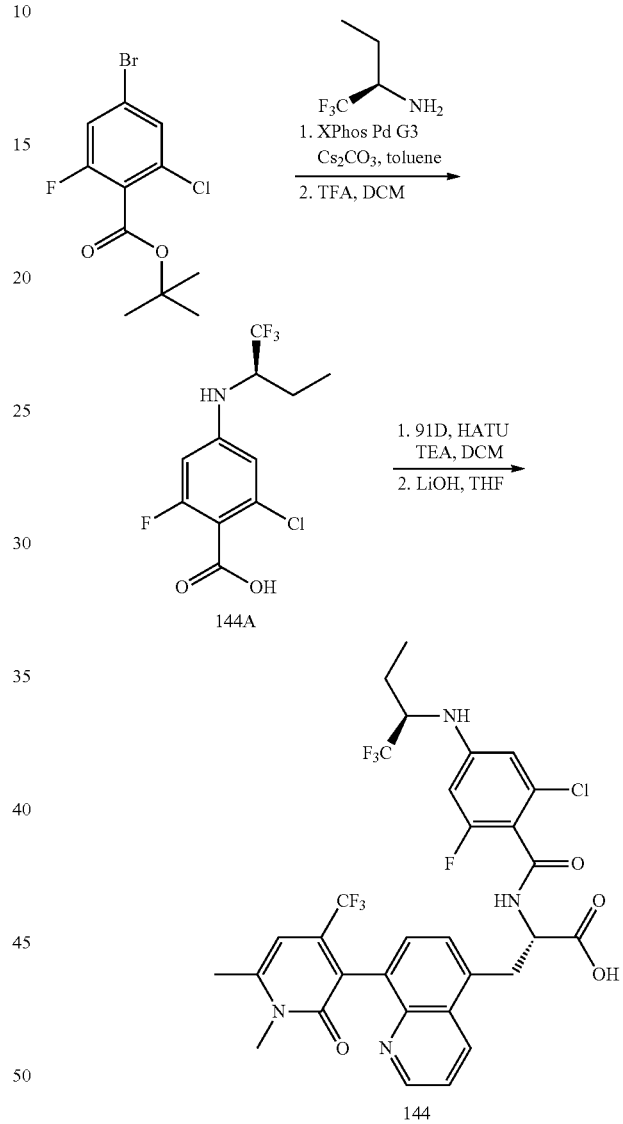

(S)-2-(2,6-dichloro-4-(((R)-1,1,1-trifluorobutan-2-yl)amino)benzamido)-3-(8-(1,6-dimethyl-2-oxo-4-(trifluoromethyl)-1,2-dihydropyridin-3-yl)quinolin-5-yl)propanoic acid (143): The title compound was prepared according to the method presented for the synthesis of compound 16A and 16 starting with 143A and 91D. MS (m/z) 703.1 [M+H]$^+$. 1H NMR (400 MHz, DMSO-d6) δ 9.01 (dd, J=26.1, 8.3 Hz, 1H), 8.82 (d, J=3.5 Hz, 1H), 8.66 (d, J=8.6 Hz, 1H), 7.65 (dd, J=18.5, 9.6 Hz, 2H), 7.43 (dd, J=7.4, 3.8 Hz, 1H), 6.77 (s, 1H), 6.55 (q, J=5.9 Hz, 2H), 4.85-4.63 (m, 1H), 4.33 (s, 1H), 3.69 (ddd, J=19.3, 14.5, 4.0 Hz, 1H), 3.49 (d, J=4.0 Hz, 3H), 3.42-3.31 (m, 1H), 2.53 (s, 3H), 1.85-1.60 (m, 1H), 1.51 (dt, J=11.8, 7.9 Hz, 1H), 0.93 (td, J=7.3, 3.0 Hz, 3H).

(S)-2-(2-chloro-6-fluoro-4-(((R)-1,1,1-trifluorobutan-2-yl)amino)benzamido)-3-(8-(1,6-dimethyl-2-oxo-4-(trifluoromethyl)-1,2-dihydropyridin-3-yl)quinolin-5-yl)propanoic acid (144): The title compound was prepared according to the method presented for the synthesis of compound 16A and 16 starting with 144A and 91D. MS (m/z) 687.2 [M+H]+. 1H NMR (400 MHz, DMSO-d6) δ 8.97 (dd, J=12.0, 8.1 Hz, 1H), 8.82 (s, 1H), 8.65 (s, 1H), 7.69-7.54 (m, 2H), 7.43 (d, J=6.2 Hz, 1H), 6.67-6.61 (m, 2H), 6.61-6.51 (m, 2H), 4.71 (dd, J=23.5, 11.8 Hz, 1H), 4.31 (s, 1H), 3.76-3.63 (m, 1H), 3.49 (d, J=3.4 Hz, 3H), 3.48-3.28 (m, 1H), 2.53 (s, 3H), 1.75 (d, J=8.3 Hz, 1H), 1.66-1.46 (m, 1H), 1.01-0.88 (m, 3H).

Example 145

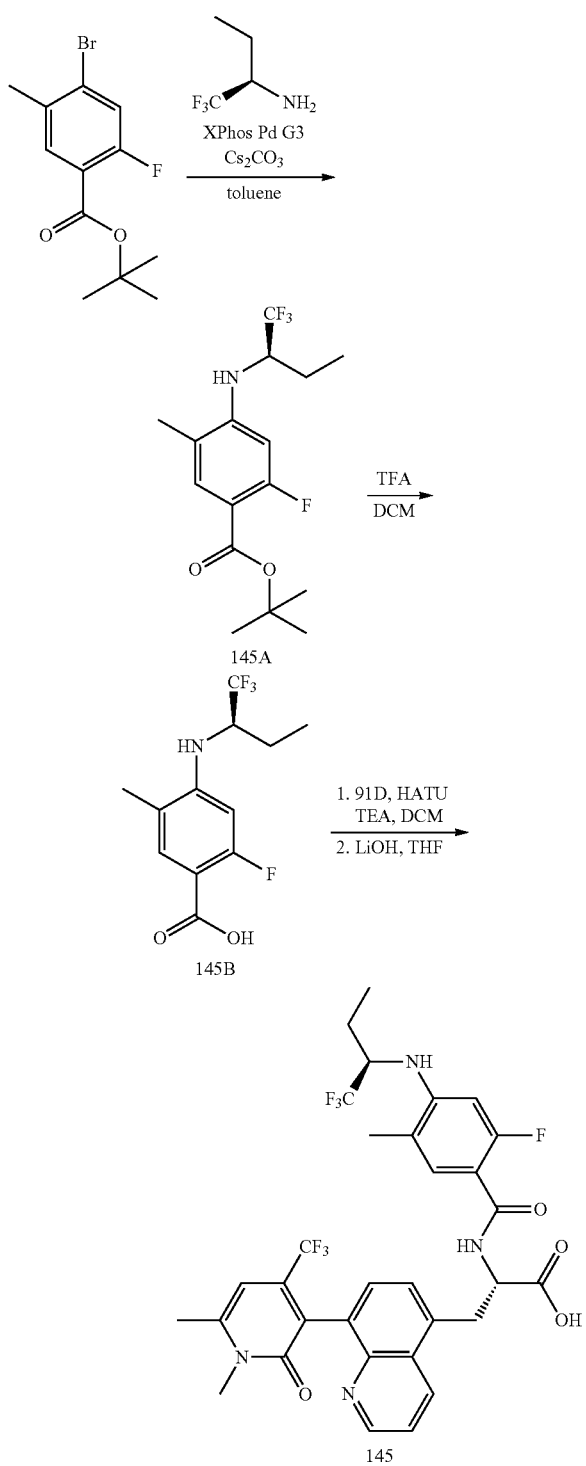

Synthesis of tert-butyl (R)-2-fluoro-5-methyl-4-((1,1,1-trifluorobutan-2-yl)amino) benzoate (145B): The title compound was prepared according to the method presented for the synthesis of compound 74B and 74C starting with tert-butyl 4-bromo-2-fluoro-5-methylbenzoate.

(S)-3-(8-(1,6-dimethyl-2-oxo-4-(trifluoromethyl)-1,2-dihydropyridin-3-yl)quinolin-5-yl)-2-(2-fluoro-5-methyl-4-(((R)-1,1,1-trifluorobutan-2-yl)amino)benzamido)propanoic acid (145): The title compound was prepared according to the method presented for the synthesis of compound 16A and 16 starting with 145B and 91D. MS (m/z) 667.2 [M+H]+. 1H NMR (400 MHz, DMSO-d6) δ 8.83 (d, J=4.0 Hz, 1H), 8.75 (t, J=11.1 Hz, 1H), 7.94 (d, J=7.2 Hz, 1H), 7.60 (dd, J=24.9, 7.1 Hz, 2H), 7.53-7.41 (m, 1H), 7.36-7.18 (m, 1H), 6.76-6.61 (m, 1H), 6.55 (s, 1H), 5.52 (d, J=8.6 Hz, 1H), 4.78 (s, 1H), 4.38 (s, 1H), 3.73 (t, J=13.5 Hz, 1H), 3.59 (dd, J=15.9, 9.6 Hz, 1H), 3.53-3.41 (m, 3H), 2.53 (d, J=2.3 Hz, 3H), 2.10 (t, J=2.9 Hz, 3H), 1.96-1.62 (m, 2H), 0.98-0.82 (m, 3H).

Example 146

Synthesis of (R)-3-bromo-2,6-difluoro-4-((1,1,1-trifluorobutan-2-yl)amino)benzoic acid (146A). To stirred solution of 74C (216 mg, 0.76 mmol) in dichloroethane (4 mL) was added TFA (0.292 mL, 3.8 mmol), and N-bromosuccinimide (143 mg, 0.80 mmol) and the mixture was heated to 50° C. After 1 h the mixture was added to silica gel and chromatographed eluting with ethyl acetate in hexanes to the title compound.

Synthesis of (trimethylsilyl)methyl 2,6-difluoro-3-((E)-3-((tetrahydro-2H-pyran-2-yl) oxy)prop-1-en-1-yl)-4-(((R)-1,1,1-trifluorobutan-2-yl)amino)benzoate (146B). To a microwave vial was added 146A (230 mg, 0.635 mmol), dioxane (4 mL), (Trimethylsilyl)diazomethane solution (1N ether) (0.635 mL, 0.635 mmol), potassium carbonate (176 mg, 1.3 mmol) palladium tetrakis triphenylphosphine (73.4 mg, 0.06 mmol), and (E)-(3-((tetrahydro-2H-pyran-2-yl)oxy)prop-1-en-1-yl)boronic acid (236.31 mg, 1.27 mmol). The vessel was sealed and heated to 110° C. for 35 minutes. The mixture was then added to silica gel and chromatographed eluting with ethyl acetate in hexanes to afford the title compound.

Synthesis of (trimethylsilyl)methyl (R)-2,6-difluoro-3-(3-hydroxypropyl)-4-((1,1,1-trifluorobutan-2-yl)amino)benzoate (146C). 146B (160 mg, 0.314 mmol), was added to a Parr shaker bottle with 5% palladium on charcoal (25 mg) and the mixture was shaken overnight under 50 PSI of H2. The mixture was filtered and HCl in methanol was added (9 mL, 3N) and the mixture was stirred for 4 h. Volatile components of the mixture were removed on a rotary evaporator, dissolved in DCM, washed with sodium bicarbonate (aq) and the residue was chromatographed on silica gel eluting with methanol in DCM to afford the title compound.

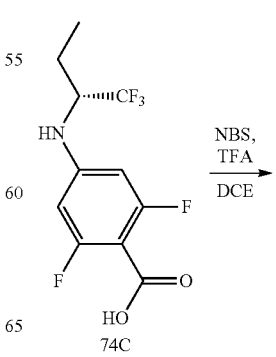

74C

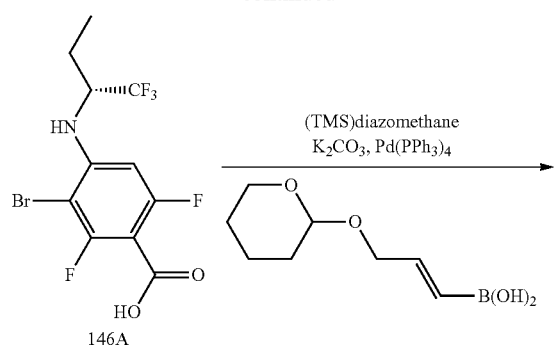

146A

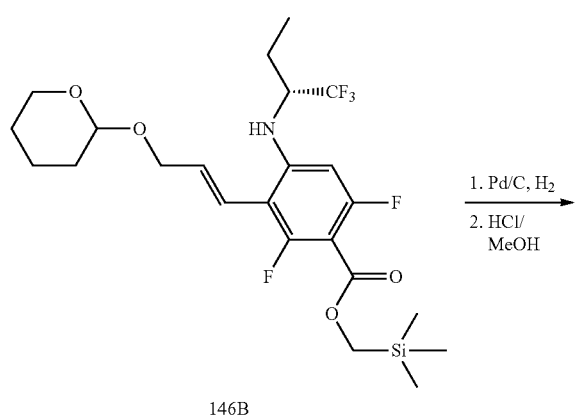

146B

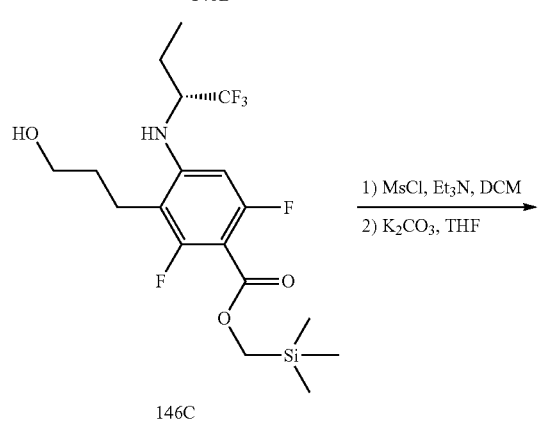

146C

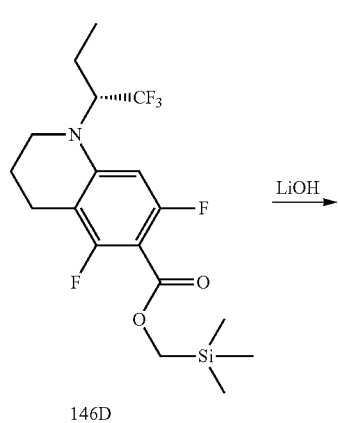

146D

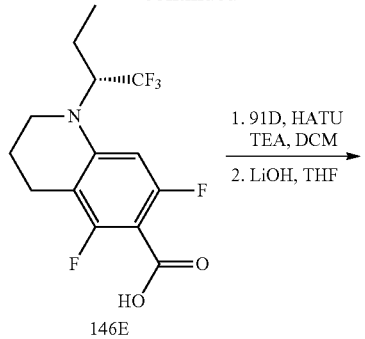

146E

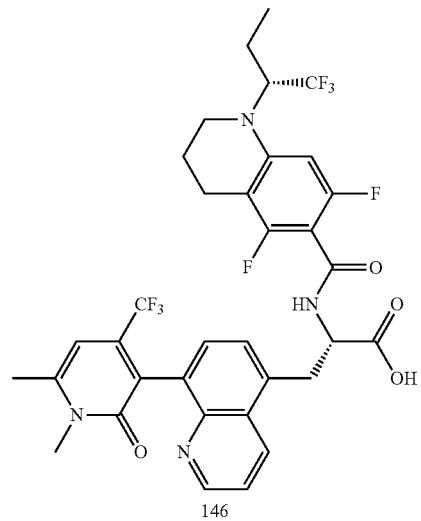

146

Synthesis of (trimethylsilyl)methyl (R)-5,7-difluoro-1-(1,1,1-trifluorobutan-2-yl)-1,2,3,4-tetrahydroquinoline-6-carboxylate (146D). To a stirred solution of 146C (107 mg, 0.215 mmol), and TEA (0.1 ml, 0.9 mmol) in DCM (1 mL) was added methanesulfonyl chloride (39 uL, 0.5 mmol) and let stir for ten minutes. The mixture was washed with sodium bicarbonate (aq) and the volatile components of the organic layer were removed on a rotary evaporator and diluted with THF (2 mL) and potassium carbonate was added (173 mg, 1.25 mmol) and the mixture was heated to 70° C. overnight. The mixture was chromatographed on silica gel eluting with ethyl acetate in hexanes to afford the title compound.

Synthesis of (R)-5,7-difluoro-1-(1,1,1-trifluorobutan-2-yl)-1,2,3,4-tetrahydroquinoline-6-carboxylic acid (146E). To 146D (95 mg, 0.2 mmol) was added methanol (10 mL) and lithium hydroxide (4 mg) and water (2 mL) and the mixture was stirred over the weekend at 85° C. The mixture was neutralized with HCl in dioxane and the solvents were removed on a rotary evaporator. The title compound thus obtained was used without further purification.

(S)-2-(5,7-difluoro-1-((R)-1,1,1-trifluorobutan-2-yl)-1,2,3,4-tetrahydroquinoline-6-carboxamido)-3-(8-(1,6-dimethyl-2-oxo-4-(trifluoromethyl)-1,2-dihydropyridin-3-yl)quinolin-5-yl)propanoic acid (146): The title compound was prepared according to the method presented for the synthesis of compound 16A and 16 starting with 91D and 146E. MS (m/z) 711.3 [M+H]+. 1 H NMR (400 MHz, Chloroform-d) δ 9.30 (dd, J=86.9, 8.7 Hz, 1H), 7.87-7.50 (m, 3H), 7.00 (d, J=35.4 Hz, 1H), 6.53 (d, J=12.4 Hz, 1H), 6.24 (dd, J=14.4, 6.2 Hz, 1H), 5.00 (dd, J=29.5, 6.2 Hz, 1H), 4.22-3.85 (m, 1H), 3.89-3.64 (m, 1H), 3.56 (d, J=7.5 Hz, 3H), 3.25 (s, 2H), 2.74-2.61 (m, 2H), 2.10-1.66 (m, 4H), 0.95 (t, J=7.4 Hz, 3H).

Example 147

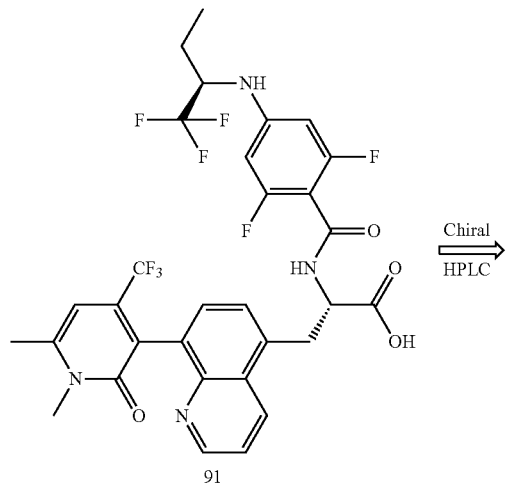

Preparation of (S)-2-(2,6-difluoro-4-(((R)-1,1,1-trifluorobutan-2-yl)amino)benzamido)-3-(8-(1,6-dimethyl-2-oxo-4-(trifluoromethyl)-1,2-dihydropyridin-3-yl)quinolin-5-yl) propanoic acid (147): 91 was separated into its 2 atropisomeric enantiomers by supercritical fluid chromatography using 30% MeOH co-solvent, at a flow rate of 60 mL/min, using an IC 5 μm 21×250 mm column. The title compound was identified as the second eluting peak. MS (m/z) 671.2 [M+H]+. 1H NMR (400 MHz, DMSO-d6) δ 8.82 (t, J=6.4 Hz, 2H), 8.67 (d, J=8.7 Hz, 1H), 7.70-7.50 (m, 2H), 7.45 (d, J=7.3 Hz, 1H), 6.76 (d, J=9.3 Hz, 1H), 6.55 (s, 1H), 6.43 (d, J=11.9 Hz, 2H), 4.68 (m, 1H), 4.37-4.24 (m, 1H), 3.67-3.63 (m, 1H), 3.48 (m, 4H), 2.52 (s, 3H), 1.74 (m, 1H), 1.53 (m, 1H), 0.91 (t, J=7.4 Hz, 3H).

Example 148

Preparation of (S)-3-(8-(2-chloro-4-cyanophenyl)quinolin-5-yl)-2-(2,6-difluoro-4-((R)-3-(trifluoromethyl)morpholino)benzamido)propanoic acid (148): 89 was separated into its 2 enantiomers by supercritical fluid chromatography using 30% EtOH/TFA co-solvent, at a flow rate of 45 mL/min, using an IE 5 μm 21×250 mm column. The title compound was identified as the second eluting peak. MS (m/z) 629.2 [M+H]+. 1H NMR (400 MHz, DMSO-d6) δ 8.86-8.75 (m, 2H), 8.63 (dd, J=8.6, 1.6 Hz, 1H), 8.15 (dd, J=1.6, 0.4 Hz, 1H), 7.89 (dd, J=7.9, 1.7 Hz, 1H), 7.66-7.51 (m, 4H), 6.92 (d, J=9.4 Hz, 1H), 6.40 (d, J=11.8 Hz, 2H), 4.67 (s, 1H), 3.97-3.89 (m, 1H), 3.72 (s, 1H), 3.40 (s, 1H), 1.03 (ddt, J=13.0, 8.1, 4.2 Hz, 1H), 0.66-0.55 (m, 1H), 0.55-0.43 (m, 2H), 0.30 (dd, J=9.7, 4.9 Hz, 1H).

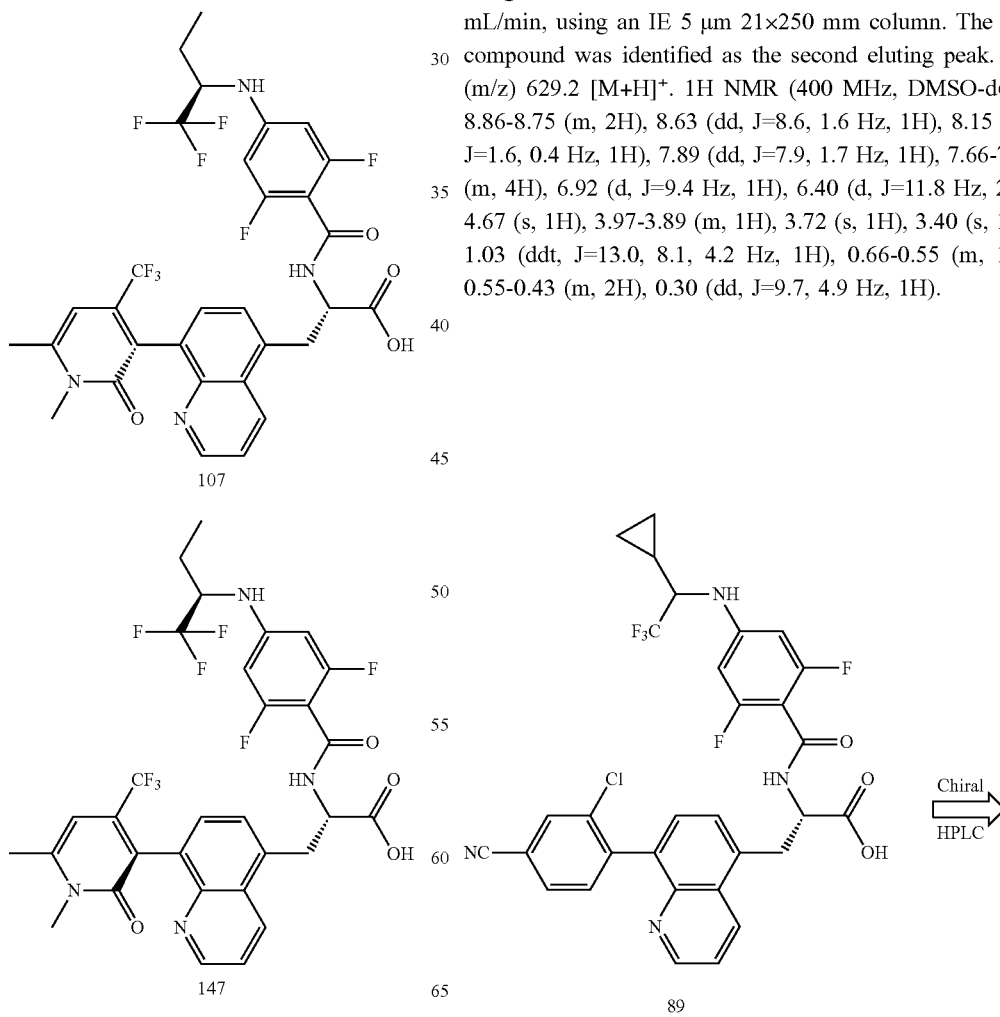

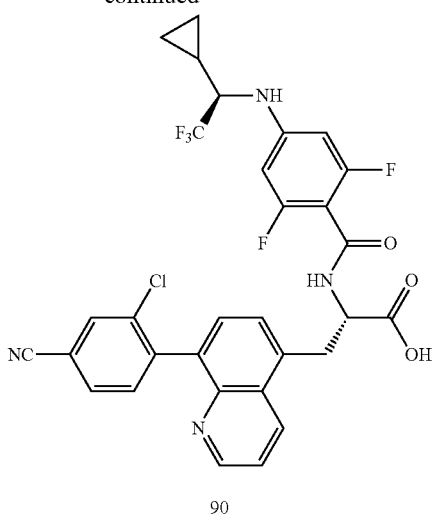

90

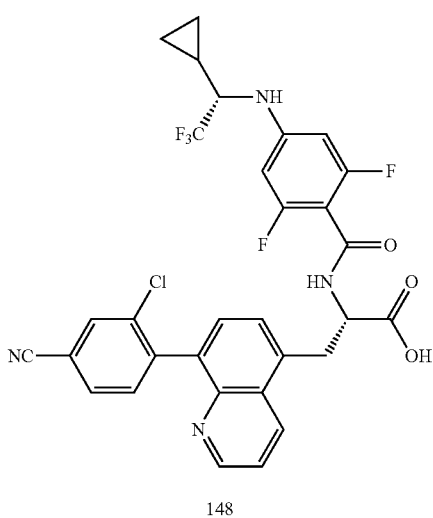

148

Example 355

Synthesis of methyl (S)-3-(8-((diphenylmethylene)amino)quinolin-5-yl)-2-(tritylamino)propanoate (355A): To a flame-dried 200 mL flask equipped with a stir bar was added 2,2'-bis(diphenylphosphino)-1,1'-binaphthalene (Binap ligand) (1.26 g, 2.029 mmol, 0.10 eq) in dioxane (101 mL, 0.2 M) and the flask was vacuum purged then flushed with $N_2$ 3 times. Bis(dibenzylideneacetone)palladium (Palladium dba) (0.93 g, 1.015 mmol, 0.05 eq) was added and the reaction was allowed to stir at room temperature for 10 minutes. Cesium carbonate (19.83 g, 60.87 mmol, 3 eq.), benzophenone imine (6.81 mL, 40.58 mmol, 2 eq.), and methyl (S)-3-(8-bromoquinolin-5-yl)-2-(tritylamino)propanoate (91A) (11.19 g, 20.29 mmol, 1 eq.) were added and the reaction was heated to 100° C. under a $N_2$ balloon and stirred overnight. The reaction was cooled to room temperature and quenched by the addition of water (100 mL). The reaction mixture was then extracted with ethyl acetate (100 mL, 3×), the combined organic phases were washed with brine (100 mL) and dry packed onto silica gel. Purification was performed via silica gel chromatography eluting with 20% EtOAc in hexanes until excess benzophenone imine was eluted (~20 min), then the percentage of EtOAc was increased to 25% in hexanes to elute product. Product containing fractions were concentrated under vacuum.

Synthesis of methyl (S)-3-(8-aminoquinolin-5-yl)-2-(tritylamino)propanoate (355B): 355A (11.19 g, 17.17 mmol, 1 eq.) was dissolved in THF (100 mL) to which was added hydroxylamine HCl (4.77 g, 68.67 mmol, 4 eq.), and sodium acetate trihydrate (14.02 g, 103.01 mmol, 6 eq.). MeOH (50 mL) was added and the reaction was allowed to stir at room temperature for 3 h. The reaction mixture was concentrated under vacuum and absorbed onto pre-packed silica gel. Purification was performed via silica gel chromatography using 20% EtOAc in Hexanes until excess hydroxyl-imine was eluted (~20 min), then the percentage of EtOAc was increased to 25% in hexanes to elute product. Product containing fractions were concentrated under vacuum.

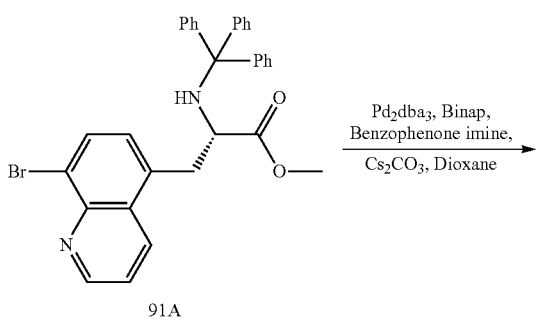

91A

-continued
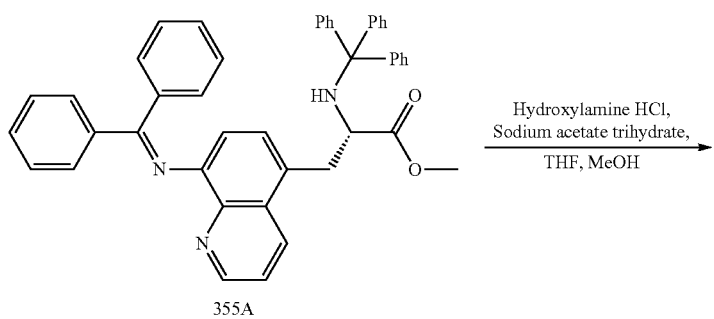
355A
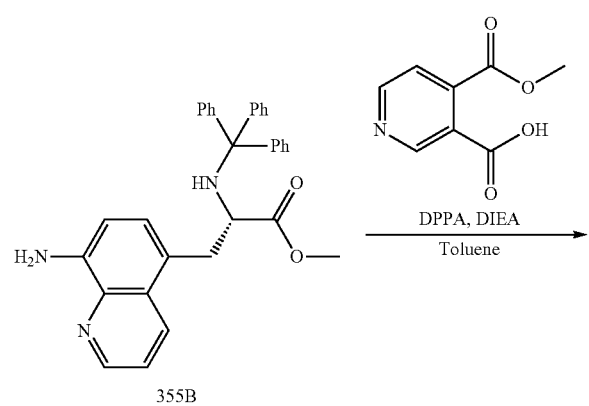
355B
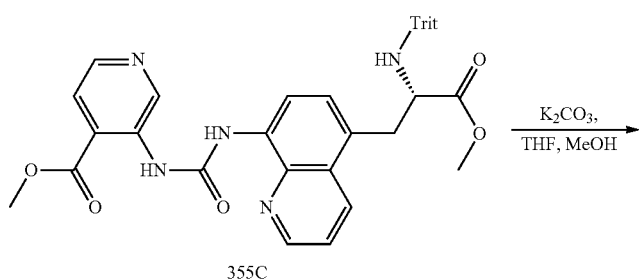
355C
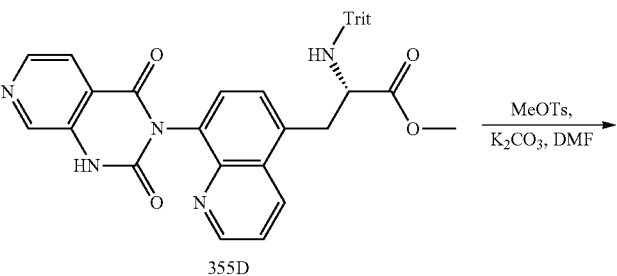
355D
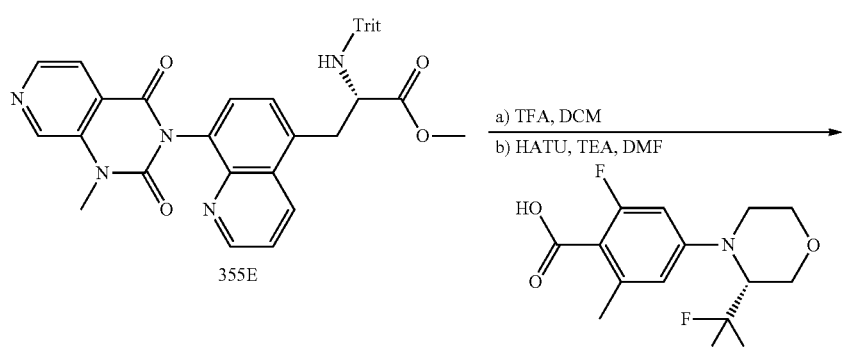
355E
141A

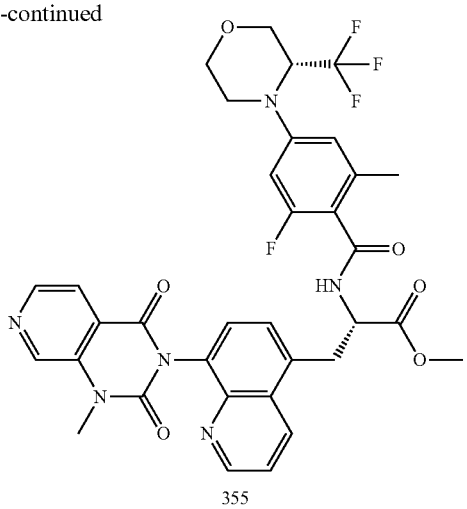

355

Synthesis of methyl (S)-3-(3-(5-(3-methoxy-3-oxo-2-(tritylamino)propyl)quinolin-8-yl)ureido)isonicotinate (355C): To a flame-dried flask equipped with a stir bar was added 4-methoxycarbonylpyridine-3-carboxylic acid (0.22 g, 1.23 mmol, 1.2 eq.), triethylamine (0.43 ml, 3.08 mmol, 3 eq.), DPPA (0.24 mL, 1.13 mmol, 1.1 eq.), 355B, and toluene (5.12 mL, 0.2 M). The reaction was affixed with a condenser (open to atmosphere) and heated to 50° C. for 2 h. The reaction was quenched with water (50 mL) and extracted with EtOAc (50 mL, 3×). The combined organic phases were washed with sat. sodium bicarbonate (25 mL), brine, and dried over anhydrous $Na_2SO_4$. Organic phases were concentrated and used without further purification.

Synthesis of methyl (S)-3-(8-(2,4-dioxo-1,4-dihydropyrido[3,4-d]pyrimidin-3(2H)-yl)quinolin-5-yl)-2-(tritylamino)propanoate (355D): 355C (0.68 g, 1.03 mmol, 1.0 eq.) was dissolved in THF (4 mL) and MeOH (4 mL), to which was added solid potassium carbonate (0.71 g, 5.13 mmol, 5 eq.). The reaction mixture was allowed to stir 1 h at room temperature. The reaction was diluted with water and sat. $NH_4Cl$ (4 mL), extracted with EtOAc (20 mL, 3×), washed with brine, and dried over $Na_2SO_4$. The combined organic phases were concentrated, EtOAc (~10 mL) was added, then hexanes was added dropwise under stirring to form a precipitate. The filtrate was collected and dried under high vacuum.

Synthesis of methyl (S)-3-(8-(1-methyl-2,4-dioxo-1,4-dihydropyrido[3,4-d]pyrimidin-3(2H)-yl)quinolin-5-yl)-2-(tritylamino)propanoate (355E): To a flame-dried flask was added Intermediate 355D (4.05 g, 6.396 mmol, 1.0 eq.), potassium carbonate (0.88 g, 6.4 mmol, 1.0 eq.) and DMF (32 mL, 0.2 M). The reaction mixture was stirred for 10 minutes at room temperature, then methyl tosylate (0.97 mL, 6.4 mmol, 1.0 eq.) was added and the reaction was allowed to stir overnight at room temperature. The reaction was concentrated and purified via silica gel chromatography eluting with DCM/MeOH 0-5%.

Synthesis of methyl (S)-2-(2-fluoro-6-methyl-4-((R)-3-(trifluoromethyl) morpholino)benzamido)-3-(8-(1-methyl-2,4-dioxo-1,4-dihydropyrido[3,4-d]pyrimidin-3(2H)-yl)quinolin-5-yl)propanoate (355): 355E (1.49 g, 2.29 mmol, 1 eq.) was dissolved in DCM (51 mL) and triethylsilane (0.44 mL, 2.75 mmol, 1.2 eq.), and TFA (0.53 ml, 6.88 mmol, 3 eq.) were added. The reaction was allowed to stir at room temperature for 2 h, then concentrated. The resulting material was re-suspended in DCM and concentrated again under vacuum to remove residual TFA. The material was used without further purification. The resulting material (1.47 g, 2.31 mmol, 1.0 eq.), 141A (0.85 g, 2.78 mmol, 1.2 eq.), and HATU (1.06 g, 2.78 mmol, 1.2 eq.) were added to a vial and dissolved in DMF (10 mL). DIEA (2.42 mL, 13.89 mmol, 6.0 eq.) was added and the reaction was allowed to stir at room temperature for 2 h. The reaction was quenched with water and extracted with EtOAc, organic phases were washed with brine, and dried over $Na_2SO_4$. The organic phases were concentrated and purified via silica gel chromatography using DCM/MeOH 0-5%. ES/MS m/z [M+H]: 695.198; 1H NMR (400 MHz, DMSO-d6) δ 9.05 (s, 1H), 8.95-8.80 (m, 2H), 8.71 (dd, J=8.7, 1.6 Hz, 1H), 8.60 (dd, J=4.9, 1.4 Hz, 1H), 7.92 (ddd, J=4.8, 3.8, 0.7 Hz, 1H), 7.77 (d, J=7.6 Hz, 1H), 7.75-7.63 (m, 2H), 6.73-6.63 (m, 2H), 4.90-4.72 (m, 2H), 4.14 (d, J=12.6 Hz, 1H), 3.94 (dd, J=11.4, 3.6 Hz, 1H), 3.83-3.69 (m, 3H), 3.66 (d, J=2.5 Hz, 3H), 3.51 (ddd, J=25.5, 13.6, 9.8 Hz, 2H), 3.35 (d, J=12.2 Hz, 1H), 3.26 (d, J=12.3 Hz, 1H), 2.09-1.95 (m, 3H).

Example 356

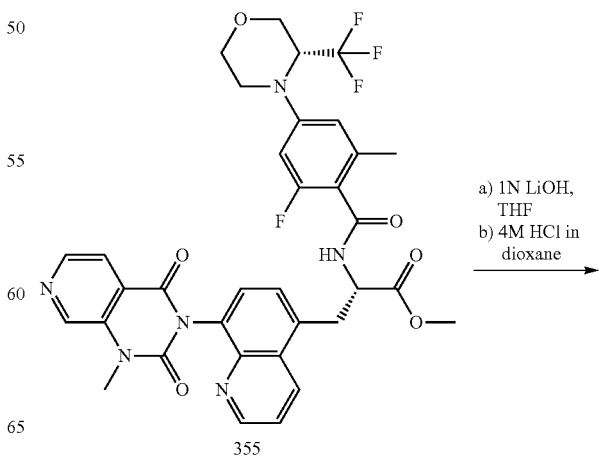

355 a) 1N LiOH, THF
b) 4M HCl in dioxane
→

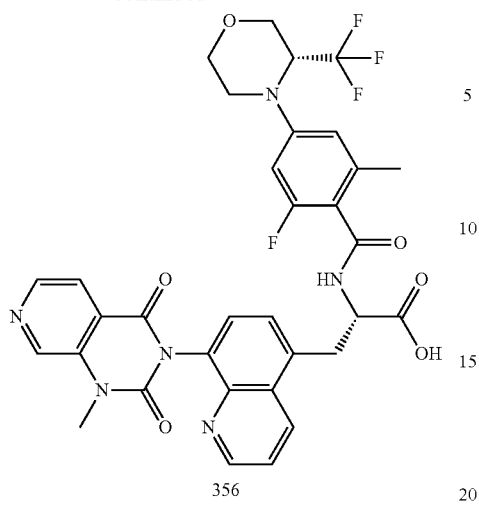

356

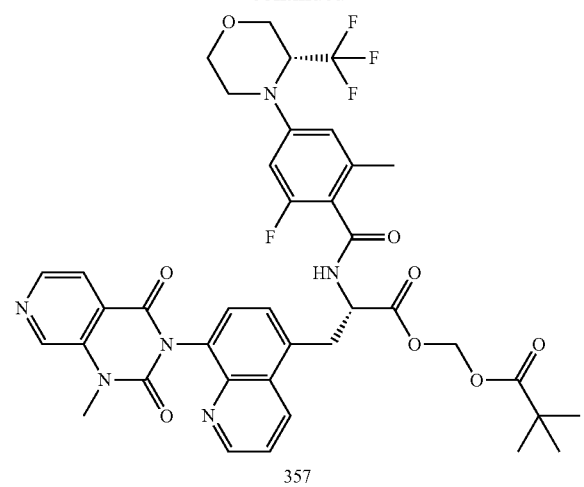

357

(S)-2-(2-fluoro-6-methyl-4-((R)-3-(trifluoromethyl)morpholino)benzamido)-3-(8-(1-methyl-2,4-dioxo-1,4-dihydropyrido[3,4-d]pyrimidin-3(2H)-yl)quinolin-5-yl)propanoic acid (356): 355 (0.49 g, 0.70 mmol, 1.0 eq.) was dissolved in THF (10 mL) and 1M LiOH (3.5 ml, 5 eq.) was added. The reaction mixture was allowed to stir at room temperature for 2 h. 4 M HCl in dioxane (1.75 mL, 10 eq.) was then added to re-cyclize, and the reaction mixture was allowed to stir for 1 h. The reaction was concentrated and purified via reverse phase HPLC, lyophilized to afford the title compound as a mono-TFA salt. ES/MS (m/z) [M+H]: 681.151 1H NMR (400 MHz, DMSO-d6) δ 9.05 (s, 1H), 8.92-8.77 (m, 2H), 8.68 (d, J=8.6 Hz, 1H), 8.60 (d, J=5.0 Hz, 1H), 7.91 (t, J=4.3 Hz, 1H), 7.76 (d, J=7.6 Hz, 1H), 7.67 (dd, J=8.3, 4.5 Hz, 2H), 6.74-6.58 (m, 2H), 5.00-4.59 (m, 2H), 4.14 (d, J=12.6 Hz, 1H), 3.99-3.91 (m, 1H), 3.66 (d, J=2.4 Hz, 4H), 3.59-3.40 (m, 1H), 3.31 (dd, J=35.1, 12.3 Hz, 3H), 2.03 (s, 3H).

(((S)-2-(2-fluoro-6-methyl-4-((R)-3-(trifluoromethyl)morpholino)benzamido)-3-(8-(1-methyl-2,4-dioxo-1,4-dihydropyrido[3,4-d]pyrimidin-3(2H)-yl)quinolin-5-yl)propanoyl)oxy)methyl pivalate (357): 356 (611 mg, 0.898 mmol) was dissolved in acetonitrile (44 mL), and added iodomethyl 2,2-dimethylpropanoate (434.6 mg, 1.8 mmol), and N,N-diisopropylethylamine (0.31 mL, 2 mmol) and stirred for 1 h. Solvents were removed on a rotary evaporator and the mixture was reverse phase chromatographed to provide the title compound as a TFA salt. ES/MS (m/z) 735.063 [M+H]; 1H NMR (400 MHz, DMSO-d6) δ 9.15-9.00 (m, 2H), 8.85 (d, J=3.9 Hz, 1H), 8.67-8.57 (m, 2H), 7.91 (ddd, J=5.0, 3.1, 0.8 Hz, 1H), 7.76 (d, J=7.5 Hz, 1H), 7.73-7.61 (m, 2H), 5.83 (s, 2H), 4.85 (d, J=9.2 Hz, 2H), 4.14 (d, J=12.6 Hz, 1H), 4.06-3.88 (m, 1H), 3.84-3.68 (m, 2H), 3.65 (d, J=2.2 Hz, 3H), 3.53 (dt, J=14.8, 9.7 Hz, 2H), 3.36 (d, J=12.3 Hz, 1H), 3.26 (d, J=12.1 Hz, 1H), 2.03 (s, 3H), 1.18 (s, 9H).

Example 357

Example 358

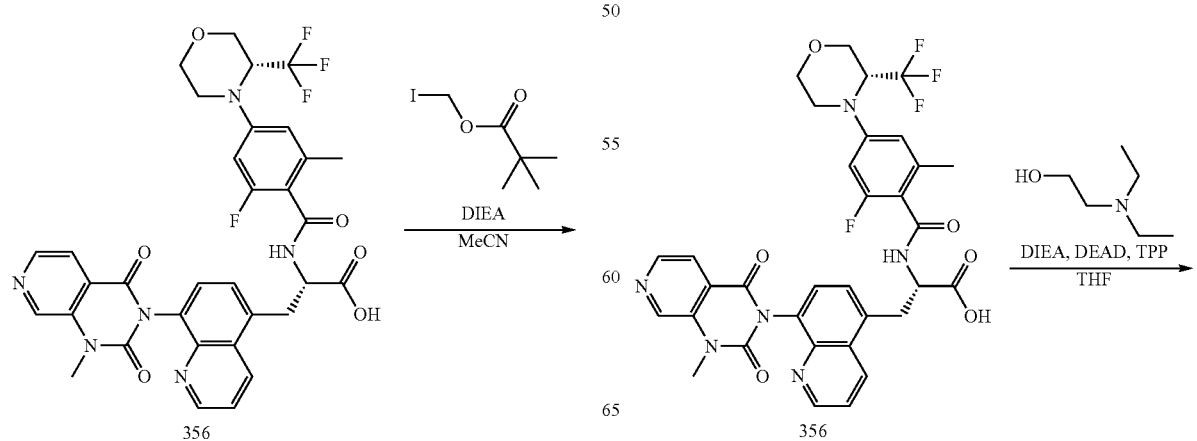

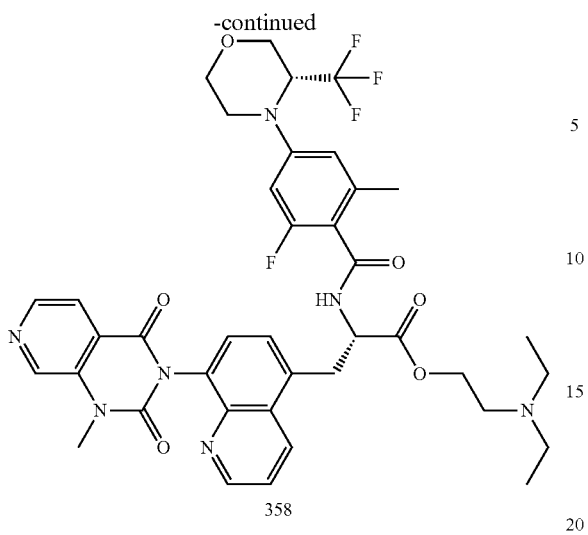

358

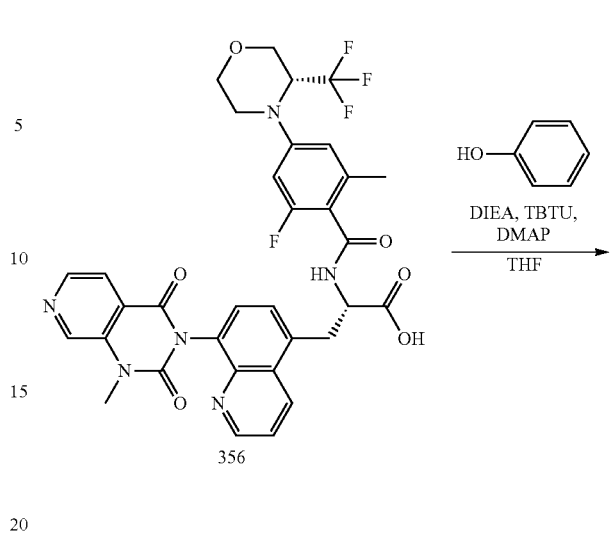

356

2-(Diethylamino)ethyl (S)-2-(2-fluoro-6-methyl-4-((R)-3-(trifluoromethyl) morpholino)benzamido)-3-(8-(1-methyl-2,4-dioxo-1,4-dihydropyrido[3,4-d]pyrimidin-3(2H)-yl)quinolin-5-yl)propanoate (358): To 356 (45 mg, 0.066 mmol), was added THF (3 mL), 2-(diethylamino) ethanol (23.24 mg, 0.2 mmol), triphenyl phosphine (0.05 g, 0.2 mmol), diethyl azodicarboxylate, 95% (0.1 ml, 0.2 mmol), and DIEA (0.41 ml, 2.28 mmol). The mixture was stirred for 1 h, then solvents were removed on a rotary evaporator, and the mixture was reverse phase chromatographed to provide the title compound as a TFA salt after lyophilization. ES/MS (m/z) 780.300 [M+H]; 1H NMR (400 MHz, Chloroform-d) δ 9.28 (dt, J=4.8, 1.6 Hz, 1H), 9.20 (ddd, J=8.7, 4.6, 1.5 Hz, 1H), 8.90 (d, J=2.2 Hz, 1H), 8.62 (dd, J=5.0, 1.6 Hz, 1H), 8.04 (dd, J=24.7, 5.0 Hz, 1H), 7.83 (dd, J=8.6, 4.7 Hz, 1H), 7.75 (d, J=1.2 Hz, 2H), 7.46 (d, J=7.0 Hz, 1H), 6.49 (d, J=2.4 Hz, 1H), 6.43-6.27 (m, 1H), 5.18 (q, J=7.6 Hz, 1H), 4.97 (dd, J=12.8, 6.4 Hz, 1H), 4.53 (td, J=9.2, 7.8, 4.6 Hz, 1H), 4.31 (d, J=12.4 Hz, 1H), 4.16 (ddt, J=19.3, 8.0, 3.3 Hz, 1H), 4.10-3.90 (m, 2H), 3.82 (dd, J=12.5, 2.2 Hz, 1H), 3.72 (d, J=9.4 Hz, 3H), 3.60 (ddt, J=32.1, 17.2, 8.3 Hz, 3H), 3.28 (d, J=12.0 Hz, 1H), 3.22-3.09 (m, 1H), 3.03 (s, 4H), 2.32 (s, 3H), 1.49-1.10 (m, 9H), 1.02 (d, J=7.6 Hz, 2H).

Example 359

Phenyl (S)-2-(2-fluoro-6-methyl-4-((R)-3-(trifluoromethyl)morpholino)benzamido)-3-(8-(1-methyl-2,4-dioxo-1,4-dihydropyrido[3,4-d]pyrimidin-3(2H)-yl)quinolin-5-yl)propanoate (359): 356 (567 mg, 0.833 mmol) was dissolved in THF (5 mL), phenol (0.12 g, 1.25 mmol), TBTU (0.4 g, 1.25 mmol), DIEA (0.44 mL, 2.5 mmol), and DMAP (0.1 g, 0.83 mmol) were added, and the reaction mixture was stirred for 1 h. The reaction mixture was then loaded directly onto silica and chromatographed eluting with ethylacetate in methanol (0-10%) to provide the title compound. ES/MS (m/z) 757.213 [M+H]; 1H NMR (400 MHz, DMSO-d6) δ 9.22 (d, J=7.1 Hz, 1H), 9.05 (s, 1H), 8.89-8.83 (m, 1H), 8.76 (d, J=8.6 Hz, 1H), 8.61 (d, J=5.0 Hz, 1H), 7.93 (d, J=5.0 Hz, 1H), 7.85-7.77 (m, 1H), 7.77-7.71 (m, 1H), 7.71-7.64 (m, 1H), 7.48-7.38 (m, 2H), 7.31-7.23 (m, 1H), 7.10-7.01 (m, 2H), 6.77-6.69 (m, 1H), 6.68 (s, 1H), 5.09-4.99 (m, 1H), 4.91-4.79 (m, 1H), 4.15 (d, J=12.7 Hz, 1H), 4.00-3.89 (m, 1H), 3.89-3.82 (m, 2H), 3.67 (s, 3H), 3.61-3.49 (m, 2H), 3.43-3.32 (m, 1H), 3.32-3.19 (m, 1H), 2.15-2.05 (m, 3H).

359

Example 360

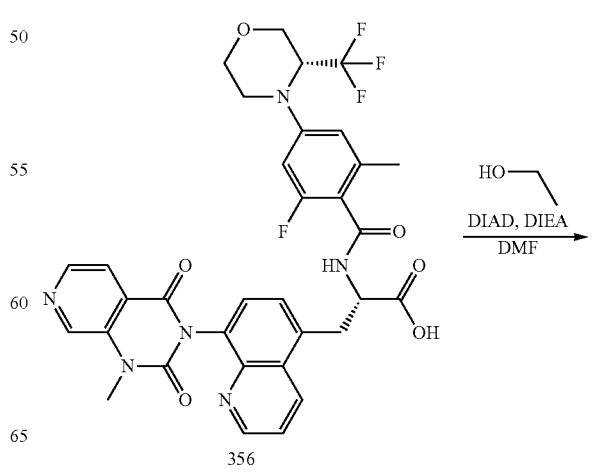

356

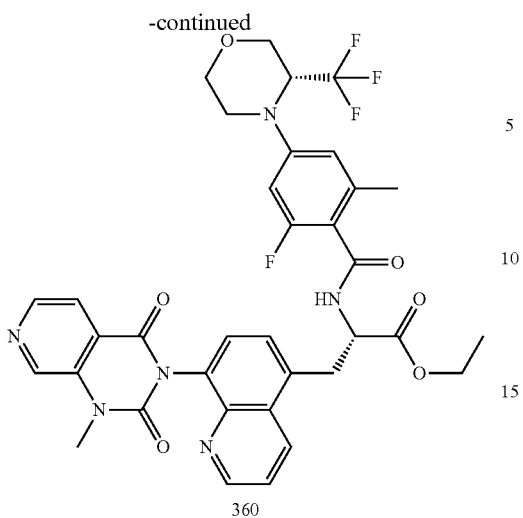

360

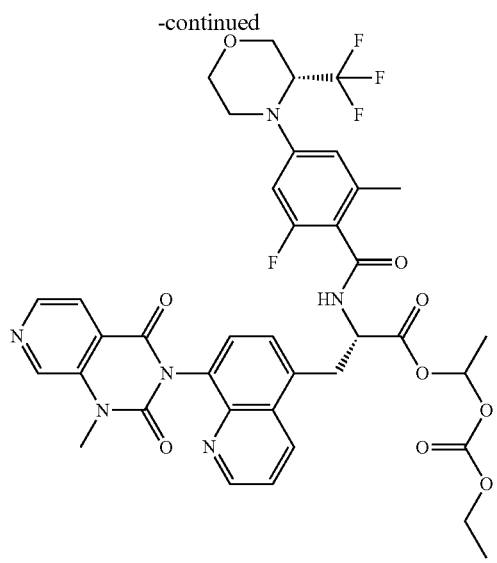

361

Ethyl (S)-2-(2-fluoro-6-methyl-4-((R)-3-(trifluoromethyl)morpholino)benzamido)-3-(8-(1-methyl-2,4-dioxo-1,4-dihydropyrido[3,4-d]pyrimidin-3(2H)-yl)quinolin-5-yl)propanoate (360): To a solution of 356 (150 mg, 0.22 mmol) in DMF (1.0 mL) was added triphenylphosphine (173 mg, 0.66 mmol) followed by DIEA (117 μL, 0.66 mmol) and ethanol (129 μL, 2.2 mmol). DIAD (217 μL, 1.1 mmol) was then added and the reaction mixture was allowed to stir for 2 hours. The reaction mixture was then diluted with EtOAc and washed with water, 10% citric acid, saturated sodium bicarbonate, and brine followed by drying the combined organics over sodium sulfate. After filtration, the solvent was removed under reduced pressure and the product was purified by normal phase using an elution gradient of 0-30%, 30-60%, and 60-100% 9:1 DCM:MeOH in DCM. ES/MS (m/z) [M+H]: 709.2. 1H NMR (400 MHz, DMSO-d6) δ 9.04 (s, 1H), 8.99 (d, J=7.7 Hz, 1H), 8.84 (dd, J=4.2, 1.4 Hz, 1H), 8.64 (dd, J=8.7, 1.6 Hz, 1H), 8.60 (d, J=4.9 Hz, 1H), 7.91 (dd, J=5.0, 2.2 Hz, 1H), 7.75 (d, J=7.5 Hz, 1H), 7.66 (dt, J=8.6, 2.5 Hz, 2H), 6.76-6.63 (m, 2H), 4.82 (td, J=14.4, 12.1, 5.3 Hz, 2H), 4.20-4.04 (m, 3H), 3.95 (dd, J=11.5, 3.6 Hz, 1H), 3.80-3.66 (m, 2H), 3.65 (d, J=1.6 Hz, 3H), 3.60-3.46 (m, 2H), 3.36 (d, J=13.7 Hz, 1H), 3.31-3.18 (m, 1H), 2.07 (s, 3H), 1.16 (td, J=7.1, 1.1 Hz, 3H).

Example 361

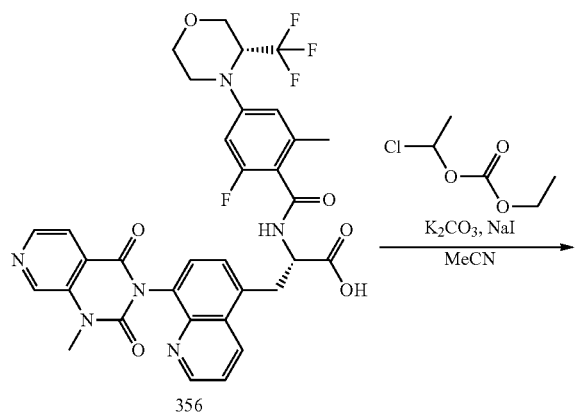

1-((Ethoxycarbonyl)oxy)ethyl (2S)-2-(2-fluoro-6-methyl-4-((R)-3-(trifluoromethyl) morpholino)benzamido)-3-(8-(1-methyl-2,4-dioxo-1,4-dihydropyrido[3,4-d]pyrimidin-3(2H)-yl)quinolin-5-yl)propanoate (361): To a solution of 356 (30 mg, 0.044 mmol) in DMF (1 mL) was added potassium carbonate (8.2 mg, 0.132 mmol), followed by sodium iodide (26 mg, 0.176 mmol) and 1-chloroethyl ethyl carbonate (20 mg, 0.132 mmol). The reaction mixture was heated to 65° C. for 2 h. Then the reaction mixture was cooled to RT and filtered. The resulting filtrate was purified by reverse phase HPLC to yield the title compound as a TFA salt. ES/MS (m/z) [M+H]: 797.2 1H NMR (400 MHz, DMSO-d6) δ 9.05 (d, J=5.5 Hz, 2H), 8.90-8.81 (m, 1H), 8.70-8.57 (m, 2H), 7.91 (d, J=5.1 Hz, 1H), 7.76 (d, J=7.6 Hz, 1H), 7.67 (d, J=7.9 Hz, 2H), 6.74-6.64 (m, 2H), 4.86 (s, 2H), 4.35-4.06 (m, 3H), 3.95 (d, J=11.0 Hz, 1H), 3.74 (d, J=13.2 Hz, 6H), 3.53 (q, J=14.3, 13.3 Hz, 2H), 3.42-3.13 (m, 2H), 2.03 (d, J=20.9 Hz, 3H), 1.53 (d, J=5.4 Hz, 1H), 1.38 (d, J=5.4 Hz, 2H), 1.23 (t, J=7.1 Hz, 3H).

Example 362

(R)-tetrahydrofuran-2-yl)methyl (S)-2-(2-fluoro-6-methyl-4-((R)-3-(trifluoromethyl) morpholino)benzamido)-3-(8-(1-methyl-2,4-dioxo-1,4-dihydropyrido[3,4-d]pyrimidin-3(2H)-yl)quinolin-5-yl)propanoate (362): 356 (0.52 g, 0.76 mmol) was dissolved in DMF (3 mL), and triphenylphosphine (0.6 g, 2.28 mmol), diisopropyl azodicarboxylate (0.46 mL, 2.28 mmol), (2R)-tetrahydrofuran-2-yl] methanol (0.23 g, 2.28 mmol), and diisopropylethylamine (0.41 ml, 2.28 mmol) were added. The mixture was stirred for 1 h and chromatographed on silica gel eluting with ethyl acetate and methanol (0-10%) to provide the title compound. ES/MS (m/z) 735.063 [M+H]; 1H NMR (400 MHz, DMSO-d6) δ 9.02 (d, J=7.5 Hz, 1H), 6.88 (d, J=7.6 Hz, 1H), 6.80 (d, J=11.8 Hz, 3H), 5.05-4.84 (m, 1H), 4.58 (q, J=7.5, 6.9 Hz, 1H), 4.17 (d, J=12.7 Hz, 1H), 4.09-3.92 (m, 7H), 3.74 (q, J=6.0 Hz, 2H), 3.70-3.54 (m, 2H), 3.24 (t, J=12.5 Hz, 1H), 3.10 (dd, J=14.5, 5.1 Hz, 1H), 2.96 (dd, J=14.4, 9.3 Hz, 1H), 2.76 (d, J=5.3 Hz, 2H), 2.32 (s, 3H), 2.26 (s, 3H), 1.86 (ddq, J=40.9, 13.8, 6.4 Hz, 6H), 1.57 (q, J=8.7, 8.1 Hz, 1H), 1.26 (d, J=12.8 Hz, 2H), 0.97-0.74 (m, 2H).

305

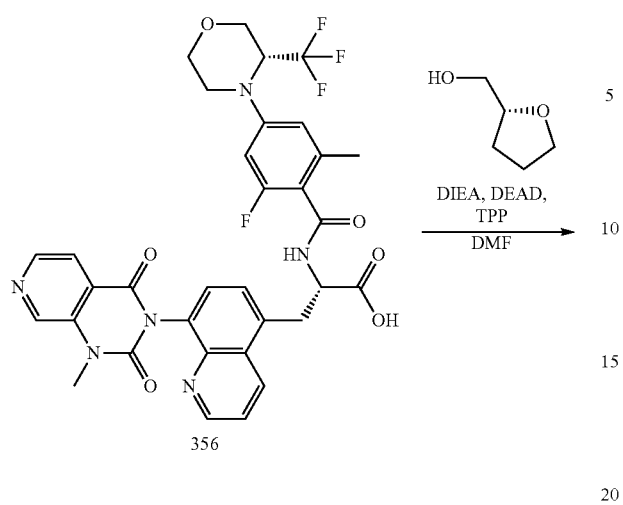

356

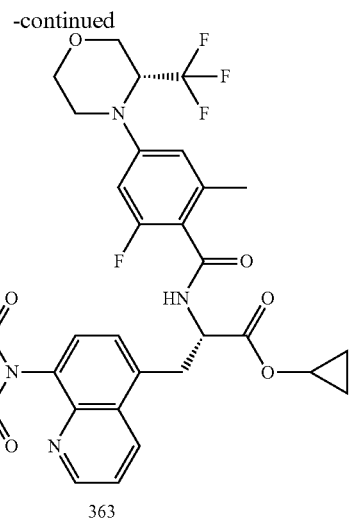

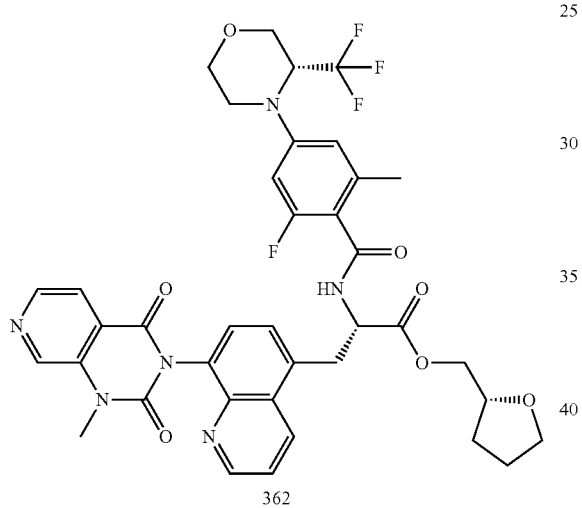

362

Example 363

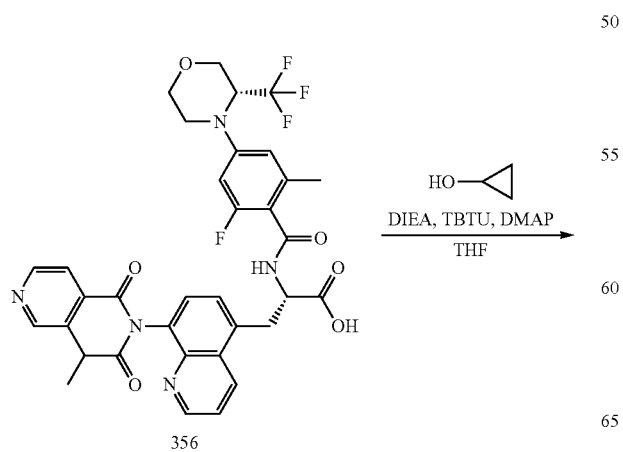

356

306

-continued

363

Cyclopropyl (S)-2-(2-fluoro-6-methyl-4-((R)-3-(trifluoromethyl) morpholino) benzamido)-3-(8-(1-methyl-2,4-dioxo-1,4-dihydropyrido[3,4-d]pyrimidin-3(2H)-yl)quinolin-5-yl)propanoate (363): To a solution of 356 (0.650 g, 0.955 mmol) in THF (4.80 mL) was added cyclopropyl alcohol (0.166 g, 2.87 mmol), DMAP (0.117 g, 0.955 mmol), DIEA (0.370 g, 2.87 mmol), and TBTU (0.920 g, 2.87 mmol) and the mixture was stirred at 50° C. for 25 min. Upon completion, the reaction mixture was diluted with EtOAc, and washed with water (×2). The organic layer was then concentrated under reduced pressure and the residue was purified using flash chromatography eluting with EtOAc in hexanes 0-100%, followed by MeOH in EtOAc 0-50%. Appropriate fractions were combined and concentrated to afford the product. The product was then dissolved in DMSO (12 mL) and purified using reverse phase HPLC to afford the title compound. ES/MS (m/z) 721.3 [M+H]; 1H NMR (400 MHz, DMSO-d6) δ 9.04 (s, 1H), 8.98 (d, J=7.6 Hz, 1H), 8.83 (d, J=4.2 Hz, 1H), 8.61 (dd, J=11.5, 6.8 Hz, 2H), 7.91 (d, J=4.9 Hz, 1H), 7.75 (d, J=7.6 Hz, 1H), 7.72-7.59 (m, 2H), 6.79-6.61 (m, 2H), 4.79 (dd, J=21.2, 12.1 Hz, 2H), 4.22-4.05 (m, 2H), 4.05-3.87 (m, 1H), 3.80-3.43 (m, 7H), 3.42-3.21 (m, 4H), 3.21-3.10 (m, 1H), 2.69 (d, J=1.3 Hz, 1H), 2.05 (d, J=7.2 Hz, 3H), 0.80-0.48 (m, 3H).

Example 364

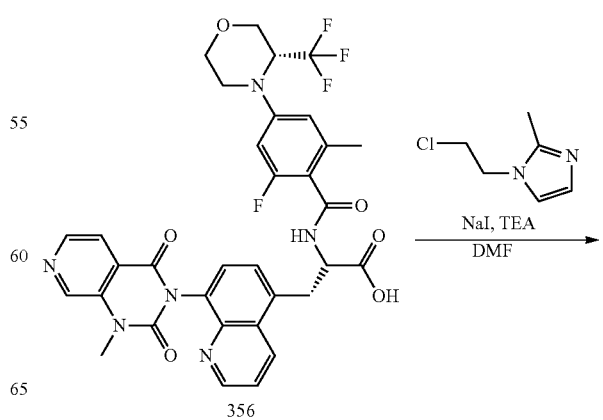

356

307

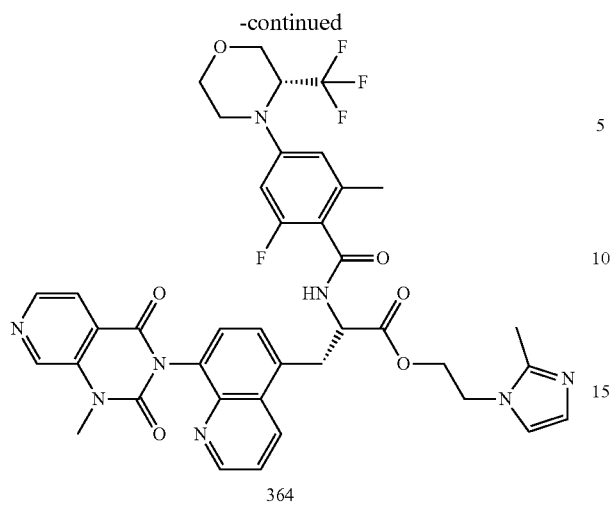

364

308

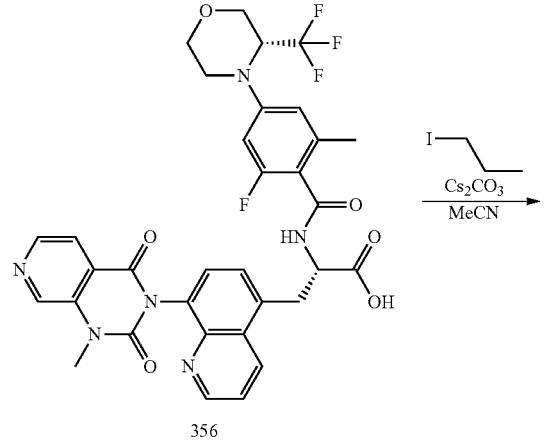

356

2-(2-Methyl-1H-imidazol-1-yl)ethyl (S)-2-(2-fluoro-6-methyl-4-((R)-3-(trifluoromethyl) morpholino)benzamido)-3-(8-(1-methyl-2,4-dioxo-1,4-dihydropyrido[3,4-d]pyrimidin-3(2H)-yl)quinolin-5-yl)propanoate (364): To a stirred solution of 356 (438.6 mg, 0.64 mmol) and 1-(2-chloroethyl)-2-methyl-1H-imidazole (279.6 mg, 1.93 mmol) in DMF (4.3 mL) was added sodium iodide (289.8 mg, 1.93 mmol), followed by triethylamine (0.27 mL, 1.93 mmol). The reaction mixture was heated using microwave irradiation at 120° C. for 45 minutes. After cooling to RT, the reaction was concentrated under reduced pressure and the material was purified using reverse phase prep HPLC to afford the title compound. MS (m/z) 789.3 [M+H]$^+$. 1 H NMR (400 MHz, DMSO-d6) δ 9.04 (d, J=8.2 Hz, 2H), 8.87 (d, J=4.1 Hz, 1H), 8.64-8.57 (m, 2H), 7.91 (t, J=4.8 Hz, 1H), 7.77 (d, 1H), 7.71-7.59 (m, 3H), 7.56 (s, 1H), 6.74-6.65 (m, 2H), 4.90-4.76 (m, 2H), 4.52-4.42 (m, 1H), 4.41-4.28 (m, 3H), 4.15 (d, J=12.6 Hz, 1H), 3.94 (d, J=3.5 Hz, 1H), 3.73 (d, J=12.7 Hz, 1H), 3.69-3.60 (m, 4H), 3.59-3.47 (m, 2H), 3.34 (d, 1H), 3.25 (t, 1H), 2.53 (s, 3H), 2.03 (s, 3H).

Example 365

Propyl (S)-2-(2-fluoro-6-methyl-4-((R)-3-(trifluoromethyl)morpholino)benzamido)-3-(8-(1-methyl-2,4-dioxo-1,4-dihydropyrido[3,4-d]pyrimidin-3(2H)-yl)quinolin-5-yl)propanoate (365): To a stirred solution of 356 (30 mg, 0.044 mmol) in acetonitrile (1 mL) was added cesium carbonate (72 mg, 0.22 mmol) and n-propyl iodide (15 mg, 0.088 mmol). The mixture was heated to 50° C. for 16 hours. The mixture was cooled to ambient temperature, diluted with dimethylsulfoxide and trifluoroacetic acid, then the mixture was purified by preparatory HPLC to yield the title compound. ES/MS (m/z) 723.3 (M+H)+0.1H NMR (400 MHz, DMSO-d6) δ 9.05 (s, 1H), 8.99 (d, J=7.8 Hz, 1H), 8.84 (d, J=4.2 Hz, 1H), 8.66 (d, J=8.6 Hz, 1H), 8.60 (d, J=5.1 Hz, 1H), 7.91 (dd, J=4.9, 2.4 Hz, 1H), 7.76 (d, J=7.5 Hz, 1H), 7.67 (dd, J=8.0, 2.7 Hz, 2H), 6.71 (dd, J=13.7, 5.1 Hz, 1H), 6.66 (s, 1H), 4.85 (s, 2H), 4.15 (d, J=12.6 Hz, 1H), 4.05 (q, J=6.3 Hz, 2H), 4.00-3.89 (m, 1H), 3.73 (d, J=13.5 Hz, 2H), 3.66 (s, 3H), 3.54 (t, J=7.7 Hz, 2H), 3.36 (d, J=12.4 Hz, 1H), 3.25 (t, J=12.1 Hz, 1H), 2.05 (d, J=6.8 Hz, 3H), 1.58 (h, J=7.2 Hz, 2H), 0.88 (t, J=7.4 Hz, 3H).

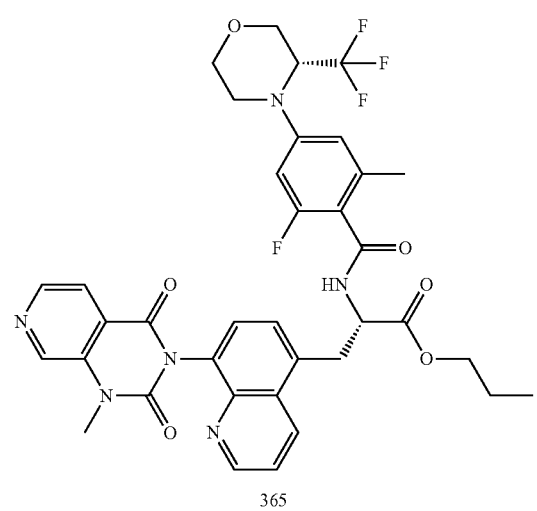

365

Example 366

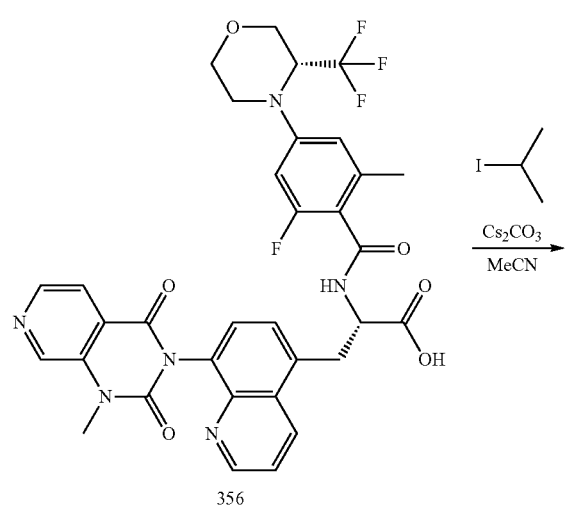

356

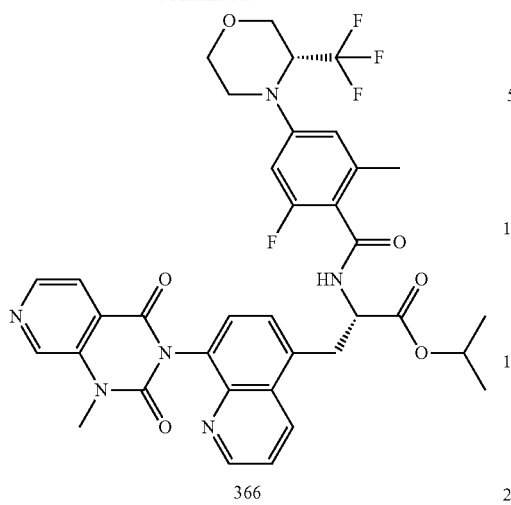

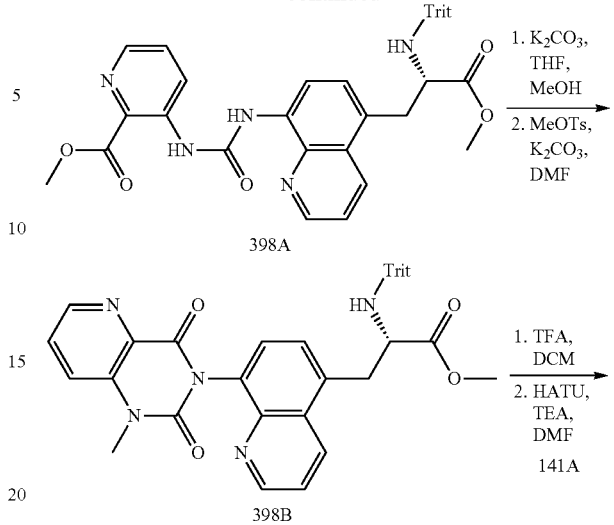

Isopropyl (S)-2-(2-fluoro-6-methyl-4-((R)-3-(trifluoromethyl)morpholino)benzamido)-3-(8-(1-methyl-2,4-dioxo-1,4-dihydropyrido[3,4-d]pyrimidin-3(2H)-yl)quinolin-5-yl)propanoate (366): To a stirred solution of 356 (30 mg, 0.044 mmol) in acetonitrile (1 mL) was added cesium carbonate (72 mg, 0.22 mmol) and isopropyl iodide (15 mg, 0.088 mmol). The mixture was heated to 50° C. for 16 hours. The mixture was cooled to ambient temperature, diluted with dimethylsulfoxide and trifluoroacetic acid, then the mixture was purified by preparatory HPLC to yield 366. ES/MS (m/z) 723.3 (M+H)+. 1H NMR (400 MHz, DMSO-d6) δ 9.05 (s, 1H), 8.97 (d, J=7.7 Hz, 1H), 8.84 (d, J=4.1 Hz, 1H), 8.65 (d, J=8.7 Hz, 1H), 8.60 (d, J=5.0 Hz, 1H), 7.91 (d, J=5.0 Hz, 1H), 7.76 (d, J=7.5 Hz, 1H), 7.71-7.62 (m, 2H), 6.71 (d, J=13.1 Hz, 1H), 6.68-6.63 (m, 1H), 4.97-4.90 (m, 1H), 4.84 (dd, J=29.2, 20.4 Hz, 2H), 4.15 (d, J=12.7 Hz, 1H), 3.95 (d, J=11.3 Hz, 1H), 3.73 (d, J=13.7 Hz, 2H), 3.66 (s, 3H), 3.53 (q, J=13.5, 11.7 Hz, 2H), 3.36 (d, J=12.3 Hz, 1H), 3.27 (d, J=12.5 Hz, 1H), 2.08 (d, J=6.7 Hz, 3H), 1.22 (d, J=6.2 Hz, 3H), 1.13 (d, J=6.3 Hz, 3H).

Example 398

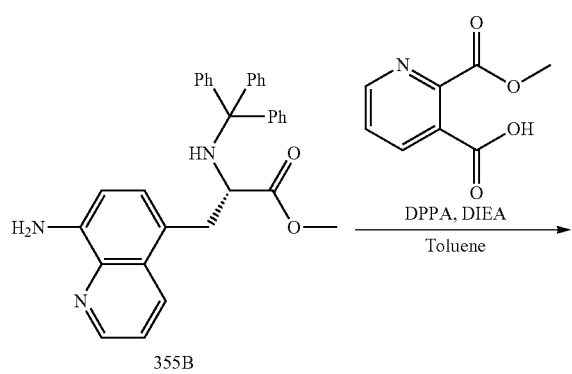

Synthesis of Methyl (S)-3-(3-(5-(3-methoxy-3-oxo-2-(tritylamino)propyl)quinolin-8-yl)ureido)picolinate (398A): To a vial was added 355B (50 mg, 0.1 mmol), 2-methoxycarbonyl pyridine-3-carboxylic acid (27.86 mg, 0.15 mmol), triethylamine (0.04 mL, 0.31 mmol), and dissolved in 0.2 M toluene (0.51 ml). DPPA (0.03 mL, 0.12 mmol) was added and reaction mixture was sealed and heated to 90° C. for 20 min. The reaction was quenched with water (20 mL), extracted with EtOAc (3×40 mL), organic phases were washed with brine (20 mL), and concentrated to afford the title compound.

Synthesis of methyl (S)-3-(8-(1-methyl-2,4-dioxo-1,4-dihydropyrido[3,2-d]pyrimidin-3(2H)-yl)quinolin-5-yl)-2-(tritylamino)propanoate (398B): The title compound was prepared according to the method presented for the synthesis of compound 355E, starting with 398A.

Methyl (S)-2-(2-fluoro-6-methyl-4-((R)-3-(trifluoromethyl)morpholino)benzamido)-3-(8-(1-methyl-2,4-dioxo-1,4-dihydropyrido[3,2-d]pyrimidin-3(2H)-yl)quinolin-5-yl)propanoate (398): The title compound was prepared according to the method presented for the synthesis of compound 355, starting with 398B. ES/MS (m/z) 695.2 (M+H)+. 1H NMR (400 MHz, DMSO-d6) δ 13.11-12.65 (s, 1H), 8.87 (d, J=8.1 Hz, 1H), 8.85-8.83 (m, 1H), 8.73-8.65 (m, 1H), 8.61 (ddd, J=4.4, 2.3, 1.2 Hz, 1H), 8.08 (dd, J=8.8, 1.3 Hz, 1H), 7.87 (dd, J=8.6, 4.4 Hz, 1H), 7.75 (d, J=7.6 Hz, 1H), 7.71-7.63 (m, 2H), 6.69 (d, J=13.4 Hz, 1H), 6.65 (s, 1H), 4.88-4.80 (m, 1H), 4.77 (d, J=11.5 Hz, 1H), 4.14 (d, J=12.6 Hz, 1H), 3.94 (dd, J=11.4, 3.6 Hz, 1H), 3.81-3.68 (m, 2H), 3.57 (d, J=2.5 Hz, 3H), 3.55-3.42 (m, 2H), 3.35 (d, J=12.4 Hz, 1H), 3.25 (t, J=12.1 Hz, 1H), 2.03 (d, J=2.5 Hz, 3H).

Hz, 1H), 7.76 (d, J=7.5 Hz, 1H), 7.67 (dt, J=7.8, 3.3 Hz, 2H), 6.70 (dd, J=13.0, 2.3 Hz, 1H), 6.66 (d, J=2.4 Hz, 1H), 4.86 (d, J=4.3 Hz, 1H), 4.83 (m, 1H), 4.14 (d, J=12.6 Hz, 1H), 3.95 (dd, J=11.3, 3.7 Hz, 1H), 3.78-3.70 (m, 2H), 3.69 (d, J=3.6 Hz, 3H), 3.57 (d, J=2.4 Hz, 3H), 3.53 (d, J=3.7 Hz, 1H), 3.51 (d, J=9.9 Hz, 1H), 3.36 (d, J=12.3 Hz, 1H), 3.25 (t, J=12.2 Hz, 1H), 2.05 (s, 3H).

Example 399

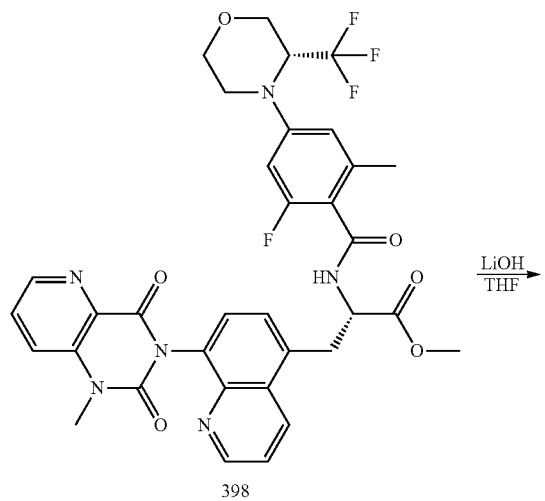

Example 400

Synthesis of methyl (S)-4-(3-(5-(3-methoxy-3-oxo-2-(tritylamino)propyl)quinolin-8-yl)ureido)nicotinate (400A): Phosgene (15% solution in toluene, 2.18 mL, 3.06 mmol, 2 eq.), was added to a flame-dried vial containing a solution of methyl 4-aminonicotinate (0.466 g, 3.06 mmol, 2 eq.), DIEA (0.8 mL, 4.59 mmol, 3 eq.), and DCM (2 mL). The combined reagents were stirred at room temperature for 1 h, then 355B (0.746 g, 1.53 mmol, 1 eq.) was added. The reaction was stirred at room temperature for 1 h. The reaction mixture was then adsorbed onto silica gel and purified by column chromatography using methanol in DCM as the eluent (0-5%). Appropriate fractions were then combined and concentrated under vacuum to afford the title compound.

Synthesis of methyl (S)-3-(8-(1-methyl-2,4-dioxo-1,4-dihydropyrido[4,3-d]pyrimidin-3(2H)-yl)quinolin-5-yl)-2-(tritylamino)propanoate (400B): The title compound was prepared according to the method presented for the synthesis of compound 355E, starting with 400A.

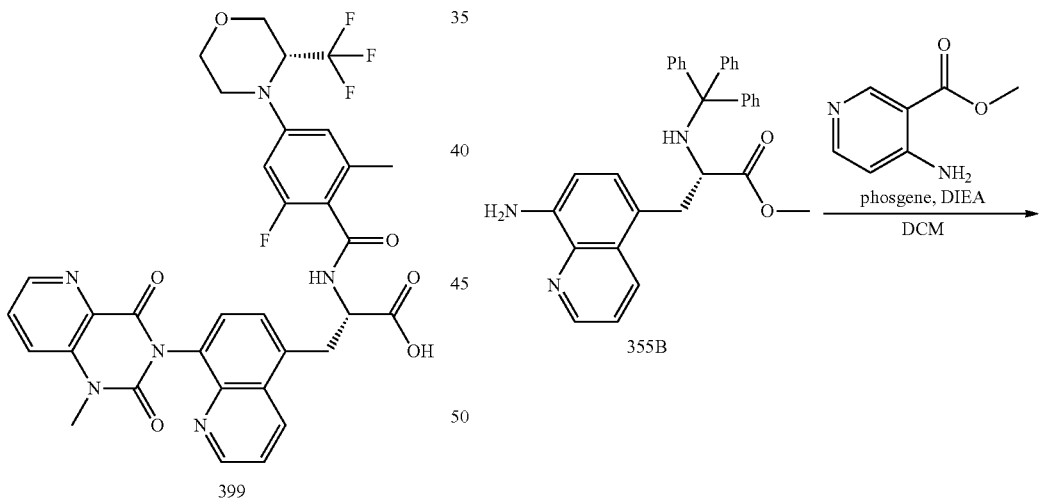

(S)-2-(2-fluoro-6-methyl-4-((R)-3-(trifluoromethyl)morpholino)benzamido)-3-(8-(1-methyl-2,4-dioxo-1,4-dihydropyrido[3,2-d]pyrimidin-3(2H)-yl)quinolin-5-yl)propanoic acid (399): The title compound was prepared according to the method presented for the synthesis of compound 356, starting with 398. ES/MS (m/z) 681.2 (M+H)+. 1H NMR (400 MHz, DMSO-d6) δ 9.00 (d, J=7.8 Hz, 1H), 8.88-8.81 (m, 1H), 8.67 (d, J=8.6 Hz, 1H), 8.61 (ddd, J=4.4, 2.1, 1.3 Hz, 1H), 8.08 (dd, J=8.8, 1.3 Hz, 1H), 7.87 (dd, J=8.6, 4.4

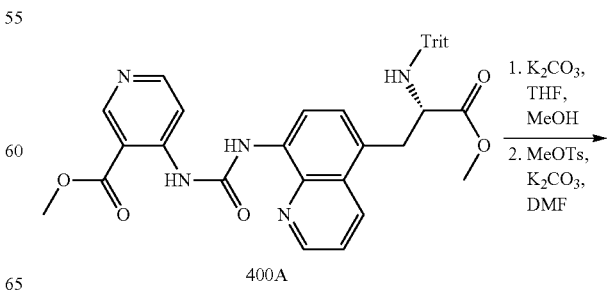

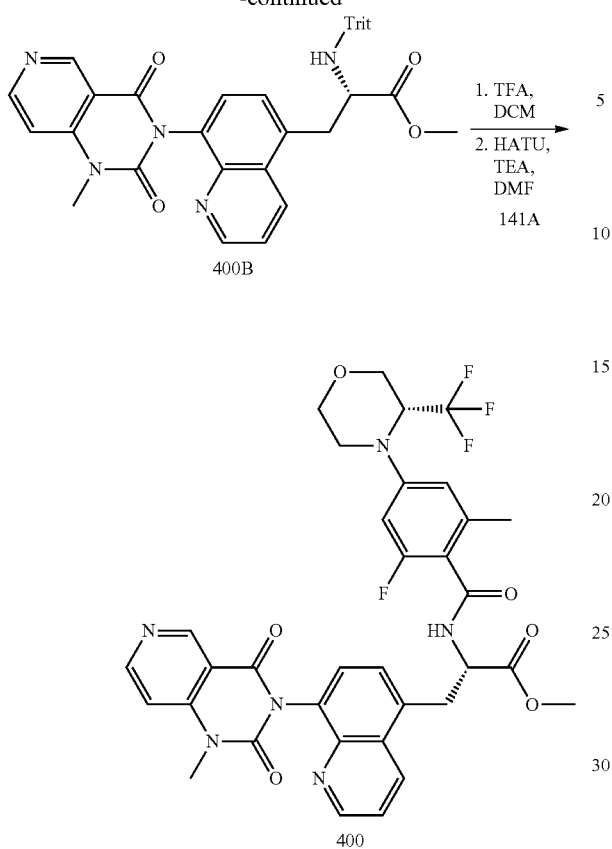

313

-continued

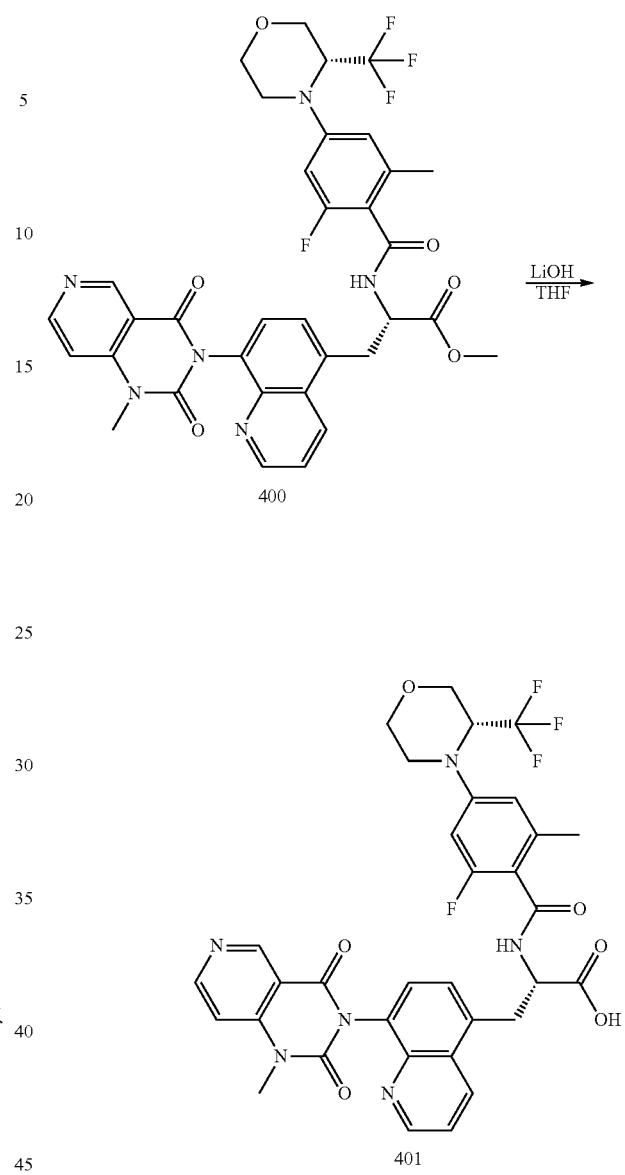

314

Methyl (S)-2-(2-fluoro-6-methyl-4-((R)-3-(trifluoromethyl)morpholino)benzamido)-3-(8-(1-methyl-2,4-dioxo-1,4-dihydropyrido[4,3-d]pyrimidin-3(2H)-yl)quinolin-5-yl)propanoate (400): The title compound was prepared according to the method presented for the synthesis of compound 355, starting with 400B. ES/MS (m/z) 695.2 (M+H)+. 1H NMR (400 MHz, DMSO-d6) δ 9.10 (d, J=3.0 Hz, 1H), 9.00 (d, J=7.7 Hz, 1H), 8.88-8.80 (m, 2H), 8.66 (dd, J=8.7, 1.6 Hz, 1H), 7.76 (d, J=7.6 Hz, 1H), 7.67 (td, J=5.8, 5.3, 2.6 Hz, 2H), 7.61 (d, J=6.1 Hz, 1H), 6.74-6.59 (m, 2H), 4.88-4.78 (m, 2H), 4.15 (d, J=12.7 Hz, 1H), 3.97-3.87 (m, 1H), 3.77-3.64 (m, 5H), 3.57 (d, J=2.2 Hz, 5H), 3.36 (d, J=12.3 Hz, 1H), 3.25 (t, J=12.1 Hz, 1H), 2.05 (s, 3H).

Example 401

(S)-2-(2-fluoro-6-methyl-4-((R)-3-(trifluoromethyl)morpholino)benzamido)-3-(8-(1-methyl-2,4-dioxo-1,4-dihydropyrido[3,2-d]pyrimidin-3(2H)-yl)quinolin-5-yl)propanoic acid (401): The title compound was prepared according to the method presented for the synthesis of compound 356, starting with 400. ES/MS (m/z) 681.2 (M+H)+. 1H NMR (400 MHz, DMSO-d6) δ 9.10 (d, J=3.6 Hz, 1H), 8.95-8.76 (m, 3H), 8.68 (d, J=8.7 Hz, 1H), 7.76 (d, J=7.5 Hz, 1H), 7.74-7.56 (m, 3H), 6.74-6.56 (m, 2H), 4.90-4.72 (m, 2H), 4.14 (d, J=12.6 Hz, 1H), 3.94 (dd, J=11.4, 3.6 Hz, 1H), 3.75 (t, J=13.4 Hz, 2H), 3.57 (d, J=2.4 Hz, 3H), 3.55-3.48 (m, 1H), 3.47 (s, 1H), 3.35 (d, J=12.6 Hz, 1H), 3.25 (t, J=12.4 Hz, 1H), 2.03 (s, 3H).

Example 402

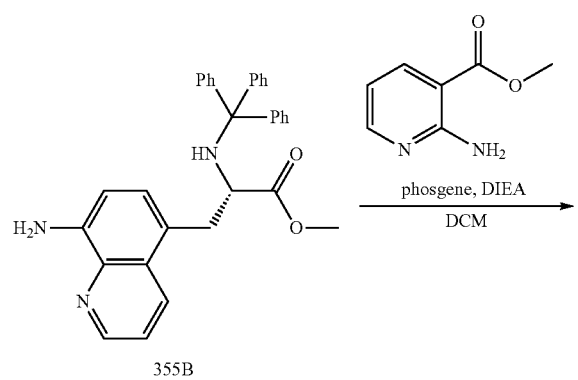

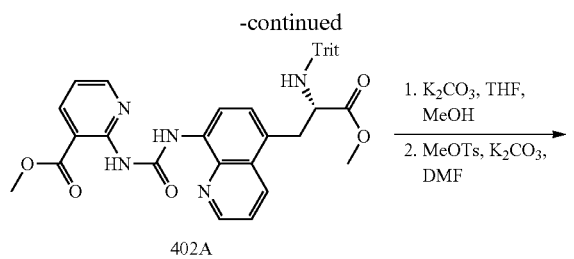

402A

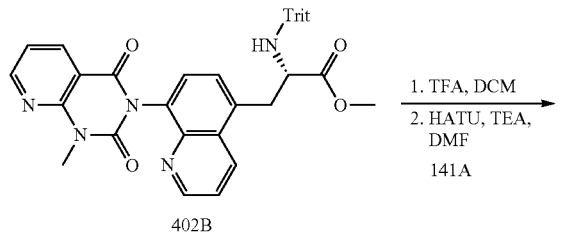

402B

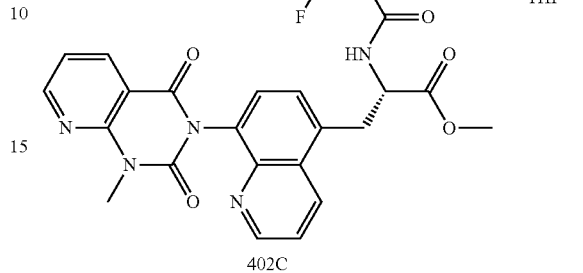

402C

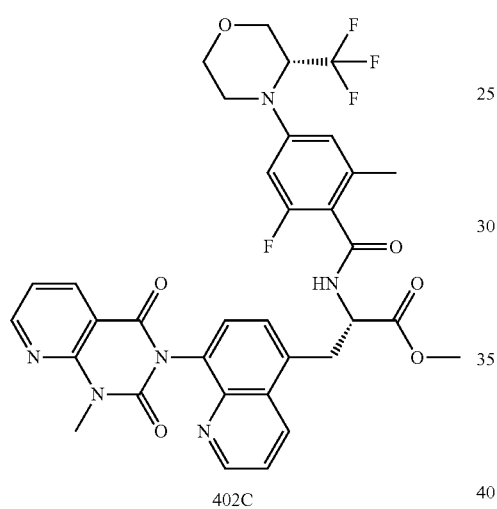

402C

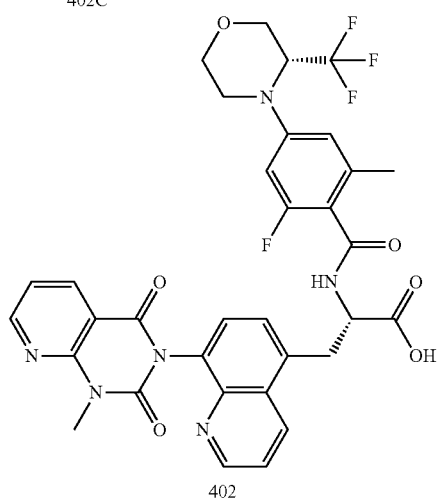

402

Synthesis of methyl (S)-2-(3-(5-(3-methoxy-3-oxo-2-(tritylamino)propyl)quinolin-8-yl)ureido)nicotinate (402A): To a solution of 355B (60.0 mg, 0.123 mmol) in DCM (0.62 mL, 0.2 mmol) in a flamed-dried vial was added methyl 2-aminonicotinate (37.0 mg, 0.246 mmol) and DIEA (48.0 mg, 0.369 mmol) and the mixture was stirred for 2 min at rt. A solution of phosgene in toluene (162 mg, 0.246 mmol) was added drop-wise and reaction mixture was stirred for an additional hour at rt. Upon completion, the solvent was removed under reduced pressure and the product was purified using flash chromatography eluting with MeOH in dichloromethane 0-20% to afford the title compound.

Synthesis of methyl (S)-3-(8-(1-methyl-2,4-dioxo-1,4-dihydropyrido[2,3-d]pyrimidin-3(2H)-yl)quinolin-5-yl)-2-(tritylamino)propanoate (400B): The title compound was prepared according to the method presented for the synthesis of compound 355E, starting with 402A.

Methyl (S)-2-(2-fluoro-6-methyl-4-((R)-3-(trifluoromethyl)morpholino)benzamido)-3-(8-(1-methyl-2,4-dioxo-1,4-dihydropyrido[2,3-d]pyrimidin-3(2H)-yl)quinolin-5-yl)propanoate (402C): The title compound was prepared according to the method presented for the synthesis of compound 355, starting with 402B.

(S)-2-(2-fluoro-6-methyl-4-((R)-3-(trifluoromethyl)morpholino)benzamido)-3-(8-(1-methyl-2,4-dioxo-1,4-dihydropyrido[3,2-d]pyrimidin-3(2H)-yl)quinolin-5-yl)propanoic acid (402): The title compound was prepared according to the method presented for the synthesis of compound 356, starting with 402C. ES/MS (m/z) 681.2 (M+H)+. 1H NMR (400 MHz, DMSO-d6) δ 8.86 (d, J=8.0 Hz, 3H), 8.68 (d, J=8.4 Hz, 1H), 8.42 (d, J=9.3 Hz, 1H), 7.76 (d, J=7.5 Hz, 1H), 7.70-7.63 (m, 2H), 7.45-7.39 (m, 1H), 6.73-6.63 (m, 2H), 4.87-4.72 (m, 3H), 4.14 (d, J=12.6 Hz, 1H), 3.99-3.91 (m, 2H), 3.74 (s, 2H), 3.63 (s, 3H), 3.58-3.51 (m, 1H), 3.50-3.42 (m, 1H), 3.38-3.31 (m, 1H), 3.28-3.21 (m, 1H), 2.03 (s, 3H).

Example 403

Synthesis of methyl (S)-3-(3-(5-(3-methoxy-3-oxo-2-(tritylamino)propyl)quinolin-8-yl)ureido)pyrazine-2-carboxylate (403A): To a vial equipped with a stir bar was added 3-(methoxycarbonyl)pyrazine-2-carboxylic acid (0.18 g, 1.01 mmol, 1.5 eq.), triethylamine (0.28 mL, 2.02 mmol, 3.0 eq.), DPPA (0.17 mL, 0.81 mmol, 1.2 eq.), 355B (0.33 g, 0.67 mmol, 1.0 eq.), and toluene (3.36 mL. 0.2 M). The reaction was then heated to 100° C. for 30 min. The reaction was quenched with water (10 mL) and extracted with EtOAc (25 mL, 3×). The combined organic phases were washed with sat. sodium bicarbonate, brine, and dried over anhydrous Na₂SO₄. Organic phases were concentrated and the product was purified by column chromatography using a stepwise elution gradient of 0-100% EtOAc in hexanes.

Synthesis of methyl (S)-3-(8-(1-methyl-2,4-dioxo-1,4-dihydropteridin-3(2H)-yl)quinolin-5-yl)-2-(tritylamino)propanoate (403B): The title compound was prepared according to the method presented for the synthesis of compound 355E, starting with 403A.

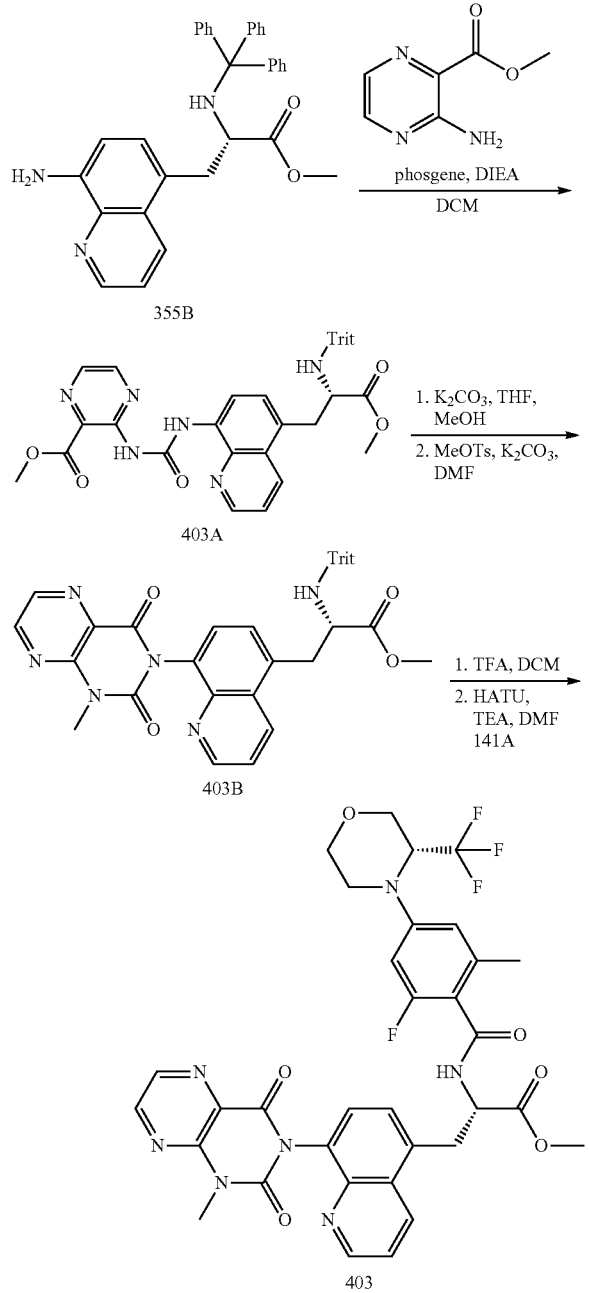

Methyl (S)-2-(2-fluoro-6-methyl-4-((R)-3-(trifluoromethyl)morpholino)benzamido)-3-(8-(1-methyl-2,4-dioxo-1,4-dihydropteridin-3(2H)-yl)quinolin-5-yl)propanoate (403): The title compound was prepared according to the method presented for the synthesis of compound 355, starting with 403B. ES/MS (m/z) 696.1 (M+H)+. 1H NMR (400 MHz, DMSO-d6) δ 9.00 (d, J=7.8 Hz, 1H), 8.92-8.86 (m, 2H), 8.73-8.68 (m, 2H), 7.78 (d, J=7.5 Hz, 1H), 7.73-7.67 (m, 2H), 6.74-6.64 (m, 2H), 4.90-4.79 (m, 2H), 4.15 (d, J=12.6 Hz, 1H), 3.95 (dd, J=11.5, 3.5 Hz, 1H), 3.80-3.65 (m, 5H), 3.61 (s, 3H), 3.55 (t, J=13.9, 7.6, 2.5 Hz, 2H), 3.36 (d, J=11.8 Hz, 1H), 3.25 (t, 1H), 2.05 (s, 3H).

Example 404

(S)-2-(2-fluoro-6-methyl-4-((R)-3-(trifluoromethyl)morpholino)benzamido)-3-(8-(1-methyl-2,4-dioxo-1,4-dihydropteridin-3(2H)-yl)quinolin-5-yl)propanoic acid (404): The title compound was prepared according to the method presented for the synthesis of compound 356, starting with 403. ES/MS (m/z) 682.7 (M+H)+. 1H NMR (400 MHz, DMSO-d6) δ 8.93-8.83 (m, 3H), 8.75-8.67 (m, 2H), 7.77 (d, J=7.5 Hz, 1H), 7.74-7.66 (m, 2H), 6.73-6.62 (m, 2H), 4.89-4.75 (m, 2H), 4.14 (d, J=12.6 Hz, 1H), 3.94 (dd, J=11.7, 3.5 Hz, 1H), 3.81-3.69 (m, 2H), 3.61 (s, 3H), 3.59-3.43 (m, 2H), 3.35 (d, J=12.2 Hz, 1H), 3.25 (t, 1H), 2.03 (d, J=2.4 Hz, 3H).

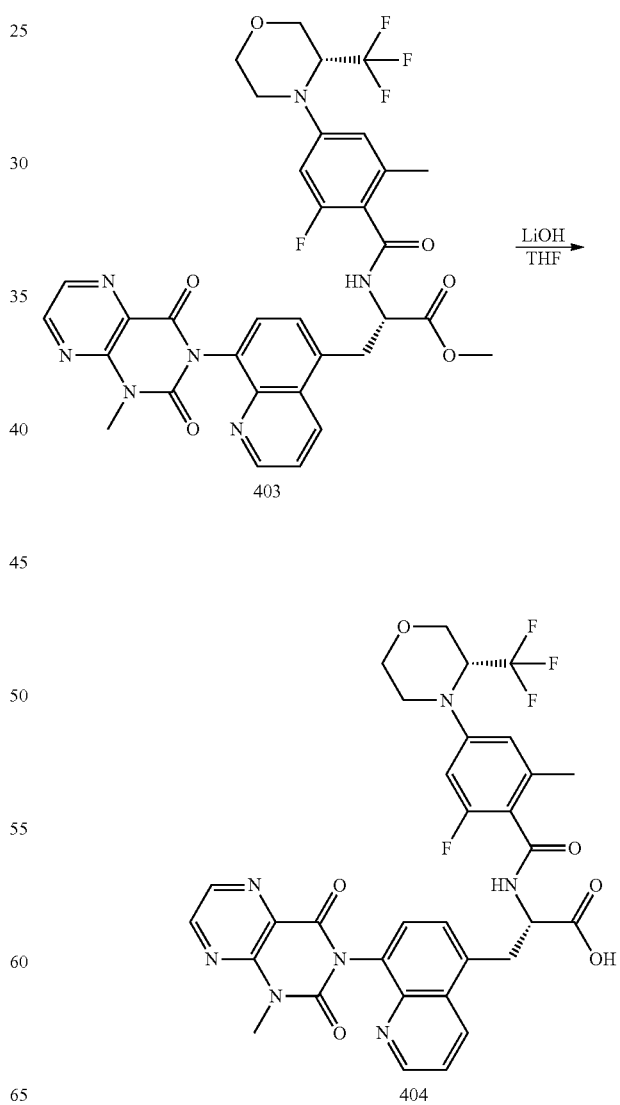

Example 405

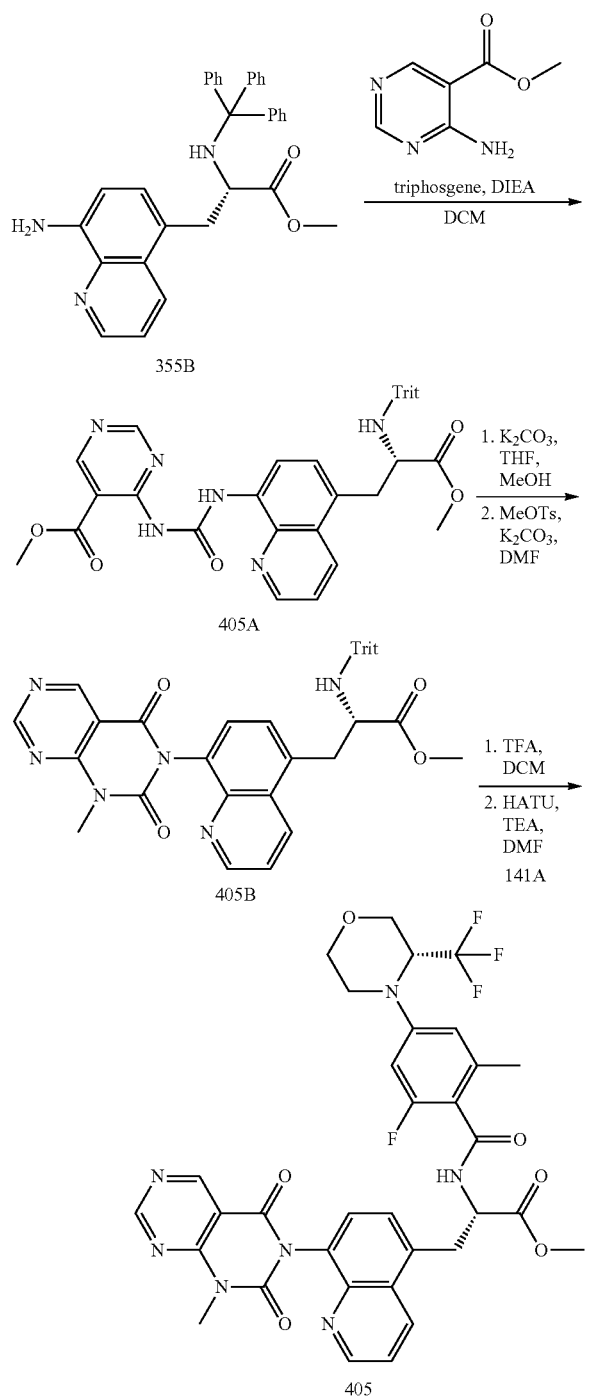

Synthesis of methyl (S)-4-(3-(5-(3-methoxy-3-oxo-2-(tritylamino)propyl)quinolin-8-yl)ureido)pyrimidine-5-carboxylate (405A): DIEA (0.5 mL, 3.1 mmol, 3 eq.) and triphosgene (212 mg, 0.72 mmol, 0.7 eq.) were added to a solution of methyl 4-aminopyrimidine-5-carboxylate (314 mg, 2.0 mmol, 2 eq.) in DCM (0.2 M). The solution was stirred at ambient temperature for 1 hour. 355B (500 mg, 1 mmol, 1 eq.) was then added to the solution and stirred for an hour at ambient temperature. The reaction mixture was concentrated directly onto silica gel and chromatographed eluting with 0-100% ethyl acetate in hexanes; the product eluted at 75%.

Synthesis of methyl (S)-3-(8-(1-methyl-2,4-dioxo-1,4-dihydropyrimido[4,5-d]pyrimidin-3(2H)-yl)quinolin-5-yl)-2-(tritylamino)propanoate (405B): The title compound was prepared according to the method presented for the synthesis of compound 355E, starting with 405A.

Methyl (S)-2-(2-fluoro-6-methyl-4-((R)-3-(trifluoromethyl)morpholino)benzamido)-3-(8-(1-methyl-2,4-dioxo-1,4-dihydropyrimido[4,5-d]pyrimidin-3(2H)-yl)quinolin-5-yl)propanoate (405): The title compound was prepared according to the method presented for the synthesis of compound 355, starting with 405B. ES/MS (m/z) 696.8 (M+H)+. 1H NMR (400 MHz, DMSO-d6) δ 9.32 (s, 1H), 9.26-9.18 (m, 1H), 8.99 (d, J=7.8 Hz, 1H), 8.91-8.84 (m, 1H), 8.67 (d, J=8.7 Hz, 1H), 7.82-7.73 (m, 1H), 7.72-7.63 (m, 2H), 6.76-6.64 (m, 2H), 4.88-4.80 (m, 2H), 4.15 (d, J=12.6 Hz, 1H), 3.98-3.91 (m, 1H), 3.78-3.70 (m, 2H), 3.68 (s, 3H), 3.61 (s, 3H), 3.58-3.51 (m, 2H), 3.42-3.32 (m, 1H), 3.30-3.18 (m, 1H), 2.04 (s, 3H).

Example 406

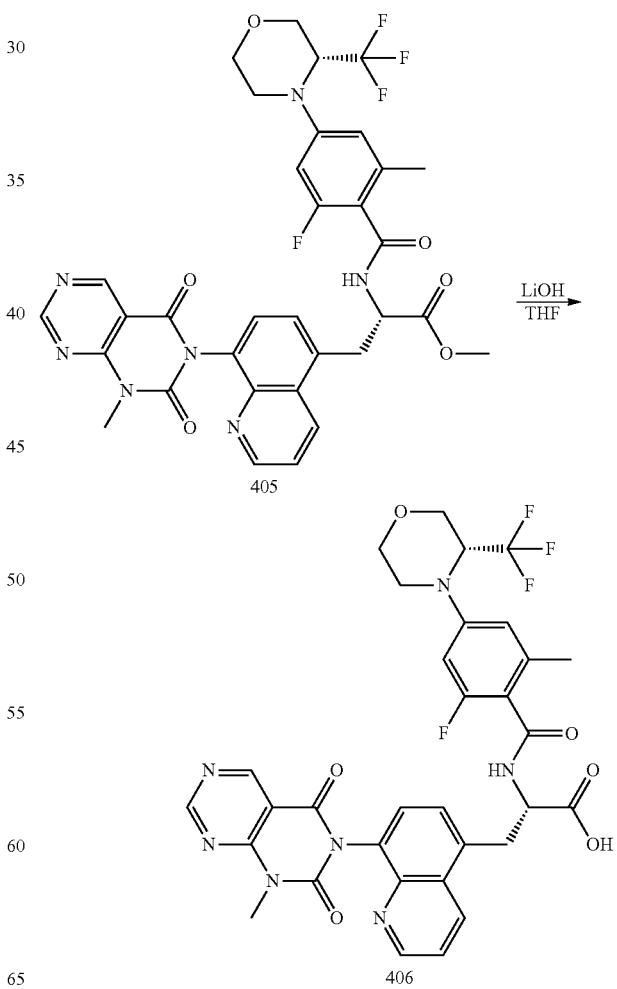

(S)-2-(2-fluoro-6-methyl-4-((R)-3-(trifluoromethyl)morpholino)benzamido)-3-(8-(1-methyl-2,4-dioxo-1,4-dihydropyrimido[4,5-d]pyrimidin-3(2H)-yl)quinolin-5-yl)propanoic acid (406): The title compound was prepared according to the method presented for the synthesis of compound 356, starting with 405. ES/MS (m/z) 682.2 (M+H)+. 1H NMR (400 MHz, DMSO-d6) δ 9.32 (s, 1H), 9.25-9.18 (m, 1H), 8.91-8.82 (m, 2H), 8.69 (d, J=8.6 Hz, 1H), 7.80-7.73 (m, 1H), 7.73-7.64 (m, 2H), 6.75-6.60 (m, 2H), 4.90-4.74 (m, 2H), 4.14 (d, J=12.6 Hz, 1H), 3.95 (d, J=10.8 Hz, 1H), 3.81-3.68 (m, 2H), 3.60 (s, 3H), 3.58-3.40 (m, 2H), 3.39-3.31 (m, 1H), 3.31-3.18 (m, 1H), 2.02 (s, 3H).

Examples 407 and 408

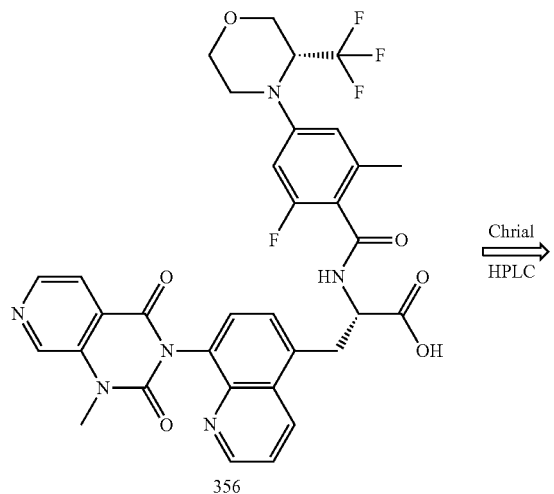

356

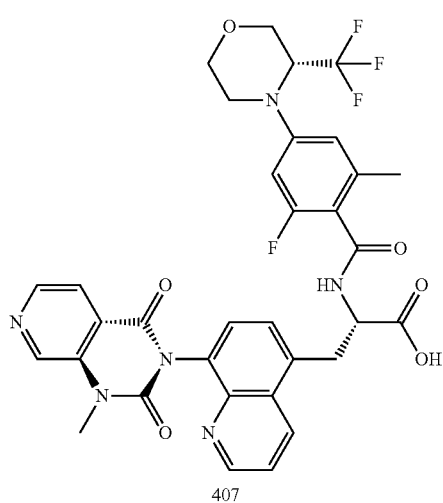

407

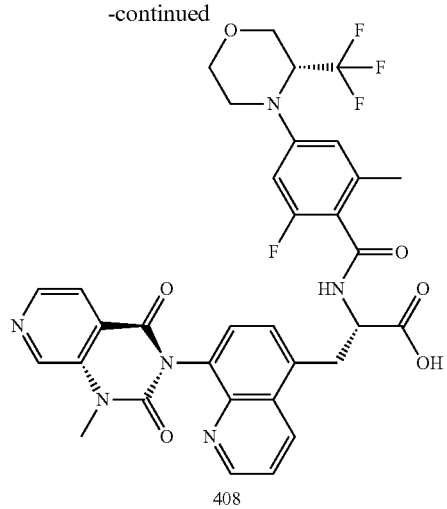

408

Preparation of (S)-2-(2-fluoro-6-methyl-4-((R)-3-(trifluoromethyl)morpholino) benzamido)-3-(8-(1-methyl-2,4-dioxo-1,4-dihydropyrido[3,4-d]pyrimidin-3(2H)-yl)quinolin-5-yl)propanoic acid (407): 356 was separated into its 2 atropisomeric enantiomers by supercritical fluid chromatography using 30% EtOH co-solvent, at a flow rate of 3 mL/min, using an AD-H 5 μm 4.6×100 mm column. The title compound was identified as the second eluting peak. ES/MS (m/z) 681.2 (M+H)+. 1H NMR (400 MHz, Chloroform-d) δ 8.84-8.72 (m, 2H), 8.66 (d, J=8.6 Hz, 1H), 8.55 (s, 1H), 8.00 (s, 1H), 7.58 (s, 2H), 7.44 (dd, J=8.6, 4.2 Hz, 1H), 6.66 (d, J=6.5 Hz, 1H), 6.46 (s, 1H), 6.37 (d, J=13.6 Hz, 1H), 5.08 (d, J=7.0 Hz, 1H), 4.29 (d, J=12.4 Hz, 1H), 4.11 (dd, J=8.2, 3.8 Hz, 1H), 4.04 (dd, J=11.3, 3.5 Hz, 1H), 3.84-3.70 (m, 3H), 3.68 (s, 3H), 3.65-3.56 (m, 1H), 3.50 (t, J=12.0 Hz, 1H), 3.26 (d, J=12.2 Hz, 1H), 2.38 (s, 3H).

Preparation (S)-2-(2-fluoro-6-methyl-4-((R)-3-(trifluoromethyl)morpholino) benzamido)-3-(8-(1-methyl-2,4-dioxo-1,4-dihydropyrido[3,4-d]pyrimidin-3(2H)-yl)quinolin-5-yl)propanoic acid (408): 356 was separated into its 2 atropisomeric enantiomers by supercritical fluid chromatography using 30% EtOH co-solvent, at a flow rate of 3 mL/min, using an AD-H 5 μm 4.6×100 mm column. The title compound was identified as the first eluting peak. ES/MS (m/z) 681.2 (M+H)+. 1H NMR (400 MHz, Chloroform-d) δ 8.83-8.72 (m, 2H), 8.64 (d, J=8.6 Hz, 1H), 8.56 (d, J=5.0 Hz, 1H), 8.03 (d, J=5.0 Hz, 1H), 7.59 (q, J=7.6 Hz, 2H), 7.46 (dd, J=8.6, 4.2 Hz, 1H), 6.63 (d, J=6.1 Hz, 1H), 6.47 (s, 1H), 6.38 (dd, J=13.4, 2.4 Hz, 1H), 5.13-5.02 (m, 1H), 4.30 (d, J=12.4 Hz, 1H), 4.12 (dd, J=8.0, 3.8 Hz, 1H), 4.04 (dd, J=11.2, 3.5 Hz, 1H), 3.86-3.78 (m, 1H), 3.72 (t, J=5.6 Hz, 2H), 3.69 (s, 3H), 3.65-3.59 (m, 1H), 3.51 (t, J=11.7 Hz, 1H), 3.27 (d, J=12.3 Hz, 1H), 2.39 (s, 3H).

Examples 487 and 488

Preparation ethyl (S)-2-(2-fluoro-6-methyl-4-((R)-3-(trifluoromethyl)morpholino) benzamido)-3-(8-(1-methyl-2,4-dioxo-1,4-dihydropyrido[3,4-d]pyrimidin-3(2H)-yl)quinolin-5-yl)propanoate (487): 360 was separated into its 2 atropisomeric enantiomers by supercritical fluid chromatography using 30% EtOH co-solvent, at a flow rate of 3 mL/min, using an AD-H 5 μm 4.6×100 mm column. The title compound was identified as the first eluting peak. ES/MS (m/z) 709.2 (M+H)+. 1H NMR (400 MHz, DMSO-d6) δ 9.04 (s, 1H), 8.99 (d, J=7.7 Hz, 1H), 8.84 (dd, J=4.1, 1.5 Hz, 1H), 8.64 (dd, J=8.6, 1.6 Hz, 1H), 8.60 (d, J=4.9 Hz, 1H), 7.91 (dd, J=4.9, 0.7 Hz, 1H), 7.75 (d, J=7.6 Hz, 1H), 7.69-7.63 (m, 2H), 6.76-6.63 (m, 2H), 4.90-4.74 (m, 2H), 4.19-4.06 (m, 3H), 3.95 (dd, J=11.4, 3.6 Hz, 1H), 3.78-3.67 (m, 2H), 3.65 (s, 3H), 3.61-3.46 (m, 2H), 3.37 (s, 1H), 3.31-3.18 (m, 1H), 2.07 (s, 3H), 1.16 (t, J=7.1 Hz, 3H).

Preparation ethyl (S)-2-(2-fluoro-6-methyl-4-((R)-3-(trifluoromethyl)morpholino) benzamido)-3-(8-(1-methyl-2,4-dioxo-1,4-dihydropyrido[3,4-d]pyrimidin-3(2H)-yl)quinolin-5-yl)propanoate (488): 360 was separated into its 2 atropisomeric enantiomers by Simulated moving bed (SMB) chromatography using EA/heptanes (80/20), using a ChiralPak IC column. The title compound was identified as the second eluting peak. ES/MS (m/z) 709.2 (M+H)+. 1H NMR (400 MHz, DMSO-d6) δ 9.04 (s, 1H), 8.99 (d, J=7.7 Hz, 1H), 8.84 (dd, J=4.2, 1.5 Hz, 1H), 8.64 (dd, J=8.7, 1.6 Hz, 1H), 8.60 (d, J=5.0 Hz, 1H), 7.91 (d, J=4.9 Hz, 1H), 7.75 (d, J=7.5 Hz, 1H), 7.69-7.63 (m, 2H), 6.75-6.62 (m, 2H), 4.91-4.75 (m, 2H), 4.20-4.07 (m, 3H), 3.95 (dd, J=11.4, 3.6 Hz, 1H), 3.78-3.67 (m, 2H), 3.66 (s, 3H), 3.60-3.47 (m, 2H), 3.36 (d, J=12.3 Hz, 1H), 3.25 (t, J=12.3 Hz, 1H), 2.07 (s, 3H), 1.16 (t, J=7.1 Hz, 3H).

α4β7 Integrin Cell Capture Assay

The potency of inhibitors in preventing α4β7 integrin interaction with MadCAM-1 was measured by monitoring the capture of α4β7 integrin expressing cells on a recombinant MadCAM-1 extracellular domain-coated plate. 384-Well plates (Corning 3702) were coated with MadCAM-1 extracellular domain by dispensing 20 µL of MAdCAM-1 at 1.0 µg/mL per well and incubating overnight at 4° C. The plates were then washed with PBS and blocked with 3% BSA for 2 hours before being washed again.

RPM18866 cells were spun down and re-suspended in assay medium (DMEM+0.5% FBS+0.5 mM $MnCl_2$) at a density of $0.5 \times 10^6$ cells/mL. The cells were then dispensed (60 µL/well) to a 384-well plate (Greiner 781280) that was previously spotted with 60 nL of test compound per well. The plates were incubated at 37° C. for 1 hour. 50 µL of cells were transferred to the blocked, MadCAM-1-coated plates and incubated for 30 minutes at 37° C. 10 µL of 12% glutaraldehyde containing Hoechst 33342 (0.06 mg/mL) was added to the cells (2% glutaraldehyde and 0.01 mg/mL final concentrations). The plates were incubated for 90 minutes at room temperature. The plates were then washed 3 times with 70 µL of PBS per well and imaged on a Cellomics ArrayScan instrument. The cells that were bound to the plate were counted and plotted against the compound concentration to determine the $EC_{50}$ of the test compounds. Results were presented in Tables 1 and 2.

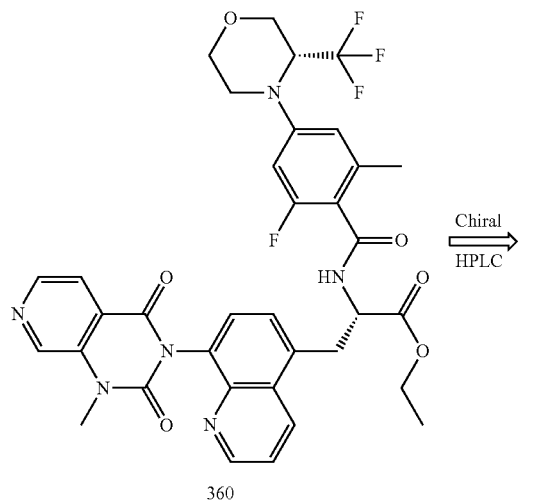

360

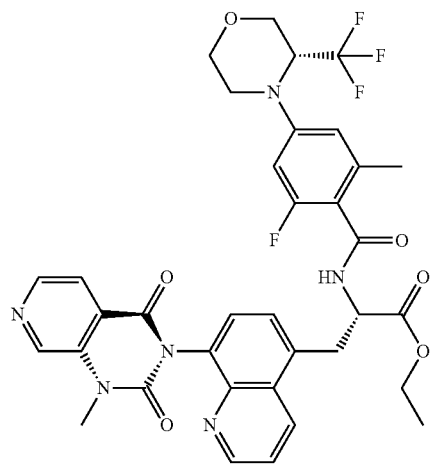

487

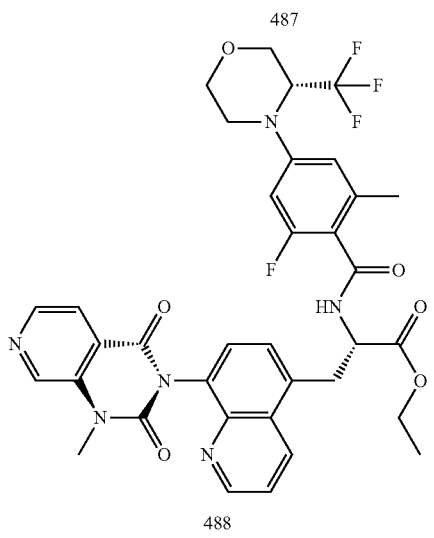

488

TABLE 1

| Example # | α4β7 $EC_{50}$ (nM) |
| --- | --- |
| 1 | 21.2 |
| 2 | 31.1 |
| 3 | 63.8 |
| 4 | 6.7 |
| 5 | 17.4 |
| 6 | 4.5 |
| 7 | 1.9 |
| 8 | 41.4 |
| 9 | 25.1 |
| 10 | 21.2 |
| 11 | 22.9 |
| 12 | 7.0 |
| 13 | 8.5 |
| 14 | 3.7 |
| 15 | 9.3 |
| 16 | 67.4 |
| 17 | 36.7 |
| 18 | 9.0 |
| 19 | 50.0 |
| 20 | 185.8 |
| 21 | 96.6 |
| 22 | 48.5 |
| 23 | 46.7 |

TABLE 1-continued

| Example # | α4β7 EC$_{50}$ (nM) |
|---|---|
| 24 | 56.7 |
| 25 | 3.3 |
| 26 | 32.8 |
| 27 | 12.8 |
| 28 | 33.5 |
| 29 | 68.7 |
| 30 | 16.9 |
| 31 | 19.3 |
| 32 | 75.9 |
| 33 | 60.5 |
| 34 | 39.5 |
| 35 | 6.2 |
| 36 | 21.0 |
| 37 | 69.6 |
| 38 | 29.7 |
| 39 | 81.6 |
| 40 | 8.6 |
| 41 | 7.7 |
| 42 | 13.4 |
| 43 | 4.6 |
| 44 | 10.9 |
| 45 | 3.4 |
| 46 | 20.0 |
| 47 | 2.4 |
| 48 | 52.1 |
| 49 | 33.7 |
| 50 | 0.4 |
| 51 | 2.9 |
| 52 | 91.5 |
| 53 | 3.0 |
| 54 | 37.4 |
| 55 | 27.4 |
| 56 | 9.1 |
| 57 | 30.0 |
| 58 | 2.0 |
| 59 | 3.2 |
| 60 | 3.0 |
| 61 | 4.2 |
| 62 | 1.8 |
| 63 | 30.5 |
| 64 | 0.8 |
| 65 | 8.4 |
| 66 | 18.9 |
| 67 | 1.6 |
| 68 | 14.0 |
| 69 | 28.9 |
| 70 | 10.7 |
| 71 | 9.5 |
| 72 | 5.5 |
| 73 | 2.5 |
| 74 | 13.6 |
| 75 | 80.4 |
| 76 | 78.4 |
| 77 | 90.7 |
| 78 | 134.3 |
| 79 | 26.1 |
| 80 | 18.1 |
| 81 | 6.0 |
| 82 | 4.7 |
| 83 | 32.9 |
| 84 | 11.7 |
| 85 | 25.4 |
| 86 | 8.3 |
| 87 | 15.0 |
| 88 | 8.2 |
| 89 | 14.4 |
| 90 | 11.3 |
| 91 | 0.3 |
| 92 | 2.0 |
| 93 | 0.4 |
| 94 | 0.5 |
| 95 | 0.3 |
| 96 | 0.2 |
| 97 | 3.2 |
| 98 | 1.4 |
| 99 | 11.2 |

TABLE 1-continued

| Example # | α4β7 EC$_{50}$ (nM) |
|---|---|
| 100 | 0.7 |
| 101 | 4.1 |
| 102 | 0.3 |
| 103 | 0.7 |
| 104 | 0.5 |
| 105 | 4.1 |
| 106 | 0.3 |
| 107 | 0.2 |
| 108 | 1.0 |
| 109 | 0.3 |
| 110 | 0.3 |
| 111 | 0.1 |
| 112 | 0.4 |
| 113 | 1.2 |
| 114 | 0.6 |
| 115 | 0.6 |
| 116 | 1.2 |
| 117 | 0.7 |
| 118 | 1.5 |
| 119 | 20.5 |
| 120 | 1.3 |
| 121 | 1.7 |
| 122 | 0.2 |
| 123 | 0.9 |
| 124 | 0.6 |
| 125 | 1.0 |
| 126 | 0.6 |
| 127 | 9.3 |
| 128 | 0.3 |
| 129 | 0.7 |
| 130 | 0.5 |
| 131 | 0.8 |
| 132 | 1.3 |
| 133 | 3.2 |
| 134 | 4.2 |
| 135 | 0.4 |
| 136 | 0.2 |
| 137 | 0.4 |
| 138 | 0.8 |
| 139 | 11.7 |
| 140 | 0.5 |
| 141 | 0.1 |
| 142 | 0.2 |
| 143 | 0.3 |
| 144 | 0.2 |
| 145 | 3.1 |
| 146 | 0.6 |
| 147 | 1.9 |
| 148 | 60.6 |

Examples 149-354 in Table 2 were prepared by processes described herein.

TABLE 2

| Example | Structure | 1H-NMR | M/Z [M + H]+ | α4β7 EC$_{50}$ (nM) |
|---|---|---|---|---|
| 149 | 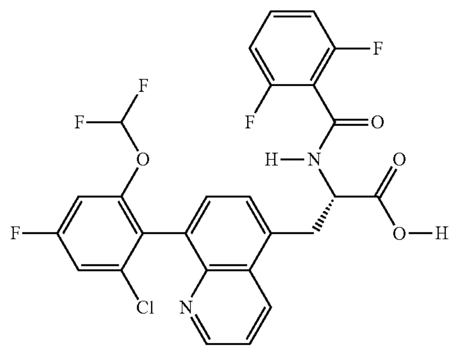 [SMILES: O=C(N[C@@H](Cc1ccc(-c2c(Cl)cc(F)cc2OC(F)F)c2ncccc12)C(=O)O)c1c(F)cccc1F] | 1H NMR (400 MHz, DMSO-d6) δ 9.26 (dd, J = 8.0, 3.2 Hz, 1H), 8.81 (dd, J = 4.2, 1.5 Hz, 1H), 8.62 (d, J = 8.9 Hz, 1H), 7.66-7.54 (m, 3H), 7.54-7.41 (m, 2H), 7.32-7.23 (m, 1H), 7.14-7.04 (m, 3H), 6.89 (d, J = 1.6 Hz, 1H), 4.78 (d, J = 2.4 Hz, 1H), 3.85-3.67 (m, 1H), 3.41 (ddd, J = 21.8, 14.7, 10.2 Hz, 1H), 1.21 (s, 1H). | 550.9 | 50.3 |
| 150 | 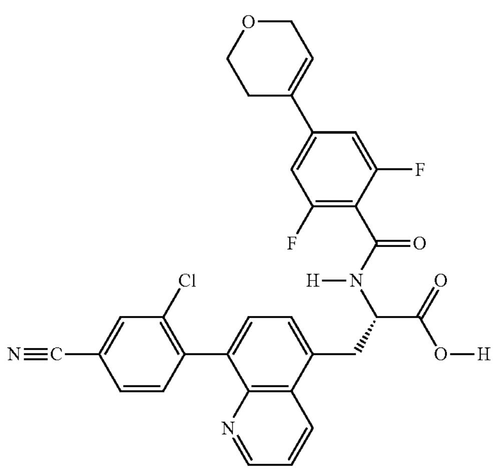 [SMILES: N#Cc1ccc(-c2ccc(C[C@H](NC(=O)c3c(F)cc(C4=CCOCC4)cc3F)C(=O)O)c3cccnc23)c(Cl)c1] | 1H NMR (400 MHz, DMSO-d6) δ 9.24 (d, J = 8.2 Hz, 1H), 8.86 (dd, J = 4.2, 1.6 Hz, 1H), 8.67 (dd, J = 8.7, 1.7 Hz, 1H), 8.17 (d, J = 1.6 Hz, 1H), 7.92 (dd, J = 7.9, 1.7 Hz, 1H), 7.70-7.61 (m, 3H), 7.58 (d, J = 7.9 Hz, 1H), 7.22 (d, J = 9.3 Hz, 2H), 6.49 (tt, J = 3.1, 1.5 Hz, 1H), 4.78 (ddd, J = 10.2, 8.1, 4.4 Hz, 1H), 4.22 (p, J = 3.4, 2.9 Hz, 2H), 3.79 (t, J = 5.4 Hz, 2H), 3.42 (s, 1H), 2.46-2.34 (m, 2H). | 573.8 | 43.6 |
| 151 | 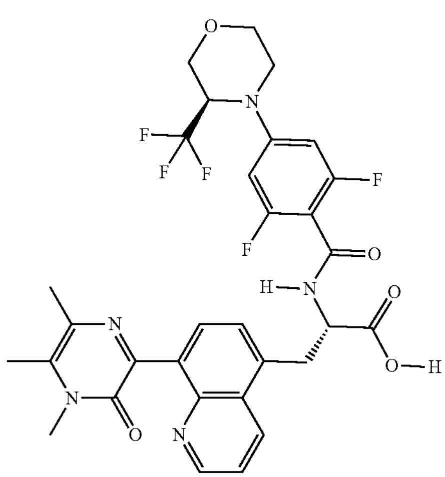 [SMILES: Cc1nc(-c2ccc(C[C@H](NC(=O)c3c(F)cc(N4CCOC[C@@H]4C(F)(F)F)cc3F)C(=O)O)c3cccnc23)c(=O)n(C)c1C] | 1H NMR (400 MHz, DMSO-d6) δ 8.96 (d, J = 8.0 Hz, 1H), 8.88 (s, 1H), 8.74 (s, 1H), 7.66 (d, J = 29.5 Hz, 3H), 6.77 (d, J = 11.8 Hz, 2H), 4.98-4.84 (m, 1H), 4.68 (s, 1H), 4.16 (d, J = 12.7 Hz, 1H), 3.99-3.90 (m, 1H), 3.72 (s, 3H), 3.52 (d, J = 1.6 Hz, 3H), 3.49-3.37 (m, 2H), 3.23 (t, J = 12.5 Hz, 1H), 2.41 (s, 3H), 2.33 (d, J = 2.0 Hz, 3H). | 646.2 | 0.2 |

TABLE 2-continued
| Example | Structure | 1H-NMR | M/Z [M + H]+ | α4β7 EC$_{50}$ (nM) |
| --- | --- | --- | --- | --- |
| 152 | 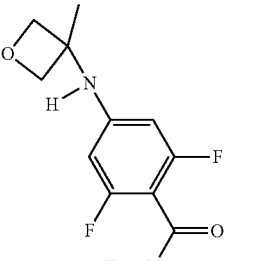 | 1H NMR (400 MHz, DMSO-d6) δ 8.83 (dd, J = 4.2, 1.6 Hz, 1H), 8.77 (d, J = 8.0 Hz, 1H), 8.64 (dd, J = 8.7, 1.7 Hz, 1H), 8.15 (d, J = 1.6 Hz, 1H), 7.89 (dd, J = 7.9, 1.6 Hz, 1H), 7.70-7.58 (m, 3H), 7.57 (d, J = 7.9 Hz, 1H), 7.01 (s, 1H), 5.94 (d, J = 11.0 Hz, 2H), 4.67 (s, 1H), 4.54 (d, J = 6.1 Hz, 2H), 4.47 (dd, J = 6.0, 1.2 Hz, 2H), 3.72 (s, 1H), 3.41 (s, 1H), 1.51 (s, 3H). | 578.1 | 51.7 |
| 153 | 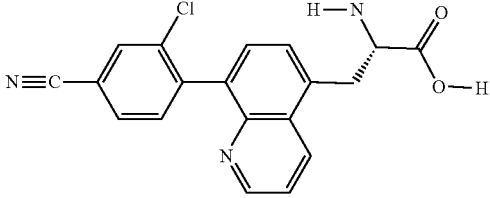 | 1H NMR (400 MHz, DMSO-d6) δ 9.25 (d, J = 8.1 Hz, 1H), 8.90 (d, J = 4.4 Hz, 1H), 8.81 (d, J = 8.4 Hz, 1H), 7.99 (s, 1H), 7.82-7.57 (m, 5H), 7.46-7.11 (m, 3H), 6.93 (dd, J = 17.5, 9.3 Hz, 3H), 4.78-4.70 (m, 1H), 3.77 (dd, J = 14.5, 4.5 Hz, 1H), 3.68 (s, 3H), 3.43 (dd, J = 14.5, 9.9 Hz, 1H). | 643.1 | 0.2 |
| 154 | 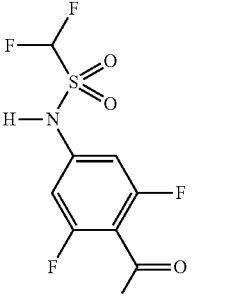 | 1H NMR (400 MHz, DMSO-d6) δ 9.38 (d, J = 8.2 Hz, 1H), 9.01 (d, J = 8.5 Hz, 1H), 8.84 (dd, J = 4.1, 1.6 Hz, 1H), 8.64 (dd, J = 8.7, 1.6 Hz, 1H), 8.16 (dd, J = 1.6, 0.4 Hz, 1H), 7.91 (d, J = 8.4 Hz, 1H), 7.68-7.53 (m, 7H), 1.34 (d, J = 7.1 Hz 4H). | 630.8 | 44.6 |

TABLE 2-continued

| Example | Structure | 1H-NMR | M/Z [M + H]+ | α4β7 EC$_{50}$ (nM) |
|---|---|---|---|---|
| 155 | 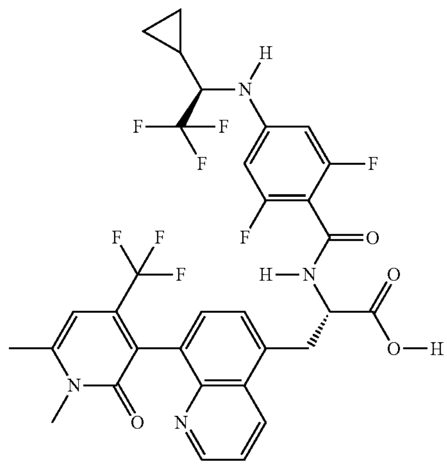 [SMILES: Cc1cc(C(F)(F)F)c(-c2ccc(C[C@H](NC(=O)c3c(F)cc(N[C@H](C4CC4)C(F)(F)F)cc3F)C(=O)O)c3cccnc23)c(=O)n1C] | 1H NMR (400 MHz, DMSO-d6) δ 8.86-8.74 (m, 2H), 8.64 (s, 1H), 7.62 (dd, J = 8.7, 4.4 Hz, 1H), 7.55 (dd, J = 7.4, 5.1 Hz, 1H), 7.42 (dd, J = 7.3, 4.2 Hz, 1H), 6.92 (dd, J = 9.5, 5.5 Hz, 1H), 6.54 (s, 1H), 6.40 (dd, J = 11.4, 4.1 Hz, 2H), 4.71-4.60 (m, 1H), 3.91 (q, J = 8.0 Hz, 1H), 3.75-3.60 (m, 1H), 3.47 (d, J = 2.4 Hz, 3H), 3.44-3.30 (m, 1H), 2.51 (s, 3H), 1.03 (ddd, J = 13.0, 8.8, 4.9 Hz, 1H), 0.68-0.56 (m, 1H), 0.54-0.41 (m, 2H), 0.30 (dd, J = 9.6, 4.8 Hz, 1H). | 682.6 | 0.3 |
| 156 | 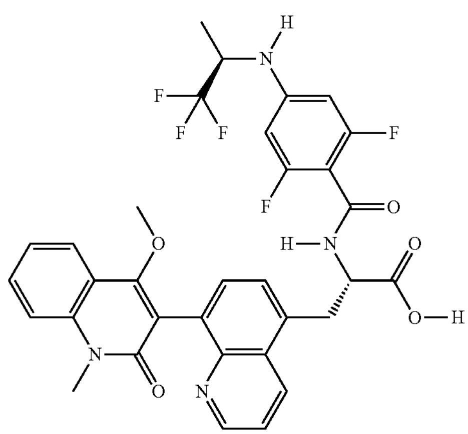 [SMILES: COc1c(-c2ccc(C[C@H](NC(=O)c3c(F)cc(N[C@H](C)C(F)(F)F)cc3F)C(=O)O)c3cccnc23)c(=O)n(C)c2ccccc12] | 1H NMR (400 MHz, DMSO-d6) δ 8.98-8.88 (m, 2H), 8.81 (d, J = 8.1 Hz, 1H), 7.96 (d, J = 8.0 Hz, 1H), 7.88-7.66 (m, 4H), 7.64 (d, J = 8.7 Hz, 1H), 7.36 (t, J = 7.6 Hz, 1H), 6.84 (d, J = 9.1 Hz, 1H), 6.48-6.36 (m, 2H), 4.80-4.69 (m, 1H), 4.58-4.43 (m, 1H), 3.87 (dd, J = 14.1, 4.0 Hz, 1H), 3.76-3.52 (m, 4H), 3.29 (d, J = 2.5 Hz, 3H), 1.28 (d, J = 6.6 Hz, 3H). | 655.3 | 0.3 |
| 157 | 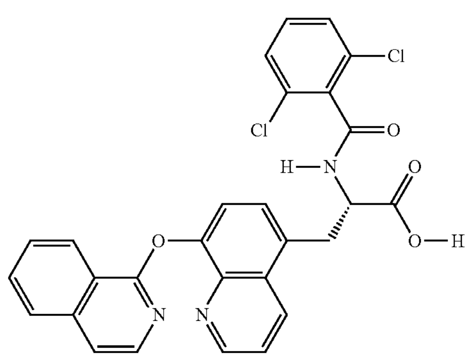 [SMILES: O=C(N[C@@H](Cc1ccc(Oc2nccc3ccccc23)c2ncccc12)C(=O)O)c1c(Cl)cccc1Cl] | 1H NMR (400 MHz, DMSO-d6) δ 9.29 (d, J = 8.4 Hz, 1H), 8.85 (dd, J = 4.1, 1.5 Hz, 1H), 8.70 (d, J = 8.7 Hz, 1H), 8.20 (d, J = 8.0 Hz, 1H), 7.83-7.72 (m, 3H), 7.69 (dd, J = 8.6, 4.2 Hz, 1H), 7.54 (ddd, J = 8.3, 6.5, 1.9 Hz, 1H), 7.46-7.35 (m, 3H), 7.27 (dd, J = 15.0, 7.3 Hz, 1H), 6.70 (t, J = 7.6 Hz, 1H), 4.85 (s, 1H), 3.42 (dd, J = 14.5, 10.3 Hz, 1H). | 532.0 | 44.0 |

TABLE 2-continued

| Example | Structure | 1H-NMR | M/Z [M + H]+ | α4β7 EC$_{50}$ (nM) |
|---|---|---|---|---|
| 158 | 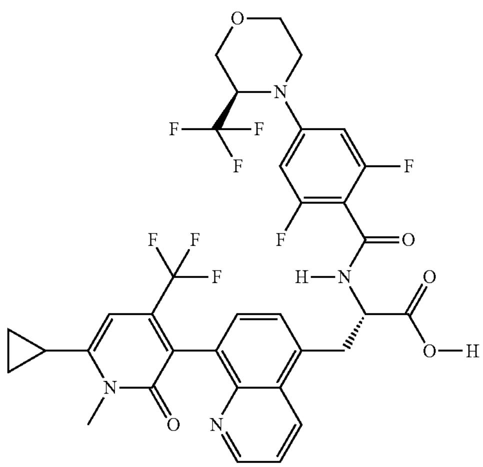 [SMILES: Cn1c(C2CC2)cc(C(F)(F)F)c(-c2ccc(C[C@H](NC(=O)c3c(F)cc(N4CCOC[C@@H]4C(F)(F)F)cc3F)C(=O)O)c3cccnc23)c1=O] | 1H NMR (400 MHz, DMSO-d6) δ 12.85 (s, 1H), 8.97 (dd, J = 8.0, 4.9 Hz, 1H), 8.86 (d, J = 4.3 Hz, 1H), 8.79-8.70 (m, 1H), 7.69 (td, J = 7.8, 4.4 Hz, 1H), 7.61 (t, J = 7.7 Hz, 1H), 7.49 (dd, J = 7.4, 3.8 Hz, 1H), 6.75 (dd, J = 11.7, 3.7 Hz, 2H), 6.34 (s, 1H), 4.90 (dt, J = 11.7, 5.8 Hz, 1H), 4.77-4.67 (m, 1H), 4.16 (d, J = 12.7 Hz, 2H), 3.95 (dd, J = 11.5, 3.7 Hz, 1H), 3.81-3.67 (m, 1H), 3.66 (s, 3H), 3.61-3.37 (m, 3H), 3.24 (t, J = 12.2 Hz, 1H), 2.17 (td, J = 8.4, 4.2 Hz, 1H), 1.10 (d, J = 8.6 Hz, 2H), 0.94 (dq, J = 17.4, 7.0, 4.0 Hz, 2H). | 725.2 | 0.3 |
| 159 | 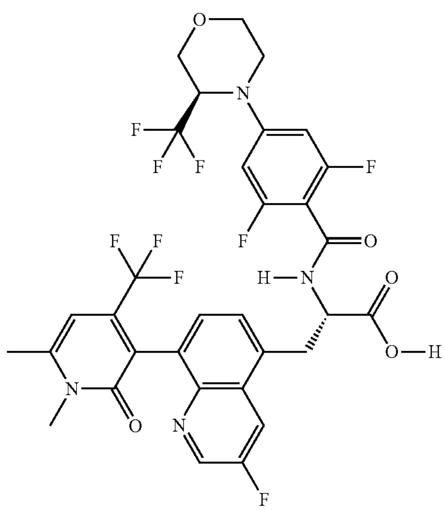 [SMILES: Cc1cc(C(F)(F)F)c(-c2ccc(C[C@H](NC(=O)c3c(F)cc(N4CCOC[C@@H]4C(F)(F)F)cc3F)C(=O)O)c3cc(F)cnc23)c(=O)n1C] | 1H NMR (400 MHz, DMSO-d6) δ 8.97 (d, J = 7.9 Hz, 1H), 8.86 (d, J = 2.7 Hz, 1H), 8.38 (dt, J = 10.6, 2.6 Hz, 1H), 7.60 (t, J = 8.2 Hz, 1H), 7.41 (dd, J = 7.3, 5.2 Hz, 1H), 6.75 (d, J = 11.7 Hz, 2H), 6.54 (s, 1H), 4.91 (dd, J = 9.0, 3.5 Hz, 1H), 4.70 (tt, J = 7.9, 3.6 Hz, 1H), 4.15 (d, J = 12.7 Hz, 1H), 3.95 (dd, J = 11.4, 3.8 Hz, 1H), 3.73 (d, J = 12.9 Hz, 1H), 3.65 (dd, J = 14.1, 4.4 Hz, 1H), 3.62-3.51 (m, 1H), 3.48 (d, J = 1.5 Hz, 3H), 3.47-3.38 (m, 2H), 3.23 (t, J = 12.4 Hz, 1H), 2.52 (s, 3H). | 717.0 | 0.3 |
| 160 | 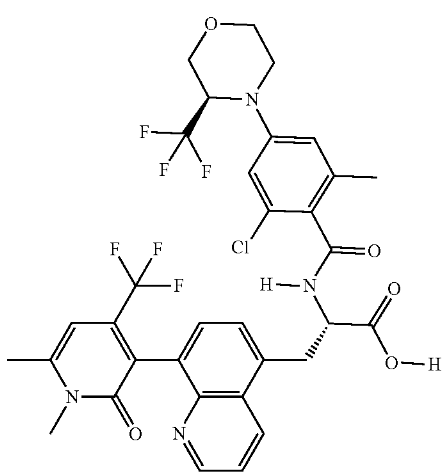 [SMILES: Cc1cc(N2CCOC[C@@H]2C(F)(F)F)cc(Cl)c1C(=O)N[C@@H](Cc1ccc(-c2c(C(F)(F)F)cc(C)n(C)c2=O)c2ncccc12)C(=O)O] | 1H NMR (400 MHz, DMSO-d6) δ 8.96-8.80 (m, 2H), 8.75-8.64 (m, 1H), 7.73-7.61 (m, 2H), 7.46 (t, J = 7.8 Hz, 1H), 6.84 (d, J = 8.7 Hz, 1H), 6.79 (d, J = 9.3 Hz, 1H), 6.56 (d, J = 4.5 Hz, 1H), 4.91-4.69 (m, 2H), 4.13 (d, J = 12.7 Hz, 1H), 3.93 (d, J = 11.3 Hz, 1H), 3.82-3.64 (m, 2H), 3.58-3.41 (m, 4H), 3.36-3.20 (m, 3H), 2.54 (s, 3H), 2.02 (s, 3H). | 711.2 | 0.3 |

TABLE 2-continued

| Example | Structure | 1H-NMR | M/Z [M + H]+ | α4β7 EC$_{50}$ (nM) |
|---|---|---|---|---|
| 161 | 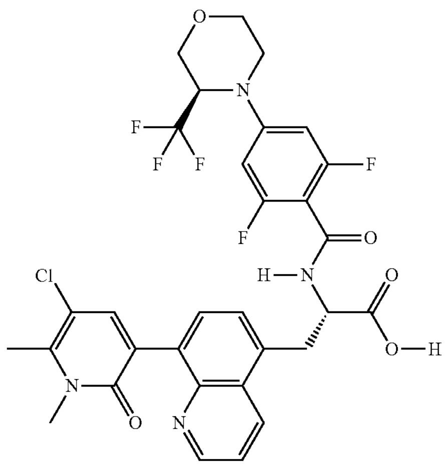 [SMILES: Cc1c(Cl)cc(-c2ccc(C[C@H](NC(=O)c3c(F)cc(N4CCOC[C@@H]4C(F)(F)F)cc3F)C(=O)O)c3cccnc23)c(=O)n1C] | 1H NMR (400 MHz, DMSO-d6) δ 8.99-8.93 (m, 2H), 8.85 (d, J = 8.7 Hz, 1H), 7.80-7.71 (m, 2H), 7.65 (d, J = 7.4 Hz, 1H), 7.57 (s, 1H), 6.76 (d, J = 11.7 Hz, 2H), 4.96-4.85 (m, 1H), 4.74-4.66 (m, 1H), 4.16 (d, J = 12.7 Hz, 1H), 3.95 (dd, J = 11.5, 3.7 Hz, 1H), 3.79-3.69 (m, 2H), 3.60-3.51 (m, 4H), 3.50-3.37 (m, 2H), 3.23 (t, 1H), 2.57 (s, 3H). | 665.2 | 0.3 |
| 162 | 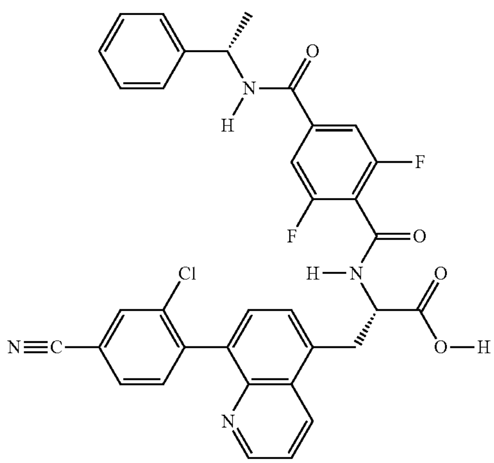 [SMILES: C[C@H](NC(=O)c1cc(F)c(C(=O)N[C@@H](Cc2ccc(-c3ccc(C#N)cc3Cl)c3ncccc23)C(=O)O)c(F)c1)c1ccccc1] | 1H NMR (400 MHz, DMSO-d6) δ 9.35 (d, J = 8.2 Hz, 1H), 8.97 (d, J = 7.9 Hz, 1H), 8.84 (dd, J = 4.1, 1.6 Hz, 1H), 8.68-8.60 (m, 1H), 8.16 (d, J = 1.6 Hz, 1H), 7.91 (d, J = 8.0 Hz, 1H), 7.60 (td, J = 15.7, 15.0, 8.2 Hz, 6H), 7.38-7.28 (m, 4H), 7.21 (t, J = 7.1 Hz, 1H), 5.11 (t, J = 7.3 Hz, 1H), 4.79 (d, J = 12.5 Hz, 1H), 3.41 (s, 1H), 2.65 (s, 1H), 2.31 (s, 1H), 1.45 (d, J = 7.0 Hz, 3H). | 639.2 | 53.5 |
| 163 | 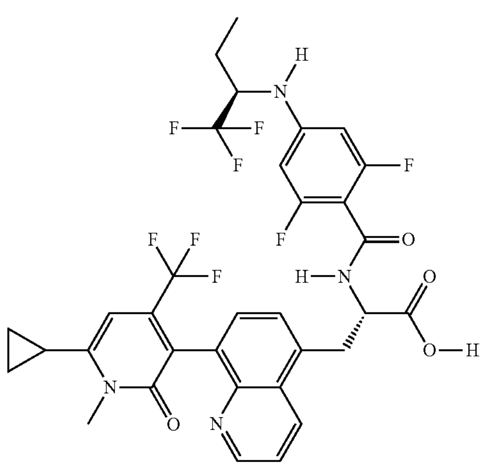 [SMILES: CC[C@@H](Nc1cc(F)c(C(=O)N[C@@H](Cc2ccc(-c3c(C(F)(F)F)cc(C4CC4)n(C)c3=O)c3ncccc23)C(=O)O)c(F)c1)C(F)(F)F] | 1H NMR (400 MHz, DMSO-d6) δ 13.00 (s, 1H), 8.86 (d, J = 3.8 Hz, 1H), 8.81 (dd, J = 7.9, 5.5 Hz, 1H), 8.73 (t, J = 7.5 Hz, 1H), 7.69 (dt, J = 8.8, 5.1 Hz, 1H), 7.60 (t, J = 6.6 Hz, 1H), 7.48 (dd, J = 7.4, 3.2 Hz, 1H), 6.76 (dd, J = 9.5, 4.7 Hz, 1H), 6.44 (dd, J = 11.4, 3.6 Hz, 2H), 6.34 (s, 1H), 4.70 (tt, J = 8.2, 4.1 Hz, 1H), 4.35-4.26 (m, 1H), 3.79-3.63 (m, 4H), 3.52-3.35 (m, 1H), 2.17 (ddd, J = 13.8, 8.4, 5.5 Hz, 1H), 1.85-1.70 (m, 1H), 1.61-1.45 (m, 1H), 1.16-1.04 (m, 2H), 1.02-0.87 (m, 2H), 0.93 (t, J = 7.3 Hz, 3H). | 697.2 | 0.4 |

TABLE 2-continued
| Example | Structure | 1H-NMR | M/Z [M + H]+ | α4β7 EC$_{50}$ (nM) |
|---|---|---|---|---|
| 164 | 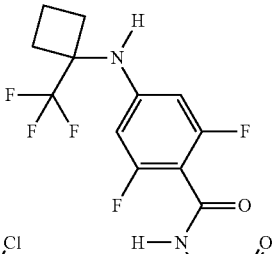 | 1H NMR (400 MHz, DMSO-d6) δ 8.86-8.79 (m, 2H), 8.63 (dd, J = 8.6, 1.7 Hz, 1H), 8.15 (dd, J = 1.7, 0.4 Hz, 1H), 7.90 (dd, J = 7.9, 1.6 Hz, 1H), 7.68-7.51 (m, 4H), 7.16 (s, 1H), 6.09 (d, J = 11.1 Hz, 2H), 4.68 (s, 1H), 3.72 (s, 1H), 3.41 (s, 1H), 2.53 (dd, J = 13.0, 6.5 Hz, 2H), 2.36-2.26 (m, 2H), 1.95 (dd, J = 15.1, 6.8 Hz, 2H). | 629.2 | 88.6 |
| 165 | 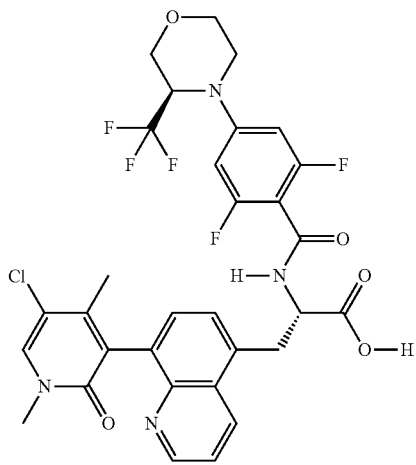 | 1H NMR (400 MHz, DMSO-d6) δ 8.98-8.88 (m, 2H), 8.84 (t, J = 8.0 Hz, 1H), 8.13 (s, 1H), 7.81-7.71 (m, 1H), 7.67 (dd, J = 15.1, 7.4 Hz, 1H), 7.57 (dd, J = 10.9, 7.3 Hz, 1H), 6.74 (dd, J = 11.7, 2.5 Hz, 2H), 4.95-4.84 (m, 1H), 4.80-4.68 (m, 1H), 4.16 (d, J = 12.7 Hz, 1H), 3.95 (dd, J = 11.5, 3.8 Hz, 1H), 3.77-3.65 (m, 1H), 3.60-3.49 (m, 2H), 3.48-3.33 (m, 5H), 3.29-3.17 (m, 1H), 1.82 (d, J = 10.8 Hz, 3H). | 665.2 | 0.4 |
| 166 | 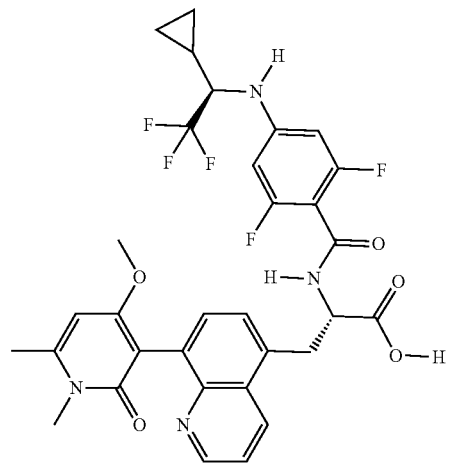 [SMILES: COc1cc(C)n(C)c(=O)c1-c1ccc(C[C@H](NC(=O)c2c(F)cc(N[C@H](C3CC3)C(F)(F)F)cc2F)C(=O)O)c2cccnc12] | 1H NMR (400 MHz, DMSO-d6) δ 9.16-9.01 (m, 1H), 8.97 (d, J = 4.7 Hz, 1H), 8.84 (d, J = 7.9 Hz, 1H), 7.98-7.82 (m, 1H), 7.76-7.63 (m, 2H), 6.96 (d, J = 9.5 Hz, 1H), 6.50-6.38 (m, 3H), 4.74-4.64 (m, 1H), 3.93 (q, J = 8.0 Hz, 1H), 3.84-3.69 (m, 1H), 3.67 (d, J = 4.4 Hz, 3H), 3.55-3.41 (m, 4H), 2.51 (s, 3H), 1.11-1.00 (m, 1H), 0.67-0.59 (m, 1H), 0.56-0.44 (m, 2H), 0.35-0.27 (m, 1H). | 645.2 | 0.4 |

TABLE 2-continued
| Example | Structure | 1H-NMR | M/Z [M + H]+ | α4β7 EC$_{50}$ (nM) |
|---|---|---|---|---|
| 167 | 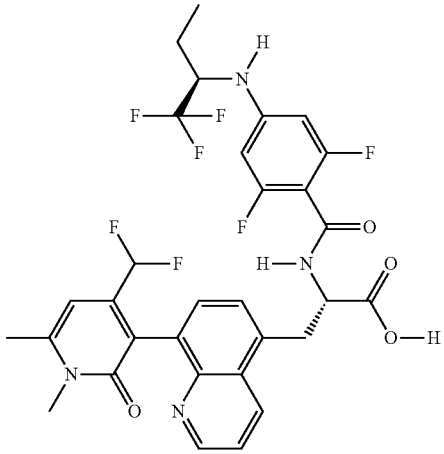 [SMILES: CC[C@@H](Nc1cc(F)c(C(=O)N[C@@H](Cc2ccc(-c3c(C(F)F)cc(C)n(C)c3=O)c3ncccc23)C(=O)O)c(F)c1)C(F)(F)F] | 1H NMR (400 MHz, DMSO-d6) δ 12.93 (s, 1H), 8.92-8.85 (m, 1H), 8.82-8.73 (m, 2H), 7.78-7.68 (m, 1H), 7.64 (dd, J = 16.6, 7.4 Hz, 1H), 7.52 (dd, J = 9.7, 7.3 Hz, 1H), 6.77 (d, J = 9.3 Hz, 1H), 6.49 (d, J = 3.0 Hz, 1H), 6.43 (dd, J = 11.4, 4.7 Hz, 2H), 6.12 (td, J = 54.6, 12.8 Hz, 1H), 4.78-4.65 (m, 1H), 4.35-4.25 (m, 1H), 3.85-3.63 (m, 1H), 3.51-3.48 (m, 3H), 3.54-3.32 (m, 1H), 2.53 (s, 3H), 1.84-1.70 (m, 1H), 1.61-1.44 (m, 1H), 0.92 (t, J = 7.3 Hz, 3H). | 653.2 | 0.4 |
| 168 | 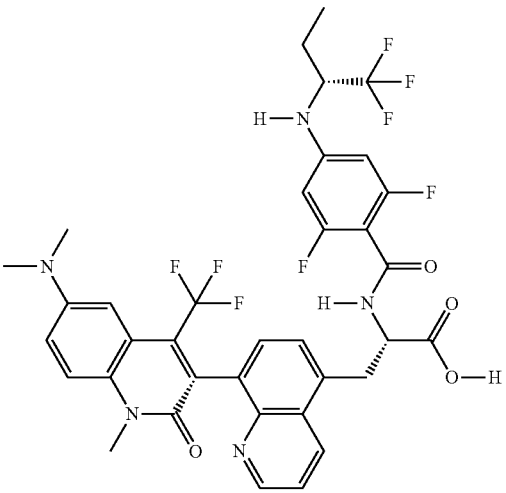 | 1H NMR (400 MHz, DMSO-d6) δ 8.75 (s, 1H), 8.61 (s, 1H), 7.58 (dd, J = 22.2, 8.5 Hz, 2H), 7.45 (d, J = 7.0 Hz, 1H), 7.36 (dd, J = 9.4, 2.7 Hz, 1H), 7.03 (s, 1H), 6.75 (d, J = 9.4 Hz, 1H), 6.53 (s, 1H), 6.45 (d, J = 11.6 Hz, 2H), 4.31 (s, 1H), 3.73 (d, J = 13.2 Hz, 1H), 3.66 (s, 3H), 2.97 (s, 5H), 2.74-2.59 (m, 1H), 2.39-2.21 (m, 1H), 1.77 (s, 1H), 1.53 (s, 1H), 0.93 (t, J = 7.3 Hz, 3H). | 750.9 | 0.5 |
| 169 | 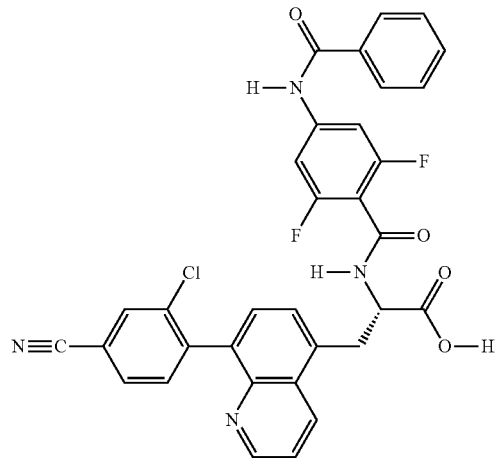 [SMILES: N#Cc1ccc(-c2ccc(C[C@H](NC(=O)c3c(F)cc(NC(=O)c4ccccc4)cc3F)C(=O)O)c3cccnc23)c(Cl)c1] | 1H NMR (400 MHz, DMSO-d6) δ 10.62 (s, 1H), 9.16 (d, J = 8.1 Hz, 1H), 8.84 (dd, J = 4.1, 1.6 Hz, 1H), 8.65 (dd, J = 8.7, 1.7 Hz, 1H), 8.16 (d, J = 1.6 Hz, 1H), 7.97-7.86 (m, 3H), 7.67-7.58 (m, 5H), 7.58-7.50 (m, 4H), 4.76 (q, J = 5.3, 4.7 Hz, 1H), 3.43 (s, 2H). | 612.2 | 88.6 |

TABLE 2-continued

| Example | Structure | 1H-NMR | M/Z [M + H]+ | α4β7 EC$_{50}$ (nM) |
|---|---|---|---|---|
| 170 | 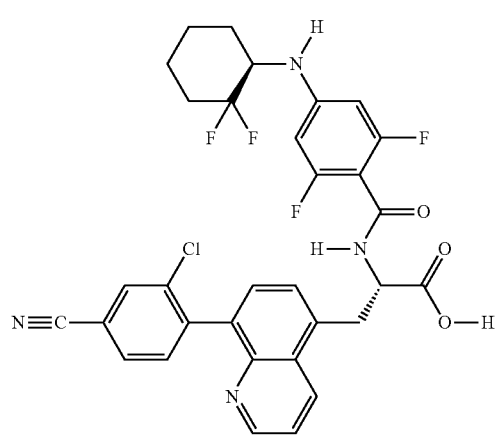 [SMILES: N#Cc1ccc(-c2ccc(C[C@H](NC(=O)c3c(F)cc(N[C@@H]4CCCCC4(F)F)cc3F)C(=O)O)c3cccnc23)c(Cl)c1] | 1H NMR (400 MHz, DMSO-d6) δ 8.83 (dd, J = 4.1, 1.6 Hz, 1H), 8.71 (d, J = 8.0 Hz, 1H), 8.64 (dd, J = 8.7, 1.7 Hz, 1H), 8.15 (d, J = 1.6 Hz, 1H), 7.90 (dd, J = 7.9, 1.7 Hz, 1H), 7.67-7.52 (m, 4H), 6.58 (d, J = 9.0 Hz, 1H), 6.34 (d, J = 12.1 Hz, 2H), 4.69 (d, J = 12.1 Hz, 1H), 3.89 (d, J = 21.4 Hz, 1H), 3.72 (s, 1H), 3.42 (s, 1H), 1.81 (s, 4H), 1.66 (s, 2H), 1.40 (s, 3H). | 625.2 | 93.7 |
| 171 | 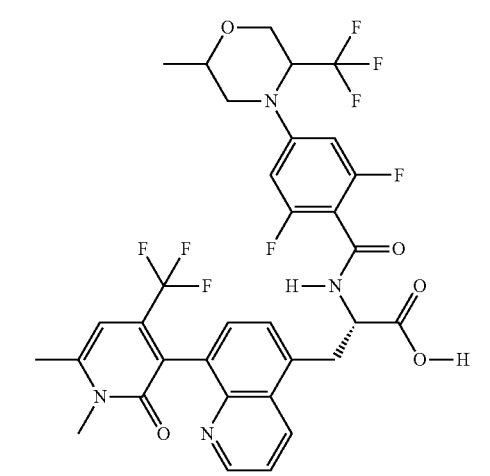 | 1H NMR (400 MHz, DMSO-d6) δ 8.96 (d, J = 7.8 Hz, 1H), 8.83 (d, J = 4.2 Hz, 1H), 8.67 (s, 1H), 7.64 (s, 1H), 7.58 (t, J = 7.3 Hz, 1H), 7.45 (d, J = 6.8 Hz, 1H), 6.76 (dd, J = 11.6, 4.1 Hz, 2H), 6.55 (s, 1H), 4.87 (d, J = 9.2 Hz, 1H), 4.71 (td, J = 8.9, 4.5 Hz, 1H), 4.17 (d, J = 12.7 Hz, 1H), 3.78 (d, J = 13.7 Hz, 1H), 3.74-3.57 (m, 1H), 3.57-3.34 (m, 5H), 2.82 (t, J = 11.7 Hz, 1H), 2.53 (s, 3H), 1.20 (d, J = 6.6 Hz, 1H), 1.15 (d, J = 6.1 Hz, 3H). | 713.0 | 0.5 |
| 172 | 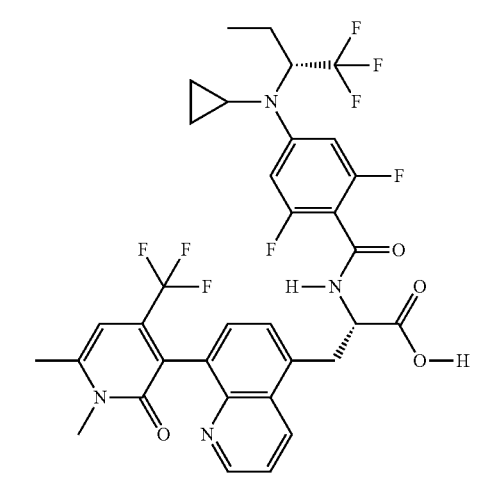 [SMILES: CC[C@@H](N(c1cc(F)c(C(=O)N[C@@H](Cc2ccc(-c3c(C(F)(F)F)cc(C)n(C)c3=O)c3ncccc23)C(=O)O)c(F)c1)C1CC1)C(F)(F)F] | 1H NMR (400 MHz, DMSO-d6) δ 8.93 (dd, J = 7.9, 3.4 Hz, 1H), 8.82 (d, J = 4.2 Hz, 1H), 8.65 (s, 1H), 7.69-7.61 (m, 1H), 7.58 (t, J = 7.4 Hz, 1H), 7.45 (d, J = 7.1 Hz, 1H), 6.64 (dd, J = 12.0, 4.1 Hz, 2H), 6.55 (d, J = 1.3 Hz, 1H), 5.67 (ddd, J = 21.8, 10.0, 4.8 Hz, 1H), 5.25-5.10 (m, 2H), 4.80 (s, 1H), 4.68 (td, J = 8.6, 7.7, 4.1 Hz, 1H), 4.00 (s, 2H), 3.71 (td, J = 14.7, 4.5 Hz, 1H), 3.54-3.31 (m, 4H), 2.53 (s, 3H), 1.91 (ddd, J = 14.2, 10.2, 7.1 Hz, 1H), 1.78 (ddd, J = 14.1, 7.2, 4.1 Hz, 1H), 0.86 (t, J = 7.3 Hz, 3H). | 711.0 | 0.5 |

TABLE 2-continued
| Example | Structure | 1H-NMR | M/Z [M + H]+ | α4β7 EC$_{50}$ (nM) |
|---|---|---|---|---|
| 173 | 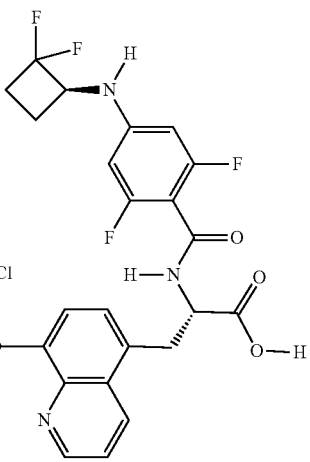 | 1H NMR (400 MHz, DMSO-d6) δ 8.80 (dd, J = 4.1, 1.6 Hz, 1H), 8.66 (d, J = 8.6 Hz, 1H), 8.55 (s, 1H), 8.14 (dd, J = 1.6, 0.4 Hz, 1H), 7.88 (dd, J = 7.9, 1.7 Hz, 1H), 7.68-7.49 (m, 4H), 7.01 (d, J = 7.5 Hz, 1H), 6.23 (d, J = 11.2 Hz, 2H), 4.58 (s, 1H), 4.46-4.30 (m, 1H), 3.70 (s, 1H), 3.45 (s, 1H), 2.42-2.28 (m, 2H), 2.21 (dt, J = 15.3, 8.8 Hz, 1H), 1.68-1.49 (m, 1H). | 598.0 | 81.5 |
| 174 | 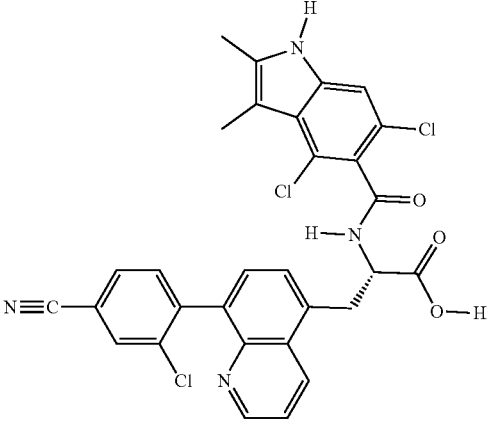 [SMILES: Cc1[nH]c2cc(Cl)c(C(=O)N[C@@H](Cc3ccc(-c4ccc(C#N)cc4Cl)c4ncccc34)C(=O)O)c(Cl)c2c1C] | 1H NMR (400 MHz, DMSO-d6) δ 11.19 (s, 1H), 8.99 (s, 1H), 8.83 (d, J = 3.6 Hz, 1H), 8.66 (d, J = 8.4 Hz, 1H), 8.17 (d, J = 1.7 Hz, 1H), 7.91 (d, J = 7.9 Hz, 1H), 7.72-7.57 (m, 2H), 7.54 (d, J = 7.9 Hz, 1H), 7.18 (s, 1H), 4.86 (s, 1H), 3.78-3.68 (m, 1H), 3.42 (s, 1H), 2.27 (d, J = 11.2 Hz, 6H). | 591.0 | 97.8 |
| 175 | 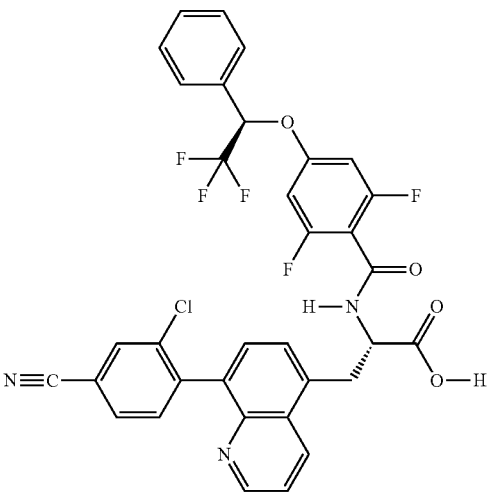 [SMILES: N#Cc1ccc(-c2ccc(C[C@H](NC(=O)c3c(F)cc(O[C@H](c4ccccc4)C(F)(F)F)cc3F)C(=O)O)c3cccnc23)c(Cl)c1] | 1H NMR (400 MHz, DMSO-d6) δ 9.12 (d, J = 8.1 Hz, 1H), 8.84 (dd, J = 4.1, 1.6 Hz, 1H), 8.62 (dd, J = 8.7, 1.7 Hz, 1H), 8.17 (dd, J = 1.6, 0.4 Hz, 1H), 7.91 (dd, J = 7.9, 1.7 Hz, 1H), 7.65-7.54 (m, 6H), 7.50-7.42 (m, 3H), 6.93 (d, J = 9.4 Hz, 2H), 6.45 (q, J = 6.6 Hz, 1H), 4.75-4.67 (m, 1H), 3.81-3.67 (m, 1H), 3.44-3.29 (m, 1H). | 666.1 | 97.1 |

TABLE 2-continued

| Example | Structure | 1H-NMR | M/Z [M + H]+ | α4β7 EC$_{50}$ (nM) |
|---|---|---|---|---|
| 176 | 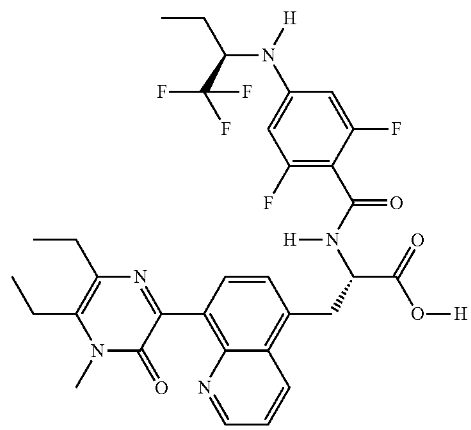 [SMILES: CCc1nc(-c2ccc(C[C@H](NC(=O)c3c(F)cc(N[C@H](CC)C(F)(F)F)cc3F)C(=O)O)c3cccnc23)c(=O)n(C)c1CC] | 1H NMR (400 MHz, DMSO-d6) δ 8.91 (d, J = 4.3 Hz, 1H), 8.79 (t, J = 10.4 Hz, 2H), 7.78-7.69 (m, 2H), 7.64 (d, J = 7.4 Hz, 1H), 6.78 (d, J = 9.4 Hz, 1H), 6.45 (d, J = 11.9 Hz, 2H), 4.78-4.58 (m, 1H), 4.30 (m, 1H), 3.72 (dd, J = 14.5, 4.6 Hz, 1H), 3.55 (d, J = 1.3 Hz, 3H), 3.45 (dd, J = 14.5, 9.7 Hz, 1H), 2.81 (q, J = 7.4 Hz, 2H), 2.66 (d, J = 7.3 Hz, 1H), 1.76 (d, J = 11.7 Hz, 1H), 1.62-1.43 (m, 1H), 1.25 (t, J = 7.4 Hz, 3H), 1.22-1.08 (m, 3H), 0.93 (t, J = 7.3 Hz, 3H). | 646.3 | 0.9 |
| 177 | 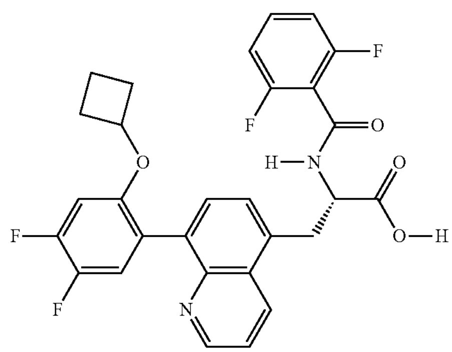 [SMILES: O=C(N[C@@H](Cc1ccc(-c2cc(F)c(F)cc2OC2CCC2)c2ncccc12)C(=O)O)c1c(F)cccc1F] | 1H NMR (400 MHz, DMSO-d6) δ 9.26 (d, J = 8.2 Hz, 1H), 8.86 (d, J = 4.1 Hz, 1H), 8.63 (d, J = 8.6 Hz, 1H), 7.67-7.59 (m, 1H), 7.57 (d, J = 7.5 Hz, 1H), 7.48 (t, J = 8.4 Hz, 1H), 7.36-7.24 (m, 1H), 7.10 (t, J = 8.0 Hz, 2H), 7.03 (dd, J = 12.9, 7.1 Hz, 1H), 4.74 (s, 1H), 4.61 (t, J = 7.0 Hz, 1H), 3.79-3.70 (m, 1H), 3.42-3.33 (m, 2H), 2.22 (s, 3H), 1.74-1.62 (m, 2H), 1.57 (d, J = 9.7 Hz, 1H), 1.51-1.42 (m, 1H). | 539.0 | 28.0 |
| 178 | 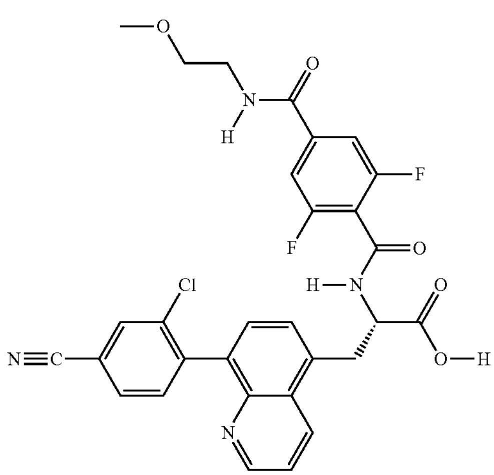 [SMILES: COCCNC(=O)c1cc(F)c(C(=O)N[C@@H](Cc2ccc(-c3ccc(C#N)cc3Cl)c3ncccc23)C(=O)O)c(F)c1] | 1H NMR (400 MHz, DMSO-d6) δ 9.35 (d, J = 8.2 Hz, 1H), 8.84 (dd, J = 4.2, 1.6 Hz, 1H), 8.74 (d, J = 5.4 Hz, 1H), 8.64 (dd, J = 8.7, 1.7 Hz, 1H), 8.16 (d, J = 1.7 Hz, 1H), 7.90 (d, J = 8.2 Hz, 1H), 7.67-7.60 (m, 3H), 7.56 (dd, J = 8.1, 6.2 Hz, 3H), 4.79 (d, J = 7.6 Hz, 1H), 3.78 (s, 1H), 3.50-3.32 (m, 3H), 3.24 (s, 3H), 2.65 (s, 1H), 2.31 (s, 1H). | 593.6 | 37.1 |

TABLE 2-continued

| Example | Structure | 1H-NMR | M/Z [M + H]+ | α4β7 EC$_{50}$ (nM) |
|---|---|---|---|---|
| 179 | 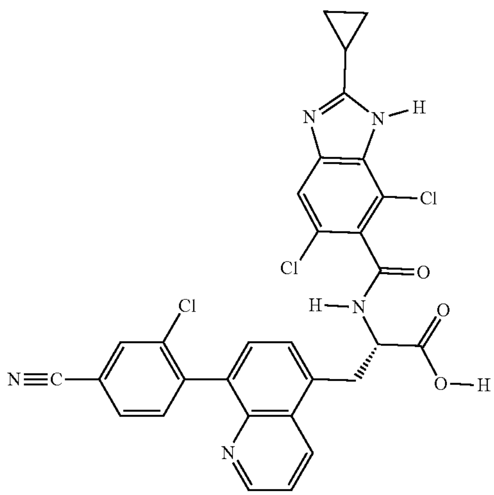 [SMILES: N#Cc1ccc(-c2ccc(C[C@H](NC(=O)c3c(Cl)cc4nc(C5CC5)[nH]c4c3Cl)C(=O)O)c3cccnc23)c(Cl)c1] | 1H NMR (400 MHz, DMSO-d6) δ 9.13 (d, J = 8.3 Hz, 1H), 8.84 (dd, J = 4.2, 1.6 Hz, 1H), 8.67 (dd, J = 8.7, 1.7 Hz, 1H), 8.17 (d, J = 1.6 Hz, 1H), 7.92 (d, J = 7.8 Hz, 1H), 7.74-7.58 (m, 3H), 7.54 (d, J = 7.9 Hz, 1H), 7.46 (s, 1H), 4.86 (s, 1H), 3.76 (dd, J = 14.3, 4.1 Hz, 1H), 3.39 (t, J = 12.7 Hz, 1H), 2.14 (ddd, J = 12.9, 8.3, 5.0 Hz, 1H), 1.19-0.98 (m, 3H). | 604.1 | 37.7 |
| 180 | 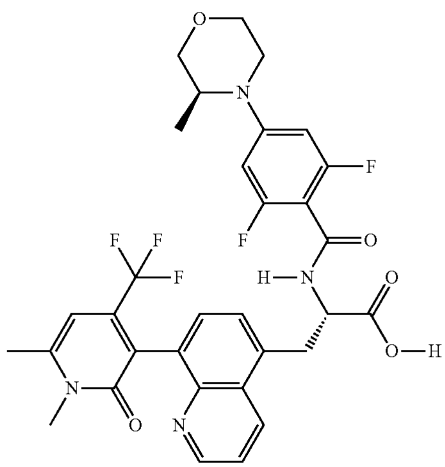 [SMILES: Cc1cc(C(F)(F)F)c(-c2ccc(C[C@H](NC(=O)c3c(F)cc(N4CCOC[C@@H]4C)cc3F)C(=O)O)c3cccnc23)c(=O)n1C] | 1H NMR (400 MHz, DMSO-d6) δ 8.90-8.81 (m, 2H), 8.74 (t, J = 7.8 Hz, 1H), 7.74-7.64 (m, 1H), 7.61 (t, J = 7.5 Hz, 1H), 7.49 (dd, J = 7.4, 2.5 Hz, 1H), 6.60-6.48 (m, 3H), 4.78-4.65 (m, 1H), 4.01-3.84 (m, 2H), 3.79-3.57 (m, 4H), 3.54-3.38 (m, 5H), 3.38-3.30 (m, 1H), 2.98 (td, J = 12.4, 3.9 Hz, 1H), 1.04 (d, J = 6.6 Hz, 3H). | 645.7 | 0.9 |
| 181 | 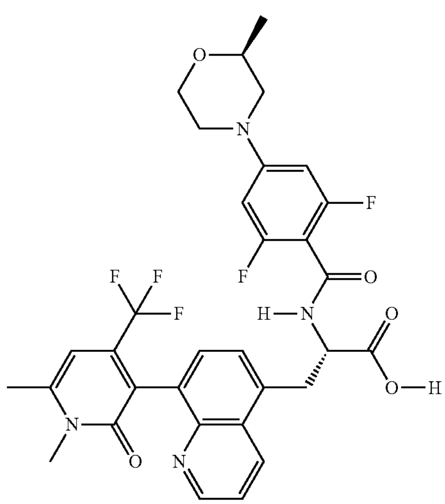 [SMILES: Cc1cc(C(F)(F)F)c(-c2ccc(C[C@H](NC(=O)c3c(F)cc(N4CCO[C@@H](C)C4)cc3F)C(=O)O)c3cccnc23)c(=O)n1C] | 1H NMR (400 MHz, DMSO-d6) δ 12.93 (s, 1H), 8.94-8.85 (m, 1H), 8.81 (dd, J = 4.2, 1.5 Hz, 1H), 8.63 (d, J = 8.5 Hz, 1H), 7.61 (dd, J = 8.5, 4.2 Hz, 1H), 7.57 (t, J = 6.9 Hz, 1H), 7.43 (dd, J = 7.4, 3.8 Hz, 1H), 6.63 (dd, J = 11.8, 4.5 Hz, 2H), 6.55 (s, 1H), 4.69 (ddd, J = 12.8, 7.9, 4.0 Hz, 1H), 3.90-3.83 (m, 1H), 3.72 (d, J = 11.8 Hz, 3H), 3.58 (s, 2H), 3.49 (d, J = 2.0 Hz, 3H), 3.47-3.36 (m, 1H), 2.76-2.64 (m, 1H), 2.53 (d, J = 4.1 Hz, 3H), 2.44-2.29 (m, 1H), 1.13 (d, J = 6.2 Hz, 3H). | 645.1 | 0.7 |

TABLE 2-continued

| Example | Structure | 1H-NMR | M/Z [M + H]+ | α4β7 EC$_{50}$ (nM) |
| --- | --- | --- | --- | --- |
| 182 | 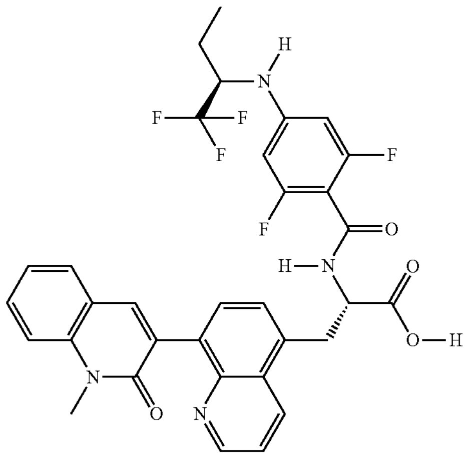 [SMILES: CC[C@@H](Nc1cc(F)c(C(=O)N[C@@H](Cc2ccc(-c3cc4ccccc4n(C)c3=O)c3ncccc23)C(=O)O)c(F)c1)C(F)(F)F] | 1H NMR (400 MHz, DMSO-d6) δ 8.93-8.86 (m, 1H), 8.83 (d, J = 8.0 Hz, 2H), 8.00 (s, 1H), 7.83-7.55 (m, 6H), 7.31 (ddd, J = 8.0, 7.1, 1.1 Hz, 1H), 6.78 (d, J = 9.4 Hz, 1H), 6.44 (d, J = 11.6 Hz, 2H), 4.72-4.57 (m, 1H), 4.30 (d, J = 8.3 Hz, 1H), 3.68 (s, 4H), 3.44 (dd, J = 14.5, 9.9 Hz, 1H), 1.75 (ddd, J = 10.6, 7.4, 3.6 Hz, 1H), 1.51 (ddd, J = 13.7, 10.4, 7.1 Hz, 1H), 0.91 (t, J = 7.3 Hz, 3H). | 639.2 | 0.9 |
| 183 | 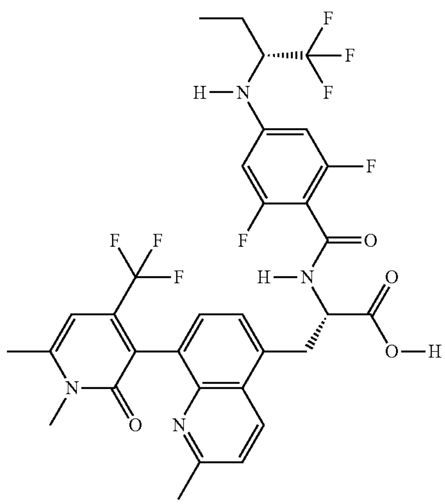 [SMILES: CC[C@@H](Nc1cc(F)c(C(=O)N[C@@H](Cc2ccc(-c3c(C(F)(F)F)cc(C)n(C)c3=O)c3nc(C)ccc23)C(=O)O)c(F)c1)C(F)(F)F] | 1H NMR (400 MHz, DMSO-d6) δ 8.78 (t, J = 7.7 Hz, 1H), 8.57 (s, 1H), 7.51 (s, 2H), 7.40 (s, 1H), 6.81-6.67 (m, 1H), 6.56 (s, 1H), 6.44 (dd, J = 11.4, 5.9 Hz, 2H), 4.66 (s, 1H), 4.29 (s, 1H), 3.67 (t, J = 16.9 Hz, 1H), 3.50 (d, J = 2.6 Hz, 3H), 3.47-3.28 (m, 1H), 2.58 (s, 3H), 2.54 (s, 3H), 1.87-1.65 (m, 1H), 1.53 (dt, J = 17.9, 7.3 Hz, 1H), 0.93 (t, J = 7.3 Hz, 3H). | 685.2 | 0.9 |
| 184 | 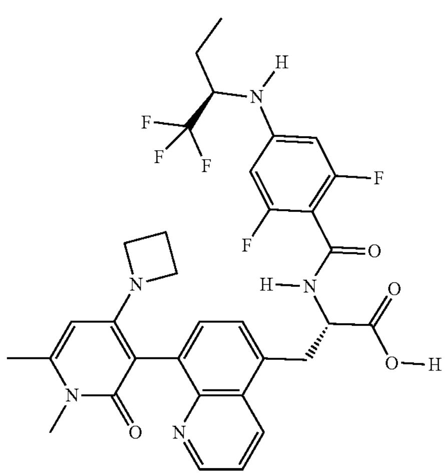 [SMILES: CC[C@@H](Nc1cc(F)c(C(=O)N[C@@H](Cc2ccc(-c3c(N4CCC4)cc(C)n(C)c3=O)c3ncccc23)C(=O)O)c(F)c1)C(F)(F)F] | 1H NMR (400 MHz, DMSO-d6) δ 9.24 (d, J = 8.5 Hz, 1H), 9.06 (d, J = 5.0 Hz, 1H), 8.74 (t, J = 7.8 Hz, 1H), 8.10-7.93 (m, 1H), 7.84-7.59 (m, 2H), 6.77 (t, J = 9.0 Hz, 1H), 6.42 (dd, J = 16.1, 11.9 Hz, 2H), 5.75 (d, J = 3.5 Hz, 1H), 4.81-4.68 (m, 1H), 4.29 (s, 2H), 3.46-3.30 (m, 5H), 3.22 (s, 3H), 2.39 (d, J = 2.3 Hz, 3H), 1.81 (ddt, J = 28.3, 13.5, 6.1 Hz, 3H), 1.60-1.43 (m, 1H), 0.92 (td, J = 7.4, 2.8 Hz, 3H). | 658.3 | 0.9 |

TABLE 2-continued

| Example | Structure | 1H-NMR | M/Z [M + H]+ | α4β7 EC$_{50}$ (nM) |
|---|---|---|---|---|
| 185 | 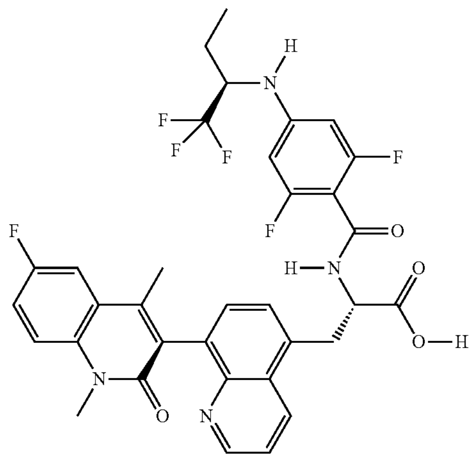 | 1H NMR (400 MHz, DMSO-d6) δ 8.86-8.65 (m, 3H), 7.75-7.49 (m, 6H), 6.76 (d, J = 9.5 Hz, 1H), 6.43 (d, J = 11.4 Hz, 2H), 4.70 (dd, J = 9.2, 5.0 Hz, 1H), 4.30 (d, J = 10.0 Hz, 1H), 3.65 (d, J = 2.4 Hz, 4H), 3.50 (dd, J = 14.5, 9.6 Hz, 1H), 2.04 (d, J = 8.8 Hz, 3H), 1.75 (ddd, J = 13.8, 7.3, 3.3 Hz, 1H), 1.57-1.47 (m, 1H), 0.91 (t, J = 7.3 Hz, 3H). | 671.2 | 1.0 |
| 186 | 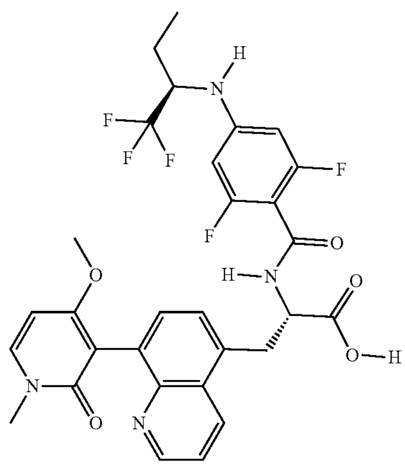 [SMILES: CC[C@@H](Nc1cc(F)c(C(=O)N[C@@H](Cc2ccc(-c3c(OC)ccn(C)c3=O)c3ncccc23)C(=O)O)c(F)c1)C(F)(F)F] | 1H NMR (400 MHz, DMSO-d6) δ 8.98 (m, J = 25.3 Hz, 2H), 8.85 (d, J = 7.9 Hz, 1H), 7.94 (d, J = 7.7 Hz, 1H), 7.91-7.81 (m, 1H), 7.74-7.62 (m, 2H), 6.79 (d, J = 9.4 Hz, 1H), 6.51-6.39 (m, 3H), 4.72-4.64 (m, 1H), 4.37-4.25 (m, 1H), 3.81-3.70 (m, 1H), 3.67 (d, J = 5.6 Hz, 3H), 3.53-3.40 (m, 4H), 1.83-1.71 (m, 1H), 1.59-1.46 (m, 1H), 0.92 (t, J = 7.3 Hz, 3H). | 619.2 | 1.0 |
| 187 | 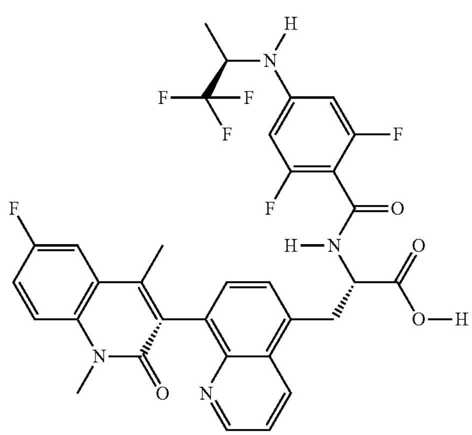 | 1H NMR (400 MHz, DMSO-d6) δ 8.81 (d, J = 7.0 Hz, 2H), 8.73 (s, 1H), 7.79-7.45 (m, 6H), 6.84 (d, J = 9.1 Hz, 1H), 6.40 (d, J = 11.4 Hz, 2H), 4.70 (dt, J = 8.8, 4.3 Hz, 1H), 4.54-4.48 (m, 1H), 3.68 (d, J = 4.9 Hz, 1H), 3.64 (d, J = 2.3 Hz, 3H), 3.50 (dd, J = 14.5, 9.7 Hz, 1H), 2.04 (d, J = 8.2 Hz, 3H), 1.26 (d, J = 6.7 Hz, 3H). | 657.2 | 1.1 |

TABLE 2-continued

| Example | Structure | 1H-NMR | M/Z [M + H]+ | α4β7 EC$_{50}$ (nM) |
|---|---|---|---|---|
| 188 | 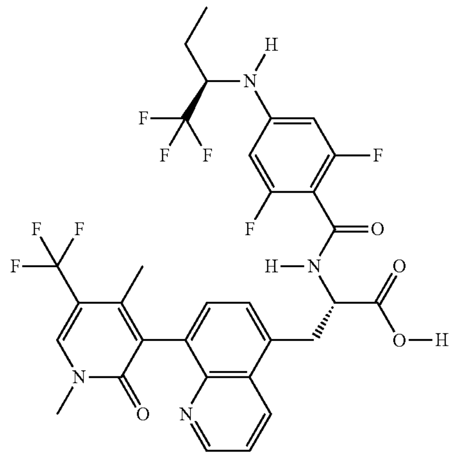 [SMILES: CC[C@@H](Nc1cc(F)c(C(=O)N[C@@H](Cc2ccc(-c3c(C)c(C(F)(F)F)cn(C)c3=O)c3ncccc23)C(=O)O)c(F)c1)C(F)(F)F] | 1H NMR (400 MHz, DMSO-d6) δ 12.92 (s, 1H), 8.87 (d, J = 4.3 Hz, 1H), 8.77 (q, J = 10.9, 9.3 Hz, 2H), 8.39 (s, 1H), 7.76-7.58 (m, 2H), 7.54 (t, J = 7.7 Hz, 1H), 6.75 (dd, J = 9.3, 6.7 Hz, 1H), 6.43 (dd, J = 11.4, 3.9 Hz, 2H), 4.71 (dt, J = 13.6, 9.5 Hz, 1H), 4.30 (d, J = 9.4 Hz, 1H), 3.74 (ddd, J = 51.1, 14.5, 4.5 Hz, 1H), 3.51 (d, J = 2.2 Hz, 3H), 3.36 (dd, J = 14.4, 10.5 Hz, 1H), 1.83 (d, J = 9.6 Hz, 3H), 1.77 (td, J = 7.4, 4.2 Hz, 1H), 1.53 (h, J = 7.4 Hz, 1H), 0.92 (t, J = 7.3 Hz, 3H). | 671.3 | 1.2 |
| 189 | 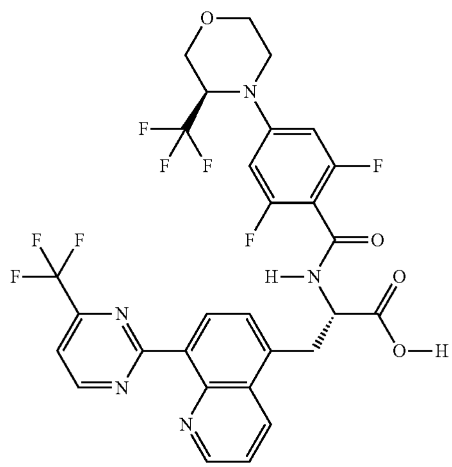 [SMILES: O=C(N[C@@H](Cc1ccc(-c2nccc(C(F)(F)F)n2)c2ncccc12)C(=O)O)c1c(F)cc(N2CCOC[C@@H]2C(F)(F)F)cc1F] | 1H NMR (400 MHz, DMSO-d6) δ 9.37 (d, J = 5.1 Hz, 1H), 9.05 (s, 1H), 8.96 (d, J = 8.2 Hz, 1H), 8.92 (s, 1H), 8.19 (s, 1H), 8.11 (d, J = 5.1 Hz, 1H), 7.83 (s, 1H), 7.78 (d, J = 7.6 Hz, 1H), 6.75 (d, J = 11.8 Hz, 2H), 4.97-4.83 (m, 1H), 4.81-4.70 (m, 1H), 4.16 (d, J = 12.8 Hz, 1H), 3.95 (dd, J = 11.5, 3.7 Hz, 1H), 3.82 (dd, J = 14.4, 4.5 Hz, 1H), 3.73 (d, J = 12.9 Hz, 1H), 3.57 (d, J = 3.3 Hz, 1H), 3.54 (s, 1H), 3.53-3.47 (m, 1H), 3.41 (d, J = 12.5 Hz, 1H), 3.29-3.16 (m, 1H), 2.54 (s, 1H). | 656.2 | 15.1 |
| 190 | 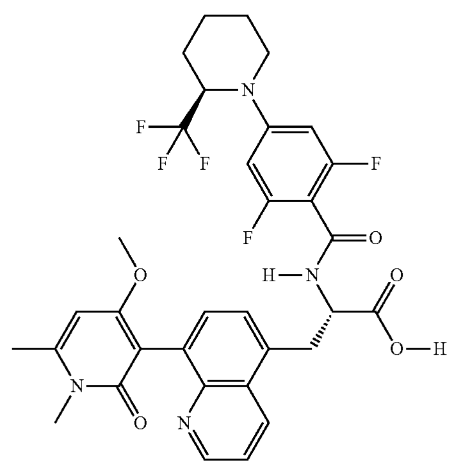 [SMILES: COc1cc(C)n(C)c(=O)c1-c1ccc(C[C@H](NC(=O)c2c(F)cc(N3CCCC[C@@H]3C(F)(F)F)cc2F)C(=O)O)c2cccnc12] | 1H NMR (400 MHz, DMSO-d6) δ 9.20 (s, 1H), 9.01 (d, J = 4.9 Hz, 1H), 8.94 (d, J = 8.0 Hz, 1H), 7.98 (s, 1H), 7.83-7.70 (m, 2H), 6.74 (d, J = 12.0 Hz, 2H), 6.48 (s, 1H), 5.00-4.88 (m, 1H), 4.78-4.69 (m, 1H), 3.79 (t, J = 12.8 Hz, 1H), 3.69 (s, 3H), 3.61 (d, J = 12.8 Hz, 1H), 3.52 (d, J = 10.8 Hz, 1H), 3.45 (s, 3H), 3.02 (t, J = 12.2 Hz, 1H), 2.52 (s, 3H), 2.02-1.89 (m, 1H), 1.86-1.68 (m, 2H), 1.67-1.42 (m, 3H). | 659.7 | 1.2 |

TABLE 2-continued

| Example | Structure | 1H-NMR | M/Z [M + H]+ | α4β7 EC$_{50}$ (nM) |
|---|---|---|---|---|
| 191 | 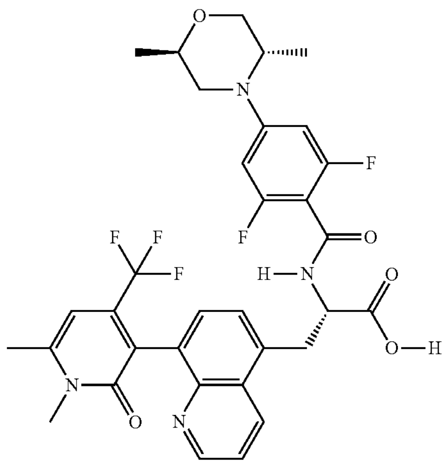 [SMILES: Cc1cc(C(F)(F)F)c(-c2ccc(C[C@H](NC(=O)c3c(F)cc(N4C[C@@H](C)OC[C@@H]4C)cc3F)C(=O)O)c3cccnc23)c(=O)n1C] | 1H NMR (400 MHz, DMSO-d6) δ 13.18-12.57 (s, 1H), 8.91 (dd, J = 7.9, 3.0 Hz, 1H), 8.81 (s, 1H), 8.63 (s, 1H), 7.58 (m, J = 18.1, 10.7 Hz, 2H), 7.43 (s, 1H), 6.62 (dd, J = 11.2, 3.9 Hz, 2H), 6.54 (s, 1H), 4.75-4.65 (m, 1H), 3.93 (m, 2H), 3.71 (t, J = 12.9 Hz, 1H), 3.63-3.54 (m, 1H), 3.49 (d, J = 2.0 Hz, 3H), 3.47-3.37 (m, 1H), 3.34 (dd, J = 11.6, 5.0 Hz, 1H), 3.27 (dd, J = 12.6, 3.6 Hz, 1H), 2.96 (dd, J = 12.5, 5.4 Hz, 1H), 2.53 (s, 3H), 1.15 (d, J = 6.4 Hz, 3H), 1.01 (d, J = 6.3 Hz, 3H). | 659.4 | 1.3 |
| 192 | 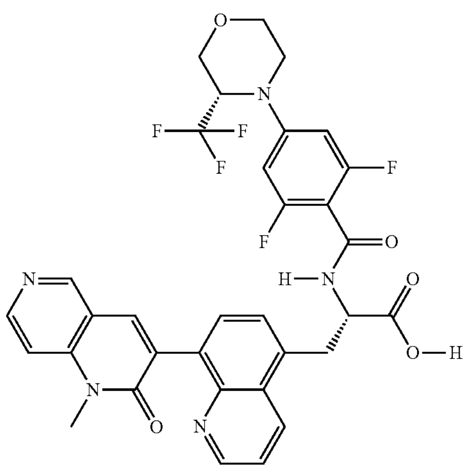 [SMILES: Cn1c(=O)c(-c2ccc(C[C@H](NC(=O)c3c(F)cc(N4CCOC[C@H]4C(F)(F)F)cc3F)C(=O)O)c3cccnc23)cc2cnccc21] | 1H NMR (400 MHz, DMSO-d6) δ 9.16 (s, 1H), 8.99 (d, J = 8.0 Hz, 1H), 8.86 (d, J = 4.1 Hz, 1H), 8.79 (d, J = 6.6 Hz, 1H), 8.68 (d, J = 8.6 Hz, 1H), 8.19 (s, 1H), 7.87 (d, J = 6.5 Hz, 1H), 7.72 (d, J = 7.3 Hz, 1H), 7.69-7.61 (m, 2H), 6.77 (d, J = 11.7 Hz, 2H), 4.96-4.84 (m, 1H), 4.70 (dt, J = 8.4, 5.3 Hz, 1H), 4.17 (d, J = 12.7 Hz, 1H), 3.96 (dd, J = 11.4, 3.7 Hz, 1H), 3.79-3.75 (m, 1H), 3.73 (m, 4H), 3.6-3.55 (m, 1H), 3.45 (dd, J = 15.3, 10.7 Hz, 2H), 3.24 (t, J = 12.2 Hz, 1H). | 668.2 | 1.4 |
| 193 | 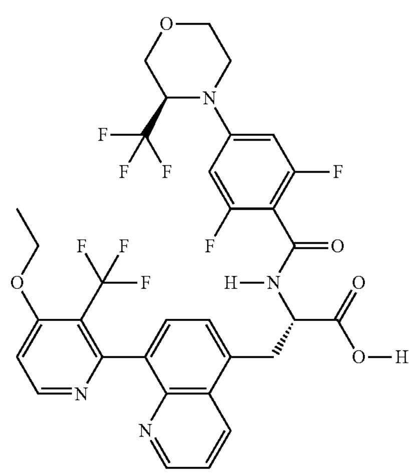 [SMILES: CCOc1ccnc(-c2ccc(C[C@H](NC(=O)c3c(F)cc(N4CCOC[C@@H]4C(F)(F)F)cc3F)C(=O)O)c3cccnc23)c1C(F)(F)F] | 1H NMR (400 MHz, DMSO-d6) δ 9.01-8.91 (m, 1H), 8.80 (s, 1H), 8.73 (d, J = 5.5 Hz, 1H), 8.64 (t, J = 7.6 Hz, 1H), 7.62 (s, 3H), 7.46 (s, 1H), 6.82-6.70 (m, 2H), 4.91 (d, J = 9.4 Hz, 1H), 4.72 (dd, J = 22.6, 8.8 Hz, 1H), 4.40 (d, J = 8.1 Hz, 2H), 4.16 (d, J = 12.8 Hz, 1H), 3.95 (d, J = 11.1 Hz, 1H), 3.73 (q, J = 14.1, 12.5 Hz, 2H), 3.61-3.35 (m, 3H), 3.24 (t, J = 12.3 Hz, 1H), 1.42 (t, J = 7.0 Hz, 3H). | 699.3 | 1.4 |

TABLE 2-continued
| Example | Structure | 1H-NMR | M/Z [M + H]+ | α4β7 EC$_{50}$ (nM) |
|---|---|---|---|---|
| 194 | 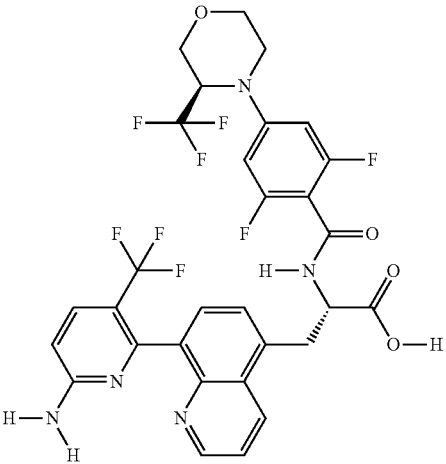 [SMILES: Nc1ccc(C(F)(F)F)c(-c2ccc(C[C@H](NC(=O)c3c(F)cc(N4CCOC[C@@H]4C(F)(F)F)cc3F)C(=O)O)c3cccnc23)n1] | 1H NMR (400 MHz, DMSO-d6) δ 8.98 (d, J = 8.0 Hz, 1H), 8.86 (dd, J = 4.3, 1.5 Hz, 1H), 8.66 (d, J = 8.6 Hz, 1H), 7.95 (d, J = 9.0 Hz, 1H), 7.73-7.54 (m, 3H), 6.74 (d, J = 11.7 Hz, 3H), 4.90 (dt, J = 8.8, 5.3 Hz, 1H), 4.75-4.56 (m, 1H), 4.15 (d, J = 12.7 Hz, 1H), 3.94 (dd, J = 11.5, 3.8 Hz, 1H), 3.80-3.63 (m, 2H), 3.62-3.46 (m, 1H), 3.41 (dd, J = 12.9, 7.8 Hz, 2H), 3.21 (t, J = 12.3 Hz, 1H). | 670.2 | 1.4 |
| 195 | 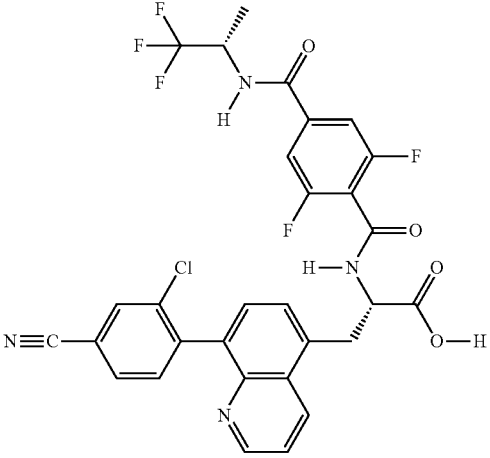 [SMILES: C[C@H](NC(=O)c1cc(F)c(C(=O)N[C@@H](Cc2ccc(-c3ccc(C#N)cc3Cl)c3ncccc23)C(=O)O)c(F)c1)C(F)(F)F] | 1H NMR (400 MHz, DMSO-d6) δ 9.38 (d, J = 8.2 Hz, 1H), 9.01 (d, J = 8.5 Hz, 1H), 8.84 (dd, J = 4.1, 1.6 Hz, 1H), 8.64 (dd, J = 8.7, 1.6 Hz, 1H), 8.16 (d, J = 1.6 Hz, 1H), 7.91 (d, J = 7.9 Hz, 1H), 7.68-7.59 (m, 5H), 7.56 (d, J = 7.9 Hz, 1H), 4.81 (d, J = 7.9 Hz, 2H), 3.79 (s, 1H), 3.41 (s, 1H), 2.65 (s, 1H), 2.31 (d, J = 1.9 Hz, 1H), 2.06 (s, 1H), 1.34 (d, J = 7.1 Hz, 3H). | 631.2 | 62.3 |
| 196 | 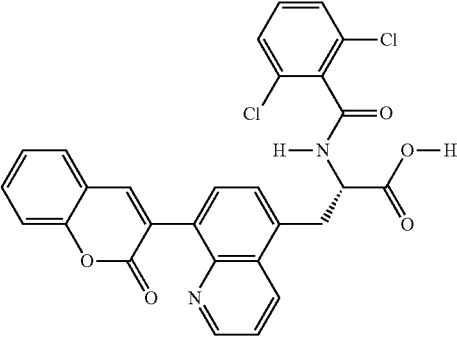 [SMILES: O=C(N[C@@H](Cc1ccc(-c2cc3ccccc3oc2=O)c2ncccc12)C(=O)O)c1c(Cl)cccc1Cl] | 1H NMR (400 MHz, DMSO-d6) δ 9.33 (dd, J = 15.0, 8.3 Hz, 1H), 8.93 (d, J = 4.2 Hz, 1H), 8.73 (d, J = 9.0 Hz, 1H), 8.12 (s, 1H), 7.86-7.79 (m, 2H), 7.77-7.65 (m, 3H), 7.53 (d, J = 8.3 Hz, 1H), 7.51-7.37 (m, 4H), 4.87 (td, J = 9.2, 4.7 Hz, 1H), 3.77 (dd, J = 14.4, 4.7 Hz, 1H), 3.46 (dd, J = 14.5, 10.0 Hz, 1H). | 533.1 | 63.1 |

TABLE 2-continued

| Example | Structure | 1H-NMR | M/Z [M + H]+ | α4β7 EC$_{50}$ (nM) |
|---|---|---|---|---|
| 197 | 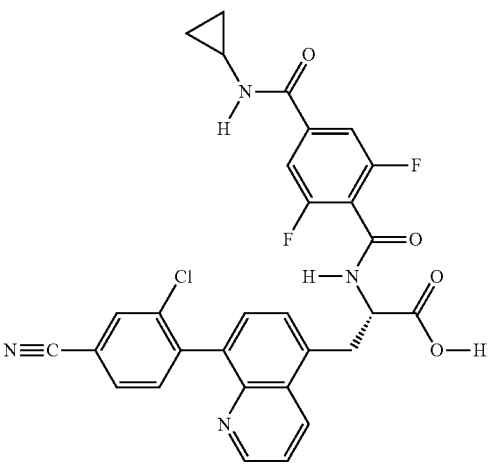 [SMILES: N#Cc1ccc(-c2ccc(C[C@H](NC(=O)c3c(F)cc(C(=O)NC4CC4)cc3F)C(=O)O)c3cccnc23)c(Cl)c1] | 1H NMR (400 MHz, DMSO-d6) δ 9.35 (d, J = 8.3 Hz, 1H), 8.83 (dd, J = 4.1, 1.6 Hz, 1H), 8.64 (d, J = 7.2 Hz, 1H), 8.60 (d, J = 4.2 Hz, 1H), 8.16 (d, J = 1.6 Hz, 1H), 7.91 (d, J = 7.8 Hz, 1H), 7.66-7.62 (m, 1H), 7.61 (d, J = 2.8 Hz, 2H), 7.56 (d, J = 7.9 Hz, 1H), 7.51 (d, J = 8.2 Hz, 2H), 4.79 (s, 1H), 2.83 (d, J = 4.0 Hz, 1H), 2.65 (s, 1H), 2.31 (s, 1H), 0.68 (dd, J = 7.0, 4.7 Hz, 2H), 0.61-0.48 (m, 2H). | 575.0 | 63.4 |
| 198 | 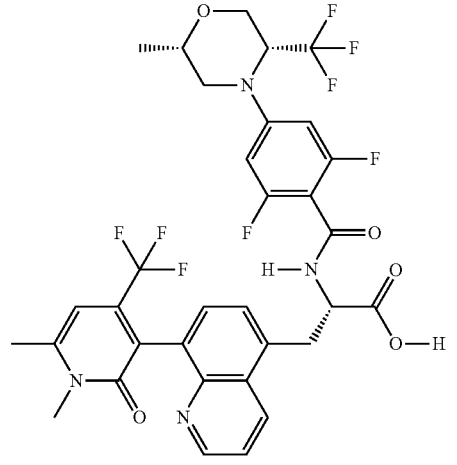 | 1H NMR (400 MHz, DMSO-d6) δ 8.96 (d, J = 8.3 Hz, 1H), 8.81 (d, J = 4.1 Hz, 1H), 8.63 (d, J = 8.7 Hz, 1H), 7.59 (ddd, J = 15.7, 8.0, 4.0 Hz, 2H), 7.44 (dd, J = 7.4, 3.9 Hz, 1H), 6.76 (dd, J = 11.6, 4.3 Hz, 3H), 6.54 (s, 1H), 4.87 (d, J = 8.8 Hz, 1H), 4.74-4.64 (m, 1H), 4.17 (d, J = 12.7 Hz, 1H), 3.82-3.57 (m, 4H), 3.53 (d, J = 12.4 Hz, 1H), 3.49 (d, J = 2.1 Hz, 4H), 3.47-3.36 (m, 1H), 3.15-3.04 (m, 1H), 2.82 (t, J = 11.6 Hz, 1H), 2.54 (d, J = 3.7 Hz, 4H), 1.18 (d, J = 7.3 Hz, 1H), 1.15 (d, J = 6.1 Hz, 4H). | 713.3 | 1.4 |
| 199 | 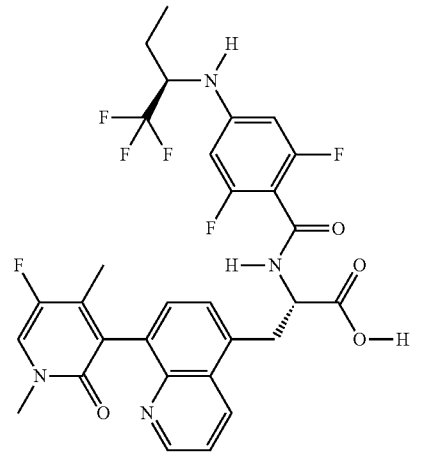 [SMILES: CC[C@@H](Nc1cc(F)c(C(=O)N[C@@H](Cc2ccc(-c3c(C)c(F)cn(C)c3=O)c3ncccc23)C(=O)O)c(F)c1)C(F)(F)F] | 1H NMR (400 MHz, DMSO-d6) δ 13.16-12.62 (s, 1H), 8.87 (s, 1H), 8.79 (t, J = 7.3 Hz, 1H), 7.99 (s, 1H), 7.76-7.45 (m, 4H), 6.76 (dd, J = 9.4, 5.7 Hz, 1H), 6.43 (dd, J = 11.4, 4.5 Hz, 2H), 4.71 (m, 1H), 4.30 (m, 1H), 3.73 (dd, J = 51.5, 14.6 Hz, 1H), 3.42 (m, J = 2.2 Hz, 4H), 1.75 (d, J = 9.1 Hz, 4H), 1.60-1.43 (m, 1H), 0.92 (t, J = 7.3 Hz, 3H). | 621.3 | 1.5 |

TABLE 2-continued

| Example | Structure | 1H-NMR | M/Z [M + H]+ | α4β7 EC$_{50}$ (nM) |
|---|---|---|---|---|
| 200 | 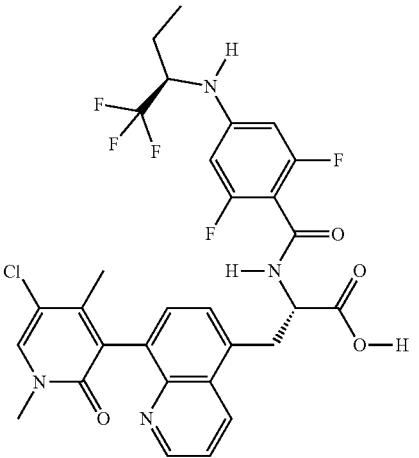 [SMILES: CC[C@@H](Nc1cc(F)c(C(=O)N[C@@H](Cc2ccc(-c3c(C)c(Cl)cn(C)c3=O)c3ncccc23)C(=O)O)c(F)c1)C(F)(F)F] | 1H NMR (400 MHz, DMSO-d6) δ 8.96-8.84 (m, 2H), 8.79 (t, J = 8.1, 6.7 Hz, 1H), 8.14 (d, J = 2.2 Hz, 1H), 7.85-7.73 (m, 1H), 7.68 (dd, J = 12.8, 7.4 Hz, 1H), 7.60 (t, J = 7.2 Hz, 1H), 6.76 (dd, J = 9.5, 5.0 Hz, 1H), 6.43 (dd, J = 11.4, 2.8 Hz, 2H), 4.72 (ddt, J = 15.3, 10.4, 4.6 Hz, 1H), 4.30 (q, J = 8.8 Hz, 1H), 3.83 (dd, J = 14.3, 4.3 Hz, 1H), 3.56-3.33 (m, 4H), 1.83 (d, J = 10.6 Hz, 3H), 1.80-1.70 (m, 1H), 1.60-1.45 (m, 1H), 0.92 (t, J = 7.3 Hz, 3H). | 637.2 | 1.5 |
| 201 | 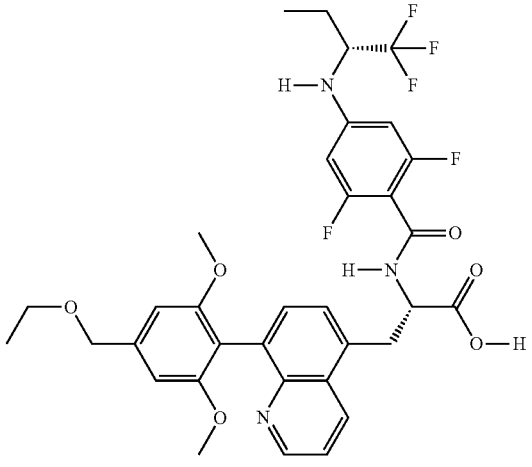 [SMILES: CCOCc1cc(OC)c(-c2ccc(C[C@H](NC(=O)c3c(F)cc(N[C@H](CC)C(F)(F)F)cc3F)C(=O)O)c3cccnc23)c(OC)c1] | 1H NMR (400 MHz, DMSO-d6) δ 8.83 (d, J = 8.1 Hz, 1H), 7.66 (s, 3H), 6.77 (d, J = 10.2 Hz, 3H), 6.44 (d, J = 11.6 Hz, 2H), 4.70 (s, 1H), 4.54 (s, 2H), 4.41-4.24 (m, 1H), 3.73 (d, J = 13.5 Hz, 1H), 3.67-3.52 (m, 6H), 3.52-3.25 (m, 1H), 1.76 (dd, J = 7.3, 3.9 Hz, 1H), 1.62-1.40 (m, 1H), 1.21 (t, J = 7.0 Hz, 3H), 0.92 (t, J = 7.3 Hz, 3H). | 676.2 | 1.5 |
| 202 | 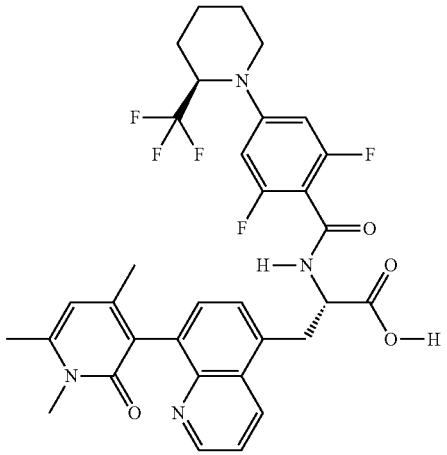 [SMILES: Cc1cc(C)n(C)c(=O)c1-c1ccc(C[C@H](NC(=O)c2c(F)cc(N3CCCC[C@@H]3C(F)(F)F)cc2F)C(=O)O)c2cccnc12] | 1H NMR (400 MHz, DMSO-d6) δ 9.03 (t, J = 9.0 Hz, 1H), 8.99-8.92 (m, 1H), 8.90 (d, J = 8.1 Hz, 1H), 7.86 (ddd, J = 17.7, 8.7, 5.0 Hz, 1H), 7.72 (dd, J = 15.8, 7.4 Hz, 1H), 7.62 (t, J = 9.0, 7.4 Hz, 1H), 6.71 (d, J = 12.0 Hz, 2H), 6.24 (d, J = 2.4 Hz, 1H), 4.99-4.86 (m, 1H), 4.81-4.68 (m, 1H), 3.85 (dd, J = 14.3, 4.3 Hz, 1H), 3.73 (dd, J = 14.6, 4.7 Hz, 1H), 3.65-3.49 (m, 2H), 3.48-3.36 (m, 4H), 3.01 (t, J = 12.3 Hz, 1H), 2.43 (s, 3H), 2.02-1.90 (m, 1H), 1.86-1.67 (m, 3H), 1.67-1.42 (m, 3H). | 643.7 | 1.5 |

TABLE 2-continued
| Example | Structure | 1H-NMR | M/Z [M + H]+ | α4β7 EC$_{50}$ (nM) |
|---|---|---|---|---|
| 203 | 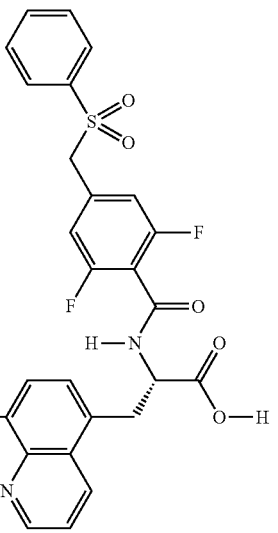 | 1H NMR (400 MHz, DMSO-d6) δ 13.08 (s, 1H), 9.28 (dd, J = 8.2, 2.8 Hz, 1H), 8.93 (dd, J = 4.5, 2.4 Hz, 1H), 8.83 (s, 1H), 7.75 (ddt, J = 6.9, 4.7, 1.5 Hz, 4H), 7.70-7.50 (m, 4H), 6.91-6.82 (m, 2H), 4.85-4.72 (m, 3H), 3.46 (d, J = 3.5 Hz, 3H), 3.22 (d, J = 2.7 Hz, 3H), 1.92 (d, J = 9.6 Hz, 3H). | 662.8 | 1.6 |
| 204 | 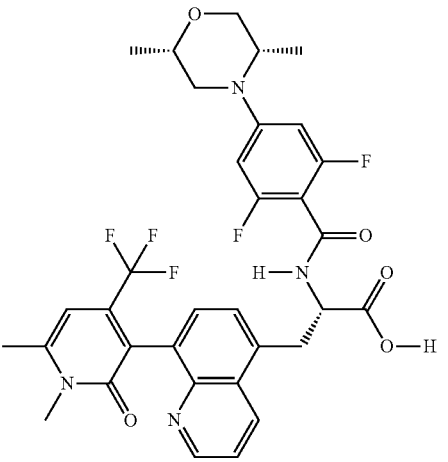 [SMILES: Cc1cc(C(F)(F)F)c(-c2ccc(C[C@H](NC(=O)c3c(F)cc(N4C[C@H](C)OC[C@@H]4C)cc3F)C(=O)O)c3cccnc23)c(=O)n1C] | 1H NMR (400 MHz, DMSO-d6) δ 13.19-12.63 (s, 1H), 8.89-8.76 (m, 2H), 8.63 (s, 1H), 7.66-7.54 (m, 2H), 7.48-7.39 (m, 1H), 6.57 (d, J = 4.6 Hz, 1H), 6.54 (s, 2H), 4.71 (d, J = 9.5 Hz, 1H), 3.93 (d, J = 7.1 Hz, 1H), 3.68 (m, J = 4.4 Hz, 3H), 3.57-3.50 (m, 1H), 3.49 (d, J = 1.8 Hz, 3H), 3.47-3.37 (m, 2H), 2.58 (d, J = 11.7 Hz, 1H), 2.53 (s, 3H), 1.16 (d, J = 6.1 Hz, 3H), 1.02 (d, J = 6.5 Hz, 3H). | 658.9 | 1.7 |
| 205 | 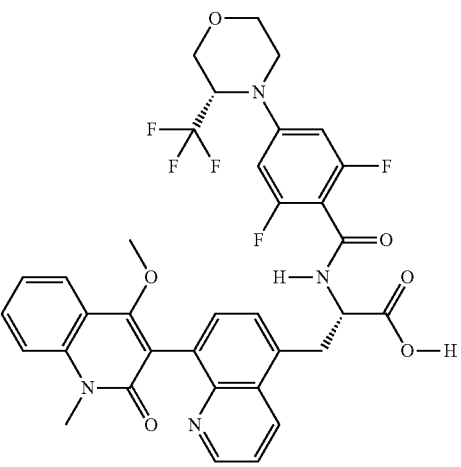 [SMILES: COc1c(-c2ccc(C[C@H](NC(=O)c3c(F)cc(N4CCOC[C@H]4C(F)(F)F)cc3F)C(=O)O)c3cccnc23)c(=O)n(C)c2ccccc12] | 1H NMR (400 MHz, DMSO-d6) δ 9.01-8.88 (m, 3H), 7.96 (d, J = 8.0 Hz, 1H), 7.88-7.69 (m, 4H), 7.64 (d, J = 8.6 Hz, 1H), 7.36 (t, J = 7.6 Hz, 1H), 6.75 (dd, J = 11.6, 8.0 Hz, 2H), 4.97-4.70 (m, 2H), 4.16 (d, J = 12.7 Hz, 1H), 4.00-3.85 (m, 2H), 3.73 (d, J = 13.9 Hz, 2H), 3.64 (d, 3H), 3.56 (t, J = 13.5, 7.5 Hz, 1H), 3.42 (d, J = 12.1 Hz, 1H), 3.30 (s, 3H), 3.25 (t, J = 13.4 Hz, 1H). | 697.3 | 1.7 |

TABLE 2-continued
| Example | Structure | 1H-NMR | M/Z [M + H]+ | α4β7 EC$_{50}$ (nM) |
|---|---|---|---|---|
| 206 | 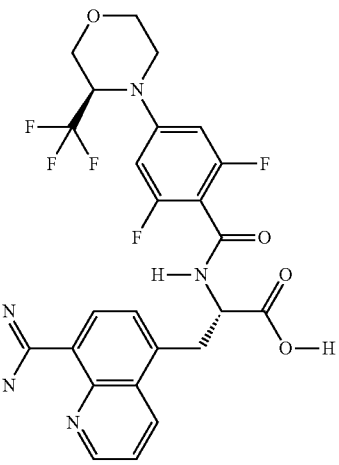 | 1H NMR (400 MHz, DMSO-d6) δ 9.41 (s, 1H), 9.34 (s, 1H), 8.96 (d, J = 8.2 Hz, 1H), 8.56 (dd, J = 9.1, 6.1 Hz, 1H), 8.27-8.07 (m, 2H), 7.98 (d, J = 3.5 Hz, 1H), 7.80 (td, J = 8.9, 2.6 Hz, 1H), 6.73 (d, J = 11.7 Hz, 2H), 4.94-4.78 (m, 2H), 4.15 (d, J = 12.7 Hz, 1H), 3.93 (dt, J = 13.7, 7.1 Hz, 2H), 3.72 (d, J = 14.8 Hz, 2H), 3.61-3.50 (m, 2H), 3.39 (d, J = 13.1 Hz, 1H), 3.21 (t, J = 15.5 Hz, 1H), 3.11 (s, 3H). | 670.2 | 1.7 |
| 207 | 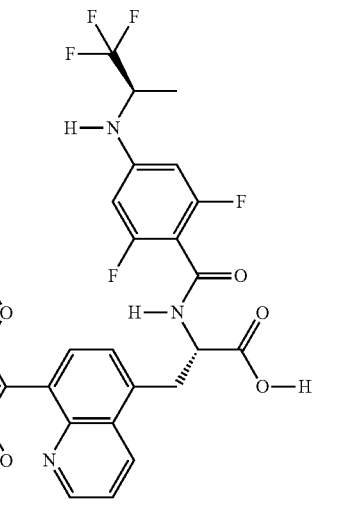 | 1H NMR (400 MHz, DMSO-d6) δ 8.88-8.80 (m, 2H), 8.71-8.62 (m, 1H), 8.27 (s, 1H), 7.69-7.49 (m, 3H), 6.86 (d, J = 9.2 Hz, 1H), 6.43 (d, J = 11.5 Hz, 2H), 4.70-4.61 (m, 1H), 4.58-4.45 (m, 1H), 3.78 (s, 3H), 3.68 (s, 3H), 3.49-3.38 (m, 2H), 1.28 (d, J = 6.7 Hz, 3H). | 606.2 | 1.7 |
| 208 | 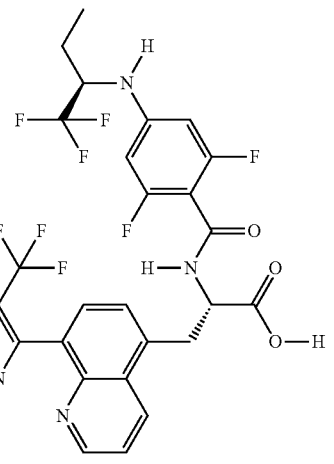 | 1H NMR (400 MHz, DMSO-d6) δ 8.82 (dd, J = 12.6, 6.1 Hz, 2H), 8.63 (d, J = 8.7 Hz, 1H), 7.90 (d, J = 9.2 Hz, 1H), 7.68-7.50 (m, 3H), 6.77 (d, J = 9.4 Hz, 1H), 6.43 (d, J = 11.5 Hz, 2H), 4.65 (td, J = 9.1, 4.5 Hz, 1H), 4.30 (s, 1H), 3.71 (d, J = 14.4 Hz, 1H), 3.45-3.32 (m, 1H), 1.89-1.61 (m, 1H), 1.66-1.34 (m, 1H), 0.91 (t, J = 7.3 Hz, 3H). | 642.1 | 1.8 |

TABLE 2-continued

| Example | Structure | 1H-NMR | M/Z [M + H]+ | α4β7 EC$_{50}$ (nM) |
|---|---|---|---|---|
| 209 | 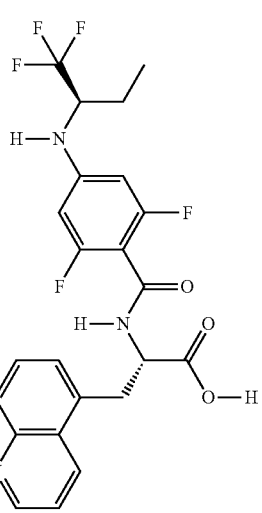 | 1H NMR (400 MHz, DMSO-d6) δ 8.89 (d, J = 4.3 Hz, 1H), 8.78 (dd, J = 20.1, 8.3 Hz, 2H), 7.79-7.67 (m, 2H), 7.62 (t, J = 3.7 Hz, 2H), 6.77 (d, J = 9.4 Hz, 1H), 6.43 (d, J = 11.5 Hz, 2H), 4.69-4.59 (m, 1H), 4.29 (d, J = 10.4 Hz, 1H), 3.71 (dd, J = 14.4, 4.6 Hz, 1H), 3.45 (s, 4H), 2.23 (d, J = 0.9 Hz, 3H), 1.75 (ddd, J = 13.9, 7.3, 3.2 Hz, 1H), 1.51 (ddd, J = 13.7, 10.4, 7.2 Hz, 1H), 0.91 (t, J = 7.3 Hz, 3H). | 604.2 | 1.9 |
| 210 | 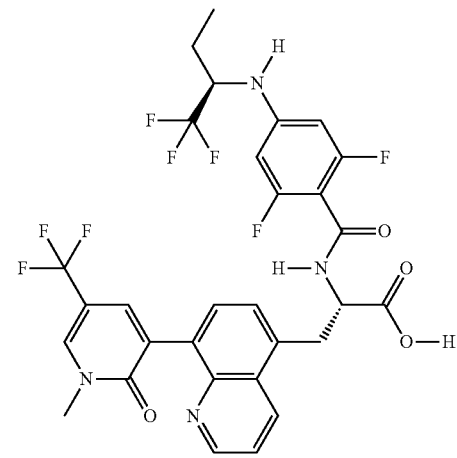 [SMILES: CC[C@@H](Nc1cc(F)c(C(=O)N[C@@H](Cc2ccc(-c3cc(C(F)(F)F)cn(C)c3=O)c3ncccc23)C(=O)O)c(F)c1)C(F)(F)F] | 1H NMR (400 MHz, DMSO-d6) δ 8.92 (dd, J = 4.4, 1.5 Hz, 1H), 8.80 (t, J = 9.0 Hz, 2H), 8.51 (dt, J = 2.8, 1.4 Hz, 1H), 7.77-7.67 (m, 3H), 7.62 (d, J = 7.5 Hz, 1H), 6.78 (d, J = 9.4 Hz, 1H), 6.43 (d, J = 11.5 Hz, 2H), 4.65 (ddd, J = 9.9, 8.0, 4.5 Hz, 1H), 4.28 (t, J = 8.9 Hz, 1H), 3.72 (dd, J = 14.4, 4.5 Hz, 1H), 3.55 (s, 3H), 3.41 (dd, J = 14.5, 9.9 Hz, 1H), 1.75 (dtt, J = 14.8, 7.4, 3.7 Hz, 1H), 1.51 (ddt, J = 17.7, 14.5, 7.3 Hz, 1H), 0.90 (t, J = 7.3 Hz, 3H). | 656.7 | 1.9 |
| 211 | 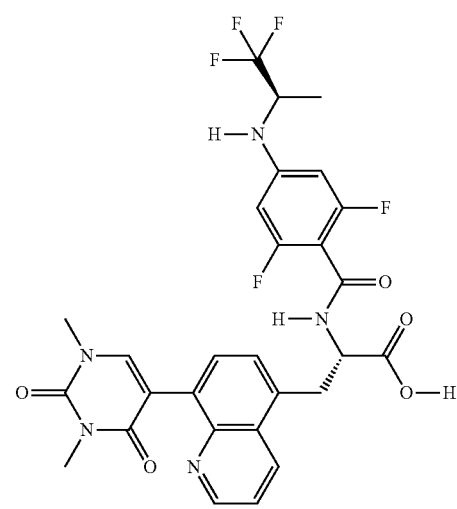 [SMILES: C[C@@H](Nc1cc(F)c(C(=O)N[C@@H](Cc2ccc(-c3cn(C)c(=O)n(C)c3=O)c3ncccc23)C(=O)O)c(F)c1)C(F)(F)F] | 1H NMR (400 MHz, DMSO-d6) δ 8.98 (dd, J = 4.4, 1.5 Hz, 1H), 8.85-8.79 (m, 2H), 7.94 (s, 1H), 7.77 (dd, J = 8.5, 4.4 Hz, 1H), 7.72 (d, J = 7.4 Hz, 1H), 7.64 (d, J = 7.4 Hz, 1H), 6.87 (d, J = 9.2 Hz, 1H), 6.43 (d, J = 11.5 Hz, 2H), 4.66 (ddd, J = 9.6, 8.1, 4.4 Hz, 1H), 4.51 (dq, J = 14.7, 7.1 Hz, 1H), 3.73 (dd, J = 14.4, 4.5 Hz, 1H), 3.47-3.38 (m, 4H), 3.26 (s, 3H), 1.28 (d, J = 6.7 Hz, 3H). | 606.2 | 1.9 |

TABLE 2-continued

| Example | Structure | 1H-NMR | M/Z [M + H]+ | α4β7 EC$_{50}$ (nM) |
|---|---|---|---|---|
| 212 | 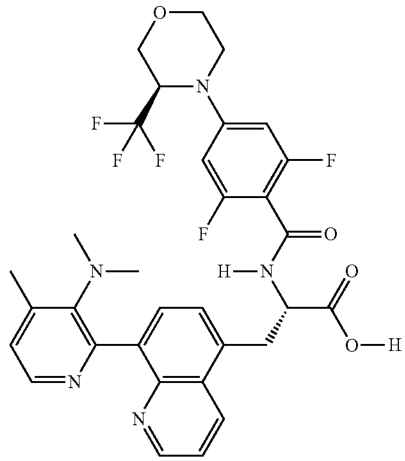 [SMILES: Cc1ccnc(-c2ccc(C[C@H](NC(=O)c3c(F)cc(N4CCOC[C@@H]4C(F)(F)F)cc3F)C(=O)O)c3cccnc23)c1N(C)C] | 1H NMR (400 MHz, DMSO-d6) δ 8.99 (d, J = 8.3 Hz, 1H), 8.93 (dd, J = 4.2, 1.6 Hz, 1H), 8.76 (dd, J = 8.7, 1.7 Hz, 1H), 8.54 (d, J = 5.8 Hz, 1H), 7.93 (d, J = 5.8 Hz, 1H), 7.84 (d, J = 7.4 Hz, 1H), 7.76 (dd, J = 7.9, 3.2 Hz, 2H), 6.74 (d, J = 11.8 Hz, 2H), 4.91 (dd, J = 8.8, 3.6 Hz, 1H), 4.77 (ddd, J = 10.4, 8.3, 4.3 Hz, 1H), 4.17 (d, J = 12.7 Hz, 1H), 3.96 (dd, J = 11.4, 3.8 Hz, 1H), 3.84 (dd, J = 14.1, 4.2 Hz, 1H), 3.73 (d, J = 12.8 Hz, 1H), 3.59-3.35 (m, 3H), 3.23 (t, J = 12.2 Hz, 1H), 2.60 (s, 3H), 2.29 (s, 6H). | 644.4 | 1.9 |
| 213 | 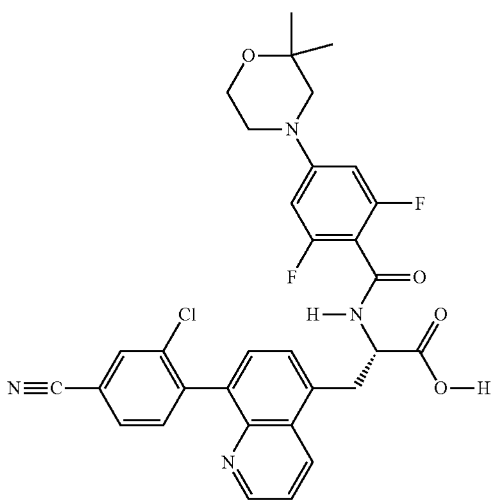 [SMILES: CC1(C)CN(c2cc(F)c(C(=O)N[C@@H](Cc3ccc(-c4ccc(C#N)cc4Cl)c4ncccc34)C(=O)O)c(F)c2)CCO1] | 1H NMR (400 MHz, DMSO-d6) δ 8.89-8.78 (m, 2H), 8.66 (dd, J = 8.6, 1.6 Hz, 1H), 8.17 (d, J = 1.6 Hz, 1H), 7.91 (dd, J = 7.9, 1.7 Hz, 1H), 7.68-7.60 (m, 3H), 7.58 (d, J = 7.9 Hz, 1H), 6.60 (d, J = 12.0 Hz, 2H), 4.77-4.66 (m, 1H), 3.75 (s, 1H), 3.68 (dd, J = 6.0, 4.1 Hz, 2H), 3.43 (s, 1H), 3.19 (t, J = 5.1 Hz, 2H), 3.11 (s, 2H), 1.16 (s, 6H). | 605.9 | 28.6 |
| 214 | 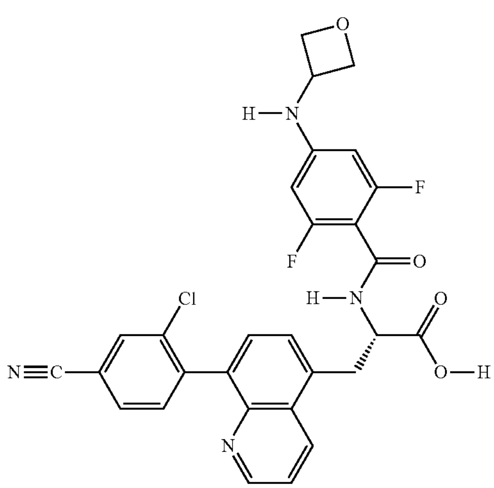 [SMILES: N#Cc1ccc(-c2ccc(C[C@H](NC(=O)c3c(F)cc(NC4COC4)cc3F)C(=O)O)c3cccnc23)c(Cl)c1] | 1H NMR (400 MHz, DMSO-d6) δ 12.98 (s, 1H), 8.84 (dd, J = 4.1, 1.6 Hz, 1H), 8.76 (d, J = 7.9 Hz, 1H), 8.64 (dd, J = 8.6, 1.7 Hz, 1H), 8.17 (d, J = 1.7 Hz, 1H), 7.91 (dd, J = 7.9, 1.7 Hz, 1H), 7.67-7.55 (m, 4H), 7.25 (d, J = 6.4 Hz, 1H), 6.12 (d, J = 11.3 Hz, 2H), 4.83 (t, J = 6.5 Hz, 2H), 4.68 (d, J = 7.3 Hz, 1H), 4.55 (h, J = 6.5 Hz, 1H), 4.36 (t, J = 6.0 Hz, 2H), 3.74 (s, 1H), 3.44 (qd, J = 7.0, 4.9 Hz, 1H). | 563.8 | 28.6 |

TABLE 2-continued
| Example | Structure | 1H-NMR | M/Z [M + H]+ | α4β7 EC$_{50}$ (nM) |
|---|---|---|---|---|
| 215 | 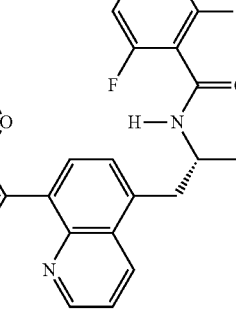 | 1H NMR (400 MHz, DMSO-d6) δ 9.27 (d, J = 8.1 Hz, 1H), 8.83 (d, J = 4.0 Hz, 1H), 8.64 (s, 1H), 7.67-7.53 (m, 3H), 7.53-7.44 (m, 2H), 7.33 (d, J = 13.3 Hz, 1H), 7.11 (t, J = 8.0 Hz, 2H), 4.74 (t, J = 9.1 Hz, 1H), 3.78-3.71 (m, 33H), 3.70 (s, 3H), 3.38 (dd, J = 14.6, 10.0 Hz, 1H). | 548.6 | 29.0 |
| 216 | 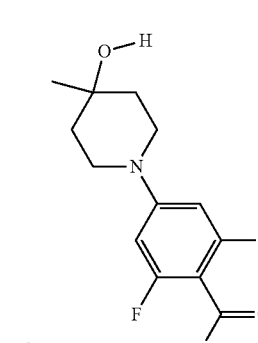 | 1H NMR (400 MHz, DMSO-d6) δ 8.83 (dd, J = 4.2, 1.6 Hz, 1H), 8.80 (d, J = 8.0 Hz, 1H), 8.64 (dd, J = 8.7, 1.7 Hz, 1H), 8.15 (dd, J = 1.6, 0.4 Hz, 1H), 7.90 (dd, J = 7.9, 1.7 Hz, 1H), 7.67-7.59 (m, 3H), 7.57 (dd, J = 7.9, 0.4 Hz, 1H), 6.56 (d, J = 12.3 Hz, 2H), 4.71 (m, 1H), 3.73 (s, 1H), 3.44 (d, J = 13.2 Hz, 3H), 3.26-3.05 (m, 2H), 1.43 (d, J = 11.2 Hz, 4H), 1.10 (s, 3H). | 605.6 | 31.0 |
| 217 | 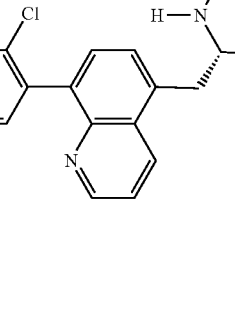 | 1H NMR (400 MHz, DMSO-d6) δ 8.88 (d, J = 7.8 Hz, 1H), 8.83 (d, J = 4.2 Hz, 1H), 8.66 (d, J = 7.9 Hz, 1H), 7.64 (dd, J = 8.6, 4.3 Hz, 1H), 7.58 (t, J = 7.0 Hz, 1H), 7.45 (dd, J = 7.5, 3.2 Hz, 1H), 6.62 (dd, J = 11.6, 4.3 Hz, 2H), 6.55 (s, 1H), 4.71 (d, J = 10.4 Hz, 1H), 3.78-3.63 (m, 5H), 3.55-3.34 (m, 4H), 3.20 (t, J = 4.9 Hz, 4H), 2.53 (s, 3H). | 631.2 | 2.0 |

TABLE 2-continued

| Example | Structure | 1H-NMR | M/Z [M + H]+ | α4β7 EC$_{50}$ (nM) |
| --- | --- | --- | --- | --- |
| 218 | 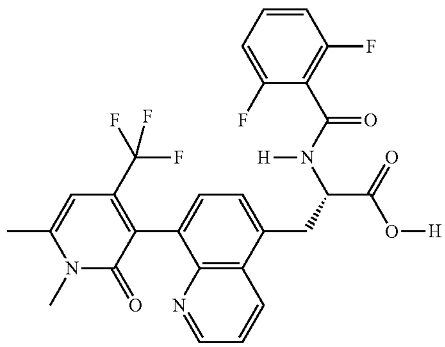 [SMILES: Cc1cc(C(F)(F)F)c(-c2ccc(C[C@H](NC(=O)c3c(F)cccc3F)C(=O)O)c3cccnc23)c(=O)n1C] | 1H NMR (400 MHz, Chloroform-d) δ 9.48-8.74 (m, 1H), 7.82-7.65 (m, 2H), 7.56 (d, J = 7.4 Hz, 1H), 7.35 (d, J = 7.9 Hz, 1H), 7.26 (d, J = 0.8 Hz, 3H), 6.91 (dt, J = 19.9, 8.1 Hz, 2H), 6.56 (d, J = 11.9 Hz, 1H), 5.04 (t, J = 9.9 Hz, 1H), 3.94 (dd, J = 14.3, 6.2 Hz, 1H), 3.59 (d, J = 14.2 Hz, 2H), 2.55 (d, J = 7.6 Hz, 3H). | 546.0 | 2.1 |
| 219 | 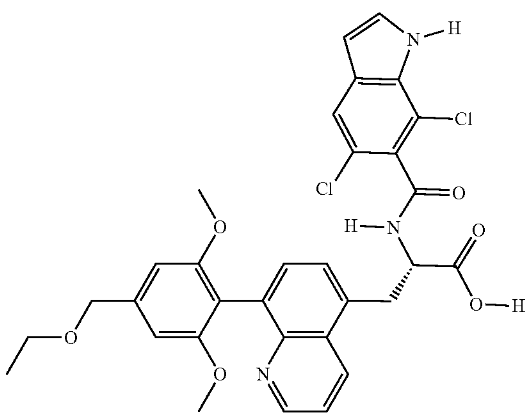 [SMILES: CCOCc1cc(OC)c(-c2ccc(C[C@H](NC(=O)c3c(Cl)cc4cc[nH]c4c3Cl)C(=O)O)c3cccnc23)c(OC)c1] | 1H NMR (400 MHz, DMSO-d6) δ 11.65 (s, 1H), 9.12 (d, J = 8.6 Hz, 1H), 8.88 (s, 1H), 7.72 (d, J = 23.5 Hz, 3H), 7.67-7.43 (m, 2H), 6.77 (d, J = 6.7 Hz, 2H), 6.50 (dd, J = 3.1, 1.9 Hz, 1H), 4.88 (d, J = 9.5 Hz, 1H), 4.54 (s, 2H), 3.79 (d, J = 14.4 Hz, 1H), 3.67-3.51 (m, 8H), 3.43 (t, J = 12.8 Hz, 1H), 1.21 (t, J = 7.0 Hz, 3H). | 621.9 | 2.1 |
| 220 | 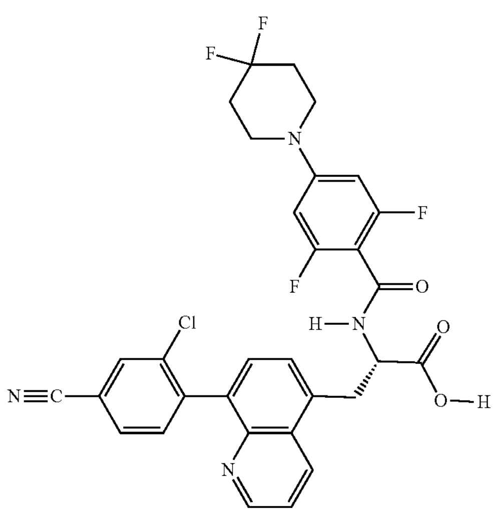 [SMILES: N#Cc1ccc(-c2ccc(C[C@H](NC(=O)c3c(F)cc(N4CCC(F)(F)CC4)cc3F)C(=O)O)c3cccnc23)c(Cl)c1] | 1H NMR (400 MHz, DMSO-d6) δ 8.88 (d, J = 8.1 Hz, 1H), 8.83 (dd, J = 4.1, 1.6 Hz, 1H), 8.64 (dd, J = 8.6, 1.7 Hz, 1H), 8.15 (d, J = 1.6 Hz, 1H), 7.90 (dd, J = 7.9, 1.7 Hz, 1H), 7.68-7.58 (m, 3H), 7.56 (d, J = 7.9 Hz, 1H), 6.70 (d, J = 11.9 Hz, 2H), 4.71 (d, J = 7.7 Hz, 1H), 3.74 (s, 1H), 3.45 (t, J = 5.8 Hz, 5H), 1.95 (tt, J = 13.7, 5.7 Hz, 5H). | 611.5 | 45.2 |

TABLE 2-continued
| Example | Structure | 1H-NMR | M/Z [M + H]+ | α4β7 EC50 (nM) |
|---|---|---|---|---|
| 221 | 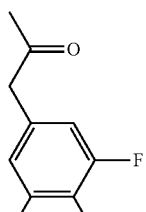 | 1H NMR (400 MHz, DMSO-d6) δ 13.04 (s, 1H), 9.24 (d, J = 8.2 Hz, 1H), 8.83 (dd, J = 4.1, 1.6 Hz, 1H), 8.63 (dd, J = 8.7, 1.7 Hz, 1H), 8.15 (d, J = 1.6 Hz, 1H), 7.90 (dd, J = 7.9, 1.7 Hz, 1H), 7.63 (d, J = 13.6 Hz, 3H), 7.56 (d, J = 7.9 Hz, 1H), 6.93 (d, J = 8.5 Hz, 2H), 4.81-4.70 (m, 1H), 3.84 (s, 2H), 3.76 (s, 1H), 2.14 (s, 3H). | 548.1 | 48.2 |
| 222 | 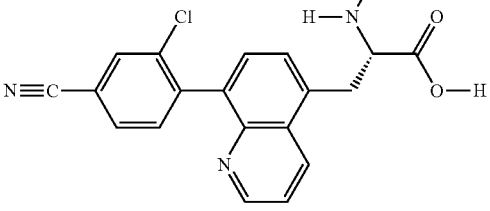 | 1H NMR (400 MHz, DMSO-d6) δ 9.21 (d, J = 8.1 Hz, 1H), 8.84 (dd, J = 4.2, 1.6 Hz, 1H), 8.64 (dd, J = 8.6, 1.6 Hz, 1H), 8.16 (dd, J = 1.6, 0.4 Hz, 1H), 7.91 (dd, J = 7.9, 1.6 Hz, 1H), 7.68-7.58 (m, 3H), 7.56 (dd, J = 7.9, 0.4 Hz, 1H), 7.48 (td, J = 8.4, 6.5 Hz, 1H), 7.15 (t, J = 8.6 Hz, 1H), 7.11-7.01 (m, 1H), 6.90 (s, 1H), 4.77 (s, 1H), 3.73 (s, 1H), 3.41 (s, 1H). | 540.1 | 48.3 |
| 223 | 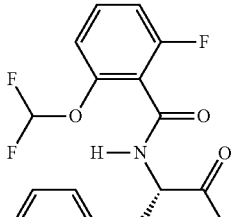 | 1H NMR (400 MHz, DMSO-d6) δ 8.97 (t, J = 7.8 Hz, 1H), 8.83-8.76 (m, 1H), 8.71 (d, J = 5.0 Hz, 1H), 8.65 (t, J = 7.7 Hz, 1H), 7.67-7.54 (m, 4H), 6.76 (dd, J = 11.6, 7.8 Hz, 2H), 4.91 (d, J = 9.3 Hz, 1H), 4.70 (d, J = 14.6 Hz, 1H), 4.16 (d, J = 12.7 Hz, 1H), 3.95 (dd, J = 11.6, 3.7 Hz, 1H), 3.75 (t, J = 14.8 Hz, 2H), 3.62-3.35 (m, 3H), 3.23 (t, J = 12.3 Hz, 1H), 2.59 (q, J = 2.3 Hz, 3H). | 669.6 | 2.2 |

//
TABLE 2-continued
| Example | Structure | 1H-NMR | M/Z [M + H]+ | α4β7 EC$_{50}$ (nM) |
|---|---|---|---|---|
| 224 | 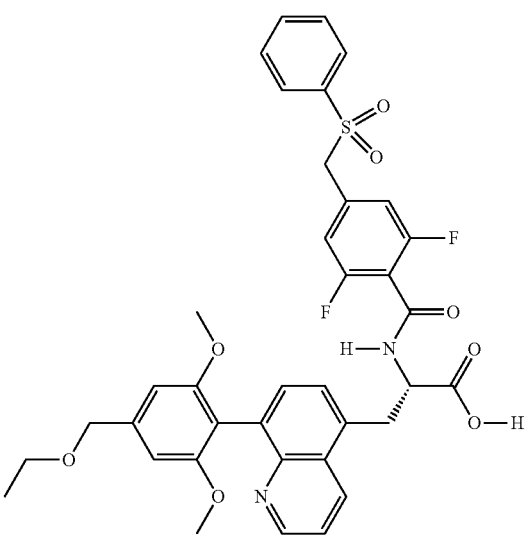 [SMILES: CCOCc1cc(OC)c(-c2ccc(C[C@H](NC(=O)c3c(F)cc(CS(=O)(=O)c4ccccc4)cc3F)C(=O)O)c3cccnc23)c(OC)c1] | 1H NMR (400 MHz, DMSO-d6) δ 13.08 (s, 1H), 9.31 (d, J = 8.1 Hz, 1H), 8.86 (d, J = 4.3 Hz, 2H), 7.93-7.70 (m, 5H), 7.62 (dd, J = 8.7, 6.9 Hz, 3H), 6.89 (d, J = 8.1 Hz, 2H), 6.76 (d, J = 4.0 Hz, 2H), 4.85-4.70 (m, 1H), 4.78 (s, 2H), 4.54 (s, 2H), 3.84-3.67 (m, 1H), 3.58 (q, J = 7.0 Hz, 2H), 3.56 (s, 3H), 3.55 (s, 3H), 3.43 (dd, J = 14.7, 10.1 Hz, 1H), 1.21 (t, J = 7.0 Hz, 3H). | 705.4 | 2.2 |
| 225 | 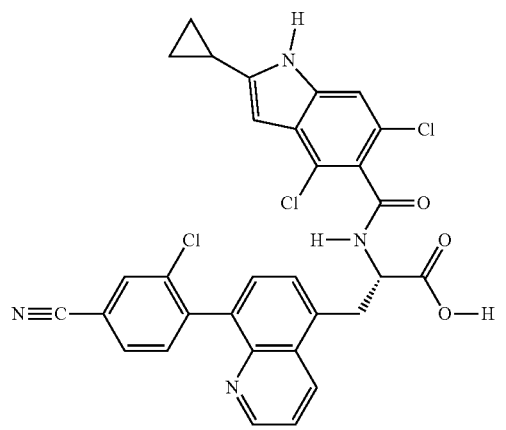 [SMILES: N#Cc1ccc(-c2ccc(C[C@H](NC(=O)c3c(Cl)cc4[nH]c(C5CC5)cc4c3Cl)C(=O)O)c3cccnc23)c(Cl)c1] | 1H NMR (400 MHz, DMSO-d6) δ 11.41 (d, J = 2.3 Hz, 1H), 9.03 (d, J = 8.3 Hz, 1H), 8.84 (dd, J = 4.1, 1.6 Hz, 1H), 8.74-8.61 (m, 1H), 8.17 (d, J = 1.7 Hz, 1H), 7.92 (s, 1H), 7.76-7.45 (m, 4H), 7.20 (d, J = 0.9 Hz, 1H), 6.10 (s, 1H), 3.74 (dd, J = 14.3, 4.1 Hz, 1H), 3.49-3.31 (m, 1H), 2.01 (td, J = 8.4, 4.2 Hz, 1H), 1.05-0.91 (m, 2H), 0.79 (ddd, J = 6.4, 5.3, 3.9 Hz, 2H). | 605.2 | 53.7 |
| 226 | 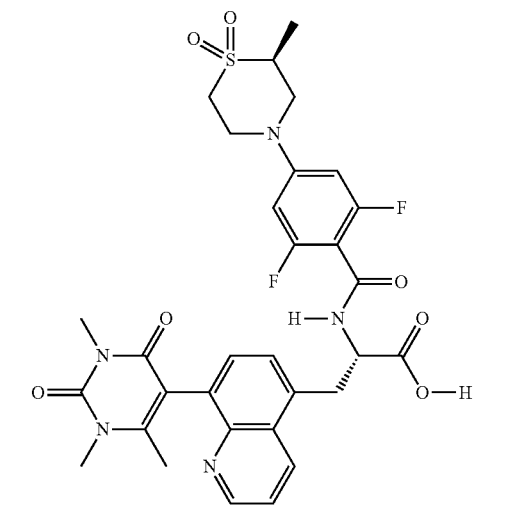 [SMILES: Cc1c(-c2ccc(C[C@H](NC(=O)c3c(F)cc(N4CCS(=O)(=O)[C@@H](C)C4)cc3F)C(=O)O)c3cccnc23)c(=O)n(C)c(=O)n1C] | 1H NMR (400 MHz, DMSO-d6) δ 8.93 (s, 1H), 8.87 (d, J = 8.1 Hz, 1H), 8.81 (s, 1H), 7.74 (s, 1H), 7.70-7.51 (m, 2H), 6.75 (dd, J = 11.6, 4.2 Hz, 2H), 4.70 (q, J = 12.2, 9.9 Hz, 1H), 4.19 (d, J = 15.1 Hz, 1H), 4.08 (d, J = 14.7 Hz, 1H), 3.87-3.62 (m, 1H), 3.57-3.30 (m, 5H), 3.30-3.14 (m, 5H), 3.14-2.94 (m, 2H), 1.92 (d, J = 9.6 Hz, 3H), 1.18 (d, J = 6.7 Hz, 3H). | 656.2 | 1.1 |

TABLE 2-continued

| Example | Structure | 1H-NMR | M/Z [M + H]+ | α4β7 EC$_{50}$ (nM) |
|---|---|---|---|---|
| 227 | 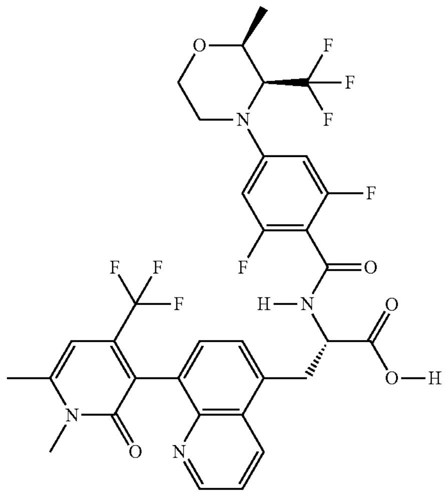 [SMILES: Cc1cc(C(F)(F)F)c(-c2ccc(C[C@H](NC(=O)c3c(F)cc(N4CCO[C@@H](C)[C@H]4C(F)(F)F)cc3F)C(=O)O)c3cccnc23)c(=O)n1C] | 1H NMR (400 MHz, DMSO-d6) δ 8.96 (d, J = 7.9 Hz, 1H), 8.86-8.77 (m, 1H), 8.62 (d, J = 8.7 Hz, 1H), 7.67-7.53 (m, 2H), 7.43 (d, J = 7.2 Hz, 1H), 6.83-6.70 (m, 2H), 6.54 (s, 1H), 4.86 (d, J = 9.3 Hz, 1H), 4.70 (d, J = 10.6 Hz, 1H), 3.94 (dd, J = 11.5, 3.6 Hz, 1H), 3.87 (s, 1H), 3.68 (dd, J = 14.7, 4.3 Hz, 1H), 3.61 (t, J = 11.0 Hz, 1H), 3.48 (d, J = 2.2 Hz, 3H), 3.43 (d, J = 14.6 Hz, 1H), 3.08 (t, J = 12.2 Hz, 1H), 2.52 (s, 5H), 2.46 (s, 1H), 1.36-1.17 (m, 3H). | 712.7 | 1.1 |
| 228 | 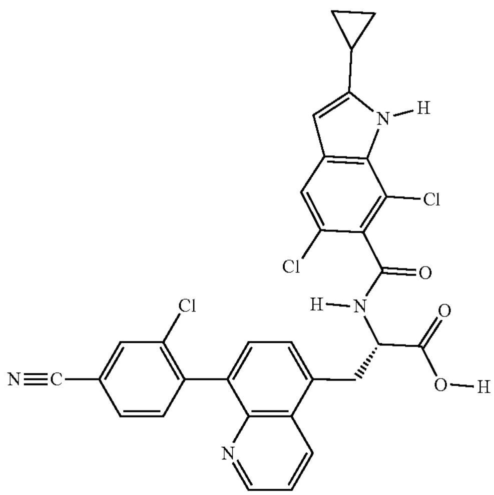 [SMILES: N#Cc1ccc(-c2ccc(C[C@H](NC(=O)c3c(Cl)cc4cc(C5CC5)[nH]c4c3Cl)C(=O)O)c3cccnc23)c(Cl)c1] | 1H NMR (400 MHz, DMSO-d6) δ 11.47 (s, 1H), 9.05 (d, J = 8.4 Hz, 1H), 8.85 (dd, J = 4.1, 1.6 Hz, 1H), 8.67 (dd, J = 8.7, 1.7 Hz, 1H), 8.17 (d, J = 1.6 Hz, 1H), 7.92 (d, J = 7.9 Hz, 1H), 7.79-7.50 (m, 4H), 7.36 (d, J = 0.6 Hz, 1H), 6.05 (d, J = 1.9 Hz, 1H), 4.86 (s, 1H), 3.75 (dd, J = 14.4, 4.1 Hz, 1H), 3.52-3.31 (m, 1H), 2.12-1.98 (m, 1H), 1.07-0.89 (m, 2H), 0.89-0.70 (m, 2H). | 604.9 | 57.8 |
| 229 | 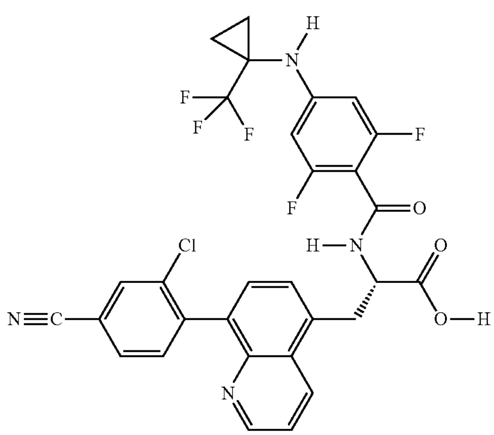 [SMILES: N#Cc1ccc(-c2ccc(C[C@H](NC(=O)c3c(F)cc(NC4(C(F)(F)F)CC4)cc3F)C(=O)O)c3cccnc23)c(Cl)c1] | 1H NMR (400 MHz, DMSO-d6) δ 8.91-8.77 (m, 2H), 8.63 (dd, J = 8.7, 1.7 Hz, 1H), 8.15 (dd, J = 1.6, 0.4 Hz, 1H), 7.90 (dd, J = 7.9, 1.7 Hz, 1H), 7.61 (s, 2H), 7.57 (dd, J = 7.9, 0.4 Hz, 1H), 7.50 (s, 1H), 6.29 (d, J = 11.2 Hz, 2H), 4.68 (s, 1H), 3.73 (s, 1H), 3.40 (s, 1H), 1.46-1.30 (m, 2H), 1.03 (s, 2H). | 615.2 | 60.5 |

TABLE 2-continued
| Example | Structure | 1H-NMR | M/Z [M + H]+ | α4β7 EC$_{50}$ (nM) |
|---|---|---|---|---|
| 230 | 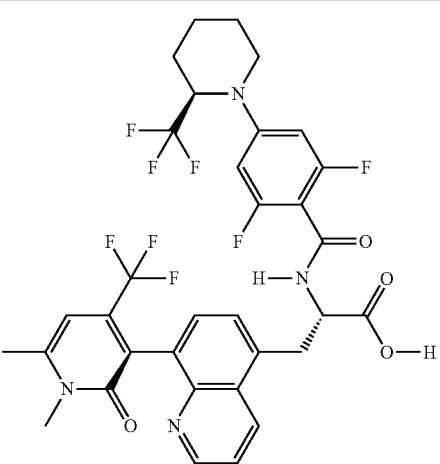 | 1H NMR (400 MHz, DMSO-d6) δ 8.72 (d, 1H), 8.67 (d, J = 8.7 Hz, 1H), 8.09 (s, 1H), 7.54-7.43 (m, 2H), 7.33 (d, J = 7.3 Hz, 1H), 6.72 (d, J = 12.1 Hz, 2H), 6.51 (s, 1H), 4.99-4.83 (m, 1H), 4.46-4.31 (m, 1H), 3.72-3.56 (m, 2H), 3.52-3.39 (m, 4H), 3.32 (s, 3H), 3.02 (t, J = 12.2 Hz, 1H), 1.95 (d, J = 14.5 Hz, 1H), 1.87-1.67 (m, 2H), 1.66-1.44 (m, 3H). | 697.3 | 2.2 |
| 231 | 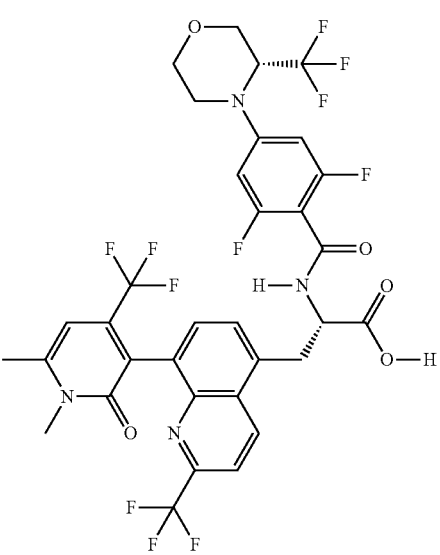 [SMILES: Cc1cc(C(F)(F)F)c(-c2ccc(C[C@H](NC(=O)c3c(F)cc(N4CCOC[C@@H]4C(F)(F)F)cc3F)C(=O)O)c3ccc(C(F)(F)F)nc23)c(=O)n1C] | 1H NMR (400 MHz, DMSO-d6) δ 8.97 (t, J = 7.2 Hz, 1H), 8.90 (d, J = 8.8 Hz, 1H), 8.01 (dd, J = 8.8, 6.1 Hz, 1H), 7.72 (dd, J = 10.6, 7.3 Hz, 1H), 7.60 (t, J = 7.6 Hz, 1H), 6.75 (dd, J = 11.5, 3.9 Hz, 2H), 6.57 (s, 1H), 4.91 (d, J = 9.1 Hz, 1H), 4.74 (s, 1H), 4.16 (d, J = 12.7 Hz, 1H), 4.01-3.90 (m, 1H), 3.85-3.64 (m, 2H), 3.63-3.37 (m, 6H), 3.23 (t, J = 12.3 Hz, 1H), 2.54 (s, 3H). | 767.2 | 0.9 |
| 232 | 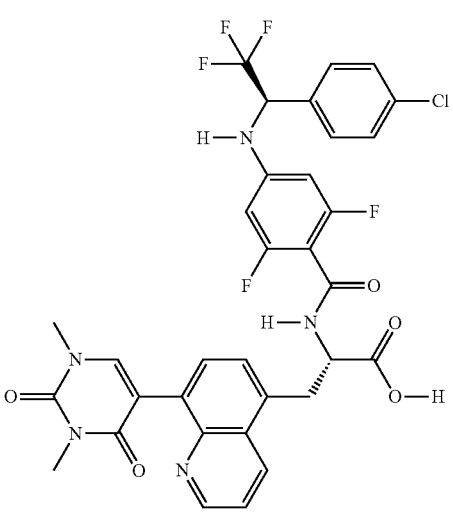 [SMILES: Cn1cc(-c2ccc(C[C@H](NC(=O)c3c(F)cc(N[C@H](c4ccc(Cl)cc4)C(F)(F)F)cc3F)C(=O)O)c3cccnc23)c(=O)n(C)c1=O] | 1H NMR (400 MHz, DMSO-d6) δ 8.91 (d, J = 3.9 Hz, 1H), 8.81 (d, J = 8.0 Hz, 1H), 8.68 (s, 1H), 7.89 (s, 1H), 7.66 (dd, J = 12.4, 5.9 Hz, 2H), 7.62-7.47 (m, 7H), 6.52 (d, J = 11.2 Hz, 2H), 5.79-5.70 (m, 1H), 4.60 (td, J = 9.2, 4.4 Hz, 1H), 3.67 (dd, J = 14.5, 4.4 Hz, 1H), 3.38 (s, 3H), 3.24 (s, 3H). | 702.1 | 0.9 |

TABLE 2-continued

| Example | Structure | 1H-NMR | M/Z [M + H]+ | α4β7 EC$_{50}$ (nM) |
|---|---|---|---|---|
| 233 | 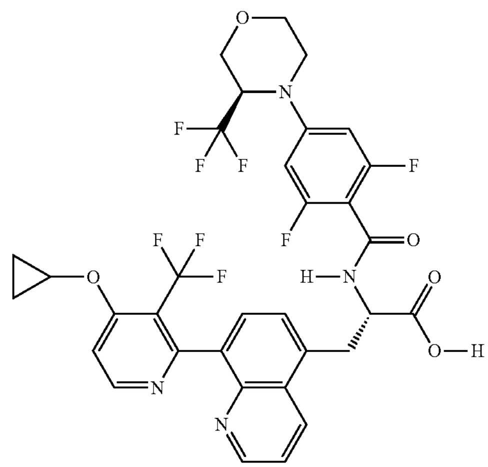 [SMILES: O=C(N[C@@H](Cc1ccc(-c2nccc(OC3CC3)c2C(F)(F)F)c2ncccc12)C(=O)O)c1c(F)cc(N2CCOC[C@@H]2C(F)(F)F)cc1F] | 1H NMR (400 MHz, DMSO-d6) δ 12.92 (br s, 1H), 8.95 (t, J = 9.3 Hz, 1H), 8.78 (d, J = 15.1 Hz, 2H), 8.63 (s, 1H), 7.70 (s, 1H), 7.60 (s, 3H), 6.76 (t, J = 10.6 Hz, 2H), 4.91 (d, J = 9.4 Hz, 1H), 4.69 (d, J = 7.4 Hz, 1H), 4.27 (s, 1H), 4.16 (d, J = 12.7 Hz, 1H), 3.99-3.91 (m, 1H), 3.73 (d, J = 13.0 Hz, 2H), 3.61-3.35 (m, 3H), 3.23 (t, J = 12.2 Hz, 1H), 0.96 (d, J = 6.1 Hz, 2H), 0.81 (q, J = 10.9, 9.6 Hz, 2H). | 711.2 | 2.2 |
| 234 | 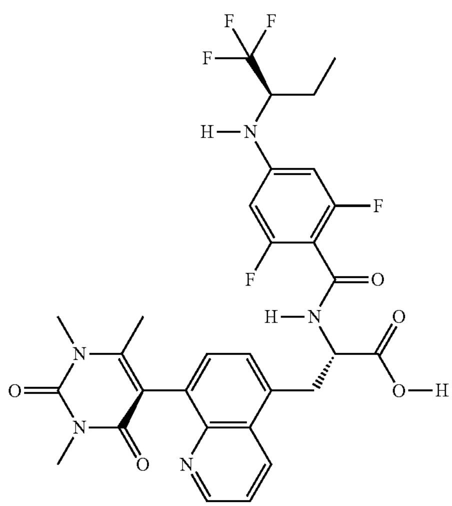 | 1H NMR (400 MHz, DMSO-d6) δ 8.92 (d, J = 4.4 Hz, 1H), 8.78 (d, J = 7.9 Hz, 1H), 7.73 (s, 1H), 7.69-7.52 (m, 2H), 6.76 (d, J = 9.4 Hz, 1H), 6.41 (d, J = 11.5 Hz, 2H), 4.68 (td, J = 9.0, 8.5, 4.6 Hz, 1H), 4.29 (s, 1H), 3.66 (dd, J = 14.3, 4.8 Hz, 1H), 3.54-3.39 (m, 4H), 3.22 (d, J = 2.4 Hz, 3H), 1.92 (d, J = 10.3 Hz, 3H), 1.75 (ddd, J = 13.8, 7.2, 3.2 Hz, 1H), 1.50 (ddd, J = 13.8, 10.4, 7.2 Hz, 1H), 0.90 (t, J = 7.3 Hz, 3H). | 634.2 | 2.3 |
| 235 | 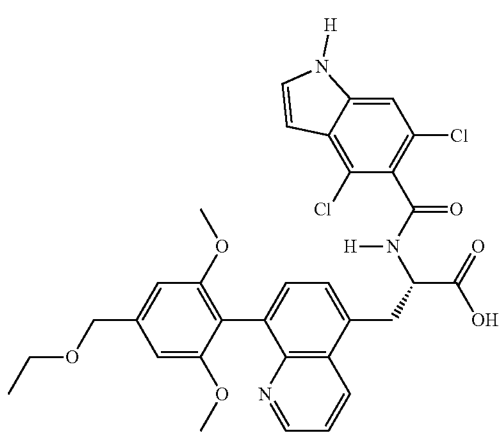 [SMILES: CCOCc1cc(OC)c(-c2ccc(C[C@H](NC(=O)c3c(Cl)cc4[nH]ccc4c3Cl)C(=O)O)c3cccnc23)c(OC)c1] | 1H NMR (400 MHz, DMSO-d6) δ 11.54 (s, 1H), 9.06 (d, J = 8.5 Hz, 1H), 8.84 (s, 1H), 7.71 (s, 2H), 7.50 (dd, J = 3.2, 2.4 Hz, 1H), 7.40 (d, J = 0.9 Hz, 1H), 6.75 (d, J = 6.2 Hz, 2H), 6.44 (d, J = 2.9 Hz, 1H), 4.88 (s, 1H), 4.54 (s, 2H), 3.76 (d, J = 14.1 Hz, 1H), 3.67-3.49 (m, 8H), 3.41 (t, J = 12.7 Hz, 1H), 1.21 (t, J = 7.0 Hz, 3H). | 622.4 | 2.3 |

TABLE 2-continued
| Example | Structure | 1H-NMR | M/Z [M + H]+ | α4β7 EC$_{50}$ (nM) |
|---|---|---|---|---|
| 236 | 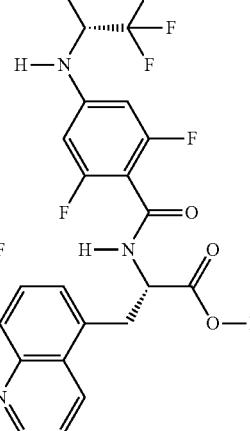 | 1H NMR (400 MHz, DMSO-d6) δ 8.93-8.73 (m, 2H), 8.62 (t, J = 8.7 Hz, 1H), 7.59 (dd, J = 11.1, 5.2 Hz, 3H), 6.76 (t, J = 8.9 Hz, 1H), 6.45 (dd, J = 11.6, 7.8 Hz, 2H), 4.68 (m, 1H), 4.31 (s, 3H), 3.80-3.59 (m, 1H), 3.54-3.32 (m, 1H), 2.54 (s, 3H), 2.46 (s, 3H), 2.35 (s, 3H), 1.76 (s, 1H), 1.52 (s, 1H), 0.92 (t, J = 7.3 Hz, 3H). | 669.2 | 2.6 |
| 237 | 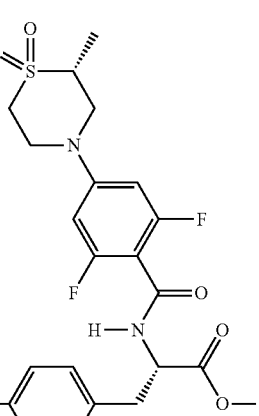 | 1H NMR (400 MHz, DMSO-d6) δ 8.94 (s, 1H), 8.88 (d, J = 8.1 Hz, 1H), 7.77 (s, 1H), 7.71-7.52 (m, 2H), 6.75 (dd, J = 11.7, 4.2 Hz, 2H), 4.72 (td, J = 14.3, 12.8, 6.6 Hz, 1H), 4.19 (d, J = 15.3 Hz, 1H), 4.08 (d, J = 14.9 Hz, 1H), 3.76 (ddd, J = 51.1, 14.4, 4.4 Hz, 1H), 3.55-3.29 (m, 6H), 3.27-3.14 (m, 5H), 3.14-2.97 (m, 2H), 1.93 (d, J = 10.5 Hz, 3H), 1.18 (d, J = 6.7 Hz, 3H). | 656.2 | 2.6 |
| 238 | 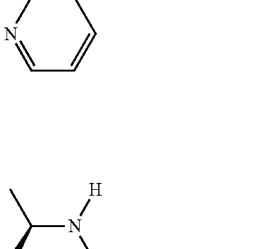 | 1H NMR (400 MHz, DMSO-d6) δ 8.91-8.73 (m, 2H), 8.64 (d, J = 8.6 Hz, 1H), 7.91 (s, 1H), 7.66-7.54 (m, 2H), 6.84 (d, J = 9.2 Hz, 1H), 6.75 (s, 1H), 6.41 (d, J = 11.4 Hz, 2H), 4.65 (td, J = 9.0, 8.2, 4.5 Hz, 1H), 4.49 (dt, J = 14.8, 7.4 Hz, 1H), 3.76-3.66 (m, 1H), 3.45-3.33 (m, 1H), 1.26 (d, J = 6.7 Hz, 3H). | 628.1 | 2.8 |

TABLE 2-continued

| Example | Structure | 1H-NMR | M/Z [M + H]+ | α4β7 EC$_{50}$ (nM) |
|---|---|---|---|---|
| 239 | 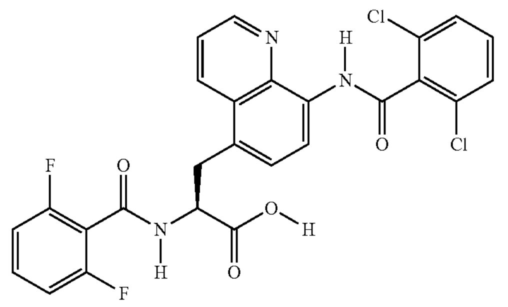 [SMILES: O=C(N[C@@H](Cc1ccc(NC(=O)c2c(Cl)cccc2Cl)c2ncccc12)C(=O)O)c1c(F)cccc1F] | 1H NMR (400 MHz, DMSO-d6) δ 10.72 (s, 1H), 9.23 (d, J = 8.1 Hz, 1H), 8.91 (dd, J = 4.2, 1.5 Hz, 1H), 8.71-8.55 (m, 2H), 7.71 (dd, J = 8.6, 4.2 Hz, 1H), 7.60-7.41 (m, 5H), 7.12 (dd, J = 8.4, 7.6 Hz, 2H), 4.68 (ddd, J = 9.6, 8.1, 4.6 Hz, 1H), 3.71-3.60 (m, 1H), 3.34 (dd, J = 14.4, 9.7 Hz, 1H). | 544.1 | 77.9 |
| 240 | 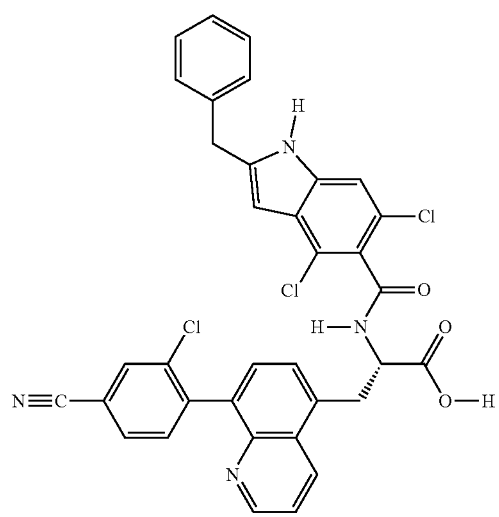 [SMILES: N#Cc1ccc(-c2ccc(C[C@H](NC(=O)c3c(Cl)cc4[nH]c(Cc5ccccc5)cc4c3Cl)C(=O)O)c3cccnc23)c(Cl)c1] | 1H NMR (400 MHz, DMSO-d6) δ 11.51 (d, J = 2.2 Hz, 1H), 9.03 (d, J = 8.3 Hz, 1H), 8.84 (dd, J = 4.1, 1.6 Hz, 1H), 8.66 (dd, J = 8.7, 1.7 Hz, 1H), 8.16 (d, J = 1.7 Hz, 1H), 7.91 (d, J = 7.9 Hz, 1H), 7.72-7.48 (m, 4H), 7.37-7.15 (m, 6H), 6.17 (s, 1H), 4.85 (s, 1H), 4.07 (s, 2H), 3.75 (dd, J = 14.5, 4.2 Hz, 1H), 3.40 (dd, J = 14.4, 10.6 Hz, 1H). | 655.2 | 79.2 |
| 241 | 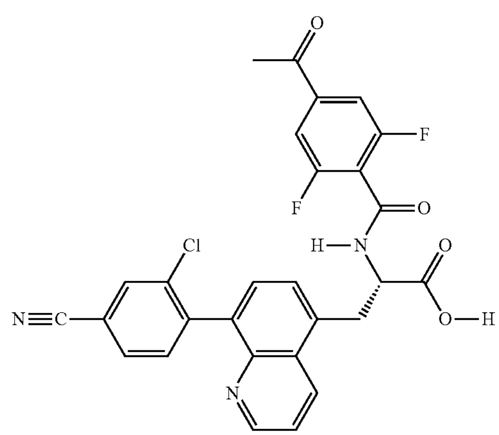 [SMILES: CC(=O)c1cc(F)c(C(=O)N[C@@H](Cc2ccc(-c3ccc(C#N)cc3Cl)c3ncccc23)C(=O)O)c(F)c1] | 1H NMR (400 MHz, DMSO-d6) δ 9.41 (d, J = 8.2 Hz, 1H), 8.84 (dd, J = 4.1, 1.6 Hz, 1H), 8.64 (dd, J = 8.6, 1.6 Hz, 1H), 8.16 (d, J = 1.7 Hz, 1H), 7.91 (d, J = 8.1 Hz, 1H), 7.68-7.42 (m, 5H), 4.98-4.59 (m, 1H), 2.58 (s, 3H), | 534.2 | 80.1 |

TABLE 2-continued

| Example | Structure | 1H-NMR | M/Z [M + H]+ | α4β7 EC$_{50}$ (nM) |
|---|---|---|---|---|
| 242 | 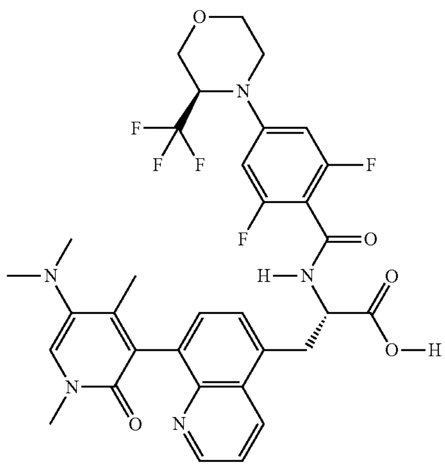 [SMILES: Cc1c(N(C)C)cn(C)c(=O)c1-c1ccc(C[C@H](NC(=O)c2c(F)cc(N3CCOC[C@@H]3C(F)(F)F)cc2F)C(=O)O)c2cccnc12] | 1H NMR (400 MHz, DMSO-d6) δ 8.95 (dd, J = 8.1, 4.0 Hz, 1H), 8.92-8.83 (m, 2H), 7.77 (ddd, J = 16.0, 8.5, 4.6 Hz, 1H), 7.67 (dd, J = 13.4, 7.4 Hz, 1H), 7.63-7.52 (m, 2H), 6.74 (d, J = 11.8 Hz, 2H), 4.95-4.85 (m, 1H), 4.74 (ddq, J = 13.1, 8.7, 4.5 Hz, 1H), 4.16 (d, J = 12.7 Hz, 1H), 3.95 (dd, J = 11.4, 3.8 Hz, 1H), 3.83 (dd, J = 14.6, 4.3 Hz, 1H), 3.73 (m, 1H), 3.45 (d, J = 2.2 Hz, 3H), 3.41-3.32 (m, 2H), 3.23 (t, J = 12.4 Hz, 1H), 3.17 (s, 1H), 2.68 (d, J = 11.0 Hz, 6H), 1.80 (d, J = 10.7 Hz, 3H). | 674.3 | 2.8 |
| 243 | 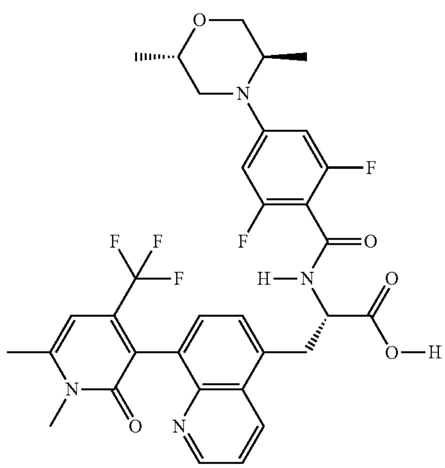 [SMILES: Cc1cc(C(F)(F)F)c(-c2ccc(C[C@H](NC(=O)c3c(F)cc(N4C[C@H](C)OC[C@H]4C)cc3F)C(=O)O)c3cccnc23)c(=O)n1C] | 1H NMR (400 MHz, DMSO-d6) δ 13.29-12.42 (s, 1H), 8.92 (dd, J = 7.9, 2.7 Hz, 1H), 8.82 (s, 1H), 8.65 (s, 1H), 7.63 (s, 1H), 7.58 (t, J = 7.0 Hz, 1H), 7.45 (s, 1H), 6.62 (dd, J = 11.3, 4.3 Hz, 2H), 6.55 (s, 1H), 4.70 (q, J = 7.8, 6.1 Hz, 1H), 3.99-3.88 (m, 2H), 3.78-3.64 (m, 1H), 3.64-3.55 (m, 1H), 3.49 (d, J = 2.1 Hz, 3H), 3.47-3.37 (m, 1H), 3.34 (dd, J = 11.6, 5.0 Hz, 1H), 3.27 (dd, J = 12.5, 3.6 Hz, 1H), 3.00-2.91 (m, 1H), 2.53 (s, 3H), 1.15 (d, J = 6.4 Hz, 3H), 1.01 (d, J = 6.3 Hz, 3H). | 659.4 | 2.9 |
| 244 | 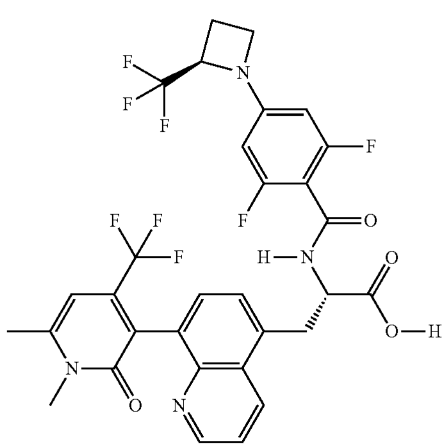 [SMILES: Cc1cc(C(F)(F)F)c(-c2ccc(C[C@H](NC(=O)c3c(F)cc(N4CC[C@@H]4C(F)(F)F)cc3F)C(=O)O)c3cccnc23)c(=O)n1C] | 1H NMR (400 MHz, DMSO-d6) δ 8.93 (dd, J = 8.0, 4.1 Hz, 1H), 8.83 (d, J = 4.2 Hz, 1H), 8.71-8.63 (m, 1H), 7.64 (dt, J = 9.1, 5.1 Hz, 1H), 7.57 (t, J = 7.2 Hz, 1H), 7.45 (dd, J = 7.3, 5.0 Hz, 1H), 6.55 (s, 1H), 6.25 (dd, J = 9.8, 4.1 Hz, 2H), 4.92 (p, J = 6.6 Hz, 1H), 4.71 (td, J = 8.6, 8.1, 4.1 Hz, 1H), 4.08 (td, J = 8.3, 5.1 Hz, 1H), 3.81-3.64 (m, 2H), 3.49 (d, J = 2.2 Hz, 3H), 2.69-2.57 (m, 1H), 2.53 (s, 3H), 2.39 (ddd, J = 14.6, 11.9, 6.6 Hz, 1H). | 669.3 | 2.9 |

TABLE 2-continued

| Example | Structure | 1H-NMR | M/Z [M + H]+ | α4β7 EC$_{50}$ (nM) |
|---|---|---|---|---|
| 245 | 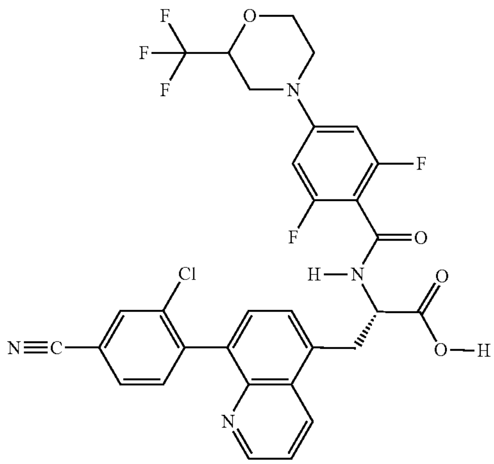 | 1H NMR (400 MHz, DMSO-d6) δ 8.93 (d, J = 8.1 Hz, 1H), 8.84 (dd, J = 4.2, 1.6 Hz, 1H), 8.66 (dd, J = 8.7, 1.7 Hz, 1H), 8.16 (d, J = 1.6 Hz, 1H), 7.90 (dd, J = 7.9, 1.7 Hz, 1H), 7.68-7.59 (m, 3H), 7.57 (d, J = 7.9 Hz, 1H), 6.75 (d, J = 11.6 Hz, 2H), 4.78-4.64 (m, 1H), 4.29 (ddd, J = 10.1, 6.8, 3.1 Hz, 1H), 4.03 (dd, J = 10.7, 3.3 Hz, 1H), 3.92-3.82 (m, 1H), 3.79-3.62 (m, 3H), 3.42 (s, 1H), 2.92-2.73 (m, 2H). | 645.8 | 33.6 |
| 246 | 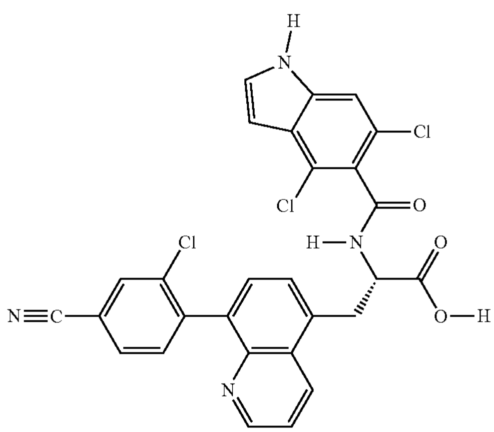 [SMILES: N#Cc1ccc(-c2ccc(C[C@H](NC(=O)c3c(Cl)cc4[nH]ccc4c3Cl)C(=O)O)c3cccnc23)c(Cl)c1] | 1H NMR (400 MHz, DMSO-d6) δ 11.55 (s, 1H), 9.06 (d, J = 8.3 Hz, 1H), 8.84 (dd, J = 4.1, 1.6 Hz, 1H), 8.67 (dd, J = 8.6, 1.6 Hz, 1H), 8.16 (d, J = 1.6 Hz, 1H), 7.92 (d, J = 7.9 Hz, 1H), 7.74-7.45 (m, 4H), 7.41 (d, J = 0.9 Hz, 1H), 6.45 (s, 1H), 4.87 (s, 1H), 3.75 (dd, J = 14.4, 4.3 Hz, 1H), 3.41 (dd, J = 14.5, 10.4 Hz, 1H). | 563.2 | 34.3 |
| 247 | 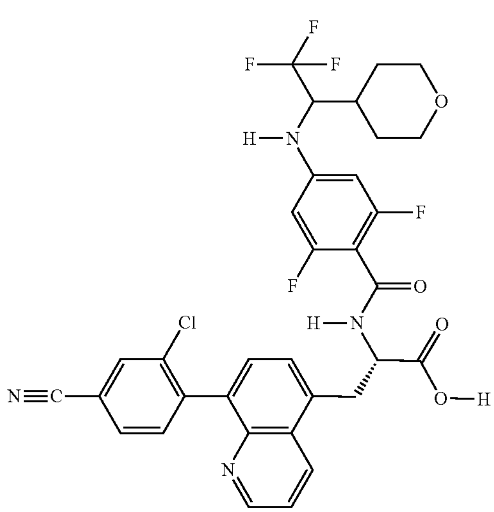 [SMILES: N#Cc1ccc(-c2ccc(C[C@H](NC(=O)c3c(F)cc(NC(C4CCOCC4)C(F)(F)F)cc3F)C(=O)O)c3cccnc23)c(Cl)c1] | 1H NMR (400 MHz, DMSO-d6) δ 8.83 (dd, J = 4.2, 1.6 Hz, 1H), 8.80 (d, J = 8.1 Hz, 1H), 8.64 (dd, J = 8.7, 1.7 Hz, 1H), 8.15 (d, J = 1.7 Hz, 1H), 7.90 (dd, J = 7.9, 1.7 Hz, 1H), 7.66-7.59 (m, 3H), 7.57 (d, J = 7.9 Hz, 1H), 6.73 (d, J = 10.2 Hz, 1H), 6.50 (d, J = 11.9 Hz, 2H), 4.69 (d, J = 7.8 Hz, 1H), 4.37 (q, J = 8.2 Hz, 1H), 3.84 (td, J = 12.2, 4.0 Hz, 2H), 3.73 (s, 1H), 3.40 (s, 1H), 3.26 (qd, J = 9.3, 8.0, 4.2 Hz, 2H), 2.05-1.89 (m, 1H), 1.55 (d, J = 13.0 Hz, 2H), 1.49-1.33 (m, 2H). | 674.4 | 35.2 |

TABLE 2-continued

| Example | Structure | 1H-NMR | M/Z [M + H]+ | α4β7 EC$_{50}$ (nM) |
|---|---|---|---|---|
| 248 | 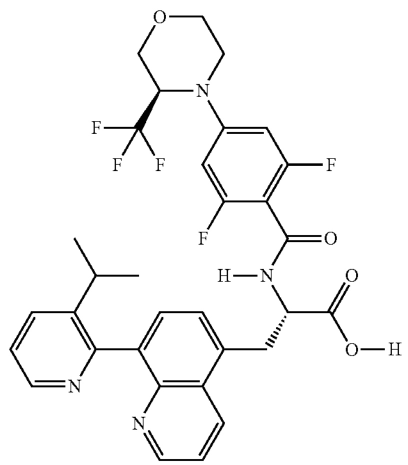 [SMILES: CC(C)c1cccnc1-c1ccc(C[C@H](NC(=O)c2c(F)cc(N3CCOC[C@@H]3C(F)(F)F)cc2F)C(=O)O)c2cccnc12] | 1H NMR (500 MHz, DMSO-d6) δ 8.98 (d, J = 8.2 Hz, 1H), 8.88 (dd, J = 4.1, 1.6 Hz, 1H), 8.79 (d, J = 5.4 Hz, 1H), 8.75 (dd, J = 8.7, 1.6 Hz, 1H), 8.63 (s, 1H), 8.02 (s, 1H), 7.91 (d, J = 7.3 Hz, 1H), 7.77-7.69 (m, 2H), 6.73 (d, J = 11.7 Hz, 2H), 4.91 (dd, J = 8.7, 3.6 Hz, 1H), 4.78 (ddd, J = 10.4, 8.3, 4.4 Hz, 1H), 4.16 (d, J = 12.7 Hz, 1H), 3.96 (dd, J = 11.6, 3.8 Hz, 1H), 3.82 (dd, J = 14.3, 4.4 Hz, 1H), 3.78-3.70 (m, 1H), 3.60-3.51 (m, 1H), 3.51-3.38 (m, 2H), 3.23 (t, J = 12.5 Hz, 1H), 2.59 (p, J = 6.9 Hz, 1H), 1.08 (dd, J = 6.9, 4.2 Hz, 6H). | 629.5 | 3.0 |
| 249 | 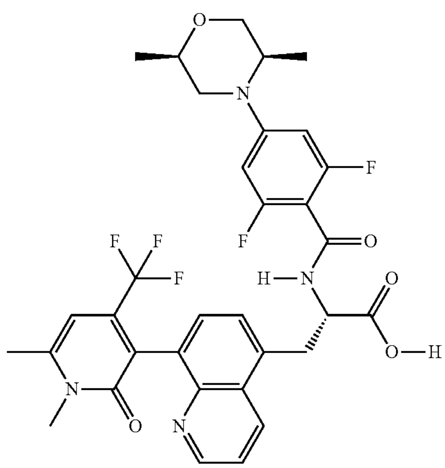 [SMILES: Cc1cc(C(F)(F)F)c(-c2ccc(C[C@H](NC(=O)c3c(F)cc(N4C[C@@H](C)OC[C@H]4C)cc3F)C(=O)O)c3cccnc23)c(=O)n1C] | 1H NMR (400 MHz, DMSO-d6) δ 13.12-12.65 (s, 1H), 8.89-8.76 (m, 2H), 8.63 (d, J = 8.4 Hz, 1H), 7.66-7.53 (m, 2H), 7.44 (d, J = 7.3 Hz, 1H), 6.57 (d, J = 4.6 Hz, 1H), 6.54 (d, J = 5.1 Hz, 2H), 4.76-4.63 (m, 1H), 3.93 (d, J = 7.3 Hz, 1H), 3.75-3.63 (m, 3H), 3.55 (d, J = 6.8 Hz, 1H), 3.49 (d, J = 1.9 Hz, 3H), 3.47-3.37 (m, 2H), 2.58 (d, J = 11.7 Hz, 1H), 2.53 (s, 3H), 1.16 (d, J = 6.1 Hz, 3H), 1.02 (d, J = 6.6 Hz, 3H). | 659.4 | 3.0 |
| 250 | 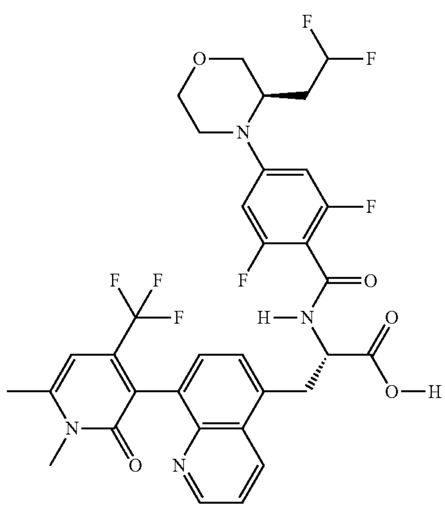 | 1H NMR (400 MHz, DMSO-d6) δ 8.89 (dd, J = 8.0, 3.1 Hz, 1H), 8.82 (dd, J = 4.5, 1.5 Hz, 1H), 8.65 (d, J = 8.4 Hz, 1H), 7.63 (dt, J = 8.4, 4.2 Hz, 1H), 7.61-7.53 (m, 1H), 7.49-7.39 (m, 1H), 6.62-6.52 (m, 3H), 6.17 (tt, J = 56.2, 4.6 Hz, 1H), 4.69 (td, J = 8.6, 7.8, 4.0 Hz, 1H), 4.08 (s, 1H), 3.89 (dd, J = 11.4, 3.6 Hz, 1H), 3.83 (d, J = 11.7 Hz, 1H), 3.71 (td, J = 14.1, 4.4 Hz, 1H), 3.61 (d, J = 11.5 Hz, 1H), 3.55-3.35 (m, 5H), 3.05 (td, J = 12.5, 3.8 Hz, 1H), 2.53 (s, 3H), 2.45-2.26 (m, 1H), 1.84 (td, J = 18.7, 14.2 Hz, 1H). | 695.2 | 3.1 |

TABLE 2-continued
| Example | Structure | 1H-NMR | M/Z [M + H]+ | α4β7 EC$_{50}$ (nM) |
|---|---|---|---|---|
| 251 | 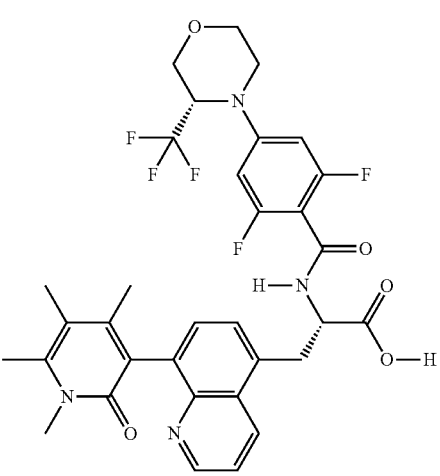 [SMILES: Cc1c(C)c(C)n(C)c(=O)c1-c1ccc(C[C@H](NC(=O)c2c(F)cc(N3CCOC[C@H]3C(F)(F)F)cc2F)C(=O)O)c2cccnc12] | 1H NMR (400 MHz, DMSO-d6) δ 8.96 (d, J = 2.2 Hz, 1H), 8.86 (s, 1H), 8.82 (d, J = 9.4 Hz, 1H), 7.78-7.70 (m, 1H), 7.65 (t, J = 7.9 Hz, 1H), 7.49 (t, J = 8.3 Hz, 1H), 6.77-6.72 (m, 2H), 4.90 (q, J = 10.1 Hz, 1H), 4.77-4.67 (m, 2H), 4.16 (d, J = 12.9 Hz, 1H), 3.95 (d, J = 8.3 Hz, 1H), 3.88-3.81 (m, 1H), 3.77-3.70 (m, 1H), 3.66 (s, 1H), 3.58-3.51 (m, 1H), 3.49 (d, J = 2.1 Hz, 3H), 3.45-3.36 (m, 2H), 3.30-3.17 (m, 1H), 2.43 (s, 3H), 2.09 (s, 3H), 1.74 (d, J = 11.0 Hz, 3H). | 658.2 | 3.1 |
| 252 | 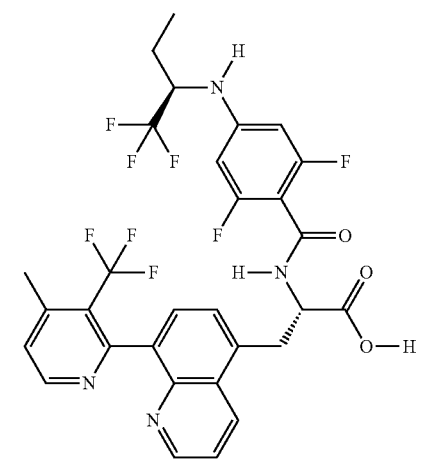 [SMILES: CC[C@@H](Nc1cc(F)c(C(=O)N[C@@H](Cc2ccc(-c3nccc(C)c3C(F)(F)F)c3ncccc23)C(=O)O)c(F)c1)C(F)(F)F] | 1H NMR (400 MHz, DMSO-d6) δ 8.85-8.77 (m, 2H), 8.71 (d, J = 5.1 Hz, 1H), 8.65 (t, J = 7.6 Hz, 1H), 7.68-7.54 (m, 4H), 6.77 (t, J = 7.6 Hz, 1H), 6.45 (dd, J = 11.7, 5.7 Hz, 2H), 4.78-4.61 (m, 1H), 4.40-4.22 (m, 1H), 3.83-3.64 (m, 1H), 3.53-3.33 (m, 1H), 2.59 (q, J = 2.3 Hz, 3H), 1.86-1.69 (m, 1H), 1.62-1.43 (m, 1H), 0.92 (t, J = 7.3 Hz, 3H). | 641.8 | 3.1 |
| 253 | 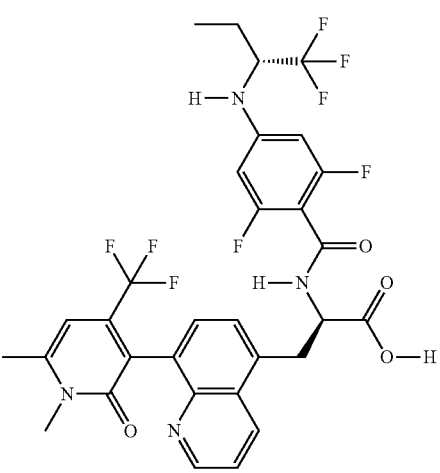 [SMILES: CC[C@@H](Nc1cc(F)c(C(=O)N[C@H](Cc2ccc(-c3c(C(F)(F)F)cc(C)n(C)c3=O)c3ncccc23)C(=O)O)c(F)c1)C(F)(F)F] | 1H NMR (400 MHz, DMSO-d6) δ 8.80 (dd, J = 12.3, 5.4 Hz, 2H), 8.64 (s, 1H), 7.74-7.51 (m, 2H), 7.44 (dd, J = 7.4, 3.7 Hz, 1H), 6.75 (dd, J = 9.5, 5.2 Hz, 1H), 6.54 (s, 1H), 6.44 (dd, J = 11.4, 3.8 Hz, 2H), 4.68 (s, 1H), 4.30 (s, 1H), 3.75-3.62 (m, 1H), 3.48 (d, J = 2.3 Hz, 3H), 3.46-3.31 (m, 1H), 2.53 (s, 3H), 1.75 (s, 1H), 1.52 (ddd, J = 13.8, 10.4, 7.0 Hz, 1H), 0.92 (t, J = 7.3 Hz, 3H). | 671.2 | 3.2 |

TABLE 2-continued
| Example | Structure | 1H-NMR | M/Z [M + H]+ | α4β7 EC$_{50}$ (nM) |
|---|---|---|---|---|
| 254 | 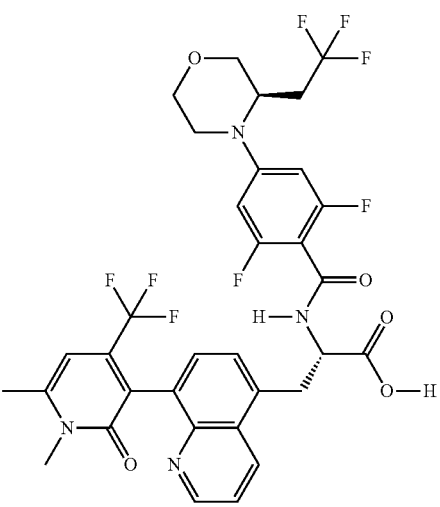 [SMILES: Cc1cc(C(F)(F)F)c(-c2ccc(C[C@H](NC(=O)c3c(F)cc(N4CCOC[C@H]4CC(F)(F)F)cc3F)C(=O)O)c3cccnc23)c(=O)n1C] | 1H NMR (400 MHz, DMSO-d6) δ 8.89 (dd, J = 7.8, 4.3 Hz, 1H), 8.85-8.78 (m, 1H), 8.64 (s, 1H), 7.60 (ddd, J = 17.6, 8.0, 4.3 Hz, 2H), 7.44 (dd, J = 7.3, 3.7 Hz, 1H), 6.66-6.49 (m, 3H), 4.69 (d, J = 11.1 Hz, 1H), 4.29 (s, 2H), 3.89 (dd, J = 11.4, 3.6 Hz, 1H), 3.85-3.59 (m, 3H), 3.57-3.38 (m, 5H), 3.08 (td, J = 12.6, 3.8 Hz, 1H), 2.77 (ddd, J = 15.4, 11.7, 8.2 Hz, 1H), 2.53 (s, 3H), 2.42-2.20 (m, 1H). | 713.2 | 3.2 |
| 255 | 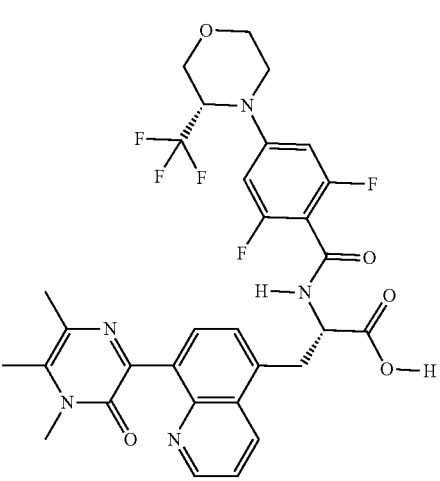 [SMILES: Cc1nc(-c2ccc(C[C@H](NC(=O)c3c(F)cc(N4CCOC[C@H]4C(F)(F)F)cc3F)C(=O)O)c3cccnc23)c(=O)n(C)c1C] | 1H NMR (400 MHz, DMSO-d6) δ 9.03-8.89 (m, 2H), 8.81 (s, 1H), 7.78 (d, J = 25.5 Hz, 2H), 7.70-7.61 (m, 1H), 6.77 (d, J = 11.7 Hz, 2H), 4.90 (d, J = 8.8 Hz, 1H), 4.69 (td, J = 9.0, 4.4 Hz, 1H), 4.16 (d, J = 12.7 Hz, 1H), 3.95 (dd, J = 11.4, 3.7 Hz, 1H), 3.82-3.68 (m, 2H), 3.63-3.35 (m, 6H), 3.24 (m, 1H), 2.42 (s, 3H), 2.34 (s, 3H). | 646.2 | 3.4 |
| 256 | 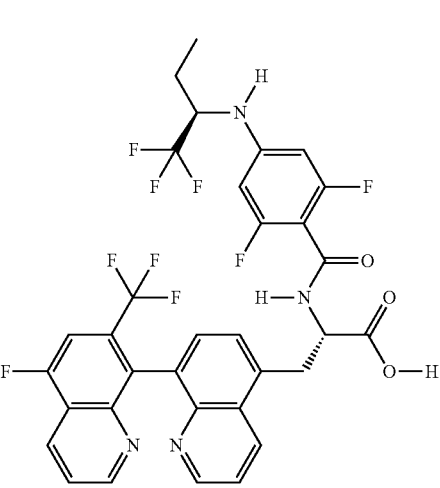 [SMILES: CC[C@@H](Nc1cc(F)c(C(=O)N[C@@H](Cc2ccc(-c3c(C(F)(F)F)cc(F)c4cccnc34)c3ncccc23)C(=O)O)c(F)c1)C(F)(F)F] | 1H NMR (400 MHz, DMSO-d6) δ 13.17-12.71 (s, 1H), 8.82 (dd, J = 15.0, 6.1 Hz, 2H), 8.63 (dd, J = 10.8, 6.2 Hz, 3H), 7.92 (d, J = 10.4 Hz, 1H), 7.73 (dd, J = 8.5, 4.2 Hz, 1H), 7.63 (d, J = 7.2 Hz, 1H), 7.56 (d, J = 7.3 Hz, 2H), 6.76 (d, J = 9.4 Hz, 1H), 6.45 (d, J = 11.7 Hz, 2H), 4.82-4.69 (m, 1H), 4.31 (m, 1H), 3.85-3.76 (m, 1H), 3.43 (dd, J = 14.6, 10.1 Hz, 1H), 1.88-1.68 (m, 1H), 1.63-1.45 (m, 1H), 0.93 (t, J = 7.3 Hz, 3H). | 695.3 | 3.5 |

TABLE 2-continued

| Example | Structure | 1H-NMR | M/Z [M + H]+ | α4β7 EC$_{50}$ (nM) |
|---|---|---|---|---|
| 257 | 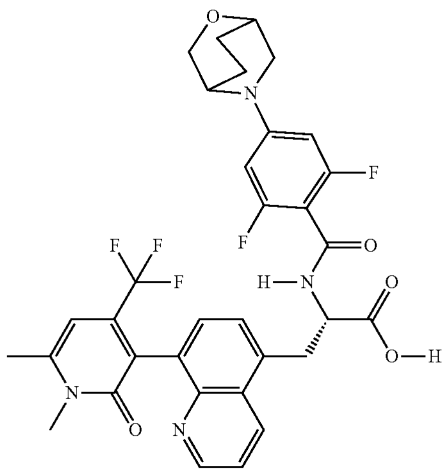 [SMILES: Cc1cc(C(F)(F)F)c(-c2ccc(C[C@H](NC(=O)c3c(F)cc(N4CC5CCC4CO5)cc3F)C(=O)O)c3cccnc23)c(=O)n1C] | 1H NMR (400 MHz, DMSO-d6) δ 8.83 (d, J = 4.3 Hz, 1H), 8.77-8.62 (m, 2H), 7.62 (dt, J = 24.9, 5.7 Hz, 2H), 7.45 (d, J = 7.3 Hz, 1H), 6.55 (s, 1H), 6.33 (dd, J = 12.2, 4.5 Hz, 2H), 4.69 (tt, J = 9.1, 5.0 Hz, 1H), 4.01 (d, J = 17.4 Hz, 2H), 3.96-3.86 (m, 2H), 3.78-3.65 (m, 1H), 3.60 (d, J = 10.9 Hz, 1H), 3.52-3.37 (m, 4H), 3.30 (d, J = 10.8 Hz, 1H), 2.53 (s, 3H), 2.09-1.94 (m, 1H), 1.87 (d, J = 8.6 Hz, 2H), 1.74-1.59 (m, 1H). | 657.3 | 3.5 |
| 258 | 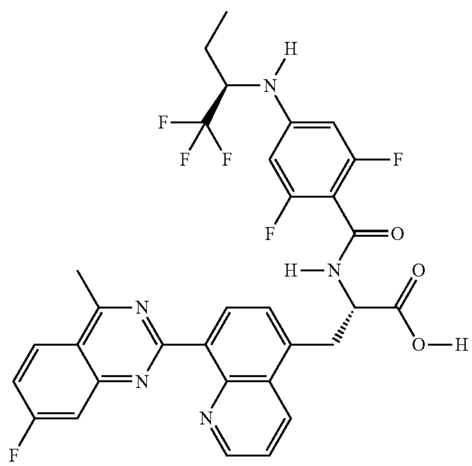 [SMILES: CC[C@@H](Nc1cc(F)c(C(=O)N[C@@H](Cc2ccc(-c3nc(C)c4ccc(F)cc4n3)c3ncccc23)C(=O)O)c(F)c1)C(F)(F)F] | 1H NMR (400 MHz, DMSO-d6) δ 9.34-9.18 (m, 1H), 8.81 (d, J = 8.1 Hz, 1H), 8.55 (dd, J = 9.0, 6.1 Hz, 1H), 8.21-8.10 (m, 2H), 7.98-7.87 (m, 1H), 7.82-7.73 (m, 1H), 6.79-6.75 (m, 1H), 6.43 (d, J = 11.5 Hz, 2H), 4.83-4.73 (m, 1H), 4.36-4.22 (m, 1H), 4.15 (d, J = 12.7 Hz, 1H), 3.93 (dt, J = 13.7, 7.1 Hz, 2H), 3.72 (d, J = 14.8 Hz, 2H), 3.61-3.50 (m, 2H), 3.39 (d, J = 13.1 Hz, 1H), 3.21 (t, J = 15.5 Hz, 1H), 3.09 (s, 3H), 1.75 (d, J = 24.4 Hz, 1H), 1.56-1.44 (m, 1H), 0.91 (t, J = 7.3 Hz, 3H). | 642.2 | 3.6 |
| 259 | 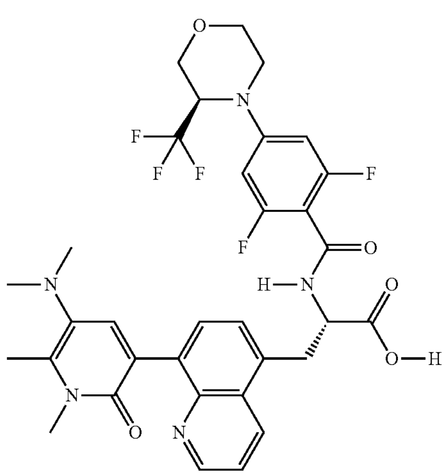 | 1H NMR (400 MHz, DMSO-d6) δ 8.97 (d, J = 8.0 Hz, 1H), 8.94 (dd, J = 4.6, 1.5 Hz, 1H), 8.86 (d, J = 8.3 Hz, 1H), 7.76 (dd, J = 14.9, 6.0 Hz, 2H), 7.71 (s, 1H), 7.66 (d, J = 7.4 Hz, 1H), 6.76 (d, J = 11.8 Hz, 2H), 4.91 (s, 1H), 4.69 (td, J = 8.8, 4.6 Hz, 1H), 4.16 (d, J = 12.7 Hz, 1H), 3.96 (dd, J = 11.5, 3.8 Hz, 1H), 3.76 (s, 1H), 3.72 (m, 1H), 3.55 (d, J = 3.6 Hz, 1H), 3.53 (s, 3H), 3.49-3.40 (m, 2H), 3.24 (t, J = 12.4 Hz, 1H), 2.65 (s, 6H), 2.52 (s, 3H). | 674.3 | 3.7 |

TABLE 2-continued

| Example | Structure | 1H-NMR | M/Z [M + H]+ | α4β7 EC$_{50}$ (nM) |
|---|---|---|---|---|
| 260 | 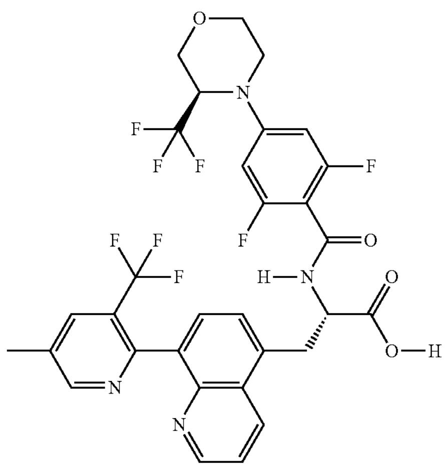 [SMILES: Cc1cnc(-c2ccc(C[C@H](NC(=O)c3c(F)cc(N4CCOC[C@@H]4C(F)(F)F)cc3F)C(=O)O)c3cccnc23)c(C(F)(F)F)c1] | 1H NMR (400 MHz, DMSO-d6) δ 12.93 (s, 1H), 8.97 (d, J = 8.0 Hz, 1H), 8.77 (dd, J = 4.1, 1.5 Hz, 1H), 8.73 (s, 1H), 8.64 (dt, J = 8.7, 1.7 Hz, 1H), 8.13 (d, J = 2.0 Hz, 1H), 7.66-7.54 (m, 3H), 6.76 (d, J = 11.7 Hz, 2H), 4.96-4.85 (m, 1H), 4.71 (ddd, J = 9.8, 8.1, 4.5 Hz, 1H), 4.16 (d, J = 12.7 Hz, 1H), 3.95 (dd, J = 11.5, 3.8 Hz, 1H), 3.79-3.70 (m, 2H), 3.62-3.49 (m, 1H), 3.44 (dd, J = 14.2, 10.4 Hz, 2H), 3.23 (t, J = 12.4 Hz, 1H), 2.50 (s, 3H). | 669.3 | 3.8 |
| 261 | 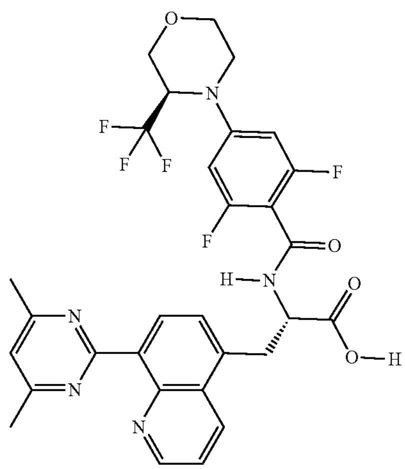 [SMILES: Cc1cc(C)nc(-c2ccc(C[C@H](NC(=O)c3c(F)cc(N4CCOC[C@@H]4C(F)(F)F)cc3F)C(=O)O)c3cccnc23)n1] | 1H NMR (400 MHz, DMSO-d6) δ 9.40 (s, 1H), 9.30 (s, 1H), 8.94 (d, J = 8.3 Hz, 1H), 8.79 (s, 1H), 8.10 (d, J = 6.8 Hz, 1H), 7.93 (d, J = 7.8 Hz, 1H), 7.48 (s, 1H), 6.73 (d, J = 11.8 Hz, 2H), 4.93-4.83 (m, 1H), 4.83-4.74 (m, 1H), 4.15 (d, J = 12.7 Hz, 1H), 3.92 (ddd, J = 25.6, 12.9, 4.1 Hz, 2H), 3.75-3.69 (m, 1H), 3.58 (s, 1H), 3.55 (d, J = 5.6 Hz, 1H), 3.38 (s, 1H), 3.22 (t, J = 12.5 Hz, 1H), 2.65 (s, 6H). | 617.3 | 4.0 |
| 262 | 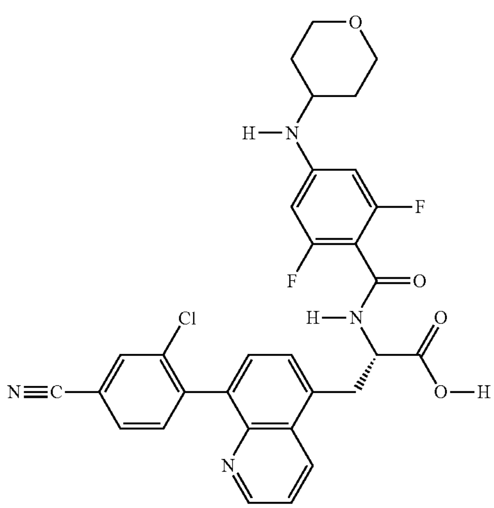 [SMILES: N#Cc1ccc(-c2ccc(C[C@H](NC(=O)c3c(F)cc(NC4CCOCC4)cc3F)C(=O)O)c3cccnc23)c(Cl)c1] | 1H NMR (400 MHz, DMSO-d6) δ 8.83 (dd, J = 4.1, 1.6 Hz, 1H), 8.71-8.61 (m, 2H), 8.15 (d, J = 1.6 Hz, 1H), 7.90 (dd, J = 7.9, 1.7 Hz, 1H), 7.67-7.59 (m, 3H), 7.57 (d, J = 7.9 Hz, 1H), 6.21 (d, J = 12.0 Hz, 2H), 4.73-4.62 (m, 1H), 3.82 (dt, J = 11.5, 3.5 Hz, 2H), 3.72 (s, 2H), 3.51-3.33 (m, 4H), 1.81 (ddt, J = 12.5, 4.4, 2.1 Hz, 2H), 1.38-1.23 (m, 2H). | 591.8 | 30.6 |

TABLE 2-continued

| Example | Structure | 1H-NMR | M/Z [M + H]+ | α4β7 EC$_{50}$ (nM) |
|---|---|---|---|---|
| 263 | 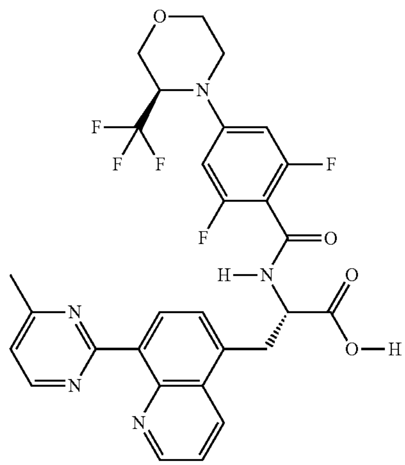 [SMILES: Cc1ccnc(-c2ccc(C[C@H](NC(=O)c3c(F)cc(N4CCOC[C@@H]4C(F)(F)F)cc3F)C(=O)O)c3cccnc23)n1] | 1H NMR (400 MHz, DMSO-d6) δ 9.35 (d, J = 22.1 Hz, 2H), 8.98-8.91 (m, 2H), 8.87 (s, 1H), 8.13 (d, J = 9.6 Hz, 1H), 7.95 (d, J = 7.7 Hz, 1H), 7.59 (d, J = 5.3 Hz, 1H), 6.73 (d, J = 11.8 Hz, 2H), 4.95-4.76 (m, 2H), 4.15 (d, J = 12.7 Hz, 1H), 3.99-3.84 (m, 2H), 3.77-3.64 (m, 2H), 3.56 (dd, J = 14.2, 10.5 Hz, 1H), 3.34 (s, 1H), 3.23 (d, J = 12.9 Hz, 1H), 2.70 (s, 3H). | 602.3 | 4.0 |
| 264 | 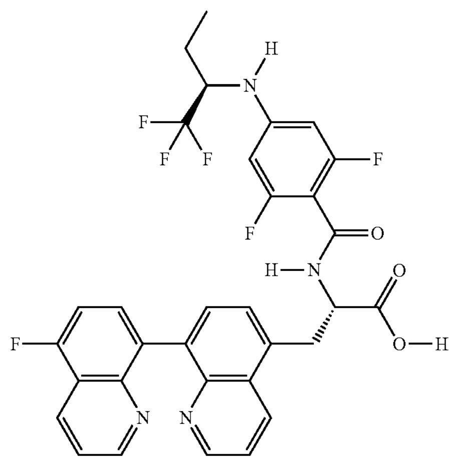 [SMILES: CC[C@@H](Nc1cc(F)c(C(=O)N[C@@H](Cc2ccc(-c3ccc(F)c4cccnc34)c3ncccc23)C(=O)O)c(F)c1)C(F)(F)F] | 1H NMR (400 MHz, DMSO-d6) δ 8.85 (t, J = 10.3 Hz, 2H), 8.79-8.71 (m, 2H), 8.59 (dd, J = 8.4, 1.8 Hz, 1H), 7.80-7.67 (m, 4H), 7.67-7.55 (m, 2H), 6.78 (d, J = 9.4 Hz, 1H), 6.46 (d, J = 11.8 Hz, 2H), 4.74 (t, J = 11.0 Hz, 1H), 4.31 (d, J = 10.3 Hz, 1H), 3.85-3.74 (m, 1H), 3.48 (dd, J = 14.5, 9.8 Hz, 1H), 1.76 (d, J = 8.2 Hz, 1H), 1.62-1.46 (m, 1H), 0.93 (t, J = 7.3 Hz, 3H). | 626.7 | 4.1 |
| 265 | 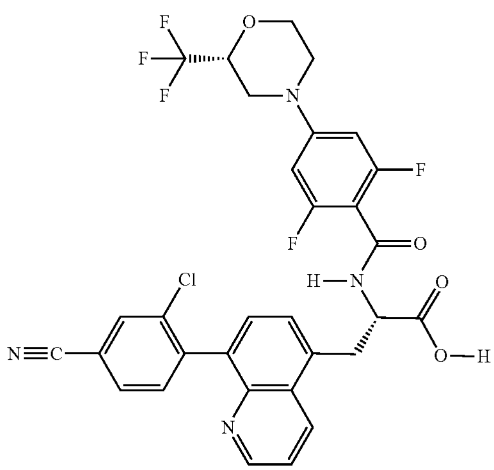 [SMILES: N#Cc1ccc(-c2ccc(C[C@H](NC(=O)c3c(F)cc(N4CCO[C@@H](C(F)(F)F)C4)cc3F)C(=O)O)c3cccnc23)c(Cl)c1] | 1H NMR (400 MHz, DMSO-d6) δ 8.93 (d, J = 8.1 Hz, 1H), 8.83 (dd, J = 4.1, 1.6 Hz, 1H), 8.64 (dd, J = 8.7, 1.7 Hz, 1H), 8.16 (d, J = 1.6 Hz, 1H), 7.90 (dd, J = 7.9, 1.7 Hz, 1H), 7.67-7.57 (m, 3H), 7.56 (d, J = 7.9 Hz, 1H), 6.75 (d, J = 11.6 Hz, 2H), 4.77-4.66 (m, 1H), 4.29 (dq, J = 6.7, 3.3 Hz, 1H), 4.03 (dd, J = 10.9, 3.3 Hz, 1H), 3.86 (d, J = 12.2 Hz, 1H), 3.75 (m, 1H), 3.69 (t, J = 10.4 Hz, 2H), 3.41 (s, 1H), 2.92-2.72 (m, 2H). | 760.0 | 68.8 |

TABLE 2-continued

| Example | Structure | 1H-NMR | M/Z [M + H]+ | α4β7 EC$_{50}$ (nM) |
|---|---|---|---|---|
| 266 | 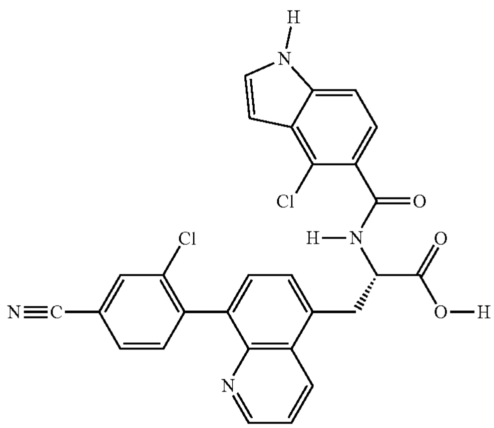 [SMILES: N#Cc1ccc(-c2ccc(C[C@H](NC(=O)c3ccc4[nH]ccc4c3Cl)C(=O)O)c3cccnc23)c(Cl)c1] | 1H NMR (400 MHz, DMSO-d6) δ 11.53 (s, 1H), 8.84 (dd, J = 4.1, 1.6 Hz, 1H), 8.68 (dd, J = 8.4, 2.4 Hz, 2H), 8.16 (d, J = 1.6 Hz, 1H), 7.91 (dd, J = 7.9, 1.6 Hz, 1H), 7.74-7.53 (m, 4H), 7.48 (t, J = 2.8 Hz, 1H), 7.34 (d, J = 8.3 Hz, 1H), 6.98 (s, 1H), 6.47 (d, J = 3.0 Hz, 1H), 4.80 (ddd, J = 10.5, 8.2, 4.2 Hz, 1H), 3.79 (dd, J = 14.4, 4.1 Hz, 1H), 3.48 (dd, J = 14.4, 10.6 Hz, 1H). | 530.6 | 72.2 |
| 267 | 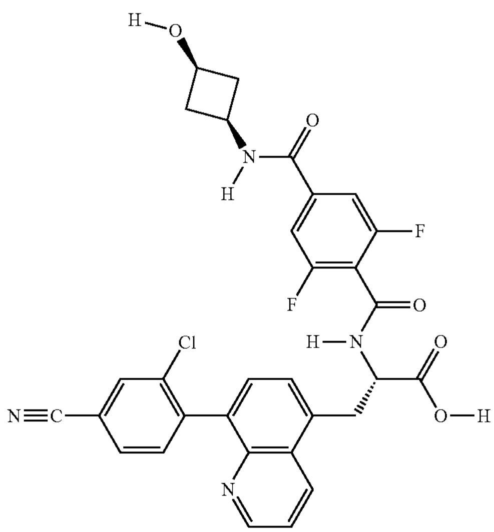 [SMILES: N#Cc1ccc(-c2ccc(C[C@H](NC(=O)c3c(F)cc(C(=O)N[C@H]4C[C@@H](O)C4)cc3F)C(=O)O)c3cccnc23)c(Cl)c1] | 1H NMR (400 MHz, DMSO-d6) δ 9.35 (d, J = 8.2 Hz, 1H), 8.87-8.80 (m, 1H), 8.74 (d, J = 7.5 Hz, 1H), 8.64 (d, J = 8.6 Hz, 1H), 8.16 (d, J = 1.7 Hz, 1H), 7.91 (d, J = 8.0 Hz, 1H), 7.66-7.60 (m, 2H), 7.58-7.53 (m, 2H), 4.79 (s, 1H), 3.95-3.78 (m, 1H), 2.65 (s, 1H), 2.31 (s, 1H), 1.88 (d, J = 10.1 Hz, 2H). | 605.2 | 77.0 |
| 268 | 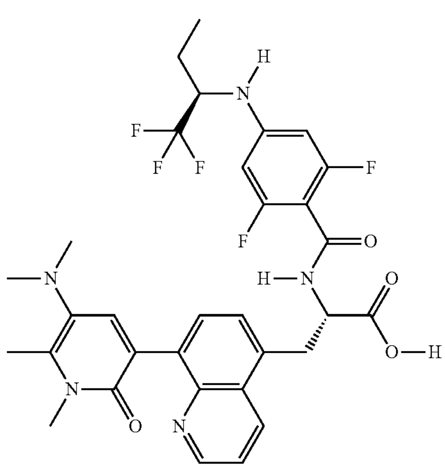 [SMILES: CC[C@@H](Nc1cc(F)c(C(=O)N[C@@H](Cc2ccc(-c3cc(N(C)C)c(C)n(C)c3=O)c3ncccc23)C(=O)O)c(F)c1)C(F)(F)F] | 1H NMR (400 MHz, DMSO-d6) δ 8.93 (d, J = 4.5 Hz, 1H), 8.89-8.76 (m, 2H), 7.82-7.59 (m, 4H), 6.79 (d, J = 9.4 Hz, 1H), 6.45 (d, J = 11.9 Hz, 2H), 4.67 (dt, J = 13.3, 6.3 Hz, 1H), 4.30 (s, 1H), 3.53 (s, 3H), 3.49-3.38 (m, 2H), 2.64 (s, 6H), 2.52 (s, 3H), 1.84-1.68 (m, 1H), 1.61-1.45 (m, 1H), 0.93 (t, J = 7.3 Hz, 3H). | 646.3 | 4.3 |

TABLE 2-continued

| Example | Structure | 1H-NMR | M/Z [M + H]+ | α4β7 EC$_{50}$ (nM) |
|---|---|---|---|---|
| 269 | 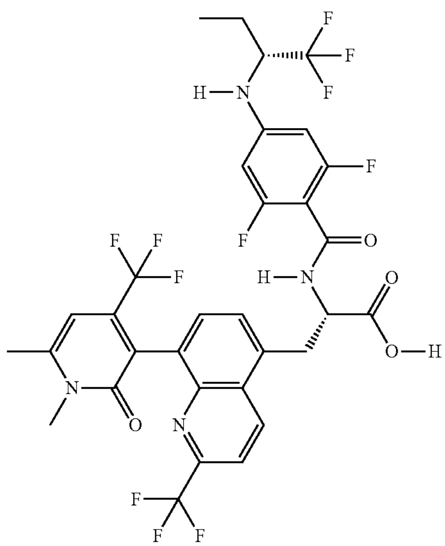 [SMILES: CC[C@@H](Nc1cc(F)c(C(=O)N[C@@H](Cc2ccc(-c3c(C(F)(F)F)cc(C)n(C)c3=O)c3nc(C(F)(F)F)ccc23)C(=O)O)c(F)c1)C(F)(F)F] | 1H NMR (400 MHz, DMSO-d6) δ 8.93-8.86 (m, 1H), 8.80 (t, J = 7.2 Hz, 1H), 8.00 (dd, J = 8.8, 3.9 Hz, 1H), 7.71 (t, J = 8.1 Hz, 1H), 7.59 (t, J = 7.4 Hz, 1H), 6.75 (dd, J = 9.5, 4.7 Hz, 1H), 6.56 (s, 1H), 6.43 (dd, J = 11.3, 3.4 Hz, 2H), 4.71 (s, 1H), 4.31 (s, 1H), 3.84-3.66 (m, 1H), 3.58-3.33 (m, 4H), 2.54 (s, 3H), 1.87-1.70 (m, 1H), 1.52 (ddd, J = 13.8, 10.1, 6.9 Hz, 1H), 0.92 (t, J = 7.3 Hz, 3H). | 739.2 | 4.4 |
| 270 | 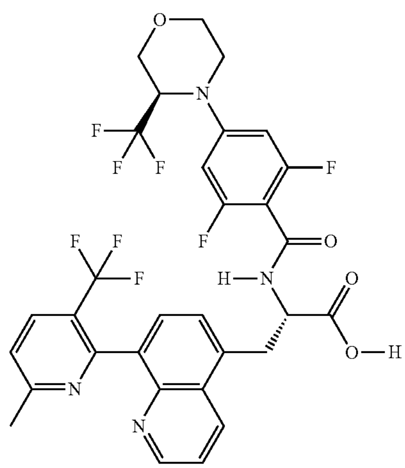 [SMILES: Cc1ccc(C(F)(F)F)c(-c2ccc(C[C@H](NC(=O)c3c(F)cc(N4CCOC[C@@H]4C(F)(F)F)cc3F)C(=O)O)c3cccnc23)n1] | 1H NMR (400 MHz, DMSO-d6) δ 8.98 (d, J = 8.0 Hz, 1H), 8.80 (dd, J = 4.2, 1.6 Hz, 1H), 8.67 (dd, J = 8.7, 1.7 Hz, 1H), 8.20 (d, J = 8.2 Hz, 1H), 7.67-7.53 (m, 4H), 6.76 (d, J = 11.7 Hz, 2H), 4.91 (dd, J = 8.8, 3.7 Hz, 1H), 4.71 (ddd, J = 9.9, 8.0, 4.5 Hz, 1H), 4.16 (d, J = 12.7 Hz, 1H), 3.95 (dd, J = 11.5, 3.8 Hz, 1H), 3.81-3.69 (m, 2H), 3.55 (td, J = 11.9, 3.3 Hz, 1H), 3.45 (dd, J = 18.1, 11.9 Hz, 2H), 3.23 (t, J = 12.1 Hz, 1H), 2.58 (s, 3H). | 669.4 | 4.4 |
| 271 | 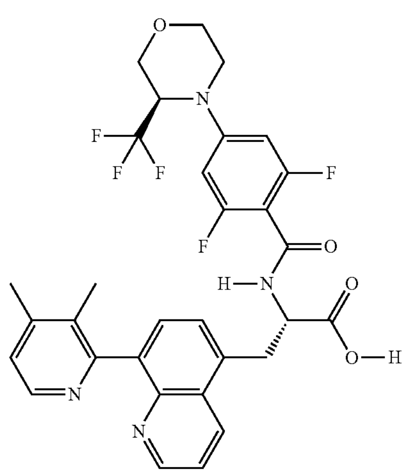 [SMILES: Cc1ccnc(-c2ccc(C[C@H](NC(=O)c3c(F)cc(N4CCOC[C@@H]4C(F)(F)F)cc3F)C(=O)O)c3cccnc23)c1C] | 1H NMR (400 MHz, DMSO-d6) δ 13.10 (s, 1H), 9.02 (d, J = 8.3 Hz, 1H), 8.90 (dd, J = 4.2, 1.6 Hz, 1H), 8.77 (dd, J = 8.7, 1.6 Hz, 1H), 8.73 (d, J = 5.9 Hz, 1H), 8.00-7.88 (m, 2H), 7.79-7.70 (m, 2H), 6.75 (d, J = 11.8 Hz, 2H), 4.90 (td, J = 8.7, 3.6 Hz, 1H), 4.77 (ddd, J = 10.4, 8.3, 4.3 Hz, 1H), 4.16 (d, J = 12.7 Hz, 1H), 3.96 (dd, J = 11.5, 3.8 Hz, 1H), 3.84 (dd, J = 14.2, 4.3 Hz, 1H), 3.78-3.69 (m, 1H), 3.60-3.37 (m, 3H), 3.23 (t, J = 12.3 Hz, 1H), 2.63 (s, 3H), 2.06-2.01 (m, 3H). | 615.2 | 4.5 |

TABLE 2-continued

| Example | Structure | 1H-NMR | M/Z [M + H]+ | α4β7 EC$_{50}$ (nM) |
|---|---|---|---|---|
| 272 | 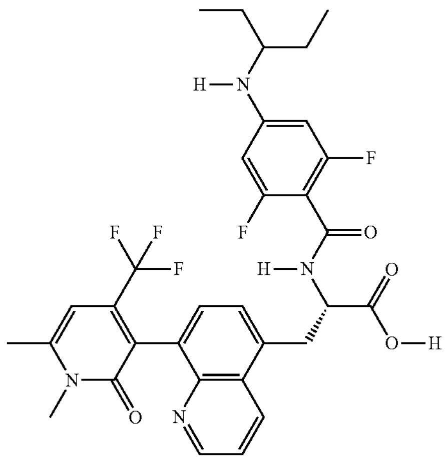 [SMILES: CCC(CC)Nc1cc(F)c(C(=O)N[C@@H](Cc2ccc(-c3c(C(F)(F)F)cc(C)n(C)c3=O)c3ncccc23)C(=O)O)c(F)c1] | 1H NMR (400 MHz, DMSO-d6) δ 8.87-8.76 (m, 1H), 8.63 (q, J = 7.1 Hz, 2H), 7.70-7.52 (m, 2H), 7.52-7.34 (m, 1H), 6.55 (s, 1H), 6.29 (s, 1H), 6.17 (dd, J = 11.9, 4.5 Hz, 2H), 4.74-4.63 (m, 1H), 3.80-3.59 (m, 1H), 3.49 (d, J = 2.1 Hz, 3H), 3.47-3.35 (m, 1H), 3.20 (s, 1H), 2.53 (s, 3H), 1.50 (ddd, J = 13.1, 7.3, 5.3 Hz, 2H), 1.37 (dp, J = 14.4, 7.4 Hz, 2H), 0.84 (t, J = 7.4 Hz, 6H). | 631.2 | 4.5 |
| 273 | 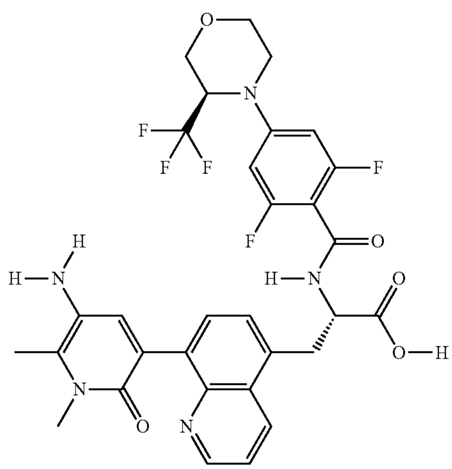 [SMILES: Cc1c(N)cc(-c2ccc(C[C@H](NC(=O)c3c(F)cc(N4CCOC[C@@H]4C(F)(F)F)cc3F)C(=O)O)c3cccnc23)c(=O)n1C] | 1H NMR (400 MHz, DMSO-d6) δ 8.97 (d, J = 8.0 Hz, 1H), 8.86 (d, J = 4.0 Hz, 1H), 8.67 (d, J = 8.6 Hz, 1H), 7.66 (dd, J = 8.1, 4.0 Hz, 2H), 7.58 (d, J = 7.4 Hz, 1H), 7.50 (s, 1H), 6.76 (d, J = 11.7 Hz, 2H), 4.90 (dt, J = 12.0, 6.0 Hz, 1H), 4.69 (td, J = 8.8, 8.3, 4.5 Hz, 1H), 4.17 (d, J = 12.7 Hz, 1H), 3.96 (dd, J = 11.6, 3.8 Hz, 1H), 3.80-3.66 (m, 2H), 3.56 (s, 4H), 3.43 (m, 1H), 3.32-3.16 (m, 2H), 2.43 (s, 3H). | 646.2 | 4.7 |
| 274 | 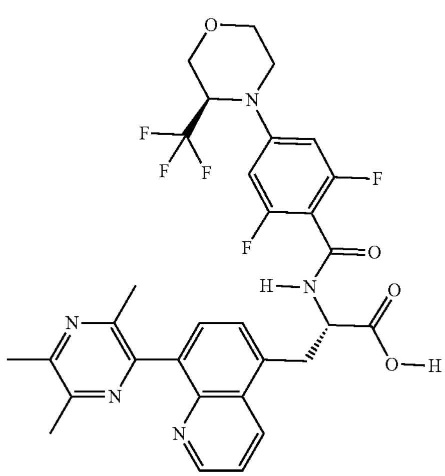 [SMILES: Cc1nc(C)c(-c2ccc(C[C@H](NC(=O)c3c(F)cc(N4CCOC[C@@H]4C(F)(F)F)cc3F)C(=O)O)c3cccnc23)nc1C] | 1H NMR (400 MHz, DMSO-d6) δ 8.93 (d, J = 8.1 Hz, 1H), 8.84 (d, J = 4.2 Hz, 1H), 8.68 (d, J = 8.7 Hz, 1H), 7.64 (d, J = 3.5 Hz, 3H), 6.75 (d, J = 11.7 Hz, 2H), 4.90 (d, J = 9.4 Hz, 1H), 4.73 (td, J = 9.0, 4.3 Hz, 1H), 4.16 (d, J = 12.7 Hz, 1H), 3.95 (dd, J = 11.5, 3.8 Hz, 1H), 3.84-3.63 (m, 2H), 3.49 (ddd, J = 45.5, 14.7, 10.8 Hz, 3H), 3.23 (s, 1H), 2.54 (s, 3H), 2.48 (s, 3H), 2.07 (s, 3H). | 630.6 | 4.8 |

TABLE 2-continued

| Example | Structure | 1H-NMR | M/Z [M + H]+ | α4β7 EC$_{50}$ (nM) |
|---|---|---|---|---|
| 275 | 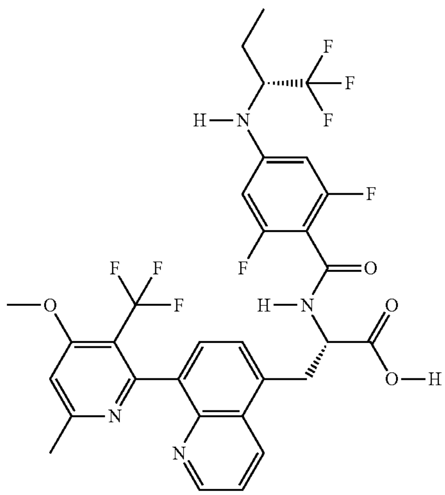 [SMILES: CC[C@@H](Nc1cc(F)c(C(=O)N[C@@H](Cc2ccc(-c3nc(C)cc(OC)c3C(F)(F)F)c3ncccc23)C(=O)O)c(F)c1)C(F)(F)F] | 1H NMR (400 MHz, DMSO-d6) δ 8.88-8.73 (m, 2H), 8.65 (t, J = 8.9 Hz, 1H), 7.63 (dd, J = 12.3, 5.2 Hz, 3H), 7.49 (s, 1H), 6.77 (t, J = 8.9 Hz, 1H), 6.45 (dd, J = 11.7, 7.9 Hz, 2H), 4.76-4.58 (m, 1H), 4.31 (s, 1H), 4.10 (s, 3H), 3.72 (ddd, J = 34.5, 14.4, 4.5 Hz, 1H), 3.44 (ddd, J = 29.6, 14.4, 9.7 Hz, 1H), 2.58 (s, 3H), 1.76 (d, J = 10.8 Hz, 1H), 1.53 (t, J = 15.8 Hz, 1H), 0.93 (t, J = 7.3 Hz, 3H). | 671.2 | 4.8 |
| 276 | 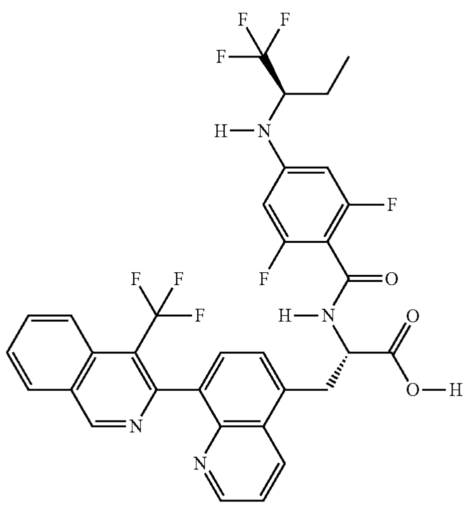 [SMILES: CC[C@@H](Nc1cc(F)c(C(=O)N[C@@H](Cc2ccc(-c3ncc4ccccc4c3C(F)(F)F)c3ncccc23)C(=O)O)c(F)c1)C(F)(F)F] | 1H NMR (400 MHz, DMSO-d6) δ 9.66-9.50 (m, 1H), 8.91-8.72 (m, 2H), 8.65 (td, J = 8.4, 1.7 Hz, 1H), 8.39 (dd, J = 8.3, 1.3 Hz, 1H), 8.18 (d, J = 8.5 Hz, 1H), 8.05 (ddd, J = 8.6, 6.9, 1.4 Hz, 1H), 7.95-7.80 (m, 1H), 7.79-7.47 (m, 3H), 6.76 (t, J = 8.3 Hz, 1H), 6.44 (dd, J = 11.5, 7.1 Hz, 2H), 4.75-4.59 (m, 1H), 4.30 (s, 1H), 3.83-3.60 (m, 1H), 3.44 (ddd, J = 25.0, 14.3, 9.9 Hz, 1H), 1.90-1.66 (m, 1H), 1.61-1.21 (m, 1H), 0.97-0.79 (m, 3H). | 677.2 | 4.9 |
| 277 | 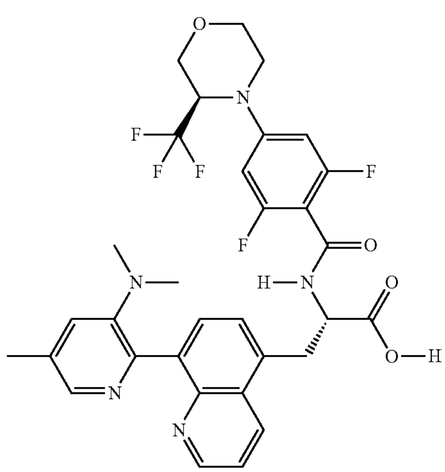 [SMILES: Cc1cnc(-c2ccc(C[C@H](NC(=O)c3c(F)cc(N4CCOC[C@@H]4C(F)(F)F)cc3F)C(=O)O)c3cccnc23)c(N(C)C)c1] | 1H NMR (400 MHz, DMSO-d6) δ 9.03-8.92 (m, 2H), 8.76 (dd, J = 8.6, 1.6 Hz, 1H), 8.22 (s, 1H), 7.99 (s, 1H), 7.90 (d, J = 7.4 Hz, 1H), 7.80-7.69 (m, 2H), 6.74 (d, J = 11.8 Hz, 2H), 4.97-4.84 (m, 1H), 4.80-4.70 (m, 1H), 4.17 (d, J = 12.7 Hz, 1H), 3.96 (dd, J = 11.5, 3.8 Hz 1H), 3.81 (dd, J = 14.3, 4.4 Hz, 1H), 3.73 (d, J = 12.8 Hz, 1H), 3.61-3.35 (m, 3H), 3.23 (t, J = 12.5 Hz, 1H). | 644.3 | 5.2 |

TABLE 2-continued

| Example | Structure | 1H-NMR | M/Z [M + H]+ | α4β7 EC$_{50}$ (nM) |
|---|---|---|---|---|
| 278 | 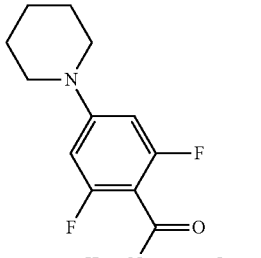 | 1H NMR (400 MHz, DMSO-d6) δ 8.85 (dd, J = 4.2, 1.6 Hz, 1H), 8.82 (d, J = 8.0 Hz, 1H), 8.67 (dd, J = 8.7, 1.7 Hz, 1H), 8.17 (d, J = 1.6 Hz, 1H), 7.92 (dd, J = 7.9, 1.7 Hz, 1H), 7.69-7.60 (m, 3H), 7.59 (d, J = 7.9 Hz, 1H), 6.56 (d, J = 12.3 Hz, 2H), 4.71 (td, J = 8.8, 8.1, 4.3 Hz, 1H), 3.77 (d, J = 18.6 Hz, 1H), 3.44 (s, 1H), 3.26 (t, J = 5.0 Hz, 4H), 1.52 (dd, J = 9.7, 5.6 Hz, 6H). | 574.8 | 82.2 |
| 279 | 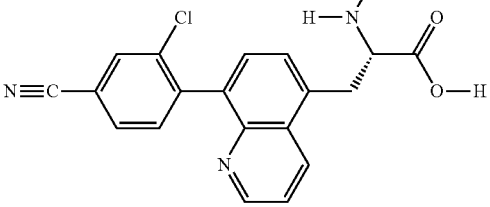 | 1H NMR (400 MHz, DMSO-d6) δ 10.35 (d, J = 1.2 Hz, 1H), 8.84 (tt, J = 3.2, 1.6 Hz, 2H), 8.50 (dd, J = 8.6, 1.7 Hz, 1H), 7.99 (s, 1H), 7.73-7.55 (m, 5H), 7.12 (t, J = 8.1 Hz, 2H), 3.30 (s, 1H). ; 1H NMR (400 MHz, DMSO-d6) δ 9.03 (d, J = 8.9 Hz, 1H), 8.85 (dd, J = 4.1, 1.5 Hz, 1H), 8.61 (dd, J = 8.7, 1.7 Hz, 1H), 7.93 (d, J = 7.5 Hz, 1H), 7.74-7.57 (m, 4H), 7.43 (tt, J = 8.4, 6.4 Hz, 1H), 7.14-6.95 (m, 2H), 6.07 (d, J = 2.8 Hz, 1H), 4.91 (dd, J = 8.9, 2.7 Hz, 1H). | 535.0 | 82.4 |
| 280 | 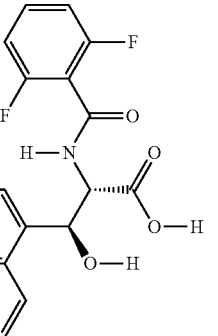 | 1H NMR (400 MHz, DMSO-d6) δ 9.31 (d, J = 8.2 Hz, 1H), 8.84 (dd, J = 4.1, 1.6 Hz, 1H), 8.64 (dd, J = 8.7, 1.7 Hz, 1H), 8.16 (dd, J = 1.6, 0.4 Hz, 1H), 7.90 (dd, J = 7.9, 1.6 Hz, 1H), 7.69-7.54 (m, 4H), 7.30 (d, J = 8.9 Hz, 2H), 6.96 (s, 1H), 4.85-4.71 (m, 1H), 3.77 (s, 1H), 3.39 (s, 1H). | 604.2 | 86.1 |

TABLE 2-continued

| Example | Structure | 1H-NMR | M/Z [M + H]+ | α4β7 EC$_{50}$ (nM) |
|---|---|---|---|---|
| 281 | 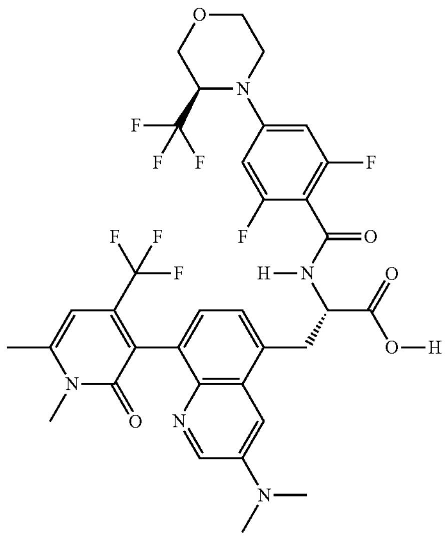 [SMILES: Cc1cc(C(F)(F)F)c(-c2ccc(C[C@H](NC(=O)c3c(F)cc(N4CCOC[C@@H]4C(F)(F)F)cc3F)C(=O)O)c3cc(N(C)C)cnc23)c(=O)n1C] | 1H NMR (400 MHz, DMSO-d6) δ 8.99 (d, J = 7.9 Hz, 1H), 8.62 (t, J = 2.7 Hz, 1H), 7.58 (s, 1H), 7.45 (t, J = 6.6 Hz, 1H), 7.12 (d, J = 7.2 Hz, 1H), 6.77 (dd, J = 11.6, 4.2 Hz, 2H), 6.55 (d, J = 2.2 Hz, 1H), 4.98-4.87 (m, 1H), 4.75-4.65 (m, 1H), 4.16 (d, J = 12.7 Hz, 1H), 3.99-3.93 (m, 1H), 3.74 (d, J = 13.1 Hz, 2H), 3.67-3.50 (m, 1H), 3.48 (d, J = 1.5 Hz, 3H), 3.46-3.18 (m, 3H), 3.10 (d, J = 4.4 Hz, 6H), 2.53 (s, 3H). | 742.6 | 5.5 |
| 282 | 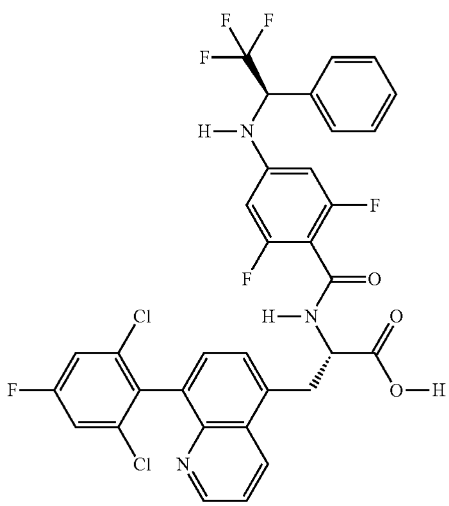 [SMILES: O=C(N[C@@H](Cc1ccc(-c2c(Cl)cc(F)cc2Cl)c2ncccc12)C(=O)O)c1c(F)cc(N[C@H](c2ccccc2)C(F)(F)F)cc1F] | 1H NMR (400 MHz, DMSO-d6) δ 8.84-8.80 (m, 2H), 8.62 (dd, J = 8.7, 1.6 Hz, 1H), 7.66-7.49 (m, 8H), 7.45-7.35 (m, 3H), 6.54 (d, J = 11.3 Hz, 2H), 5.70 (p, J = 8.3 Hz, 1H), 4.70 (ddd, J = 10.1, 8.0, 4.4 Hz, 1H), 3.72 (dd, J = 14.4, 4.4 Hz, 1H), 3.39 (dd, J = 14.5, 10.3 Hz, 1H). | 692.0 | 26.8 |
| 283 | 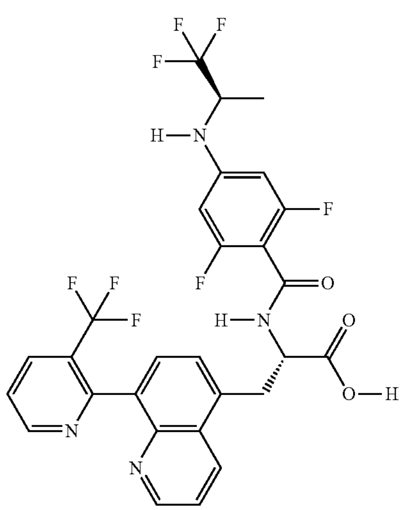 [SMILES: C[C@@H](Nc1cc(F)c(C(=O)N[C@@H](Cc2ccc(-c3ncccc3C(F)(F)F)c3ncccc23)C(=O)O)c(F)c1)C(F)(F)F] | 1H NMR (400 MHz, DMSO-d6) δ 8.90 (ddd, J = 4.8, 1.6, 0.7 Hz, 1H), 8.81 (d, J = 8.0 Hz, 1H), 8.78 (dd, J = 4.2, 1.6 Hz, 1H), 8.64 (dd, J = 8.7, 1.7 Hz, 1H), 8.33-8.29 (m, 1H), 7.70 (ddd, J = 8.0, 4.8, 0.9 Hz, 1H), 7.64-7.59 (m, 3H), 6.84 (d, J = 9.2 Hz, 1H), 6.42 (d, J = 11.4 Hz, 2H), 4.73-4.66 (m, 1H), 4.51 (td, J = 14.3, 6.9 Hz, 1H), 3.74 (dd, J = 14.3, 4.4 Hz, 1H), 3.44 (dd, J = 14.4, 10.1 Hz, 1H), 1.27 (d, J = 6.7 Hz, 3H). | 613.1 | 5.7 |

TABLE 2-continued
| Example | Structure | 1H-NMR | M/Z [M + H]+ | α4β7 EC$_{50}$ (nM) |
|---|---|---|---|---|
| 284 | 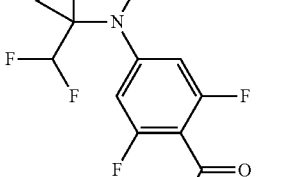 | 1H NMR (400 MHz, DMSO-d6) δ 8.86-8.75 (m, 2H), 8.63 (dd, J = 8.7, 1.7 Hz, 1H), 8.15 (dd, J = 1.6, 0.4 Hz, 1H), 7.90 (dd, J = 7.9, 1.7 Hz, 1H), 7.67-7.53 (m, 4H), 7.25 (s, 1H), 6.27 (d, J = 11.5 Hz, 2H), 5.81 (t, J = 55.6 Hz, 1H), 4.67 (s, 1H), 3.72 (s, 1H), 3.41 (s, 1H), 1.18-1.10 (m, 2H), 0.85 (s, 2H). | 597.2 | 45.9 |
| 285 | 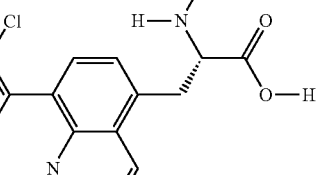 | 1H NMR (400 MHz, DMSO-d6) δ 9.08 (d, J = 8.4 Hz, 1H), 8.84 (dd, J = 4.2, 1.6 Hz, 1H), 8.76-8.61 (m, 1H), 8.17 (d, J = 1.6 Hz, 1H), 7.91 (s, 1H), 7.72-7.58 (m, 3H), 7.55 (d, J = 7.9 Hz, 1H), 7.48 (d, J = 3.2 Hz, 1H), 6.44 (d, J = 3.1 Hz, 1H), 4.87 (s, 1H), 3.77 (s, 3H), 3.74 (d, J = 4.2 Hz, 1H), 3.48-3.34 (m, 1H). | 577.0 | 46.2 |
| 286 | 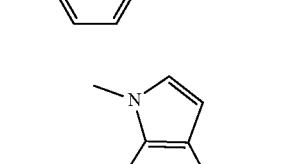 | 1H NMR (400 MHz, DMSO-d6) δ 9.18 (d, J = 8.1 Hz, 1H), 8.84 (dd, J = 4.2, 1.6 Hz, 1H), 8.64 (dd, J = 8.6, 1.6 Hz, 1H), 8.16 (d, J = 1.6 Hz, 1H), 7.90 (dd, J = 7.9, 1.6 Hz, 1H), 7.68-7.59 (m, 3H), 7.57 (d, J = 7.9 Hz, 1H), 6.94 (d, J = 8.8 Hz, 2H), 4.80-4.69 (m, 1H), 3.80 (pd, J = 8.9, 7.6, 3.0 Hz, 2H), 3.40 (s, 1H), 2.62 (d, J = 6.2 Hz, 2H), 1.02 (d, J = 6.1 Hz, 3H). | 550.2 | 47.3 |

TABLE 2-continued

| Example | Structure | 1H-NMR | M/Z [M + H]+ | α4β7 EC$_{50}$ (nM) |
|---|---|---|---|---|
| 287 | 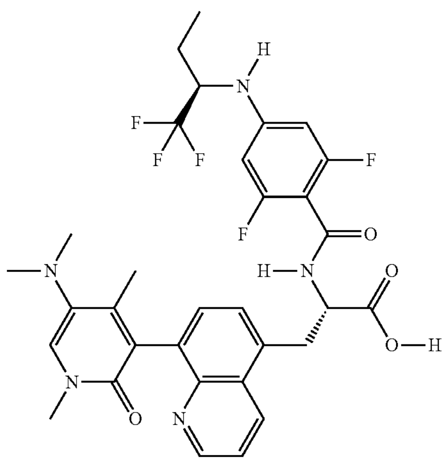 [SMILES: CC[C@@H](Nc1cc(F)c(C(=O)N[C@@H](Cc2ccc(-c3c(C)c(N(C)C)cn(C)c3=O)c3ncccc23)C(=O)O)c(F)c1)C(F)(F)F] | 1H NMR (400 MHz, DMSO-d6) δ 8.93 (dd, J = 11.1, 6.5 Hz, 2H), 8.80 (dd, J = 8.1, 4.4 Hz, 1H), 7.81 (ddd, J = 15.3, 8.5, 4.8 Hz, 1H), 7.72-7.63 (m, 2H), 7.59 (t, J = 6.5 Hz, 1H), 6.76 (dd, J = 9.4, 4.1 Hz, 1H), 6.48-6.33 (m, 2H), 4.72 (qd, J = 10.7, 4.5 Hz, 1H), 4.30 (d, J = 8.8 Hz, 1H), 3.70 (dd, J = 14.6, 4.8 Hz, 1H), 3.57-3.32 (m, 4H), 2.75-2.62 (m, 6H), 1.82 (d, J = 11.0 Hz, 3H), 1.75 (dd, J = 7.1, 3.5 Hz, 1H), 1.53 (ddd, J = 13.7, 10.4, 7.1 Hz, 1H), 0.92 (t, J = 7.3 Hz, 3H). | 646.3 | 5.7 |
| 288 | 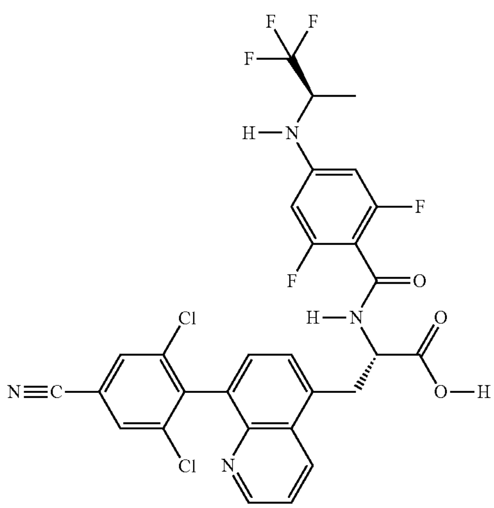 [SMILES: C[C@@H](Nc1cc(F)c(C(=O)N[C@@H](Cc2ccc(-c3c(Cl)cc(C#N)cc3Cl)c3ncccc23)C(=O)O)c(F)c1)C(F)(F)F] | 1H NMR (400 MHz, DMSO-d6) δ 8.83-8.79 (m, 2H), 8.65 (dd, J = 8.7, 1.7 Hz, 1H), 8.23-8.22 (m, 2H), 7.68-7.59 (m, 3H), 6.84 (d, J = 9.2 Hz, 1H), 6.41 (d, J = 11.4 Hz, 2H), 4.73 (ddd, J = 10.1, 8.0, 4.5 Hz, 1H), 4.51 (dq, J = 14.2, 6.9 Hz, 1H), 3.75 (dd, J = 14.6, 4.5 Hz, 1H), 3.44 (dd, J = 14.5, 10.2 Hz, 1H), 1.27 (d, J = 6.7 Hz, 3H). | 637.1 | 5.8 |
| 289 | 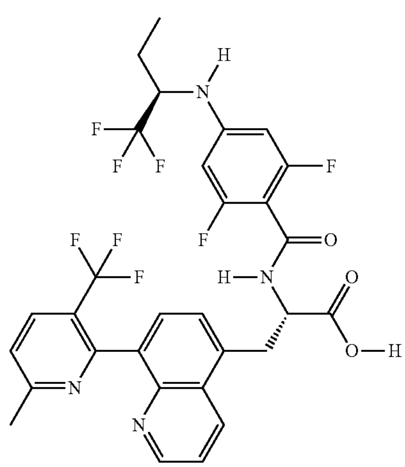 [SMILES: CC[C@@H](Nc1cc(F)c(C(=O)N[C@@H](Cc2ccc(-c3nc(C)ccc3C(F)(F)F)c3ncccc23)C(=O)O)c(F)c1)C(F)(F)F] | 1H NMR (400 MHz, DMSO-d6) δ 12.86 (s, 1H), 8.86-8.78 (m, 2H), 8.66 (dd, J = 8.7, 1.7 Hz, 1H), 8.20 (d, J = 8.2 Hz, 1H), 7.66-7.59 (m, 3H), 7.56 (d, J = 8.2 Hz, 1H), 6.78 (d, J = 9.4 Hz, 1H), 6.45 (d, J = 11.5 Hz, 2H), 4.69 (ddd, J = 9.8, 7.9, 4.5 Hz, 1H), 4.38-4.25 (m, 1H), 3.74 (dd, J = 14.3, 4.5 Hz, 1H), 3.44 (dd, J = 14.4, 9.9 Hz, 1H), 2.58 (s, 3H), 1.76 (ddt, J = 13.1, 10.5, 5.3 Hz, 1H), 1.52 (ddq, J = 14.4, 10.4, 7.3 Hz, 1H), 0.92 (t, J = 7.3 Hz, 3H). | 641.8 | 6.5 |

TABLE 2-continued

| Example | Structure | 1H-NMR | M/Z [M + H]+ | α4β7 EC$_{50}$ (nM) |
|---|---|---|---|---|
| 290 | 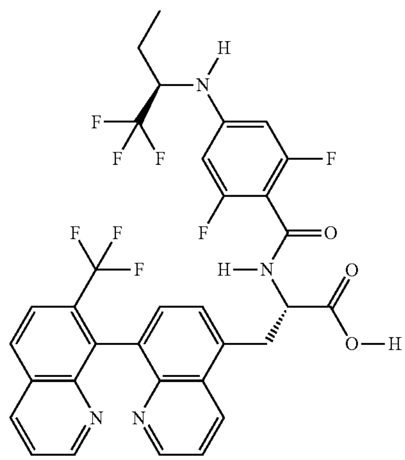 [SMILES: CC[C@@H](Nc1cc(F)c(C(=O)N[C@@H](Cc2ccc(-c3c(C(F)(F)F)ccc4cccnc34)c3ncccc23)C(=O)O)c(F)c1)C(F)(F)F] | 1H NMR (400 MHz, DMSO-d6) δ 8.87 (dd, J = 14.3, 7.8 Hz, 1H), 8.72 (ddd, J = 8.7, 4.1, 1.8 Hz, 1H), 8.68-8.58 (m, 2H), 8.55 (dt, J = 8.4, 1.8 Hz, 1H), 8.29 (d, J = 8.8 Hz, 1H), 8.01 (d, J = 8.8 Hz, 1H), 7.67-7.51 (m, 3H), 6.76 (dd, J = 9.5, 5.2 Hz, 1H), 6.53-6.38 (m, 2H), 4.75 (t, J = 11.1 Hz, 1H), 4.31 (s, 1H), 3.70 (d, J = 5.3 Hz, 1H), 1.77 (s, 1H), 1.53 (q, J = 13.4, 10.2 Hz, 1H), 1.02-0.83 (m, 3H). | 677.2 | 6.5 |
| 291 | 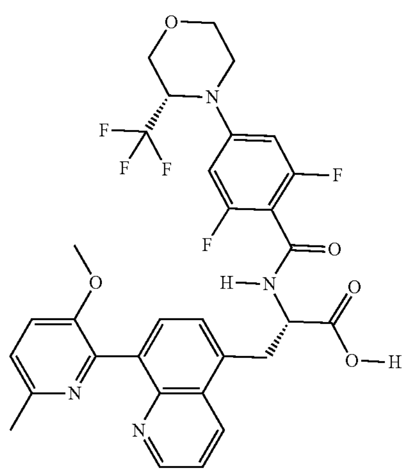 [SMILES: COc1ccc(C)nc1-c1ccc(C[C@H](NC(=O)c2c(F)cc(N3CCOC[C@H]3C(F)(F)F)cc2F)C(=O)O)c2cccnc12] | 1H NMR (400 MHz, DMSO-d6) δ 9.03 (d, J = 8.1 Hz, 1H), 8.89 (d, J = 4.1 Hz, 1H), 8.74 (d, J = 8.6 Hz, 1H), 8.15 (s, 1H), 7.85 (d, J = 27.1 Hz, 2H), 7.74-7.67 (m, 2H), 6.77 (d, J = 12.0 Hz, 2H), 4.91 (d, J = 9.4 Hz, 1H), 4.72 (m, 1H), 4.17 (d, J = 12.7 Hz, 1H), 3.95 (m, 1H), 3.76 (m, 4H), 3.60-3.38 (m, 4H), 3.24 (t, J = 12.6 Hz, 1H), 2.62 (s, 3H). | 631.2 | 6.9 |
| 292 | 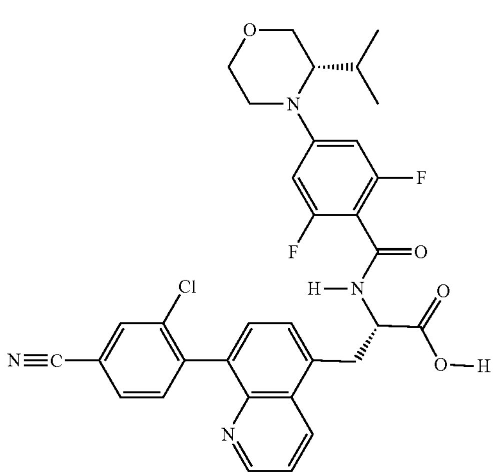 [SMILES: CC(C)[C@H]1COCCN1c1cc(F)c(C(=O)N[C@@H](Cc2ccc(-c3ccc(C#N)cc3Cl)c3ncccc23)C(=O)O)c(F)c1] | 1H NMR (400 MHz, DMSO-d6) δ 8.83 (dd, J = 4.2, 1.6 Hz, 1H), 8.76 (d, J = 8.0 Hz, 1H), 8.65 (dd, J = 8.7, 1.7 Hz, 1H), 8.15 (d, J = 1.7 Hz, 1H), 7.90 (dd, J = 7.9, 1.7 Hz, 1H), 7.69-7.58 (m, 3H), 7.57 (d, J = 7.9 Hz, 1H), 6.50 (d, J = 12.8 Hz, 2H), 4.69 (d, J = 8.0 Hz, 1H), 3.90 (d, J = 11.7 Hz, 1H), 3.84-3.64 (m, 2H), 3.48 (t, J = 11.7 Hz, 2H), 3.38 (dtd, J = 11.4, 5.8, 3.0 Hz, 2H), 3.13 (td, J = 12.7, 3.7 Hz, 1H), 2.39-2.23 (m, 1H), 0.94 (d, J = 6.6 Hz, 3H), 0.68 (d, J = 6.8 Hz, 3H). | 620.4 | 26.9 |

TABLE 2-continued

| Example | Structure | 1H-NMR | M/Z [M + H]+ | α4β7 EC$_{50}$ (nM) |
|---|---|---|---|---|
| 293 | 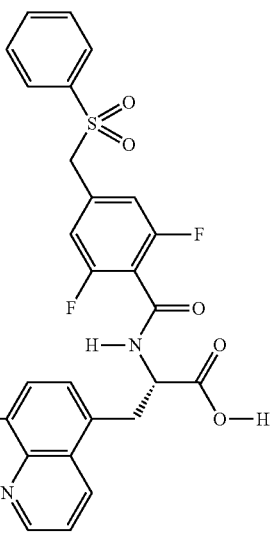 | 1H NMR (400 MHz, DMSO-d6) δ 9.29 (d, J = 8.2 Hz, 1H), 8.81 (dd, J = 4.2, 1.6 Hz, 1H), 8.64 (dd, J = 8.7, 1.7 Hz, 1H), 8.22 (q, J = 1.6 Hz, 2H), 7.75 (dtd, J = 9.1, 3.1, 1.6 Hz, 3H), 7.68-7.56 (m, 5H), 6.91-6.81 (m, 2H), 4.84-4.73 (m, 3H), 3.77 (dd, J = 14.5, 4.4 Hz, 1H), 3.41 (dd, J = 14.6, 10.5 Hz, 1H). | 680.2 | 6.9 |
| 294 | 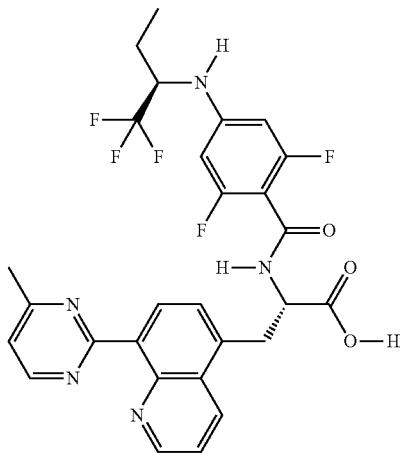 [SMILES: CC[C@@H](Nc1cc(F)c(C(=O)N[C@@H](Cc2ccc(-c3nccc(C)n3)c3ncccc23)C(=O)O)c(F)c1)C(F)(F)F] | 1H NMR (400 MHz, DMSO-d6) δ 9.39 (d, J = 4.9 Hz, 1H), 9.35 (d, J = 8.8 Hz, 1H), 8.95 (d, J = 5.2 Hz, 1H), 8.90 (s, 1H), 8.79 (d, J = 8.3 Hz, 1H), 8.14 (dd, J = 8.6, 5.0 Hz, 1H), 7.96 (d, J = 7.8 Hz, 1H), 7.60 (d, J = 5.2 Hz, 1H), 6.77 (d, J = 9.4 Hz, 1H), 6.41 (d, J = 11.6 Hz, 2H), 4.78 (ddd, J = 10.3, 8.3, 4.5 Hz, 1H), 4.29 (d, J = 8.9 Hz, 1H), 3.89 (dd, J = 14.4, 4.5 Hz, 1H), 3.55 (dd, J = 14.4, 10.4 Hz, 1H), 2.71 (s, 3H), 1.77 (ddd, J = 13.7, 7.3, 3.3 Hz, 1H), 1.52 (ddd, J = 13.8, 10.4, 7.1 Hz, 1H), 0.91 (t, J = 7.3 Hz, 3H). | 575.3 | 7.4 |
| 295 | 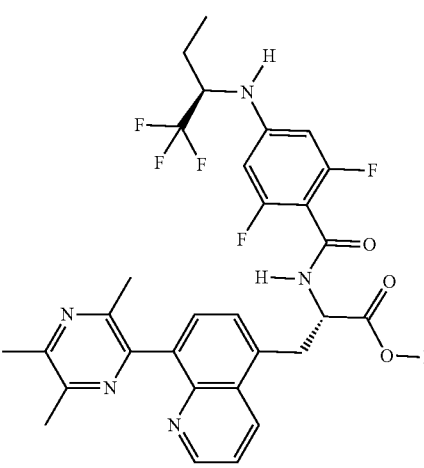 | 1H NMR (400 MHz, DMSO-d6) δ 8.84 (dd, J = 4.2, 1.5 Hz, 1H), 8.78 (d, J = 8.1 Hz, 1H), 8.67 (dd, J = 8.7, 1.7 Hz, 1H), 7.65 (d, J = 9.3 Hz, 3H), 6.76 (d, J = 9.4 Hz, 1H), 6.44 (d, J = 11.6 Hz, 2H), 4.70 (td, J = 9.2, 8.1, 4.5 Hz, 1H), 4.31 (d, J = 3.2 Hz, 1H), 3.74 (dd, J = 14.3, 4.6 Hz, 1H), 3.43 (dd, J = 14.4, 10.0 Hz, 1H), 2.54 (s, 3H), 2.48 (s, 3H), 2.07 (s, 3H), 1.77 (ddd, J = 14.0, 7.4, 3.4 Hz, 1H), 1.52 (ddt, J = 17.6, 14.2, 7.3 Hz, 1H), 0.92 (t, J = 7.3 Hz, 3H). | 602.2 | 7.4 |

TABLE 2-continued

| Example | Structure | 1H-NMR | M/Z [M + H]+ | α4β7 EC$_{50}$ (nM) |
| --- | --- | --- | --- | --- |
| 296 | 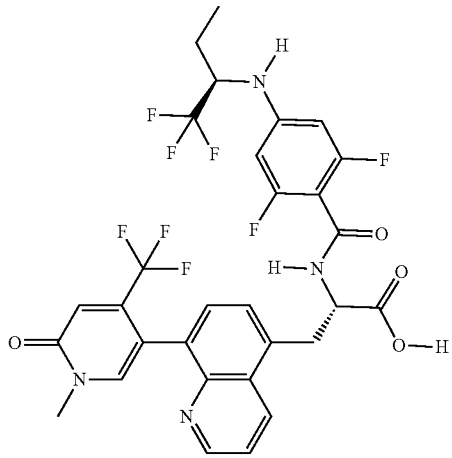 [SMILES: CC[C@@H](Nc1cc(F)c(C(=O)N[C@@H](Cc2ccc(-c3cn(C)c(=O)cc3C(F)(F)F)c3ncccc23)C(=O)O)c(F)c1)C(F)(F)F] | 1H NMR (400 MHz, DMSO-d6) δ 8.89 (d, J = 4.1 Hz, 1H), 8.79 (t, J = 10.0 Hz, 1H), 8.64 (d, J = 9.2 Hz, 1H), 7.87 (d, J = 10.9 Hz, 1H), 7.66-7.57 (m, 2H), 6.89 (d, J = 10.7 Hz, 1H), 6.76 (d, J = 9.2 Hz, 1H), 6.44 (d, J = 11.9 Hz, 2H), 4.66 (s, 1H), 4.30 (d, J = 8.8 Hz, 1H), 3.75 (d, J = 14.2 Hz, 1H), 3.51 (s, 3H), 3.45-3.30 (m, 1H), 1.76 (ddd, J = 13.8, 7.3, 3.3 Hz, 1H), 1.58-1.45 (m, 1H), 0.92 (t, J = 7.3 Hz, 3H). | 657.2 | 7.7 |
| 297 | 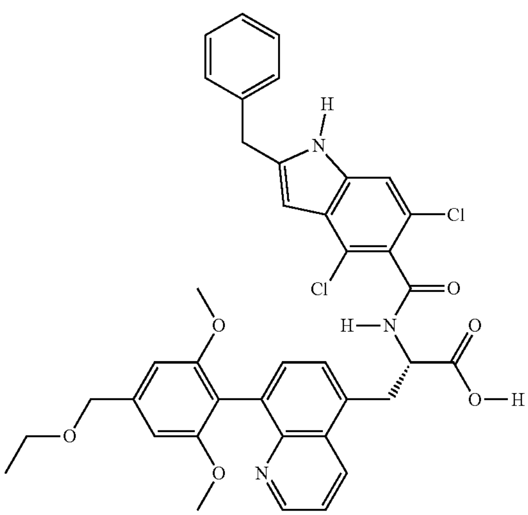 [SMILES: CCOCc1cc(OC)c(-c2ccc(C[C@H](NC(=O)c3c(Cl)cc4[nH]c(Cc5ccccc5)cc4c3Cl)C(=O)O)c3cccnc23)c(OC)c1] | 1H NMR (400 MHz, DMSO-d6) δ 11.52 (d, J = 2.2 Hz, 1H), 9.03 (d, J = 8.6 Hz, 1H), 8.90 (d, J = 4.3 Hz, 1H), 7.95-7.71 (m, 2H), 7.64 (s, 1H), 7.36-7.17 (m, 6H), 6.78 (d, J = 6.0 Hz, 2H), 6.17 (dd, J = 2.2, 1.0 Hz, 1H), 4.89 (ddd, J = 10.7, 8.5, 4.0 Hz, 1H), 4.55 (s, 2H), 4.07 (s, 2H), 3.79 (dd, J = 14.5, 4.0 Hz, 1H), 3.61 (s, 3H), 3.59 (q, J = 7.0 Hz, 2H), 3.57 (s, 3H), 3.51-3.37 (m, 1H), 1.22 (t, J = 7.0 Hz, 3H). | 712.5 | 7.9 |
| 298 | 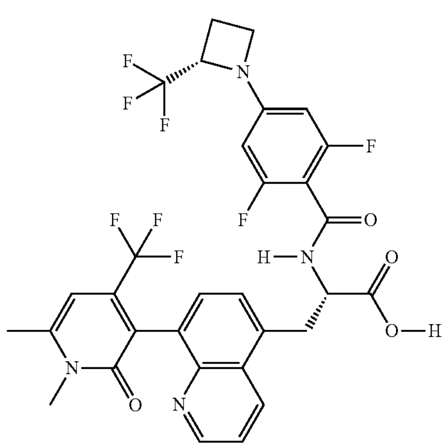 [SMILES: Cc1cc(C(F)(F)F)c(-c2ccc(C[C@H](NC(=O)c3c(F)cc(N4CC[C@H]4C(F)(F)F)cc3F)C(=O)O)c3cccnc23)c(=O)n1C] | 1H NMR (400 MHz, DMSO-d6) δ 8.93 (dd, J = 7.9, 4.5 Hz, 1H), 8.83 (d, J = 4.2 Hz, 1H), 8.71-8.64 (m, 1H), 7.68-7.61 (m, 1H), 7.58 (t, J = 6.8 Hz, 1H), 7.46 (dd, J = 7.4, 3.7 Hz, 1H), 6.55 (s, 1H), 6.26 (dd, J = 9.9, 5.2 Hz, 2H), 4.99-4.87 (m, 1H), 4.75-4.65 (m, 1H), 4.12-4.03 (m, 1H), 3.80-3.65 (m, 2H), 3.49 (d, J = 2.3 Hz, 3H), 2.69-2.56 (m, 1H), 2.53 (s, 3H), 2.44-2.34 (m, 1H). | 669.3 | 7.9 |

TABLE 2-continued

| Example | Structure | 1H-NMR | M/Z [M + H]+ | α4β7 EC$_{50}$ (nM) |
|---|---|---|---|---|
| 299 | 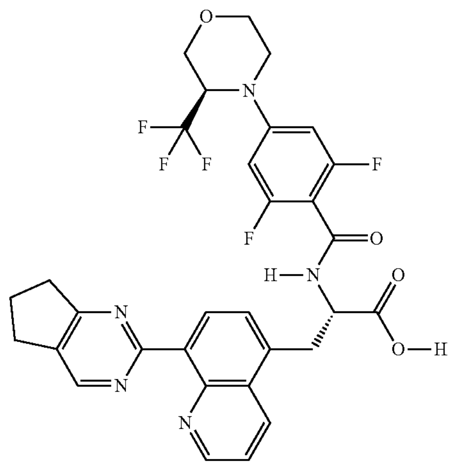 [SMILES: O=C(N[C@@H](Cc1ccc(-c2ncc3c(n2)CCC3)c2ncccc12)C(=O)O)c1c(F)cc(N2CCOC[C@@H]2C(F)(F)F)cc1F] | 1H NMR (400 MHz, DMSO-d6) δ 13.11 (s, 1H), 9.40 (t, J = 8.4 Hz, 2H), 9.03-8.92 (m, 2H), 8.90 (s, 1H), 8.17 (dd, J = 8.7, 5.1 Hz, 1H), 7.98 (d, J = 7.8 Hz, 1H), 6.72 (d, J = 11.8 Hz, 2H), 4.93-4.77 (m, 2H), 4.15 (d, J = 12.7 Hz, 1H), 3.93 (td, J = 15.3, 13.6, 4.2 Hz, 2H), 3.74-3.68 (m, 1H), 3.61-3.48 (m, 2H), 3.40 (d, J = 12.7 Hz, 1H), 3.28-3.05 (m, 5H), 2.20 (p, J = 7.7 Hz, 2H). | 628.3 | 8.2 |
| 300 | 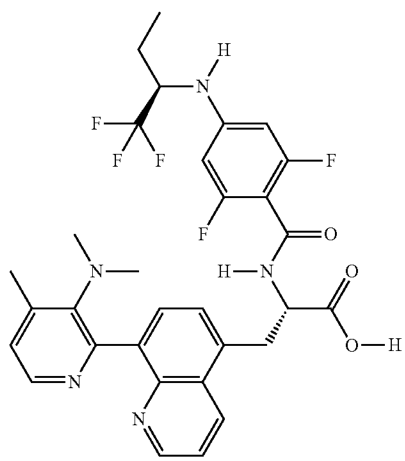 [SMILES: CC[C@@H](Nc1cc(F)c(C(=O)N[C@@H](Cc2ccc(-c3nccc(C)c3N(C)C)c3ncccc23)C(=O)O)c(F)c1)C(F)(F)F] | 1H NMR (400 MHz, DMSO-d6) δ 8.93 (dd, J = 4.2, 1.6 Hz, 1H), 8.83 (d, J = 8.3 Hz, 1H), 8.76 (dd, J = 8.7, 1.7 Hz, 1H), 8.54 (d, J = 5.8 Hz, 1H), 7.93 (d, J = 5.8 Hz, 1H), 7.84 (d, J = 7.3 Hz, 1H), 7.76 (dd, J = 8.3, 4.3 Hz, 2H), 6.78 (d, J = 9.4 Hz, 1H), 6.44 (d, J = 11.5 Hz, 2H), 4.73 (td, J = 9.2, 8.3, 4.2 Hz, 1H), 4.31 (d, J = 9.7 Hz, 1H), 3.83 (dd, J = 14.2, 4.3 Hz, 1H), 3.45 (dd, J = 14.2, 10.4 Hz, 1H), 2.60 (s, 3H), 2.29 (s, 6H), 1.78 (ddd, J = 13.7, 7.3, 3.3 Hz, 1H), 1.53 (ddd, J = 13.8, 10.4, 7.2 Hz, 1H), 0.92 (t, J = 7.3 Hz, 3H). | 616.1 | 8.4 |
| 301 | 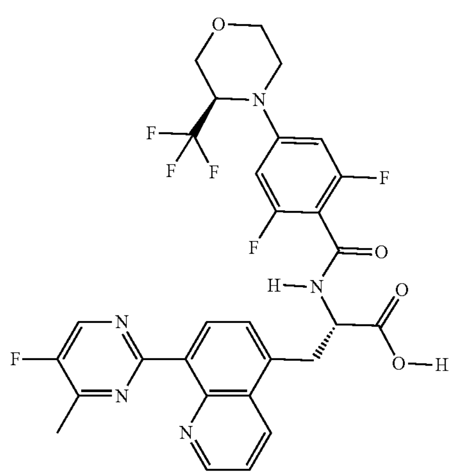 [SMILES: Cc1nc(-c2ccc(C[C@H](NC(=O)c3c(F)cc(N4CCOC[C@@H]4C(F)(F)F)cc3F)C(=O)O)c3cccnc23)ncc1F] | 1H NMR (400 MHz, DMSO-d6) δ 9.24-9.17 (m, 1H), 9.18-9.09 (m, 1H), 8.95 (s, 1H), 8.94 (s, 1H), 8.51-8.40 (m, 1H), 8.02-7.92 (m, 1H), 7.87-7.80 (m, 1H), 6.74 (d, J = 11.7 Hz, 2H), 4.95-4.85 (m, 1H), 4.82-4.72 (m, 1H), 4.15 (d, J = 12.6 Hz, 1H), 3.95 (dd, J = 11.6, 3.6 Hz, 1H), 3.85 (dd, J = 14.4, 4.2 Hz, 1H), 3.72 (d, J = 12.6 Hz, 1H), 3.59-3.46 (m, 2H), 3.44-3.38 (m, 1H), 3.27-3.15 (m, 1H), 2.65 (s, 3H). | 620.2 | 9.4 |

TABLE 2-continued

| Example | Structure | 1H-NMR | M/Z [M + H]+ | α4β7 EC$_{50}$ (nM) |
|---|---|---|---|---|
| 302 | 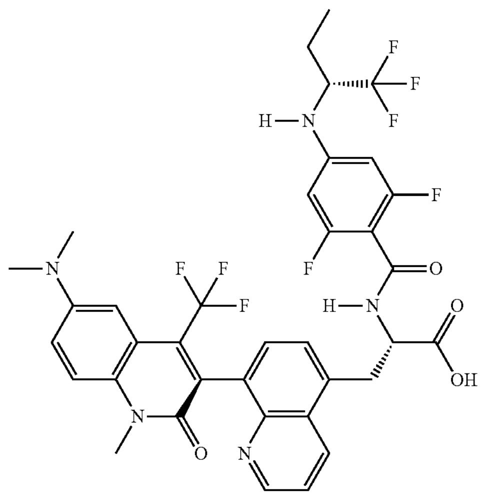 | 1H NMR (400 MHz, DMSO-d6) δ 8.82 (d, J = 7.7 Hz, 1H), 8.80-8.75 (m, 1H), 8.61 (d, J = 8.6 Hz, 1H), 7.60 (td, J = 8.7, 7.7, 4.9 Hz, 3H), 7.49 (d, J = 7.3 Hz, 1H), 7.37 (d, J = 10.1 Hz, 1H), 7.03 (s, 1H), 6.77 (d, J = 9.3 Hz, 1H), 6.46 (d, J = 11.6 Hz, 2H), 4.67 (d, J = 11.0 Hz, 1H), 4.31 (s, 1H), 3.67 (s, 4H), 2.97 (s, 6H), 1.53 (s, 1H), 0.93 (t, J = 7.3 Hz, 3H). | 750.9 | 9.4 |
| 303 | 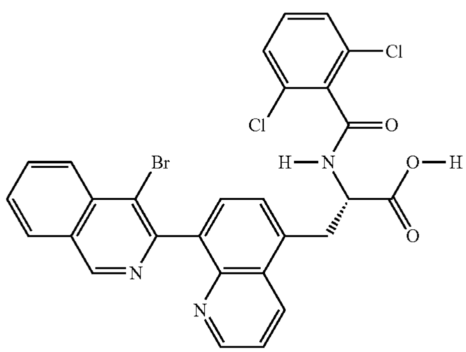 [SMILES: O=C(N[C@@H](Cc1ccc(-c2ncc3ccccc3c2Br)c2ncccc12)C(=O)O)c1c(Cl)cccc1Cl] | 1H NMR (400 MHz, DMSO-d6) δ 9.41 (d, J = 0.8 Hz, 1H), 9.33-9.23 (m, 1H), 8.83-8.68 (m, 2H), 8.34-8.18 (m, 2H), 8.02 (ddd, J = 8.4, 7.0, 1.3 Hz, 1H), 7.86 (ddd, J = 8.1, 6.9, 1.1 Hz, 1H), 7.81-7.58 (m, 3H), 7.47-7.33 (m, 3H), 4.92-4.81 (m, 1H), 3.79 (dd, J = 14.5, 4.3 Hz, 1H), 3.45 (dd, J = 14.5, 10.4 Hz, 1H). | 594.1 | 9.4 |
| 304 | 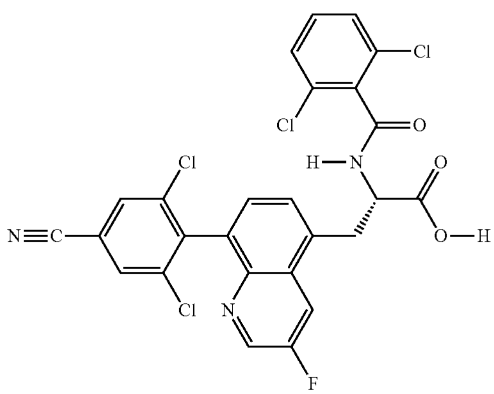 [SMILES: N#Cc1cc(Cl)c(-c2ccc(C[C@H](NC(=O)c3c(Cl)cccc3Cl)C(=O)O)c3cc(F)cnc23)c(Cl)c1] | 1H NMR (400 MHz, DMSO-d6) δ 9.27 (d, J = 8.6 Hz, 1H), 8.89 (d, J = 2.8 Hz, 1H), 8.46 (dd, J = 10.5, 2.8 Hz, 1H), 8.25-8.18 (m, 1H), 7.78 (d, J = 7.4 Hz, 1H), 7.62 (d, J = 7.3 Hz, 1H), 7.47-7.28 (m, 2H), 4.85 (s, 1H), 3.73-3.65 (m, 1H), 3.41 (d, J = 11.0 Hz, 1H). | 576.0 | 9.6 |

TABLE 2-continued

| Example | Structure | 1H-NMR | M/Z [M + H]+ | α4β7 EC$_{50}$ (nM) |
|---|---|---|---|---|
| 305 | 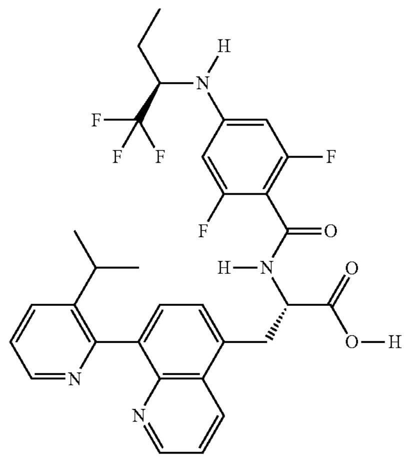 [SMILES: CC[C@@H](Nc1cc(F)c(C(=O)N[C@@H](Cc2ccc(-c3ncccc3C(C)C)c3ncccc23)C(=O)O)c(F)c1)C(F)(F)F] | 1H NMR (400 MHz, DMSO-d6) δ 13.01 (s, 1H), 8.88 (dd, J = 4.2, 1.5 Hz, 1H), 8.85-8.70 (m, 3H), 8.61 (s, 1H), 8.01 (s, 1H), 7.90 (d, J = 7.3 Hz, 1H), 7.72 (dd, J = 8.3, 4.1 Hz, 2H), 6.77 (d, J = 9.4 Hz, 1H), 6.43 (d, J = 11.7 Hz, 2H), 4.76 (td, J = 9.4, 8.4, 4.2 Hz, 1H), 4.30 (s, 2H), 3.82 (dd, J = 14.3, 4.3 Hz, 1H), 3.45 (dd, J = 14.4, 10.3 Hz, 1H), 2.62-2.56 (m, 1H), 1.77 (ddd, J = 14.0, 7.4, 3.2 Hz, 1H), 1.52 (ddd, J = 13.6, 10.3, 7.0 Hz, 1H), 1.08 (d, J = 6.8 Hz, 6H), 0.92 (t, J = 7.3 Hz, 3H). | 601.1 | 10.2 |
| 306 | 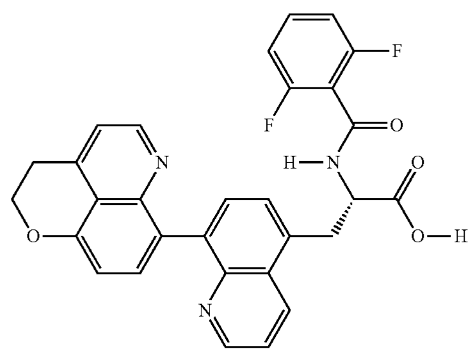 [SMILES: O=C(N[C@@H](Cc1ccc(-c2ccc3c4c(ccnc24)CCO3)c2ncccc12)C(=O)O)c1c(F)cccc1F] | 1H NMR (400 MHz, DMSO-d6) δ 9.35 (d, J = 8.1 Hz, 1H), 8.88 (s, 1H), 8.77 (dd, J = 4.4, 1.5 Hz, 1H), 8.68 (d, J = 4.9 Hz, 1H), 7.89-7.68 (m, 3H), 7.51 (tt, J = 8.4, 6.5 Hz, 1H), 7.29 (d, J = 8.0 Hz, 1H), 7.15 (dd, J = 8.4, 7.6 Hz, 2H), 4.83 (td, J = 9.3, 4.3 Hz, 1H), 4.58 (t, J = 5.9 Hz, 2H), 3.85 (dd, J = 14.5, 4.4 Hz, 1H), 3.57-3.36 (m, 3H). | 525.9 | 11.2 |
| 307 | 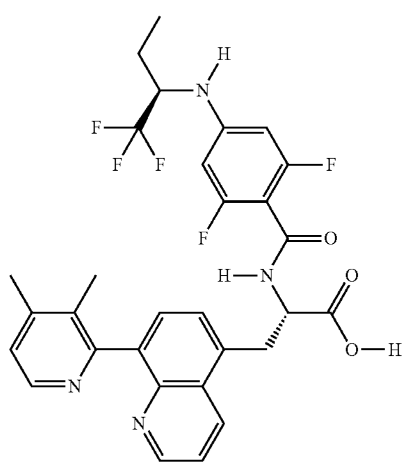 [SMILES: CC[C@@H](Nc1cc(F)c(C(=O)N[C@@H](Cc2ccc(-c3nccc(C)c3C)c3ncccc23)C(=O)O)c(F)c1)C(F)(F)F] | 1H NMR (400 MHz, DMSO-d6) δ 13.05 (s, 1H), 8.90 (dd, J = 4.2, 1.6 Hz, 1H), 8.86 (d, J = 8.2 Hz, 1H), 8.80-8.70 (m, 2H), 7.98 (d, J = 6.0 Hz, 1H), 7.92 (d, J = 7.3 Hz, 1H), 7.79-7.71 (m, 2H), 6.80 (d, J = 9.4 Hz, 1H), 6.44 (d, J = 11.5 Hz, 2H), 4.79-4.69 (m, 1H), 4.39-4.23 (m, 1H), 3.83 (dd, J = 14.2, 4.3 Hz, 1H), 3.45 (dd, J = 14.3, 10.3 Hz, 1H), 2.63 (s, 3H), 2.04 (s, 3H), 1.85-1.70 (m, 1H), 1.61-1.44 (m, 1H), 0.92 (t, J = 7.3 Hz, 3H). | 587.5 | 11.4 |

TABLE 2-continued

| Example | Structure | 1H-NMR | M/Z [M + H]+ | α4β7 EC$_{50}$ (nM) |
|---|---|---|---|---|
| 308 | 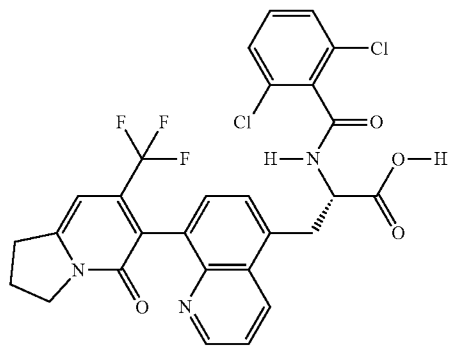 [SMILES: O=C(N[C@@H](Cc1ccc(-c2c(C(F)(F)F)cc3n(c2=O)CCC3)c2ncccc12)C(=O)O)c1c(Cl)cccc1Cl] | 1H NMR (400 MHz, DMSO-d6) δ 9.29 (dd, J = 25.4, 8.3 Hz, 1H), 8.87 (p, J = 4.1, 1.9 Hz, 1H), 8.72 (d, J = 8.6 Hz, 1H), 7.74-7.61 (m, 2H), 7.52-7.33 (m, 4H), 6.59 (dt, J = 4.7, 1.2 Hz, 1H), 4.83 (dddd, J = 36.2, 10.6, 8.3, 3.9 Hz, 1H), 4.10-3.98 (m, 2H), 3.81-3.68 (m, 1H), 3.50-3.33 (m, 1H), 3.33-3.15 (m, 2H), 2.27-2.13 (m, 2H). | 589.8 | 11.9 |
| 309 | 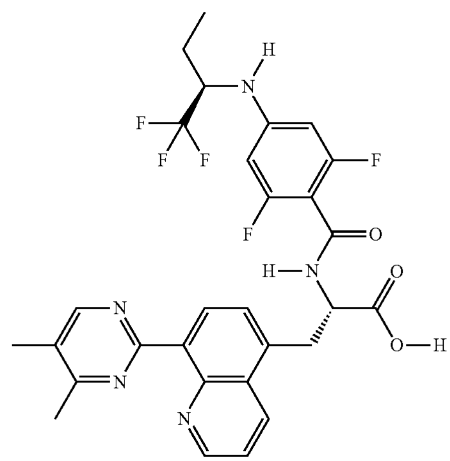 [SMILES: CC[C@@H](Nc1cc(F)c(C(=O)N[C@@H](Cc2ccc(-c3ncc(C)c(C)n3)c3ncccc23)C(=O)O)c(F)c1)C(F)(F)F] | 1H NMR (400 MHz, DMSO-d6) δ 9.51-9.46 (m, 1H), 9.44 (d, J = 8.8 Hz, 1H), 9.05 (d, J = 7.7 Hz, 1H), 8.82 (s, 1H), 8.79 (d, J = 8.4 Hz, 1H), 8.21 (dd, J = 8.7, 5.2 Hz, 1H), 8.00 (d, J = 7.8 Hz, 1H), 6.78 (d, J = 9.4 Hz, 1H), 6.41 (d, J = 11.6 Hz, 2H), 4.80 (ddd, J = 10.3, 8.3, 4.5 Hz, 1H), 4.28 (d, J = 8.8 Hz, 1H), 3.90 (dd, J = 14.3, 4.6 Hz, 1H), 3.56 (dd, J = 14.4, 10.3 Hz, 1H), 2.70 (s, 3H), 2.41 (s, 3H), 1.76 (dtd, J = 14.7, 7.4, 3.2 Hz, 1H), 1.52 (dtd, J = 13.8, 7.2, 3.1 Hz, 1H), 0.91 (t, J = 7.3 Hz, 3H). | 589.6 | 11.9 |
| 310 | 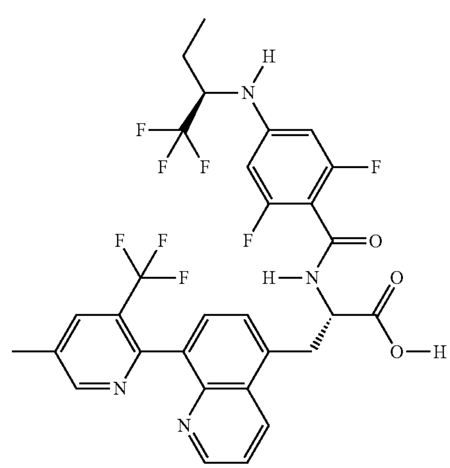 [SMILES: CC[C@@H](Nc1cc(F)c(C(=O)N[C@@H](Cc2ccc(-c3ncc(C)cc3C(F)(F)F)c3ncccc23)C(=O)O)c(F)c1)C(F)(F)F] | 1H NMR (400 MHz, DMSO-d6) δ 12.86 (s, 1H), 8.81 (d, J = 8.0 Hz, 1H), 8.78 (dd, J = 4.2, 1.5 Hz, 1H), 8.73 (d, J = 1.9 Hz, 1H), 8.64 (dt, J = 8.7, 1.7 Hz, 1H), 8.14 (d, J = 2.0 Hz, 1H), 7.67-7.55 (m, 3H), 6.77 (d, J = 9.4 Hz, 1H), 6.44 (d, J = 11.6 Hz, 2H), 4.74-4.65 (m, 1H), 4.31 (d, J = 9.7 Hz, 1H), 3.73 (dd, J = 14.5, 4.5 Hz, 1H), 3.43 (dd, J = 14.5, 10.0 Hz, 1H), 2.50 (s, 3H), 1.77 (ddd, J = 13.9, 7.2, 3.3 Hz, 1H), 1.52 (ddd, J = 13.7, 10.4, 7.1 Hz, 1H), 0.92 (t, J = 7.3 Hz, 3H). | 641.8 | 12.3 |

TABLE 2-continued

| Example | Structure | 1H-NMR | M/Z [M + H]+ | α4β7 EC50 (nM) |
|---|---|---|---|---|
| 311 | 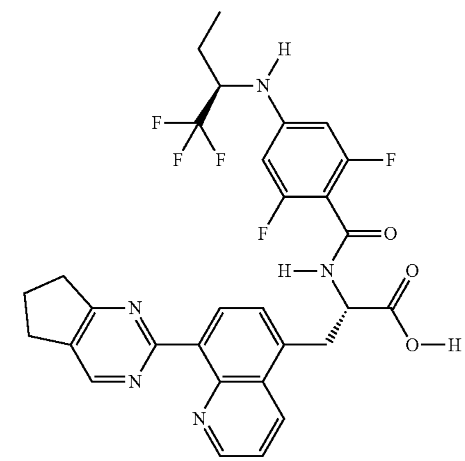 [SMILES: CC[C@@H](Nc1cc(F)c(C(=O)N[C@@H](Cc2ccc(-c3ncc4c(n3)CCC4)c3ncccc23)C(=O)O)c(F)c1)C(F)(F)F] | 1H NMR (400 MHz, DMSO-d6) δ 13.03 (s, 1H), 9.26 (d, J = 28.9 Hz, 2H), 8.86 (s, 1H), 8.79 (d, J = 8.2 Hz, 1H), 8.73 (s, 1H), 8.05 (s, 1H), 7.89 (d, J = 7.6 Hz, 1H), 6.77 (d, J = 9.4 Hz, 1H), 6.42 (d, J = 11.7 Hz, 2H), 4.75 (d, J = 12.0 Hz, 1H), 4.29 (d, J = 9.4 Hz, 1H), 3.86 (d, J = 14.2 Hz, 1H), 3.57-3.48 (m, 1H), 3.09 (q, J = 7.6 Hz, 4H), 2.19 (p, J = 7.6 Hz, 2H), 1.76 (ddd, J = 10.6, 7.4, 3.6 Hz, 1H), 1.52 (ddd, J = 13.7, 10.3, 7.1 Hz, 1H), 0.91 (t, J = 7.3 Hz, 3H). | 600.2 | 12.3 |
| 312 | 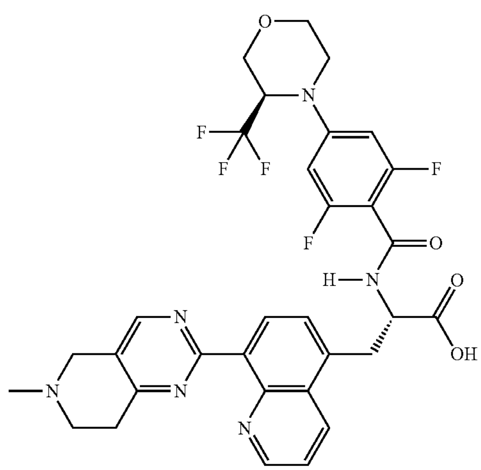 [SMILES: CN1CCc2nc(-c3ccc(C[C@H](NC(=O)c4c(F)cc(N5CCOC[C@@H]5C(F)(F)F)cc4F)C(=O)O)c4cccnc34)ncc2C1] | 1H NMR (400 MHz, DMSO-d6) δ 9.19 (d, 1H), 9.12 (d, J = 7.7 Hz, 1H), 8.96 (d, J = 8.3 Hz, 1H), 8.92 (s, 1H), 8.47 (s, 1H), 7.97 (dd, J = 8.5, 4.7 Hz, 1H), 7.85 (d, J = 7.6 Hz, 1H), 6.74 (d, J = 11.9 Hz, 2H), 4.95-4.84 (m, 1H), 4.83-4.73 (m, 1H), 4.54 (s, 1H), 4.16 (d, J = 12.7 Hz, 1H), 4.00-3.67 (m, 4H), 3.60-3.46 (m, 4H), 3.40 (d, J = 12.4 Hz, 1H), 3.33 (t, 2H), 3.28-3.18 (m, 1H), 3.05 (s, 3H). | 657.2 | 12.5 |
| 313 | 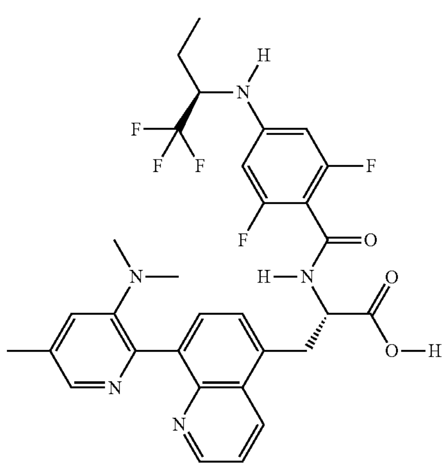 [SMILES: CC[C@@H](Nc1cc(F)c(C(=O)N[C@@H](Cc2ccc(-c3ncc(C)cc3N(C)C)c3ncccc23)C(=O)O)c(F)c1)C(F)(F)F] | 1H NMR (400 MHz, DMSO-d6) δ 8.95 (dd, J = 4.2, 1.4 Hz, 1H), 8.82 (d, J = 8.3 Hz, 1H), 8.75 (dd, J = 8.8, 1.6 Hz, 1H), 8.22 (s, 1H), 7.98 (s, 1H), 7.90 (d, J = 7.4 Hz, 1H), 7.81-7.68 (m, 2H), 6.78 (d, J = 9.4 Hz, 1H), 6.43 (d, J = 11.6 Hz, 2H), 4.72 (ddd, J = 10.1, 8.1, 4.4 Hz, 1H), 4.30 (d, J = 8.4 Hz, 2H), 3.80 (dd, J = 14.2, 4.4 Hz, 1H), 3.44 (dd, J = 14.2, 10.3 Hz, 1H), 1.85-1.69 (m, 1H), 1.62-1.43 (m, 1H), 0.92 (t, J = 7.3 Hz, 3H). | 616.3 | 13.3 |

TABLE 2-continued

| Example | Structure | 1H-NMR | M/Z [M + H]+ | α4β7 EC50 (nM) |
|---|---|---|---|---|
| 314 | 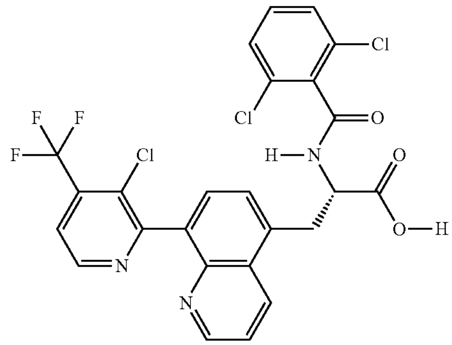 [SMILES: O=C(N[C@@H](Cc1ccc(-c2nccc(C(F)(F)F)c2Cl)c2ncccc12)C(=O)O)c1c(Cl)cccc1Cl] | 1H NMR (400 MHz, DMSO-d6) δ 9.29 (d, J = 8.4 Hz, 1H), 8.90 (d, J = 5.0, 0.7 Hz, 1H), 8.86 (dd, J = 4.2, 1.6 Hz, 1H), 8.70 (dd, J = 8.7, 1.7 Hz, 1H), 7.97 (d, J = 5.1 Hz, 1H), 7.76-7.64 (m, 3H), 7.46-7.35 (m, 3H), 4.92-4.83 (m, 1H), 3.79 (dd, J = 14.5, 4.2 Hz, 1H), 3.44 (dd, J = 14.6, 10.6 Hz, 1H). | 569.4 | 13.4 |
| 315 | 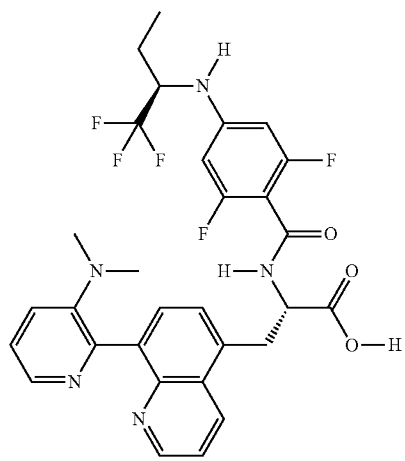 [SMILES: CC[C@@H](Nc1cc(F)c(C(=O)N[C@@H](Cc2ccc(-c3ncccc3N(C)C)c3ncccc23)C(=O)O)c(F)c1)C(F)(F)F] | 1H NMR (400 MHz, DMSO-d6) δ 8.96 (d, J = 4.2 Hz, 1H), 8.82 (d, J = 8.2 Hz, 1H), 8.76 (d, J = 8.6 Hz, 1H), 8.31 (d, J = 5.3 Hz, 1H), 8.10 (s, 1H), 7.92 (d, J = 7.7 Hz, 1H), 7.81-7.67 (m, 2H), 6.78 (d, J = 9.4 Hz, 1H), 6.44 (d, J = 11.6 Hz, 2H), 4.80-4.67 (m, 1H), 4.30 (s, 1H), 3.81 (dd, J = 14.1, 4.4 Hz, 1H), 3.45 (dd, J = 14.2, 10.3 Hz, 1H), 1.78 (ddd, J = 13.7, 7.3, 3.3 Hz, 1H), 1.54 (dt, J = 10.2, 6.8 Hz, 1H), 0.92 (t, J = 7.3 Hz, 3H). | 602.3 | 13.6 |
| 316 | 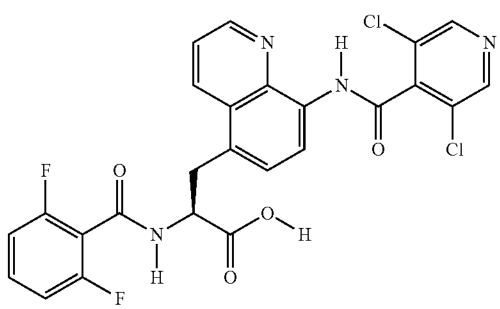 [SMILES: O=C(N[C@@H](Cc1ccc(NC(=O)c2c(Cl)cncc2Cl)c2ncccc12)C(=O)O)c1c(F)cccc1F] | 1H NMR (400 MHz, DMSO-d6) δ 11.26 (s, 1H), 9.23 (d, J = 8.1 Hz, 1H), 8.93 (dd, J = 4.2, 1.5 Hz, 1H), 8.73 (s, 1H), 8.67-8.54 (m, 2H), 7.71 (dd, J = 8.6, 4.2 Hz, 1H), 7.57-7.38 (m, 2H), 7.12 (dd, J = 8.5, 7.6 Hz, 2H), 4.68 (td, J = 9.0, 4.6 Hz, 1H), 3.66 (dd, J = 14.3, 4.6 Hz, 1H), 3.34 (dd, J = 14.4, 9.8 Hz, 1H). | 545.1 | 13.7 |
| 317 | 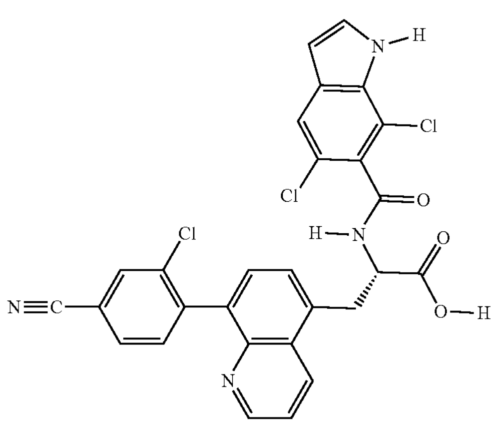 [SMILES: N#Cc1ccc(-c2ccc(C[C@H](NC(=O)c3c(Cl)cc4cc[nH]c4c3Cl)C(=O)O)c3cccnc23)c(Cl)c1] | 1H NMR (400 MHz, DMSO-d6) δ 11.67 (s, 1H), 9.11 (d, J = 8.4 Hz, 1H), 8.84 (dd, J = 4.2, 1.6 Hz, 1H), 8.67 (dd, J = 8.7, 1.7 Hz, 1H), 8.17 (d, J = 1.6 Hz, 1H), 7.92 (d, J = 7.9 Hz, 1H), 7.80-7.39 (m, 5H), 6.50 (dd, J = 3.1, 1.9 Hz, 1H), 4.87 (s, 1H), 3.76 (dd, J = 14.4, 4.1 Hz, 1H), 3.41 (dd, J = 14.5, 10.7 Hz, 1H). | 565.0 | 13.8 |

TABLE 2-continued

| Example | Structure | 1H-NMR | M/Z [M + H]+ | α4β7 EC$_{50}$ (nM) |
|---|---|---|---|---|
| 318 | 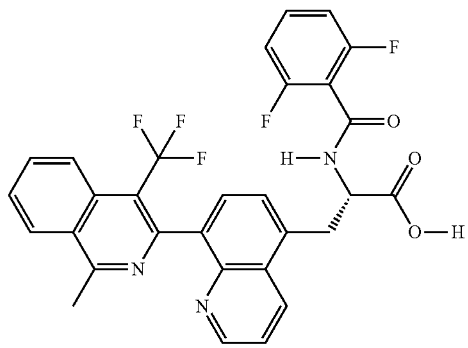 [SMILES: Cc1nc(-c2ccc(C[C@H](NC(=O)c3c(F)cccc3F)C(=O)O)c3cccnc23)c(C(F)(F)F)c2ccccc12] | 1H NMR (400 MHz, DMSO-d6) δ 9.42-9.22 (m, 1H), 8.78 (dt, J = 3.8, 1.8 Hz, 1H), 8.68 (t, J = 8.2 Hz, 1H), 8.48 (d, J = 8.4 Hz, 1H), 8.20 (d, J = 8.6 Hz, 1H), 8.05 (ddd, J = 8.5, 6.9, 1.3 Hz, 1H), 7.91 (t, J = 7.7 Hz, 1H), 7.79-7.58 (m, 3H), 7.56-7.45 (m, 1H), 7.14 (q, J = 7.9 Hz, 2H), 4.91-4.66 (m, 1H), 3.78 (ddd, J = 28.6, 14.5, 4.7 Hz, 1H), 3.47 (ddd, J = 24.2, 14.5, 9.8 Hz, 1H), 2.99 (d, J = 2.0 Hz, 3H). | 566.2 | 14.3 |
| 319 | 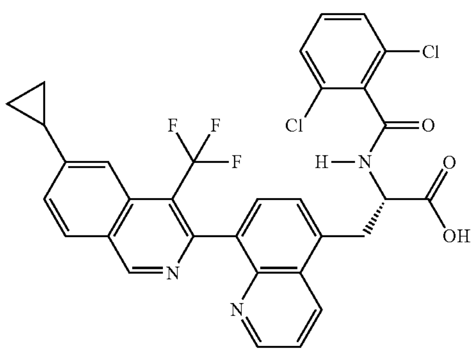 [SMILES: O=C(N[C@@H](Cc1ccc(-c2ncc3ccc(C4CC4)cc3c2C(F)(F)F)c2ncccc12)C(=O)O)c1c(Cl)cccc1Cl] | 1H NMR (400 MHz, DMSO-d6) δ 13.02 (s, 1H), 9.46 (d, J = 4.4 Hz, 1H), 9.16 (br, 1H), 8.78-8.62 (m, 2H), 8.24 (d, J = 8.6 Hz, 1H), 7.85 (s, 1H), 7.68-7.56 (m, 3H), 7.50 (dd, J = 8.5, 1.5 Hz, 1H), 7.46-7.35 (m, 3H), 4.75 (m, 1H), 3.85-3.58 (m, 1H), 3.43 (t, J = 11.9 Hz, 1H), 2.37-2.19 (m, 1H), 1.24-1.10 (m, 2H), 0.99-0.79 (m, 2H). | 626.0 | 14.4 |
| 320 | 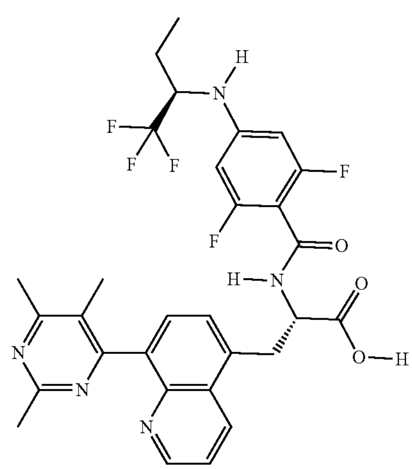 [SMILES: CC[C@@H](Nc1cc(F)c(C(=O)N[C@@H](Cc2ccc(-c3nc(C)nc(C)c3C)c3ncccc23)C(=O)O)c(F)c1)C(F)(F)F] | 1H NMR (400 MHz, DMSO-d6) δ 8.85 (d, J = 4.2 Hz, 1H), 8.78 (d, J = 8.1 Hz, 1H), 8.69 (d, J = 8.6 Hz, 1H), 7.71-7.45 (m, 3H), 6.76 (d, J = 9.3 Hz, 1H), 6.44 (d, J = 11.6 Hz, 2H), 4.71 (td, J = 9.0, 4.4 Hz, 1H), 4.30 (d, J = 9.9 Hz, 1H), 3.76 (dd, J = 14.3, 4.5 Hz, 1H), 3.43 (dd, J = 14.3, 10.1 Hz, 1H), 2.61 (s, 3H), 2.54 (s, 3H), 1.85 (s, 3H), 1.77 (ddd, J = 13.8, 7.2, 3.2 Hz, 1H), 1.53 (ddt, J = 17.6, 14.4, 7.3 Hz, 1H), 0.92 (t, J = 7.3 Hz, 3H). | 602.2 | 15.3 |

TABLE 2-continued

| Example | Structure | 1H-NMR | M/Z [M + H]+ | α4β7 EC$_{50}$ (nM) |
|---|---|---|---|---|
| 321 | 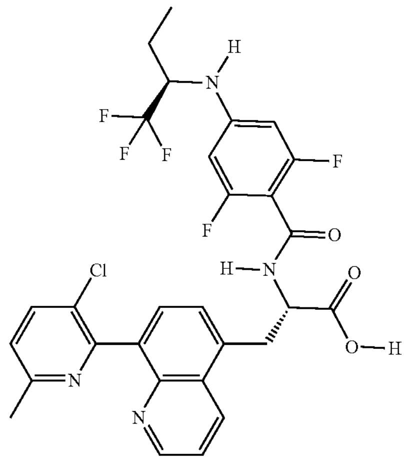 [SMILES: CC[C@@H](Nc1cc(F)c(C(=O)N[C@@H](Cc2ccc(-c3nc(C)ccc3Cl)c3ncccc23)C(=O)O)c(F)c1)C(F)(F)F] | 1H NMR (400 MHz, DMSO-d6) δ 8.85-8.79 (m, 2H), 8.66-8.61 (m, 1H), 7.90 (d, J = 8.2 Hz, 1H), 7.65-7.60 (m, 2H), 7.36 (d, J = 8.2 Hz, 1H), 6.78 (d, J = 9.4 Hz, 1H), 6.45 (d, J = 11.5 Hz, 2H), 4.73-4.61 (m, 1H), 4.38-4.23 (m, 1H), 3.78-3.69 (m, 1H), 3.48-3.38 (m, 1H), 2.50 (s, 3H), 1.84-1.69 (m, 1H), 1.61-1.45 (m, 1H), 0.92 (t, J = 7.3 Hz, 3H). | 607.2 | 15.8 |
| 322 | 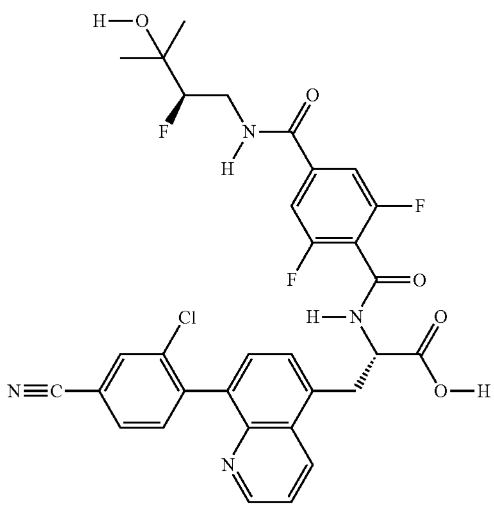 [SMILES: CC(C)(O)[C@H](F)CNC(=O)c1cc(F)c(C(=O)N[C@@H](Cc2ccc(-c3ccc(C#N)cc3Cl)c3ncccc23)C(=O)O)c(F)c1] | 1H NMR (400 MHz, DMSO-d6) δ 9.36 (d, J = 8.2 Hz, 1H), 8.91-8.79 (m, 2H), 8.64 (d, J = 8.8 Hz, 1H), 8.16 (d, J = 1.6 Hz, 1H), 7.90 (d, J = 8.0 Hz, 1H), 7.69-7.59 (m, 2H), 7.57 (d, J = 8.3 Hz, 3H), 4.80 (s, 1H), 4.30 (d, J = 39.4 Hz, 1H), 3.38 (s, 2H), 2.65 (s, 1H), 2.31 (s, 1H). | 639.3 | 16.2 |
| 323 | 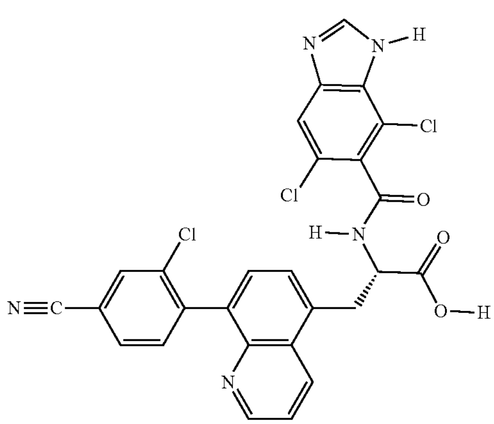 [SMILES: N#Cc1ccc(-c2ccc(C[C@H](NC(=O)c3c(Cl)cc4nc[nH]c4c3Cl)C(=O)O)c3cccnc23)c(Cl)c1] | 1H NMR (400 MHz, DMSO-d6) δ 9.17 (d, J = 8.5 Hz, 1H), 8.84 (dd, J = 4.2, 1.5 Hz, 1H), 8.67 (dd, J = 8.7, 1.7 Hz, 1H), 8.41 (s, 1H), 8.17 (d, J = 1.6 Hz, 1H), 7.92 (d, J = 7.8 Hz, 1H), 7.72-7.58 (m, 4H), 7.55 (d, J = 7.9 Hz, 1H), 4.87 (s, 1H), 3.77 (dd, J = 14.4, 4.2 Hz, 1H), 3.49-3.33 (m, 1H). | 564.0 | 17.1 |

TABLE 2-continued
| Example | Structure | 1H-NMR | M/Z [M + H]+ | α4β7 EC50 (nM) |
|---|---|---|---|---|
| 324 | 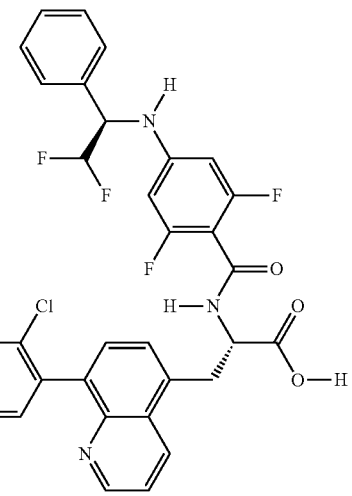 | 1H NMR (400 MHz, DMSO-d6) δ 8.85-8.72 (m, 2H), 8.60 (dd, J = 8.7, 1.6 Hz, 1H), 8.15 (dd, J = 1.7, 0.4 Hz, 1H), 7.89 (dd, J = 7.9, 1.7 Hz, 1H), 7.66-7.50 (m, 4H), 7.49-7.41 (m, 2H), 7.41-7.24 (m, 4H), 6.43-6.11 (m, 3H), 5.16-5.04 (m, 1H), 4.64 (s, 1H), 3.70 (s, 1H), 3.37 (s, 1H). | 647.1 | 18.7 |
| 325 | 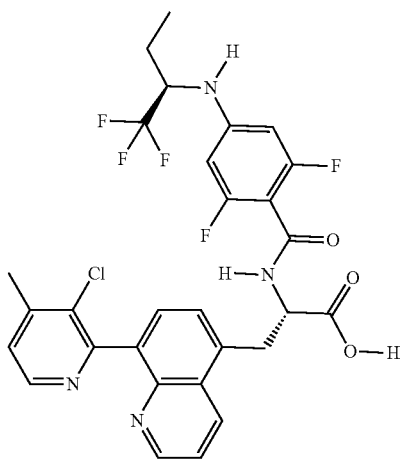 [SMILES: CC[C@@H](Nc1cc(F)c(C(=O)N[C@@H](Cc2ccc(-c3nccc(C)c3Cl)c3ncccc23)C(=O)O)c(F)c1)C(F)(F)F] | 1H NMR (400 MHz, DMSO-d6) δ 8.86-8.80 (m, 2H), 8.67-8.62 (m, 1H), 8.47 (d, J = 4.9 Hz, 1H), 7.63-7.60 (m, 2H), 7.49 (d, J = 5.0 Hz, 1H), 6.78 (d, J = 9.4 Hz, 1H), 6.45 (d, J = 11.6 Hz, 2H), 4.74-4.60 (m, 1H), 4.39-4.25 (m, 1H), 3.74 (dd, J = 14.5, 4.5 Hz, 1H), 3.47-3.37 (m, 1H), 2.45 (s, 3H), 1.85-1.70 (m, 1H), 1.52 (dt, J = 17.7, 7.2 Hz, 1H), 0.92 (t, J = 7.3 Hz, 3H). | 607.1 | 18.8 |
| 326 | 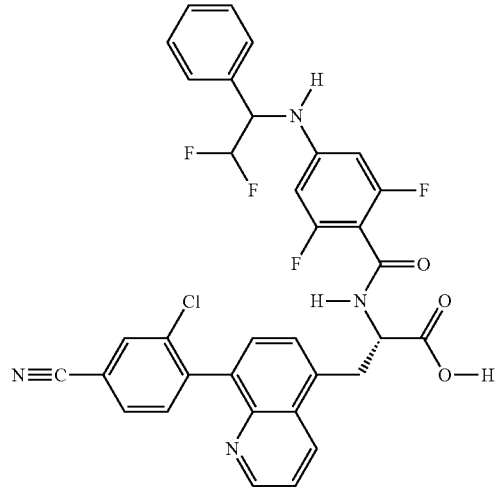 [SMILES: N#Cc1ccc(-c2ccc(C[C@H](NC(=O)c3c(F)cc(NC(c4ccccc4)C(F)F)cc3F)C(=O)O)c3cccnc23)c(Cl)c1] | 1H NMR (400 MHz, DMSO-d6) δ 8.85-8.73 (m, 2H), 8.61 (d, J = 8.7 Hz, 1H), 8.15 (dd, J = 1.7, 0.4 Hz, 1H), 7.89 (dd, J = 7.9, 1.6 Hz, 1H), 7.66-7.52 (m, 4H), 7.49-7.42 (m, 2H), 7.41-7.26 (m, 4H), 6.44-6.10 (m, 3H), 5.10 (q, J = 12.3 Hz, 1H), 4.64 (s, 1H), 3.70 (s, 1H), 3.37 (s, 1H). | 647.2 | 19.1 |

TABLE 2-continued
| Example | Structure | 1H-NMR | M/Z [M + H]+ | α4β7 EC$_{50}$ (nM) |
|---|---|---|---|---|
| 327 | 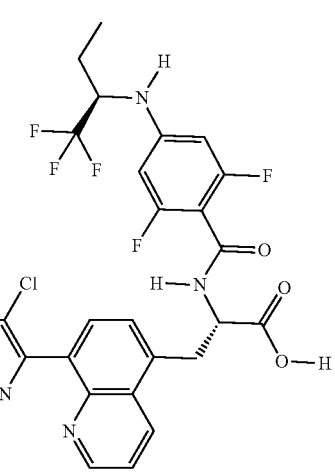 | 1H NMR (400 MHz, DMSO-d6) δ 8.84-8.79 (m, 2H), 8.62 (dd, J = 8.7, 1.7 Hz, 1H), 8.47-8.43 (m, 1H), 7.88-7.85 (m, 1H), 7.64-7.59 (m, 2H), 6.78 (d, J = 9.4 Hz, 1H), 6.45 (d, J = 11.5 Hz, 2H), 4.73-4.63 (m, 1H), 4.37-4.24 (m, 1H), 3.77-3.67 (m, 1H), 3.48-3.36 (m, 1H), 2.41 (s, 3H), 1.83-1.69 (m, 1H), 1.59-1.45 (m, 1H), 0.92 (t, J = 7.3 Hz, 3H), . | 607.2 | 19.3 |
| 328 | 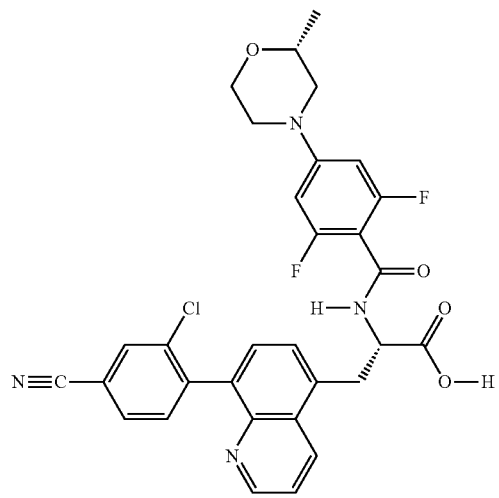 [SMILES: C[C@@H]1CN(c2cc(F)c(C(=O)N[C@@H](Cc3ccc(-c4ccc(C#N)cc4Cl)c4ncccc34)C(=O)O)c(F)c2)CCO1] | 1H NMR (400 MHz, DMSO-d6) δ 8.88 (d, J = 8.1 Hz, 1H), 8.85 (dd, J = 4.1, 1.6 Hz, 1H), 8.66 (dd, J = 8.7, 1.7 Hz, 1H), 8.17 (d, J = 1.7 Hz, 1H), 7.91 (dd, J = 7.9, 1.7 Hz, 1H), 7.68-7.60 (m, 3H), 7.58 (d, J = 7.9 Hz, 1H), 6.62 (d, J = 11.9 Hz, 2H), 4.72 (td, J = 9.1, 8.7, 4.3 Hz, 1H), 3.91-3.83 (m, 1H), 3.71 (d, J = 12.3 Hz, 1H), 3.65-3.49 (m, 3H), 3.43 (s, 2H), 2.70 (td, J = 12.1, 3.7 Hz, 1H), 2.38 (dd, J = 12.4, 10.4 Hz, 1H), 1.13 (d, J = 6.2 Hz, 3H). | 591.8 | 19.4 |
| 329 | 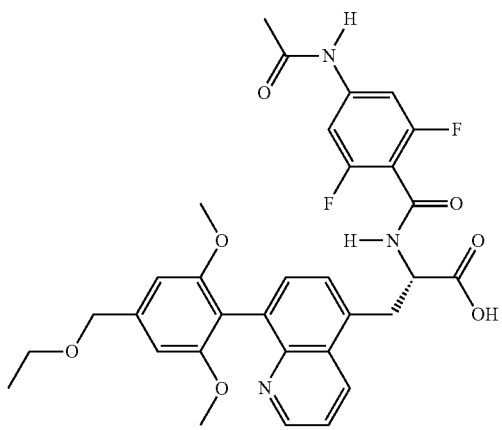 [SMILES: CCOCc1cc(OC)c(-c2ccc(C[C@H](NC(=O)c3c(F)cc(NC(C)=O)cc3F)C(=O)O)c3cccnc23)c(OC)c1] | 1H NMR (400 MHz, DMSO-d6) δ 10.38 (s, 1H), 9.13 (d, J = 8.1 Hz, 1H), 8.86 (d, J = 4.6 Hz, 1H), 7.91-7.45 (m, 3H), 7.37-7.16 (m, 2H), 6.75 (d, J = 3.0 Hz, 2H), 4.76 (td, J = 8.8, 8.1, 4.5 Hz, 1H), 4.53 (s, 2H), 3.79-3.73 (m, 1H), 3.57 (dd, J = 8.2, 7.4 Hz, 8H), 3.49-3.38 (m, 1H), 2.05 (s, 3H), 1.21 (t, J = 7.0 Hz, 3H). | 608.4 | 20.1 |

TABLE 2-continued

| Example | Structure | 1H-NMR | M/Z [M + H]+ | α4β7 EC$_{50}$ (nM) |
|---|---|---|---|---|
| 330 | 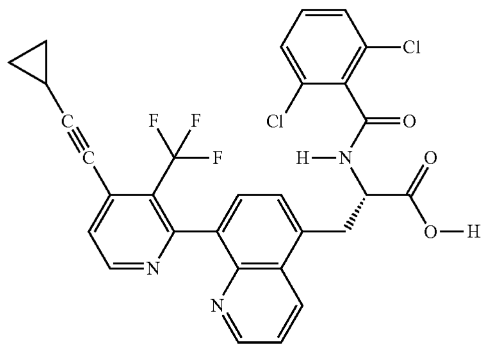 [SMILES: O=C(N[C@@H](Cc1ccc(-c2nccc(C#CC3CC3)c2C(F)(F)F)c2ncccc12)C(=O)O)c1c(Cl)cccc1Cl] | 1H NMR (400 MHz, DMSO-d6) δ 9.29 (t, J = 9.2 Hz, 1H), 8.83-8.74 (m, 2H), 8.65 (dd, J = 8.7, 1.6 Hz, 1H), 7.68-7.58 (m, 4H), 7.48-7.34 (m, 3H), 4.90-4.74 (m, 1H), 3.74 (dt, J = 14.8 Hz, 1H), 3.42 (dd, J = 14.5, 10.2 Hz, 1H), 1.68 (ddd, J = 13.2, 8.4, 4.9 Hz, 1H), 1.07-0.95 (m, 2H), 0.87-0.78 (m, 2H). | 599.7 | 21.0 |
| 331 | 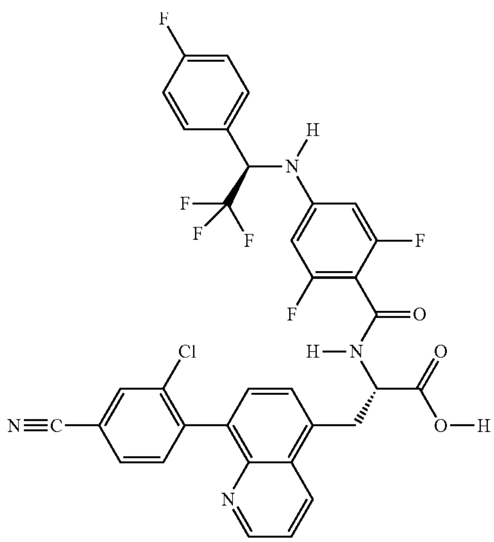 [SMILES: N#Cc1ccc(-c2ccc(C[C@H](NC(=O)c3c(F)cc(N[C@H](c4ccc(F)cc4)C(F)(F)F)cc3F)C(=O)O)c3cccnc23)c(Cl)c1] | 1H NMR (400 MHz, DMSO-d6) δ 8.90-8.74 (m, 2H), 8.61 (dd, J = 8.7, 1.7 Hz, 1H), 8.15 (dd, J = 1.6, 0.4 Hz, 1H), 7.89 (dd, J = 7.9, 1.7 Hz, 1H), 7.69-7.43 (m, 6H), 7.31-7.21 (m, 2H), 6.52 (d, J = 11.4 Hz, 2H), 5.73 (p, J = 8.3 Hz, 1H), 4.66 (s, 1H), 3.71 (s, 1H), 3.37 (s, 1H). | 683.1 | 22.9 |
| 332 | 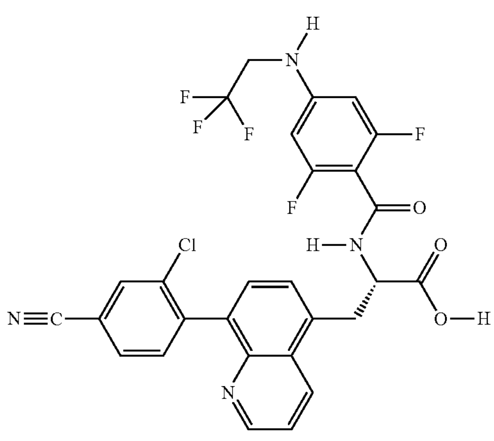 [SMILES: N#Cc1ccc(-c2ccc(C[C@H](NC(=O)c3c(F)cc(NCC(F)(F)F)cc3F)C(=O)O)c3cccnc23)c(Cl)c1] | 1H NMR (400 MHz, DMSO-d6) δ 8.86-8.76 (m, 2H), 8.63 (dd, J = 8.8, 1.6 Hz, 1H), 8.15 (d, J = 1.7 Hz, 1H), 7.89 (dd, J = 7.9, 1.7 Hz, 1H), 7.61 (s, 2H), 7.57 (d, J = 7.9 Hz, 1H), 7.02 (t, J = 6.9 Hz, 1H), 6.42 (d, J = 11.4 Hz, 2H), 4.78-4.59 (m, 1H), 4.08-3.95 (m, 2H), 3.72 (s, 1H), 3.41 (s, 1H). | 589.1 | 23.7 |

TABLE 2-continued

| Example | Structure | 1H-NMR | M/Z [M + H]+ | α4β7 EC$_{50}$ (nM) |
|---|---|---|---|---|
| 333 | 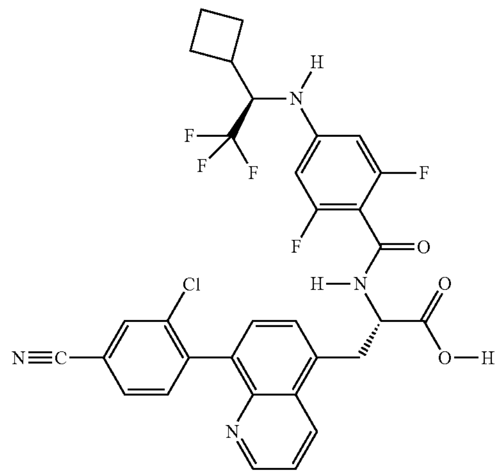 [SMILES: N#Cc1ccc(-c2ccc(C[C@H](NC(=O)c3c(F)cc(N[C@H](C4CCC4)C(F)(F)F)cc3F)C(=O)O)c3cccnc23)c(Cl)c1] | 1H NMR (400 MHz, DMSO-d6) δ 8.86-8.76 (m, 2H), 8.63 (dd, J = 8.7, 1.7 Hz, 1H), 8.16 (dd, J = 1.6, 0.4 Hz, 1H), 7.90 (dd, J = 7.9, 1.7 Hz, 1H), 7.68-7.49 (m, 4H), 6.70 (d, J = 9.7 Hz, 1H), 6.47 (d, J = 11.7 Hz, 2H), 4.68 (s, 1H), 4.42 (d, J = 8.1 Hz, 2H), 3.73 (s, 1H), 3.41 (s, 1H), 2.61 (q, J = 8.2 Hz, 1H), 1.98-1.71 (m, 6H). | 643.2 | 24.1 |
| 334 | 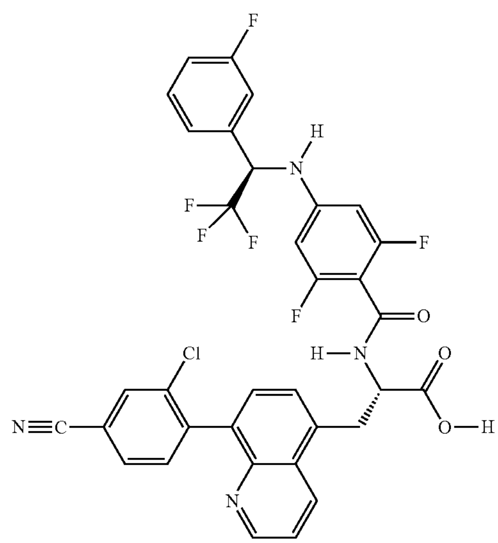 [SMILES: N#Cc1ccc(-c2ccc(C[C@H](NC(=O)c3c(F)cc(N[C@H](c4cccc(F)c4)C(F)(F)F)cc3F)C(=O)O)c3cccnc23)c(Cl)c1] | 1H NMR (400 MHz, DMSO-d6) δ 8.86-8.79 (m, 2H), 8.62 (dd, J = 8.7, 1.7 Hz, 1H), 8.15 (dd, J = 1.6, 0.4 Hz, 1H), 7.89 (dd, J = 7.9, 1.7 Hz, 1H), 7.66-7.37 (m, 8H), 7.28-7.18 (m, 1H), 6.53 (d, J = 11.4 Hz, 2H), 5.76 (p, J = 8.1 Hz, 1H), 4.65 (d, J = 10.7 Hz, 1H), 3.77-3.65 (m, 1H), 3.36 (s, 1H). | 683.2 | 24.2 |
| 335 | 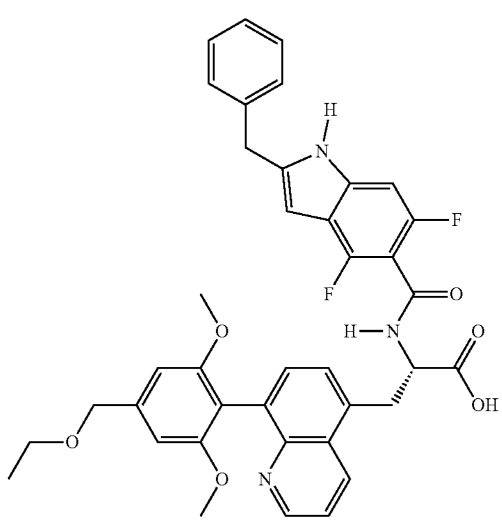 [SMILES: CCOCc1cc(OC)c(-c2ccc(C[C@H](NC(=O)c3c(F)cc4[nH]c(Cc5ccccc5)cc4c3F)C(=O)O)c3cccnc23)c(OC)c1] | 1H NMR (400 MHz, DMSO-d6) δ 12.96 (s, 1H), 11.47 (s, 1H), 9.00 (d, J = 8.0 Hz, 1H), 8.85 (s, 1H), 7.63 (d, J = 40.1 Hz, 2H), 7.40-7.12 (m, 5H), 6.94 (d, J = 9.8 Hz, 1H), 6.85-6.69 (m, 2H), 6.22 (d, J = 2.0 Hz, 1H), 4.76 (d, J = 11.0 Hz, 1H), 4.53 (s, 2H), 4.04 (s, 2H), 3.75 (d, J = 13.8 Hz, 1H), 3.57 (dd, J = 9.5, 6.9 Hz, 1H), 1.21 (t, J = 7.0 Hz, 3H). | 680.3 | 25.1 |

TABLE 2-continued
| Example | Structure | 1H-NMR | M/Z [M + H]+ | α4β7 EC50 (nM) |
|---|---|---|---|---|
| 336 | 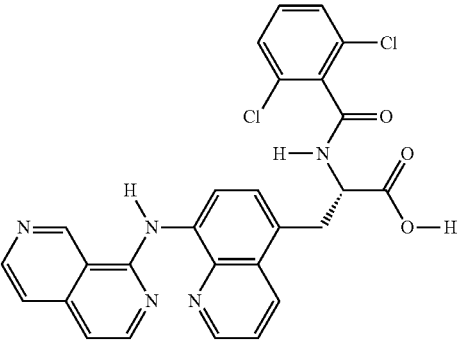 [SMILES: O=C(N[C@@H](Cc1ccc(Nc2nccc3ccncc23)c2ncccc12)C(=O)O)c1c(Cl)cccc1Cl] | 1H NMR (400 MHz, DMSO-d6) δ 9.92 (s, 1H), 9.27 (d, J = 8.3 Hz, 1H), 9.01 (dd, J = 4.2, 1.5 Hz, 1H), 8.81 (d, J = 5.8 Hz, 1H), 8.75-8.68 (m, 1H), 8.61 (s, 1H), 8.22 (s, 1H), 7.97 (d, J = 5.9 Hz, 1H), 7.78 (dd, J = 8.6, 4.2 Hz, 1H), 7.66 (d, J = 8.0 Hz, 1H), 7.47-7.30 (m, 4H), 4.81 (td, J = 8.9, 4.9 Hz, 1H), 3.39 (dd, J = 14.5, 9.7 Hz, 2H). | 532.0 | 26.1 |
| 337 | 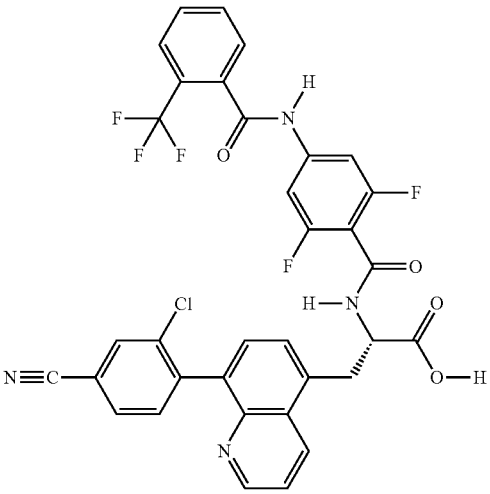 [SMILES: N#Cc1ccc(-c2ccc(C[C@H](NC(=O)c3c(F)cc(NC(=O)c4ccccc4C(F)(F)F)cc3F)C(=O)O)c3cccnc23)c(Cl)c1] | 1H NMR (400 MHz, DMSO-d6) δ 11.02 (s, 1H), 9.16 (d, J = 8.2 Hz, 1H), 8.84 (dd, J = 4.2, 1.6 Hz, 1H), 8.64 (dd, J = 8.7, 1.7 Hz, 1H), 8.15 (dd, J = 1.7, 0.4 Hz, 1H), 7.92-7.85 (m, 2H), 7.81 (t, J = 7.6 Hz, 1H), 7.77-7.70 (m, 2H), 7.67-7.59 (m, 3H), 7.57 (dd, J = 7.9, 0.4 Hz, 1H), 7.38 (d, J = 9.7 Hz, 2H), 4.76 (s, 1H), 3.8 (br, 1H). | 679.1 | 26.2 |
| 338 | 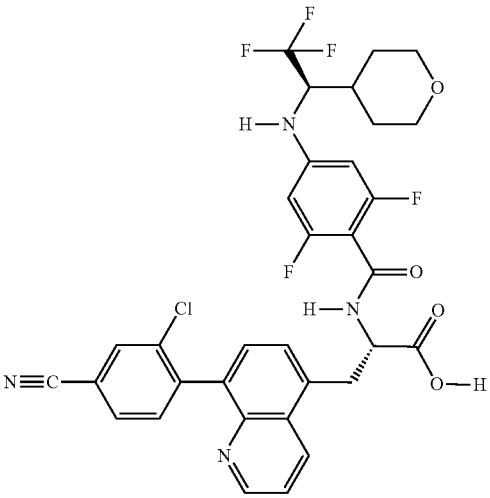 [SMILES: N#Cc1ccc(-c2ccc(C[C@H](NC(=O)c3c(F)cc(N[C@H](C4CCOCC4)C(F)(F)F)cc3F)C(=O)O)c3cccnc23)c(Cl)c1] | 1H NMR (400 MHz, DMSO-d6) δ 8.86-8.74 (m, 2H), 8.63 (dd, J = 8.7, 1.7 Hz, 1H), 8.15 (dd, J = 1.6, 0.4 Hz, 1H), 7.90 (dd, J = 7.9, 1.6 Hz, 1H), 7.67-7.59 (m, 3H), 7.57 (dd, J = 7.9, 0.4 Hz, 1H), 6.73 (d, J = 10.2 Hz, 1H), 6.50 (d, J = 11.8 Hz, 2H), 4.65-4.72 (m, 1H), 4.44-4.32 (m, 1H), 3.84 (td, J = 12.2, 4.2 Hz, 2H), 3.72 (s, 1H), 3.40 (s, 1H), 3.33-3.21 (m, 2H), 1.97 (d, J = 10.8 Hz, 1H), 1.55 (d, J = 13.2 Hz, 2H), 1.48-1.32 (m, 2H). | 788.1 | 26.5 |

TABLE 2-continued

| Example | Structure | 1H-NMR | M/Z [M + H]+ | α4β7 EC$_{50}$ (nM) |
|---|---|---|---|---|
| 339 | 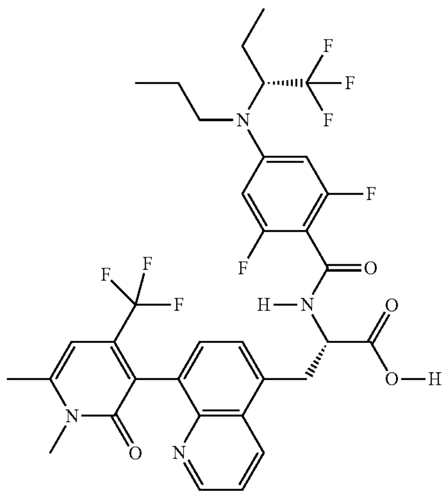 [SMILES: CCCN(c1cc(F)c(C(=O)N[C@@H](Cc2ccc(-c3c(C(F)(F)F)cc(C)n(C)c3=O)c3ncccc23)C(=O)O)c(F)c1)[C@H](CC)C(F)(F)F] | 1H NMR (400 MHz, DMSO-d6) δ 8.92 (dd, J = 7.9, 4.3 Hz, 1H), 8.84 (dd, J = 4.3, 1.4 Hz, 1H), 8.68 (d, J = 8.0 Hz, 1H), 7.66 (dt, J = 8.7, 4.4 Hz, 1H), 7.60 (t, J = 7.7 Hz, 1H), 7.46 (dd, J = 7.3, 2.1 Hz, 1H), 6.63 (dd, J = 12.0, 4.7 Hz, 2H), 6.56 (d, J = 1.8 Hz, 1H), 4.69 (ddd, J = 13.2, 8.8, 4.9 Hz, 2H), 3.80-3.63 (m, 1H), 3.49 (d, J = 2.2 Hz, 3H), 3.48-3.34 (m, 1H), 3.34-3.21 (m, 1H), 3.21-3.07 (m, 1H), 2.54 (s, 3H), 1.90 (ddd, J = 14.2, 10.5, 7.1 Hz, 1H), 1.76 (ddt, J = 11.2, 7.3, 4.0 Hz, 1H), 1.61-1.34 (m, 2H), 0.86 (dt, J = 10.9, 7.3 Hz, 6H). | 713.2 | 0.6 |
| 340 | 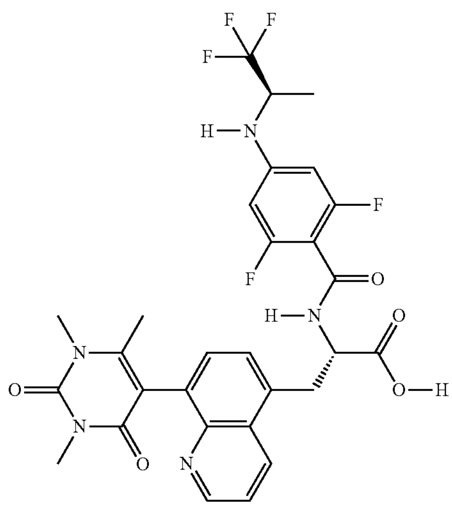 [SMILES: Cc1c(-c2ccc(C[C@H](NC(=O)c3c(F)cc(N[C@H](C)C(F)(F)F)cc3F)C(=O)O)c3cccnc23)c(=O)n(C)c(=O)n1C] | 1H NMR (400 MHz, DMSO-d6) δ 8.93 (d, J = 4.4 Hz, 1H), 8.89-8.71 (m, 2H), 7.75 (s, 1H), 7.62 (td, J = 18.5, 17.8, 7.5 Hz, 2H), 6.93-6.77 (m, 1H), 6.38 (dd, J = 11.3, 2.7 Hz, 2H), 4.76-4.61 (m, 1H), 4.49 (q, J = 7.5 Hz, 1H), 3.87-3.74 (m, 1H), 3.66 (dd, J = 14.5, 4.8 Hz, 1H), 3.54-3.48 (m, 1H), 3.45 (d, J = 1.7 Hz, 3H), 3.34 (dd, J = 14.4, 10.6 Hz, 1H), 3.22 (d, J = 2.5 Hz, 3H), 1.93 (d, J = 9.9 Hz, 3H), 1.25 (d, J = 6.7 Hz, 3H). | 620.2 | 0.6 |
| 341 | 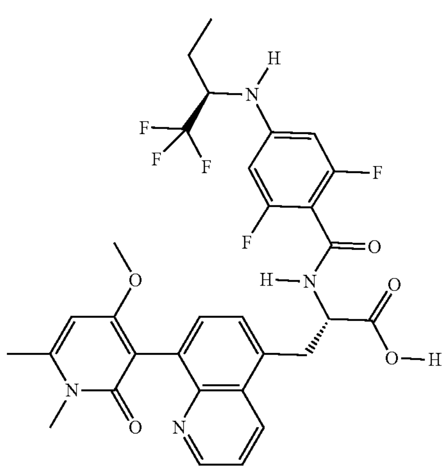 [SMILES: CC[C@@H](Nc1cc(F)c(C(=O)N[C@@H](Cc2ccc(-c3c(OC)cc(C)n(C)c3=O)c3ncccc23)C(=O)O)c(F)c1)C(F)(F)F] | 1H NMR (400 MHz, DMSO-d6) δ 12.97 (s, 1H), 9.06 (s, 1H), 8.96 (s, 1H), 8.84 (d, J = 8.0 Hz, 1H), 7.89 (s, 1H), 7.78-7.60 (m, 2H), 6.79 (d, J = 9.4 Hz, 1H), 6.51-6.38 (m, 3H), 4.69 (s, 1H), 4.31 (d, J = 9.6 Hz, 1H), 3.74 (d, J = 11.7 Hz, 1H), 3.67 (d, J = 4.4 Hz, 3H), 3.45 (s, 4H), 1.78 (dt, J = 10.8, 3.7 Hz, 1H), 1.53 (ddd, J = 13.8, 10.5, 7.1 Hz, 1H), 0.92 (t, J = 7.3 Hz, 3H). | 633.2 | 0.6 |

TABLE 2-continued

| Example | Structure | 1H-NMR | M/Z [M + H]+ | α4β7 EC$_{50}$ (nM) |
|---|---|---|---|---|
| 342 | 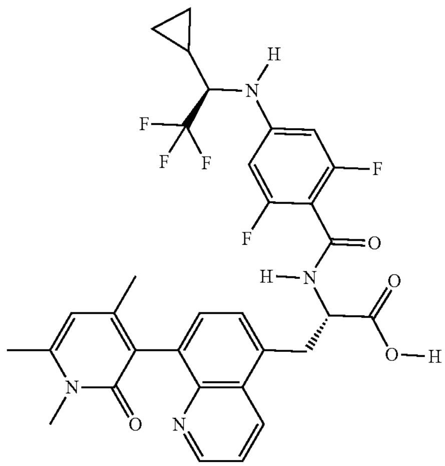 [SMILES: Cc1cc(C)n(C)c(=O)c1-c1ccc(C[C@H](NC(=O)c2c(F)cc(N[C@H](C3CC3)C(F)(F)F)cc2F)C(=O)O)c2cccnc12] | 1H NMR (400 MHz, DMSO-d6) δ 8.95-8.83 (m, 2H), 8.80 (d, J = 8.0 Hz, 1H), 7.84-7.70 (m, 1H), 7.70-7.61 (m, 1H), 7.61-7.50 (m, 1H), 6.94 (dd, J = 9.5, 4.6 Hz, 1H), 6.40 (dd, J = 11.4, 3.6 Hz, 2H), 6.21 (d, J = 2.7 Hz, 1H), 4.77-4.65 (m, 1H), 3.99-3.87 (m, 1H), 3.84-3.64 (m, 1H), 3.53-3.32 (m, 4H), 2.42 (s, 3H), 1.80-1.70 (m, 3H), 1.11-0.98 (m, 1H), 0.68-0.58 (m, 1H), 0.55-0.44 (m, 2H), 0.35-0.27 (m, 1H). | 629.2 | 0.7 |
| 343 | 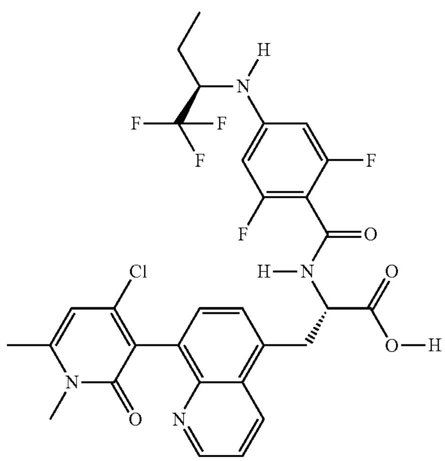 [SMILES: CC[C@@H](Nc1cc(F)c(C(=O)N[C@@H](Cc2ccc(-c3c(Cl)cc(C)n(C)c3=O)c3ncccc23)C(=O)O)c(F)c1)C(F)(F)F] | 1H NMR (400 MHz, DMSO-d6) δ 8.87 (d, J = 4.3 Hz, 1H), 8.85-8.79 (m, 1H), 8.75 (d, J = 8.7 Hz, 1H), 7.74-7.65 (m, 1H), 7.63 (dd, J = 7.4, 3.1 Hz, 1H), 7.54 (d, J = 7.4 Hz, 1H), 6.77 (dd, J = 9.3, 3.8 Hz, 1H), 6.52-6.42 (m, 3H), 4.68 (qd, J = 8.4, 4.5 Hz, 1H), 4.38-4.19 (m, 1H), 3.74-3.66 (m, 1H), 3.53-3.37 (m, 4H), 2.46 (s, 3H), 1.77 (ddd, J = 13.6, 7.2, 3.2 Hz, 1H), 1.61-1.45 (m, 1H), 0.93 (t, J = 7.3 Hz, 4H). | 639.2 | 0.7 |
| 344 | 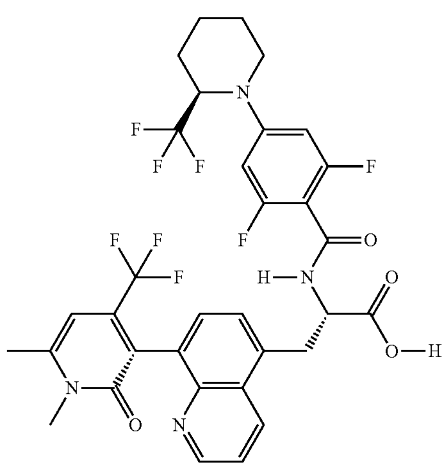 | 1H NMR (400 MHz, DMSO-d6) δ 8.76-8.64 (m, 2H), 7.54-7.42 (m, 2H), 7.32 (d, J = 7.3 Hz, 1H), 6.72 (d, J = 12.1 Hz, 2H), 6.51 (s, 1H), 5.00-4.85 (m, 1H), 4.36 (s, 1H), 3.73-3.55 (m, 2H), 3.48 (s, 3H), 3.29 (s, 3H), 3.02 (t, J = 12.1 Hz, 1H), 1.95 (d, J = 14.7 Hz, 1H), 1.87-1.67 (m, 2H), 1.67-1.43 (m, 3H), 0.91-0.77 (m, 2H). | 697.2 | 0.8 |

TABLE 2-continued

| Example | Structure | 1H-NMR | M/Z [M + H]+ | α4β7 EC$_{50}$ (nM) |
|---|---|---|---|---|
| 345 | 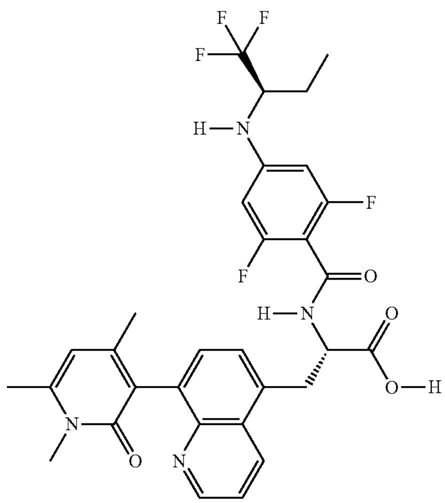 [SMILES: CC[C@@H](Nc1cc(F)c(C(=O)N[C@@H](Cc2ccc(-c3c(C)cc(C)n(C)c3=O)c3ncccc23)C(=O)O)c(F)c1)C(F)(F)F] | 1H NMR (400 MHz, DMSO-d6) δ 8.89 (s, 2H), 8.79 (d, J = 8.0 Hz, 1H), 7.78 (d, J = 11.8 Hz, 1H), 7.65 (dd, J = 11.1, 7.4 Hz, 1H), 7.54 (t, J = 6.8 Hz, 1H), 6.75 (dd, J = 9.5, 4.3 Hz, 1H), 6.41 (dd, J = 11.3, 3.2 Hz, 2H), 6.20 (d, J = 2.9 Hz, 1H), 4.69 (dt, J = 13.3, 9.3 Hz, 1H), 4.29 (d, J = 9.7 Hz, 1H), 3.74 (ddd, J = 46.6, 14.4, 4.6 Hz, 1H), 3.55-3.30 (m, 4H), 2.41 (s, 3H), 1.74 (d, J = 11.1 Hz, 3H), 1.50 (ddd, J = 13.9, 10.5, 7.1 Hz, 1H), 0.90 (t, J = 7.3 Hz, 3H). | 617.2 | 0.8 |
| 346 | 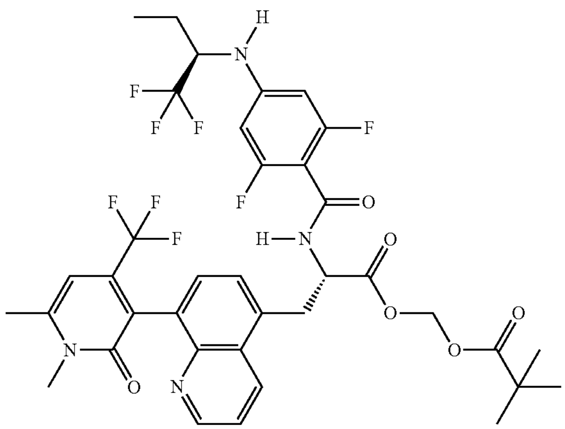 [SMILES: CC[C@@H](Nc1cc(F)c(C(=O)N[C@@H](Cc2ccc(-c3c(C(F)(F)F)cc(C)n(C)c3=O)c3ncccc23)C(=O)OCOC(=O)C(C)(C)C)c(F)c1)C(F)(F)F] | 1H NMR (400 MHz, DMSO-d6) δ 9.00 (dd, J = 12.1, 7.5 Hz, 1H), 8.82 (d, J = 4.2 Hz, 1H), 8.57 (d, J = 8.7 Hz, 1H), 7.68-7.56 (m, 2H), 7.44 (dd, J = 7.2, 2.9 Hz, 1H), 6.81-6.73 (m, 1H), 6.55 (s, 1H), 6.45 (dd, J = 11.5, 5.6 Hz, 2H), 5.76 (dd, J = 11.1, 6.1 Hz, 2H), 4.74 (dd, J = 13.7, 7.1 Hz, 1H), 4.34 (d, J = 2.1 Hz, 1H), 3.70-3.61 (m, 1H), 3.51 (s, 3H), 3.43 (d, J = 10.0 Hz, 1H), 2.53 (s, 3H), 1.76 (d, J = 8.0 Hz, 1H), 1.53 (dq, J = 13.7, 7.1 Hz, 1H), 1.16 (d, J = 1.9 Hz, 9H), 0.92 (t, J = 7.3 Hz, 3H). | 785.2 | NA |
| 347 | 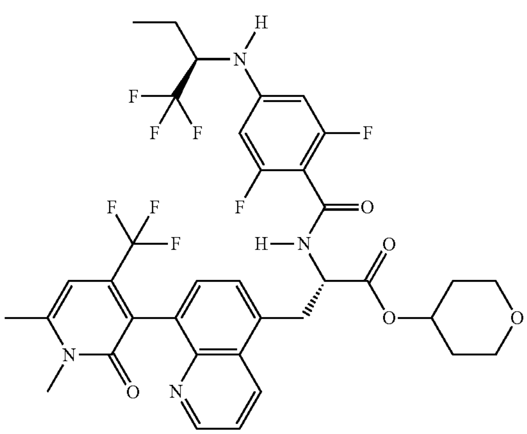 [SMILES: CC[C@@H](Nc1cc(F)c(C(=O)N[C@@H](Cc2ccc(-c3c(C(F)(F)F)cc(C)n(C)c3=O)c3ncccc23)C(=O)OC2CCOCC2)c(F)c1)C(F)(F)F] | 1H NMR (400 MHz, DMSO-d6) δ 8.98 (t, J = 6.8 Hz, 1H), 8.82 (d, J = 4.2 Hz, 1H), 8.62 (d, J = 8.6 Hz, 1H), 7.63 (dd, J = 8.5, 4.3 Hz, 1H), 7.56 (d, J = 7.4 Hz, 1H), 7.45 (d, J = 7.3 Hz, 1H), 6.79 (dd, J = 9.5, 4.4 Hz, 1H), 6.55 (s, 1H), 6.47 (dd, J = 11.4, 3.9 Hz, 2H), 4.86 (d, J = 9.4 Hz, 1H), 4.69 (d, J = 13.6 Hz, 1H), 4.35-4.28 (m, 1H), 3.82-3.60 (m, 3H), 3.57-3.36 (m, 6H), 2.53 (s, 3H), 1.85-1.65 (m, 3H), 1.53 (ddd, J = 17.2, 8.9, 5.3 Hz, 2H), 1.39 (t, J = 9.7 Hz, 1H), 0.93 (t, J = 7.3 Hz, 3H). | 755.2 | NA |

TABLE 2-continued

| Example | Structure | 1H-NMR | M/Z [M + H]+ | α4β7 EC$_{50}$ (nM) |
|---|---|---|---|---|
| 348 | 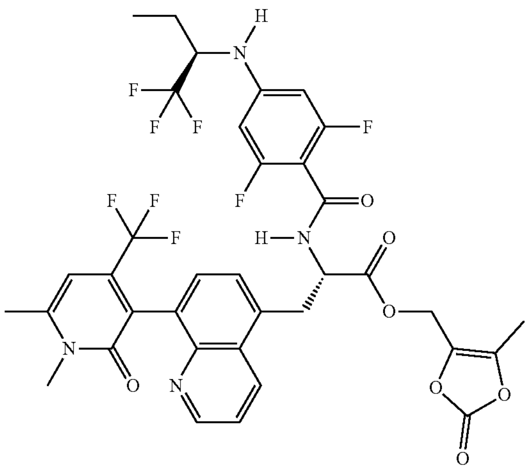 | 1H NMR (400 MHz, DMSO-d6) δ 9.00 (t, J = 7.1 Hz, 1H), 8.83 (d, J = 4.2 Hz, 1H), 8.63 (s, 1H), 7.62 (dd, J = 8.9, 4.6 Hz, 1H), 7.55 (t, J = 7.0 Hz, 1H), 7.44 (t, J = 6.6 Hz, 1H), 6.78 (d, J = 9.8 Hz, 1H), 6.55 (s, 1H), 6.45 (d, J = 11.9 Hz, 2H), 5.06-4.96 (m, 2H), 4.74 (d, J = 7.9 Hz, 1H), 4.32 (d, J = 9.2 Hz, 1H), 3.67 (dt, J = 12.6, 5.8 Hz, 1H), 3.49 (s, 4H), 2.53 (s, 3H), 2.14 (d, J = 3.7 Hz, 3H), 1.76 (d, J = 10.4 Hz, 1H), 1.53 (d, J = 9.1 Hz, 1H), 0.93 (t, J = 7.3 Hz, 3H). | 783.2 | NA |
| 349 | 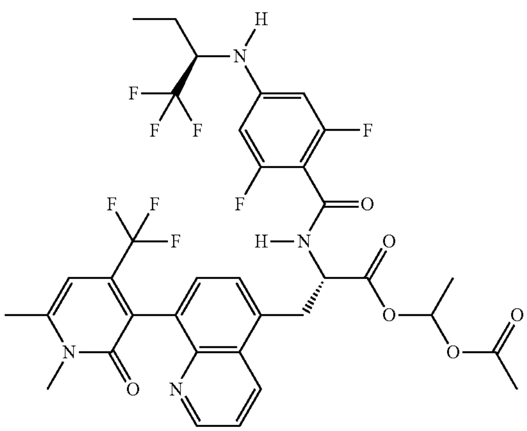 [SMILES: CC[C@@H](Nc1cc(F)c(C(=O)N[C@@H](Cc2ccc(-c3c(C(F)(F)F)cc(C)n(C)c3=O)c3ncccc23)C(=O)OC(C)OC(C)=O)c(F)c1)C(F)(F)F] | 1H NMR (400 MHz, DMSO-d6) δ 9.06-8.93 (m, 1H), 8.81 (d, J = 4.0 Hz, 1H), 8.56 (t, J = 10.6 Hz, 1H), 7.65-7.51 (m, 2H), 7.44 (d, J = 6.4 Hz, 1H), 6.85-6.69 (m, 2H), 6.54 (s, 1H), 6.50-6.35 (m, 2H), 4.79-4.65 (m, 1H), 4.32 (s, 1H), 3.63 (d, J = 13.8 Hz, 1H), 3.49 (s, 4H), 2.53 (s, 3H), 2.08-1.97 (m, 2H), 1.77 (s, 1H), 1.55 (d, J = 15.3 Hz, 1H), 1.44 (t, J = 5.0 Hz, 1H), 1.29 (d, J = 5.4 Hz, 1H), 0.93 (q, J = 6.5, 5.8 Hz, 2H), −0.00 (d, J = 1.6 Hz, 3H). | 757.2 | NA |
| 350 | 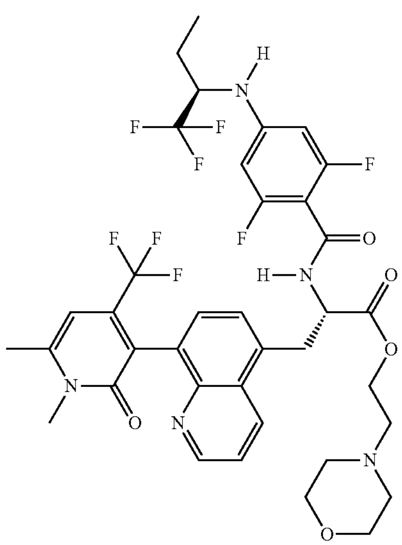 [SMILES: CC[C@@H](Nc1cc(F)c(C(=O)N[C@@H](Cc2ccc(-c3c(C(F)(F)F)cc(C)n(C)c3=O)c3ncccc23)C(=O)OCCN2CCOCC2)c(F)c1)C(F)(F)F] | 1H NMR (400 MHz, DMSO-d6) δ 9.81 (d, J = 41.6 Hz, 1H), 9.08 (t, J = 8.0 Hz, 1H), 8.83 (t, J = 5.3 Hz, 1H), 8.58 (dd, J = 37.4, 9.3 Hz, 1H), 7.66-7.56 (m, 1H), 7.46 (dd, J = 9.5, 6.6 Hz, 1H), 6.85 (d, J = 9.6 Hz, 1H), 6.58 (d, J = 8.8 Hz, 1H), 6.49 (dd, J = 11.5, 2.6 Hz, 2H), 4.86-4.76 (m, 1H), 4.47-4.37 (m, 1H), 4.38-4.29 (m, 1H), 4.24-4.14 (m, 1H), 3.99-3.90 (m, 1H), 3.73 (dd, J = 15.6, 4.8 Hz, 1H), 3.70-3.60 (m, 2H), 3.59-3.52 (m, 1H), 3.50 (s, 2H), 3.43-3.34 (m, 1H), 3.34-3.26 (m, 2H), 3.22-3.08 (m, 2H), 2.54 (d, J = 2.3 Hz, 3H), 1.83-1.72 (m, 1H), 1.57-1.46 (m, 1H), 0.96-0.90 (m, 3H). | 784.2 | NA |

TABLE 2-continued

| Example | Structure | 1H-NMR | M/Z [M + H]+ | α4β7 EC₅₀ (nM) |
|---|---|---|---|---|
| 351 | 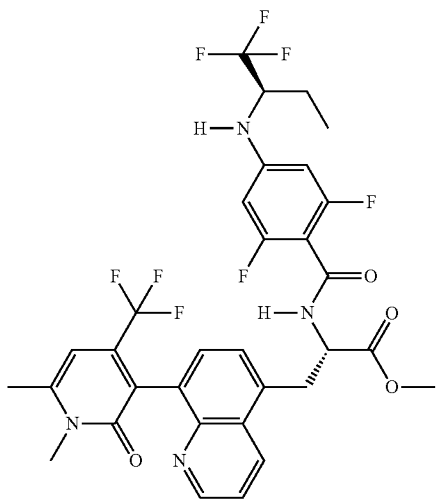 | 1H NMR (400 MHz, DMSO-d6) δ 9.01-8.91 (m, 1H), 8.79 (d, J = 4.3 Hz, 1H), 8.57 (d, J = 8.5 Hz, 1H), 7.60 (dd, J = 8.5, 4.2 Hz, 1H), 7.51 (t, J = 7.9 Hz, 1H), 7.42 (d, J = 7.6 Hz, 1H), 6.78 (dd, J = 9.4, 6.0 Hz, 1H), 6.53 (d, J = 0.9 Hz, 1H), 6.44 (dd, J = 11.5, 5.7 Hz, 2H), 4.72 (dd, J = 10.4, 7.2 Hz, 1H), 4.30 (s, 1H), 3.72-3.29 (m, 6H), 2.51 (s, 3H), 1.80-1.71 (m, 1H), 1.58-1.45 (m, 1H), 0.91 (t, J = 7.3 Hz, 3H). | 685.2 | NA |
| 352 | 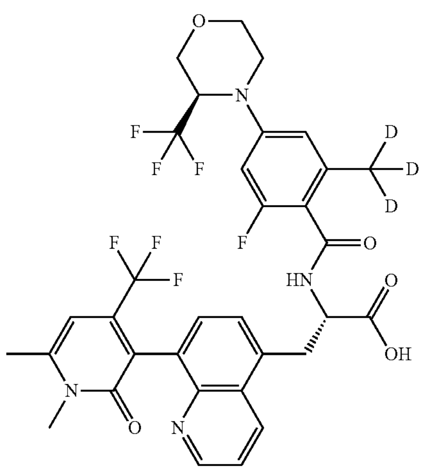 [SMILES: [2H]C([2H])([2H])c1cc(N2CCOC[C@@H]2C(F)(F)F)cc(F)c1C(=O)N[C@@H](Cc1ccc(-c2c(C(F)(F)F)cc(C)n(C)c2=O)c2ncccc12)C(=O)O] | 1H NMR (400 MHz, DMSO-d6) δ 8.88-8.77 (m, 2H), 8.66 (d, J = 8.7 Hz, 1H), 7.70-7.56 (m, 2H), 7.45 (t, J = 7.2 Hz, 1H), 6.71-6.60 (m, 2H), 6.55 (d, J = 3.3 Hz, 1H), 4.89-4.69 (m, 2H), 4.14 (d, J = 12.6 Hz, 1H), 3.99-3.89 (m, 1H), 3.81-3.73 (m, 2H), 3.55-3.42 (m, 4H), 3.41-3.30 (m, 1H), 3.30-3.17 (m, 1H), 2.53 (s, 3H). | 698.13 | NA |
| 353 | 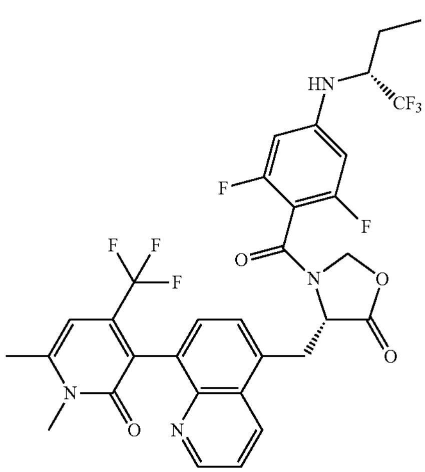 [SMILES: CC[C@@H](Nc1cc(F)c(C(=O)N2COC(=O)[C@@H]2Cc2ccc(-c3c(C(F)(F)F)cc(C)n(C)c3=O)c3ncccc23)c(F)c1)C(F)(F)F] | 1H NMR (400 MHz, DMSO-d6) δ 8.78 (s, 1H), 8.64 (d, J = 8.5 Hz, 1H), 7.54 (s, 1H), 7.52-7.35 (m, 2H), 7.00 (t, J = 10.6 Hz, 1H), 6.50 (d, J = 30.6 Hz, 3H), 5.31 (d, J = 6.2 Hz, 1H), 5.08 (s, 1H), 4.67 (s, 1H), 4.57 (s, 1H), 4.35 (s, 1H), 3.49 (s, 3H), 2.53 (s, 3H), 1.78 (s, 1H), 1.53 (d, J = 15.1 Hz, 1H), 1.25 (d, J = 6.4 Hz, 1H), 0.93 (d, J = 6.2 Hz, 3H). | 683.2 | NA |

TABLE 2-continued

| Example | Structure | 1H-NMR | M/Z [M + H]+ | α4β7 EC$_{50}$ (nM) |
|---|---|---|---|---|
| 354 | 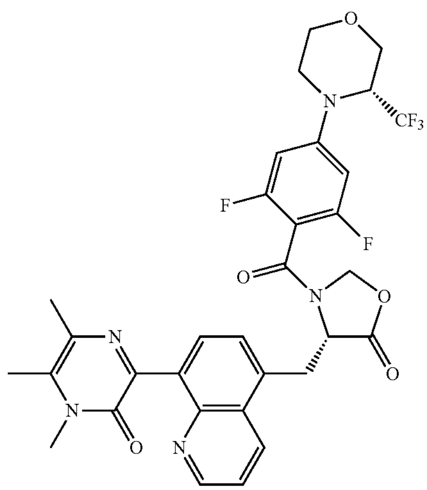 [SMILES: Cc1nc(-c2ccc(C[C@H]3C(=O)OCN3C(=O)c3c(F)cc(N4CCOC[C@@H]4C(F)(F)F)cc3F)c3cccnc23)c(=O)n(C)c1C] | 1H NMR (400 MHz, DMSO-d6) δ 8.86 (m, 2H), 7.75 (s, 1H), 7.67 (s, 1H), 7.60 (d, J = 7.5 Hz, 1H), 7.03 (d, J = 9.4 Hz, 1H), 6.54 (d, J = 12.4 Hz, 2H), 5.36 (d, J = 4.4 Hz, 1H), 5.03 (m, 2H), 3.79 (d, J = 6.2 Hz, 1H), 3.53 (s, 3H), 2.42 (s, 3H), 2.34 (s, 3H), 1.79 (m, 1H), 1.55 (s, 1H), 0.94 (t, J = 7.4 Hz, 3H) | 630.2 | NA |

Examples 355-406 in Table 3 were prepared by processes described herein.

TABLE 3

| Example | Structure | 1H-NMR | M/Z [M + H]+ | α4β7 EC$_{50}$ (nM) |
|---|---|---|---|---|
| 355 | 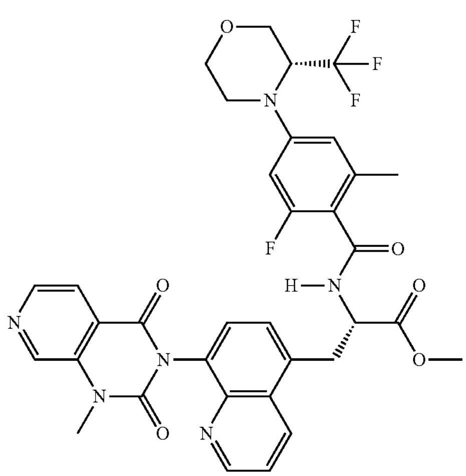 [SMILES: COC(=O)[C@H](Cc1ccc(-n2c(=O)c3ccncc3n(C)c2=O)c2ncccc12)NC(=O)c1c(C)cc(N2CCOC[C@@H]2C(F)(F)F)cc1F] | 1H NMR (400 MHz, DMSO-d6) δ 9.05 (s, 1H), 9.00 (d, J = 7.7 Hz, 1H), 8.85 (d, J = 4.1 Hz, 1H), 8.66 (dd, J = 8.7, 1.5 Hz, 1H), 8.60 (d, J = 4.9 Hz, 1H), 7.91 (dd, J = 4.9, 3.2 Hz, 1H), 7.77 (d, J = 7.5 Hz, 1H), 7.72-7.58 (m, 2H), 6.79-6.61 (m, 2H), 4.83 (td, J = 9.2, 8.4, 4.4 Hz, 2H), 4.15 (d, J = 12.6 Hz, 1H), 3.93 (d, J = 3.7 Hz, 1H), 3.68 (s, 3H), 3.66 (d, J = 2.3 Hz, 4H), 3.53 (dp, J = 14.9, 5.8, 5.2 Hz, 2H), 3.40-3.18 (m, 2H), 2.05 (s, 3H). | 695.2 | NA |

TABLE 3-continued

| Example | Structure | 1H-NMR | M/Z [M + H]+ | α4β7 EC$_{50}$ (nM) |
|---|---|---|---|---|
| 356 | 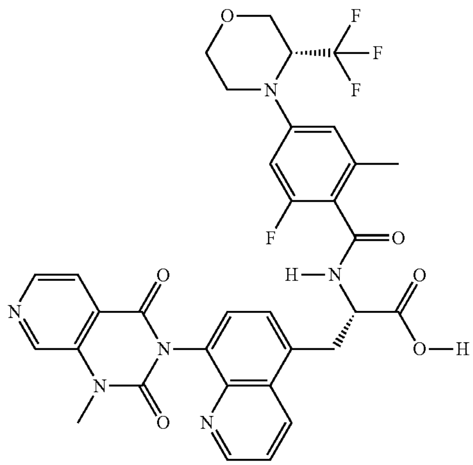 | 1H NMR (400 MHz, DMSO-d6) δ 9.05 (s, 1H), 8.92-8.77 (m, 2H), 8.68 (d, J = 8.6 Hz, 1H), 8.60 (d, J = 5.0 Hz, 1H), 7.91 (t, J = 4.3 Hz, 1H), 7.76 (d, J = 7.6 Hz, 1H), 7.67 (dd, J = 8.3, 4.5 Hz, 2H), 6.74-6.58 (m, 2H), 5.00-4.59 (m, 2H), 4.14 (d, J = 12.6 Hz, 1H), 3.99-3.91 (m, 1H), 3.66 (d, J = 2.4 Hz, 4H), 3.59-3.40 (m, 1H), 3.31 (dd, J = 35.1, 12.3 Hz, 3H), 2.03 (s, 3H). | 681.2 | 0.05 |
| 357 | 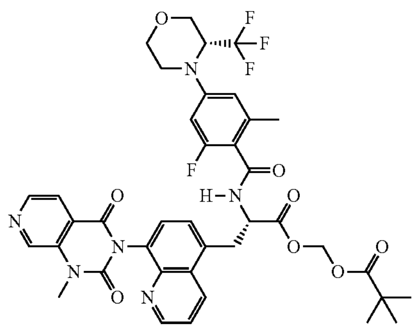 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)OCOC(=O)C(C)(C)C] | 1H NMR (400 MHz, DMSO-d6) δ 9.15-9.00 (m, 2H), 8.85 (d, J = 3.9 Hz, 1H), 8.67-8.57 (m, 2H), 7.91 (ddd, J = 5.0, 3.1, 0.8 Hz, 1H), 7.76 (d, J = 7.5 Hz, 1H), 7.73-7.61 (m, 2H), 5.83 (s, 2H), 4.85 (d, J = 9.2 Hz, 2H), 4.14 (d, J = 12.6 Hz, 1H), 4.06-3.88 (m, 1H), 3.84-3.68 (m, 2H), 3.65 (d, J = 2.2 Hz, 3H), 3.53 (dt, J = 14.8, 9.7 Hz, 2H), 3.36 (d, J = 12.3 Hz, 1H), 3.26 (d, J = 12.1 Hz, 1H), 2.03 (s, 3H), 1.18 (s, 9H). | 795.3 | NA |
| 358 | 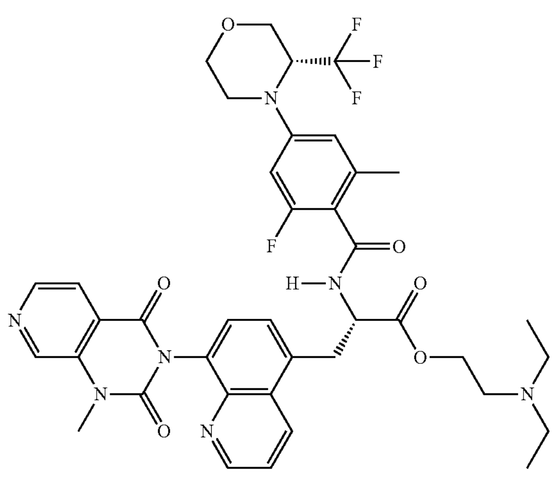 [SMILES: CCN(CC)CCOC(=O)[C@H](Cc1ccc(-n2c(=O)c3ccncc3n(C)c2=O)c2ncccc12)NC(=O)c1c(C)cc(N2CCOC[C@@H]2C(F)(F)F)cc1F] | 1H NMR (400 MHz, Chloroform-d) δ 9.28 (dt, J = 4.8, 1.6 Hz, 1H), 9.20 (ddd, J = 8.7, 4.6, 1.5 Hz, 1H), 8.90 (d, J = 2.2 Hz, 1H), 8.62 (dd, J = 5.0, 1.6 Hz, 1H), 8.04 (dd, J = 24.7, 5.0 Hz, 1H), 7.83 (dd, J = 8.6, 4.7 Hz, 1H), 7.75 (d, J = 1.2 Hz, 2H), 7.46 (d, J = 7.0 Hz, 1H), 6.49 (d, J = 2.4 Hz, 1H), 6.43-6.27 (m, 1H), 5.18 (q, J = 7.6 Hz, 1H), 4.97 (dd, J = 12.8, 6.4 Hz, 1H), 4.53 (td, J = 9.2, 7.8, 4.6 Hz, 1H), 4.31 (d, J = 12.4 Hz, 1H), 4.16 (ddt, J = 19.3, 8.0, 3.3 Hz, 1H), 4.10-3.90 (m, 2H), 3.82 (dd, J = 12.5, 2.2 Hz, 1H), 3.72 (d, J = 9.4 Hz, 3H), 3.60 (ddt, J = 32.1, 17.2, 8.3 Hz, 3H), 3.28 (d, J = 12.0 Hz, 1H), 3.22-3.09 (m, 1H), 3.03 (s, 4H), 2.32 (s, 3H), 1.49-1.10 (m, 9H), 1.02 (d, J = 7.6 Hz, 2H). | 780.3 | NA |

TABLE 3-continued

| Example | Structure | 1H-NMR | M/Z [M + H]+ | α4β7 EC$_{50}$ (nM) |
|---|---|---|---|---|
| 359 | 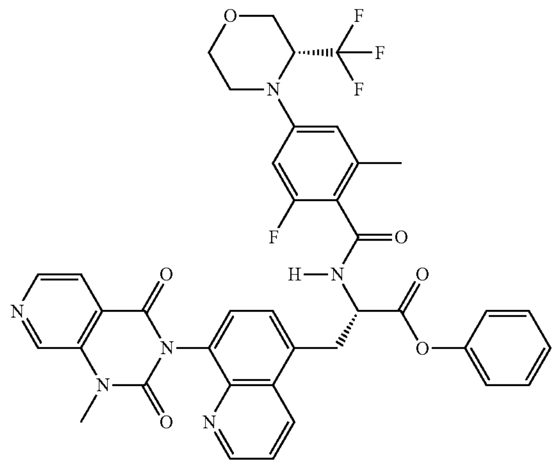 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)Oc1ccccc1] | 1H NMR (400 MHz, DMSO-d6) δ 9.22 (d, J = 7.1 Hz, 1H), 9.05 (s, 1H), 8.86 (dd, J = 4.1, 1.5 Hz, 1H), 8.76 (dd, J = 8.7, 1.5 Hz, 1H), 8.61 (d, J = 4.9 Hz, 1H), 7.93 (d, J = 4.9 Hz, 1H), 7.81 (d, J = 7.5 Hz, 1H), 7.73 (d, J = 7.6 Hz, 1H), 7.68 (dd, J = 8.6, 4.2 Hz, 1H), 7.44 (td, J = 8.4, 7.9, 1.4 Hz, 2H), 7.28 (t, J = 7.4 Hz, 1H), 7.06 (ddd, J = 8.5, 2.3, 1.1 Hz, 2H), 6.73 (d, J = 13.4 Hz, 1H), 6.70-6.64 (m, 1H), 5.05 (q, J = 7.3 Hz, 1H), 4.93-4.78 (m, 1H), 4.15 (d, J = 12.5 Hz, 1H), 3.95 (dd, J = 11.4, 3.6 Hz, 1H), 3.86 (dd, J = 14.6, 5.6 Hz, 1H), 3.72 (dd, J = 14.3, 9.9 Hz, 2H), 3.67 (s, 3H), 3.60-3.49 (m, 1H), 3.37 (d, J = 12.4 Hz, 1H), 3.26 (t, J = 12.1 Hz, 1H), 2.10 (d, J = 1.7 Hz, 3H). | 757.2 | NA |
| 360 | 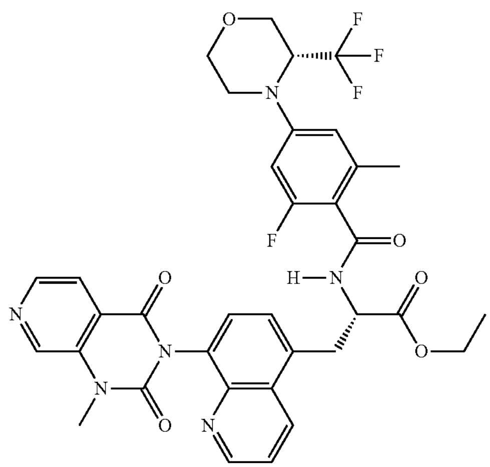 [SMILES: CCOC(=O)[C@H](Cc1ccc(-n2c(=O)c3ccncc3n(C)c2=O)c2ncccc12)NC(=O)c1c(C)cc(N2CCOC[C@@H]2C(F)(F)F)cc1F] | 1H NMR (400 MHz, DMSO-d6) δ 9.04 (s, 1H), 8.99 (d, J = 7.7 Hz, 1H), 8.84 (dd, J = 4.2, 1.4 Hz, 1H), 8.64 (dd, J = 8.7, 1.6 Hz, 1H), 8.60 (d, J = 4.9 Hz, 1H), 7.91 (dd, J = 5.0, 2.2 Hz, 1H), 7.75 (d, J = 7.5 Hz, 1H), 7.66 (dt, J = 8.6, 2.5 Hz, 2H), 6.76-6.63 (m, 2H), 4.82 (td, J = 14.4, 12.1, 5.3 Hz, 2H), 4.20-4.04 (m, 3H), 3.95 (dd, J = 11.5, 3.6 Hz, 1H), 3.80-3.66 (m, 2H), 3.65 (d, J = 1.6 Hz, 3H), 3.60-3.46 (m, 2H), 3.36 (d, J = 13.7 Hz, 1H), 3.31-3.18 (m, 1H), 2.07 (s, 3H), 1.16 (td, J = 7.1, 1.1 Hz, 3H). | 709.2 | NA |
| 361 | 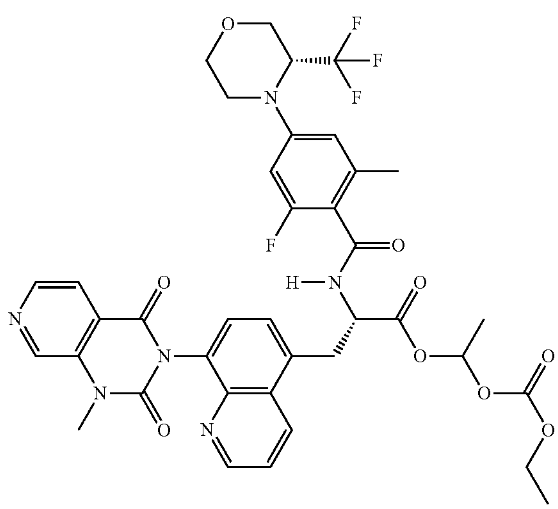 [SMILES: CCOC(=O)OC(C)OC(=O)[C@H](Cc1ccc(-n2c(=O)c3ccncc3n(C)c2=O)c2ncccc12)NC(=O)c1c(C)cc(N2CCOC[C@@H]2C(F)(F)F)cc1F] | 1H NMR (400 MHz, DMSO-d6) δ 9.05 (d, J = 5.5 Hz, 2H), 8.90-8.81 (m, 1H), 8.70-8.57 (m, 2H), 7.91 (d, J = 5.1 Hz, 1H), 7.76 (d, J = 7.6 Hz, 1H), 7.67 (d, J = 7.9 Hz, 2H), 6.74-6.64 (m, 2H), 4.86 (s, 2H), 4.35-4.06 (m, 3H), 3.95 (d, J = 11.0 Hz, 1H), 3.74 (d, J = 13.2 Hz, 6H), 3.53 (q, J = 14.3, 13.3 Hz, 2H), 3.42-3.13 (m, 2H), 2.03 (d, J = 20.9 Hz, 3H), 1.53 (d, J = 5.4 Hz, 1H), 1.38 (d, J = 5.4 Hz, 2H), 1.23 (t, J = 7.1 Hz, 3H). | 797.2 | NA |

TABLE 3-continued

| Example | Structure | 1H-NMR | M/Z [M + H]+ | α4β7 EC$_{50}$ (nM) |
|---|---|---|---|---|
| 362 | 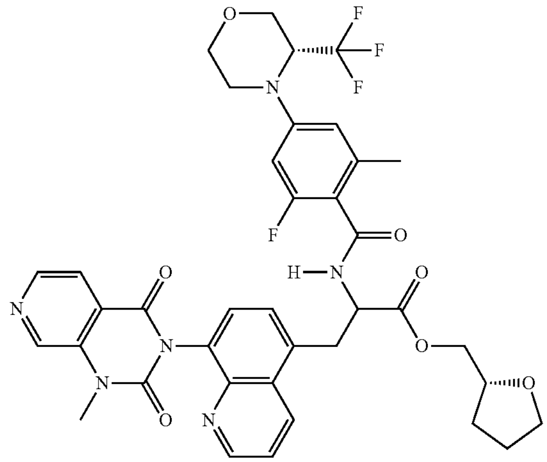 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)OC[C@H]1CCCO1] | 1H NMR (400 MHz, DMSO-d6) δ 9.03 (d, J = 13.5 Hz, 2H), 8.85 (d, J = 4.3 Hz, 1H), 8.65 (d, J = 8.7 Hz, 1H), 8.60 (d, J = 5.0 Hz, 1H), 7.96-7.88 (m, 1H), 7.77 (d, J = 7.7 Hz, 1H), 7.72-7.61 (m, 2H), 6.81-6.59 (m, 2H), 4.86 (d, J = 11.5 Hz, 2H), 4.21-4.05 (m, 2H), 3.95 (dd, J = 11.7, 3.9 Hz, 1H), 3.75 (dd, J = 15.2, 9.4 Hz, 3H), 3.66 (s, 4H), 3.36 (q, J = 13.6 Hz, 1H), 3.27 (d, J = 11.9 Hz, 1H), 2.41-2.22 (m, 1H), 2.07 (d, J = 6.2 Hz, 2H), 1.87 (ddt, J = 33.9, 14.4, 7.2 Hz, 2H), 1.76-1.36 (m, 1H). | 765.3 | NA |
| 363 | 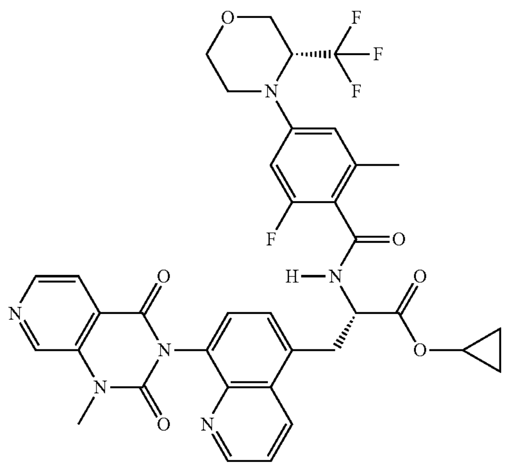 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)OC1CC1] | 1H NMR (400 MHz, DMSO-d6) δ 9.04 (s, 1H), 8.98 (d, J = 7.6 Hz, 1H), 8.83 (dd, J = 4.1, 1.5 Hz, 1H), 8.68-8.56 (m, 2H), 7.91 (dt, J = 4.9, 1.0 Hz, 1H), 7.75 (d, J = 7.6 Hz, 1H), 7.71-7.60 (m, 2H), 6.76-6.59 (m, 2H), 4.89-4.72 (m, 2H), 4.14 (dt, J = 9.3, 3.7 Hz, 2H), 3.95 (dd, J = 11.1, 3.6 Hz, 1H), 3.80-3.62 (m, 5H), 3.52 (q, J = 14.4, 13.6 Hz, 2H), 3.36 (d, J = 12.2 Hz, 1H), 3.22 (s, 1H), 2.04 (s, 3H), 0.75-0.52 (m, 4H). | 721.3 | NA |
| 364 | 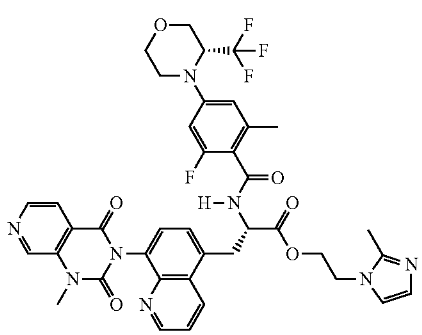 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)OCCn1ccnc1C] | 1H NMR (400 MHz, DMSO-d6) δ 9.04 (d, J = 8.2 Hz, 2H), 8.87 (d, J = 4.1 Hz, 1H), 8.64-8.57 (m, 2H), 7.91 (t, J = 4.8 Hz, 1H), 7.77 (d, 1H), 7.71-7.59 (m, 3H), 7.56 (s, 1H), 6.74-6.65 (m, 2H), 4.90-4.76 (m, 2H), 4.52-4.42 (m, 1H), 4.41-4.28 (m, 3H), 4.15 (d, J = 12.6 Hz, 1H), 3.94 (d, J = 3.5 Hz, 1H), 3.73 (d, J = 12.7 Hz, 1H), 3.69-3.60 (m, 4H), 3.59-3.47 (m, 2H), 3.34 (d, 1H), 3.25 (t, 1H), 2.53 (s, 3H), 2.03 (s, 3H). | 789.3 | NA |

TABLE 3-continued

| Example | Structure | 1H-NMR | M/Z [M + H]+ | α4β7 EC$_{50}$ (nM) |
|---|---|---|---|---|
| 365 | 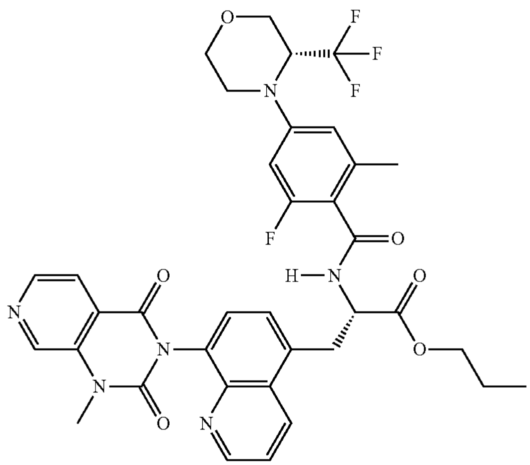 [SMILES: CCCOC(=O)[C@H](Cc1ccc(-n2c(=O)c3ccncc3n(C)c2=O)c2ncccc12)NC(=O)c1c(C)cc(N2CCOC[C@@H]2C(F)(F)F)cc1F] | 1H NMR (400 MHz, DMSO-d6) δ 9.04 (d, J = 2.1 Hz, 1H), 8.99 (d, J = 7.8 Hz, 1H), 8.89-8.79 (m, 1H), 8.67 (d, J = 8.6 Hz, 1H), 8.60 (d, J = 5.0 Hz, 1H), 7.91 (dt, J = 4.9, 2.4 Hz, 1H), 7.77 (dd, J = 7.5, 2.1 Hz, 1H), 7.71-7.63 (m, 2H), 6.76-6.61 (m, 2H), 4.84 (d, J = 9.4 Hz, 2H), 4.14 (d, J = 12.6 Hz, 1H), 4.05 (q, J = 6.7 Hz, 2H), 3.95 (d, J = 11.3 Hz, 1H), 3.73 (dd, J = 14.0, 4.4 Hz, 2H), 3.65 (d, J = 2.3 Hz, 3H), 3.54 (t, J = 8.7 Hz, 2H), 3.36 (d, J = 12.4 Hz, 1H), 3.25 (t, J = 12.6 Hz, 1H), 2.05 (s, 3H), 1.58 (h, J = 7.0 Hz, 2H), 0.88 (td, J = 7.4, 2.1 Hz, 3H). | 723.3 | NA |
| 366 | 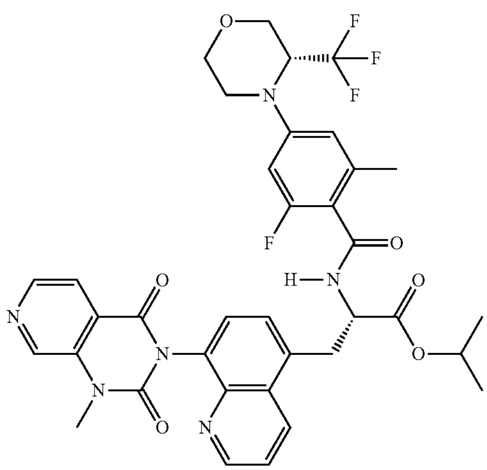 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)OC(C)C] | 1H NMR (400 MHz, DMSO-d6) δ 9.05 (s, 1H), 8.97 (d, J = 7.7 Hz, 1H), 8.84 (d, J = 4.1 Hz, 1H), 8.65 (d, J = 8.7 Hz, 1H), 8.60 (d, J = 5.0 Hz, 1H), 7.91 (d, J = 5.0 Hz, 1H), 7.76 (d, J = 7.5 Hz, 1H), 7.71-7.62 (m, 2H), 6.71 (d, J = 13.1 Hz, 1H), 6.68-6.63 (m, 1H), 4.97-4.90 (m, 1H), 4.84 (dd, J = 29.2, 20.4 Hz, 2H), 4.15 (d, J = 12.7 Hz, 1H), 3.95 (d, J = 11.3 Hz, 1H), 3.73 (d, J = 13.7 Hz, 2H), 3.66 (s, 3H), 3.53 (q, J = 13.5, 11.7 Hz, 2H), 3.36 (d, J = 12.3 Hz, 1H), 3.27 (d, J = 12.5 Hz, 1H), 2.08 (d, J = 6.7 Hz, 3H), 1.22 (d, J = 6.2 Hz, 3H), 1.13 (d, J = 6.3 Hz, 3H). | 723.3 | NA |
| 367 | 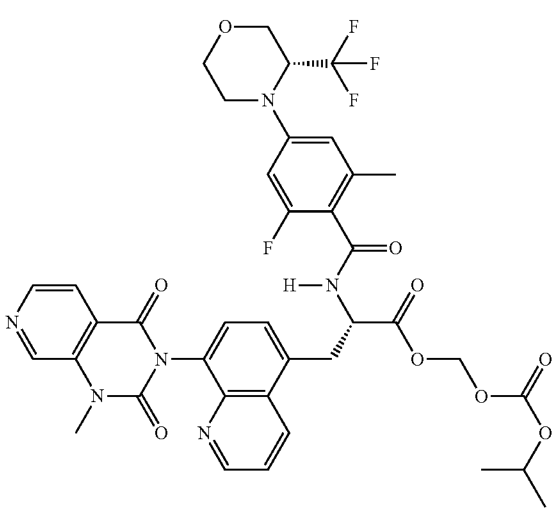 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)OCOC(=O)OC(C)C] | 1H NMR (400 MHz, DMSO-d6) δ 9.15-9.00 (m, 2H), 8.85 (d, J = 3.9 Hz, 1H), 8.67-8.57 (m, 2H), 7.91 (ddd, J = 5.0, 3.1, 0.8 Hz, 1H), 7.76 (d, J = 7.5 Hz, 1H), 7.73-7.61 (m, 2H), 5.83 (s, 2H), 4.85 (d, J = 9.2 Hz, 2H), 4.14 (d, J = 12.6 Hz, 1H), 4.06-3.88 (m, 1H), 3.84-3.68 (m, 2H), 3.65 (d, J = 2.2 Hz, 3H), 3.53 (dt, J = 14.8, 9.7 Hz, 2H), 3.36 (d, J = 12.3 Hz, 1H), 3.26 (d, J = 12.1 Hz, 1H), 2.03 (s, 3H), 1.18 (s, 9H). | 795.3 | NA |

TABLE 3-continued

| Example | Structure | 1H-NMR | M/Z [M + H]+ | α4β7 EC$_{50}$ (nM) |
|---|---|---|---|---|
| 368 | 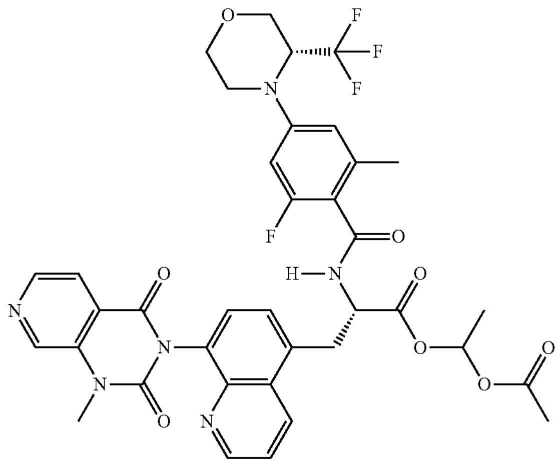 [SMILES: CC(=O)OC(C)OC(=O)[C@H](Cc1ccc(-n2c(=O)c3ccncc3n(C)c2=O)c2ncccc12)NC(=O)c1c(C)cc(N2CCOC[C@@H]2C(F)(F)F)cc1F] | 1H NMR (400 MHz, DMSO-d6) δ 9.02 (d, J = 18.4 Hz, 2H), 8.85 (d, J = 4.1 Hz, 1H), 8.63 (dd, J = 22.3, 7.3 Hz, 2H), 7.92 (d, J = 4.9 Hz, 1H), 7.77 (d, J = 7.6 Hz, 1H), 7.68 (t, J = 6.5 Hz, 2H), 6.82 (dq, J = 27.7, 5.5 Hz, 1H), 6.75-6.63 (m, 2H), 4.84 (d, J = 10.7 Hz, 2H), 4.15 (d, J = 12.7 Hz, 1H), 3.95 (d, J = 11.4 Hz, 1H), 3.81-3.61 (m, 5H), 3.53 (q, J = 13.5, 12.8 Hz, 2H), 3.36 (d, J = 12.5 Hz, 1H), 3.26 (d, J = 12.5 Hz, 1H), 2.15-1.96 (m, 6H), 1.42 (dd, J = 53.9, 5.5 Hz, 3H). | 767.2 | NA |
| 369 | 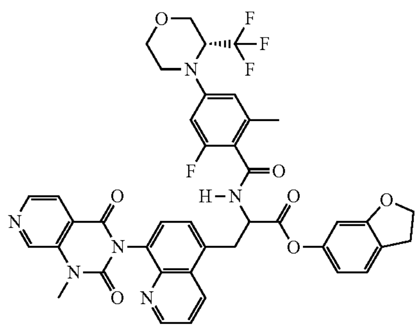 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)Oc1ccc2c(c1)OCC2] | 1H NMR (400 MHz, DMSO-d6) δ 9.19 (d, J = 7.3 Hz, 1H), 9.05 (s, 1H), 8.86 (d, J = 4.1 Hz, 1H), 8.75 (d, J = 8.6 Hz, 1H), 8.61 (d, J = 5.0 Hz, 1H), 7.92 (d, J = 5.0 Hz, 1H), 7.80 (d, J = 7.6 Hz, 1H), 7.73 (d, J = 7.7 Hz, 1H), 7.68 (dd, J = 8.7, 4.2 Hz, 1H), 7.24 (d, J = 8.0 Hz, 1H), 6.73 (d, J = 13.7 Hz, 1H), 6.67 (s, 1H), 6.56-6.47 (m, 2H) 5.00 (s, 1H) 4.90-4.79 (m, 1H), 4.59 (t, J = 8.7 Hz, 2H), 4.15 (d, J = 12.7 Hz, 1H), 3.99-3.91 (m, 1H), 3.85 (dd, J = 14.8, 5.2 Hz, 1H), 3.72 (t, J = 11.9 Hz, 2H), 3.66 (s, 3H), 3.54 (dd, J = 13.2, 9.8 Hz, 1H), 3.36 (d, J = 12.3 Hz, 1H), 3.27 (d, J = 12.0 Hz, 1H), 3.17 (t, J = 8.7 Hz, 2H), 2.08 (d, J = 7.3 Hz, 3H). | 799.2 | NA |
| 370 | 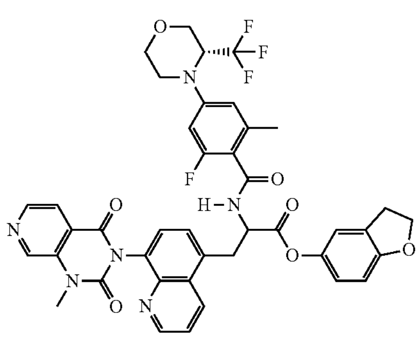 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)Oc1ccc2c(c1)CCO2] | 1H NMR (400 MHz, DMSO-d6) δ 9.20 (d, J = 7.0 Hz, 1H), 9.05 (s, 1H), 8.86 (d, J = 4.1 Hz, 1H), 8.74 (d, J = 8.5 Hz, 1H), 8.61 (d, J = 5.0 Hz, 1H), 7.93 (d, J = 5.0 Hz, 1H), 7.80 (d, J = 7.5 Hz, 1H), 7.74-7.64 (m, 2H), 6.85 (s, 1H), 6.79-6.64 (m, 4H), 4.99 (s, 1H), 4.85 (d, J = 9.7 Hz, 1H), 4.54 (t, J = 8.7 Hz, 2H), 4.15 (d, J = 12.7 Hz, 1H), 3.96 (d, J = 11.5 Hz, 2H), 3.81 (dd, J = 14.7, 6.2 Hz, 1H), 3.77-3.69 (m, 1H), 3.67 (s, 3H), 3.55 (t, J = 11.3 Hz, 1H), 3.40-3.33 (m, 1H), 3.27 (d, J = 12.5 Hz, 1H), 3.19 (t, J = 8.8 Hz, 2H), 2.12 (d, J = 6.0 Hz, 3H). | 799.2 | NA |

TABLE 3-continued

| Example | Structure | 1H-NMR | M/Z [M + H]+ | α4β7 EC$_{50}$ (nM) |
|---|---|---|---|---|
| 371 | 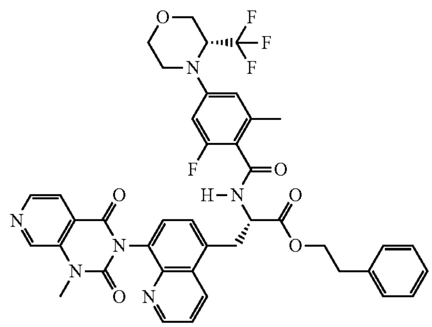 | 1H NMR (400 MHz, DMSO-d6) δ 9.05 (s, 1H), 8.99 (d, J = 7.7 Hz, 1H), 8.85 (d, J = 4.2 Hz, 1H), 8.60 (d, J = 5.0 Hz, 1H), 8.52 (d, J = 8.6 Hz, 1H), 7.91 (t, J = 4.4 Hz, 1H), 7.75 (d, J = 7.5 Hz, 1H), 7.64 (dt, J = 16.5, 5.8 Hz, 2H), 7.30 (d, J = 4.5 Hz, 5H), 7.23 (dt, J = 8.8, 4.9 Hz, 1H), 6.76-6.60 (m, 2H), 4.84 (d, J = 8.8 Hz, 1H), 4.75 (d, J = 11.5 Hz, 1H), 4.31 (m, 1H), 4.15 (d, J = 12.6 Hz, 1H), 3.95 (d, J = 9.8 Hz, 1H), 3.79-3.69 (m, 2H), 3.56 (dt, J = 20.4, 9.0 Hz, 2H), 3.48-3.31 (m, 2H), 3.31-3.18 (m, 1H), 2.90 (t, J = 6.9 Hz, 2H), 2.05 (s, 3H). | 785.2 | NA |
| 372 | 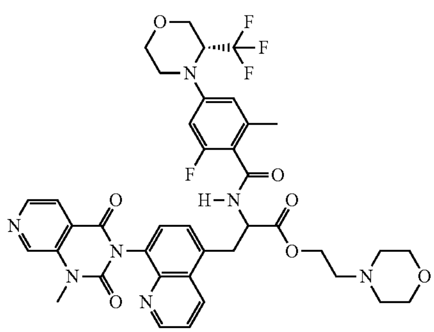 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)OCCN1CCOCC1] | 1H NMR (400 MHz, DMSO-d6) δ 9.82 (s, 1H), 9.10-9.04 (m, 2H), 8.86 (d, J = 4.2 Hz, 1H), 8.66 (d, J = 8.6 Hz, 1H), 8.61 (d, J = 5.0 Hz, 1H), 7.92 (d, J = 5.1 Hz, 1H), 7.79 (d, J = 7.5 Hz, 1H), 7.67 (dt, J = 7.9, 3.9 Hz, 2H), 6.78-6.64 (m, 2H), 4.96-4.81 (m, 2H), 4.43 (s, 1H), 4.38-4.26 (m, 1H), 4.16 (d, J = 12.6 Hz, 1H), 3.96 (d, J = 11.8 Hz, 3H), 3.74 (d, J = 12.6 Hz, 2H), 3.65-3.51 (m, 4H), 3.37 (d, J = 12.0 Hz, 4H), 3.27 (d, J = 13.6 Hz, 2H), 3.10 (d, J = 43.0 Hz, 2H), 2.10 (d, J = 2.4 Hz, 3H). | 794.3 | NA |
| 373 | 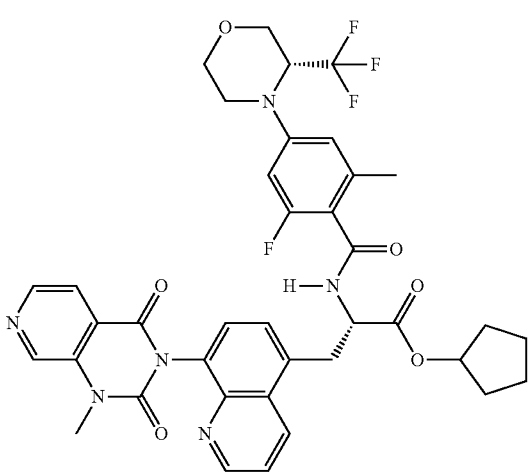 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)OC1CCCC1] | 1H NMR (400 MHz, DMSO-d6) δ 9.04 (s, 1H), 8.95 (d, J = 7.7 Hz, 1H), 8.84 (d, J = 4.1 Hz, 1H), 8.65 (d, J = 8.8 Hz, 1H), 8.60 (d, J = 4.8 Hz, 1H), 7.91 (d, J = 4.8 Hz, 1H), 7.76 (d, J = 7.5 Hz, 1H), 7.67 (d, J = 6.7 Hz, 2H), 6.71 (d, J = 13.1 Hz, 1H), 6.66 (s, 1H), 5.16-5.10 (m, 1H), 4.88-4.75 (m, 2H), 4.15 (d, J = 12.8 Hz, 1H), 3.95 (d, J = 12.5 Hz, 1H), 3.76-3.67 (m, 2H), 3.65 (s, 3H), 3.58-3.46 (m, 2H), 3.36 (d, J = 12.1 Hz, 1H), 3.27 (d, J = 11.5 Hz, 1H), 2.04 (s, 2H), 1.90-1.75 (m, 2H), 1.72-1.50 (m, 6H). | 749.3 | NA |

TABLE 3-continued

| Example | Structure | 1H-NMR | M/Z [M + H]+ | α4β7 EC$_{50}$ (nM) |
| --- | --- | --- | --- | --- |
| 374 | 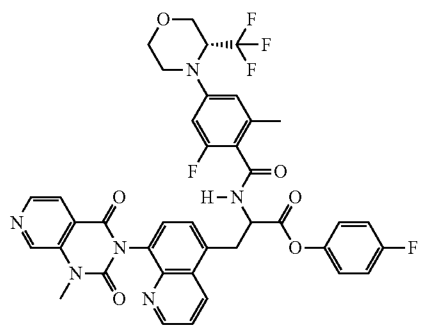 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)Oc1ccc(F)cc1] | 1H NMR (400 MHz, DMSO-d6) δ 9.23 (d, J = 7.0 Hz, 1H), 9.05 (s, 1H), 8.85 (d, J = 4.1 Hz, 1H), 8.75 (d, J = 8.6 Hz, 1H), 8.61 (d, J = 5.0 Hz, 1H), 7.93 (t, J = 4.4 Hz, 1H), 7.80 (d, J = 7.5 Hz, 1H), 7.72 (d, J = 7.7 Hz, 1H), 7.68 (dd, J = 8.9, 4.2 Hz, 1H), 7.26 (t, J = 8.6 Hz, 2H), 7.14-7.02 (m, 2H), 6.74 (d, J = 13.3 Hz, 1H), 6.68 (s, 1H), 5.03 (s, 1H), 4.85 (d, J = 9.4 Hz, 1H), 4.15 (d, J = 12.7 Hz, 1H), 3.95 (d, J = 11.2 Hz, 1H), 3.84 (d, J = 10.6 Hz, 1H), 3.74 (d, J = 13.2 Hz, 2H), 3.67 (s, 3H), 3.55 (t, J = 11.7 Hz, 1H), 3.37 (d, J = 12.2 Hz, 1H), 3.27 (d, J = 12.8 Hz, 1H), 2.11 (d, J = 6.3 Hz, 3H). | 775.2 | NA |
| 375 | 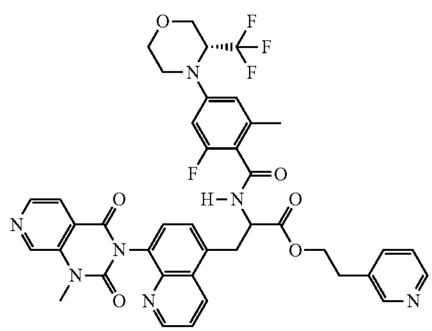 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)OCCc1cccnc1] | 1H NMR (400 MHz, DMSO-d6) δ 9.05 (s, 1H), 9.00 (d, J = 7.6 Hz, 1H), 8.86 (d, J = 4.2 Hz, 1H), 8.75 (s, 1H), 8.68 (d, J = 5.3 Hz, 1H), 8.60 (d, J = 5.0 Hz, 1H), 8.55 (d, J = 8.6 Hz, 1H), 8.25 (s, 1H), 7.91 (t, J = 3.7 Hz, 1H), 7.76 (d, J = 7.6 Hz, 2H), 7.65 (td, J = 9.1, 3.2 Hz, 2H), 6.76-6.62 (m, 2H), 4.92-4.70 (m, 2H), 4.45-4.28 (m, 2H), 4.15 (d, J = 12.7 Hz, 1H), 3.95 (d, J = 10.9 Hz, 1H), 3.73 (d, J = 12.6 Hz, 1H), 3.65 (s, 3H), 3.63-3.44 (m, 2H), 3.36 (d, J = 12.3 Hz, 1H), 3.25 (t, J = 12.3 Hz, 1H), 3.03 (d, J = 6.2 Hz, 2H), 2.04 (d, J = 5.4 Hz, 3H). | 786.2 | NA |
| 376 | 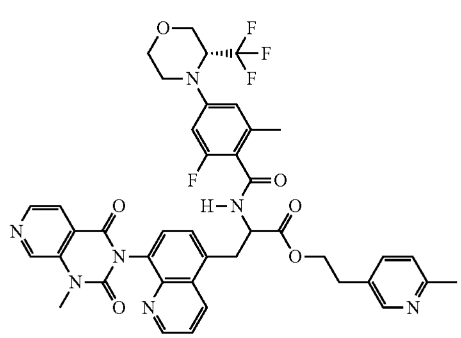 [SMILES: Cc1ccc(CCOC(=O)C(Cc2ccc(-n3c(=O)c4ccncc4n(C)c3=O)c3ncccc23)NC(=O)c2c(C)cc(N3CCOC[C@@H]3C(F)(F)F)cc2F)cn1] | 1H NMR (400 MHz, DMSO-d6) δ 9.05 (d, J = 4.4 Hz, 1H), 9.01 (d, J = 7.4 Hz, 1H), 8.86 (d, J = 4.4 Hz, 1H), 8.68 (s, 1H), 8.59 (dd, J = 14.4, 6.8 Hz, 2H), 8.30 (d, J = 8.3 Hz, 1H), 7.90 (dd, J = 4.8, 2.4 Hz, 1H), 7.77 (d, J = 8.0 Hz, 2H), 7.66 (td, J = 9.4, 8.6, 5.8 Hz, 2H), 6.79-6.60 (m, 3H), 4.94-4.69 (m, 2H), 4.38 (s, 1H), 4.31 (dt, J = 11.4, 6.2 Hz, 1H), 4.15 (d, J = 12.6 Hz, 1H), 3.95 (d, J = 10.9 Hz, 1H), 3.73 (d, J = 12.4 Hz, 1H), 3.65 (s, 3H), 3.63-3.45 (m, 3H), 3.36 (d, J = 12.4 Hz, 1H), 3.27 (d, J = 12.4 Hz, 1H), 3.12-2.92 (m, 2H), 2.63 (s, 3H), 2.04 (d, J = 4.7 Hz, 3H). | 800.2 | NA |

TABLE 3-continued

| Example | Structure | 1H-NMR | M/Z [M + H]+ | α4β7 EC$_{50}$ (nM) |
|---|---|---|---|---|
| 377 | 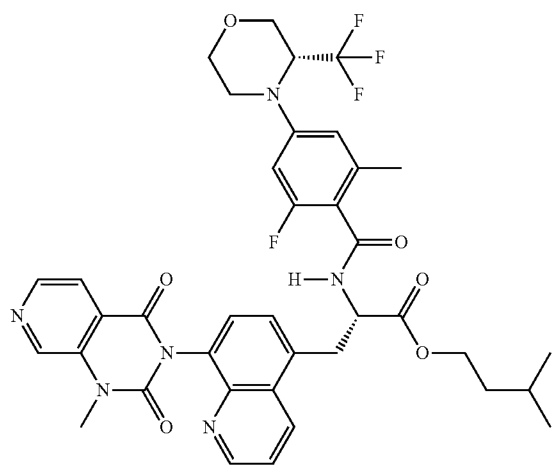 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)OCCC(C)C] | 1H NMR (400 MHz, DMSO-d6) δ 9.05 (d, J = 2.6 Hz, 1H), 9.01-8.94 (m, 1H), 8.84 (d, J = 3.4 Hz, 1H), 8.65 (d, J = 8.6 Hz, 1H), 8.60 (t, J = 3.7 Hz, 1H), 7.91 (q, J = 3.7 Hz, 1H), 7.81-7.73 (m, 1H), 7.68 (dd, J = 8.0, 2.9 Hz, 2H), 6.80-6.62 (m, 2H), 4.83 (s, 2H), 4.20-4.05 (m, 3H), 3.95 (d, J = 11.4 Hz, 1H), 3.79-3.60 (m, 5H), 3.54 (s, 2H), 3.36 (d, J = 12.5 Hz, 1H), 3.27 (d, J = 12.4 Hz, 1H), 2.05 (s, 3H), 1.66 (q, J = 6.8 Hz, 1H), 1.51-1.35 (m, 2H), 0.89 (dd, J = 6.8, 2.3 Hz, 6H). | 751.3 | NA |
| 378 | 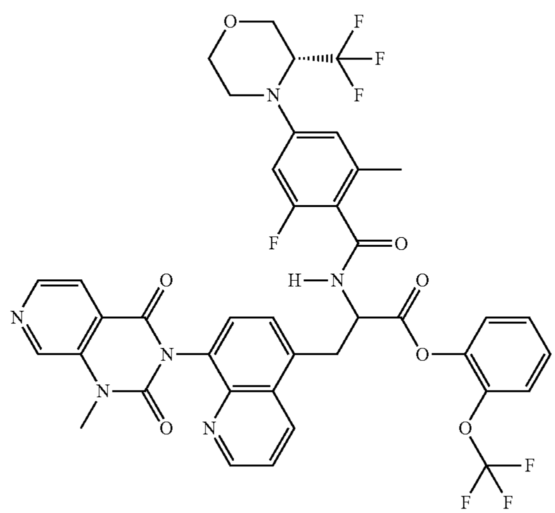 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)Oc1ccccc1OC(F)(F)F] | 1H NMR (400 MHz, DMSO-d6) δ 9.23 (d, J = 7.7 Hz, 1H), 9.06 (s, 1H), 8.87 (d, J = 4.1 Hz, 1H), 8.71 (d, J = 8.7 Hz, 1H), 8.61 (d, J = 5.0 Hz, 1H), 7.93 (d, J = 5.0 Hz, 1H), 7.82 (d, J = 7.5 Hz, 1H), 7.77 (d, J = 7.8 Hz, 1H), 7.71 (dd, J = 8.6, 4.2 Hz, 1H), 7.57 (d, J = 8.0 Hz, 1H), 7.54-7.41 (m, 2H), 7.29 (d, J = 8.1, 2.7 Hz, 1H), 6.72 (dd, J = 13.2, 6.7 Hz, 1H), 6.66 (s, 1H), 5.24-.12 (m, 1H), 4.91-4.76 (m, 1H), 4.14 (d, J = 12.6 Hz, 1H), 4.00-3.87 (m, 2H), 3.72 (d, 2H), 3.67 (s, 3H), 3.54 (t, J = 3.0 Hz, 1H), 3.34 (d, 1H), 3.25 (t, 1H), 2.05 (d, J = 7.6 Hz, 3H). | 841.1 | NA |
| 379 | 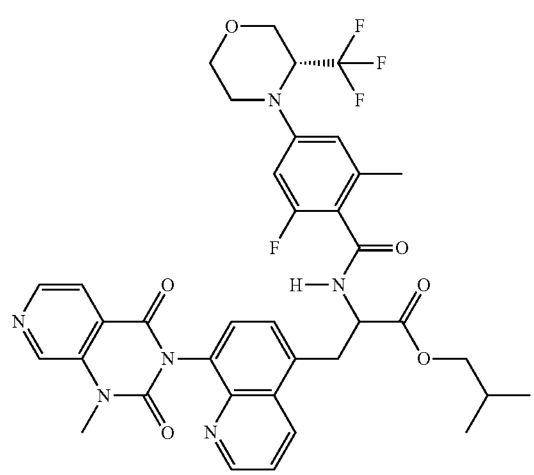 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)OCC(C)C] | 1H NMR (400 MHz, DMSO-d6) δ 9.04 (s, 1H), 8.99 (d, J = 7.8 Hz, 1H), 8.84 (d, J = 4.2 Hz, 1H), 8.65 (d, J = 8.7 Hz, 1H), 8.60 (d, J = 5.0 Hz, 1H), 7.91 (d, J = 4.3 Hz, 1H), 7.76 (d, J = 7.6 Hz, 1H), 7.67 (d, J = 8.0 Hz, 2H), 6.71 (d, J = 13.4 Hz, 1H), 6.65 (s, 1H), 4.86 (s, 2H), 4.14 (d, J = 12.7 Hz, 1H), 3.98-3.82 (m, 3H), 3.73 (d, J = 13.3 Hz, 2H), 3.66 (s, 3H), 3.53 (d, J = 9.2 Hz, 2H), 3.36 (d, J = 12.5 Hz, 1H), 3.27 (d, J = 12.7 Hz, 1H), 2.03 (d, J = 6.9 Hz, 3H), 1.89 (p, J = 6.6 Hz, 1H), 0.90 (d, J = 6.7 Hz, 6H). | 737.3 | NA |

TABLE 3-continued

| Example | Structure | 1H-NMR | M/Z [M + H]+ | α4β7 EC$_{50}$ (nM) |
|---|---|---|---|---|
| 380 | 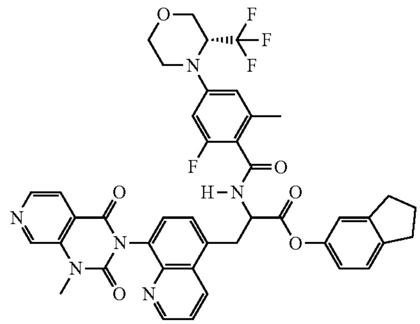 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)Oc1ccc2c(c1)CCC2] | 1H NMR (400 MHz, DMSO-d6) δ 9.20 (d, J = 7.1 Hz, 1H), 9.05 (s, 1H), 8.90-8.82 (m, 1H), 8.75 (d, J = 8.6 Hz, 1H), 8.64-8.57 (m, 1H), 7.92 (d, J = 5.0 Hz, 1H), 7.81 (d, J = 7.6 Hz, 1H), 7.73 (d, J = 7.8 Hz, 1H), 7.68 (dd, J = 8.7, 4.2 Hz, 1H), 7.24 (d, J = 8.1 Hz, 1H), 6.88 (s, 1H), 6.81-6.69 (m, 2H), 6.68 (s, 1H), 5.00 (d, J = 8.7 Hz, 2H), 4.85 (d, J = 9.7 Hz, 1H), 4.15 (d, J = 12.6 Hz, 1H), 3.95 (d, J = 11.5 Hz, 1H), 3.84 (dd, J = 14.6, 5.7 Hz, 1H), 3.73 (d, J = 10.6 Hz, 2H), 3.67 (s, 3H), 3.55 (t, J = 11.4 Hz, 1H), 3.42-3.32 (m, 1H), 3.26 (t, J = 12.1 Hz, 1H), 2.85 (q, J = 8.1 Hz, 4H), 2.11 (d, J = 6.3 Hz, 3H), 2.04 (p, J = 7.5 Hz, 2H). | 797.3 | NA |
| 381 | 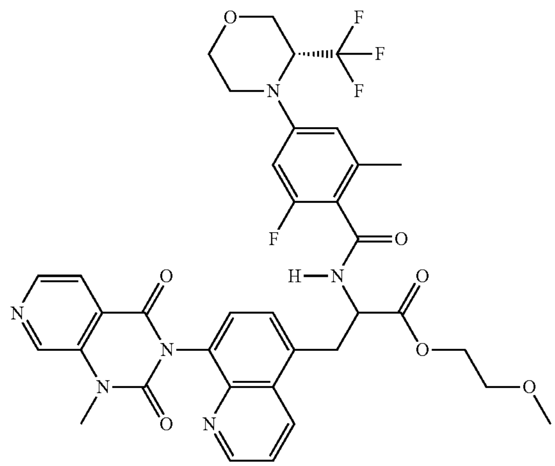 [SMILES: COCCOC(=O)C(Cc1ccc(-n2c(=O)c3ccncc3n(C)c2=O)c2ncccc12)NC(=O)c1c(C)cc(N2CCOC[C@@H]2C(F)(F)F)cc1F] | 1H NMR (400 MHz, DMSO-d6) δ 9.12-8.95 (m, 2H), 8.84 (d, J = 4.2 Hz, 1H), 8.65 (d, J = 8.7 Hz, 1H), 8.60 (d, J = 5.1 Hz, 1H), 7.97-7.86 (m, 1H), 7.76 (d, J = 7.5 Hz, 1H), 7.67 (d, J = 7.8 Hz, 2H), 6.71 (dd, J = 20.6, 7.9 Hz, 2H), 4.82 (d, J = 8.7 Hz, 2H), 4.21 (t, J = 5.0 Hz, 2H), 4.15 (d, J = 12.6 Hz, 1H), 3.95 (d, J = 11.2 Hz, 1H), 3.73 (d, J = 14.0 Hz, 2H), 3.52 (d, J = 7.9 Hz, 4H), 3.36 (d, J = 12.6 Hz, 1H), 3.27 (d, J = 1.5 Hz, 4H), 2.09 (d, J = 6.3 Hz, 3H). | 739.2 | NA |
| 382 | 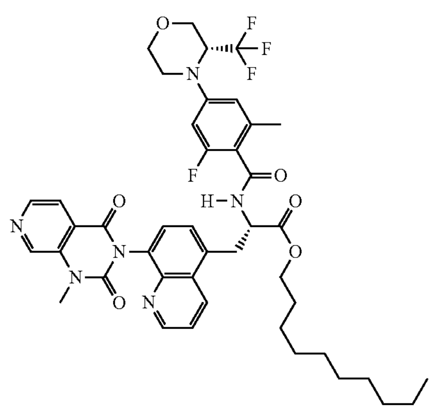 [SMILES: CCCCCCCCCCOC(=O)[C@H](Cc1ccc(-n2c(=O)c3ccncc3n(C)c2=O)c2ncccc12)NC(=O)c1c(C)cc(N2CCOC[C@@H]2C(F)(F)F)cc1F] | 1H NMR (400 MHz, DMSO-d6) δ 9.05 (s, 1H), 8.98 (d, J = 7.7 Hz, 1H), 8.86 (d, J = 4.1 Hz, 1H), 8.67 (d, J = 8.6 Hz, 1H), 8.60 (d, J = 5.0 Hz, 1H), 7.91 (t, J = 4.2 Hz, 1H), 7.77 (d, J = 7.5 Hz, 1H), 7.68 (d, J = 7.7 Hz, 2H), 6.81-6.57 (m, 2H), 4.84 (dt, J = 10.6, 6.3 Hz, 2H), 4.15 (d, J = 12.7 Hz, 1H), 4.07 (q, J = 6.4 Hz, 2H), 3.95 (dd, J = 11.5, 3.5 Hz, 1H), 3.72 (dd, J = 14.4, 5.6 Hz, 2H), 3.53 (tt, J = 9.3, 5.5 Hz, 2H), 3.36 (d, J = 12.4 Hz, 1H), 3.30-3.18 (m, 1H), 2.06 (s, 3H), 1.55 (p, J = 6.8 Hz, 2H), 1.25 (d, J = 13.8 Hz, 14H), 0.83 (t, J = 6.5 Hz, 3H). | 821.4 | NA |

TABLE 3-continued

| Example | Structure | 1H-NMR | M/Z [M + H]+ | α4β7 EC$_{50}$ (nM) |
|---|---|---|---|---|
| 383 | 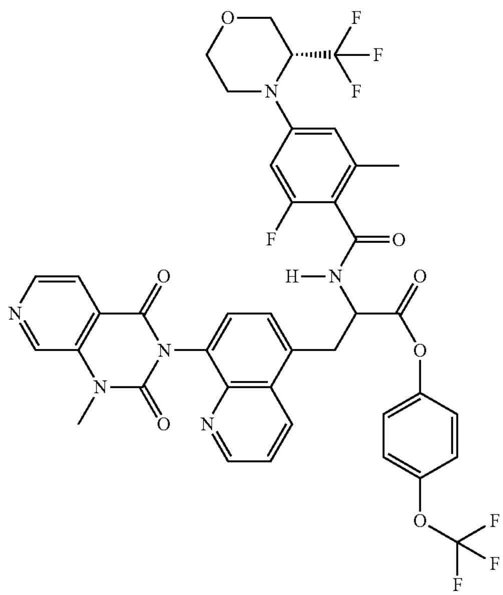 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)Oc1ccc(OC(F)(F)F)cc1] | 1H NMR (400 MHz, DMSO-d6) δ 9.26 (d, J = 6.9 Hz, 1H), 9.06 (s, 1H), 8.86 (d, J = 4.1 Hz, 1H), 8.77 (d, J = 8.7 Hz, 1H), 8.61 (d, J = 5.0 Hz, 1H), 7.93 (d, J = 4.9 Hz, 1H), 7.81 (d, J = 7.6 Hz, 1H), 7.77-7.65 (m, 2H), 7.45 (d, J = 8.4 Hz, 2H), 7.16 (dd, J = 9.0, 3.5 Hz, 2H), 6.78-6.71 (m, 1H), 6.68 (s, 1H), 5.04 (d, J = 7.2 Hz, 1H), 4.91-4.79 (m, 1H), 4.15 (d, J = 12.6 Hz, 1H), 3.95 (d, J = 11.3 Hz, 1H), 3.85 (d, J = 9.5 Hz, 1H), 3.74 (d, J = 13.1 Hz, 2H), 3.67 (s, 3H), 3.55 (t, J = 11.5 Hz, 1H), 3.37 (d, J = 12.4 Hz, 1H), 3.26 (t, J = 12.4 Hz, 1H), 2.12 (d, J = 6.2 Hz, 3H). | 841.1 | NA |
| 384 | 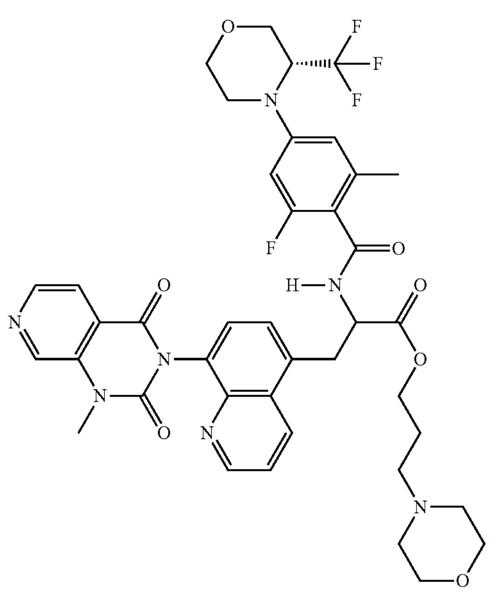 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)OCCCN1CCOCC1] | 1H NMR (400 MHz, DMSO-d6) δ 9.66 (s, 1H), 9.07 (d, J = 7.2 Hz, 2H), 8.86 (s, 1H), 8.63 (dd, J = 16.9, 6.9 Hz, 2H), 7.91 (s, 1H), 7.78 (d, J = 7.6 Hz, 1H), 7.67 (d, J = 7.1 Hz, 2H), 6.79-6.65 (m, 2H), 4.84 (s, 2H), 4.16 (d, J = 12.5 Hz, 2H), 4.08-3.90 (m, 4H), 3.79-3.48 (m, 8H), 3.37 (d, J = 11.6 Hz, 3H), 3.27 (d, J = 13.1 Hz, 1H), 3.13-2.92 (m, 5H), 2.11 (d, J = 5.1 Hz, 3H), 1.94 (s, 2H). | 808.0 | NA |

TABLE 3-continued

| Example | Structure | 1H-NMR | M/Z [M + H]+ | α4β7 EC$_{50}$ (nM) |
|---|---|---|---|---|
| 385 | 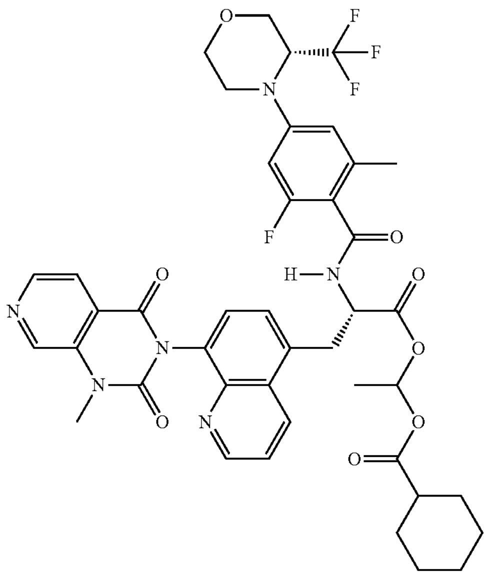 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)OC(C)OC(=O)C1CCCCC1] | 1H NMR (400 MHz, DMSO-d6) δ 9.03 (d, J = 16.1 Hz, 2H), 8.86 (d, J = 4.2 Hz, 1H), 8.69-8.56 (m, 2H), 7.92 (d, J = 4.7 Hz, 1H), 7.78 (d, J = 7.6 Hz, 1H), 7.69 (dd, J = 7.9, 4.8 Hz, 2H), 6.71 (dt, J = 24.9, 7.3 Hz, 3H), 4.84 (d, J = 9.1 Hz, 2H), 4.15 (d, J = 12.7 Hz, 1H), 3.95 (d, J = 11.4 Hz, 1H), 3.78-3.62 (m, 5H), 3.61-3.43 (m, 2H), 3.36 (d, J = 12.5 Hz, 1H), 3.27 (d, J = 12.6 Hz, 1H), 2.34 (ddd, J = 20.9, 13.2, 7.6 Hz, 1H), 2.08 (s, 1H), 2.02 (s, 1H), 1.81 (s, 4H), 1.74 (d, J = 5.7 Hz, 1H), 1.65 (s, 2H), 1.57 (dd, J = 10.5, 4.6 Hz, 1H), 1.50 (d, J = 5.4 Hz, 1H), 1.30 (tq, J = 20.3, 9.9, 9.4 Hz, 6H). | 835.0 | NA |
| 386 | 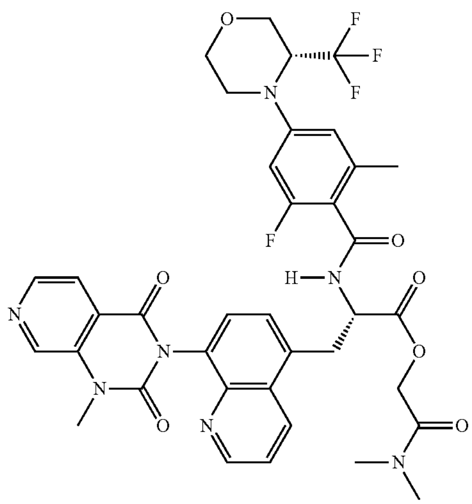 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)OCC(=O)N(C)C] | 1H NMR (400 MHz, DMSO-d6) δ 9.06 (d, J = 7.0 Hz, 2H), 8.86 (d, J = 4.2 Hz, 1H), 8.66 (d, J = 8.6 Hz, 1H), 8.60 (d, J = 4.9 Hz, 1H), 7.92 (t, J = 4.6 Hz, 1H), 7.80-7.66 (m, 3H), 6.73-6.62 (m, 2H), 5.06 (d, J = 14.8 Hz, 1H), 4.95-4.77 (m, 3H), 4.15 (d, J = 12.6 Hz, 1H), 4.01-3.90 (m, 2H), 3.73 (d, J = 12.7 Hz, 1H), 3.66 (t, J = 2.0 Hz, 3H), 3.53 (qd, J = 14.9, 13.4, 6.7 Hz, 2H), 3.36 (d, J = 12.3 Hz, 1H), 3.25 (t, J = 12.5 Hz, 1H), 2.98 (s, 3H), 2.88 (s, 3H), 2.02 (s, 3H). | 766.6 | NA |
| 387 | 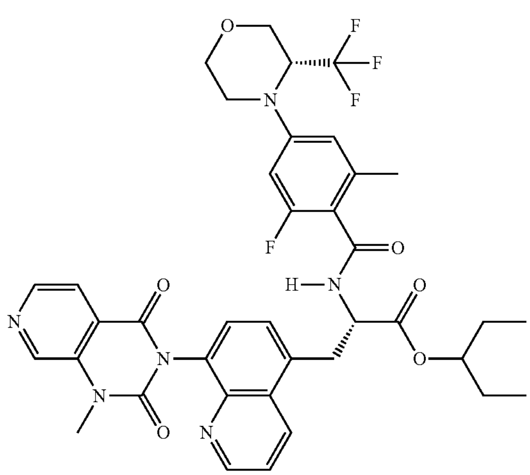 [SMILES: CCC(CC)OC(=O)[C@H](Cc1ccc(-n2c(=O)c3ccncc3n(C)c2=O)c2ncccc12)NC(=O)c1c(C)cc(N2CCOC[C@@H]2C(F)(F)F)cc1F] | 1H NMR (400 MHz, DMSO-d6) δ 9.05 (s, 1H), 8.98 (d, J = 7.9 Hz, 1H), 8.85 (d, J = 4.2 Hz, 1H), 8.65 (d, J = 8.7 Hz, 1H), 8.60 (d, J = 5.0 Hz, 1H), 7.91 (dd, J = 5.1, 2.5 Hz, 1H), 7.76 (d, J = 7.5 Hz, 1H), 7.69 (d, J = 7.6 Hz, 2H), 6.74-6.61 (m, 2H), 4.86 (s, 2H), 4.75 (q, J = 6.7, 6.2 Hz, 1H), 4.15 (d, J = 12.6 Hz, 1H), 3.95 (d, J = 10.2 Hz, 1H), 3.73 (d, J = 13.3 Hz, 2H), 3.53 (q, J = 11.6 Hz, 2H), 3.36 (d, J = 12.7 Hz, 1H), 3.25 (t, J = 12.7 Hz, 1H), 2.03 (s, 3H), 1.54 (dtt, J = 29.8, 14.0, 7.1 Hz, 4H), 0.89 (t, J = 7.4 Hz, 3H), 0.82 (t, J = 7.5 Hz, 3H). | 751.3 | NA |

TABLE 3-continued

| Example | Structure | 1H-NMR | M/Z [M + H]+ | α4β7 EC$_{50}$ (nM) |
|---|---|---|---|---|
| 388 | 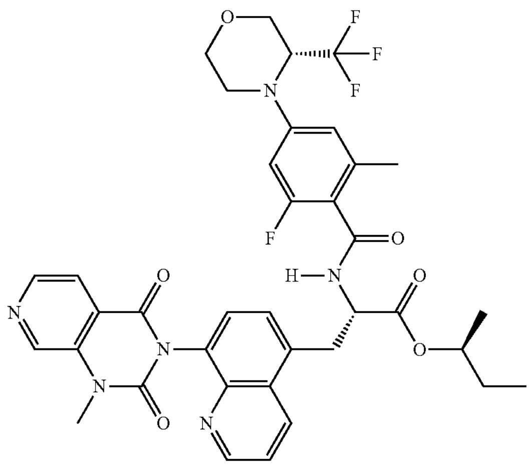 [SMILES: CC[C@H](C)OC(=O)[C@H](Cc1ccc(-n2c(=O)c3ccncc3n(C)c2=O)c2ncccc12)NC(=O)c1c(C)cc(N2CCOC[C@@H]2C(F)(F)F)cc1F] | 1H NMR (400 MHz, DMSO-d6) δ 9.05 (s, 1H), 8.98 (d, J = 8.0 Hz, 1H), 8.86-8.83 (m, 1H), 8.65 (d, J = 9.0 Hz, 1H), 8.60 (d, J = 5.1 Hz, 1H), 7.91 (d, J = 4.9 Hz, 1H), 7.76 (d, J = 7.6 Hz, 1H), 7.68 (d, J = 7.9 Hz, 2H), 6.71 (d, J = 13.3 Hz, 1H), 6.67 (s, 1H), 4.82 (d, J = 22.8 Hz, 3H), 4.15 (d, J = 12.6 Hz, 1H), 3.95 (d, J = 13.7 Hz, 1H), 3.76-3.68 (m, 2H), 3.65 (s, 3H), 3.53 (q, J = 11.1, 10.3 Hz, 2H), 3.36 (d, J = 13.6 Hz, 1H), 3.30-3.20 (m, 1H), 2.07 (s, 3H), 1.58-1.50 (m, 2H), 1.07 (d, J = 6.2 Hz, 3H), 0.87 (t, J = 7.3 Hz, 3H). | 737.2 | NA |
| 389 | 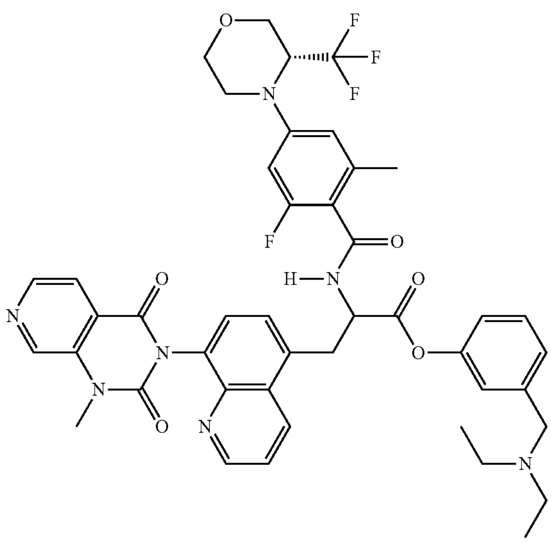 [SMILES: CCN(CC)Cc1cccc(OC(=O)C(Cc2ccc(-n3c(=O)c4ccncc4n(C)c3=O)c3ncccc23)NC(=O)c2c(C)cc(N3CCOC[C@@H]3C(F)(F)F)cc2F)c1] | 1H NMR (400 MHz, DMSO-d6) δ 9.33 (s, 1H), 9.26 (d, J = 6.8 Hz, 1H), 9.06 (s, 1H), 8.86 (d, J = 4.1 Hz, 1H), 8.73 (d, J = 8.6 Hz, 1H), 8.61 (d, J = 4.9 Hz, 1H), 7.92 (d, J = 5.1 Hz, 1H), 7.81 (d, J = 7.6 Hz, 1H), 7.74 (d, J = 7.6 Hz, 1H), 7.68 (dd, J = 8.9, 4.1 Hz, 1H), 7.55 (t, J = 7.9 Hz, 1H), 7.44 (d, J = 7.8 Hz, 1H), 7.25 (s, 1H), 7.13 (d, J = 8.3 Hz, 1H), 6.74 (d, J = 13.4 Hz, 1H), 6.69 (s, 1H), 5.04 (d, J = 8.3 Hz, 1H), 4.85 (d, J = 9.1 Hz, 1H), 4.35 (d, J = 5.3 Hz, 2H), 4.16 (d, J = 12.7 Hz, 1H), 3.96 (d, J = 11.1 Hz, 1H), 3.90-3.80 (m, 1H), 3.76 (t, J = 12.0 Hz, 2H), 3.67 (s, 3H), 3.55 (t, J = 11.5 Hz, 1H), 3.37 (d, J = 12.2 Hz, 1H), 3.27 (d, J = 12.4 Hz, 1H), 3.08 (s, 4H), 2.13 (d, J = 5.0 Hz, 3H), 1.22 (t, J = 7.2 Hz, 6H). | 842.3 | NA |
| 390 | 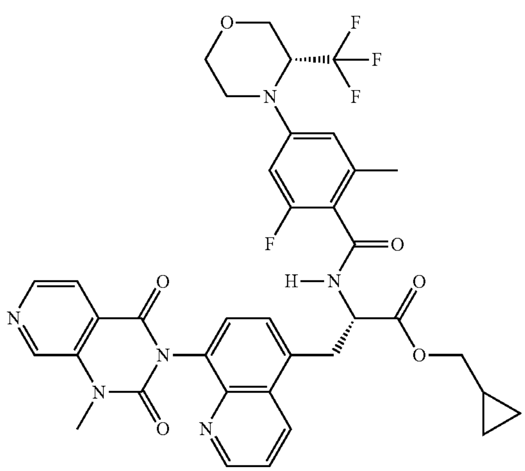 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)OCC1CC1] | 1H NMR (400 MHz, DMSO-d6) δ 9.02 (d, J = 19.3 Hz, 2H), 8.86 (d, J = 4.1 Hz, 1H), 8.69 (d, J = 8.7 Hz, 1H), 8.60 (d, J = 5.0 Hz, 1H), 7.92 (dt, J = 4.8, 2.1 Hz, 1H), 7.78 (d, J = 7.4 Hz, 1H), 7.72-7.60 (m, 2H), 6.75-6.57 (m, 2H), 4.84 (d, J = 7.6 Hz, 2H), 4.15 (d, J = 12.7 Hz, 1H), 3.94 (t, J = 7.0 Hz, 3H), 3.76-3.59 (m, 5H), 3.54 (dd, J = 13.9, 10.1 Hz, 2H), 3.31 (dd, J = 36.7, 12.3 Hz, 2H), 2.09 (s, 3H), 1.10-0.98 (m, 1H), 0.51 (d, J = 7.9 Hz, 2H), 0.27 (d, J = 4.5 Hz, 2H). | 735.3 | NA |

TABLE 3-continued

| Example | Structure | 1H-NMR | M/Z [M + H]+ | α4β7 EC$_{50}$ (nM) |
|---|---|---|---|---|
| 391 | 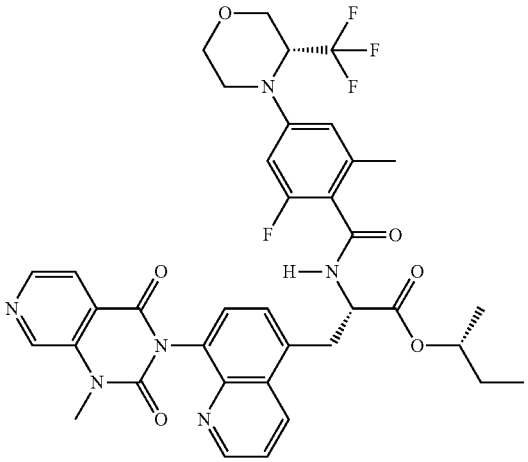 | 1H NMR (400 MHz, DMSO-d6) δ 9.04 (s, 1H), 8.96 (d, J = 7.9 Hz, 1H), 8.84 (d, J = 4.1 Hz, 1H), 8.65 (d, J = 8.7 Hz, 1H), 8.60 (d, J = 4.9 Hz, 1H),7.91 (d, J = 4.7 Hz, 1H), 7.76 (d, J = 7.2 Hz, 1H), 7.68 (d, J = 7.5 Hz, 2H), 6.72 (s, 1H), 6.65 (s, 1H), 4.88-4.79 (m, 3H), 4.15 (d, J = 12.5 Hz, 1H), 3.95 (d, J = 10.8 Hz, 1H), 3.75 (s, 2H), 3.65 (s, 3H), 3.56-3.48 (m, 2H), 3.36 (d, J = 10.2 Hz, 1H), 3.25 (t, J = 11.4 Hz, 1H), 2.04 (s, 3H), 1.58-1.47 (m, 2H), 1.22 (d, J = 6.1 Hz, 3H), 0.87-0.81 (m, 3H). | 737.2 | NA |
| 392 | 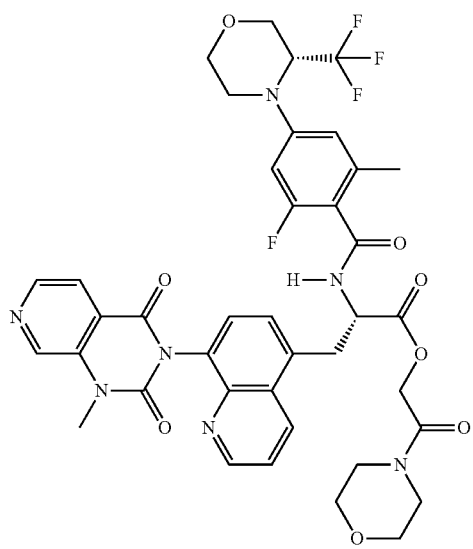 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)OCC(=O)N1CCOCC1] | 1H NMR (400 MHz, DMSO-d6) δ 9.06 (d, J = 7.8 Hz, 2H), 8.86 (d, J = 4.1 Hz, 1H), 8.64 (d, J = 8.7 Hz, 1H), 8.60 (d, J = 5.1 Hz, 1H), 7.91 (d, J = 4.9 Hz, 1H), 7.76 (dd, J = 9.5, 7.6 Hz, 2H), 7.71-7.67 (m, 1H), 6.69 (d, J = 13.7 Hz, 1H), 6.66 (s, 1H), 5.08 (d, J = 14.9 Hz, 1H), 4.92 (d, J = 14.9 Hz, 2H), 4.85 (d, J = 16.2 Hz, 2H), 4.15 (d, J = 12.6 Hz, 1H), 3.97 (s, 1H), 3.93 (s, 1H), 3.73 (d, J = 12.7 Hz, 1H), 3.66 (d, J = 2.3 Hz, 3H), 3.64-3.55 (m, 4H), 3.48 (dd, J = 23.3, 15.5 Hz, 5H), 3.36 (d, J = 12.4 Hz, 1H), 3.26 (d, J = 12.6 Hz, 1H), 2.02 (s, 3H). | 808.3 | NA |
| 393 | 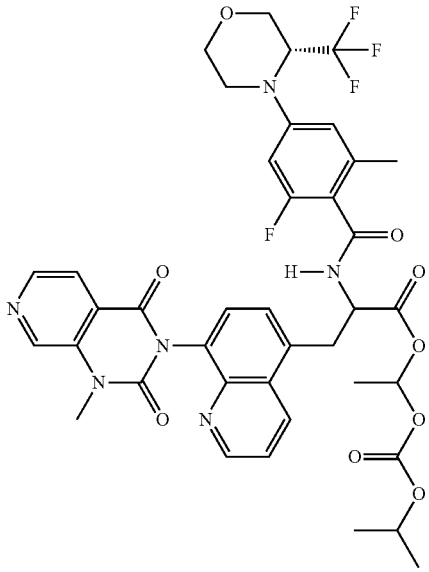 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)OC(C)OC(=O)OC(C)C] | 1H NMR (400 MHz, DMSO-d6) δ 9.02 (d, J = 16.9 Hz, 2H), 8.85 (d, J = 3.9 Hz, 1H), 8.66-8.57 (m, 2H), 7.92 (d, J = 4.9 Hz, 1H), 7.81-7.73 (m, 1H), 7.68 (d, J = 8.8 Hz, 2H), 6.71-6.62 (m, 2H), 4.93-4.75 (m, 3H), 4.15 (d, J = 12.6 Hz, 1H), 3.95 (d, J = 11.1 Hz, 1H), 3.73 (d, J = 13.5 Hz, 6H), 3.53 (q, J = 14.6, 13.8 Hz, 2H), 3.36 (d, J = 12.8 Hz, 1H), 3.26 (d, J = 12.5 Hz, 1H), 2.03 (d, J = 23.8 Hz, 3H), 1.57-1.31 (m, 3H), 1.25 (dd, J = 6.3, 2.9 Hz, 6H). | 811.3 | NA |

TABLE 3-continued

| Example | Structure | 1H-NMR | M/Z [M + H]+ | α4β7 EC$_{50}$ (nM) |
|---|---|---|---|---|
| 394 | 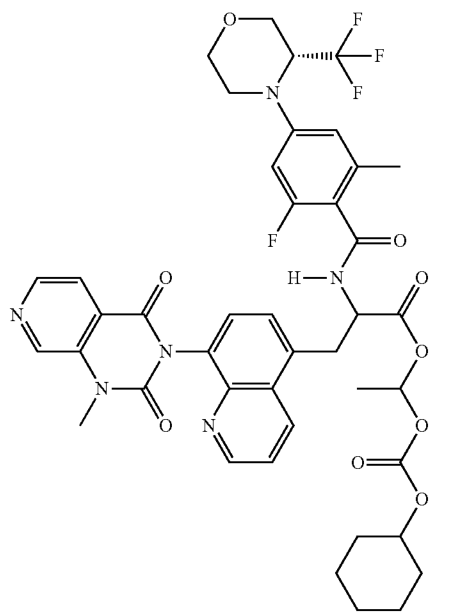 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)OC(C)OC(=O)OC1CCCCC1] | 1H NMR (400 MHz, DMSO-d6) δ 9.10-8.99 (m, 2H), 8.85 (t, J = 3.0 Hz, 1H), 8.62 (dd, J = 16.4, 6.9 Hz, 2H), 7.92 (d, J = 4.9 Hz, 1H), 7.77 (d, J = 7.5 Hz, 1H), 7.67 (dd, J = 8.9, 4.9 Hz, 2H), 6.66 (d, J = 8.2 Hz, 2H), 4.86 (s, 1H), 4.62-4.57 (m, 1H), 4.15 (d, J = 12.6 Hz, 1H), 3.95 (d, J = 11.4 Hz, 1H), 3.73 (d, J = 13.3 Hz, 5H), 3.54 (t, J = 12.6 Hz, 2H), 3.36 (d, J = 12.6 Hz, 1H), 3.26 (d, J = 12.5 Hz, 1H), 2.03 (d, J = 22.0 Hz, 3H), 1.84 (d, J = 7.9 Hz, 2H), 1.76 (dd, J = 5.8, 2.0 Hz, 2H), 1.64 (s, 2H), 1.53 (d, J = 5.5 Hz, 2H), 1.48-1.41 (m, 3H), 1.36 (t, J = 8.1 Hz, 3H), 1.26-1.20 (m, 1H). | 851.3 | NA |
| 395 | 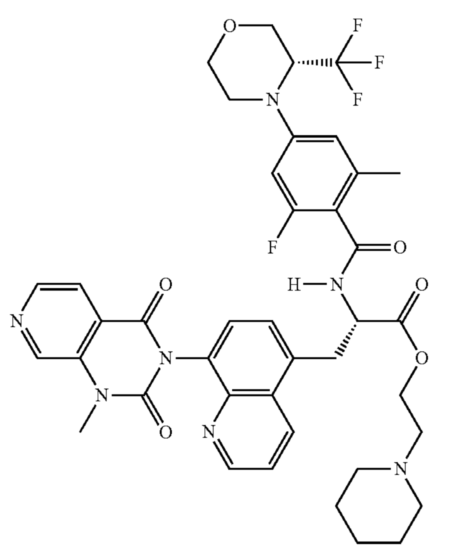 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncccc12)C(=O)OCCN1CCCCC1] | 1H NMR (400 MHz, DMSO-d6) δ 9.17 (s, 1H), 9.14-9.00 (m, 2H), 8.86 (t, J = 2.7 Hz, 1H), 8.66 (d, J = 8.8 Hz, 1H), 8.63-8.54 (m, 1H), 7.91 (d, J = 5.0 Hz, 1H), 7.78 (dd, J = 7.6, 1.9 Hz, 1H), 7.67 (d, J = 7.6 Hz, 2H), 6.77-6.66 (m, 2H), 4.88 (dd, J = 20.8, 9.6 Hz, 2H), 4.40 (s, 1H), 4.32 (s, 1H), 4.16 (d, J = 12.6 Hz, 1H), 3.96 (d, J = 11.8 Hz, 1H), 3.74 (d, J = 11.3 Hz, 2H), 3.56 (dd, J = 23.8, 12.5 Hz, 2H), 3.47-3.34 (m, 3H), 3.32-3.17 (m, 3H), 2.94 (d, J = 11.3 Hz, 1H), 2.84 (s, 1H), 2.11 (s, 3H), 1.77 (t, J = 16.7 Hz, 2H), 1.67-1.52 (m, 3H), 1.33 (d, J = 12.7 Hz, 1H). | 792.3 | NA |

TABLE 3-continued

| Example | Structure | 1H-NMR | M/Z [M + H]+ | α4β7 EC$_{50}$ (nM) |
|---|---|---|---|---|
| 396 | 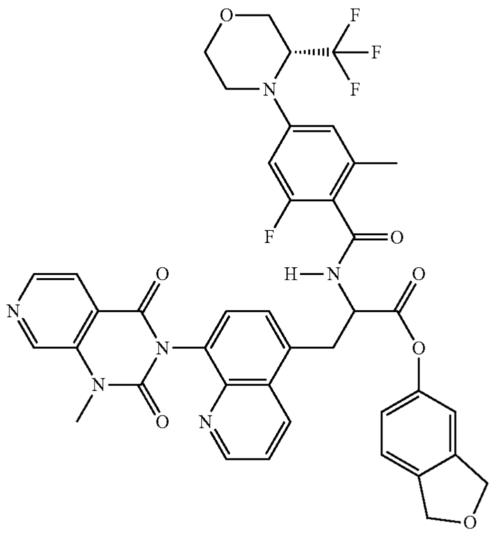 [SMILES: Cc1cc(N2CCOC[C@@H]2C(F)(F)F)cc(F)c1C(=O)NC(Cc1ccc(-n2c(=O)c3ccncc3n(C)c2=O)c2ncccc12)C(=O)Oc1ccc2c(c1)COC2] | 1H NMR (400 MHz, DMSO-d6) δ 9.24 (d, J = 6.8 Hz, 1H), 9.06 (s, 1H), 8.86 (t, J = 3.0 Hz, 1H), 8.76 (d, J = 8.7 Hz, 1H), 8.65-8.57 (m, 1H), 7.93 (d, J = 5.0 Hz, 1H), 7.81 (d, J = 7.5 Hz, 1H), 7.71 (dd, J = 17.1, 7.8 Hz, 2H), 7.33 (d, J = 8.1 Hz, 1H), 6.90 (dd, J = 15.0, 5.8 Hz, 2H), 6.75 (d, J = 13.1 Hz, 1H), 6.69 (s, 1H), 5.03 (m, 1H), 4.99 (s, 4H), 4.88-4.86 (m, 1H), 4.15 (d, J = 12.7 Hz, 1H), 3.96 (d, J = 11.4 Hz, 1H), 3.84-3.69 (m, 3H), 3.67 (s, 3H), 3.55 (t, J = 11.7 Hz, 1H), 3.37 (d, J = 12.4 Hz, 1H), 3.26 (t, J = 12.9 Hz, 1H), 2.14 (d, J = 5.4 Hz, 3H). | 799.2 | NA |
| 397 | 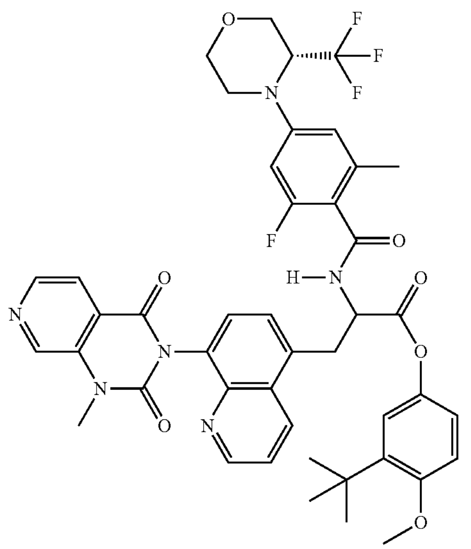 [SMILES: COc1ccc(OC(=O)C(Cc2ccc(-n3c(=O)c4ccncc4n(C)c3=O)c3ncccc23)NC(=O)c2c(C)cc(N3CCOC[C@@H]3C(F)(F)F)cc2F)cc1C(C)(C)C] | 1H NMR (400 MHz, DMSO-d6) δ 9.17 (d, J = 7.4 Hz, 1H), 9.06 (s, 1H), 8.87 (s, 1H), 8.77 (d, J = 8.5 Hz, 1H), 8.61 (s, 1H), 7.92 (s, 1H), 7.76 (dt, J = 25.0, 12.6 Hz, 3H), 7.02 (d, J = 8.5 Hz, 1H), 6.91 (d, J = 10.1 Hz, 2H), 6.73 (d, J = 13.9 Hz, 1H), 6.67 (s, 1H), 5.03 (s, 1H), 4.85 (s, 1H), 4.15 (d, J = 12.7 Hz, 1H), 3.95 (d, J = 11.0 Hz, 1H), 3.86 (s, 2H), 3.83 (s, 3H), 3.73 (d, J = 12.4 Hz, 1H), 3.66 (s, 3H), 3.54 (s, 1H), 3.36 (d, J = 10.4 Hz, 1H), 3.32-3.12 (m, 1H), 2.08 (d, J = 7.2 Hz, 3H), 1.32 (s, 9H). | 843.1 | NA |
| 398 | 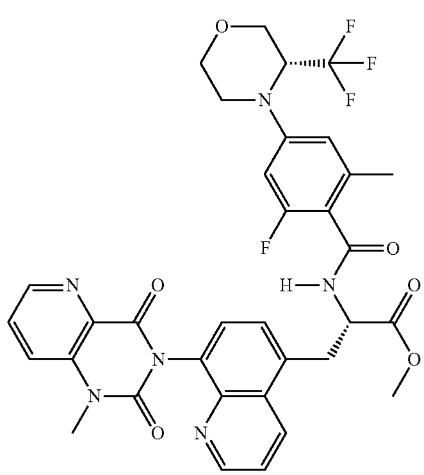 [SMILES: COC(=O)[C@H](Cc1ccc(-n2c(=O)c3ncccc3n(C)c2=O)c2ncccc12)NC(=O)c1c(C)cc(N2CCOC[C@@H]2C(F)(F)F)cc1F] | 1H NMR (400 MHz, DMSO-d6) δ 9.00 (d, J = 7.8 Hz, 1H), 8.88-8.81 (m, 1H), 8.67 (d, J = 8.6 Hz, 1H), 8.61 (ddd, J = 4.4, 2.1, 1.3 Hz, 1H), 8.08 (dd, J = 8.8, 1.3 Hz, 1H), 7.87 (dd, J = 8.6, 4.4 Hz, 1H), 7.76 (d, J = 7.5 Hz, 1H), 7.67 (dt, J = 7.8, 3.3 Hz, 2H), 6.70 (dd, J = 13.0, 2.3 Hz, 1H), 6.66 (d, J = 2.4 Hz, 1H), 4.86 (d, J = 4.3 Hz, 1H), 4.83 (m, 1H), 4.14 (d, J = 12.6 Hz, 1H), 3.95 (dd, J = 11.3, 3.7 Hz, 1H), 3.78-3.70 (m, 2H), 3.69 (d, J = 3.6 Hz, 3H), 3.57 (d, J = 2.4 Hz, 3H), 3.53 (d, J = 3.7 Hz, 1H), 3.51 (d, J = 9.9 Hz, 1H), 3.36 (d, J = 12.3 Hz, 1H), 3.25 (t, J = 12.2 Hz, 1H), 2.05 (s, 3H). | 695.2 | NA |

TABLE 3-continued

| Example | Structure | 1H-NMR | M/Z [M + H]+ | α4β7 EC$_{50}$ (nM) |
|---|---|---|---|---|
| 399 | 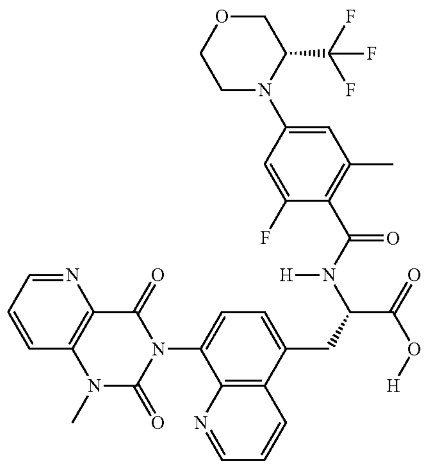 | 1H NMR (400 MHz, DMSO-d6) δ 13.11-12.65 (s, 1H), 8.87 (d, J = 8.1 Hz, 1H), 8.85-8.83 (m, 1H), 8.73-8.65 (m, 1H), 8.61 (ddd, J = 4.4, 2.3, 1.2 Hz, 1H), 8.08 (dd, J = 8.8, 1.3 Hz, 1H), 7.87 (dd, J = 8.6, 4.4 Hz, 1H), 7.75 (d, J = 7.6 Hz, 1H), 7.71-7.63 (m, 2H), 6.69 (d, J = 13.4 Hz, 1H), 6.65 (s, 1H), 4.88-4.80 (m, 1H), 4.77 (d, J = 11.5 Hz, 1H), 4.14 (d, J = 12.6 Hz, 1H), 3.94 (dd, J = 11.4, 3.6 Hz, 1H), 3.81-3.68 (m, 2H), 3.57 (d, J = 2.5 Hz, 3H), 3.55-3.42 (m, 2H), 3.35 (d, J = 12.4 Hz, 1H), 3.25 (t, J = 12.1 Hz, 1H), 2.03 (d, J = 2.5 Hz, 3H). | 681.2 | 0.1 |
| 400 | 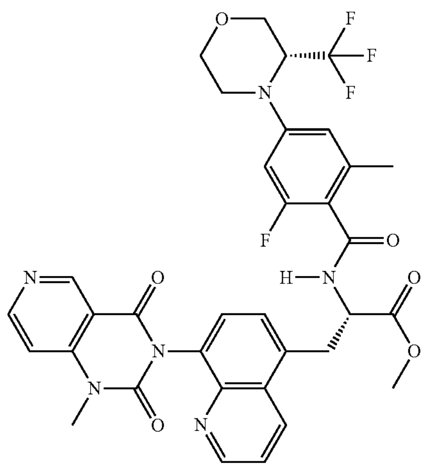 [SMILES: COC(=O)[C@H](Cc1ccc(-n2c(=O)c3cnccc3n(C)c2=O)c2ncccc12)NC(=O)c1c(C)cc(N2CCOC[C@@H]2C(F)(F)F)cc1F] | 1H NMR (400 MHz, DMSO-d6) δ 9.10 (d, J = 3.0 Hz, 1H), 9.00 (d, J = 7.7 Hz, 1H), 8.88-8.80 (m, 2H), 8.66 (dd, J = 8.7, 1.6 Hz, 1H), 7.76 (d, J = 7.6 Hz, 1H), 7.67 (td, J = 5.8, 5.3, 2.6 Hz, 2H), 7.61 (d, J = 6.1 Hz, 1H), 6.74-6.59 (m, 2H), 4.88-4.78 (m, 2H), 4.15 (d, J = 12.7 Hz, 1H), 3.97-3.87 (m, 1H), 3.77-3.64 (m, 5H), 3.57 (d, J = 2.2 Hz, 5H), 3.36 (d, J = 12.3 Hz, 1H), 3.25 (t, J = 12.1 Hz, 1H), 2.05 (s, 3H). | 695.2 | NA |
| 401 | 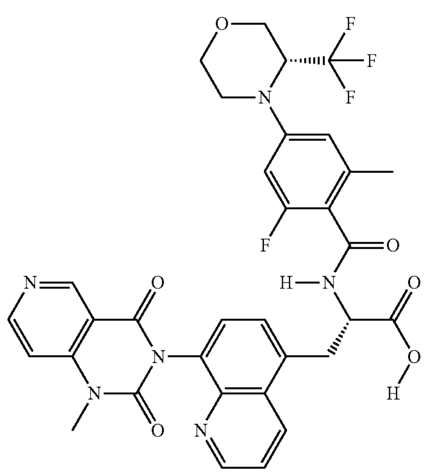 | 1H NMR (400 MHz, DMSO-d6) δ 9.10 (d, J = 3.6 Hz, 1H), 8.95-8.76 (m, 3H), 8.68 (d, J = 8.7 Hz, 1H), 7.76 (d, J = 7.5 Hz, 1H), 7.74-7.56 (m, 3H), 6.74-6.56 (m, 2H), 4.90-4.72 (m, 2H), 4.14 (d, J = 12.6 Hz, 1H), 3.94 (dd, J = 11.4, 3.6 Hz, 1H), 3.75 (t, J = 13.4 Hz, 2H), 3.57 (d, J = 2.4 Hz, 3H), 3.55-3.48 (m, 1H), 3.47 (s, 1H), 3.35 (d, J = 12.6 Hz, 1H), 3.25 (t, J = 12.4 Hz, 1H), 2.03 (s, 3H). | 681.2 | 0.1 |

TABLE 3-continued
| Example | Structure | 1H-NMR | M/Z [M + H]+ | α4β7 EC$_{50}$ (nM) |
|---|---|---|---|---|
| 402 | 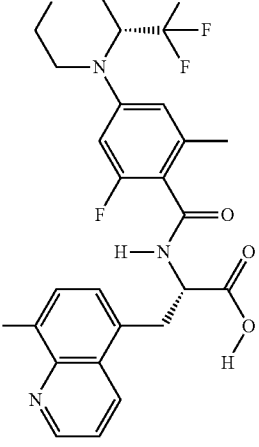 | 1H NMR (400 MHz, DMSO-d6) δ 8.86 (d, J = 8.0 Hz, 3H), 8.68 (d, J = 8.4 Hz, 1H), 8.42 (d, J = 9.3 Hz, 1H), 7.76 (d, J = 7.5 Hz, 1H), 7.70-7.63 (m, 2H), 7.45-7.39 (m, 1H), 6.73-6.63 (m, 2H), 4.87-4.72 (m, 3H), 4.14 (d, J = 2.6 Hz, 1H), 3.99-3.91 (m, 2H), 3.74 (s, 2H), 3.63 (s, 3H), 3.58-3.51 (m, 1H), 3.50-3.42 (m, 1H), 3.38-3.31 (m, 1H), 3.28-3.21 (m, 1H), 2.03 (s, 3H). | 681.2 | 0.1 |
| 403 | 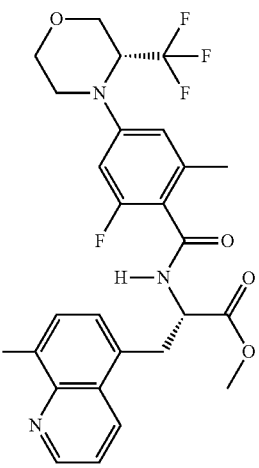 | 1H NMR (400 MHz, DMSO-d6) δ 9.00 (d, J = 7.8 Hz, 1H), 8.92-8.86 (m, 2H), 8.73-8.68 (m, 2H), 7.78 (d, J = 7.5 Hz, 1H), 7.73-7.67 (m, 2H), 6.74-6.64 (m, 2H), 4.90-4.79 (m, 2H), 4.15 (d, J = 12.6 Hz, 1H), 3.95 (dd, J = 11.5, 3.5 Hz, 1H), 3.80-3.65 (m, 5H), 3.61 (s, 3H), 3.55 (t, J = 13.9, 7.6, 2.5 Hz, 2H), 3.36 (d, J = 11.8 Hz, 1H), 3.25 (t, 1H), 2.05 (s, 3H). | 696.8 | NA |
| 404 | 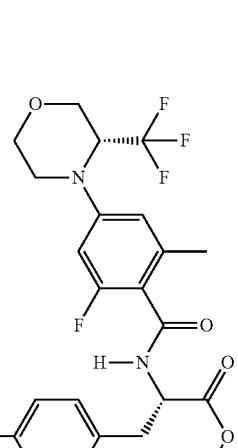 | 1H NMR (400 MHz, DMSO-d6) δ 8.93-8.83 (m, 3H), 8.75-8.67 (m, 2H), 7.77 (d, J = 7.5 Hz, 1H), 7.74-7.66 (m, 2H), 6.73-6.62 (m, 2H), 4.89-4.75 (m, 2H), 4.14 (d, J = 12.6 Hz, 1H), 3.94 (dd, J = 11.7, 3.5 Hz, 1H), 3.81-3.69 (m, 2H), 3.61 (s, 3H), 3.59-3.43 (m, 2H), 3.35 (d, J = 12.2 Hz, 1H), 3.25 (t, 1H), 2.03 (d, J = 2.4 Hz, 3H). | 682.7 | 0.1 |

TABLE 3-continued

| Example | Structure | 1H-NMR | M/Z [M + H]+ | α4β7 EC$_{50}$ (nM) |
|---|---|---|---|---|
| 405 | 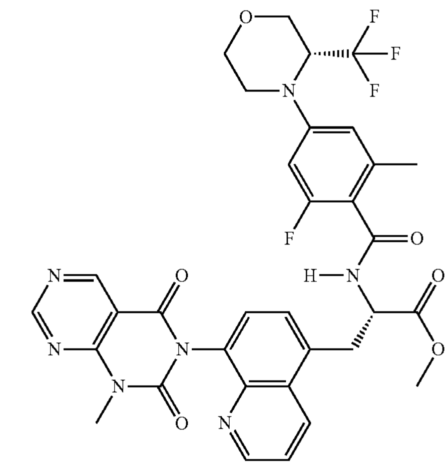 [SMILES: COC(=O)[C@H](Cc1ccc(-n2c(=O)c3cncnc3n(C)c2=O)c2ncccc12)NC(=O)c1c(C)cc(N2CCOC[C@@H]2C(F)(F)F)cc1F] | 1H NMR (400 MHz, DMSO-d6) δ 9.32 (s, 1H), 9.26-9.18 (m, 1H), 8.99 (d, J = 7.8 Hz, 1H), 8.91-8.84 (m, 1H), 8.67 (d, J = 8.7 Hz, 1H), 7.82-7.73 (m, 1H), 7.72-7.63 (m, 2H), 6.76-6.64 (m, 2H), 4.88-4.80 (m, 2H), 4.15 (d, J = 12.6 Hz, 1H), 3.98-3.91 (m, 1H), 3.78-3.70 (m, 2H), 3.68 (s, 3H), 3.61 (s, 3H), 3.58-3.51 (m, 2H), 3.42-3.32 (m, 1H), 3.30-3.18 (m, 1H), 2.04 (s, 3H). | 696.8 | NA |
| 406 | 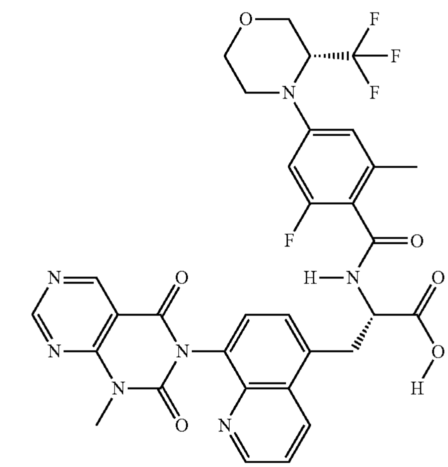 [SMILES: Cc1cc(N2CCOC[C@@H]2C(F)(F)F)cc(F)c1C(=O)N[C@@H](Cc1ccc(-n2c(=O)c3cncnc3n(C)c2=O)c2ncccc12)C(=O)O] | 1H NMR (400 MHz, DMSO-d6) δ 9.32 (s, 1H), 9.25-9.18 (m, 1H), 8.91-8.82 (m, 2H), 8.69 (d, J = 8.6 Hz, 1H), 7.80-7.73 (m, 1H), 7.73-7.64 (m, 2H), 6.75-6.60 (m, 2H), 4.90-4.74 (m, 2H), 4.14 (d, J = 12.6 Hz, 1H), 3.95 (d, J = 10.8 Hz, 1H), 3.81-3.68 (m, 2H), 3.60 (s, 3H), 3.58-3.40 (m, 2H), 3.39-3.31 (m, 1H), 3.31-3.18 (m, 1H), 2.02 (s, 3H). | 682.2 | 0.08 |
| 407 | 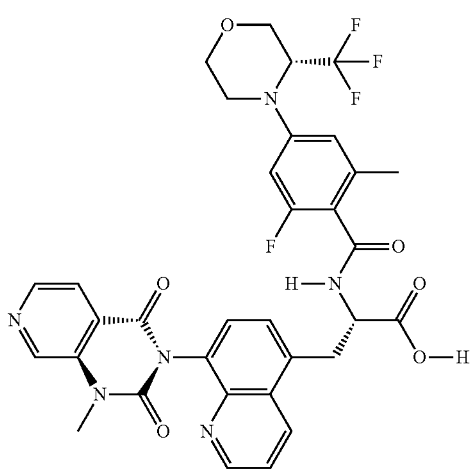 | 1H NMR (400 MHz, Chloroform-d) δ 8.84-8.72 (m, 2H), 8.66 (d, J = 8.6 Hz, 1H), 8.55 (s, 1H), 8.00 (s, 1H), 7.58 (s, 2H), 7.44 (dd, J = 8.6, 4.2 Hz, 1H), 6.66 (d, J = 6.5 Hz, 1H), 6.46 (s, 1H), 6.37 (d, J = 13.6 Hz, 1H), 5.08 (d, J = 7.0 Hz, 1H), 4.29 (d, J = 12.4 Hz, 1H), 4.11 (dd, J = 8.2, 3.8 Hz, 1H), 4.04 (dd, J = 11.3, 3.5 Hz, 1H), 3.84-3.70 (m, 3H), 3.68 (s, 3H), 3.65-3.56 (m, 1H), 3.50 (t, J = 12.0 Hz, 1H), 3.26 (d, J = 12.2 Hz, 1H), 2.38 (s, 3H). | 681.2 | 0.162 |

TABLE 3-continued

| Example | Structure | 1H-NMR | M/Z [M + H]+ | α4β7 EC$_{50}$ (nM) |
|---|---|---|---|---|
| 408 | 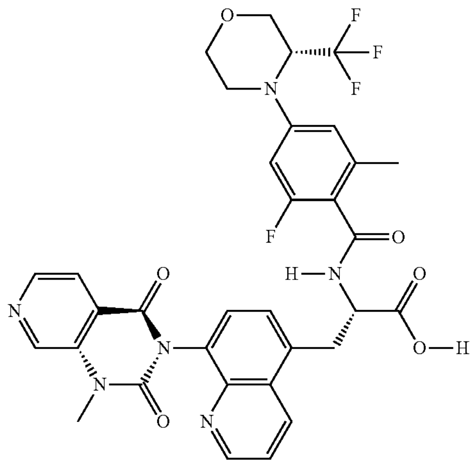 | 1H NMR (400 MHz, Chloroform-d) δ 8.8-8.72 (m, 2H), 8.64 (d, J = 8.6 Hz, 1H), 8.56 (d, J = 5.0 Hz, 1H), 8.03 (d, J = 5.0 Hz, 1H), 7.59 (q, J = 7.6 Hz, 2H), 7.46 (dd, J = 8.6, 4.2 Hz, 1H), 6.63 (d, J = 6.1 Hz, 1H), 6.47 (s, 1H), 6.38 (dd, J = 13.4, 2.4 Hz, 1H), 5.13-5.02 (m, 1H), 4.30 (d, J = 12.4 Hz, 1H), 4.12 (dd, J = 8.0, 3.8 Hz, 1H), 4.04 (dd, J = 11.2, 3.5 Hz, 1H), 3.86-3.78 (m, 1H), 3.72 (t, J = 5.6 Hz, 2H), 3.69 (s, 3H), 3.65-3.59 (m, 1H), 3.51 (t, J = 11.7 Hz, 1H), 3.27 (d, J = 12.3 Hz, 1H), 2.39 (s, 3H). | 681.2 | 0.049 |
| 409 | 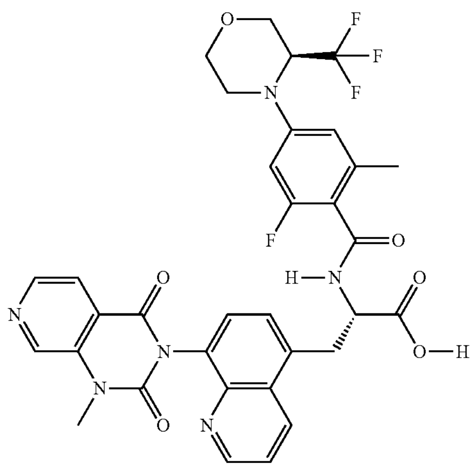 [SMILES: Cc1cc(N2CCOC[C@H]2C(F)(F)F)cc(F)c1C(=O)N[C@@H](Cc1ccc(-n2c(=O)c3ccncc3n(C)c2=O)c2ncccc12)C(=O)O] | 1H NMR (400 MHz, DMSO-d6) δ 13.21-12.53 (s, 1H), 9.05 (s, 1H), 8.87 (d, J = 7.9 Hz, 1H), 8.84 (dd, J = 4.2, 1.4 Hz, 1H), 8.71-8.65 (m, 1H), 8.60 (dd, J = 4.9, 1.8 Hz, 1H), 7.91 (ddd, J = 5.0, 3.4, 0.7 Hz, 1H), 7.76 (d, J = 7.6 Hz, 1H), 7.71-7.65 (m, 2H), 6.70 (d, J = 13.1 Hz, 1H), 6.64 (s, 1H), 4.83 (d, J = 6.1 Hz, 1H), 4.81-4.73 (m, 1H), 4.14 (d, J = 12.6 Hz, 1H), 3.94 (dd, J = 11.2, 3.6 Hz, 1H), 3.81-3.69 (m, 2H), 3.66 (d, J = 2.6 Hz, 3H), 3.60-3.51 (m, 1H), 3.46 (dd, J = 14.7, 10.6 Hz, 1H), 3.35 (d, J = 12.3 Hz, 1H), 3.25 (t, J = 12.2 Hz, 1H), 2.08-2.01 (m, 3H). | 681.2 | 0.401 |
| 410 | 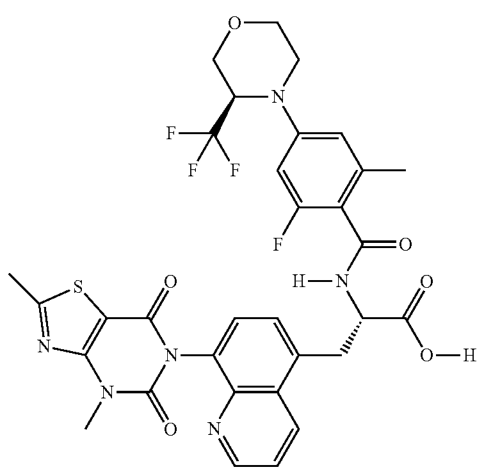 [SMILES: Cc1nc2c(s1)c(=O)n(-c1ccc(C[C@H](NC(=O)c3c(C)cc(N4CCOC[C@@H]4C(F)(F)F)cc3F)C(=O)O)c3cccnc13)c(=O)n2C] | 1H NMR (400 MHz, DMSO-d6) δ 8.91-8.82 (m, 2H), 8.68 (d, J = 8.6 Hz, 1H), 7.73 (d, 1H), 7.71-7.63 (m, 2H), 6.72-6.61 (m, 2H), 4.92-4.71 (m, 2H), 4.14 (d, J = 12.6 Hz, 1H), 3.94 (d, J = 11.4 Hz, 1H), 3.80-3.68 (m, 2H), 3.61 (s, 3H), 3.59-3.40 (m, 2H), 3.35 (d, J = 12.7 Hz, 1H), 3.26 (t, 1H), 2.86 (d, J = 1.9 Hz, 3H), 2.01 (d, 3H). | 701.7 | 0.054 |

TABLE 3-continued

| Example | Structure | 1H-NMR | M/Z [M + H]+ | α4β7 EC$_{50}$ (nM) |
|---|---|---|---|---|
| 411 | 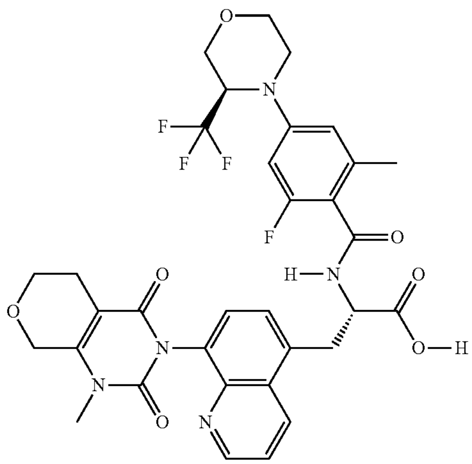 [SMILES: Cc1cc(N2CCOC[C@@H]2C(F)(F)F)cc(F)c1C(=O)N[C@@H](Cc1ccc(-n2c(=O)c3c(n(C)c2=O)COCC3)c2ncccc12)C(=O)O] | 1H NMR (400 MHz, DMSO-d6) δ 8.89-8.82 (m, 2H), 8.65 (d, J = 8.4 Hz, 1H), 7.67 (d, J = 3.8 Hz, 1H), 7.62 (s, 2H), 6.68 (d, J = 13.1 Hz, 1H), 6.64 (s, 1H), 4.84 (d, J = 2.8 Hz, 1H), 4.78-4.72 (m, 1H), 4.71-4.61 (m, 2H), 4.16 (s, 1H), 3.93 (s, 1H), 3.82 (s, 2H), 3.73 (d, J = 14.0 Hz, 2H), 3.55 (d, J = 11.7 Hz, 1H), 3.50-3.38 (m, 1H), 3.35 (d, J = 12.4 Hz, 1H), 3.25 (s, 4H), 2.34 (d, J = 8.3 Hz, 2H), 2.03 (s, 3H). | 686.2 | 0.06 |
| 412 | 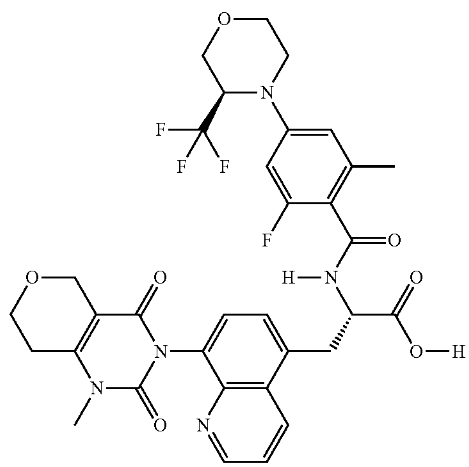 [SMILES: Cc1cc(N2CCOC[C@@H]2C(F)(F)F)cc(F)c1C(=O)N[C@@H](Cc1ccc(-n2c(=O)c3c(n(C)c2=O)CCOC3)c2ncccc12)C(=O)O] | 1H NMR (400 MHz, DMSO-d6) δ 8.88-8.82 (m, 2H), 8.64 (d, J = 9.0 Hz, 1H), 7.68-7.64 (m, 1H), 7.62 (s, 2H), 6.68 (d, J = 13.3 Hz, 1H), 6.64 (s, 1H), 4.88-4.79 (m, 1H), 4.79-4.70 (m, 1H), 4.30 (m, 2H), 4.14 (d, J = 12.9 Hz, 1H), 3.93 (m, 3H), 3.73 (d, J = 14.6 Hz, 2H), 3.55 (d, J = 8.1 Hz, 1H), 3.49-3.38 (m, 2H), 3.34 (s, 3H), 3.24 (t, J = 13.0 Hz, 1H), 2.87-2.68 (m, 1H), 2.02 (s, 3H). | 686.2 | 0.091 |
| 413 | 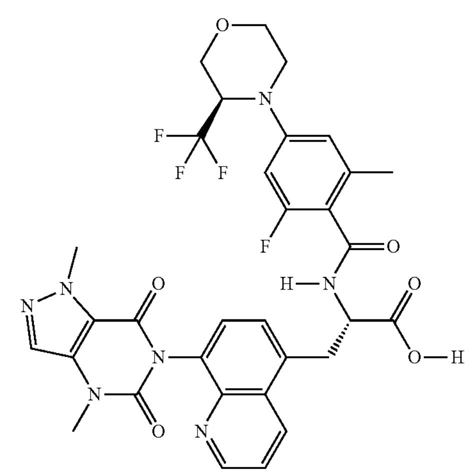 [SMILES: Cc1cc(N2CCOC[C@@H]2C(F)(F)F)cc(F)c1C(=O)N[C@@H](Cc1ccc(-n2c(=O)c3c(cnn3C)n(C)c2=O)c2ncccc12)C(=O)O] | 1H NMR (400 MHz, DMSO-d6) δ 8.86 (t, J = 5.9 Hz, 2H), 8.68 (d, J = 8.6 Hz, 1H), 8.10 (d, J = 1.6 Hz, 1H), 7.67 (td, J = 8.1, 4.9 Hz, 3H), 6.73-6.60 (m, 2H), 4.90-4.71 (m, 2H), 4.14 (d, J = 12.6 Hz, 1H), 4.05 (s, 3H), 3.99-3.91 (m, 1H), 3.74 (d, J = 12.8 Hz, 2H), 3.50 (ddd, J = 35.8, 13.4, 9.9 Hz, 2H), 3.37 (d, J = 2.3 Hz, 4H), 3.25 (t, J = 12.5 Hz, 1H), 2.03 (s, 3H). | 684.3 | 0.529 |

TABLE 3-continued

| Example | Structure | 1H-NMR | M/Z [M + H]+ | α4β7 EC$_{50}$ (nM) |
|---|---|---|---|---|
| 414 | 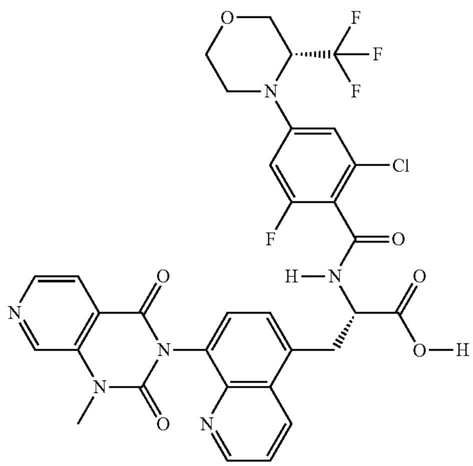 [SMILES: Cn1c(=O)n(-c2ccc(C[C@H](NC(=O)c3c(F)cc(N4CCOC[C@@H]4C(F)(F)F)cc3Cl)C(=O)O)c3cccnc23)c(=O)c2ccncc21] | 1H NMR (400 MHz, DMSO-d6) δ 9.12 (d, J = 8.2 Hz, 1H), 9.05 (d, J = 1.6 Hz, 1H), 8.88 (d, J = 4.0 Hz, 1H), 8.76 (t, J = 7.7 Hz, 1H), 8.61 (d, J = 5.0 Hz, 1H), 7.92 (p, J = 2.0 Hz, 1H), 7.79 (dd, J = 7.7, 2.5 Hz, 1H), 7.72 (t, J = 5.9 Hz, 2H), 6.91 (t, J = 6.2 Hz, 2H), 4.92 (h, J = 7.9 Hz, 1H), 4.87-4.75 (m, 1H), 4.15 (d, J = 12.7 Hz, 1H), 3.95 (dd, J = 11.7, 3.6 Hz, 1H), 3.86-3.69 (m, 2H), 3.60-3.34 (m, 3H), 3.25 (t, J = 12.2 Hz, 1H). | 701.1 | 0.048 |
| 415 | 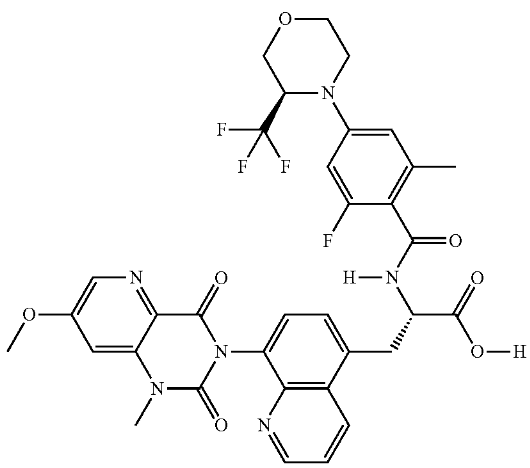 [SMILES: COc1cnc2c(=O)n(-c3ccc(C[C@H](NC(=O)c4c(C)cc(N5CCOC[C@@H]5C(F)(F)F)cc4F)C(=O)O)c4cccnc34)c(=O)n(C)c2c1] | 1H NMR (400 MHz, DMSO-d6) δ 8.86 (d, J = 8.0 Hz, 2H), 8.70 (d, J = 8.6 Hz, 1H), 8.34-8.30 (m, 1H), 7.75 (d, 1H), 7.72-7.65 (m, 2H), 7.46-7.42 (m, 1H), 6.73-6.62 (m, 2H), 4.90-4.73 (m, 2H), 4.14 (d, J = 12.7 Hz, 1H), 4.06 (s, 3H), 3.94 (d, J = 11.2 Hz, 1H), 3.75 (t, 2H), 3.62-3.41 (m, 5H), 3.35 (d, J = 12.3 Hz, 1H), 3.26 (t, 1H), 2.03 (s, 3H). | 711.3 | 0.091 |
| 416 | 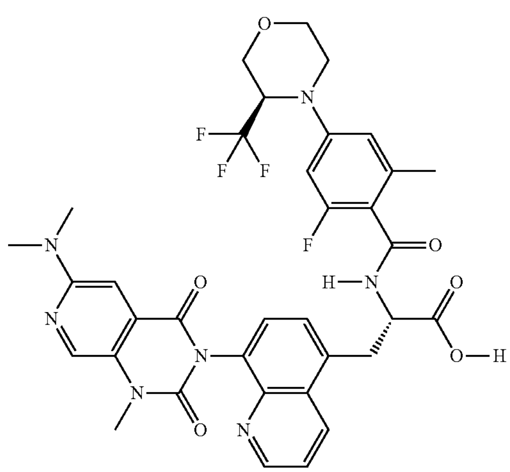 [SMILES: Cc1cc(N2CCOC[C@@H]2C(F)(F)F)cc(F)c1C(=O)N[C@@H](Cc1ccc(-n2c(=O)c3cc(N(C)C)ncc3n(C)c2=O)c2ncccc12)C(=O)O] | 1H NMR (400 MHz, DMSO-d6) δ 8.90-8.82 (m, 2H), 8.68 (d, J = 8.6 Hz, 1H), 8.57 (s, 1H), 7.73 (d, J = 7.6 Hz, 1H), 7.67 (d, J = 7.8 Hz, 2H), 7.04 (t, J = 2.5 Hz, 1H), 6.72-6.62 (m, 2H), 4.82 (s, 1H), 4.79 (d, J = 8.9 Hz, 1H), 4.14 (d, J = 12.6 Hz, 1H), 3.94 (d, J = 11.3 Hz, 1H), 3.80-3.67 (m, 2H), 3.60-3.53 (m, 4H), 3.47 (dd, J = 23.9, 11.6 Hz, 1H), 3.35 (d, J = 12.4 Hz, 1H), 3.26 (d, J = 12.0 Hz, 1H), 3.09 (s, 6H), 2.02 (s, 3H). | 724.2 | 0.126 |

TABLE 3-continued

| Example | Structure | 1H-NMR | M/Z [M + H]+ | α4β7 EC$_{50}$ (nM) |
|---|---|---|---|---|
| 417 | 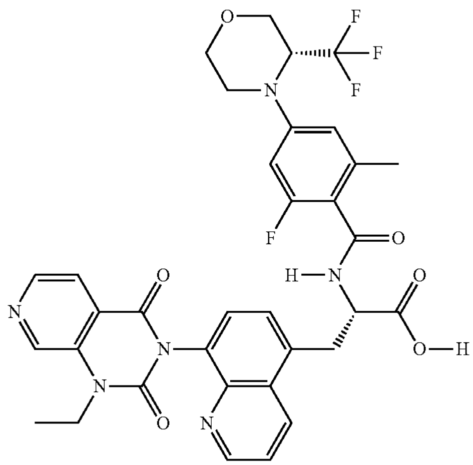 [SMILES: CCn1c(=O)n(-c2ccc(C[C@H](NC(=O)c3c(C)cc(N4CCOC[C@@H]4C(F)(F)F)cc3F)C(=O)O)c3cccnc23)c(=O)c2ccncc21] | 1H NMR (400 MHz, DMSO-d6) δ 13.12-12.64 (s, 1H), 9.10 (s, 1H), 8.85 (t, J = 6.8 Hz, 2H), 8.68 (d, J = 8.6 Hz, 1H), 8.58 (d, J = 5.1 Hz, 1H), 7.92 (d, J = 4.6 Hz, 1H), 7.78 (d, J = 7.5 Hz, 1H), 7.72-7.63 (m, 2H), 6.69 (d, J = 13.3 Hz, 1H), 6.65 (s, 1H), 4.84 (d, J = 8.6 Hz, 1H), 4.79 (d, J = 11.1 Hz, 2H), 4.27 (d, J = 7.5 Hz, 2H), 4.14 (d, J = 12.7 Hz, 1H), 3.95 (d, J = 11.1 Hz, 1H), 3.79-3.69 (m, 2H), 3.54 (t, J = 12.5 Hz, 1H), 3.50-3.41 (m, 1H), 3.35 (d, J = 12.4 Hz, 1H), 3.25 (t, J = 12.3 Hz, 1H), 2.03 (s, 3H), 1.30 (t, J = 7.2 Hz, 3H). | 695.3 | 0.117 |
| 418 | 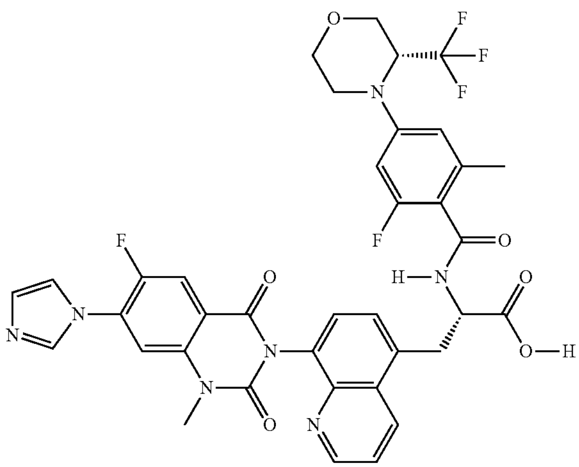 [SMILES: Cc1cc(N2CCOC[C@@H]2C(F)(F)F)cc(F)c1C(=O)N[C@@H](Cc1ccc(-n2c(=O)c3cc(F)c(-n4ccnc4)cc3n(C)c2=O)c2ncccc12)C(=O)O] | 1H NMR (400 MHz, DMSO-d6) δ 12.94 (s, 1H), 8.87 (d, J = 7.9 Hz, 1H), 8.84 (d, J = 4.2 Hz, 1H), 8.67 (d, J = 8.8 Hz, 1H), 8.07 (s, 2H), 7.93 (s, 1H), 7.77 (d, J = 7.6 Hz, 1H), 7.68 (d, J = 7.1 Hz, 2H), 7.66 (s, 1H), 6.73-6.63 (m, 2H), 4.90-4.72 (m, 3H), 4.15 (d, J = 12.6 Hz, 1H), 3.95 (d, J = 11.3 Hz, 1H), 3.82-3.70 (m, 2H), 3.64 (s, 3H), 3.50 (dt, J = 33.6, 12.1 Hz, 3H), 3.35 (d, J = 13.4 Hz, 1H), 3.27 (d, J = 12.8 Hz, 1H), 2.04 (s, 3H). | 764.4 | 0.104 |
| 419 | 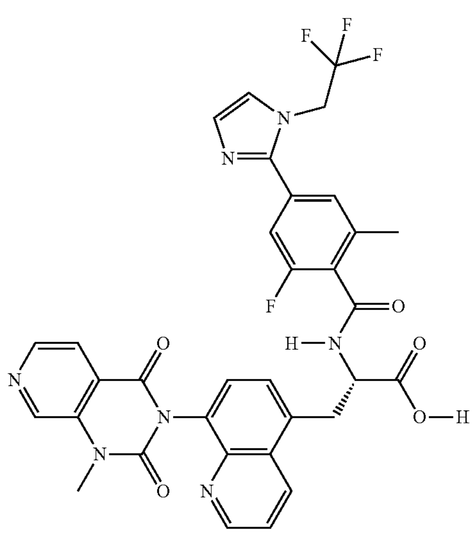 [SMILES: Cc1cc(-c2nccn2CC(F)(F)F)cc(F)c1C(=O)N[C@@H](Cc1ccc(-n2c(=O)c3ccncc3n(C)c2=O)c2ncccc12)C(=O)O] | 1H NMR (400 MHz, DMSO-d6) δ 9.27 (d, J = 8.1 Hz, 1H), 9.05 (s, 1H), 8.85 (d, J = 3.8 Hz, 1H), 8.70 (d, J = 8.6 Hz, 1H), 8.60 (d, J = 5.0 Hz, 1H), 7.91 (d, J = 5.2 Hz, 1H), 7.78 (d, J = 7.6 Hz, 1H), 7.72-7.63 (m, 3H), 7.53-7.41 (m, 2H), 7.39 (s, 1H), 5.21 (dd, J = 13.7, 5.4 Hz, 2H), 4.88 (s, 1H), 3.82 (d, J = 15.3 Hz, 1H), 3.66 (d, J = 2.9 Hz, 3H), 3.48 (dd, J = 14.7, 10.9 Hz, 1H), 2.14 (s, 3H). | 676.2 | 0.369 |

TABLE 3-continued

| Example | Structure | 1H-NMR | M/Z [M + H]+ | α4β7 EC$_{50}$ (nM) |
|---|---|---|---|---|
| 420 | 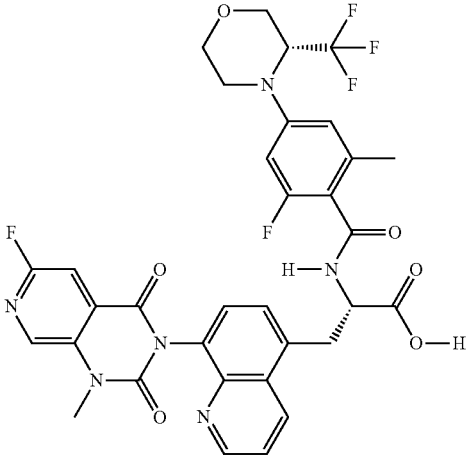 [SMILES: Cc1cc(N2CCOC[C@@H]2C(F)(F)F)cc(F)c1C(=O)N[C@@H](Cc1ccc(-n2c(=O)c3cc(F)ncc3n(C)c2=O)c2ncccc12)C(=O)O] | 1H NMR (400 MHz, DMSO-d6) δ 8.85 (t, J = 6.2 Hz, 2H), 8.68 (d, J = 5.8 Hz, 2H), 7.76 (d, J = 7.5 Hz, 1H), 7.68 (dd, J = 8.2, 4.8 Hz, 3H), 6.71-6.61 (m, 2H), 4.88-4.73 (m, 2H), 4.14 (d, J = 12.7 Hz, 1H), 3.97-3.92 (m, 2H), 3.75 (m, 1H), 3.63 (d, J = 2.5 Hz, 3H), 3.56 (dd, J = 13.0, 2.7 Hz, 1H), 3.46 (dd, J = 14.6, 10.8 Hz, 1H), 3.35 (d, J = 12.6 Hz, 1H), 3.26 (d, J = 12.4 Hz, 1H), 2.02 (s, 3H). | 699.1 | 0.116 |
| 421 | 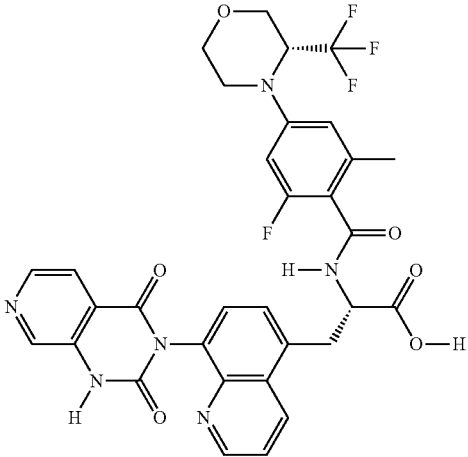 | 1H NMR (400 MHz, DMSO-d6) δ 13.31-12.61 (s, 1H), 11.90 (d, J = 3.2 Hz, 1H), 8.87 (d, J = 8.2 Hz, 2H), 8.72 (s, 1H), 8.68 (d, J = 8.8 Hz, 1H), 8.48 (d, J = 5.1 Hz, 1H), 7.82 (s, 1H), 7.77 (d, J = 7.6 Hz, 1H), 7.68 (d, J = 7.9 Hz, 2H), 6.69 (d, J = 13.3 Hz, 1H), 6.65 (s, 1H), 4.84 (d, J = 9.4 Hz, 1H), 4.77 (s, 1H), 4.14 (d, J = 12.7 Hz, 1H), 3.95 (d, J = 11.4 Hz, 1H), 3.76 (d, J = 10.6 Hz, 2H), 3.54 (t, J = 12.0 Hz, 1H), 3.46 (t, J = 12.8 Hz, 1H), 3.35 (d, J = 12.5 Hz, 1H), 3.25 (t, J = 12.2 Hz, 1H), 2.04 (s, 3H). | 667.2 | 0.191 |
| 422 | 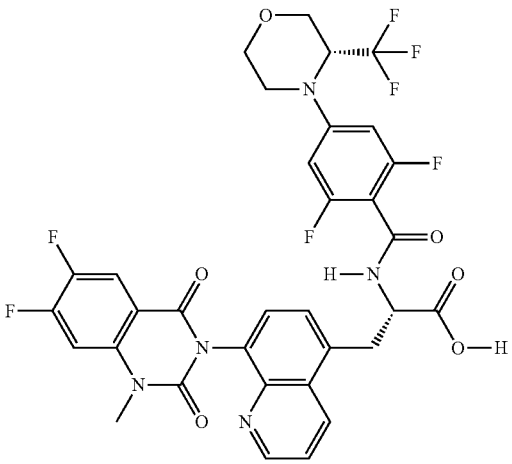 [SMILES: Cn1c(=O)n(-c2ccc(C[C@H](NC(=O)c3c(F)cc(N4CCOC[C@@H]4C(F)(F)F)cc3F)C(=O)O)c3cccnc23)c(=O)c2cc(F)c(F)cc21] | 1H NMR (400 MHz, DMSO-d6) δ 13.10-12.83, (s, 1H), 9.01 (d, J = 7.8 Hz, 1H), 8.84 (d, J = 4.2 Hz, 1H), 8.65 (d, J = 8.7 Hz, 1H), 8.00 (t, J = 9.1 Hz, 1H), 7.80 (dd, J = 12.1, 6.4 Hz, 1H), 7.73 (d, J = 7.6 Hz, 1H), 7.65 (d, J = 7.5 Hz, 2H), 6.78 (d, J = 11.8 Hz, 2H), 4.92 (d, J = 9.8 Hz, 1H), 4.70 (s, 1H), 4.16 (d, J = 12.8 Hz, 1H), 3.99-3.91 (m, 1H), 3.74 (d, J = 13.7 Hz, 2H), 3.57 (s, 1H), 3.55 (s, 3H), 3.44 (d, J = 12.1 Hz, 2H), 3.26 (d, J = 12.7 Hz, 1H). | 720.1 | 0.231 |

TABLE 3-continued

| Example | Structure | 1H-NMR | M/Z [M + H]+ | α4β7 EC$_{50}$ (nM) |
|---|---|---|---|---|
| 423 | 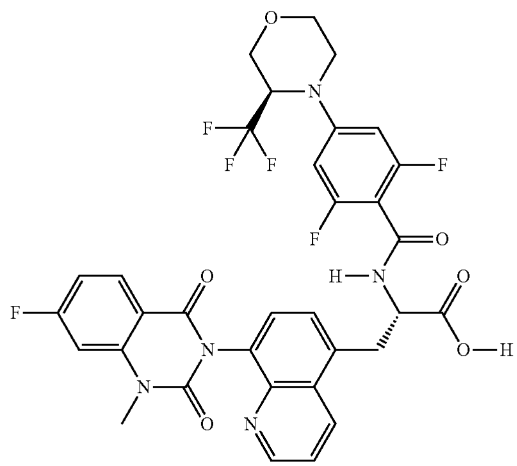 [SMILES: Cn1c(=O)n(-c2ccc(C[C@H](NC(=O)c3c(F)cc(N4CCOC[C@@H]4C(F)(F)F)cc3F)C(=O)O)c3cccnc23)c(=O)c2ccc(F)cc21] | 1H NMR (400 MHz, DMSO-d6) δ 9.01 (d, J = 7.8 Hz, 1H), 8.87-8.82 (m, 1H), 8.67 (d, J = 8.6 Hz, 1H), 8.14-8.06 (m, 1H), 7.74 (d, J = 7.6 Hz, 1H), 7.70-7.62 (m, 2H), 7.53-7.46 (m, 1H), 7.21 (t, J = 8.4 Hz, 1H), 6.78 (d, J = 11.8 Hz, 2H), 4.96-4.86 (m, 1H), 4.76-4.65 (m, 1H), 4.16 (d, J = 12.7 Hz, 1H), 4.00-3.90 (m, 1H), 3.78-3.70 (m, 2H), 3.62-3.39 (m, 6H), 3.24 (t, J = 12.3 Hz, 1H). | 702.2 | 0.08 |
| 424 | 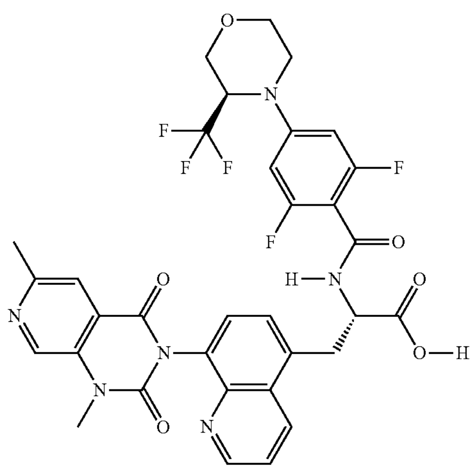 [SMILES: Cc1cc2c(=O)n(-c3ccc(C[C@H](NC(=O)c4c(F)cc(N5CCOC[C@@H]5C(F)(F)F)cc4F)C(=O)O)c4cccnc34)c(=O)n(C)c2cn1] | 1H NMR (400 MHz, DMSO-d6) δ 9.02 (d, J = 7.8 Hz, 1H), 8.90 (s, 1H), 8.84 (d, J = 4.2 Hz, 1H), 8.68 (d, J = 8.6 Hz, 1H), 7.80-7.72 (m, 2H), 7.67 (t, J = 6.7 Hz, 2H), 6.78 (d, J = 11.8 Hz, 2H), 4.92 (dd, J = 10.0, 3.4 Hz, 1H), 4.71 (s, 1H), 4.16 (d, J = 12.7 Hz, 1H), 4.01-3.90 (m, 1H), 3.74 (d, J = 13.3 Hz, 2H), 3.63 (s, 3H), 3.50 (dt, J = 42.0, 12.4 Hz, 3H), 3.24 (t, J = 12.3 Hz, 1H), 2.60 (s, 3H). | 700.1 | 0.15 |
| 425 | 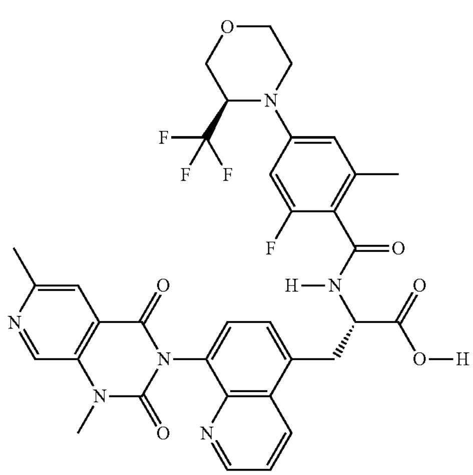 [SMILES: Cc1cc2c(=O)n(-c3ccc(C[C@H](NC(=O)c4c(C)cc(N5CCOC[C@@H]5C(F)(F)F)cc4F)C(=O)O)c4cccnc34)c(=O)n(C)c2cn1] | 1H NMR (400 MHz, DMSO-d6) δ 8.93-8.81 (m, 3H), 8.68 (d, J = 8.6 Hz, 1H), 7.81-7.71 (m, 2H), 7.67 (dd, J = 8.4, 4.2 Hz, 2H), 6.73-6.61 (m, 2H), 4.91-4.71 (m, 2H), 4.14 (d, J = 12.6 Hz, 1H), 3.99-3.89 (m, 1H), 3.80-3.68 (m, 2H), 3.63 (t, J = 1.8 Hz, 3H), 3.50 (ddd, J = 33.4, 13.8, 10.0 Hz, 2H), 3.35 (d, J = 12.3 Hz, 1H), 3.25 (t, J = 12.5 Hz, 1H), 2.60 (s, 3H), 2.02 (s, 3H). | 695.2 | 0.185 |

TABLE 3-continued
| Example | Structure | 1H-NMR | M/Z [M + H]+ | α4β7 EC$_{50}$ (nM) |
|---|---|---|---|---|
| 426 | 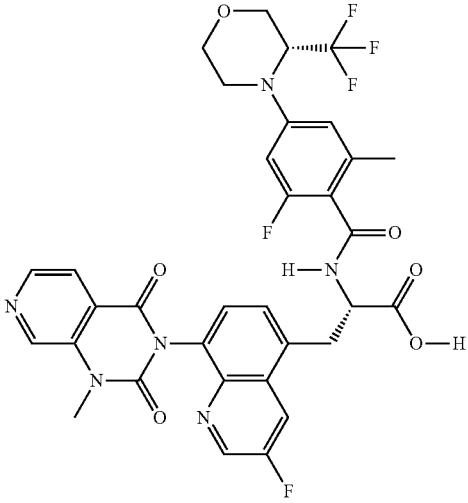 [SMILES: Cc1cc(N2CCOC[C@@H]2C(F)(F)F)cc(F)c1C(=O)N[C@@H](Cc1ccc(-n2c(=O)c3ccncc3n(C)c2=O)c2ncc(F)cc12)C(=O)O] | 1H NMR (400 MHz, DMSO-d6) δ 9.04 (s, 1H), 8.90 (t, J = 1.8 Hz, 1H), 8.85 (d, J = 8.1 Hz, 1H), 8.60 (d, J = 5.0 Hz, 1H), 8.51-8.44 (m, 1H), 7.91 (t, J = 3.9 Hz, 1H), 7.75 (d, J = 2.5 Hz, 2H), 6.82-6.68 (m, 3H), 6.65 (d, J = 7.6 Hz, 2H), 4.97-4.73 (m, 4H), 4.15 (dd, J = 12.7, 7.7 Hz, 2H), 4.03-3.87 (m, 3H), 3.84-3.68 (m, 1H), 3.65 (s, 3H), 3.59-3.40 (m, 2H), 3.40-3.16 (m, 3H), 2.01 (s, 3H). | 699.2 | 0.096 |
| 427 | 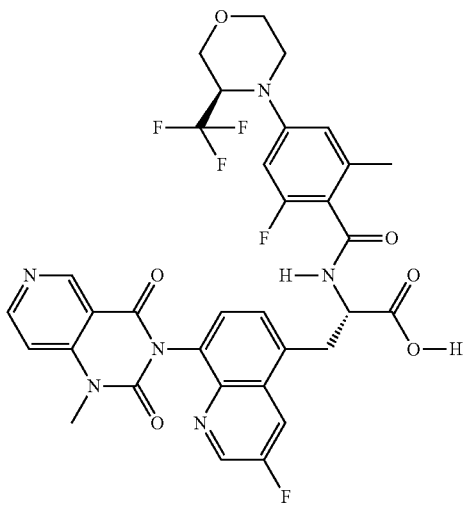 [SMILES: Cc1cc(N2CCOC[C@@H]2C(F)(F)F)cc(F)c1C(=O)N[C@@H](Cc1ccc(-n2c(=O)c3cnccc3n(C)c2=O)c2ncc(F)cc12)C(=O)O] | 1H NMR (400 MHz, DMSO-d6) δ 9.10 (s, 1H), 8.91 (d, J = 2.5 Hz, 1H), 8.88-8.83 (m, 2H), 8.49 (d, J = 10.3 Hz, 1H), 7.75 (d, J = 1.7 Hz, 2H), 7.60 (d, J = 6.0 Hz, 1H), 6.73-6.60 (m, 2H), 4.81 (d, J = 11.0 Hz, 2H), 4.14 (d, J = 12.5 Hz, 1H), 3.94 (d, J = 11.8 Hz, 1H), 3.72 (s, 1H), 3.68 (d, J = 4.5 Hz, 1H), 3.60-3.42 (m, 5H), 3.35 (d, J = 12.4 Hz, 1H), 3.25 (t, J = 12.1 Hz, 1H), 2.02 (d, J = 7.4 Hz, 3H). | 699.2 | 0.355 |
| 428 | 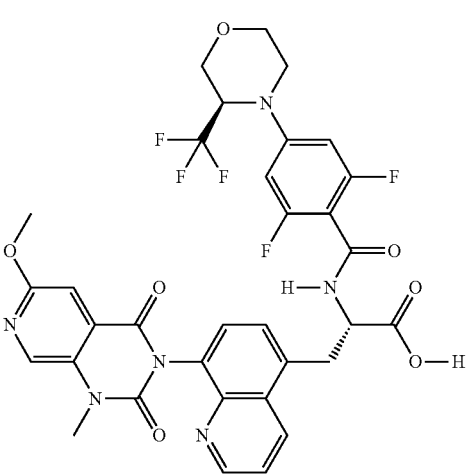 [SMILES: COc1cc2c(=O)n(-c3ccc(C[C@H](NC(=O)c4c(F)cc(N5CCOC[C@@H]5C(F)(F)F)cc4F)C(=O)O)c4cccnc34)c(=O)n(C)c2cn1] | 1H NMR (400 MHz, DMSO-d6) δ 9.01 (d, J = 7.8 Hz, 1H), 8.85 (d, J = 4.2, 1.4 Hz, 1H), 8.69 (d, J = 8.6 Hz, 1H), 8.61 (s, 1H), 7.76 (d, J = 7.5 Hz, 1H), 7.71-7.64 (m, 2H), 7.29 (d, J = 2.3 Hz, 1H), 6.78 (d, J = 11.7 Hz, 2H), 4.97-4.86 (m, 1H), 4.76-4.67 (m, 1H), 4.16 (d, J = 12.7 Hz, 1H), 3.99-3.91 (m, 4H), 3.75 (dd, J = 14.4, 4.4 Hz, 2H), 3.60 (s, 3H), 3.58-3.39 (m, 3H), 3.25 (t, J = 11.2 Hz, 1H). | 715.3 | 0.18 |

TABLE 3-continued

| Example | Structure | 1H-NMR | M/Z [M + H]+ | α4β7 EC$_{50}$ (nM) |
|---|---|---|---|---|
| 429 | 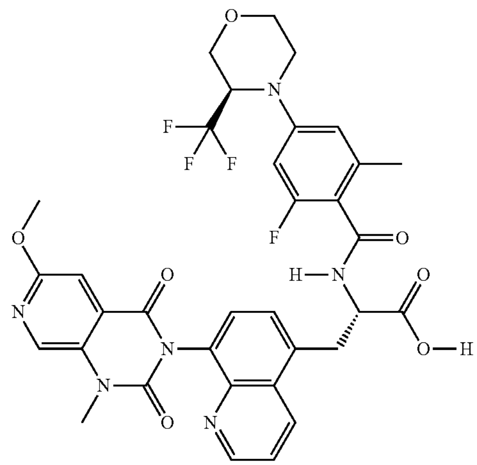 [SMILES: COc1cc2c(=O)n(-c3ccc(C[C@H](NC(=O)c4c(C)cc(N5CCOC[C@@H]5C(F)(F)F)cc4F)C(=O)O)c4cccnc34)c(=O)n(C)c2cn1] | 1H NMR (400 MHz, DMSO-d6) δ 8.88-8.84 (m, 2H), 8.70 (d, J = 8.6 Hz, 1H), 8.62 (s, 1H), 7.76 (d, J = 7.5 Hz, 1H), 7.71-7.66 (m, 2H), 7.29 (d, J = 3.4 Hz, 1H), 6.72-6.63 (m, 2H), 4.89-4.73 (m, 2H), 4.14 (d, J = 12.6 Hz, 1H), 3.99-3.90 (m, 4H), 3.81-3.69 (m, 2H), 3.60 (d, J = 2.5 Hz, 3H), 3.58-3.41 (m, 2H), 3.35 (d, J = 10.6 Hz, 1H), 3.26 (d, J = 12.3 Hz, 1H), 2.03 (s, 3H). | 711.4 | 0.162 |
| 430 | 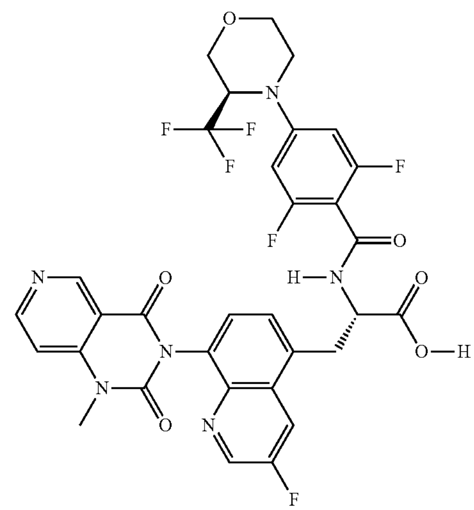 | 1H NMR (400 MHz, DMSO-d6) δ 9.09 (s, 1H), 9.01 (d, J = 7.9 Hz, 1H), 8.91 (d, J = 2.5 Hz, 1H), 8.85 (d, J = 6.0 Hz, 1H), 8.54-8.41 (m, 1H), 7.74 (q, J = 7.8 Hz, 2H), 7.59 (d, J = 6.1 Hz, 1H), 6.77 (d, J = 11.8 Hz, 2H), 4.98-4.85 (m, 1H), 4.73 (tt, J = 9.3, 4.3 Hz, 1H), 4.16 (d, J = 12.7 Hz, 1H), 3.95 (dd, J = 11.7, 3.7 Hz, 1H), 3.76 (s, 2H), 3.66 (m, 1H), 3.57 (s, 3H), 3.43 (d, J = 14.8 Hz, 2H), 3.30-3.17 (m, 1H). | 703.8 | 0.469 |
| 431 | 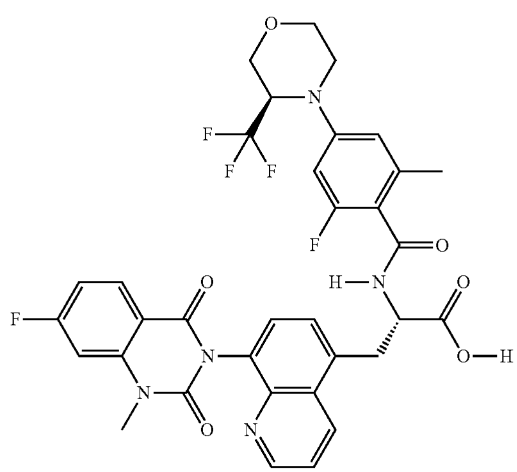 [SMILES: Cc1cc(N2CCOC[C@@H]2C(F)(F)F)cc(F)c1C(=O)N[C@@H](Cc1ccc(-n2c(=O)c3ccc(F)cc3n(C)c2=O)c2ncccc12)C(=O)O] | 1H NMR (400 MHz, DMSO-d6) δ 8.87 (d, J = 8.1 Hz, 1H), 8.86-8.83 (m, 1H), 8.70-8.65 (m, 1H), 8.14-8.07 (m, 1H), 7.75-7.72 (m, 1H), 7.70-7.64 (m, 2H), 7.53-7.46 (m, 1H), 7.25-7.17 (m, 1H), 6.72-6.63 (m, 2H), 4.89-4.80 (m, 1H), 4.80-4.72 (m, 1H), 4.14 (d, J = 12.6 Hz, 1H), 3.97-3.91 (m, 1H), 3.80-3.69 (m, 2H), 3.61-3.53 (m, 3H), 3.53-3.42 (m, 1H), 3.35 (d, J = 12.6 Hz, 1H), 3.26 (d, J = 15.6 Hz, 2H), 2.03 (s, 3H). | 698.2 | 0.094 |

TABLE 3-continued
| Example | Structure | 1H-NMR | M/Z [M + H]+ | α4β7 EC$_{50}$ (nM) |
|---|---|---|---|---|
| 432 | 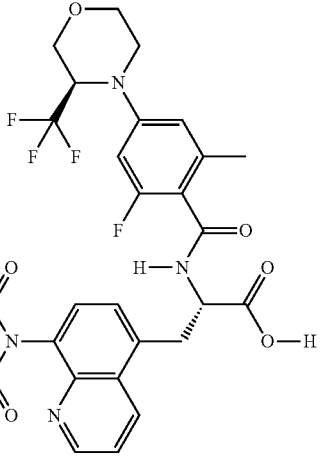 | 1H NMR (400 MHz, DMSO-d6) δ 8.86 (d, J = 8.0 Hz, 3H), 8.68 (d, J = 8.4 Hz, 1H), 8.42 (d, J = 9.3 Hz, 1H), 7.76 (d, J = 7.5 Hz, 1H), 7.70-7.63 (m, 2H), 7.45-7.39 (m, 1H), 6.73-6.63 (m, 2H), 4.87-4.72 (m, 3H), 4.14 (d, J = 12.6 Hz, 1H), 3.99-3.91 (m, 2H), 3.74 (s, 2H), 3.63 (s, 3H), 3.58-3.51 (m, 1H), 3.50-3.42 (m, 1H), 3.38-3.31 (m, 1H), 3.28-3.21 (m, 1H), 2.03 (s, 3H). | 681.2 | 0.11 |
| 433 | 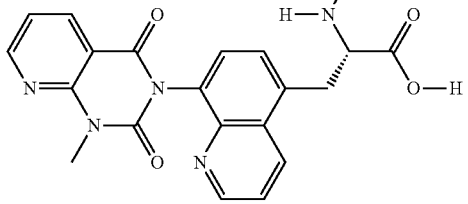 | 1H NMR (400 MHz, DMSO-d6) δ 9.07 (s, 1H), 8.88 (dd, J = 8.2, 3.2 Hz, 2H), 8.69 (dd, J = 8.7, 1.5 Hz, 1H), 8.63 (dd, J = 5.0, 1.4 Hz, 1H), 7.94 (t, J = 4.4 Hz, 1H), 7.69 (td, J = 9.8, 9.3, 3.4 Hz, 2H), 6.79-6.60 (m, 2H), 4.81 (dtd, J = 12.0, 7.6, 3.7 Hz, 2H), 4.14 (d, J = 12.6 Hz, 1H), 3.94 (dd, J = 11.5, 3.6 Hz, 1H), 3.83 (dd, J = 14.7, 3.9 Hz, 1H), 3.77-3.64 (m, 4H), 3.64-3.41 (m, 2H), 3.35 (d, J = 12.3 Hz, 1H), 3.31-3.18 (m, 1H), 2.04 (d, J = 7.5 Hz, 3H). | 699.2 | 0.076 |
| 434 | 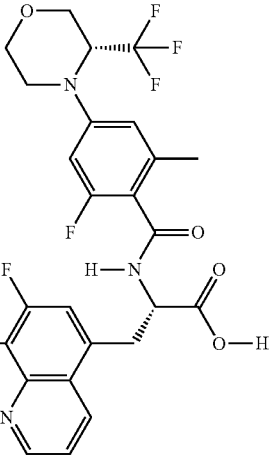 | 1H NMR (400 MHz, DMSO-d6) δ 9.10 (d, J = 3.6 Hz, 1H), 8.95-8.76 (m, 3H), 8.68 (d, J = 8.7 Hz, 1H), 7.76 (d, J = 7.5 Hz, 1H), 7.74-7.56 (m, 3H), 6.74-6.56 (m, 2H), 4.90-4.72 (m, 2H), 4.14 (d, J = 12.6 Hz, 1H), 3.94 (dd, J = 11.4, 3.6 Hz, 1H), 3.75 (t, J = 13.4 Hz, 2H), 3.57 (d, J = 2.4 Hz, 3H), 3.55-3.48 (m, 1H), 3.47 (s, 1H), 3.35 (d, J = 12.6 Hz, 1H), 3.25 (t, J = 12.4 Hz, 1H), 2.03 (s, 3H). | 681.2 | 0.103 |

TABLE 3-continued

| Example | Structure | 1H-NMR | M/Z [M + H]+ | α4β7 EC$_{50}$ (nM) |
|---|---|---|---|---|
| 435 | 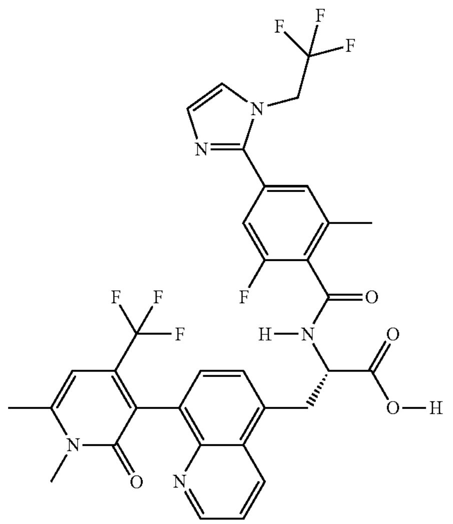 [SMILES: Cc1cc(-c2nccn2CC(F)(F)F)cc(F)c1C(=O)N[C@@H](Cc1ccc(-c2c(C(F)(F)F)cc(C)n(C)c2=O)c2ncccc12)C(=O)O] | 1H NMR (400 MHz, DMSO-d6) δ 9.23 (t, J = 9.0 Hz, 1H), 8.82 (dt, J = 4.0, 1.9 Hz, 1H), 8.64 (d, J = 8.7 Hz, 1H), 7.69-7.55 (m, 3H), 7.42 (ddd, J = 24.4, 15.8, 6.8 Hz, 4H), 6.55 (d, J = 2.9 Hz, 1H), 5.24-5.16 (m, 2H), 4.90-4.80 1H), 3.86-3.70 (m, 1H), 3.49 (s, 2H), 3.51-3.32 (m, 2H), 2.53 (s, 4H), 2.18 (t, J = 7.3 Hz, 2H), 2.10 (d, J = 3.5 Hz, 3H), 1.52-1.43 (m, 3H), 0.85 (t, J = 6.6 Hz, 4H). | 690.2 | 0.524 |
| 436 | 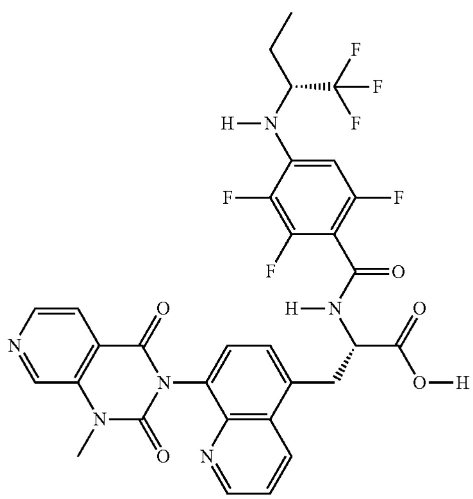 [SMILES: CC[C@@H](Nc1cc(F)c(C(=O)N[C@@H](Cc2ccc(-n3c(=O)c4ccncc4n(C)c3=O)c3ncccc23)C(=O)O)c(F)c1F)C(F)(F)F] | 1H NMR (400 MHz, DMSO-d6) δ 9.05 (d, J = 2.1 Hz, 1H), 8.93-8.80 (m, 1H), 8.75 (d, J = 8.1 Hz, 1H), 8.68 (d, J = 8.6 Hz, 1H), 8.60 (d, J = 5.0 Hz, 1H), 7.92 (dt, J = 5.3, 3.3 Hz, 1H), 7.76 (dd, J = 7.7, 2.2 Hz, 1H), 7.73-7.61 (m, 2H), 6.39 (d, J = 7.7 Hz, 2H) 6.30 (d, J = 9.2 Hz, 1H), 4.74 (d, J = 10.0 Hz, 1H), 4.18 (s, 2H), 3.75 (d, J = 16.7 Hz, 1H), 3.66 (d, J = 2.6 Hz, 3H), 3.44 (dd, J = 14.6, 10.8 Hz, 1H), 1.98 (s, 3H), 1.85-1.68 (m, 1H), 1.53 (dt, J = 15.8, 8.1 Hz, 1H), 1.01-0.87 (m, 3H). | 653.3 | 0.076 |
| 437 | 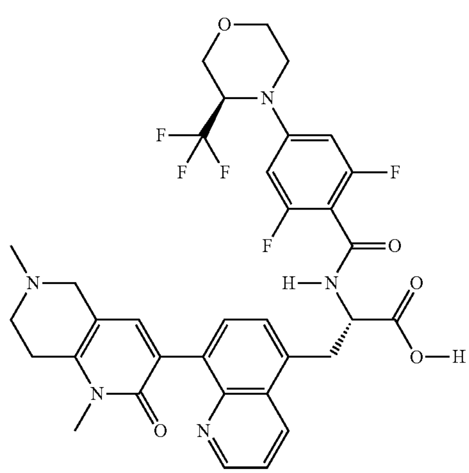 [SMILES: CN1CCc2c(cc(-c3ccc(C[C@H](NC(=O)c4c(F)cc(N5CCOC[C@@H]5C(F)(F)F)cc4F)C(=O)O)c4cccnc34)c(=O)n2C)C1] | 1H NMR (400 MHz, DMSO-d6) δ 10.19 (s, 1H), 8.97 (d, J = 8.0 Hz, 1H), 8.86 (dd, J = 4.2, 1.5 1H), 8.68 (dd, J = 8.8, 1.7 Hz, 1H), 7.69-7.56 (m, 3H), 7.35 (s, 1H), 6.76 (d, J = 11.7 Hz, 2H), 4.98-4.85 (m, 1H), 4.73-4.63 (m, 1H), 4.31 (d, J = 14.7 Hz, 1H), 4.21-4.06 (m, 2H), 3.96 (dd, J = 11.5, 3.8 Hz, 1H), 3.81-3.66 (m, 3H), 3.61-3.47 (m, 4H), 3.47-3.36 (m, 3H), 3.31-3.06 (m, 3H), 2.97 (s, 3H). | 686.3 | 0.261 |

US 12,053,462 B2

521                                                                            522

TABLE 3-continued

| Example | Structure | 1H-NMR | M/Z [M + H]+ | α4β7 EC$_{50}$ (nM) |
|---|---|---|---|---|
| 438 | 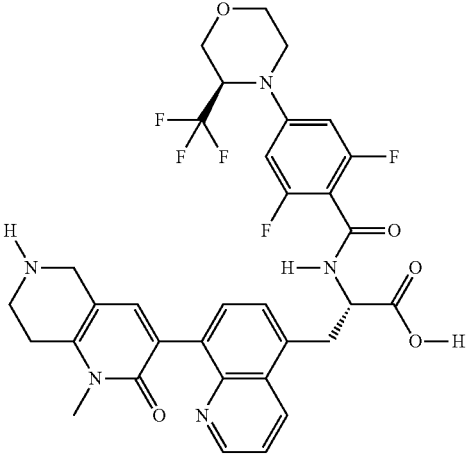 [SMILES: Cn1c2c(cc(-c3ccc(C[C@H](NC(=O)c4c(F)cc(N5CCOC[C@@H]5C(F)(F)F)cc4F)C(=O)O)c4cccnc34)c1=O)CNCC2] | 1H NMR (400 MHz, DMSO-d6) δ 9.11 (s, 2H), 8.97 (d, J = 8.0 Hz, 1H), 8.88-8.82 (m, 1H), 8.67 (d, J = 8.7 Hz, 1H), 7.69-7.55 (m, 3H), 7.37 (s, 1H), 6.76 (d, J = 12.0 Hz, 2H), 4.96-4.86 (m, 1H), 4.73-4.63 (m, 1H), 4.17 (d, J = 12.8 Hz, 1H), 4.09 (s, 2H), 3.96 (d, J = 11.6 Hz, 1H), 3.73 (t, J = 12.0 Hz, 2H), 3.61-3.52 (m, 1H), 3.51-3.46 (m, 4H), 3.46-3.37 (m, 2H), 3.25 (t, J = 12.6 Hz, 1H), 3.10-3.02 (m, 2H). | 672.3 | 0.291 |
| 439 | 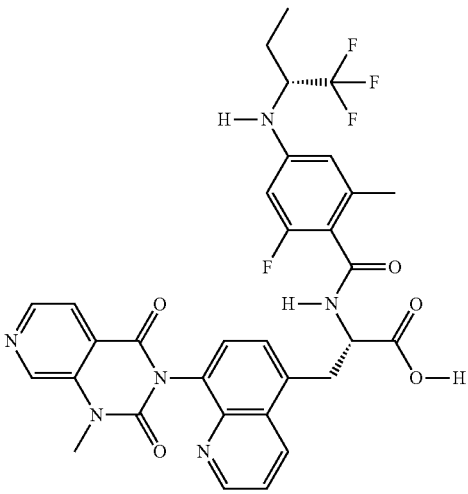 [SMILES: CC[C@@H](Nc1cc(C)c(C(=O)N[C@@H](Cc2ccc(-n3c(=O)c4ccncc4n(C)c3=O)c3ncccc23)C(=O)O)c(F)c1)C(F)(F)F] | 1H NMR (400 MHz, DMSO-d6) δ 9.05 (d, J = 2.1 Hz, 1H), 8.93-8.80 (m, 1H), 8.75 (d, J = 8.1 Hz, 1H), 8.68 (d, J = 8.6 Hz, 1H), 8.60 (d, J = 5.0 Hz, 1H), 7.92 (dt, J = 5.3, 3.3 Hz, 1H), 7.76 (dd, J = 7.7, 2.2 Hz, 1H), 7.73-7.61 (m, 2H), 6.39 (d, J = 7.7 Hz, 2H), 6.30 (d, J = 9.2 Hz, 1H), 4.74 (d, J = 10.0 Hz, 1H), 4.18 (s, 2H), 3.75 (d, J = 16.7 Hz, 1H), 3.66 (d, J = 2.6 Hz, 3H), 3.44 (dd, J = 14.6, 10.8 Hz, 1H), 1.98 (s, 3H), 1.85-1.68 (m, 1H), 1.53 (dt, J = 15.8, 8.1 Hz, 1H), 1.01-0.87 (m, 3H). | 653.3 | 0.049 |
| 440 | 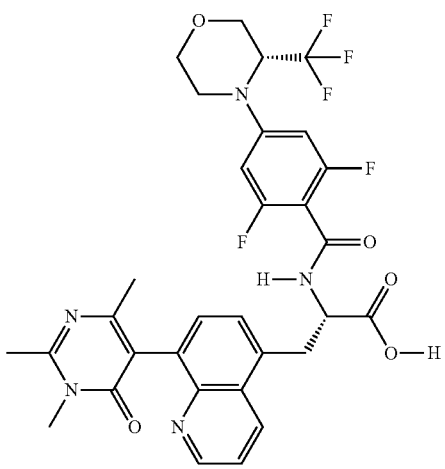 [SMILES: Cc1nc(C)n(C)c(=O)c1-c1ccc(C[C@H](NC(=O)c2c(F)cc(N3CCOC[C@@H]3C(F)(F)F)cc2F)C(=O)O)c2cccnc12] | 1H NMR (400 MHz, DMSO-d6) δ 13.18-12.55 (s, 1H), 8.94 (s, 1H), 8.87 (s, 1H), 8.72 (s, 1H), 7.64 (dd, J = 18.1, 9.8 Hz, 2H), 7.56 (d, J = 8.1 Hz, 1H), 6.74 (d, J = 12.2 Hz, 2H), 4.90 (d, J = 9.7 Hz, 1H), 4.72 (s, 1H), 4.16 (d, J = 12.7 Hz, 1H), 3.95 (d, J = 11.5 Hz, 1H), 3.81 (s, 1H), 3.71 (t, J = 14.1 Hz, 2H), 3.55 (t, J = 11.9 Hz, 1H), 3.48 (s, 3H), 3.45-3.33 (m, 1H), 3.25 (d, J = 12.7 Hz, 1H), 2.62 (d, J = 2.6 Hz, 3H), 1.86 (d, J = 10.0 Hz, 3H). | 646.3 | 0.25 |

TABLE 3-continued

| Example | Structure | 1H-NMR | M/Z [M + H]+ | α4β7 EC$_{50}$ (nM) |
|---|---|---|---|---|
| 441 | 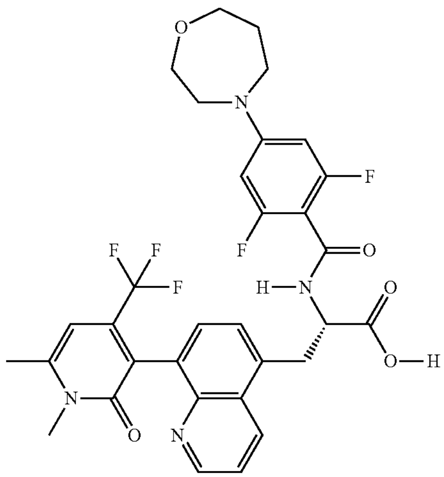 [SMILES: Cc1cc(C(F)(F)F)c(-c2ccc(C[C@H](NC(=O)c3c(F)cc(N4CCCOCC4)cc3F)C(=O)O)c3cccnc23)c(=O)n1C] | 1H NMR (400 MHz, DMSO-d6) δ 8.84 (d, J = 4.2 Hz, 1H), 8.76 (dd, J = 7.8, 2.7 Hz, 1H), 8.69 (d, J = 7.9 Hz, 1H), 7.66 (dd, J = 8.6, 4.3 Hz, 1H), 7.60 (t, J = 7.3 Hz, 1H), 7.46 (d, J = 7.3 Hz, 1H), 6.56 (s, 1H), 6.42 (dd, J = 11.9, 4.3 Hz, 2H), 4.69 (tt, J = 9.9, 5.6 Hz, 1H), 3.77-3.62 (m, 3H), 3.56 (dt, J = 11.9, 5.6 Hz, 6H), 3.49 (s, 4H), 2.54 (s, 3H), 1.84 (p, J = 5.9 Hz, 2H). | 645.2 | 0.412 |
| 442 | 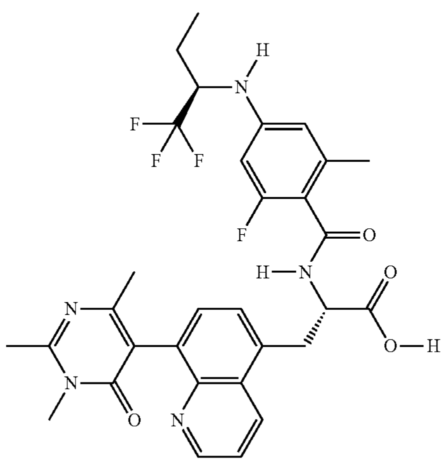 [SMILES: CC[C@@H](Nc1cc(C)c(C(=O)N[C@@H](Cc2ccc(-c3c(C)nc(C)n(C)c3=O)c3ncccc23)C(=O)O)c(F)c1)C(F)(F)F] | 1H NMR (400 MHz, DMSO-d6) δ 8.90-8.82 (m, 1H), 8.73-8.63 (m, 2H), 7.73-7.58 (m, 2H), 7.58-7.50 (m, 1H), 6.41-6.32 (m, 2H), 6.28 (d, J = 9.2 Hz, 1H), 4.80-4.68 (m, 1H), 4.25-4.11 (m, 1H), 3.87-3.72 (m, 1H), 3.51-3.44 (m, 3H), 3.38-3.27 1H), 2.60 (s, 3H), 1.92 (s, 3H), 1.89-1.79 (m, 3H), 1.81-1.67 (m, 1H), 1.60-1.46 (m, 1H), 0.92 (t, J = 7.3 Hz, 3H). | 614.3 | 0.227 |
| 443 | 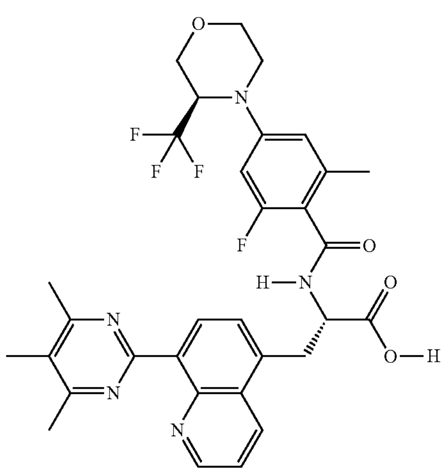 [SMILES: Cc1cc(N2CCOC[C@@H]2C(F)(F)F)cc(F)c1C(=O)N[C@@H](Cc1ccc(-c2nc(C)c(C)c(C)n2)c2ncccc12)C(=O)O] | 1H NMR (400 MHz, DMSO-d6) δ 9.44 (t, J = 8.3 Hz, 1H), 9.36-9.27 (m, 1H), 8.81 (d, J = 8.4 Hz, 1H), 8.18-8.11 (m, 1H), 7.96 (d, J = 7.3 Hz, 1H), 6.63 (t, J = 5.8 Hz, 2H), 4.86-4.76 (m, 3H), 4.14 (d, J = 12.7 Hz, 1H), 3.95-3.86 (m, 3H), 3.72 (m, 1H), 3.53 (d, J = 11.5 Hz, 2H), 3.32 (d, J = 12.1 Hz, 1H), 3.24 (d, J = 9.8 Hz, 1H), 2.69 (s, 6H), 2.36 (s, 3H), 2.01 (s, 3H). | 626.2 | 0.714 |

TABLE 3-continued
| Example | Structure | 1H-NMR | M/Z [M + H]+ | α4β7 EC$_{50}$ (nM) |
|---|---|---|---|---|
| 444 | 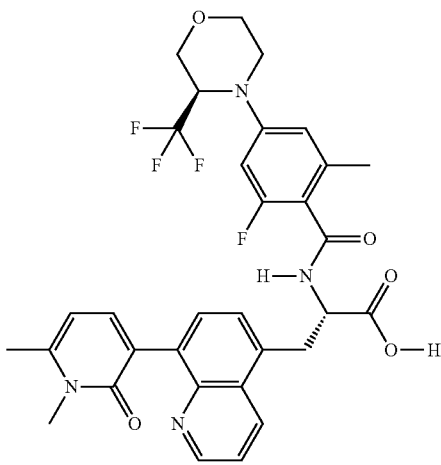 [SMILES: Cc1cc(N2CCOC[C@@H]2C(F)(F)F)cc(F)c1C(=O)N[C@@H](Cc1ccc(-c2ccc(C)n(C)c2=O)c2ncccc12)C(=O)O] | 1H NMR (400 MHz, DMSO-d6) δ 8.93 (s, 1H), 8.91-8.78 (m, 2H), 7.77 (s, 1H), 7.72-7.62 (m, 2H), 7.40 (d, J = 7.0 Hz, 1H), 6.72-6.61 (m, 2H), 6.31 (d, J = 7.1 Hz, 1H), 4.89-4.70 (m, 1H), 4.14 (d, J = 12.6 Hz, 1H), 3.94 (dd, J = 11.2, 3.6 Hz, 1H), 3.81-3.69 (m, 2H), 3.50 (s, 4H), 3.47-3.18 (m, 3H), 2.46 (s, 3H), 2.00 (s, 3H). | 627.1 | 0.161 |
| 445 | 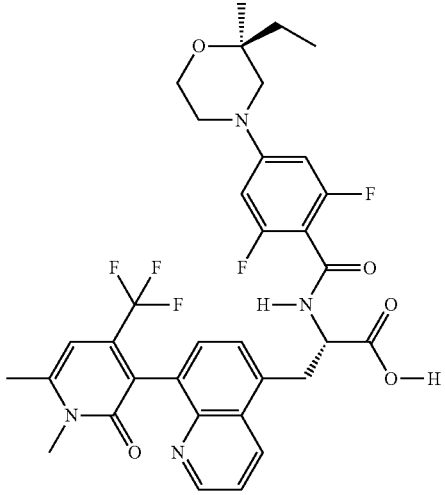 [SMILES: CC[C@@]1(C)CN(c2cc(F)c(C(=O)N[C@@H](Cc3ccc(-c4c(C(F)(F)F)cc(C)n(C)c4=O)c4ncccc34)C(=O)O)c(F)c2)CCO1] | 1H NMR (400 MHz, DMSO-d6) δ 8.93-8.77 (m, 2H), 8.65 (s, 1H), 7.74-7.52 (m, 2H), 7.43 (dd, J = 7.4, 3.3 Hz, 1H), 6.69-6.48 (m, 3H), 4.75-4.59 (m, 1H), 3.77-3.56 (m, 3H), 3.55-3.33 (m, 4H), 3.19 (d, J = 7.1 Hz, 2H), 3.17-3.03 (m, 2H), 2.53 (s, 3H), 1.66 (dq, J = 14.8, 7.4 Hz, 1H), 1.40 (dq, J = 14.6, 7.4 Hz, 1H), 1.09 (s, 3H), 0.83 (t, J = 7.5 Hz, 3H). | 673.2 | 0.984 |
| 446 | 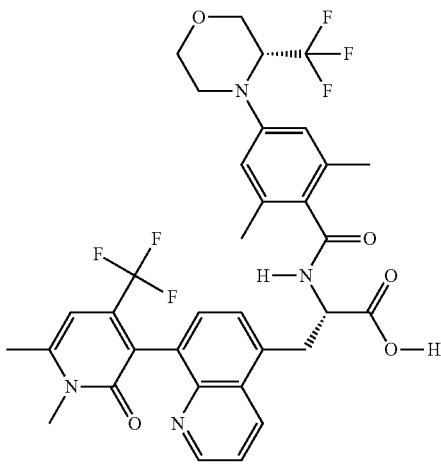 [SMILES: Cc1cc(N2CCOC[C@@H]2C(F)(F)F)cc(C)c1C(=O)N[C@@H](Cc1ccc(-c2c(C(F)(F)F)cc(C)n(C)c2=O)c2ncccc12)C(=O)O] | 1H NMR (400 MHz, DMSO-d6) δ 12.92 (s, 1H), 8.80 (t, J = 5.3 Hz, 1H), 8.68 (d, J = 8.3 Hz, 1H), 8.61 (d, J = 8.4 Hz, 1H), 7.67-7.54 (m, 2H), 7.42 (dd, J = 11.0, 7.2 Hz, 1H), 6.59 (d, J = 11.2 Hz, 2H), 6.54 (d, J = 5.6 Hz, 1H), 4.90 (s, 1H), 4.84-4.63 (m, 2H), 4.12 (d, J = 13.4 Hz, 1H), 3.92 (d, J = 11.3 Hz, 2H), 3.80 (d, J = 15.7 Hz, 1H), 3.71 (d, J = 15.7 Hz, 1H), 3.70 (m, 1H), 3.49 (d, J = 3.6 Hz, 3H), 3.31 (d, J = 11.7 Hz, 1H), 3.26 (s, 3H), 1.93 (d, J = 6.7 Hz, 6H). | 691.2 | 0.318 |

TABLE 3-continued

| Example | Structure | 1H-NMR | M/Z [M + H]+ | α4β7 EC$_{50}$ (nM) |
|---|---|---|---|---|
| 447 | 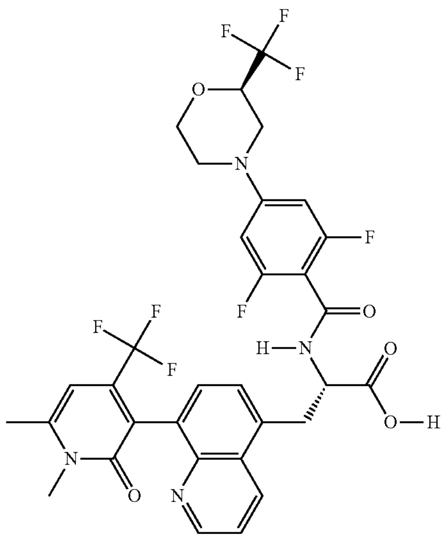 [SMILES: Cc1cc(C(F)(F)F)c(-c2ccc(C[C@H](NC(=O)c3c(F)cc(N4CCO[C@@H](C(F)(F)F)C4)cc3F)C(=O)O)c3cccnc23)c(=O)n1C] | 1H NMR (400 MHz, DMSO-d6) δ 8.94 (d, J = 7.8 Hz, 1H), 8.84-8.77 (m, 1H), 8.68-8.59 (m, 1H), 7.66-7.53 (m, 2H), 7.43 (dd, J = 7.4, 4.0 Hz, 1H), 6.76 (dd, J = 11.5, 4.1 Hz, 2H), 6.54 (s, 1H), 4.75-4.65 (m, 1H), 4.38-4.24 (m, 1H), 4.09-4.01 (m, 1H), 3.92-3.85 (m, 1H), 3.78-3.62 (m, 3H), 3.53-3.37 (m, 4H), 2.92-2.77 (m, 2H), 2.53 (s, 3H). | 699.2 | 0.271 |
| 448 | 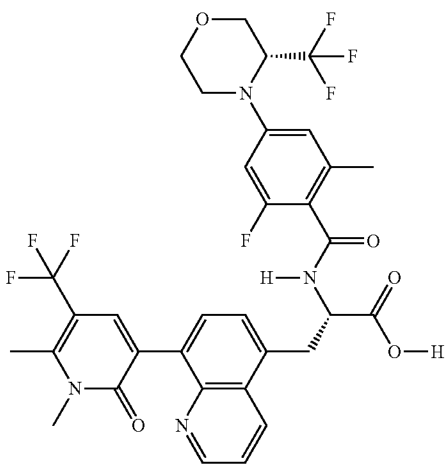 [SMILES: Cc1cc(N2CCOC[C@@H]2C(F)(F)F)cc(F)c1C(=O)N[C@@H](Cc1ccc(-c2cc(C(F)(F)F)c(C)n(C)c2=O)c2ncccc12)C(=O)O] | 1H NMR (400 MHz, DMSO-d6) δ 13.07-12.69 (s, 1H), 8.87 (d, J = 4.1 Hz, 1H), 8.81 (d, J = 8.2 Hz, 1H), 8.68 (d, J = 8.6 Hz, 1H), 7.69 (d, J = 7.4 Hz, 1H), 7.67-7.63 (m, 1H), 7.60 (m, 2H), 6.66 (d, J = 16.6 Hz, 2H), 4.83 (d, J = 9.5 Hz, 1H), 4.76 (d, J = 11.4 Hz, 1H), 4.14 (d, J = 12.6 Hz, 1H), 3.94 (d, J = 11.5 Hz, 1H), 3.73 (d, J = 13.3 Hz, 2H), 3.60 (s, 3H), 3.54 (dd, J = 13.7, 10.4 Hz, 1H), 3.44-3.38 (m, 1H), 3.35 (d, J = 16.3 Hz, 1H), 3.26 (d, J = 12.4 Hz, 1H), 2.60 (s, 3H), 2.00 (s, 3H). | 695.1 | 0.307 |
| 449 | 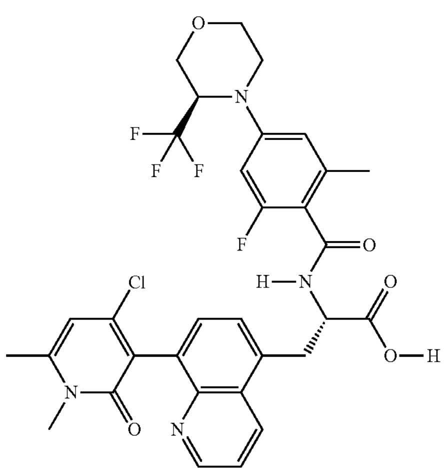 [SMILES: Cc1cc(N2CCOC[C@@H]2C(F)(F)F)cc(F)c1C(=O)N[C@@H](Cc1ccc(-c2c(Cl)cc(C)n(C)c2=O)c2ncccc12)C(=O)O] | 1H NMR (400 MHz, DMSO-d6) δ 8.88 (d, J = 3.5 Hz, 1H), 8.83 (t, J = 7.6 Hz, 1H), 8.75 (d, J = 8.6 Hz, 1H), 7.74-7.68 (m, 1H), 7.65 (t, J = 6.8 Hz, 1H), 7.55 (dd, J = 7.3, 4.5 Hz, 1H), 6.70-6.61 (m, 2H), 6.49 (d, J = 4.1 Hz, 1H), 4.79 (dtd, J = 19.1, 11.2, 9.8, 5.4 Hz, 2H), 4.14 (d, J = 12.6 Hz, 1H), 3.94 (dd, J = 11.5, 3.6 Hz, 1H), 3.81-3.69 (m, 4H), 3.45 (d, J = 3.3 Hz, 3H), 3.40-3.32 (m, 1H), 3.24 (t, J = 12.5 Hz, 1H), 2.46 (s, 3H), 1.98 (d, J = 6.2 Hz, 3H). | 661.1 | 0.092 |

TABLE 3-continued

| Example | Structure | 1H-NMR | M/Z [M + H]+ | α4β7 EC$_{50}$ (nM) |
|---|---|---|---|---|
| 450 | 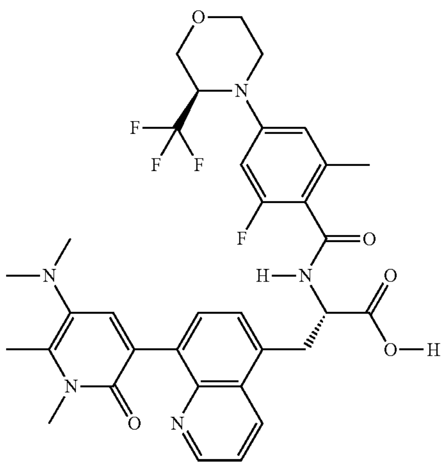 [SMILES: Cc1cc(N2CCOC[C@@H]2C(F)(F)F)cc(F)c1C(=O)N[C@@H](Cc1ccc(-c2cc(N(C)C)c(C)n(C)c2=O)c2ncccc12)C(=O)O] | 1H NMR (400 MHz, DMSO-d6) δ 8.95 (d, J = 4.5 Hz, 1H), 8.89 (d, J = 8.1 Hz, 1H), 8.83 (d, J = 8.1 Hz, 1H), 7.82-7.72 (m, 2H), 7.68 (d, J = 8.0 Hz, 2H), 6.67 (d, J = 13.0 Hz, 2H), 4.82 (dt, J = 10.8, 5.4 Hz, 1H), 4.79-4.70 1H), 4.15 (d, J = 12.6 Hz, 1H), 3.98-3.92 (m, 2H), 3.75 (s, 1H), 3.53 (s, 4H), 3.44 (dd, J = 14.6, 10.2 Hz, 1H), 3.34 (d, J = 12.1 Hz, 1H), 3.29-3.20 (m, 1H), 2.66 (s, 6H), 2.53 (s, 4H), 2.03 (s, 3H). | 670.3 | 1.02 |
| 451 | 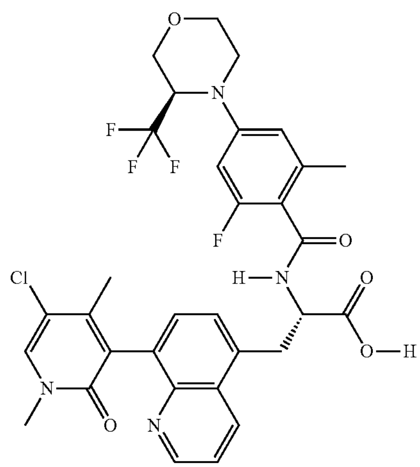 [SMILES: Cc1cc(N2CCOC[C@@H]2C(F)(F)F)cc(F)c1C(=O)N[C@@H](Cc1ccc(-c2c(C)c(Cl)cn(C)c2=O)c2ncccc12)C(=O)O] | 1H NMR (400 MHz, DMSO-d6) δ 8.90 (t, J = 4.3 Hz, 1H), 8.87-8.78 (m, 2H), 8.12 (d, J = 1.9 Hz, 1H), 7.81-7.65 (m, 2H), 7.57 (t, J = 7.8 Hz, 1H), 6.70-6.60 (m, 2H), 4.88-4.73 (m, 2H), 4.14 (d, J = 12.6 Hz, 1H), 3.94 (dd, J = 11.6, 3.7 Hz, 1H), 3.84 (dd, J = 14.4, 3.9 Hz, 1H), 3.76-3.66 (m, 2H), 3.58-3.48 (m, 1H), 3.45 (d, J = 2.8 Hz, 3H), 3.41-3.29 (m, 1H), 3.29-3.18 (m, 1H), 1.98 (d, J = 3.5 Hz, 3H), 1.82 (d, J = 12.7 Hz, 3H). | 661.1 | 0.208 |
| 452 | 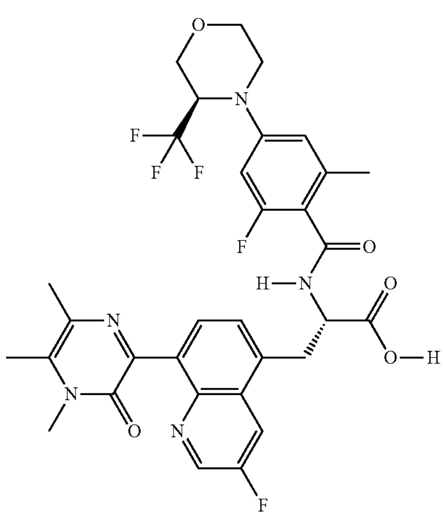 [SMILES: Cc1cc(N2CCOC[C@@H]2C(F)(F)F)cc(F)c1C(=O)N[C@@H](Cc1ccc(-c2nc(C)c(C)n(C)c2=O)c2ncc(F)cc12)C(=O)O] | 1H NMR (400 MHz, DMSO-d6) δ 8.86 (d, J = 2.7 Hz, 1H), 8.81 (d, J = 8.1 Hz, 1H), 8.40 (dd, J = 10.7, 2.8 Hz, 1H), 7.64 (d, J = 7.4 Hz, 1H), 7.56 (d, J = 7.3 Hz, 1H), 6.67 (d, J = 14.5 Hz, 2H), 4.87-4.79 (m, 1H), 4.73 (ddd, J = 10.1, 8.1, 4.4 Hz, 1H), 4.14 (d, J = 12.6 Hz, 1H), 3.94 (dd, J = 11.5, 3.6 Hz, 1H), 3.73 (dt, J = 12.0, 2.9 Hz, 1H), 3.65 (dd, J = 14.6, 4.4 Hz, 1H), 3.55 (dd, J = 12.0, 3.5 Hz, 1H), 3.51 (s, 3H), 3.42 (dd, J = 14.6, 10.0 Hz, 1H), 3.35 (d, J = 12.2 Hz, 1H), 3.25 (t, J = 12.2 Hz, 1H), 2.40 (s, 3H), 2.31 (s, 3H), 2.06 (d, J = 8.9 Hz, 3H). | 660.2 | 0.232 |

TABLE 3-continued
| Example | Structure | 1H-NMR | M/Z [M + H]+ | α4β7 EC$_{50}$ (nM) |
|---|---|---|---|---|
| 453 | 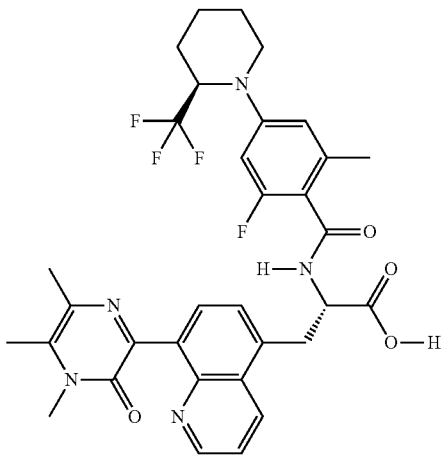 [SMILES: Cc1cc(N2CCCC[C@@H]2C(F)(F)F)cc(F)c1C(=O)N[C@@H](Cc1ccc(-c2nc(C)c(C)n(C)c2=O)c2ncccc12)C(=O)O] | 1H NMR (400 MHz, DMSO-d6) δ 8.88 (d, J = 4.2 Hz, 1H), 8.82-8.70 (m, 2H), 7.77-7.66 (m, 2H), 7.64 (d, J = 7.3 Hz, 1H), 6.69-6.60 (m, 2H), 4.90-4.77 (m, 1H), 4.77-4.66 (m, 1H), 3.74 (dd, J = 14.3, 4.3 Hz, 1H), 3.59-3.48 (m, 4H), 3.44 (dd, J = 14.5, 10.2 Hz, 1H), 3.03 (t, J = 12.0 Hz, 1H), 2.42 (s, 3H), 2.33 (s, 3H), 2.05 (s, 3H), 1.99-1.89 (m, 1H), 1.86-1.67 (m, 2H), 1.67-1.41 (m, 3H). | 640.2 | 0.677 |
| 454 | 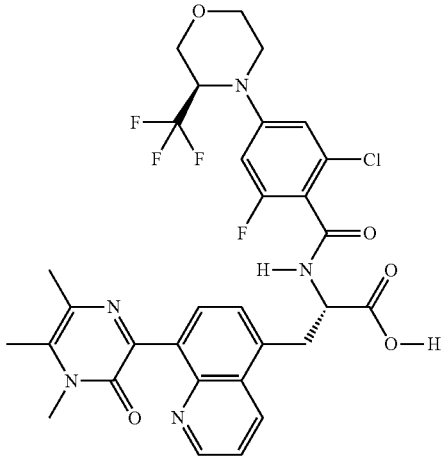 | 1H NMR (400 MHz, DMSO-d6) δ 9.09 (d, J = 8.1 Hz, 1H), 8.92-8.83 (m, 1H), 8.78-8.67 (m, 1H), 7.77-7.58 (m, 3H), 6.95-6.85 (m, 2H), 4.98-4.86 (m, 1H), 4.80-4.69 (m, 1H), 4.15 (d, J = 12.6 Hz, 1H), 3.99-3.91 1H), 3.77-3.69 (m, 2H), 3.52 (s, 3H), 3.42-3.35 (m, 2H), 3.30-3.15 (m, 2H), 2.41 (s, 3H), 2.33 (s, 3H). | 663.2 | 0.14 |
| 455 | 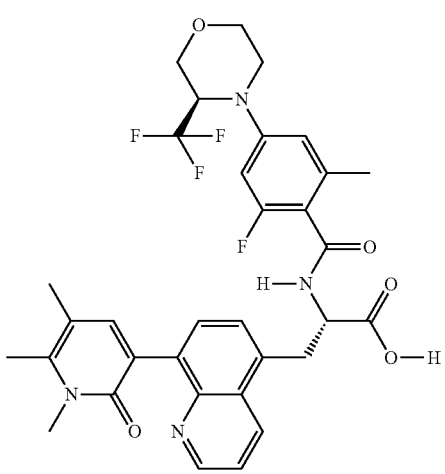 [SMILES: Cc1cc(N2CCOC[C@@H]2C(F)(F)F)cc(F)c1C(=O)N[C@@H](Cc1ccc(-c2cc(C)c(C)n(C)c2=O)c2ncccc12)C(=O)O] | 1H NMR (400 MHz, DMSO-d6) δ 8.93 (dd, J = 17.1, 6.7 Hz, 2H), 8.81 (d, J = 8.2 Hz, 1H), 7.95-7.54 (m, 3H), 7.38 (s, 1H), 6.66 (d, J = 13.4 Hz, 2H), 4.86-4.73 (m, 2H), 4.14 (d, J = 12.7 Hz, 1H), 3.94 (dd, J = 11.4, 3.6 Hz, 1H), 3.78-3.67 (m, 2H), 3.57 (d, J = 3.2 Hz, 3H), 3.51-3.16 (m, 4H), 2.40 (s, 3H), 2.15 (s, 3H), 2.01 (s, 3H). | 641.2 | 0.211 |

TABLE 3-continued

| Example | Structure | 1H-NMR | M/Z [M + H]+ | α4β7 EC$_{50}$ (nM) |
|---|---|---|---|---|
| 456 | 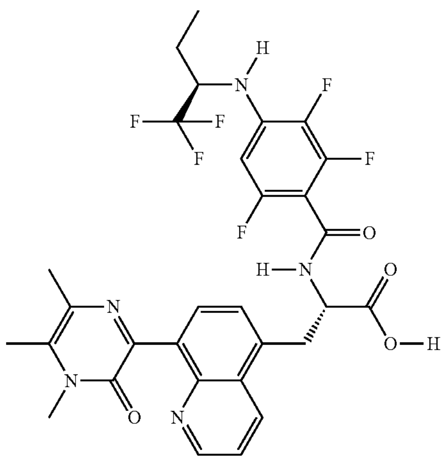 [SMILES: CC[C@@H](Nc1cc(F)c(C(=O)N[C@@H](Cc2ccc(-c3nc(C)c(C)n(C)c3=O)c3ncccc23)C(=O)O)c(F)c1F)C(F)(F)F] | 1H NMR (400 MHz, DMSO-d6) δ 8.98 (d, J = 8.0 Hz, 1H), 8.91 (s, 1H), 8.78 (s, 1H), 7.75 (d, J = 18.6 Hz, 2H), 7.63 (d, J = 7.4 Hz, 1H), 6.83 (dd, J = 12.3, 6.4 Hz, 1H), 6.71 (d, J = 9.3 Hz, 1H), 4.68 (dd, J = 9.0, 4.8 Hz, 1H), 4.38-4.36 (m, 1H), 3.75 (dd, J = 14.5, 4.5 Hz, 1H), 3.53 (s, 3H), 3.44 (dd, J = 14.5, 9.9 Hz, 1H), 2.42 (s, 3H), 2.34 (s, 3H), 1.83-1.70 (m, 2H), 0.92 (t, J = 7.3 Hz, 3H). | 636.2 | 0.248 |
| 457 | 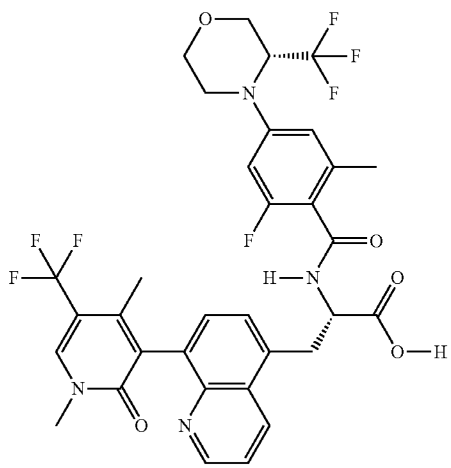 [SMILES: Cc1cc(N2CCOC[C@@H]2C(F)(F)F)cc(F)c1C(=O)N[C@@H](Cc1ccc(-c2c(C)c(C(F)(F)F)cn(C)c2=O)c2ncccc12)C(=O)O] | 1H NMR (400 MHz, DMSO-d6) δ 13.07-12.67 (s, 1H), 8.85 (s, 1H), 8.81 (dd, J = 8.3, 5.2 Hz, 1H), 8.69 (s, 1H), 8.38 (s, 1H), 7.75-7.59 (s, 2H), 7.56-7.47 (s, 1H), 6.71-6.57 (m, 2H), 4.83 (s, 1H), 4.80 (s, 2H), 4.14 (d, J = 12.6 Hz, 1H), 3.94 (d, J = 10.2 Hz, 1H), 3.82 (d, J = 14.7 Hz, 1H), 3.70 (t, J = 14.2 Hz, 1H), 3.56 (s, 1H), 3.51 (d, J = 2.7 Hz, 3H), 3.33 (d, J = 11.6 Hz, 1H), 3.25 (d, J = 13.0 Hz, 1H), 1.97 (s, 3H), 1.83 (d, J = 12.7 Hz, 3H). | 695.2 | 0.238 |
| 458 | 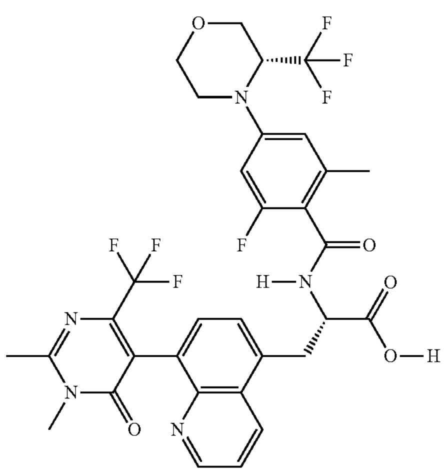 [SMILES: Cc1cc(N2CCOC[C@@H]2C(F)(F)F)cc(F)c1C(=O)N[C@@H](Cc1ccc(-c2c(C(F)(F)F)nc(C)n(C)c2=O)c2ncccc12)C(=O)O] | 1H NMR (400 MHz, DMSO-d6) δ 13.24-12.52 (s, 1H), 8.88-8.77 (m, 2H), 8.67-8.59 (m, 1H), 7.62 (ddd, J = 17.7, 8.6, 5.0 Hz, 2H), 7.49 (t, J = 6.9 Hz, 1H), 6.72-6.59 (m, 2H), 4.83 (d, J = 12.2 Hz, 1H), 4.80-4.70 (m, 1H), 4.14 (d, J = 12.6 Hz, 1H), 3.94 (dd, J = 11.9, 3.6 Hz, 1H), 3.73 (q, J = 12.6, 11.1 Hz, 2H), 3.53 (d, J = 4.4 Hz, 1H), 3.51 (d, J = 3.3 Hz, 3H), 3.49-3.38 (m, 1H), 3.34 (d, J = 12.1 Hz, 1H), 3.26 (d, J = 12.5 Hz, 1H), 2.66 (s, 3H), 1.96 (s, 3H). | 696.2 | 0.09 |

TABLE 3-continued
| Example | Structure | 1H-NMR | M/Z [M + H]+ | α4β7 EC$_{50}$ (nM) |
|---|---|---|---|---|
| 459 | 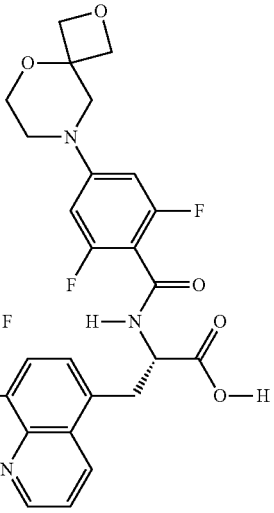 | 1H NMR (400 MHz, DMSO-d6) δ 8.90 (d, J = 7.9 Hz, 1H), 8.84 (s, 1H), 8.69 (s, 1H), 7.73-7.55 (m, 2H), 7.46 (s, 1H), 6.73 (dd, J = 11.5, 4.1 Hz, 2H), 6.56 (s, 1H), 4.70 (d, J = 11.3 Hz, 1H), 4.45 (d, J = 6.8 Hz, 2H), 4.41 (d, J = 6.3 Hz, 2H), 3.82-3.61 (m, 3H), 3.57-3.34 (m, 6H), 3.15 (t, J = 5.0 Hz, 2H), 2.54 (s, 3H). | 673.2 | 2.066 |
| 460 | 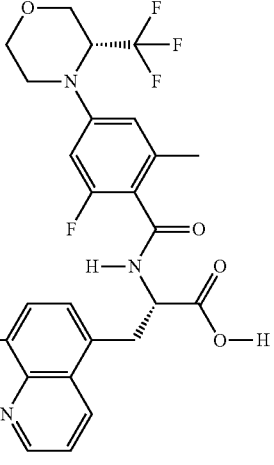 | 1H NMR (400 MHz, DMSO-d6) δ 13.31-12.56 (s, 1H), 8.88 (s, 1H), 8.81 (dd, J = 8.3, 6.2 Hz, 1H), 8.75 (s, 1H), 7.67 (dd, J = 17.8, 10.3 Hz, 1H), 7.58 (d, J = 6.9 Hz, 1H), 6.67 (s, 1H), 6.66-6.59 (m, 2H), 4.88-4.73 (m, 2H), 4.14 (d, J = 12.6 Hz, 1H), 3.98-3.90 1H), 3.81 (d, J = 12.8 Hz, 1H), 3.72 (d, J = 13.4 Hz, 2H), 3.53 (dd, J = 12.1, 8.6 Hz, 1H), 3.49 (d, J = 3.3 Hz, 3H), 3.34 (d, J = 14.5 Hz, 1H), 3.24 (t, J = 12.4 Hz, 1H), 2.63 (s, 3H), 1.96 (d, J = 8.2 Hz, 3H), 1.92 (s, 3H). | 642.2 | 0.15 |
| 461 | 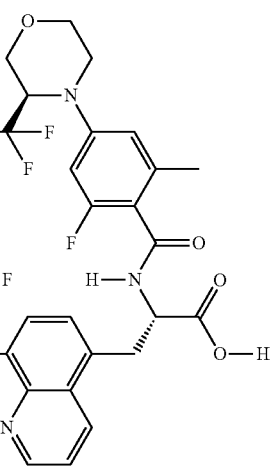 | 1H NMR (400 MHz, DMSO-d6) δ 8.93-8.75 (m, 2H), 8.61 (d, J = 8.7 Hz, 1H), 7.68-7.56 (m, 2H), 7.42 (t, J = 7.2 Hz, 1H), 6.72-6.61 (m, 2H), 6.54 (d, J = 3.1 Hz, 1H), 4.86-4.68 (m, 2H), 4.14 (d, J = 12.5 Hz, 1H), 3.94 (d, J = 11.1 Hz, 1H), 3.65 (m, 3H), 3.49 (d, J = 3.3 Hz, 4H), 3.30 (dd, J = 33.7, 11.9 Hz, 3H), 2.53 (s, 3H), 1.98 (d, J = 3.0 Hz, 3H). | 695.2 | 0.093 |

TABLE 3-continued

| Example | Structure | 1H-NMR | M/Z [M + H]+ | α4β7 EC$_{50}$ (nM) |
|---|---|---|---|---|
| 462 | 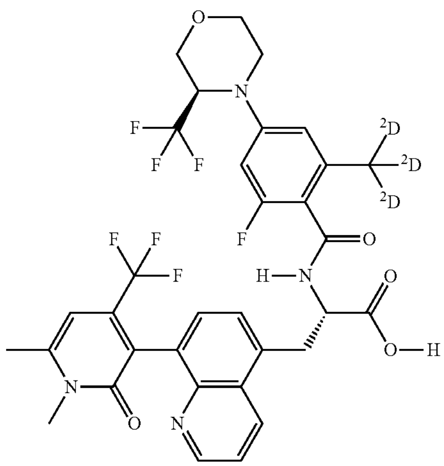 [SMILES: [2H]C([2H])([2H])c1cc(N2CCOC[C@@H]2C(F)(F)F)cc(F)c1C(=O)N[C@@H](Cc1ccc(-c2c(C(F)(F)F)cc(C)n(C)c2=O)c2ncccc12)C(=O)O] | 1H NMR (400 MHz, DMSO-d6) δ 8.88-8.77 (m, 2H), 8.66 (d, J = 8.7 Hz, 1H), 7.70-7.56 (m, 2H), 7.45 (t, J = 7.2 Hz, 1H), 6.71-6.60 (m, 2H), 6.55 (d, J = 3.3 Hz, 1H), 4.89-4.69 (m, 2H), 4.14 (d, J = 12.6 Hz, 1H), 3.99-3.89 (m, 1H), 3.81-3.73 (m, 2H), 3.55-3.42 (m, 4H), 3.41-3.30 (m, 1H), 3.30-3.17 (m, 1H), 2.53 (s, 3H). | 698.1 | 0.102 |
| 463 | 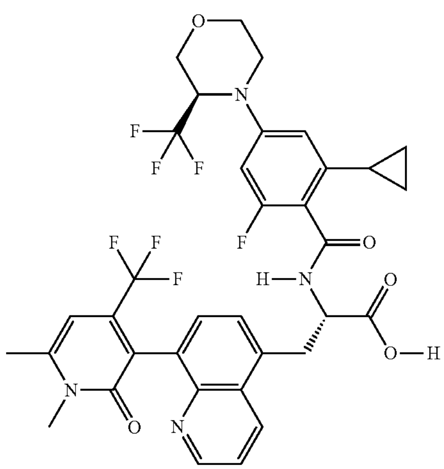 [SMILES: Cc1cc(C(F)(F)F)c(-c2ccc(C[C@H](NC(=O)c3c(F)cc(N4CCOC[C@@H]4C(F)(F)F)cc3C3CC3)C(=O)O)c3cccnc23)c(=O)n1C] | 1H NMR (400 MHz, DMSO-d6) δ 8.95 (dd, J = 8.0, 2.7 Hz, 1H), 8.84 (dd, J = 4.3, 1.5 Hz, 1H), 8.74-8.65 (m, 1H), 7.70-7.64 (m, 1H), 7.62 (dd, J = 7.5, 1.7 Hz, 1H), 7.45 (d, J = 7.3 Hz, 1H), 6.62 (ddd, J = 12.8, 4.2, 2.2 Hz, 1H), 6.57-6.53 (m, 1H), 6.18 (dd, J = 13.7, 2.2 Hz, 1H), 4.93-4.71 (m, 2H), 4.13 (d, J = 12.6 Hz, 1H), 3.93 (dd, J = 11.5, 3.6 Hz, 1H), 3.77-3.66 (m, 2H), 3.58-3.39 (m, 5H), 3.35-3.17 (m, 3H), 2.54 (s, 3H), 1.87-1.68 (m, 1H), 0.71 (dd, J = 8.2, 3.5 Hz, 2H), 0.65-0.51 (m, 1H). | 721.2 | 0.205 |
| 464 | 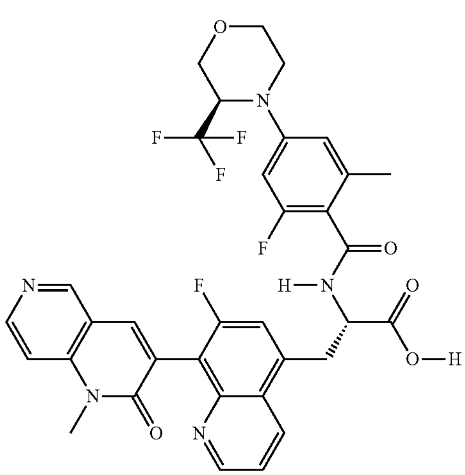 [SMILES: Cc1cc(N2CCOC[C@@H]2C(F)(F)F)cc(F)c1C(=O)N[C@@H](Cc1cc(F)c(-c2cc3cnccc3n(C)c2=O)c2ncccc12)C(=O)O] | 1H NMR (400 MHz, DMSO-d6) δ 9.16 (d, J = 8.4 Hz, 1H), 8.88-8.82 (m, 2H), 8.80 (d, J = 6.5 Hz, 1H), 8.67 (dd, J = 8.7, 1.7 Hz, 1H), 8.22 (s, 1H), 7.90-7.81 (m, 1H), 7.70-7.52 (m, 2H), 6.73-6.62 (m, 2H), 4.90-4.72 (m, 2H), 4.14 (d, J = 12.6 Hz, 1H), 3.98-3.92 (m, 1H), 3.85 (d, J = 14.3 Hz, 1H), 3.80 (d, J = 4.2 Hz, 1H), 3.74 (s, 3H), 3.54 (dd, J = 13.7, 10.4 Hz, 1H), 3.48-3.40 (m, 1H), 3.40-3.31 (m, 1H), 3.26 (d, J = 12.5 Hz, 1H), 2.04 (d, J = 6.4 Hz, 3H). | 682.1 | 0.13 |

TABLE 3-continued

| Example | Structure | 1H-NMR | M/Z [M + H]+ | α4β7 EC$_{50}$ (nM) |
|---|---|---|---|---|
| 465 | 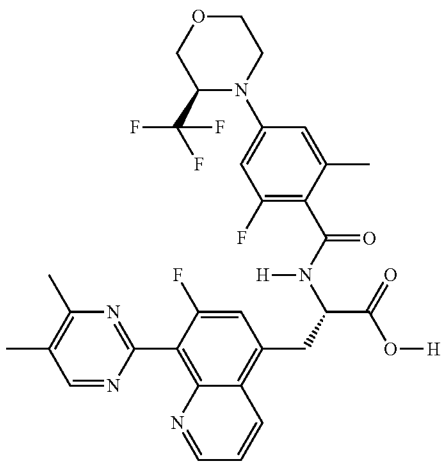 [SMILES: Cc1cnc(-c2c(F)cc(C[C@H](NC(=O)c3c(C)cc(N4CCOC[C@@H]4C(F)(F)F)cc3F)C(=O)O)c3cccnc23)nc1C] | 1H NMR (400 MHz, DMSO-d6) δ 8.86-8.77 (m, 2H), 8.69-8.56 (m, 2H), 7.62 (dd, J = 8.6, 4.2 Hz, 1H), 7.56 (d, J = 10.2 Hz, 1H), 6.75-6.62 (m, 2H), 4.83 (dd, J = 8.9, 3.4 Hz, 1H), 4.75 (ddd, J = 11.7, 8.1, 3.9 Hz, 1H) 4.14 (d, J = 12.6 Hz, 1H), 3.95 (s, 1H), 3.75 (s, 1H), 3.71 (s, 1H), 3.54 (td, J = 11.6, 3.3 Hz, 1H), 3.43 (dd, J = 14.5, 10.8 Hz, 1H), 3.35 (d, J = 11.8 Hz, 1H), 3.24 (t, J = 12.4 Hz, 1H), 2.49 (s, 3H), 2.34 (s, 3H), 2.07 (s, 3H). | 630.1 | 1.527 |
| 466 | 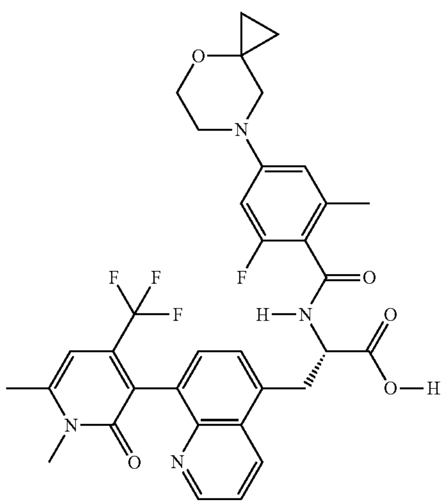 [SMILES: Cc1cc(N2CCOC3(CC3)C2)cc(F)c1C(=O)N[C@@H](Cc1ccc(-c2c(C(F)(F)F)cc(C)n(C)c2=O)c2ncccc12)C(=O)O] | 1H NMR (400 MHz, DMSO-d6) δ 8.87-8.72 (m, 2H), 8.64 (d, J = 8.6 Hz, 1H), 7.69-7.54 (m, 2H), 7.44 (t, J = 6.9 Hz, 1H), 6.58-6.44 (m, 3H), 4.75 (dd, J = 19.5, 9.1 Hz, 1H), 3.81-3.56 (m, 3H), 3.56-3.25 (m, 4H), 3.19 (s, 2H), 3.12 (s, 1H), 2.53 (s, 3H), 1.97 (s, 3H), 0.66 (d, J = 38.0 Hz, 4H). | 653.2 | 0.581 |
| 467 | 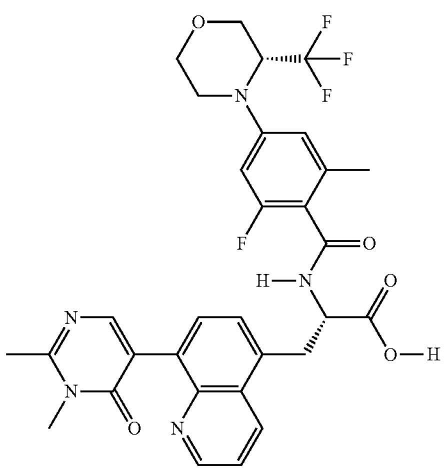 [SMILES: Cc1cc(N2CCOC[C@@H]2C(F)(F)F)cc(F)c1C(=O)N[C@@H](Cc1ccc(-c2cnc(C)n(C)c2=O)c2ncccc12)C(=O)O] | 1H NMR (400 MHz, DMSO-d6) δ 13.14-12.59 (s, 1H), 8.89 (dd, J = 4.4, 1.4 Hz, 1H), 8.81 (d, J = 8.2 Hz, 1H), 8.70 (d, J = 8.6 Hz, 1H), 7.93 (s, 1H), 7.69 (d, J = 7.4 Hz, 2H), 7.61 (d, J = 7.4 Hz, 1H), 6.74-6.55 (m, 2H), 4.83 (d, J = 7.2 Hz, 1H), 4.78-4.70 (m, 1H), 4.14 (d, J = 12.6 Hz, 1H), 3.94 (dd, J = 11.5, 3.7 Hz, 1H), 3.78-3.68 (m, 2H), 3.54 (s, 4H), 3.41 (dd, J = 14.5, 10.5 Hz, 1H), 3.34 (d, J = 12.0 Hz, 1H), 3.24 (t, J = 12.1 Hz, 1H), 2.63 (s, 3H), 1.99 (s, 3H). | 628.2 | 0.238 |

TABLE 3-continued

| Example | Structure | 1H-NMR | M/Z [M + H]+ | α4β7 EC$_{50}$ (nM) |
|---|---|---|---|---|
| 468 | 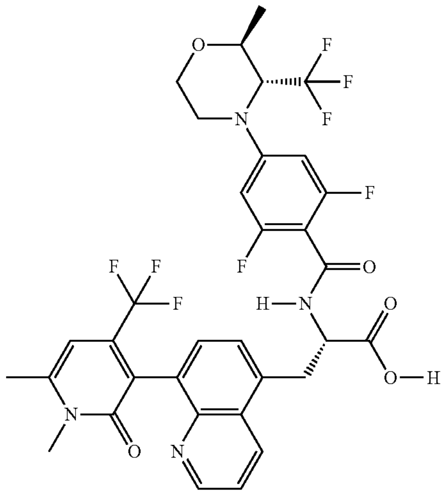 [SMILES: Cc1cc(C(F)(F)F)c(-c2ccc(C[C@H](NC(=O)c3c(F)cc(N4CCO[C@@H](C)[C@@H]4C(F)(F)F)cc3F)C(=O)O)c3cccnc23)c(=O)n1C] | 1H NMR (400 MHz, DMSO-d6) δ 12.90 (s, 1H), 8.95 (d, J = 8.1 Hz, 1H), 8.80 (d, J = 5.1 Hz, 1H), 8.62 (s, 1H), 7.65-7.52 (m, 2H), 7.43 (d, J = 5.8 Hz, 1H), 6.79 (dd, J = 11.5, 4.4 Hz, 2H), 6.54 (s, 1H), 4.69 (t, J = 8.4 Hz, 2H), 4.29 (q, J = 6.7 Hz, 1H), 3.91-3.81 (m, 1H), 3.73 (d, J = 14.7 Hz, 1H), 3.65 (dd, J = 11.9, 4.3 Hz, 1H), 3.49 (d, J = 2.2 Hz, 3H), 3.46 (s, 1H), 3.38 (d, J = 14.3 Hz, 1H), 3.23 (t, J = 12.5 Hz, 1H), 2.53 (s, 3H), 1.37 (d, J = 6.6 Hz, 3H). | 713.3 | 0.189 |
| 469 | 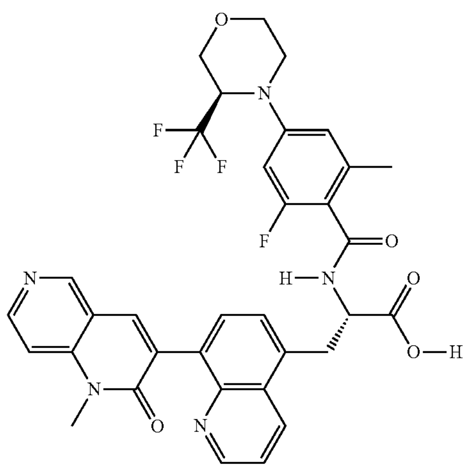 [SMILES: Cc1cc(N2CCOC[C@@H]2C(F)(F)F)cc(F)c1C(=O)N[C@@H](Cc1ccc(-c2cc3cnccc3n(C)c2=O)c2ncccc12)C(=O)O] | 1H NMR (400 MHz, DMSO-d6) δ 9.20 (s, 1H), 8.88-8.84 (m, 1H), 8.83-8.78 (m, 1H), 8.69 (dd, J = 8.7, 1.7 Hz, 1H), 8.19 (s, 1H), 7.90 (d, J = 6.7 Hz, 1H), 7.72 (d, J = 7.3 Hz, 1H), 7.70-7.62 (m, 2H), 6.71-6.61 (m, 2H), 4.92-4.70 (m, 2H), 4.15 (d, J = 12.6 Hz, 1H), 3.95 (dd, J = 11.2, 3.6 Hz, 1H), 3.78 (d, J = 4.2 Hz, 1H), 3.74 (s, 4H), 3.60-3.50 (m, 1H), 3.43 (dd, J = 14.5, 10.5 Hz, 1H), 3.34 (d, J = 12.3 Hz, 1H), 3.25 (t, J = 12.4 Hz, 1H), 2.02 (s, 3H). | 664.4 | 0.103 |
| 470 | 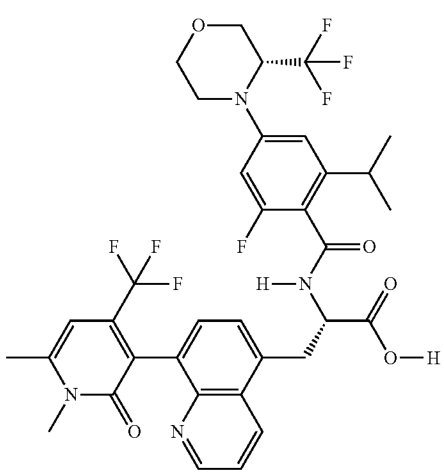 [SMILES: Cc1cc(C(F)(F)F)c(-c2ccc(C[C@H](NC(=O)c3c(F)cc(N4CCOC[C@@H]4C(F)(F)F)cc3C(C)C)C(=O)O)c3cccnc23)c(=O)n1C] | 1H NMR (400 MHz, DMSO-d6) δ 8.92 (dd, J = 8.0, 4.6 Hz, 1H), 8.84 (d, J = 4.2 Hz, 1H), 8.68 (d, J = 8.6 Hz, 1H), 7.73-7.55 (m, 2H), 7.46 (d, J = 7.3 Hz, 1H), 6.71 (d, J = 6.4 Hz, 1H), 6.64 (d, J = 13.0 Hz, 1H), 6.56 (d, J = 2.7 Hz, 1H), 4.91 (d, J = 9.3 Hz, 1H), 4.74 (q, J = 12.2, 10.6 Hz, 1H), 4.15 (d, J = 12.6 Hz, 1H), 3.95 (d, J = 10.8 Hz, 1H), 3.72 (t, J = 14.4 Hz, 2H), 3.55 (t, J = 11.2 Hz, 1H), 3.49 (d, J = 3.1 Hz, 3H), 3.46-3.17 (m, 2H), 2.84 (dq, J = 13.7, 6.7 Hz, 1H), 2.54 (s, 3H), 1.05 (dt, J = 11.2, 5.8 Hz, 6H). | 723.2 | 0.181 |

TABLE 3-continued

| Example | Structure | 1H-NMR | M/Z [M + H]+ | α4β7 EC$_{50}$ (nM) |
| --- | --- | --- | --- | --- |
| 471 | 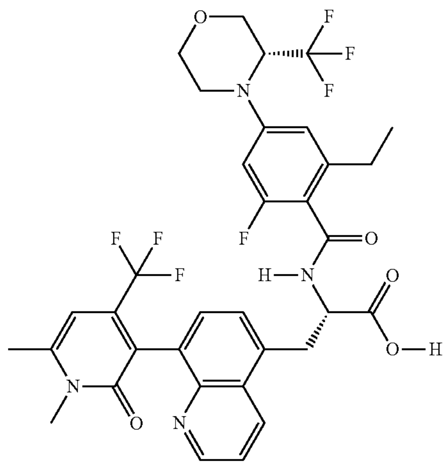 [SMILES: CCc1cc(N2CCOC[C@@H]2C(F)(F)F)cc(F)c1C(=O)N[C@@H](Cc1ccc(-c2c(C(F)(F)F)cc(C)n(C)c2=O)c2ncccc12)C(=O)O] | 1H NMR (400 MHz, DMSO-d6) δ 8.85 (dd, J = 12.2, 6.2 Hz, 2H), 8.68 (d, J = 8.7 Hz, 1H), 7.73-7.55 (m, 2H), 7.46 (d, J = 7.0 Hz, 1H), 6.66 (d, J = 11.4 Hz, 2H), 6.56 (s, 1H), 4.94-4.66 (m, 2H), 4.14 (d, J = 12.6 Hz, 1H), 3.95 (d, J = 11.3 Hz, 1H), 3.72 (t, J = 14.9 Hz, 2H), 3.63-3.31 (m, 5H), 3.27 (d, J = 12.4 Hz, 1H), 2.54 (s, 3H), 2.39 (q, J = 7.5 Hz, 2H), 1.06-0.90 (m, 3H). | 709.2 | 0.179 |
| 472 | 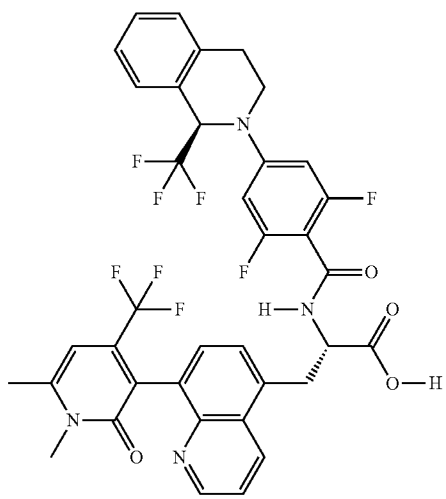 [SMILES: Cc1cc(C(F)(F)F)c(-c2ccc(C[C@H](NC(=O)c3c(F)cc(N4CCc5ccccc5[C@@H]4C(F)(F)F)cc3F)C(=O)O)c3cccnc23)c(=O)n1C] | 1H NMR (400 MHz, DMSO-d6) δ 8.94 (d, J = 7.8 Hz, 1H), 8.83 (s, 1H), 8.68 (s, 1H), 7.78-7.54 (m, 3H), 7.48 (t, J = 9.3 Hz, 2H), 7.34 (dq, J = 16.4, 7.8 Hz, 3H), 6.82 (dd, J = 12.1, 3.7 Hz, 2H), 6.56 (d, J = 5.4 Hz, 1H), 6.00 (q, J = 7.9 Hz, 1H), 4.71 (s, 1H), 3.71 (dt, J = 12.2, 5.8 Hz, 2H), 3.49 (s, 4H), 3.01 (t, J = 6.4 Hz, 2H), 2.54 (s, 3H). | 745.2 | 0.331 |
| 473 | 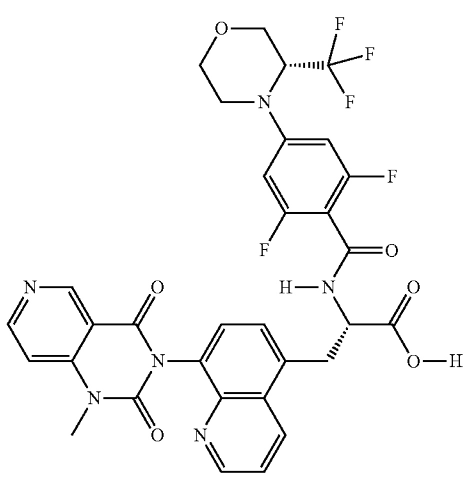 [SMILES: Cn1c(=O)n(-c2ccc(C[C@H](NC(=O)c3c(F)cc(N4CCOC[C@@H]4C(F)(F)F)cc3F)C(=O)O)c3cccnc23)c(=O)c2cnccc21] | 1H NMR (400 MHz, DMSO-d6) δ 9.12 (t, J = 1.7 Hz, 1H), 9.02 (d, J = 7.8 Hz, 1H), 8.86 (t, J = 4.7 Hz, 2H), 8.69 (d, J = 8.6 Hz, 1H), 7.77 (d, J = 7.5 Hz, 1H), 7.71-7.47 (m, 3H), 6.78 (d, J = 11.7 Hz, 2H), 4.91 (dd, J = 8.8, 3.6 Hz, 1H), 4.71 (dt, J = 8.6, 4.6 Hz, 1H), 4.16 (d, J = 12.7 Hz, 1H), 3.96 (dd, J = 11.6, 3.7 Hz, 1H), 3.86-3.70 (m, 3H), 3.62-3.38 (m, 7H), 3.35-3.14 (m, 1H). | 685.4 | 0.196 |

TABLE 3-continued

| Example | Structure | 1H-NMR | M/Z [M + H]+ | α4β7 EC$_{50}$ (nM) |
|---|---|---|---|---|
| 474 | 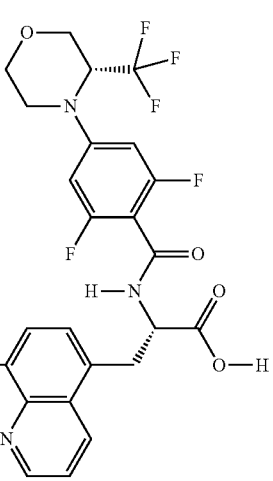 | 1H NMR (400 MHz, DMSO-d6) δ 13.24-12.63 (bs, 1H), 9.05 (s, 1H), 9.02 (d, J = 7.9 Hz, 1H), 8.84 (d, J = 4.1 Hz, 1H), 8.68 (d, J = 8.7 Hz, 1H), 8.60 (d, J = 5.1 Hz, 1H), 7.91 (dd, J = 5.0, 2.3 Hz, 1H), 7.76 (dd, J = 7.6, 1.8 Hz, 1H), 7.67 (d, J = 7.6 Hz, 2H), 6.78 (d, J = 11.9 Hz, 2H), 4.91 (d, J = 9.9 Hz, 1H), 4.71 (s, 1H), 4.16 (d, J = 12.7 Hz, 1H), 4.00-3.92 (m, 1H), 3.74 (d, J = 13.0 Hz, 2H), 3.65 (s, 3H), 3.61-3.40 (m, 3H), 3.26 (d, J = 12.4 Hz, 1H). | 685.3 | 0.112 |
| 475 | 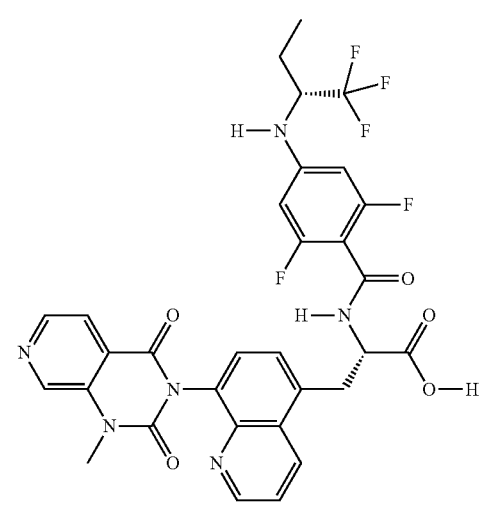 [SMILES: CC[C@@H](Nc1cc(F)c(C(=O)N[C@@H](Cc2ccc(-n3c(=O)c4ccncc4n(C)c3=O)c3ncccc23)C(=O)O)c(F)c1)C(F)(F)F] | 1H NMR (400 MHz, DMSO-d6) δ 9.05 (s, 1H), 9.02 (d, J = 7.9 Hz, 1H), 8.85 (d, J = 4.2 Hz, 1H), 8.68 (d, J = 8.6 Hz, 1H), 8.60 (d, J = 5.0 Hz, 1H), 7.95-7.86 (m, 1H), 7.76 (d, J = 7.5 Hz, 1H), 7.68 (t, J = 6.5 Hz, 2H), 6.80 (dd, J = 17.6, 12.4 Hz, 5H), 4.93 (ddt, J = 17.8, 8.9, 4.6 Hz, 2H), 4.78-4.55 (m, 1H), 4.17 (dd, J = 12.8, 4.3 Hz, 3H), 4.00-3.91 (m, 3H), 3.75 (dd, J = 14.4, 4.2 Hz, 4H), 3.65 (s, 3H), 3.54 (td, J = 14.7, 13.3, 9.5 Hz, 4H), 3.44 (d, J = 15.1 Hz, 1H), 3.31-3.14 (m, 2H). | 657.2 | 0.157 |
| 476 | 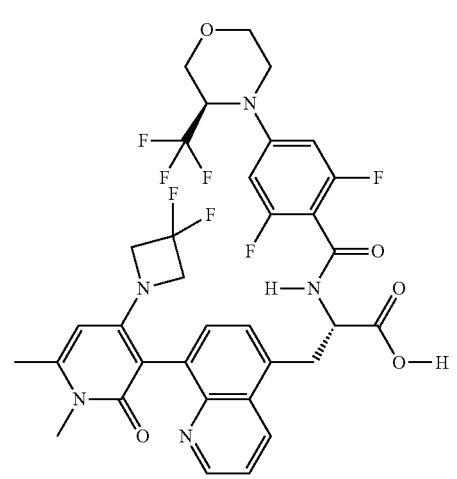 [SMILES: Cc1cc(N2CC(F)(F)C2)c(-c2ccc(C[C@H](NC(=O)c3c(F)cc(N4CCOC[C@@H]4C(F)(F)F)cc3F)C(=O)O)c3cccnc23)c(=O)n1C] | 1H NMR (400 MHz, DMSO-d6) δ 9.12 (dd, J = 18.2, 8.5 Hz, 1H), 9.02 (d, J = 4.8 Hz, 1H), 8.92 (dd, J = 10.8, 8.3 Hz, 1H), 7.93 (dt, J = 32.7, 6.7 Hz, 1H), 7.82-7.55 (m, 2H), 6.70 (dd, J = 14.9, 11.7 Hz, 2H), 5.84 (d, J = 6.9 Hz, 1H), 4.97-4.84 (m, 1H), 4.83-4.69 (m, 1H), 4.15 (dd, J = 12.8, 3.1 Hz, 1H), 3.94 (dd, J = 9.7, 5.7 Hz, 2H), 3.66 (ddt, J = 51.3, 42.1, 11.8 Hz, 7H), 3.37 (d, J = 6.2 Hz, 4H), 3.26 (d, J = 26.6 Hz, 2H), 2.41 (d, J = 2.9 Hz, 3H). | 722.3 | 0.337 |

TABLE 3-continued

| Example | Structure | 1H-NMR | M/Z [M + H]+ | α4β7 EC$_{50}$ (nM) |
|---|---|---|---|---|
| 477 | 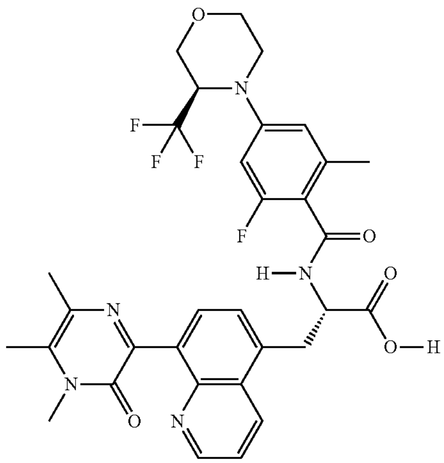 [SMILES: Cc1cc(N2CCOC[C@@H]2C(F)(F)F)cc(F)c1C(=O)N[C@@H](Cc1ccc(-c2nc(C)c(C)n(C)c2=O)c2ncccc12)C(=O)O] | 1H NMR (400 MHz, DMSO-d6) δ 8.88 (d, J = 4.2 Hz, 1H), 8.82 (d, J = 8.1 Hz, 1H), 8.74 (d, J = 8.6 Hz, 1H), 7.71 (s, 2H), 7.64 (d, J = 7.4 Hz, 1H), 6.67 (d, J = 14.4 Hz, 2H), 4.83 (d, J = 9.6 Hz, 1H), 4.78-4.70 (m, 1H), 4.14 (s, 1H), 3.93 (s, 1H), 3.73 (s, 1H), 3.55 (d, J = 9.6 Hz, 4H), 3.44 (dd, J = 14.5, 10.2 Hz, 2H), 3.33 (s, 1H), 3.26 (d, J = 12.4 Hz, 1H), 2.41 (s, 3H), 2.33 (s, 3H), 2.05 (s, 3H). | 642.2 | 0.115 |
| 478 | 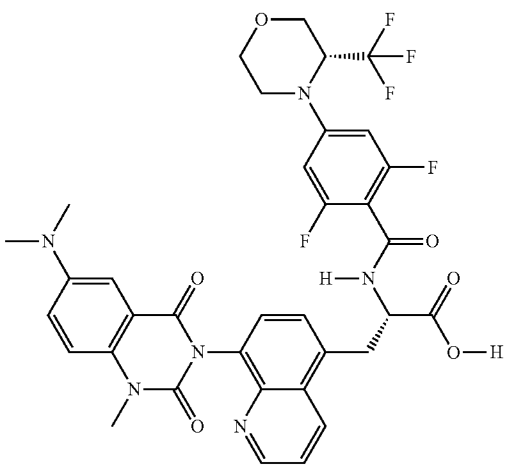 [SMILES: CN(C)c1ccc2c(c1)c(=O)n(-c1ccc(C[C@H](NC(=O)c3c(F)cc(N4CCOC[C@@H]4C(F)(F)F)cc3F)C(=O)O)c3cccnc13)c(=O)n2C] | 1H NMR (400 MHz, DMSO-d6) δ 9.02 (d, J = 7.8 Hz, 1H), 8.83 (d, J = 4.2 Hz, 1H), 8.68 (d, J = 8.6 Hz, 1H), 7.78-7.61 (m, 3H), 7.46 (d, J = 9.2 Hz, 1H), 7.39 (dd, J = 9.2, 3.0 Hz, 1H), 7.28 (t, J = 2.9 Hz, 1H), 6.78 (d, J = 11.7 Hz, 2H), 4.91 (dd, J = 9.0, 3.7 Hz, 1H), 4.71 (td, J = 8.7, 4.3 Hz, 1H), 4.16 (d, J = 12.7 Hz, 1H), 3.95 (dd, J = 11.5, 3.8 Hz, 1H), 3.76 (d, J = 3.2 Hz, 2H), 3.53 (s, 4H), 3.46 (dd, J = 19.1, 8.8 Hz, 2H), 3.24 (d, J = 3.4 Hz, 1H), 2.96 (s, 6H). | 727.3 | 0.394 |
| 479 | 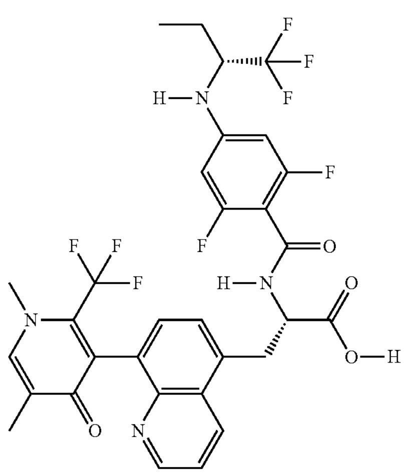 [SMILES: CC[C@@H](Nc1cc(F)c(C(=O)N[C@@H](Cc2ccc(-c3c(C(F)(F)F)n(C)cc(C)c3=O)c3ncccc23)C(=O)O)c(F)c1)C(F)(F)F] | 1H NMR (400 MHz, DMSO-d6) δ 8.85-8.74 (m, 2H), 8.62 (d, J = 8.6 Hz, 1H), 7.99 (s, 1H), 7.61 (dt, J = 8.8, 4.5 Hz, 1H), 7.54 (t, J = 7.2 Hz, 1H), 7.36 (dd, J = 10.4, 7.3 Hz, 1H), 6.76 (t, J = 8.6 Hz, 1H), 6.44 (dd, J = 11.4, 6.3 Hz, 2H), 4.75-4.56 (m, 1H), 4.31 (s, 1H), 3.88-3.79 (m, 4H), 3.68 (ddd, J = 44.6, 14.4, 4.7 Hz, 1H), 3.35 (m, 1H), 1.90 (t, J = 1.3 Hz, 3H), 1.77 (t, J = 10.1 Hz, 1H), 1.64-1.41 (m, 1H), 0.93 (t, J = 7.3 Hz, 3H). | 671.2 | 1.188 |

TABLE 3-continued

| Example | Structure | 1H-NMR | M/Z [M + H]+ | α4β7 EC$_{50}$ (nM) |
|---|---|---|---|---|
| 480 | 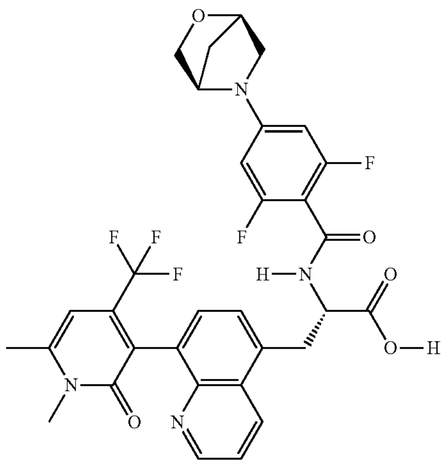 [SMILES: Cc1cc(C(F)(F)F)c(-c2ccc(C[C@H](NC(=O)c3c(F)cc(N4C[C@H]5C[C@@H]4CO5)cc3F)C(=O)O)c3cccnc23)c(=O)n1C] | 1H NMR (400 MHz, DMSO-d6) δ 8.89-8.60 (m, 3H), 7.73-7.55 (m, 2H), 7.46 (d, J = 7.0 Hz, 1H), 6.56 (s, 1H), 6.32 (d, J = 12.2 Hz, 2H), 4.77-4.61 (m, 3H), 3.78-3.64 (m, 2H), 3.59 (d, J = 7.5 Hz, 1H), 3.49 (d, J = 1.8 Hz, 3H), 3.48-3.38 (m, 1H), 3.00 (d, J = 9.7 Hz, 1H), 2.54 (s, 3H), 1.94-1.87 (m, 1H), 1.84 (d, J = 9.9 Hz, 1H). | 643.2 | 0.297 |
| 481 | 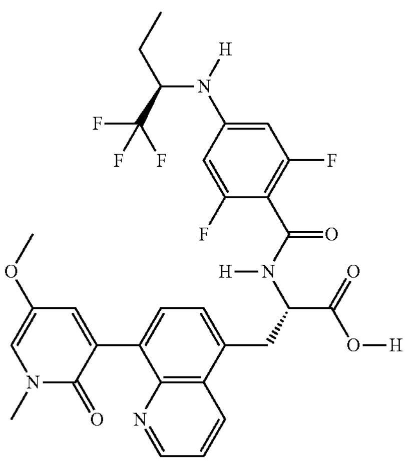 [SMILES: CC[C@@H](Nc1cc(F)c(C(=O)N[C@@H](Cc2ccc(-c3cc(OC)cn(C)c3=O)c3ncccc23)C(=O)O)c(F)c1)C(F)(F)F] | 1H NMR (400 MHz, DMSO-d6) δ 12.93 (s, 1H), 8.93 (dd, J = 4.4, 1.5 Hz, 1H), 8.81 (dd, J = 8.3, 3.0 Hz, 2H), 7.77-7.69 (m, 2H), 7.62 (d, J = 7.4 Hz, 1H), 7.52 (d, J = 3.3 Hz, 1H), 7.38 (d, J = 3.3 Hz, 1H), 6.78 (d, J = 9.4 Hz, 1H), 6.45 (d, J = 11.5 Hz, 2H), 4.67 (ddd, J = 9.8, 7.9, 4.6 Hz, 1H), 4.31 (d, J = 9.2 Hz, 1H), 3.74 (d, J = 4.7 Hz, 1H), 3.71 (s, 3H), 3.49 (s, 3H), 3.43 (dd, J = 14.5, 9.8 Hz, 1H), 1.77 (ddq, J = 11.6, 7.5, 4.3, 3.8 Hz, 1H), 1.53 (ddt, J = 17.5, 14.3, 7.2 Hz, 1H), 0.93 (t, J = 7.3 Hz, 3H). | 619.3 | 1.483 |
| 482 | 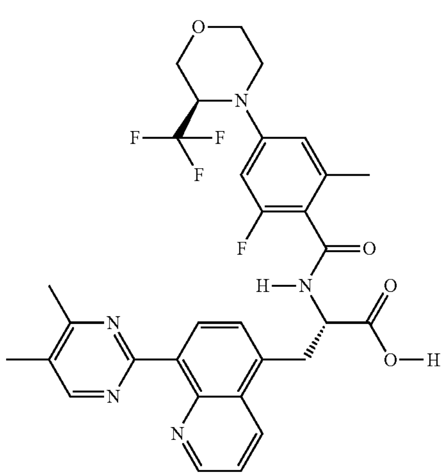 [SMILES: Cc1cnc(-c2ccc(C[C@H](NC(=O)c3c(C)cc(N4CCOC[C@@H]4C(F)(F)F)cc3F)C(=O)O)c3cccnc23)nc1C] | 1H NMR (400 MHz, DMSO-d6) δ 9.39 (s, 1H), 9.34 (d, J = 9.2 Hz, 1H), 8.88 (s, 1H), 8.83-8.76 (m, 2H), 8.13 (d, J = 6.7 Hz, 1H), 7.96 (d, J = 7.7 Hz, 1H), 6.69-6.57 (m, 2H), 4.83 (ddt, J = 16.3, 8.2, 3.9 Hz, 2H), 4.14 (d, J = 12.6 Hz, 1H), 3.97-3.82 (m, 2H), 3.71 (d, J = 12.9 Hz, 1H), 3.59-3.54 (m, 1H), 3.31 (s, 1H), 3.24 (d, J = 13.4 Hz, 2H), 2.67 (s, 3H), 2.40 (s, 3H), 2.01 (s, 3H). | 612.3 | 1.496 |

TABLE 3-continued

| Example | Structure | 1H-NMR | M/Z [M + H]+ | α4β7 EC$_{50}$ (nM) |
|---|---|---|---|---|
| 483 | 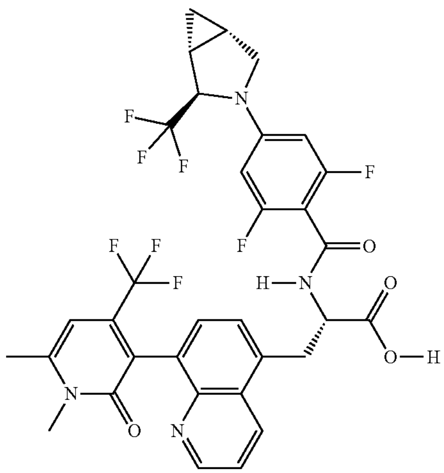 [SMILES: Cc1cc(C(F)(F)F)c(-c2ccc(C[C@H](NC(=O)c3c(F)cc(N4C[C@H]5C[C@H]5[C@@H]4C(F)(F)F)cc3F)C(=O)O)c3cccnc23)c(=O)n1C] | 1H NMR (400 MHz, DMSO-d6) δ 12.98 (s, 1H), 8.96 (dd, J = 8.0, 5.0 Hz, 1H), 8.85 (dd, J = 4.3, 1.5 Hz, 1H), 8.70 (d, J = 7.8 Hz, 1H), 7.72-7.63 (m, 1H), 7.59 (t, J = 7.7 Hz, 1H), 7.47 (dd, J = 7.3, 4.9 Hz, 1H), 6.59-6.49 (m, 3H), 5.02 (p, J = 5.7 Hz, 1H), 4.72 (dddd, J = 10.0, 7.4, 4.5, 2.2 Hz, 1H), 3.80-3.74 (m, 1H), 3.74-3.65 (m, 1H), 3.49 (d, J = 2.5 Hz, 3H), 3.48-3.36 (m, 2H), 2.54 (s, 3H), 2.07-1.98 (m, 1H), 1.90 (dq, J = 13.1, 7.8, 6.1 Hz, 1H), 0.88 (td, J = 8.1, 5.1 Hz, 1H), 0.79 (s, 1H). | 695.3 | 0.544 |
| 484 | 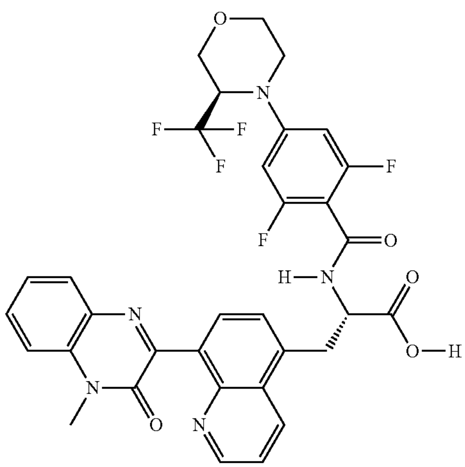 [SMILES: Cn1c(=O)c(-c2ccc(C[C@H](NC(=O)c3c(F)cc(N4CCOC[C@@H]4C(F)(F)F)cc3F)C(=O)O)c3cccnc23)nc2ccccc21] | 1H NMR (400 MHz, DMSO-d6) δ 8.99 (d, J = 7.9 Hz, 1H), 8.85 (d, J = 4.2 Hz, 1H), 8.73 (d, J = 8.6 Hz, 1H), 7.87 (d, J = 8.0 Hz, 1H), 7.81 (d, J = 7.2 Hz, 1H), 7.75-7.62 (m, 4H), 7.44 (t, J = 7.5 Hz, 1H), 6.78 (d, J = 11.8 Hz, 2H), 4.97-4.86 (m, 1H), 4.75-4.67 (m, 1H), 4.16 (d, J = 12.7 Hz, 1H), 4.00-3.90 (m, 1H), 3.80-3.71 (m, 2H), 3.69 (s, 3H), 3.61-3.40 (m, 3H), 3.31-3.18 (m, 1H). | 668.2 | 0.143 |
| 485 | 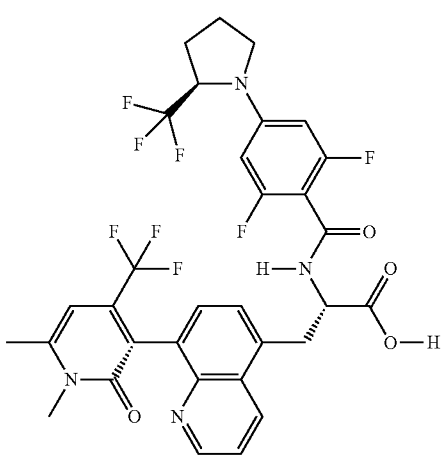 | 1H NMR (400 MHz, DMSO-d6) δ 9.03 (d, J = 7.7 Hz, 1H), 8.79 (d, J = 4.1 Hz, 1H), 8.55 (d, J = 8.6 Hz, 1H), 7.58 (dd, J = 8.7, 4.2 Hz, 1H), 7.52 (d, J = 7.3 Hz, 1H), 7.40 (d, J = 7.2 Hz, 1H), 6.60-6.45 (m, 3H), 4.86-4.69 (m, 2H), 3.67 (dd, J = 14.5, 5.5 Hz, 1H), 3.63-3.55 (m, 1H), 3.52-3.40 (m, 4H), 3.19 (q, J = 8.7 Hz, 1H), 2.52 (s, 3H), 2.17-1.96 (m, 4H). | 683.3 | 0.233 |

TABLE 3-continued

| Example | Structure | 1H-NMR | M/Z [M + H]+ | α4β7 EC$_{50}$ (nM) |
|---|---|---|---|---|
| 486 | 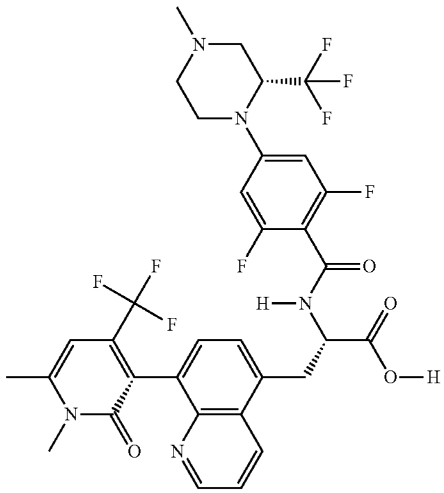 | 1H NMR (400 MHz, DMSO-d6) δ 9.01 (d, J = 8.0 Hz, 1H), 8.80 (d, J = 4.2 Hz, 1H), 8.60 (d, J = 8.5 Hz, 1H), 7.60 (m, 1H), 7.55 (d, J = 7.3 Hz, 1H), 7.41 (d, J = 7.2 Hz, 1H), 6.83 (d, J = 11.5 Hz, 2H), 6.53 (s, 1H), 5.37 (s, 1H), 4.70 (m, 1H), 3.83-3.91 (m, 4H), 3.73 (dd, J = 14.5, 4.1 Hz, 1H), 3.48 (s, 3H), 3.44-3.35 (m, 1H), 3.32 (s, 1H), 2.83 (bs, 3H), 2.53 (s, 3). | 712.2 | 1.307 |
| 487 | 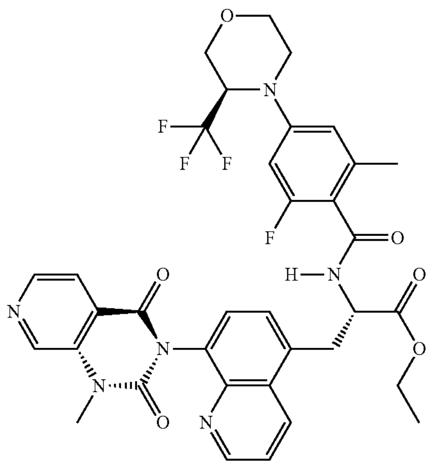 | 1H NMR (400 MHz, DMSO-d6) δ 9.04 (s, 1H), 8.99 (d, J = 7.7 Hz, 1H), 8.84 (dd, J = 4.1, 1.5 Hz, 1H), 8.64 (dd, J = 8.6, 1.6 Hz, 1H), 8.60 (d, J = 4.9 Hz, 1H), 7.91 (dd, J = 4.9, 0.7 Hz, 1H), 7.75 (d, J = 7.6 Hz, 1H), 7.69-7.63 (m, 2H), 6.76-6.63 (m, 2H), 4.90-4.74 (m, 2H), 4.19-4.06 (m, 3H), 3.95 (dd, J = 11.4, 3.6 Hz, 1H), 3.78-3.67 (m, 2H), 3.65 (s, 3H), 3.61-3.46 (m, 2H), 3.37 (s, 1H), 3.31-3.18 (m, 1H), 2.07 (s, 3H), 1.16 (t, J = 7.1 Hz, 3H). | 709.2 | NA |
| 488 | 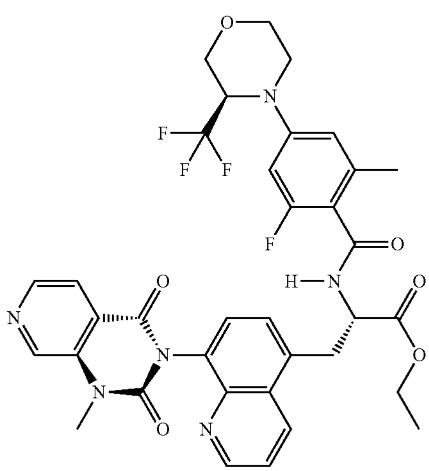 | 1H NMR (400 MHz, DMSO-d6) δ 9.04 (s, 1H), 8.99 (d, J = 7.7 Hz, 1H), 8.84 (dd, J = 4.2, 1.5 Hz, 1H), 8.64 (dd, J = 8.7, 1.6 Hz, 1H), 8.60 (d, J = 5.0 Hz, 1H), 7.91 (d, J = 4.9 Hz, 1H), 7.75 (d, J = 7.5 Hz, 1H), 7.69-7.63 (m, 2H), 6.75-6.62 (m, 2H), 4.91-4.75 (m, 2H), 4.20-4.07 (m, 3H), 3.95 (dd, J = 11.4, 3.6 Hz, 1H), 3.78-3.67 (m, 2H), 3.66 (s, 3H), 3.60-3.47 (m, 2H), 3.36 (d, J = 12.3 Hz, 1H), 3.25 (t, J = 12.3 Hz, 1H), 2.07 (s, 3H), 1.16 (t, J = 7.1 Hz, 3H). | 709.2 | NA |

TABLE 3-continued

| Example | Structure | 1H-NMR | M/Z [M + H]+ | α4β7 EC$_{50}$ (nM) |
|---|---|---|---|---|
| 489 | 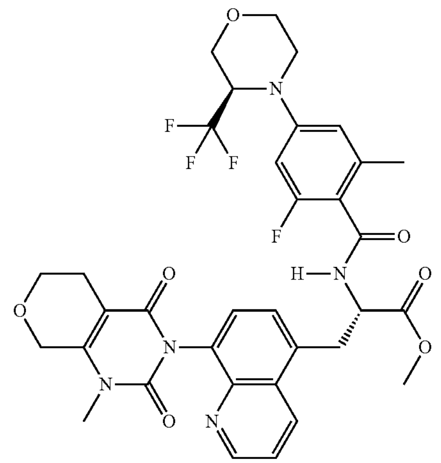 [SMILES: COC(=O)[C@H](Cc1ccc(-n2c(=O)c3c(n(C)c2=O)COCC3)c2ncccc12)NC(=O)c1c(C)cc(N2CCOC[C@@H]2C(F)(F)F)cc1F] | 1H NMR (400 MHz, DMSO-d6) δ 8.99 (d, J = 7.6 Hz, 1H), 8.87 (s, 1H), 8.62 (d, J = 8.4 Hz, 1H), 7.67 (s, 1H), 7.61 (s, 2H), 6.70 (d, J = 13.0 Hz, 1H), 6.66 (s, 1H), 4.89-4.77 (m, 2H), 4.76-4.61 (m, 2H), 4.18-4.12 (m, 1H), 3.93 (s, 1H), 3.87-3.79 (m, 2H), 3.73 (d, J = 12.9 Hz, 2H), 3.67 (s, 4H), 3.60-3.46 (m, 2H), 3.35 (d, J = 9.6 Hz, 1H), 3.37 (m, 1H), 3.25 (s, 4H), 2.37 (d, J = 10.2 Hz, 3H), 2.05 (s, 3H). | 700.2 | NA |
| 490 | 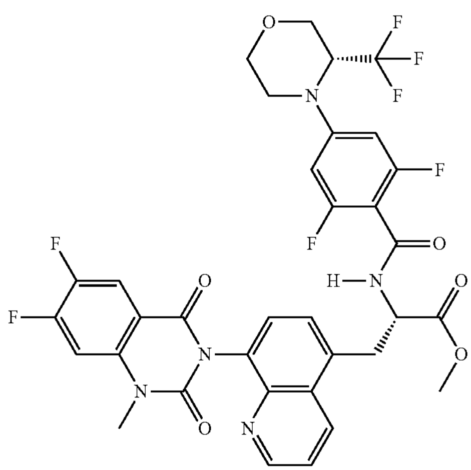 [SMILES: COC(=O)[C@H](Cc1ccc(-n2c(=O)c3cc(F)c(F)cc3n(C)c2=O)c2ncccc12)NC(=O)c1c(F)cc(N2CCOC[C@@H]2C(F)(F)F)cc1F] | 1H NMR (400 MHz, DMSO-d6) δ 9.15 (d, J = 7.5 Hz, 1H), 8.85 (d, J = 4.2 Hz, 1H), 8.65 (d, J = 8.6 Hz, 1H), 8.00 (t, J = 9.2 Hz, 1H), 7.80 (dd, J = 12.3, 6.4 Hz, 1H), 7.74 (d, J = 7.5 Hz, 1H), 7.69-7.60 (m, 2H), 6.79 (d, J = 11.8 Hz, 2H), 5.01-4.86 (m, 1H), 4.76 (q, J = 7.9 Hz, 1H), 4.17 (d, J = 12.7 Hz, 1H), 3.96 (dd, J = 11.9, 3.6 Hz, 1H), 3.80-3.67 (m, 2H), 3.64 (s, 3H), 3.58 (s, 1H), 3.55 (s, 3H), 3.44 (d, J = 12.9 Hz, 1H), 3.24 (t, J = 12.4 Hz, 1H), 2.53 (s, 1H). | 733.7 | NA |
| 491 | 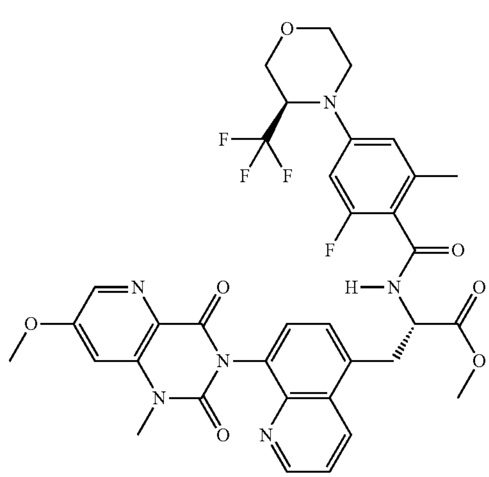 [SMILES: COC(=O)[C@H](Cc1ccc(-n2c(=O)c3ncc(OC)cc3n(C)c2=O)c2ncccc12)NC(=O)c1c(C)cc(N2CCOC[C@@H]2C(F)(F)F)cc1F] | 1H NMR (400 MHz, DMSO-d6) δ 9.00 (d, J = 7.7 Hz, 1H), 8.85 (d, J = 4.1 Hz, 1H), 8.67 (d, J = 8.6 Hz 1H), 8.34-8.30 (m, 1H), 7.75 (d, J = 7.5 Hz, 1H), 7.71-7.63 (m, 2H), 7.46-7.42 (m, 1H), 6.74-6.64 (m, 2H), 4.90-4.78 (m, 3H), 4.14 (d, J = 12.6 Hz, 1H), 4.06 (s, 3H), 3.95 (d, J = 11.7 Hz, 1H), 3.79-3.65 (m, 5H), 3.62-3.47 (m, 6H), 3.34 (d, 1H), 3.25 (t, J = 12.6 Hz, 1H), 2.05 (s, 3H). | 725.8 | NA |

TABLE 3-continued

| Example | Structure | 1H-NMR | M/Z [M + H]+ | α4β7 EC$_{50}$ (nM) |
|---|---|---|---|---|
| 492 | 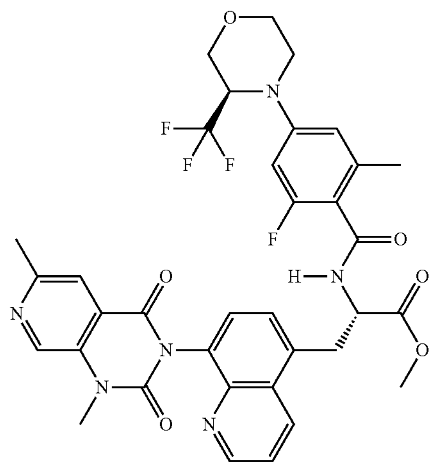 [SMILES: COC(=O)[C@H](Cc1ccc(-n2c(=O)c3cc(C)ncc3n(C)c2=O)c2ncccc12)NC(=O)c1c(C)cc(N2CCOC[C@@H]2C(F)(F)F)cc1F] | 1H NMR (400 MHz, DMSO-d6) δ 9.00 (d, J = 7.7 Hz, 1H), 8.90 (s, 1H), 8.84 (d, J = 4.2 Hz, 1H), 8.66 (d, J = 8.6 Hz, 1H), 7.80-7.73 (m, 2H), 7.67 (t, J = 6.7 Hz, 2H), 6.75-6.61 (m, 2H), 4.84 (d, J = 10.4 Hz, 2H), 4.15 (d, J = 12.7 Hz, 1H), 3.99-3.89 (m, 1H), 3.77-3.70 (m, 2H), 3.68 (s, 2H), 3.63 (t, J = 1.7 Hz, 3H), 3.53 (dt, J = 14.6, 9.9 Hz, 2H), 3.34 (s, 1H), 2.59 (s, 3H), 2.05 (s, 3H). | 709.6 | NA |
| 493 | 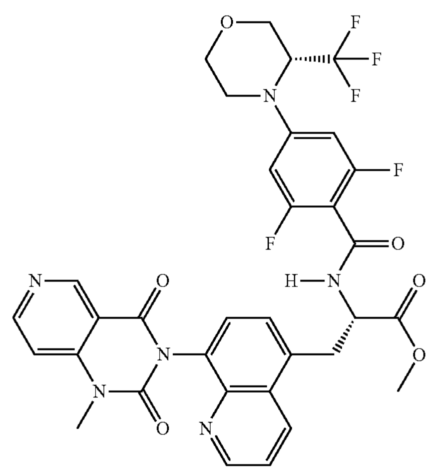 [SMILES: COC(=O)[C@H](Cc1ccc(-n2c(=O)c3cnccc3n(C)c2=O)c2ncccc12)NC(=O)c1c(F)cc(N2CCOC[C@@H]2C(F)(F)F)cc1F] | 1H NMR (400 MHz, DMSO-d6) δ 9.26-9.06 (m, 2H), 8.88 (d, J = 6.8 Hz, 2H), 8.68 (d, J = 8.7 Hz, 1H), 7.78 (d, J = 7.6 Hz, 1H), 7.67 (t, J = 8.3 Hz, 3H), 6.79 (d, J = 12.1 Hz, 2H), 4.92 (d, J = 9.3 Hz, 1H), 4.78 (q, J = 7.7 Hz, 1H), 4.17 (d, J = 12.7 Hz, 1H), 3.94 (s, 2H), 3.65 (s, 3H), 3.58 (m, 4H), 3.44 (d, J = 12.9 Hz, 1H), 3.26 (d, J = 12.7 Hz, 1H). | 699.8 | NA |
| 494 | 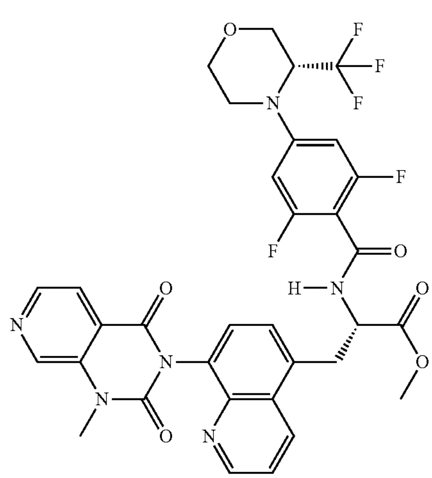 [SMILES: COC(=O)[C@H](Cc1ccc(-n2c(=O)c3ccncc3n(C)c2=O)c2ncccc12)NC(=O)c1c(F)cc(N2CCOC[C@@H]2C(F)(F)F)cc1F] | 1H NMR (400 MHz, DMSO-d6) δ 9.15 (d, J = 7.5 Hz, 1H), 9.05 (s, 1H), 8.86 (d, J = 4.2 Hz, 1H), 8.64 (dd, J = 28.6, 6.8 Hz, 2H), 7.91 (dd, J = 4.9, 1.9 Hz, 1H), 7.77 (d, J = 7.5 Hz, 1H), 7.72-7.55 (m, 2H), 6.79 (d, J = 11.8 Hz, 2H), 4.96-4.82 (m, 1H), 4.77 (q, J = 8.0 Hz, 1H), 4.17 (d, J = 12.7 Hz, 1H), 3.96 (dd, J = 11.6, 3.6 Hz, 1H), 3.82-3.68 (m, 2H), 3.56 (dd, J = 14.0, 9.9 Hz, 2H), 3.44 (d, J = 13.3 Hz, 1H), 3.24 (t, J = 12.0 Hz, 1H) | 699.2 | NA |

TABLE 3-continued

| Example | Structure | 1H-NMR | M/Z [M + H]+ | α4β7 EC$_{50}$ (nM) |
|---|---|---|---|---|
| 495 | 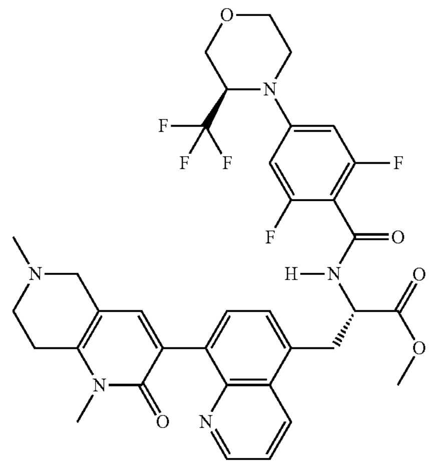 [SMILES: COC(=O)[C@H](Cc1ccc(-c2cc3c(n(C)c2=O)CCN(C)C3)c2ncccc12)NC(=O)c1c(F)cc(N2CCOC[C@@H]2C(F)(F)F)cc1F] | 1H NMR (400 MHz, DMSO-d6) δ 10.19 (s, 1H), 9.11 (d, J = 7.7 Hz, 1H), 8.86 (dd, J = 4.2, 1.6 Hz, 1H), 8.65 (dd, J = 8.7, 1.6 Hz, 1H), 7.69-7.54 (m, 3H), 7.34 (s, 1H), 6.78 (d, J = 11.8 Hz, 2H), 4.97-4.86 (m, 1H), 4.80-4.69 (m, 1H), 4.31 (d, J = 14.6 Hz, 1H), 4.21-4.06 (m, 2H), 3.96 (dd, J = 11.6, 3.8 Hz, 1H), 3.81-3.70 (m, 2H), 3.70-3.64 (m, 3H), 3.61-3.35 (m, 9H), 3.30-3.08 (m, 2H), 2.97 (s, 3H). | 700.3 | NA |
| 496 | 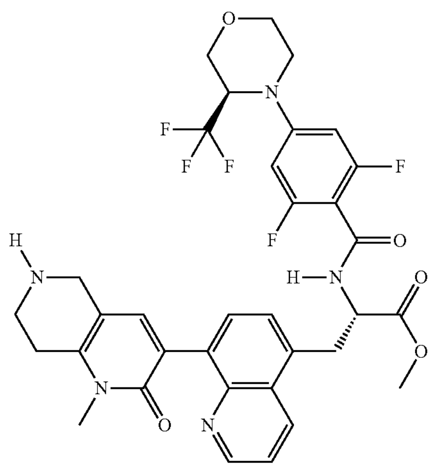 [SMILES: COC(=O)[C@H](Cc1ccc(-c2cc3c(n(C)c2=O)CCNC3)c2ncccc12)NC(=O)c1c(F)cc(N2CCOC[C@@H]2C(F)(F)F)cc1F] | 1H NMR (400 MHz, DMSO-d6) δ 9.11 (d, J = 7.4 Hz, 3H), 8.85 (t, J = 3.1 Hz, 1H), 8.63 (d, J = 8.6 1H), 7.60 (dtd, J = 23.9, 7.6, 2.8 Hz, 3H), 7.36 (d, J = 2.4 Hz, 1H), 6.78 (d, J = 12.3 Hz, 2H), 4.91 (d, J = 9.3 Hz, 1H), 4.74 (q, J = 7.8 Hz, 1H), 4.17 (d, J = 12.7 Hz, 2H), 3.96 (d, J = 11.7 Hz, 1H), 3.79-3.62 (m, 5H), 3.61-3.38 (m, 8H), 3.24 (t, J = 12.6 Hz, 1H), 3.07 (d, J = 6.3 Hz, 2H). | 686.4 | NA |

α4β1 Cell Capture Assay

The potency of inhibitors in preventing α4β1 integrin interaction with VCAM-1 was measured by monitoring the capture of α4β1 expressing cells to a recombinant VCAM-1 extracellular domain-coated plate.

384-well plates (Corning 3702) were coated with VCAM-1 extracellular domain by dispensing 20 μL of VCAM-1 at 0.5 μg/ml per well and incubating overnight at 4° C. The plates were then washed with PBS and blocked with 3% BSA for 2 hours before being washed again.

Jurkat cells were spun down and re-suspended in assay medium (DMEM+0.5% FBS+0.5 mM MnCl$_2$) at a density of 0.5×106 cells/ml. The cells were then dispensed (60 μL/well) to a 384-well plate (Greiner 781280) that was previously spotted with 60 nL of test compound per well. The plates were incubated at 37° C. for 1 hour. 50 μL of cells were transferred to the blocked, VCAM-1-coated plates and incubated for 30 minutes at 37° C. 10 μL of 12% glutaraldehyde containing Hoechst 33342 (0.06 mg/mL) was added to the cells (2% glutaraldehyde and 0.01 mg/mL Hoechst 33342 final concentrations). The plates were incubated for 90 minutes at room temperature. The plates were then washed 3 times with 70 μL of PBS per well and imaged on a Cellomics ArrayScan instrument. The cells that were bound to the plate were counted and plotted against the compound concentration to determine the EC$_{50}$ of the test compounds.

The parent carboxylic acids in Table 3 display at least 70 folds selectivity over α4β1, as calculated from the ratio of EC$_{50}$ values in cell capture assays for α4β1 and α4β7. These assays measure the capture of α4β1 or α4β7 expressing cells by a recombinant VCAM-1 or MadCAM-1 extracellular domain-coated plate, respectively.

Dog Bioavailability Experiments

Pharmacokinetic studies for were performed in non-naïve male beagle dogs (three animals per dosing route) following federal and Institutional Animal Care and Use Committee in humans (IACUC) guidelines. Intravenous (iv) administration was dosed via infusion over 30 minutes. The intravenous dose for dogs was formulated in a sterile solution. One solution formulation was 20% polyethylene glycol 300 and 80% water, pH 8-9. Oral dosing in dogs was administered by gavage as a solution. One formulation for dog was 72% 10 mM HCl, 5% N-methylpyrrolidone, 20% polyethylene glycol 200, and 3% Vitamin E TPGS, pH 2-3. Blood samples were collected over a 24 h period post-dose, plasma was isolated, and the concentration of the test compound in plasma was determined with LC/MS/MS after protein precipitation with acetonitrile. Non-compartmental pharmacokinetic analysis was performed on the plasma concentration-time data.

Bioavailability (% F) is defined as the area under the concentration/time curve (AUC) of parent carboxylic acid in systemic circulation following oral administration of ester prodrug divided by the AUC of amount of parent carboxylic acid in circulation following intravenous administration of the parent carboxylic acid, normalized to the same dose. Results for dog oral bioavailability are presented in Table 4.

TABLE 4

| Prodrug Example | % F | Parent carboxylic acid |
|---|---|---|
| 346 | 5 | Example 91 |
| 347 | 11 | Example 91 |
| 348 | 3 | Example 91 |
| 349 | 9 | Example 91 |
| 351 | 35 | Example 91 |
| 355 | 18 | Example 356 |
| 357 | 9 | Example 356 |
| 358 | 2 | Example 356 |
| 359 | 12 | Example 356 |
| 360 | 37 | Example 356 |
| 361 | 5 | Example 356 |
| 363 | 37 | Example 356 |
| 364 | 3 | Example 356 |
| 365 | 16 | Example 356 |
| 368 | 8 | Example 356 |
| 487 | 20 | Example 408 |
| 494 | 8 | Example 474 |

What is claimed is:
1. A compound of formula (J):

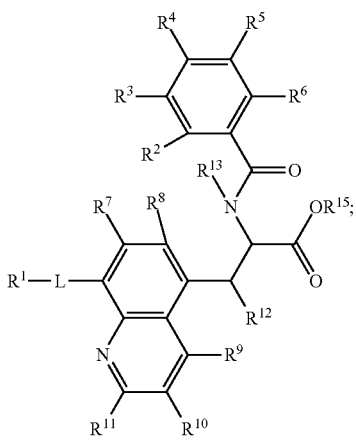

or a pharmaceutically acceptable salt thereof, wherein:
L is selected from a bond, —O—, —O—C(O)—*, —NH—, —C(O)—N(H)—*, and —N(H)—C(O)—*; wherein * indicates the point of attachment of L to $R^1$;
$R^1$ is selected from $A^1$, $A^2$, $A^3$, and $A^4$;
  $A^1$ is 5-10 membered heteroaryl containing one to five heteroatoms independently selected from S, N, and O; wherein $A^1$ optionally comprises one to three C(O); and wherein $A^1$ is optionally substituted with one to six $R^a$;
  $A^2$ is $C_{6-10}$aryl, optionally substituted with one to six $R^a$;
  $A^3$ is $C_{5-10}$cycloalkyl or 5-14 membered heterocyclyl; wherein $A^3$ is optionally substituted with one to four groups independently selected from oxo and $R^a$; and
  $A^4$ is —$NR^{a1}R^{a2}$;
    wherein each $R^a$ is independently selected from halo, cyano, hydroxyl, —$NR^{a1}R^{a2}$, $C_{1-6}$ alkyl, $C_{2-6}$alkenyl, $C_{2-6}$alkynyl, $C_{1-6}$alkoxyl, $C_{1-6}$haloalkyl, $C_{1-6}$haloalkoxyl, —$S(O)_m$—$C_{1-6}$alkyl, $C_{3-8}$ cycloalkyl, 3-6 membered heterocyclyl, $C_{6-10}$ aryl, 5-6 membered heteroaryl, —O—$C_{3-8}$ cycloalkyl, —O-(3-6 membered heterocyclyl), —O—$C_{1-4}$ alkylene-$C_{3-8}$cycloalkyl, and —O-phenyl;
    wherein each $C_{3-8}$ cycloalkyl, 3-6 membered heterocyclyl, $C_{6-10}$aryl, 5-6 membered heteroaryl, —O—$C_{3-8}$cycloalkyl, —O-(3-6 membered heterocyclyl), —O—$C_{1-4}$alkylene-$C_{3-8}$cycloalkyl, and —O-phenyl of $R^a$ is independently optionally substituted with one to three groups independently selected from halo, cyano, hydroxyl, —$NR^{a1}R^{a2}$, $C_{1-6}$ alkyl, $C_{1-6}$haloalkyl, $C_{1-6}$alkoxyl, and $C_{1-6}$ haloalkoxyl; and
    wherein each $C_{1-6}$alkyl, $C_{2-6}$alkenyl, $C_{2-6}$alkynyl, $C_{1-6}$alkoxyl, $C_{1-6}$haloalkyl, $C_{1-6}$ haloalkoxyl, and —$S(O)_m$—$C_{1-6}$alkyl of $R^a$ is optionally substituted with one to three $R^{a3}$, wherein each $R^{a3}$ is independently selected from halo, cyano, hydroxyl, —$NR^{a1}R^{a2}$, $C_{1-6}$ alkoxyl, $C_{3-8}$cycloalkyl, and 3-6 membered heterocyclyl;
    wherein each $C_{3-8}$ cycloalkyl and 3-6 membered heterocyclyl of $R^{a3}$ is optionally substituted with one to three Rao; and each Rao is independently selected from halo, cyano, hydroxyl, —$NR^{a1}R^{a2}$, $C_{1-6}$alkyl, $C_{1-6}$haloalkyl, $C_{1-6}$alkoxyl, $C_{1-6}$haloalkoxyl, $C_{3-8}$cycloalkyl, and 3-6 membered heterocyclyl;
each $R^2$, $R^3$, $R^4$, $R^5$, and $R^6$ is independently selected from H, halo, cyano, hydroxyl, $C_{1-6}$alkyl, $C_{2-6}$ alkenyl, $C_{2-6}$ alkynyl, $C_{1-6}$ alkoxyl, $C_{1-8}$ haloalkyl, $C_{1-8}$ haloalkoxyl, —$NR^{b1}R^{b2}$, —$R^{b3}S(O)_mR^{b4}$, —$S(O)_mR^{b4}$, —$NR^{b1}S(O)_nR^{b4}$, —$COOR^{b1}$, —$CONR^{b1}R^{b2}$, —$NR^{b1}COOR^{b2}$, —$NR^{b1}COR^{b4}$, —$R^{b3}NR^{b1}R^{b2}$, —$S(O)_nNR^{b1}R^{b2}$, $C_{3-12}$cycloalkyl, $C_{6-10}$aryl, 5-6 membered heteroaryl, and 3-12 membered heterocyclyl;
wherein each $C_{1-6}$alkyl, $C_{2-6}$alkenyl, $C_{2-6}$alkynyl, $C_{1-6}$alkoxyl, $C_{1-8}$haloalkyl, and $C_{1-8}$haloalkoxyl of $R^2$, $R^3$, $R^4$, $R^5$, and $R^6$ is optionally substituted with one to two $R^c$; wherein each $R^c$ is independently selected from azido, oxo, cyano, halo, hydroxyl, —$NR^{a1}R^{a2}$, $C_{1-4}$alkoxyl, $C_{3-8}$cycloalkyl, $C_{6-10}$aryl, 5-6 membered heteroaryl, and 4-6 membered heterocyclyl; wherein each $C_{3-8}$cycloalkyl, $C_{6-10}$aryl, 5-6 membered heteroaryl, and 4-6 membered heterocyclyl of $R^c$ is optionally substituted with one to three groups independently selected from halo, cyano, hydroxyl, —$NR^{a1}R^{a2}$, —$C_{1-4}$ alkyl, $C_{1-6}$haloalkyl, $C_{1-4}$alkoxyl, and $C_{3-6}$cycloalkyl;
wherein each $C_{6-10}$ aryl, and 5-6 membered heteroaryl of $R^2$, $R^3$, $R^4$, $R^5$, and $R^6$ is independently optionally substituted with one to five $R^b$; and
wherein each $C_{3-12}$cycloalkyl, and 3-12 membered heterocyclyl of $R^2$, $R^3$, $R^4$, $R^5$, and $R^6$ is independently optionally substituted with one to six groups independently selected from —$CR^{b1}R^{b2}$ and $R^b$;
  wherein each $R^b$ is independently selected from azido, cyano, halo, hydroxyl, —$NR^{a1}R^{a2}$, $C_{1-6}$ alkyl, $C_{1-8}$ haloalkyl, $C_{1-6}$alkoxyl, $C_{3-6}$cycloalkyl, $C_{6-10}$aryl, 5-6 membered heteroaryl, and 4-6 membered heterocyclyl; wherein each $C_{3-6}$cycloalkyl, $C_{6-10}$aryl, 5-6 membered heteroaryl, and 4-6 membered heterocyclyl of $R^b$ is independently optionally substituted with one to three groups independently selected from halo, cyano, hydroxyl, —$NR^{a1}R^{a2}$, $C_{1-4}$ alkyl, $C_{1-4}$haloalkyl, and $C_{1-4}$alkoxyl;

wherein each $R^{b1}$ and $R^{b2}$ is independently selected from H, $C_{1-8}$alkyl, $C_{1-8}$ haloalkyl, $C_{3-8}$cycloalkyl, $C_{6-10}$aryl, 5-6 membered heteroaryl, and 3-8 membered heterocyclyl;

wherein each $C_{3-8}$cycloalkyl, $C_{6-10}$aryl, 5-6 membered heteroaryl, and 4-6 membered heterocyclyl of $R^{b1}$ and $R^{b2}$ is independently optionally substituted with one to three groups independently selected from halo, cyano, hydroxyl, —$NR^{a1}R^{a2}$, $C_{1-8}$ alkyl, $C_{1-8}$ haloalkyl, $C_{1-6}$alkoxyl, $C_{3-6}$cycloalkyl, $C_{6-10}$aryl, 5-6 membered heteroaryl, and 4-6 membered heterocyclyl; and wherein each $C_{1-8}$ alkyl and $C_{1-8}$ haloalkyl of $R^{b1}$ and $R^{b2}$ is optionally substituted with one to two $R^{b5}$;

wherein $R^{b3}$ is $C_{1-4}$alkylene;

wherein $R^{b4}$ is selected from $C_{1-4}$alkyl, $C_{1-4}$haloalkyl, $C_{3-6}$cycloalkyl, $C_{6-10}$aryl, 5-6 membered heteroaryl, and 4-6 membered heterocyclyl; wherein each $C_{1-4}$alkyl, $C_{1-4}$haloalkyl, $C_{3-8}$cycloalkyl, $C_{6-10}$aryl, 5-6 membered heteroaryl, and the 4-6 membered heterocyclyl of $R^{b4}$ is optionally substituted with one to three $R^{b6}$;

wherein each $R^{b5}$ is independently selected from cyano, hydroxyl, $C_{1-4}$alkoxyl, $C_{3-8}$cycloalkyl, $C_{6-10}$aryl, 5-6 membered heteroaryl, and 4-6 membered heterocyclyl; and each $C_{1-4}$alkoxyl, $C_{3-8}$cycloalkyl, $C_{6-10}$aryl, 5-6 membered heteroaryl, and 4-6 membered heterocyclyl of $R^{b5}$ is optionally substituted with one to three groups independently selected from halo, cyano, hydroxyl, —$NR^{a1}R^{a2}$, $C_{1-4}$alkyl, $C_{1-4}$haloalkyl, $C_{1-4}$alkoxyl, and phenyl; and wherein each $R^{b6}$ is independently selected from halo, cyano, $C_{1-4}$alkyl, $C_{1-4}$haloalkyl, $C_{1-4}$alkoxyl, $C_{3-6}$cycloalkyl, phenyl, 4-6 membered heterocyclyl, and 5-6 membered heteroaryl; wherein each $C_{3-6}$ cycloalkyl, 4-6 membered heterocyclyl, and 5-6 membered heteroaryl of $R^{b6}$ is independently optionally substituted with one to three groups independently selected from halo, cyano, —$NR^{a1}R^{a2}$, $C_{1-4}$ alkyl, $C_{1-4}$haloalkyl, and $C_{1-4}$ alkoxyl; or $R^2$ and $R^3$, $R^3$ and $R^4$, or $R^5$ and $R^6$ together with the atoms to which they are attached form a $C_{6-10}$aryl, 5-6 membered heteroaryl, $C_{3-6}$cycloalkyl, or 5-6 membered heterocyclyl; wherein each $C_{6-10}$aryl, 5-6 membered heteroaryl, $C_{3-6}$cycloalkyl, and 5-6 membered heterocyclyl is independently optionally substituted with one to three groups independently selected from halo, cyano, —$NR^{a1}R^{a2}$, $C_{1-6}$ alkyl, $C_{1-6}$alkoxyl, $C_{1-6}$haloalkyl, $C_{3-8}$ cycloalkyl, 3-6 membered heterocyclyl, $C_{6-10}$aryl, 5-6 membered heteroaryl, $C_{1-4}$alkylene-$C_{3-8}$cycloalkyl, $C_{1-4}$alkylene-$C_{6-10}$aryl, and $C_{1-4}$ alkylene-(5-6 membered heteroaryl);

each $R^7$, $R^8$, $R^9$, $R^{10}$, $R^{11}$, and $R^{12}$ is independently selected from H, halo, hydroxyl, cyano, $C_{1-6}$ alkyl, $C_{1-6}$alkoxyl, $C_{1-6}$haloalkyl, $C_{1-6}$haloalkoxyl, and —$NR^{a1}R^{a2}$;

$R^{13}$ is selected from H, $C_{1-4}$alkyl, and $C_{1-4}$haloalkyl; and $R^{15}$ is selected from $C_{6-10}$aryl, 5-10 membered heteroaryl, and -$L^1$-$R^{16}$;

wherein $L^1$ is selected from —$C_{1-4}$ alkylene; and wherein $R^{16}$ is selected from $C_{6-10}$aryl, and 5-10 membered heteroaryl;

wherein each $C_{6-10}$ aryl, and 5-10 membered heteroaryl of $R^{15}$ and $R^{16}$ is optionally substituted with one to four groups independently selected from halo, hydroxyl, —$COOR^{b7}$, $NR^{a1}R^{a2}$, —$S(O)_2R^{a5}$, $C_{1-4}$alkyl, $C_{1-4}$alkoxyl, $C_{1-4}$haloalkyl, $C_{1-4}$haloalkoxyl, and —$C_{1-4}$ alkylene-$NR^{a1}R^{a2}$;

each $R^{a1}$ and $R^{a2}$ is independently selected from H, $C_{1-6}$alkyl, and $C_{1-6}$haloalkyl;

$R^{a5}$ is $C_{1-6}$alkyl;

$R^{b7}$ is independently selected from H and $C_{1-6}$alkyl;

m is selected from 0, 1, and 2; and n is selected from 1, and 2.

2. The compound of claim 1, or a pharmaceutically acceptable salt thereof, wherein the compound is of formula (Ja):

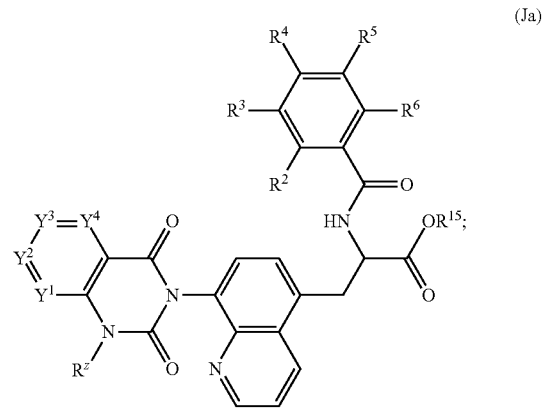

(Ja)

wherein $Y^1$, $Y^2$, $Y^3$, and $Y^4$ is independently selected from $CR^y$, and N, wherein each $R^y$ is independently selected from H and $R^a$; and $R^z$ is selected from H, $C_{1-6}$alkyl, $C_{2-6}$alkenyl, $C_{2-6}$alkynyl, $C_{1-6}$ haloalkyl, $C_{3-8}$ cycloalkyl, and 3-6 membered heterocyclyl.

3. The compound of claim 1, or a pharmaceutically acceptable salt thereof, wherein the compound is of formula (Jd):

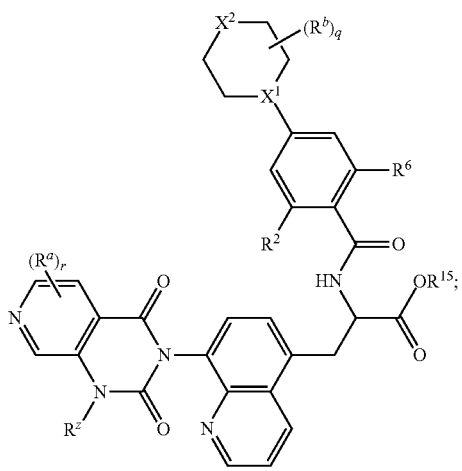

wherein $R^z$ is selected from H, —CH$_3$, —CD$_3$, —CH$_2$F, —CHF$_2$, —CF$_3$, and —CH$_2$CH$_3$;

$X^1$ is selected from CR$^{x1}$, and N;

$X^2$ is selected from CR$^{x1}$R$^{x2}$, NR$^{x2}$, O, and S(O)$_2$, wherein R$^{x1}$ is selected from H, and R$^b$, wherein R$^{x2}$ is selected from H, C$_{1-4}$alkyl, and C$_{1-4}$haloalkyl;

q is selected from 0, 1, 2, and 3; and r is selected from 0, 1, 2, and 3.

4. The compound of claim 1, or a pharmaceutically acceptable salt thereof; wherein R$^1$ is selected from

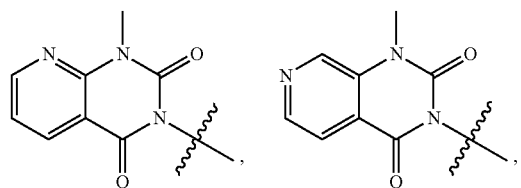

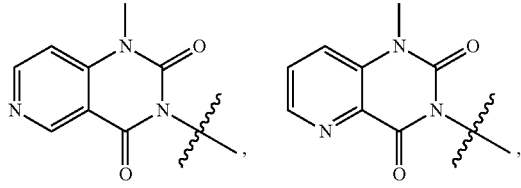

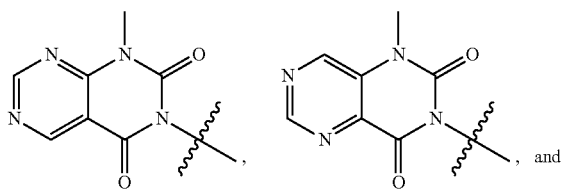

and

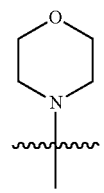 [SMILES: *N1CCOCC1]

5. The compound of claim 1, or a pharmaceutically acceptable salt thereof; wherein R$^3$ and R$^5$ are H.

6. The compound of claim 1, or a pharmaceutically acceptable salt thereof, wherein each R$^2$ and R$^6$ is independently selected from F and —CH$_3$.

7. The compound of claim 1, or a pharmaceutically acceptable salt thereof, wherein R$^2$ is F, and R$^6$ is —CH$_3$.

8. The compound of claim 1, or a pharmaceutically acceptable salt thereof, wherein R$^4$ is

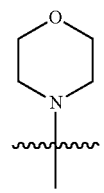 [SMILES: *N1CCOCC1]

substituted with one to three R$^b$.

9. The compound of claim 1, or a pharmaceutically acceptable salt thereof, wherein R$^4$ is

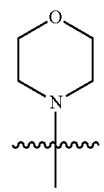 [SMILES: *N1CCOCC1]

substituted with one to three R$^b$; and wherein each R$^b$ is independently selected from C$_{1-4}$alkyl, C$_{1-4}$alkoxyl, C$_{1-4}$haloalkyl, and C$_{1-4}$haloalkoxyl.

10. The compound of claim 1, or a pharmaceutically acceptable salt thereof, wherein R$^4$ is

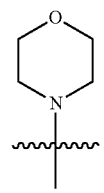

substituted with —CF$_3$.

11. The compound of claim 2, or a pharmaceutically acceptable salt thereof, wherein Y$^2$ is N.

12. The compound of claim 2, or a pharmaceutically acceptable salt thereof, wherein Y$^4$ is CH.

13. The compound of claim 2 or 3, or a pharmaceutically acceptable salt thereof, wherein R$^z$ is —CH$_3$.

14. The compound of claim 3, or a pharmaceutically acceptable salt thereof, wherein $X^1$ is N.

15. The compound of claim 3, or a pharmaceutically acceptable salt thereof, wherein $X^2$ is O.

16. The compound of claim 3, or a pharmaceutically acceptable salt thereof, wherein q is 1, and $R^b$ is $CF_3$.

17. The compound of claim 1, or a pharmaceutically acceptable salt thereof, wherein $R^{15}$ is selected from

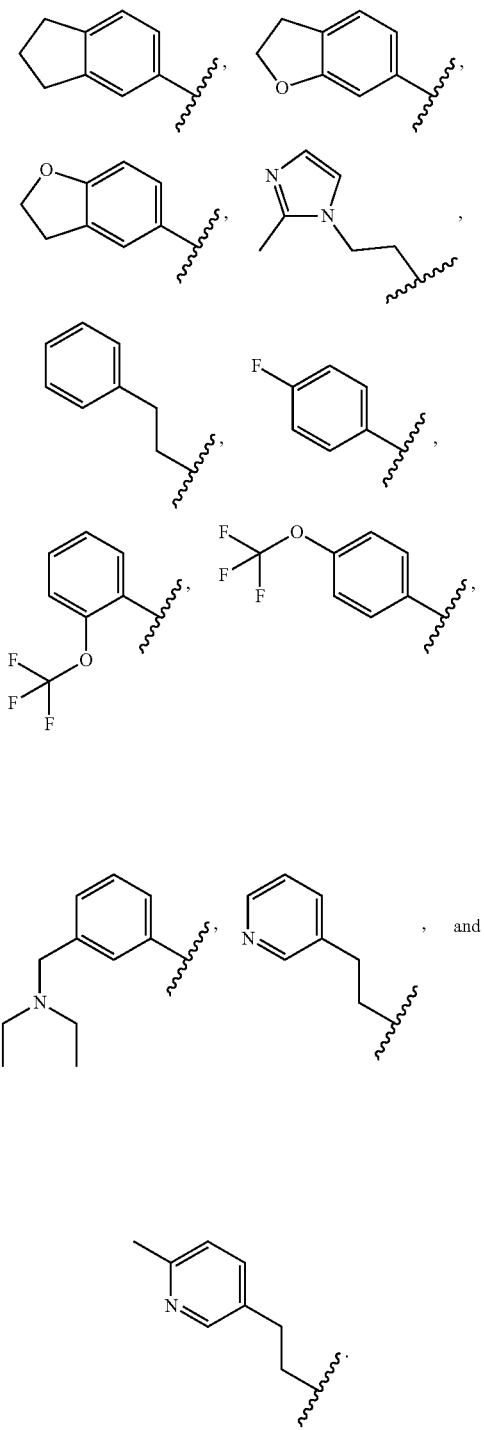

18. The compound of claim 1, or a pharmaceutically acceptable salt thereof, wherein the compound is selected from:

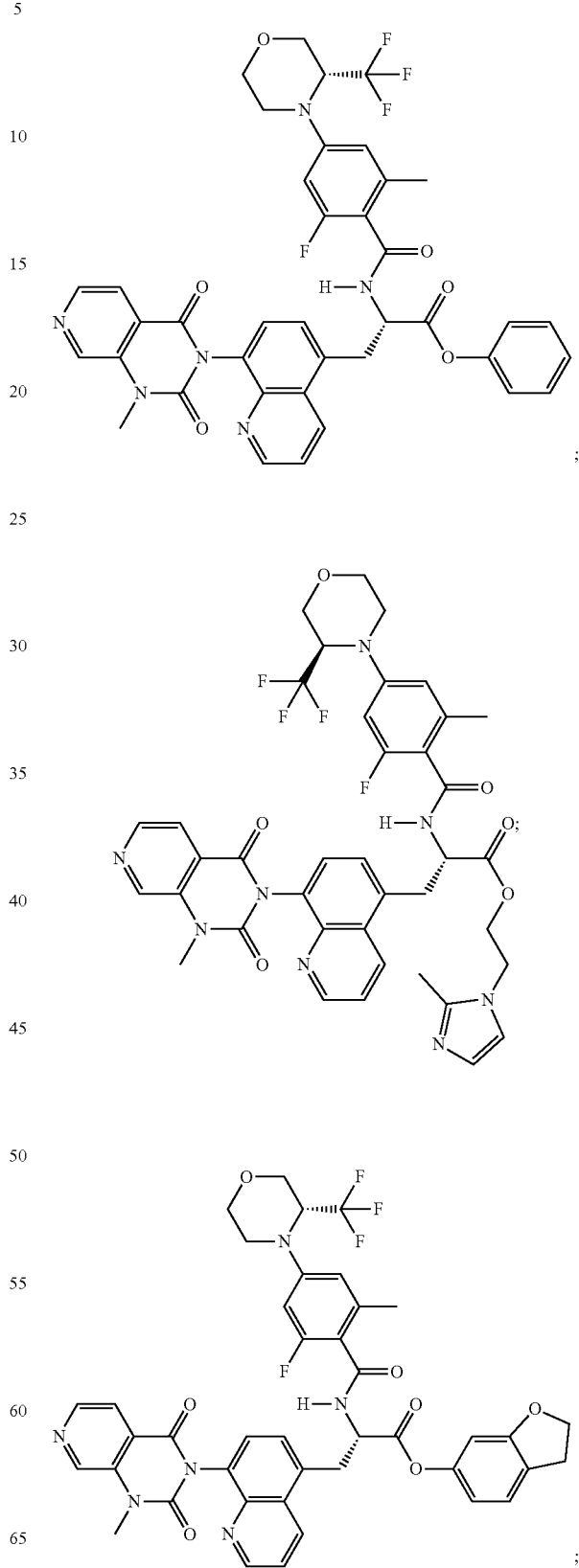

569
-continued
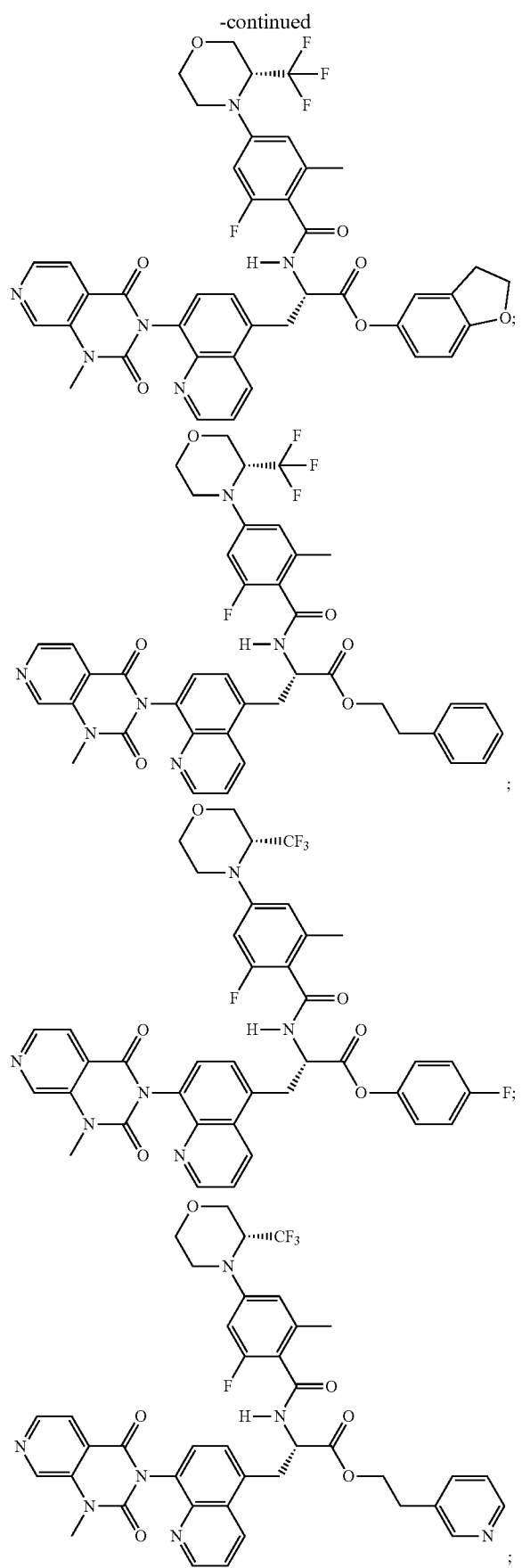
570
-continued
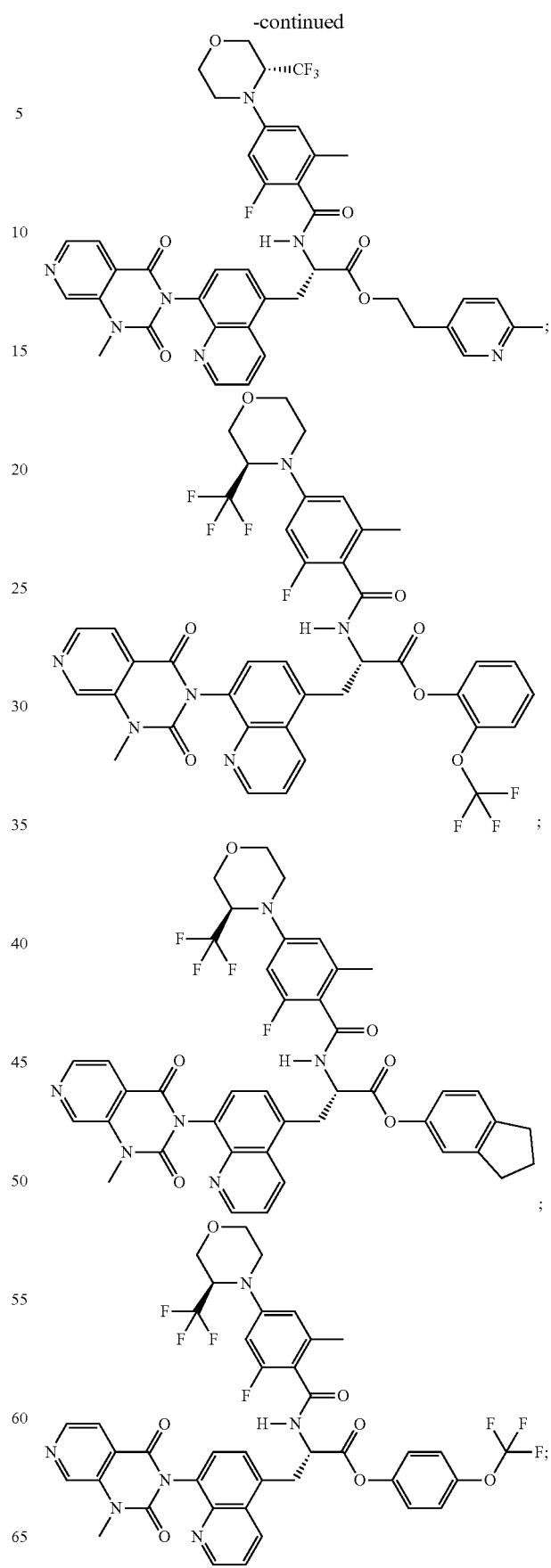

571
-continued
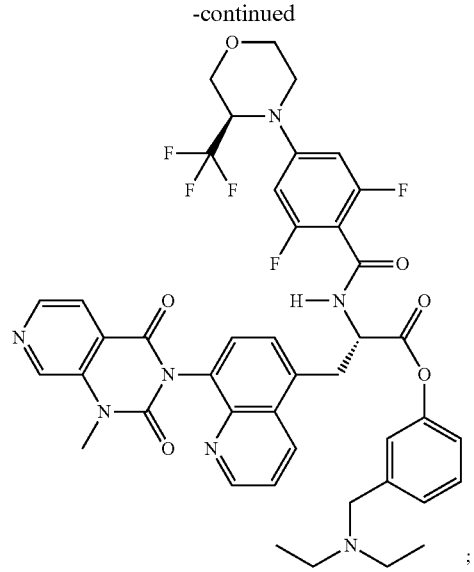
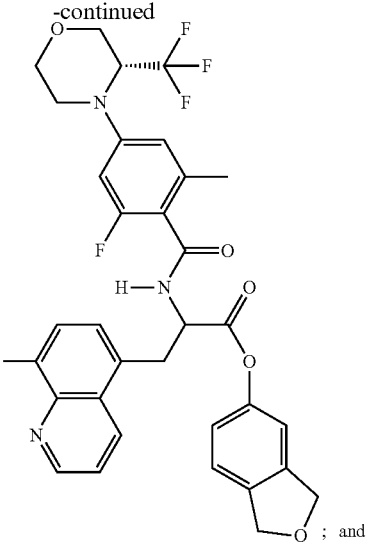; and
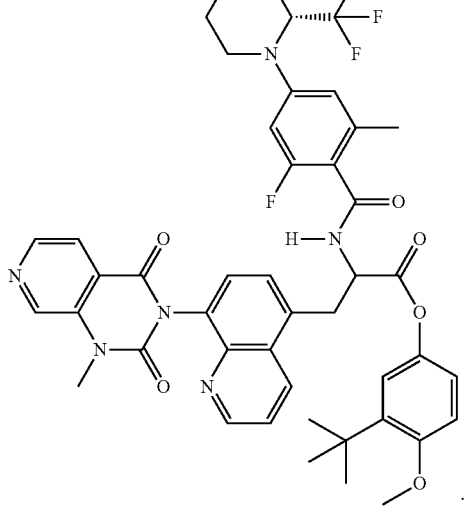
* * * * *